US009315820B2

(12) United States Patent
Dühring et al.

(10) Patent No.: US 9,315,820 B2
(45) Date of Patent: Apr. 19, 2016

(54) METABOLICALLY ENHANCED CYANOBACTERIUM WITH SEQUENTIALLY INDUCIBLE PRODUCTION GENES FOR THE PRODUCTION OF A FIRST CHEMICAL COMPOUND

(71) Applicant: Algenol Biofuels Inc., Fort Myers, GA (US)

(72) Inventors: Ulf Dühring, Fredersdorf (DE); Alexandra Friedrich, Fort Myers, FL (US); Kerstin Baier, Kleinmachnow (DE); Heike Enke, Berlin (DE); Dan Kramer, Berlin (DE)

(73) Assignee: Algenol Biotech LLC, Fort Myers, FL (US)

( * ) Notice: Subject to any disclaimer, the term of this patent is extended or adjusted under 35 U.S.C. 154(b) by 0 days.

(21) Appl. No.: 14/320,477

(22) Filed: Jun. 30, 2014

(65) Prior Publication Data

US 2014/0322799 A1 Oct. 30, 2014

Related U.S. Application Data

(63) Continuation of application No. PCT/EP2012/076786, filed on Dec. 21, 2012.

(60) Provisional application No. 61/583,580, filed on Jan. 5, 2012, provisional application No. 61/581,976, filed on Dec. 30, 2011.

(51) Int. Cl.
*C12N 15/74* (2006.01)
*C12N 15/82* (2006.01)
*C12P 7/06* (2006.01)

(52) U.S. Cl.
CPC ............ *C12N 15/8243* (2013.01); *C12N 15/74* (2013.01); *C12P 7/065* (2013.01); *Y02E 50/17* (2013.01)

(58) Field of Classification Search
None
See application file for complete search history.

(56) References Cited

U.S. PATENT DOCUMENTS 5,750,380 A 5/1998 Itakura et al.
6,472,184 B1 10/2002 Hegemann

FOREIGN PATENT DOCUMENTS

WO WO/2009098089 8/2009
WO WO/2013098265 7/2013

OTHER PUBLICATIONS

Holland-Staley et al. (2000), "Aerobic Activity of *Escherichia coli* Alcohol Dehydrogenase is Determined by a Single Amino Acid," Jour. Bacteriology 182:6049-6054.

Hoppner, et al. (1983) "Purification and Kinetic Characteristics of Pyruvate Decarboxylase and Ethanol Dehydrogenase from Zymomonas mobilis in Relation to Ethanol Production," Eur. J. Appl. Microbiol. Biotechnol. 17:152-157.

Karlin, et al. (1993), "Applications and Statistics for Multiple High-scoring Segments in Molecular Sequences," Proc. Natl. Acad. Sci. U.S.A. 90:5873-5877.

Karlin, et al. (1990), "Methods for Assessing the Statistical Significance of Molecular Sequence Features by Using General Scoring Schemes," Proc. Natl. Acad. Sci. U.S.A. 87:2264-2268.

Nakamura, et al. (2000), "CyanoBase, theGenome Database for *Synechocystis* sp. Strain PCC6803: Status for the Year 2000," Nucleic Acids Res. 28:72.

Ruffing, A.M. (2011), "Engineered Cyanobacteria: Teaching an Old Bug New Tricks," Bioengineered Bugs 2:136-149.

Takahama, et al. (2003), "Construction and Analysis of a Recombinant Cyanobacterium Expressing a Chromosomally Inserted Gene for an Ethylene-Forming Enzyme at the psbAl Locus," J. Bioscience Bioengineering 95:302-305.

Thompson, et al. (1994), "Clustal W: Improving the Sensitivity of Progressive Multiple Sequence Alignment Through Sequence Weighting, Position-specific Gap Penalties and Weight Matrix Choice," Nucleic Acids Res. 22:4673-4680.

Tumer et al. (1983), "Different Promoters for the Anabaena Glutamine Synthetase Gene During Growth Using Molecular or Fixed Nitrogen," Nature 306:337-342.

Deng et al. (1999), "Ethanol Synthesis by Genetic Engineering in Cyanobacteria," Applied and Environmental Microbiology 65:523-528.

Dexter et al. (2009), "Metabolic Engineering of Cyanobacteria for Ethanol Production," Energy and Environmental Science 2:857-864.

International Patent Application Publication No. WO/2013098265; International Search Report (ISR).

International Patent Application Publication No. WO/2013098265; Written Opinion.

International Patent Application Publication No. WO/2013098265; International Preliminary Report on Patentability (IPRP).

*Primary Examiner* — Brian J Gangle
(74) *Attorney, Agent, or Firm* — Lawrence B. Ebert; Suzanne G. Jepson

(57) ABSTRACT

This invention provides a metabolically enhanced cyanobacterium for the production of a chemical compound of interest, having at least two first production genes encoding first biocatalysts for the production of the first chemical compound. One of the two first production genes is under the transcriptional control of a first promoter for the first production gene, whereas the other of the two first production genes is under the transcriptional control of a second promoter for the first production gene. The first promoter and second promoter are separately inducible under different conditions and the at least two first biocatalysts catalyze the same chemical reaction. Metabolically enhanced cyanobacteria according to the present invention allow prolonged production of first chemical compounds. Further provisions of the present invention include, inter alia, a method for producing the metabolically enhanced cyanobacterium and a method for producing a first chemical compound by culturing the metabolically enhanced cyanobacterium.

25 Claims, 68 Drawing Sheets

A

B

A

B

A

B

A

B

A

B

A

B

METABOLICALLY ENHANCED CYANOBACTERIUM WITH SEQUENTIALLY INDUCIBLE PRODUCTION GENES FOR THE PRODUCTION OF A FIRST CHEMICAL COMPOUND

CROSS-REFERENCE TO RELATED APPLICATIONS

This application is a continuation of International Application No. PCT/EP2012/076786, filed Dec. 21, 2012, which claims priority to U.S. Provisional Application No. 61/583,580, filed Jan. 5, 2012, and also claims priority to U.S. Provisional Application No. 61/581,976, filed Dec. 30, 2011, all of which are incorporated herein by reference.

STATEMENT REGARDING FEDERALLY SPONSORED RESEARCH

Not Applicable.

REFERENCE TO SEQUENCE LISTING

This application contains a sequence listing submitted by EFS-Web, thereby satisfying the requirements of 37 C.F.R. §§1.821-1.825. The sequence listing, created on Jun. 30, 2014, contains 84 sequences and is 486 KB in size.

FIELD OF THE INVENTION

This invention is related to the field of production of chemical compounds by using metabolically enhanced cyanobacterial cells.

BACKGROUND OF THE INVENTION

Various chemical compounds of interest, such as biofuels like fatty acid esters or alcohols, functional foods, vitamins, pharmaceuticals such as lactams, peptides and polyketides or terpenes and terpenoids and also biopolymers such as polyhydroxyalkanoates can be produced via metabolically enhanced cyanobacteria. One of these compounds is ethanol. In this context, the PCT patent application WO 2009/098089 A2 discloses the use of ethanologenic genes, for example pyruvate decarboxylase and alcohol dehydrogenase for the production of ethanol.

Typically, the cyanobacterial host cells for the production of a specific chemical compound of interest are metabolically enhanced hybrid lines, which have been transformed with genetic elements containing corresponding production genes under the control of either constitutive or inducible promoters. In the case of inducible promoters, transcription of the production genes is coupled to specific induction conditions, for instance the addition or depletion of certain metals such as Cu, Zn etc. to, or from, the culture medium.

It is a known problem in the art that such metabolically enhanced cyanobacteria produce such chemical compounds, e.g. ethanol, for a certain period of time, before the productivity decreases due to mutations in the respective production genes. For example, Takahama and colleagues (2003) investigated the time-related productivity of a recombinant *Synechococcus elongatus* PCC 7942 harboring a heterologous gene for an ethylene-forming enzyme. They found that the rate of ethylene production in the recombinant culture decreased as a result of competition with faster growing ethylene-non-forming mutants that carried short nucleotide insertions within the coding sequence of the gene for the ethylene forming enzyme.

Therefore, there is a need for improved cyanobacterial hybrid strains for prolonged production of first chemical compounds.

This task is solved by providing a metabolically enhanced cyanobacterium according to base claim 1. Further claims are directed to advantageous embodiments of the metabolically enhanced cyanobacteria, to a method of producing the metabolically enhanced cyanobacteria, and to a method of producing a first chemical compound by culturing the metabolically enhanced cyanobacteria.

SUMMARY OF THE INVENTION

The invention described herein discloses a metabolically enhanced cyanobacterium for the production of a first chemical compound, comprising:

- at least two first production genes encoding first biocatalysts for the production of the first chemical compound;
- wherein one of the two first production genes is under the transcriptional control of a first promoter for the first production gene;
- wherein the other of the two first production genes is under the transcriptional control of a second promoter for the first production gene;
- wherein the first promoter and second promoter are separately inducible under different conditions;
- wherein the at least two first biocatalysts catalyze the same chemical reaction.

This invention further discloses a method for producing a metabolically enhanced cyanobacterium as above, comprising the method steps of:

- a) Providing the following at least two transformable nucleic acid sequences:
  - said first production gene under the transcriptional control of said first promoter for the first production gene;
  - said first production gene under the transcriptional control of said second promoter for the first production gene;
- b) Transforming said at least two transformable nucleic acid sequences into the cyanobacteria cells.

This invention also discloses a method for producing a first chemical compound using any of the metabolically enhanced cyanobacterium as above, comprising the method steps of:

- A) Culturing the metabolically enhanced cyanobacterium under conditions for induction of the first promoter for the first production gene, the cyanobacterium producing the first chemical compound;
- B) Culturing the metabolically enhanced cyanobacterium under conditions for induction of the second promoter for the first production gene, the cyanobacterium producing the first chemical compound;
- wherein method step A) and method step B) are temporally separated;
- wherein the second promoter for the first production gene of method step B) is maintained in an uninduced state during method step A).

This invention further discloses a metabolically enhanced cyanobacterium for the production of a first chemical compound, comprising:

- at least a first and second first production gene encoding first biocatalysts for the production of the first chemical compound;

wherein both first production genes are under the transcriptional control of the same inducible promoter for the first production genes;

wherein the inducible promoter for the first production genes is gradually inducible in a dose-dependent manner;

wherein said first biocatalysts catalyze the same chemical reaction.

Finally, this invention discloses a method for producing a first chemical compound using any of the metabolically enhanced cyanobacteria above, comprising the method steps of:

A1) Culturing the metabolically enhanced cyanobacterium under a first condition for induction of the promoter for the first production genes, the cyanobacterium producing the first chemical compound;

A2) Culturing the metabolically enhanced cyanobacterium under a second condition for induction of the promoter for the first production genes, the cyanobacterium producing the first chemical compound;

wherein method step A1) and method step A2) are temporally separated;

wherein the first condition for induction results in a lower induction of the promoter for the first production genes than the second condition of induction.

BRIEF DESCRIPTION OF THE FIGURES

The following figures schematically show, inter alia, several maps of plasmids used in representative embodiments of the present invention. Some of these plasmids harbour only one first production gene under the transcriptional control of an inducible promoter for the first production gene, for example the plasmids shown in FIGS. 7-9, 14-16 and 19. The use of one of these plasmids for generating a metabolically enhanced cyanobacterium according to the present invention therefore requires that at least a second first production gene under the transcriptional control of a second inducible promoter for the first production gene is present in the cyanobacteria, e.g. on a different genetic element, to obtain a metabolically enhanced cyanobacterium according to the present invention.

In contrast, some other plasmids harbor already two first production genes under the transcriptional control of a first and a second inducible promoter for the first production gene according to the present invention, for instance plasmids shown in FIGS. 10, 17 and 18. For production of ethanol as the first chemical compound, however, the corresponding metabolically enhanced cyanobacteria have to comprise at least one second production gene encoding an alcohol dehydrogenase enzyme located on another genetic element in addition to the first production genes encoding pyruvate decarboxylases shown in FIGS. 10, 17 and 18.

Plasmid maps shown in the following include restriction sites for the correspondingly denoted restriction endonucleases. “Gm” denotes a gene conferring resistance to Gentamycin, and “aph (KanR2)” denotes a gene coding for aminoglycoside (3') phosphotransferase conferring resistance to Kanamycin. “Sp/Sm” designates a gene imparting resistance for spectinomycin/streptomycin and “Cm” depicts a gene conferring resistance to Chloramphenicol. The bold circumferential arrows in the plasmid maps illustrate the position and the orientation of inserted genes. Note that the regulator genes generally run in antisense orientation from 3' to 5'. The protruding angled arrows illustrate the position of the specified promoter sequence.

In general, plasmids were generated by inserting DNA constructs comprising the promoters and the production genes into the plasmids pVZ322a, pVZ324 and pVZ325a as well as pGEM via the multiple cloning site using corresponding restriction/ligation protocols. The shown plasmids can, however, alternatively be synthetically produced by gene synthesis.

FIG. 1A and FIG. 1B schematically illustrate the problem of genetic instability and the corresponding decrease of production of the first chemical compound under long-term cultivation conditions using conventional cyanobacterial hybrid strains. FIG. 1A schematically shows a metabolically enhanced cyanobacterial cell. FIG. 1B shows the same metabolically enhanced cyanobacterial cell after long term cultivation.

FIG. 2A schematically shows a metabolically enhanced cyanobacterial cell according to the principles of the present invention, wherein the production genes are co-located on one genetic element prior to, or at the start of, method step A).

FIG. 2B shows the cyanobacterial cell with the production genes co-located on one genetic element in the transition phase from method step A) to method step B).

FIG. 2C shows the cyanobacterial cell with the production genes co-located on one genetic element in the transition phase from method step B) to method step C).

FIG. 3A schematically illustrates a metabolically enhanced cyanobacterium according to the principles of the present invention, wherein the different production genes are located on different genetic elements, prior to, or at the start of, method step A).

FIG. 3B shows the cyanobacterial cell with the different production genes located on different genetic elements in the transition phase from method step A) to method step B).

FIG. 3C shows the cyanobacterial cell with the different production genes located on different genetic elements in the transition phase from method step B) to method step C).

Figure 4:
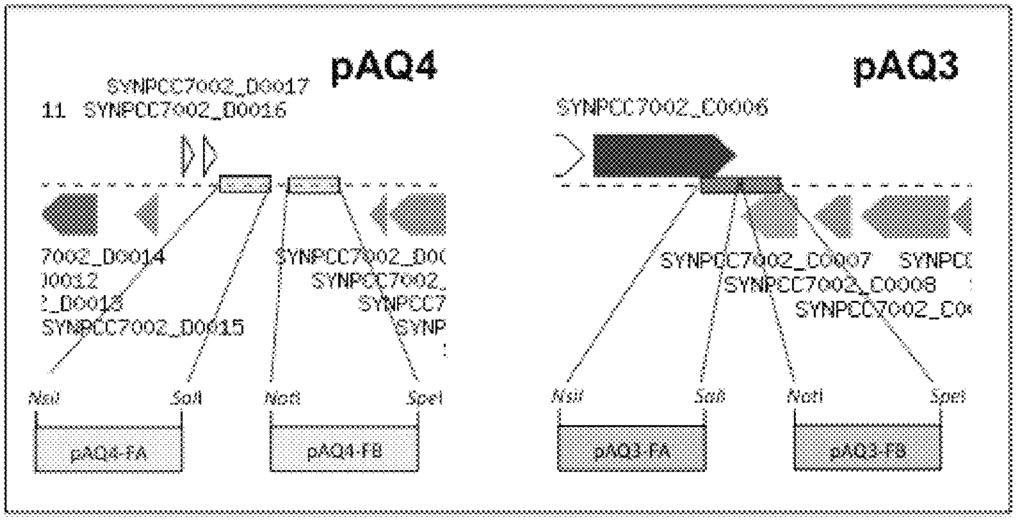

FIG. 4 illustrates the chosen integration site for homologous recombination of genetic constructs into the endogenous plasmid pAQ4, and a previously published integration site into the endogenous plasmid pAQ3 of *Synechococcus* PCC7002/ABCC 1535 via recombined flanking regions FA and FB.

Figure 5:
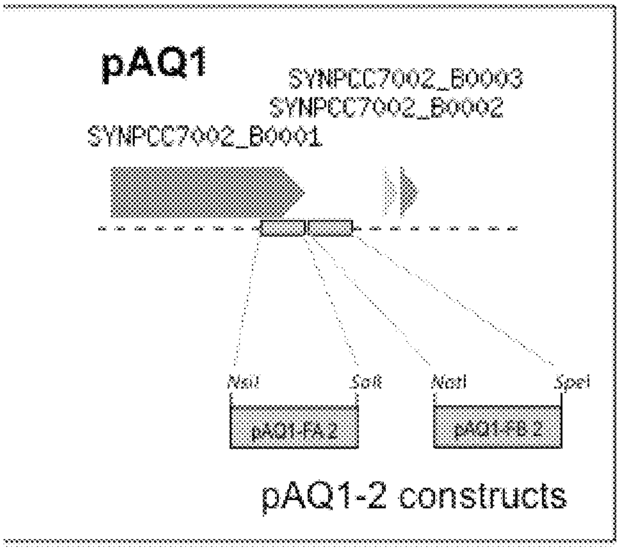

FIG. 5 illustrates the chosen integration site for homologous recombination of genetic constructs into the endogenous plasmid pAQ1 of *Synechococcus* PCC7002 via recombined flanking regions FA2 and FB2.

Figure 6:
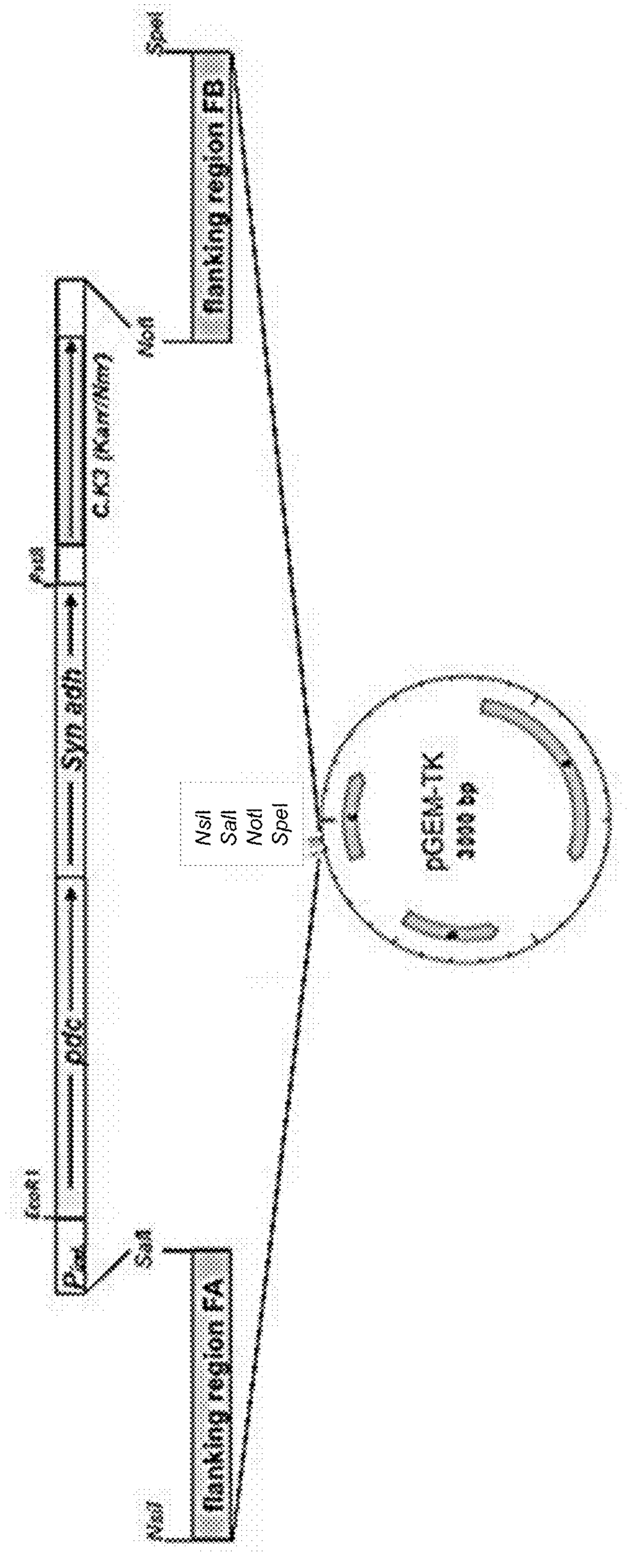

FIG. 6 illustrates the generation of a transformable genetic construct harboring an operon comprising a first production gene encoding a Pdc enzyme and a second production gene encoding an Adh enzyme under the control of an inducible promoter as well as an antibiotic resistance cassette C.K3. The construct is ligated into the cloning vector pGEM-TK in between flanking regions FA and FB, amplified, cut-out at restriction sites NsiI and SpeI to incorporate the flanking regions and can then be transformed via homologous recombination into e.g. pQ4, pAQ3 or pAQ1 depending on the chosen flanking regions.

Figure 7:
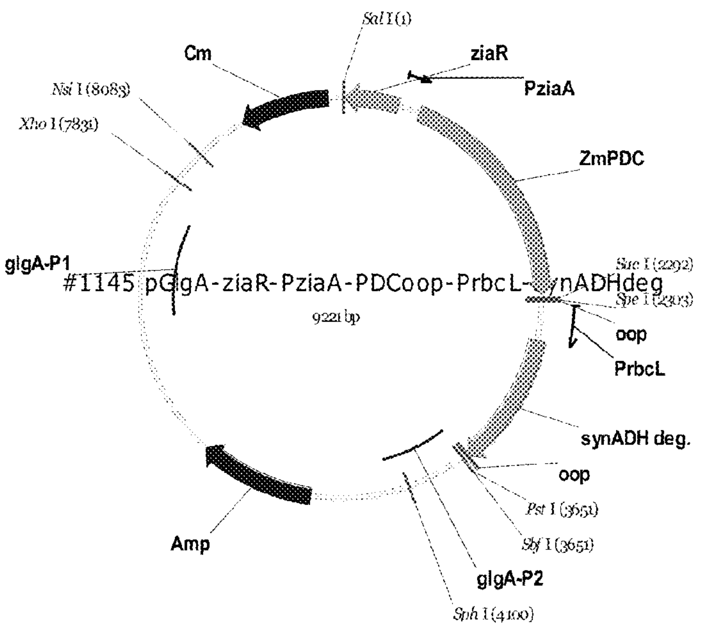
Figure 7:
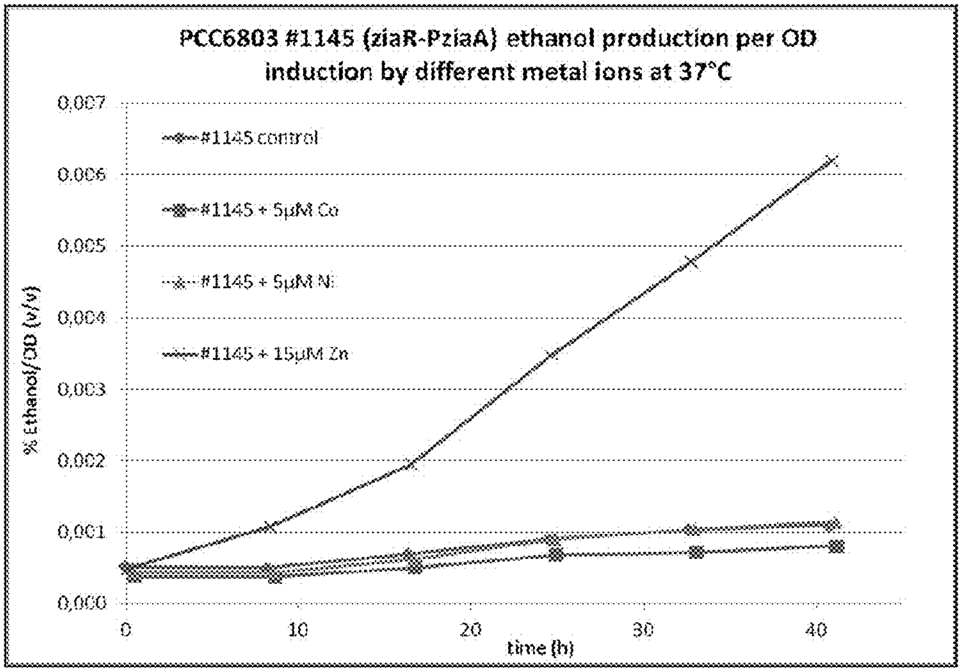

FIG. 7A depicts the map of construct #1145 for chromosomal integration comprising a pdc gene from *Zymomonas mobilis* under the transcriptional control of the $Zn^{2+}$-inducible promoter ziaR-PziaA and a degenerated adh from *Synechocystis* PCC 6803 under the transcriptional control of the constitutive promoter Prbc.

FIG. 7B shows the ethanol production per OD of *Synechocystis* PCC 6803 strain #1145 after induction with Co, Ni or Zn as well as a control without addition of these metal ions.

Figure 8:
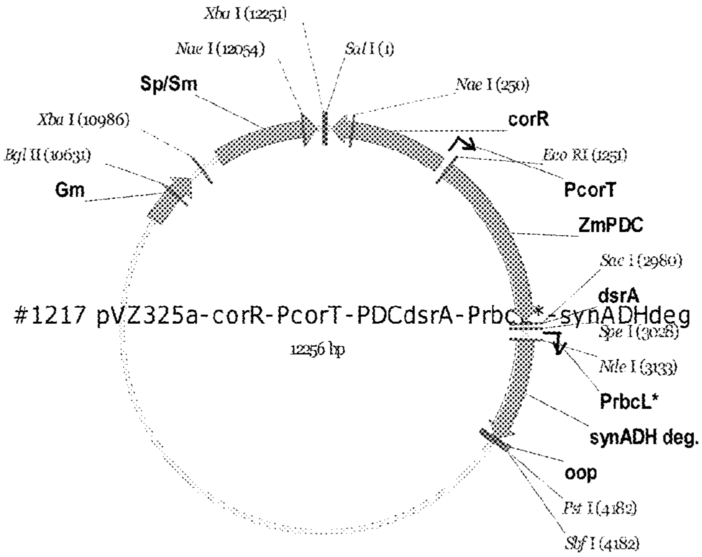
Figure 8:
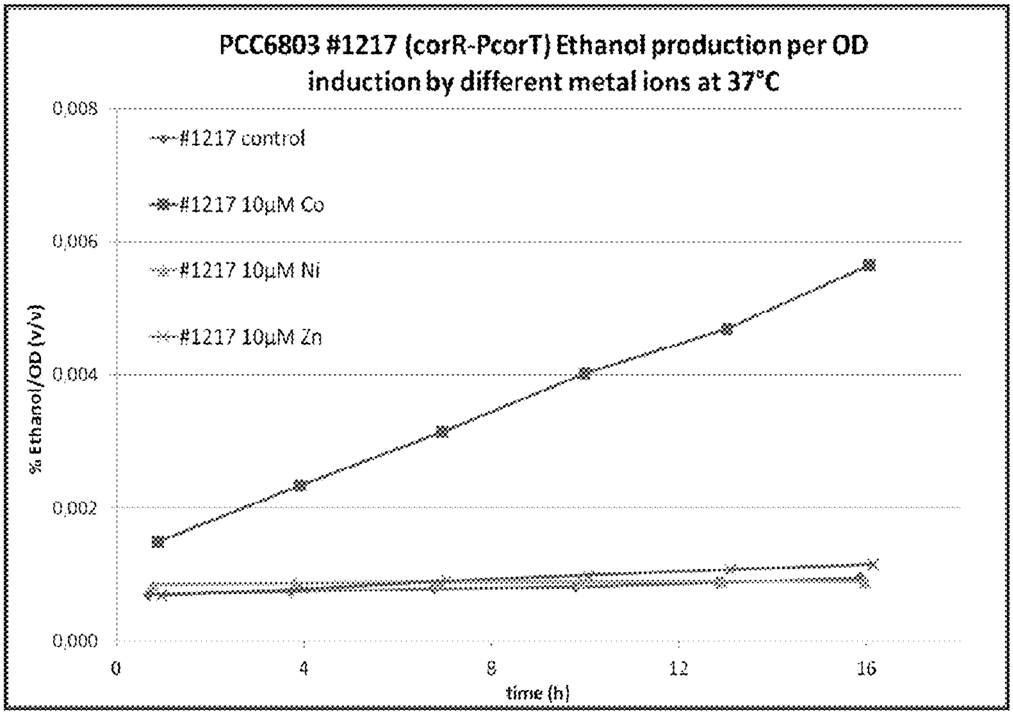

FIG. 8A depicts the map of the self-replicating broad host range vector pVZ325 #1217 comprising a pdc from *Zymomonas mobilis* under the transcriptional control of the $Co^{2+}$-inducible promoter corR-PcorT and a degenerated adh from *Synechocystis* PCC 6803 under the transcriptional control of the constitutive promoter Prbc*.

FIG. 8B shows the ethanol production per $OD_{750\ nm}$ of *Synechocystis* PCC 6803 strain #1217 after induction with Co, Ni or Zn as well as a control without addition of these metals.

FIG. 9A depicts the map of self-replicating broad host range vector pVZ325 #1227 comprising a pdc from *Zymomonas mobilis* under the transcriptional control of the $Ni^{2+}$-inducible promoter nrsR-PnrsB and a degenerated adh from *Synechocystis* PCC 6803 under the transcriptional control of the constitutive promoter Prbc*.

FIG. 9B shows the ethanol production per OD of *Synechocystis* PCC 6803 strain #1227 after induction with Co, Ni or Zn as well as a control without addition of these metal ions.

Figure 10A:
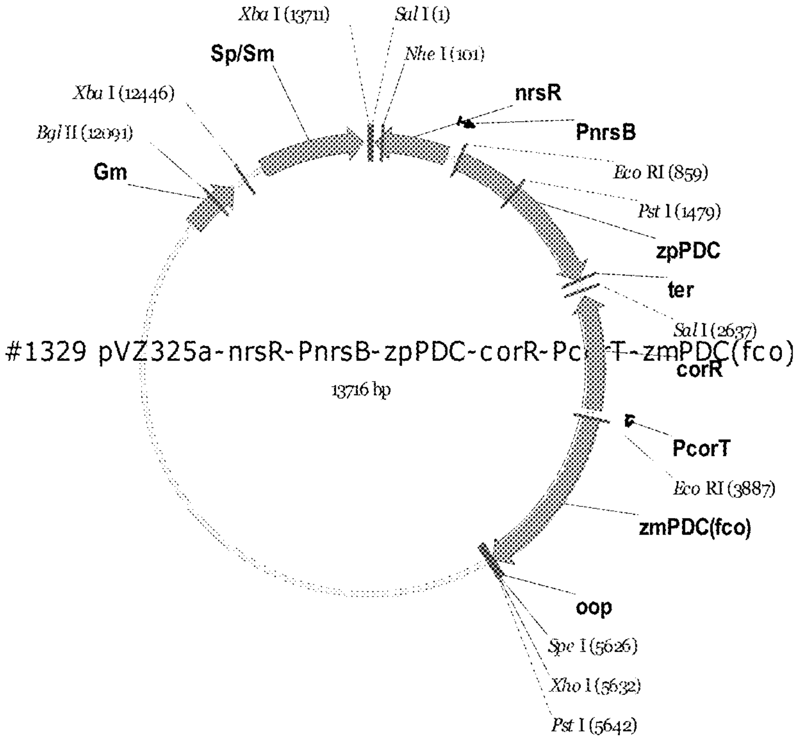

FIG. 10A depicts the map of self-replicating broad host range vector pVZ325 #1329 comprising a first production gene encoding a pdc from *Zymomobacter palmae* under the transcriptional control of the $Ni^{2+}$-inducible promoter nrsR-PnrsB and a second first production gene encoding a codon-optimised pdc from *Zymomonas mobilis* under the transcriptional control of the $Co^{2+}$-inducible promoter corR-PcorT.

Figure 10B:
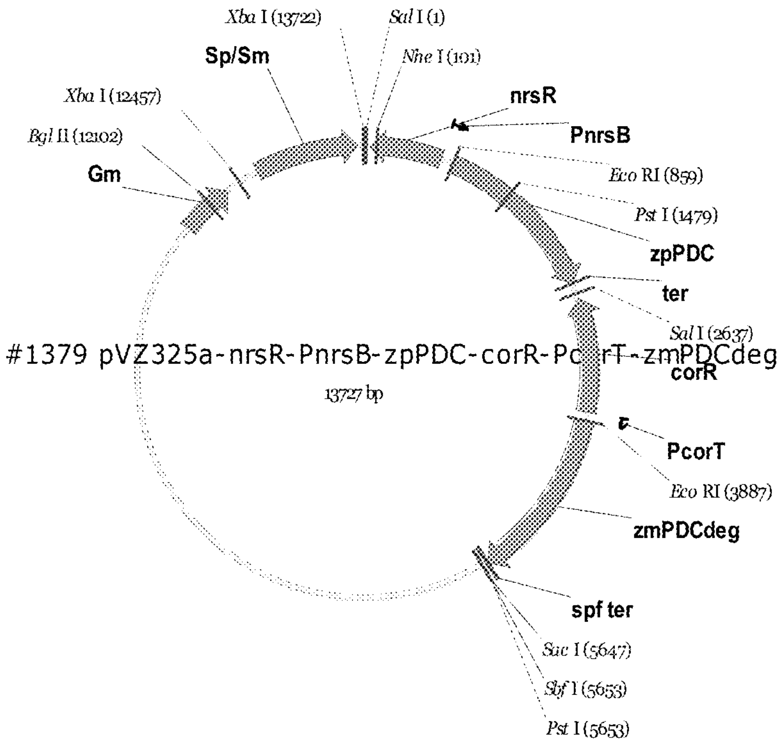

FIG. 10B depicts the map of self-replicating broad host range vector pVZ325 #1379 comprising a first production gene encoding a pdc from *Zymomobacter palmae* under the transcriptional control of the $Ni^{2+}$-inducible promoter nrsR-PnrsB and a second first production gene encoding a degenerated pdc from *Zymomonas mobilis* under the transcriptional control of the $Co^{2+}$-inducible promoter corR-PcorT.

Figure 11:
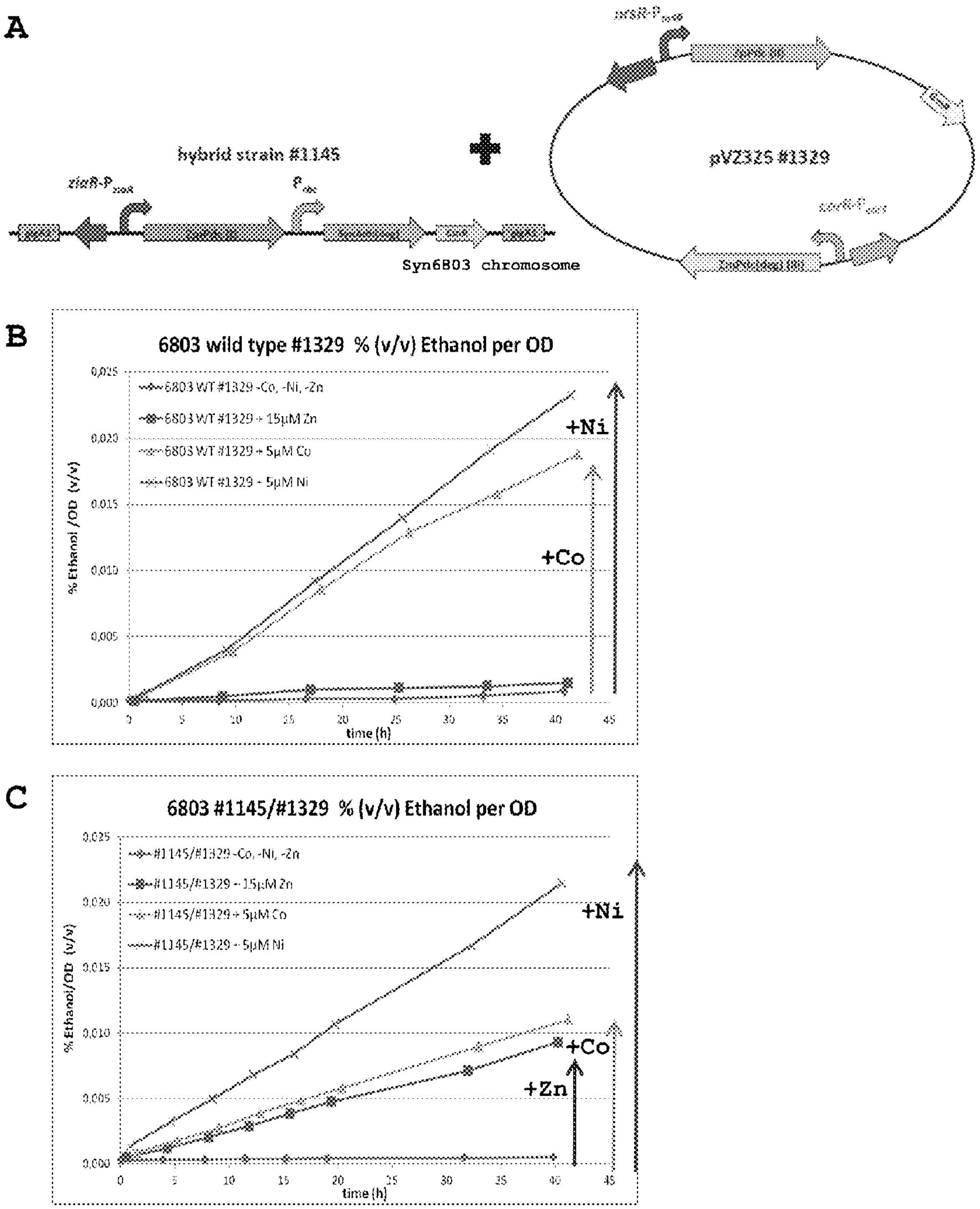

FIG. 11A illustrates the genetic constructs used to generate the *Synechocystis* PCC 6803 strain #1145/#1329. Strain #1145 harboring a first production gene encoding a pdc enzyme from *Zymomonas mobilis* under the transcriptional control of the $Zn^{2+}$-inducible first promoter ziaR-PziaA and a second production gene which is a degenerated adh-gene from *Synechocystis* PCC 6803 under the transcriptional control of the constitutive Prbc promoter recombined into its chromosome was further transformed with the self-replicating broad host range vector pVZ325 #1329 comprising a second first production gene encoding a Pdc enzyme from *Zymobacter palmae* under the transcriptional control of the $Ni^{2+}$-inducible second promoter nrsR-PnrsB and a third first production gene which is a codon-optimised pdc gene from *Zymomonas mobilis* under the transcriptional control of the $Co^{2+}$-inducible third promoter corR-PcorT.

FIG. 11B shows the ethanol production per OD of a wild type *Synechocystis* PCC 6803 transformed with construct #1329 after selective induction with Zn, Co and Ni as well as a control without addition of these metal ions.

FIG. 11C shows the ethanol production per OD of *Synechocystis* PCC 6803 strain #1145/#1329 after selective induction with Zn, Co and Ni as well as a control without addition of these metal ions.

Figure 12:
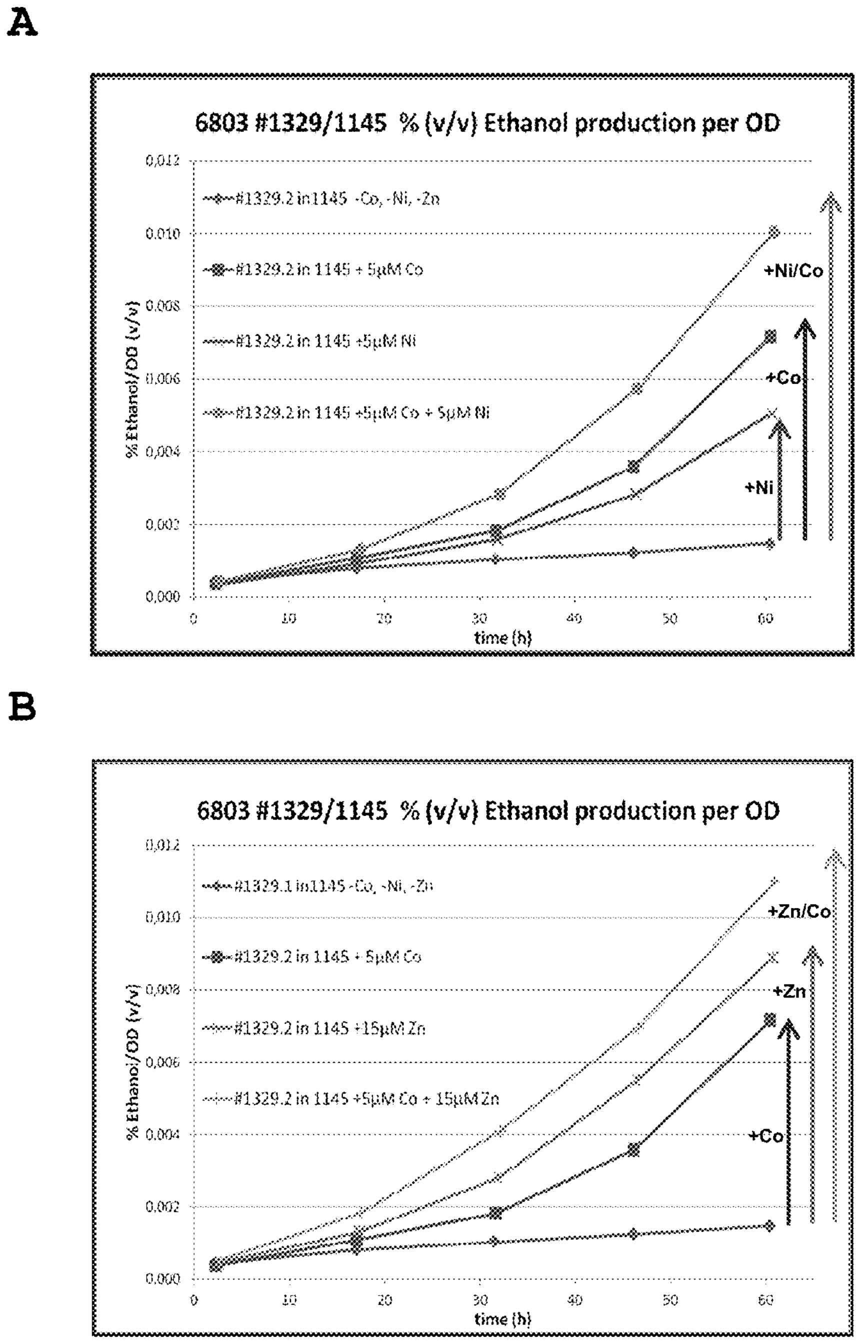

FIG. 12A shows the ethanol production per OD of *Synechocystis* PCC 6803 strain #1145/#1329 without induction, after induction with $Ni^{2+}$, after induction with $Co^{2+}$, and after combined induction with $Ni^{2+}$ and $Co^{2+}$.

FIG. 12B shows the ethanol production per OD of *Synechocystis* PCC 6803 strain #1145/#1329 without induction, after induction with $Co^{2+}$, after induction with $Zn^{2+}$, and after combined induction with $Zn^{2+}$ and $Co^{2+}$.

Figure 13:
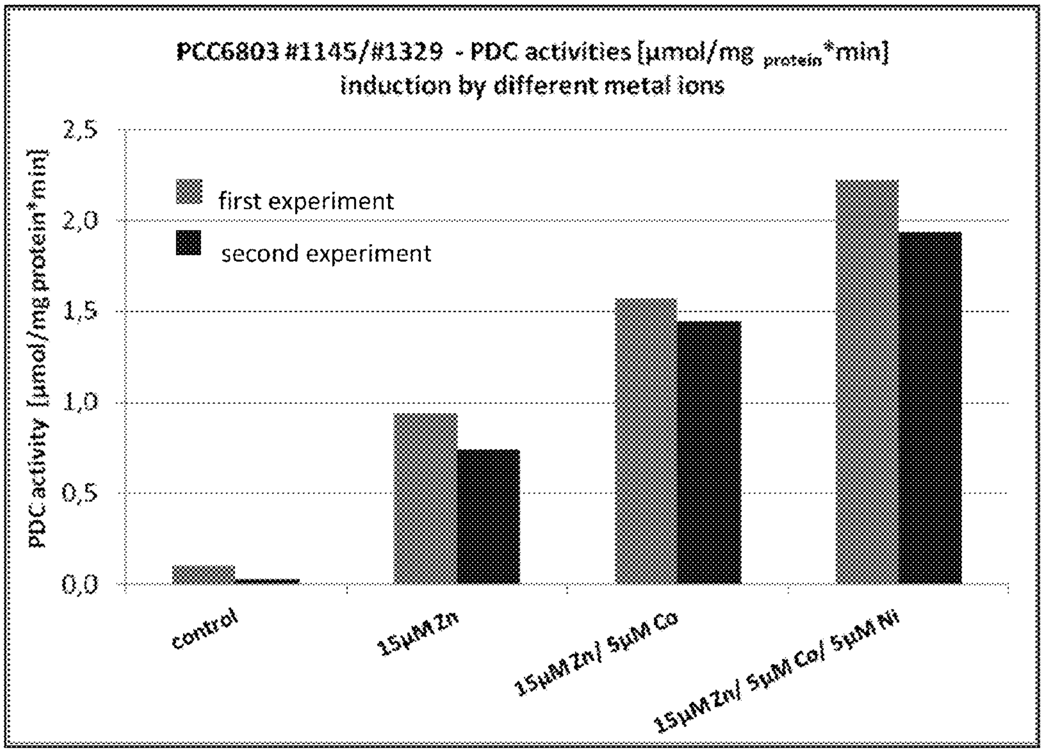

FIG. 13 shows the specific Pdc activities of *Synechocystis* PCC 6803 #1145/#1329 without induction, after selective induction with $Zn^{2+}$, $Zn^{2+}+Co^{2+}$, and $Zn^{2+}+Co^{2+}+Ni^{2+}$.

Figure 14A:
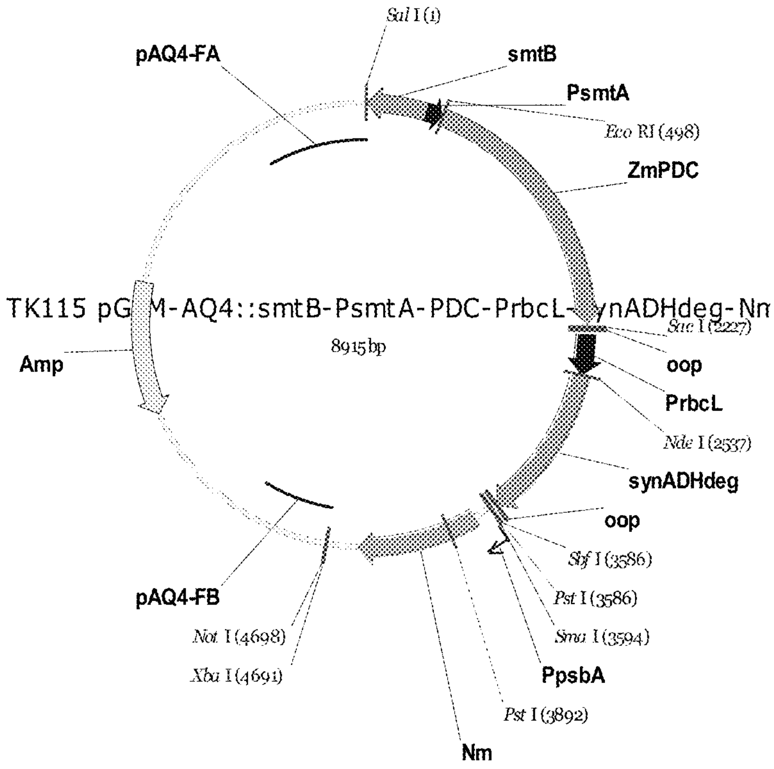

FIG. 14A depicts the map of construct TK115 for integration into the endogenous pAQ4 plasmid comprising a first production gene encoding a pdc from *Zymomonas mobilis* under the transcriptional control of the $Zn^{2+}$-inducible promoter smtB-PsmtA and a degenerated adh-encoding gene from *Synechocystis* PCC 6803 as second production gene under the transcriptional control of the constitutive promoter Prbc.

Figure 14B:
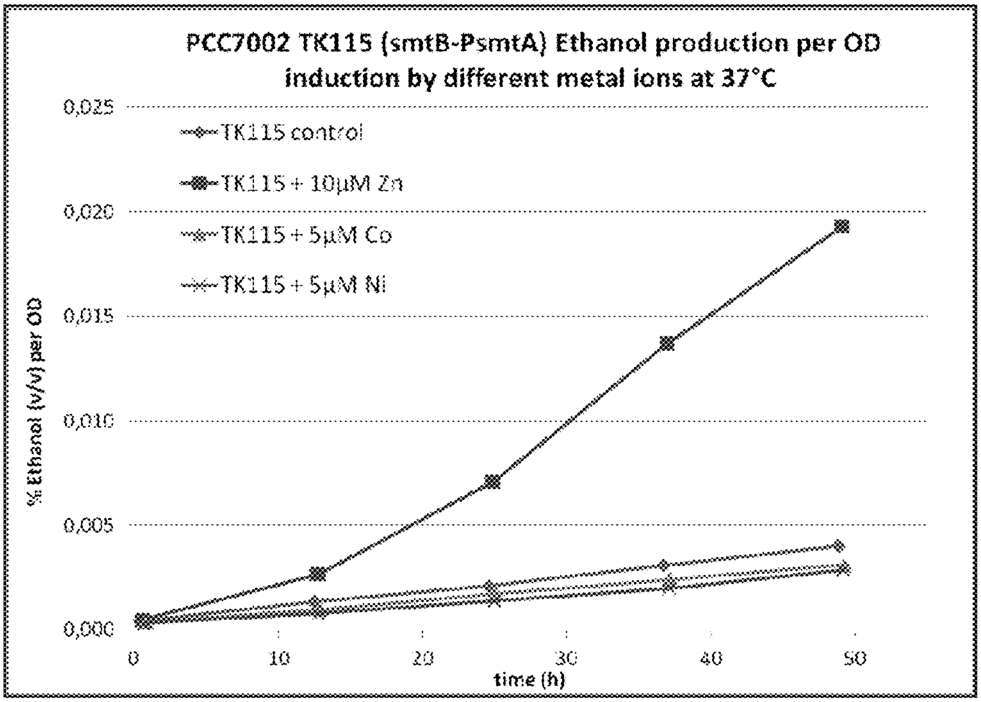

FIG. 14B shows the ethanol production per OD of *Synechococcus* PCC 7002 strain TK115 without induction and after selective induction with Zn, Co or Ni, respectively.

FIG. 15A depicts the map of the self-replicating pVZ325a vector #1217.4 comprising a first production gene encoding a pdc from *Zymomonas mobilis* under the transcriptional control of the $Co^{2+}$-inducible promoter corR-PcorT and a degenerated adh-encoding gene from *Synechocystis* PCC 6803 as second production gene under the transcriptional control of the constitutive promoter Prbc*.

FIG. 15B shows the ethanol production per OD of *Synechococcus* PCC 7002 strain #1217.4 without induction and after selective induction with Zn, Co or Ni, respectively.

Figure 16:
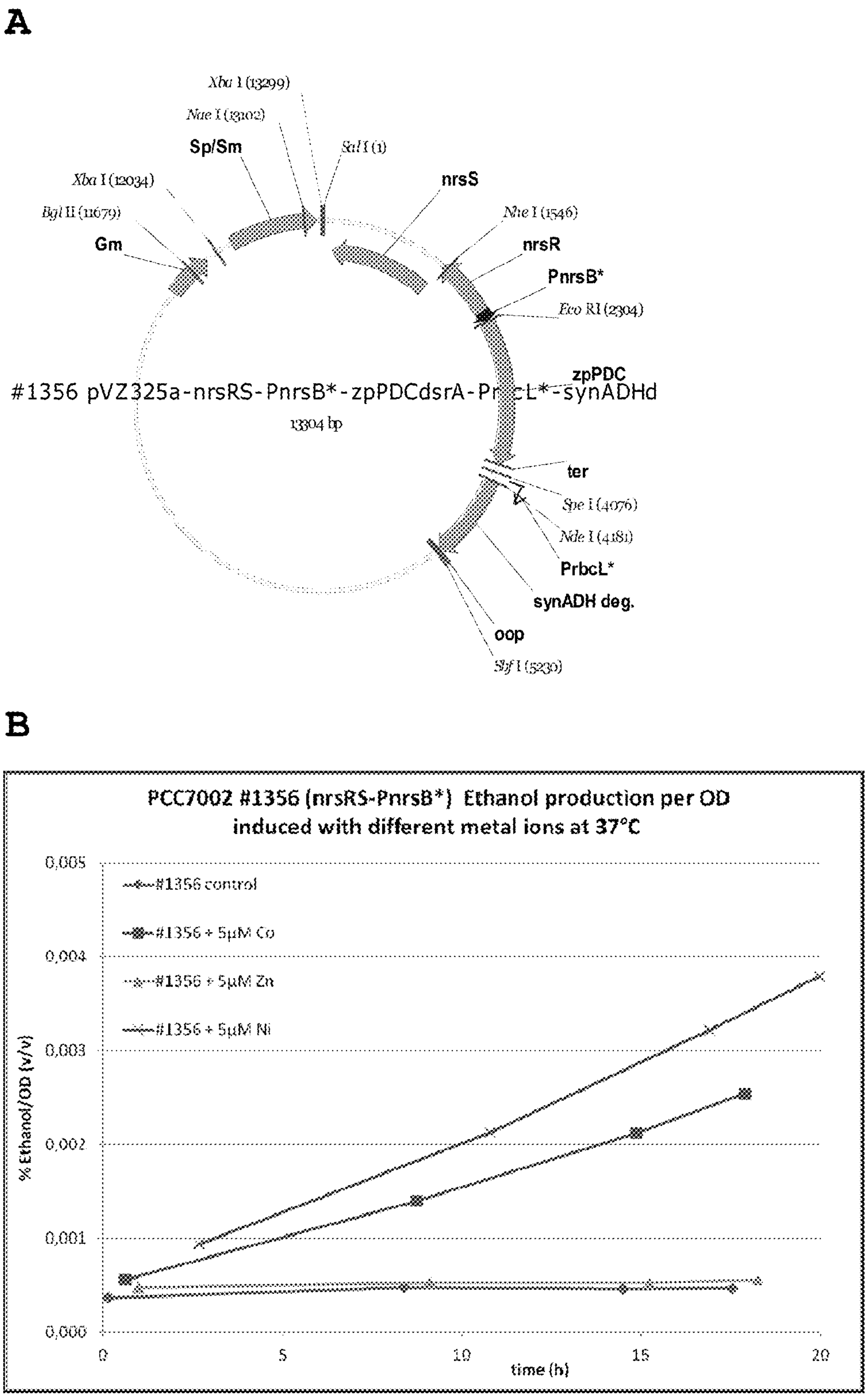

FIG. 16A depicts the map of the self-replicating pVZ325a vector #1356 comprising a first production gene encoding a pdc from *Zymobacter palmae* under the transcriptional control of the $Ni^{2+}$-inducible promoter nrsRS-PnrsB* and a degenerated adh-encoding gene from *Synechocystis* PCC 6803 as second production gene under the transcriptional control of the constitutive promoter Prbc*.

FIG. 16B shows the ethanol production per OD of *Synechococcus* PCC 7002 strain #1356 without induction and after selective induction with Zn, Co or Ni, respectively.

Figure 17A:
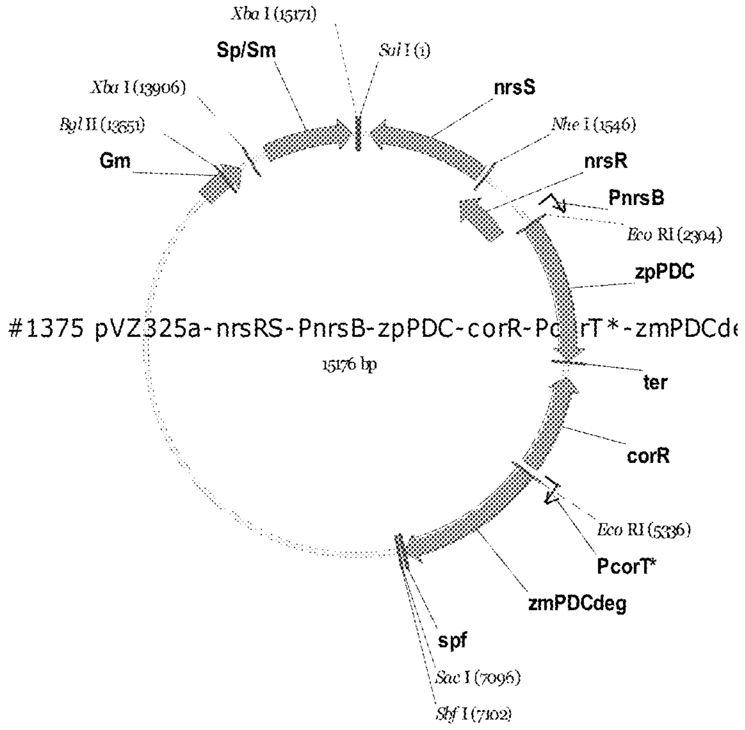

FIG. 17A depicts the map of self-replicating pVZ325a vector #1375 comprising a first production gene encoding a pdc from *Zymobacter palmae* under the transcriptional control of the $Ni^{2+}$-inducible first promoter nrsRS-PnrsB and a second first production gene which is a degenerated pdc-encoding gene from *Zymomonas mobilis* under the transcriptional control of the $Co^{2+}$-inducible second promoter corR-PcorT*.

Figure 17B:
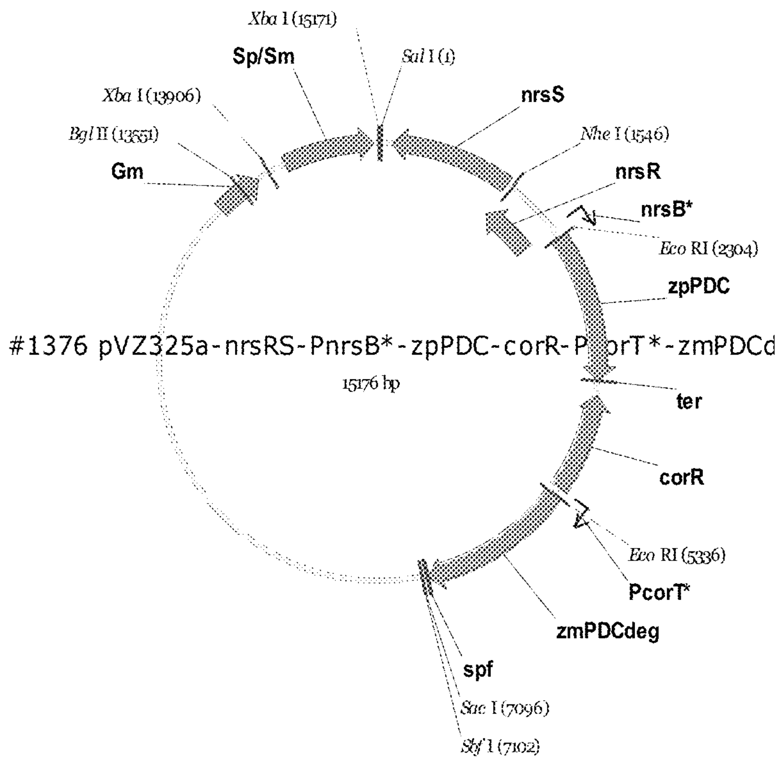

FIG. 17B depicts the map of self-replicating pVZ325a vector #1376 comprising a first production gene encoding a pdc from *Zymobacter palmae* under the transcriptional control of the $Ni^{2+}$-inducible first promoter nrsRS-PnrsB* and a second first production gene which is a degenerated pdc-encoding gene from *Zymomonas mobilis* under the transcriptional control of the $Co^{2+}$-inducible second promoter corR-PcorT*.

Figure 18A:
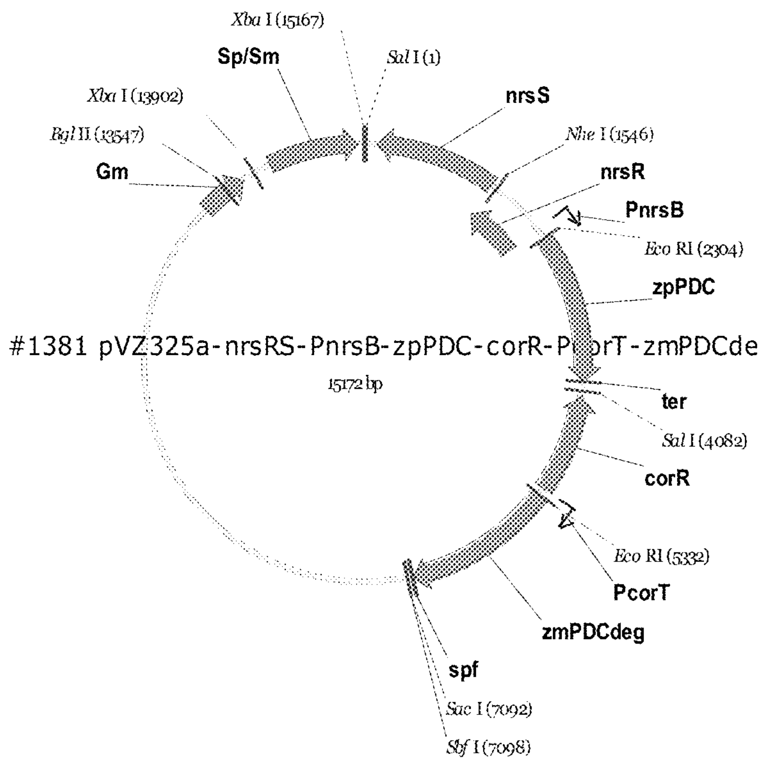

FIG. 18A depicts the map of self-replicating pVZ325a vector #1381 comprising a first production gene encoding a pdc from *Zymobacter palmae* under the transcriptional control of the $Ni^{2+}$-inducible first promoter nrsRS-PnrsB and a second first production gene which is a degenerated pdc-encoding gene from *Zymomonas mobilis* under the transcriptional control of the $Co^{2+}$-inducible second promoter corR-PcorT.

Figure 18B:
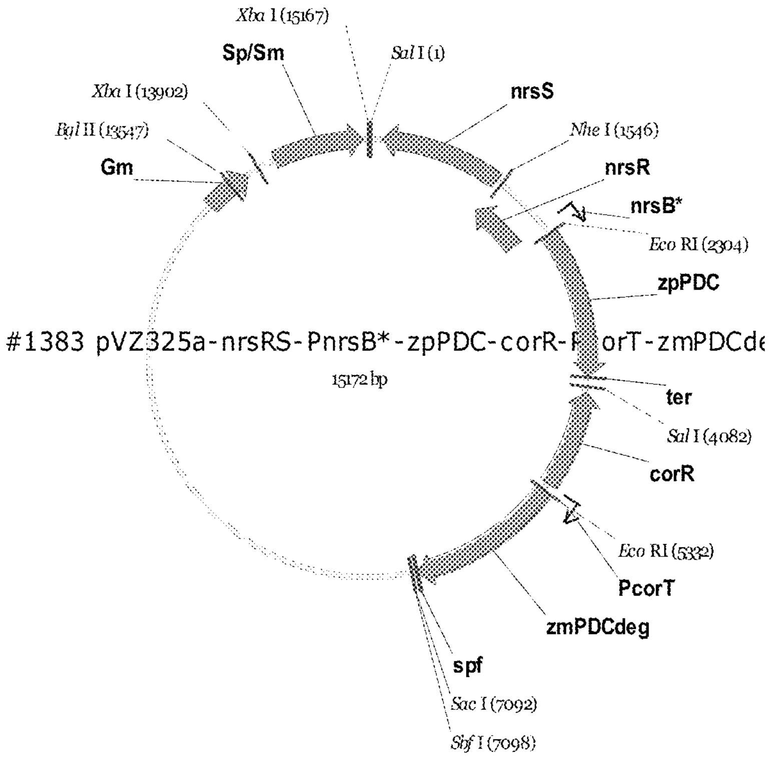

FIG. 18B depicts the map of self-replicating pVZ325a vector #1383 comprising a first production gene encoding a pdc from *Zymobacter palmae* under the transcriptional control of the $Ni^{2+}$-inducible first promoter nrsRS-PnrsB* and a second first production gene which is a degenerated pdc-encoding gene from *Zymomonas mobilis* under the transcriptional control of the $Co^{2+}$-inducible second promoter corR-PcorT.

Figure 19:
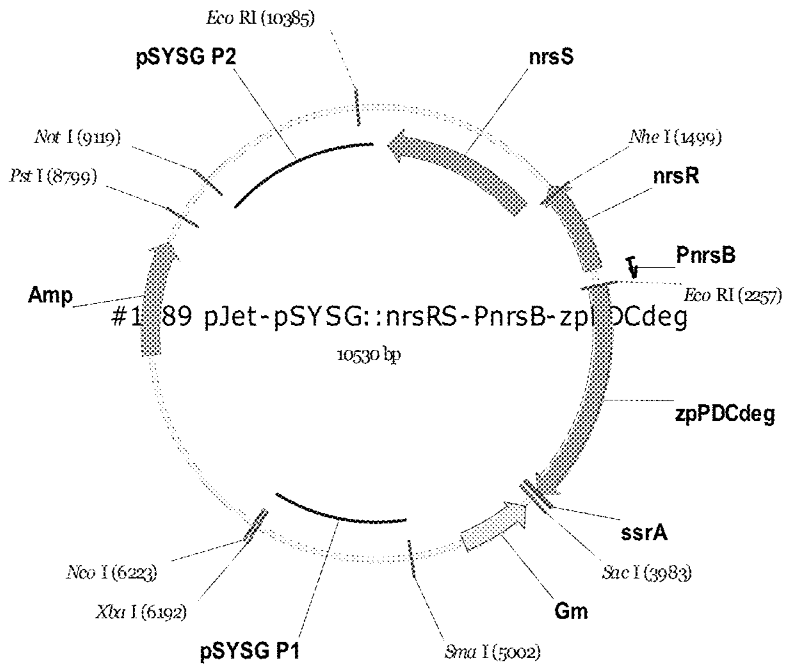
Figure 19:
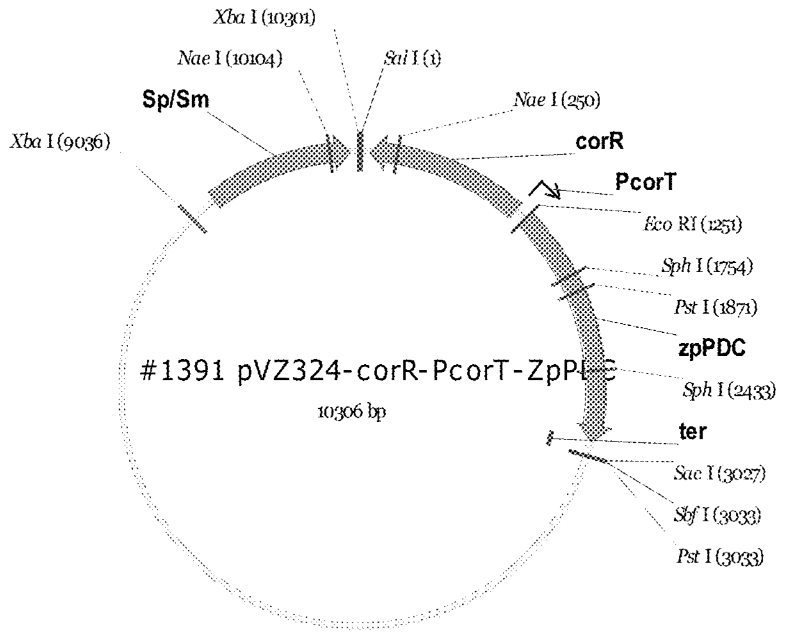

FIG. 19A depicts the map of construct #1389 for integration into the endogenous pSYSG plasmid comprising a first production gene which is a degenerated pdc-encoding gene from *Zymobacter palmae* under the transcriptional control of the $Ni^{2+}$-inducible promoter nrsRS-PnrsB.

FIG. 19B depicts the map of self-replicating pVZ324 vector #1391 comprising a first production gene which is a pdc from *Zymomobacter palmae* under the transcriptional control of the Co2+-inducible promoter corR-PcorT.

Figure 20:
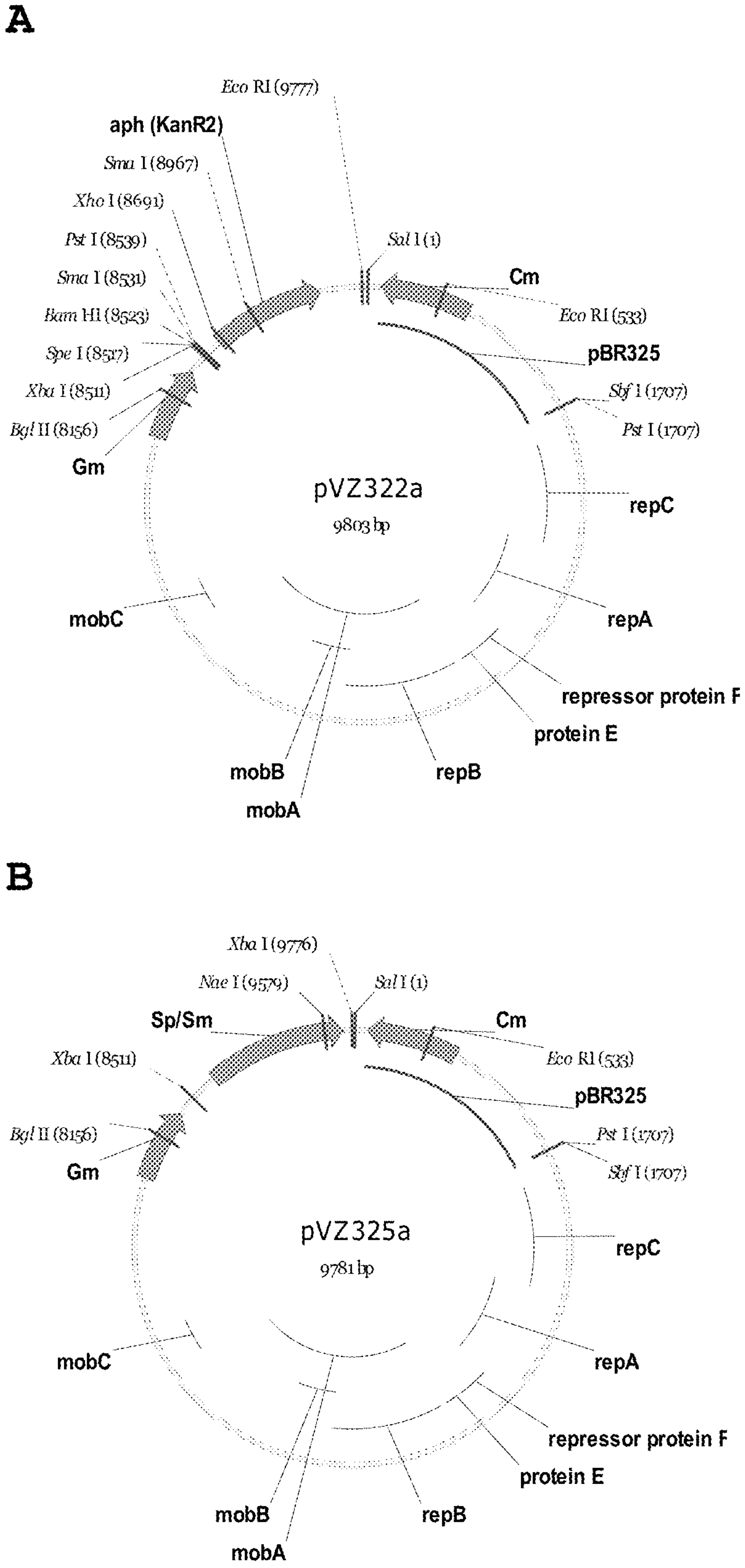

FIG. 20A depicts the map of self-replicating broad host range vector pVZ322a with Gm (gentamycin), Cm (chloramphenicol) and aph (kanamycin/neomycin) antibiotic resistance cassettes, based on the RSF1010 plasmid backbone.

FIG. 20B depicts the map of self-replicating broad host range vector pVZ325a with Gm (gentamycin), Cm (chloramphenicol) and Sp/Sm (spectinomycin/streptomycin) antibiotic resistance cassettes, based on the RSF1010 plasmid backbone.

Figure 21:
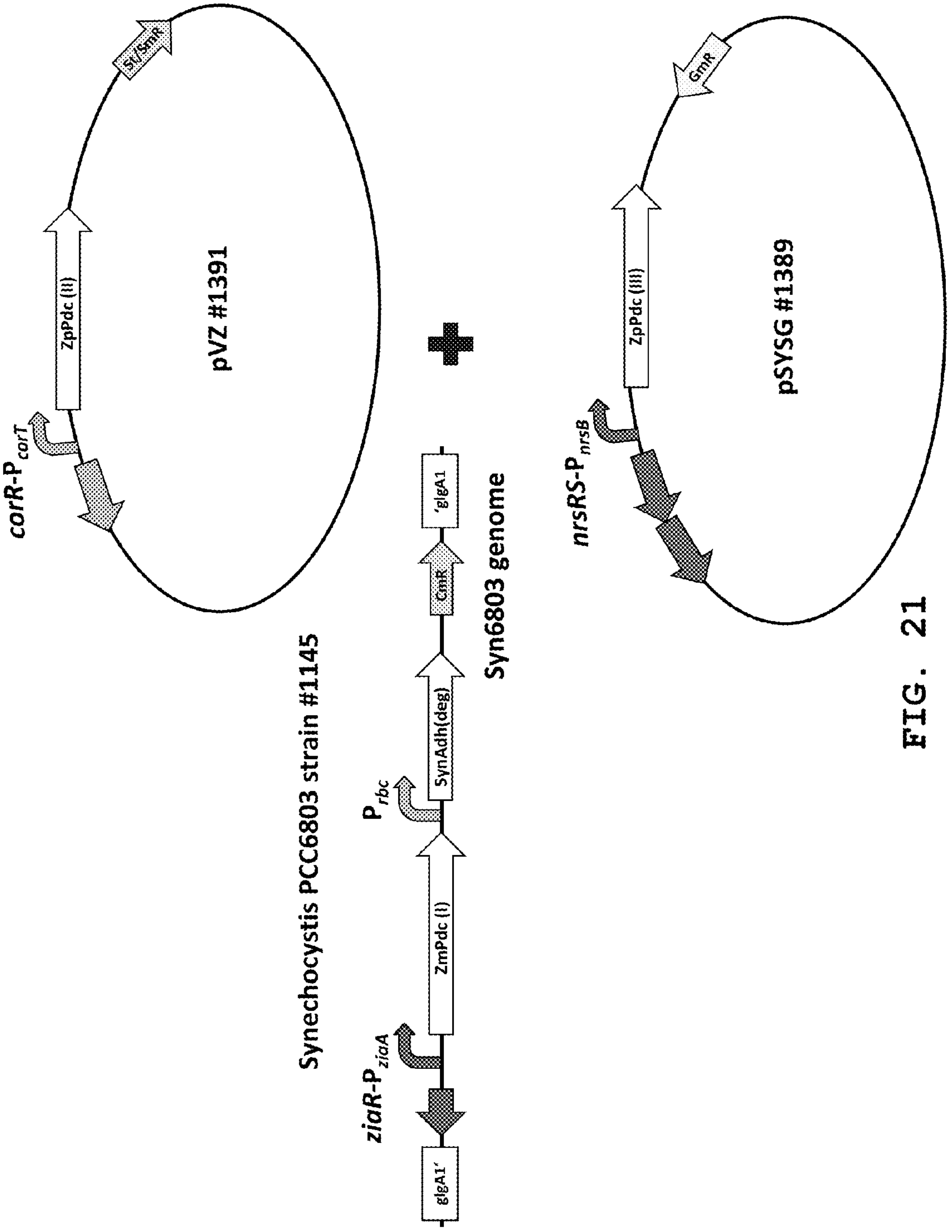

FIG. 21 illustrates the genetic constructs used to generate the *Synechocystis* PCC 6803 strain #1145/#1391/#1389. Strain #1145 harboring a first production gene encoding a pdc enzyme from *Zymomonas mobilis* under the transcriptional control of the $Zn^{2+}$-inducible first promoter ziaR-PziaA and a second production gene which is a degenerated adh-encoding gene from *Synechocystis* PCC 6803 under the transcriptional control of the constitutive Prbc promoter recombined into its chromosome was further transformed with the self-replicating vector pVZ324 #1391 comprising a second first production gene encoding a pdc enzyme from *Zymobacter palmae* under the transcriptional control of the $Co^{2+}$-inducible second promoter corR-PcorT and with the plasmid pSYSG #1389 for integration into the endogenous pSYSG plasmid comprising a third first production gene which is a degenerated gene encoding the pdc enzyme from *Zymobacter palmae* under the transcriptional control of the $Ni^{2+}$-inducible third promoter nrsRS-PnrsB.

Figure 22:
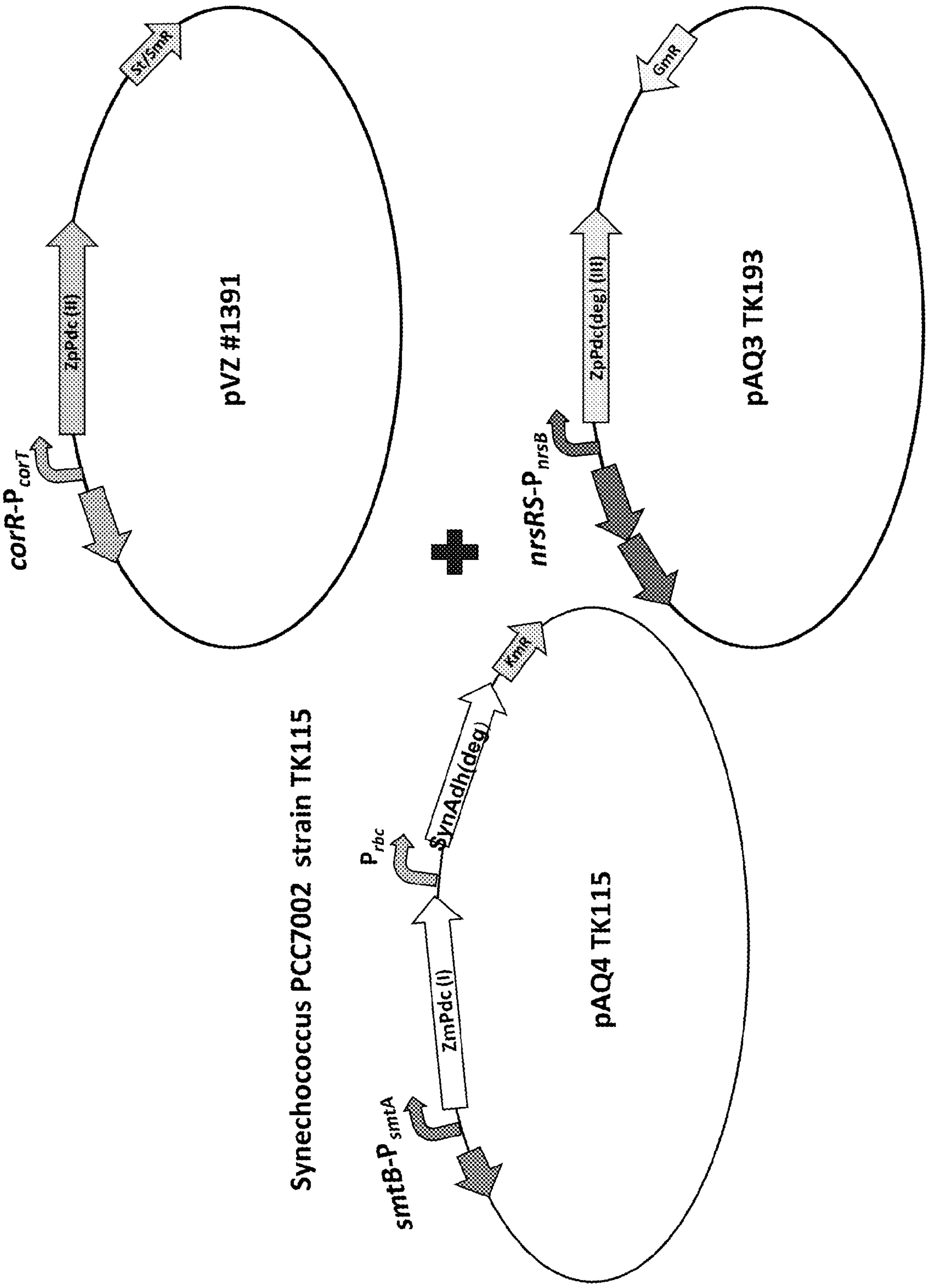

FIG. 22 illustrates the genetic constructs used to generate the *Synechococcus* PCC 7002 strain TK115/#1391/TK193. Strain TK115 harboring a first production gene encoding a pdc enzyme from *Zymomonas mobilis* under the transcriptional control of the $Zi^{2+}$-inducible first promoter smtB-PsmtA and a second production gene which is a degenerated adh-encoding gene from *Synechocystis* PCC 6803 under the transcriptional control of the constitutive Prbc promoter recombined into its endogenous pAQ4 plasmid was further transformed with the self-replicating vector pVZ324 #1391 comprising a second first production gene encoding a pdc enzyme from *Zymobacter palmae* under the transcriptional control of the $Co^{2+}$-inducible second promoter corR-PcorT and with a further third first production gene which is a degenerated gene encoding the pdc enzyme from *Zymobacter palmae* under the transcriptional control of the $Ni^{2+}$-inducible third promoter nrsRS-PnrsB integrated into its endogenous pAQ3 plasmid.

Figure 23:
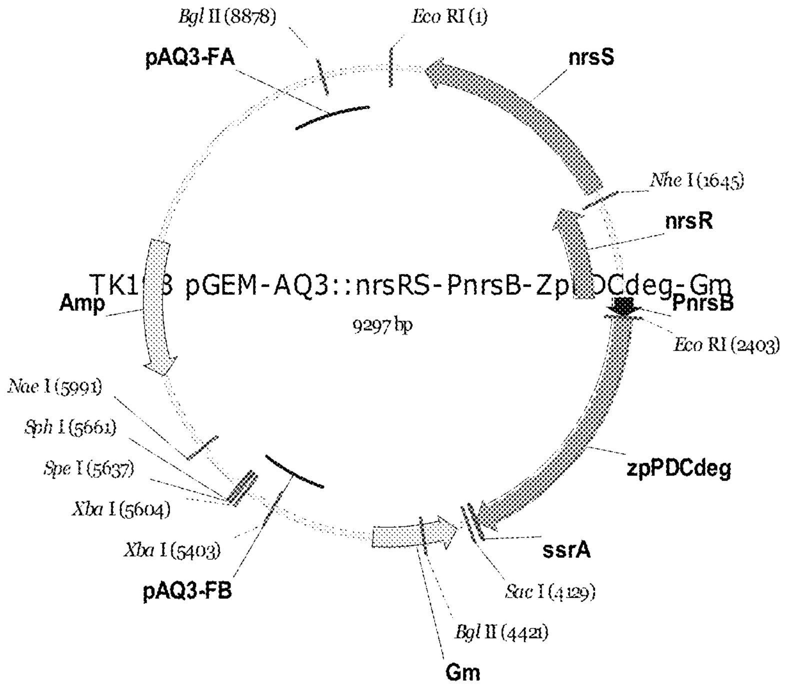

FIG. 23 shows the map of the plasmid TK193 pGEM-AQ3::nrsRS-PnrsB-zpPDC(deg)-Gm designed for integration into the endogenous plasmid pAQ3 of *Synechococcus* sp. PCC 7002, comprising a first production gene encoding a pdc from *Zymobacter palmae* under the transcriptional control of the $Ni^{2+}$-inducible promoter nrsRS-PnrsB. This plasmid is used with other constructs to generate *Synechococcus* PCC 7002 strain TK115/#1391/TK193.

Figure 24:
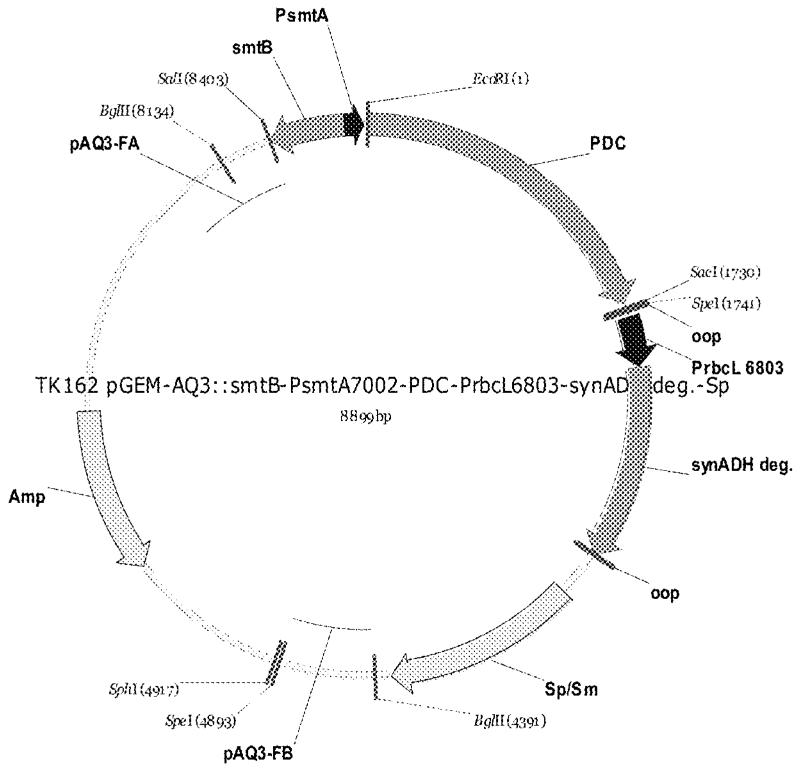

FIG. 24 depicts the map of construct TK162 pGEM-AQ3::smtB-PsmtA-zmPDC_oop-PrbcL-synADHdeg_oop for integration into the endogenous pAQ3 plasmid of *Synechococcus* sp. 7002, comprising a first production gene encoding a pdc from *Zymomonas mobilis* under the transcriptional control of the $Zn^{2+}$-inducible promoter smtB-PsmtA and a degenerated adh-encoding gene from *Synechocystis* sp. PCC 6803 as second production gene under the transcriptional control of the constitutive promoter Prbc.

Figure 25:
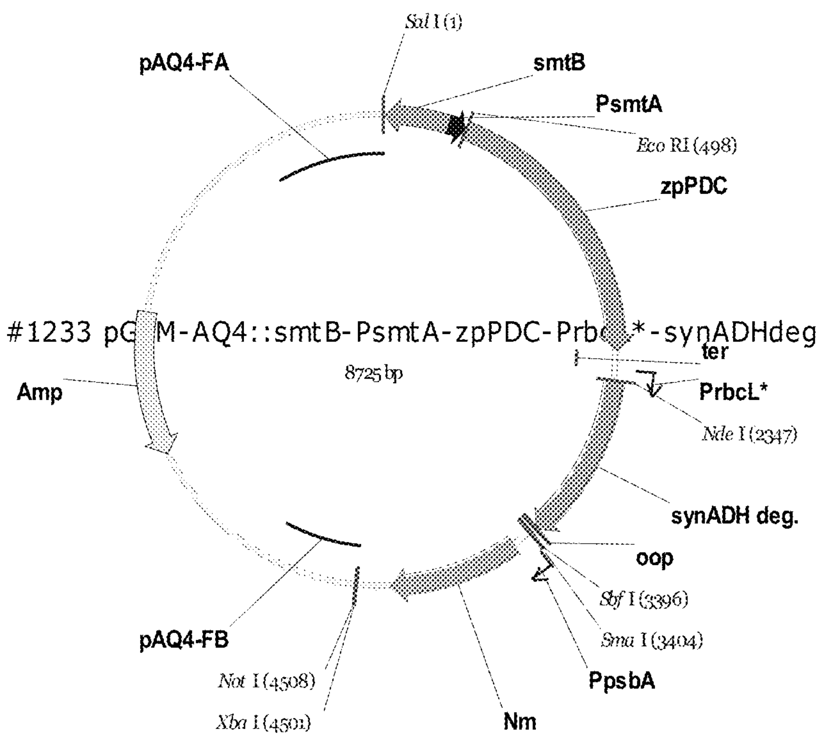

FIG. 25 depicts the map of construct #1233 pGEM-AQ4::smtB-PsmtA-zpPDC-PrbcL*-synADHdeg for integration into the endogenous pAQ4 plasmid of *Synechococcus* sp. 7002, comprising a first production gene encoding a pdc from *Zymomobacter palmae* under the transcriptional control of the $Zn^{2+}$-inducible promoter smtB-PsmtA and a degenerated adh-encoding gene from *Synechocystis* sp. PCC 6803 as second production gene under the transcriptional control of the constitutive promoter Prbc.

Figure 26:
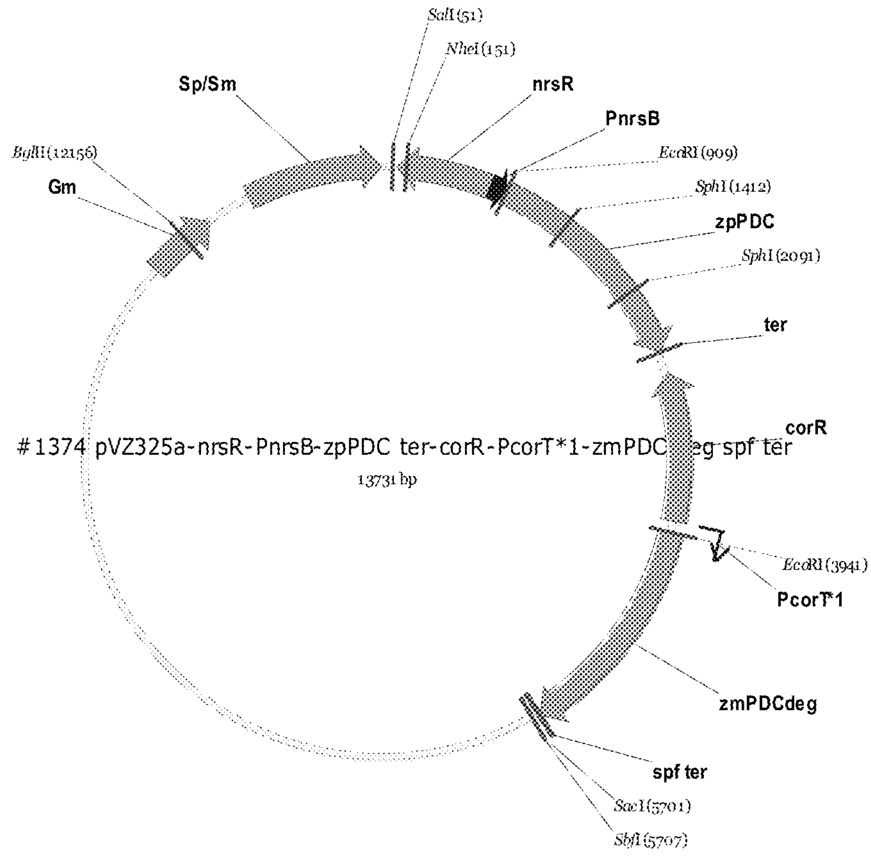

FIG. 26 depicts the map of self-replicating broad host range vector pVZ325a-based construct #1374 pVZ325a-nrsR-PnrsB-zpPDC ter-corR-PcorT*1-zmPDCdeg spf ter for transformation of *Synechocystis* sp. PCC6803 comprising a first production gene encoding a pdc from *Zymomobacter palmae* under the transcriptional control of the $Ni^{2+}$-inducible promoter nrsR-PnrsB and a second first production gene encoding a degenerated pdc from *Zymomonas mobilis* under the transcriptional control of the $Co^{2+}$-inducible promoter corR-PcorT*1 construct having an optimised RBS in comparison to the native corR-PcorT.

Figure 27A:
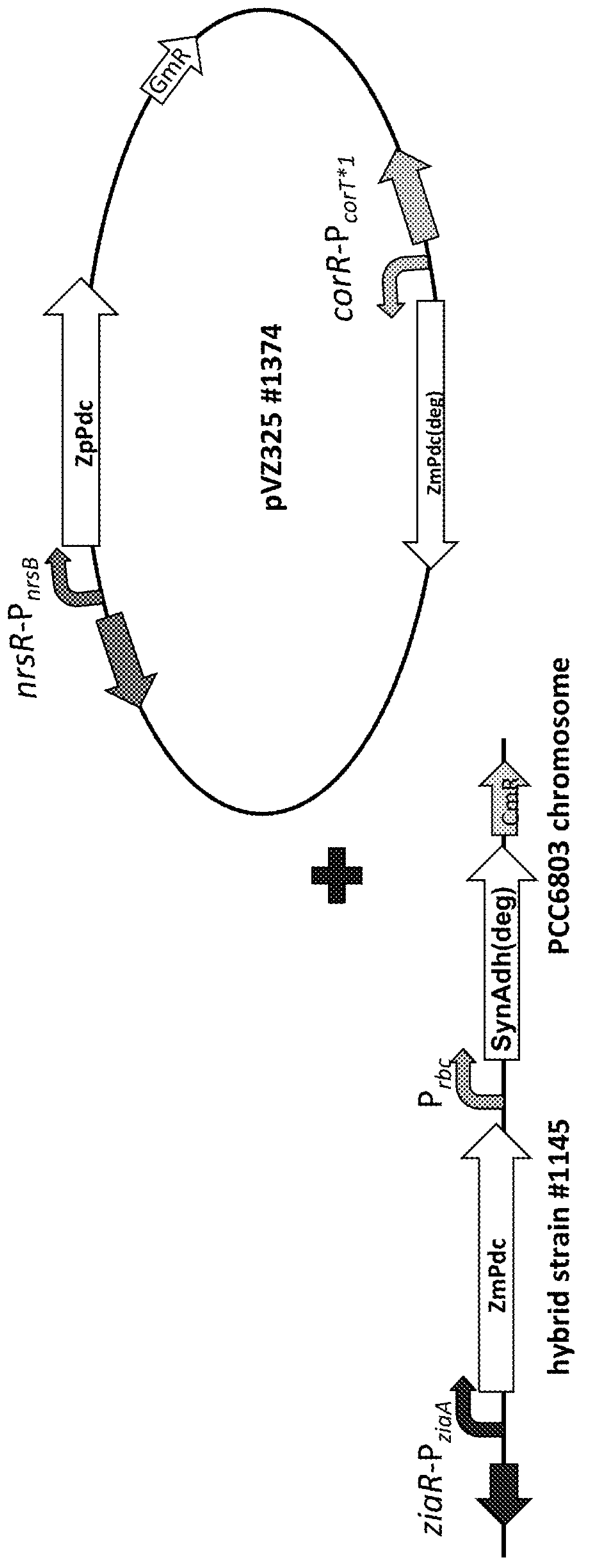

FIG. 27A schematically illustrates the genetic constructs used to generate the *Synechocystis* PCC 6803 strain #1145/#1374. Strain #1145 harboring, recombined into its chromosome, a first production gene encoding a pdc enzyme from *Zymomonas mobilis* under the transcriptional control of the $Zn^{2+}$-inducible first promoter ziaR-PziaA and a second production gene which is a degenerated adh-gene from *Synechocystis* PCC 6803 under the transcriptional control of the constitutive Prbc promoter was further transformed with the self-replicating vector pVZ325a #1374 comprising a second first production gene encoding a Pdc enzyme from *Zymobacter palmae* under the transcriptional control of the $Ni^{2+}$-inducible second promoter nrsR-PnrsB and a third first production gene which is a codon-degenerated pdc gene from *Zymomonas mobilis* under the transcriptional control of the $Co^{2+}$-inducible third promoter corR-PcorT*1.

Figure 27B:
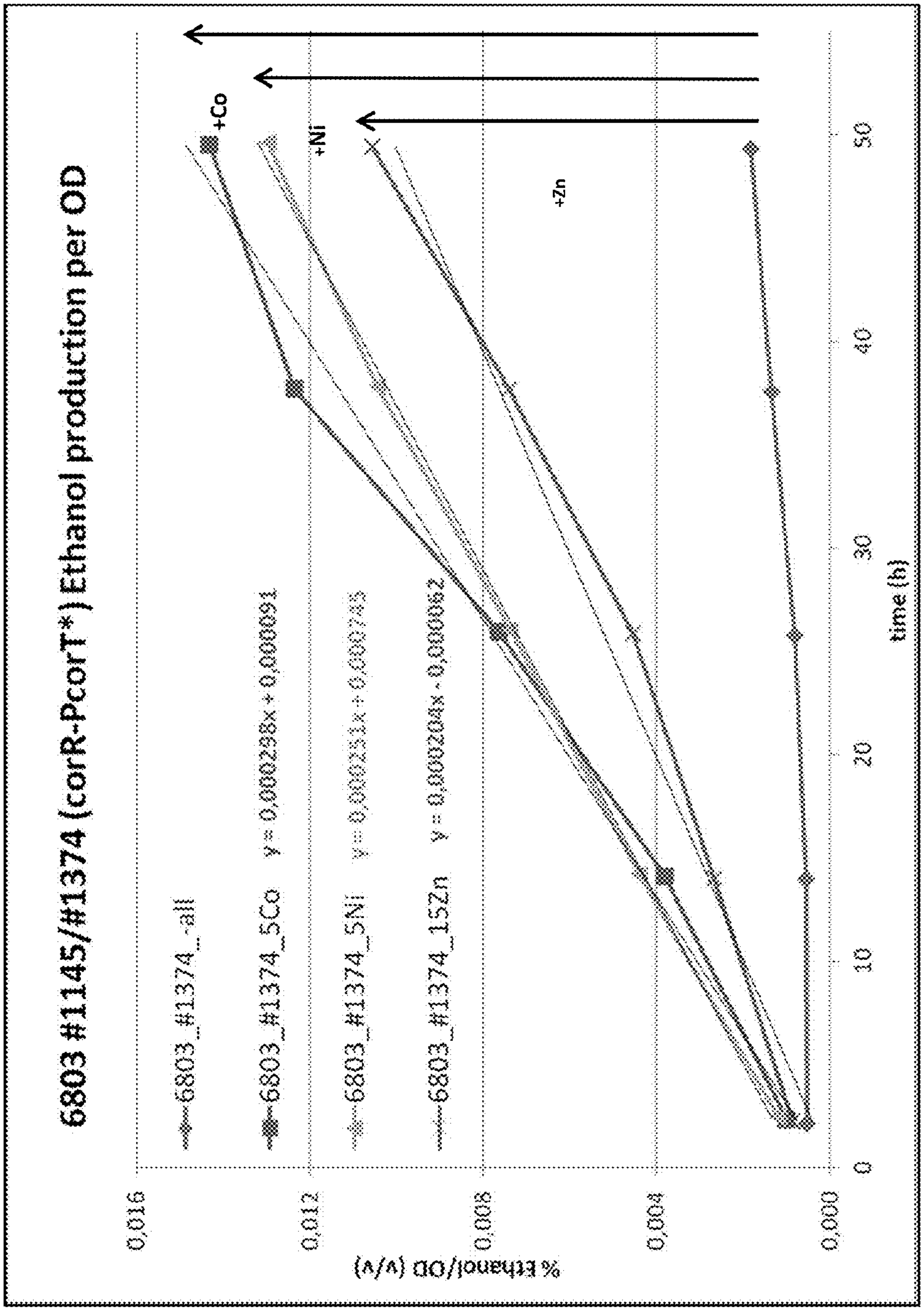

FIG. 27B shows the specific ethanol production per OD of the metabolically enhanced *Synechocystis* sp. PCC 6803 strain #1145/#1374 as a function of time after selective induction with Zn, Co and Ni as well as a control without addition of these metal ions.

Figure 27C:
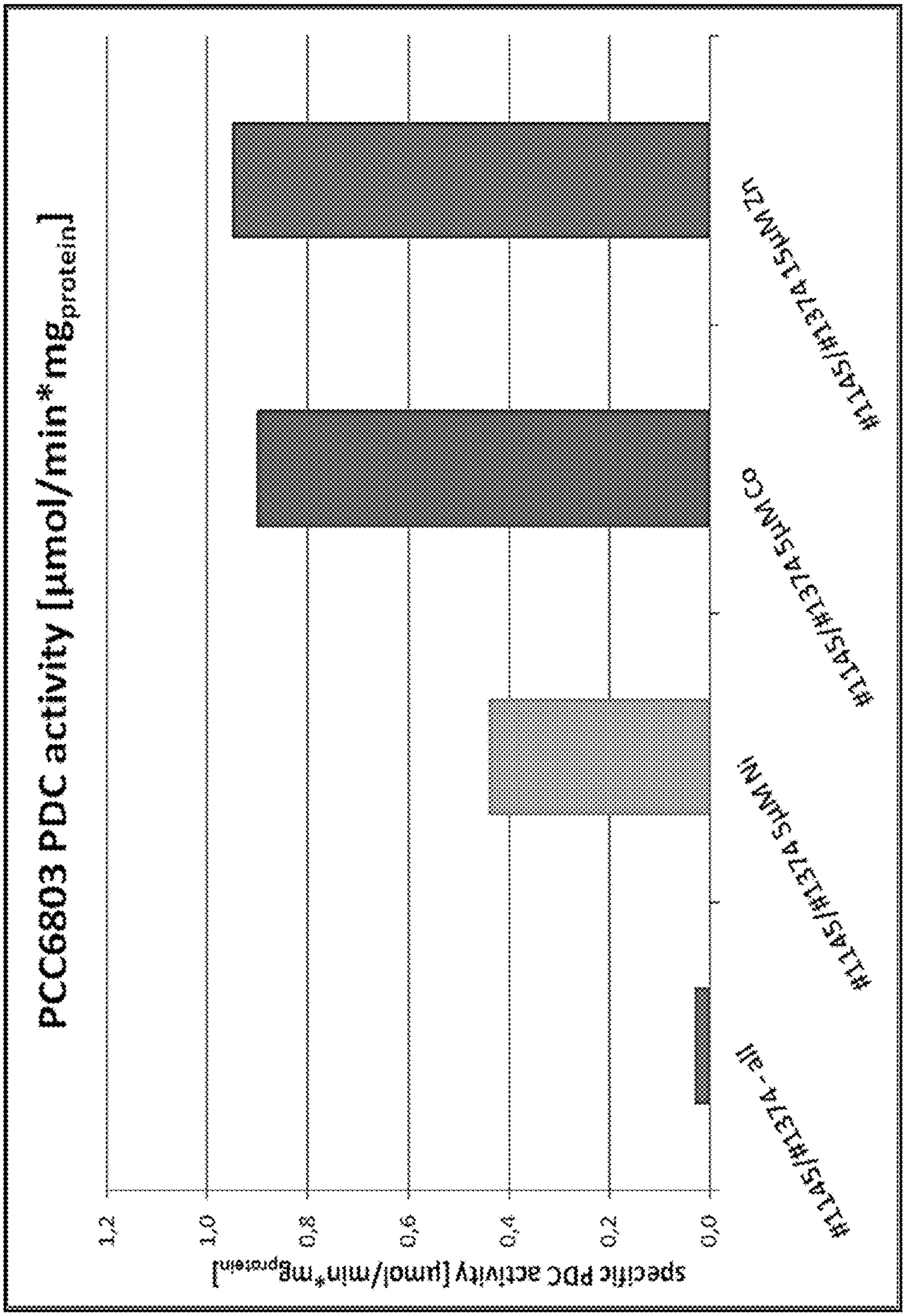

FIG. 27C illustrates the specific activity of the three different Pdc enzymes of *Synechocystis* PCC 6803 strain #1145/#1374 in terms of μmol per min and mg protein after selective induction with Ni, Co and Zn in comparison to a control without addition of these metal ions.

Figure 28:
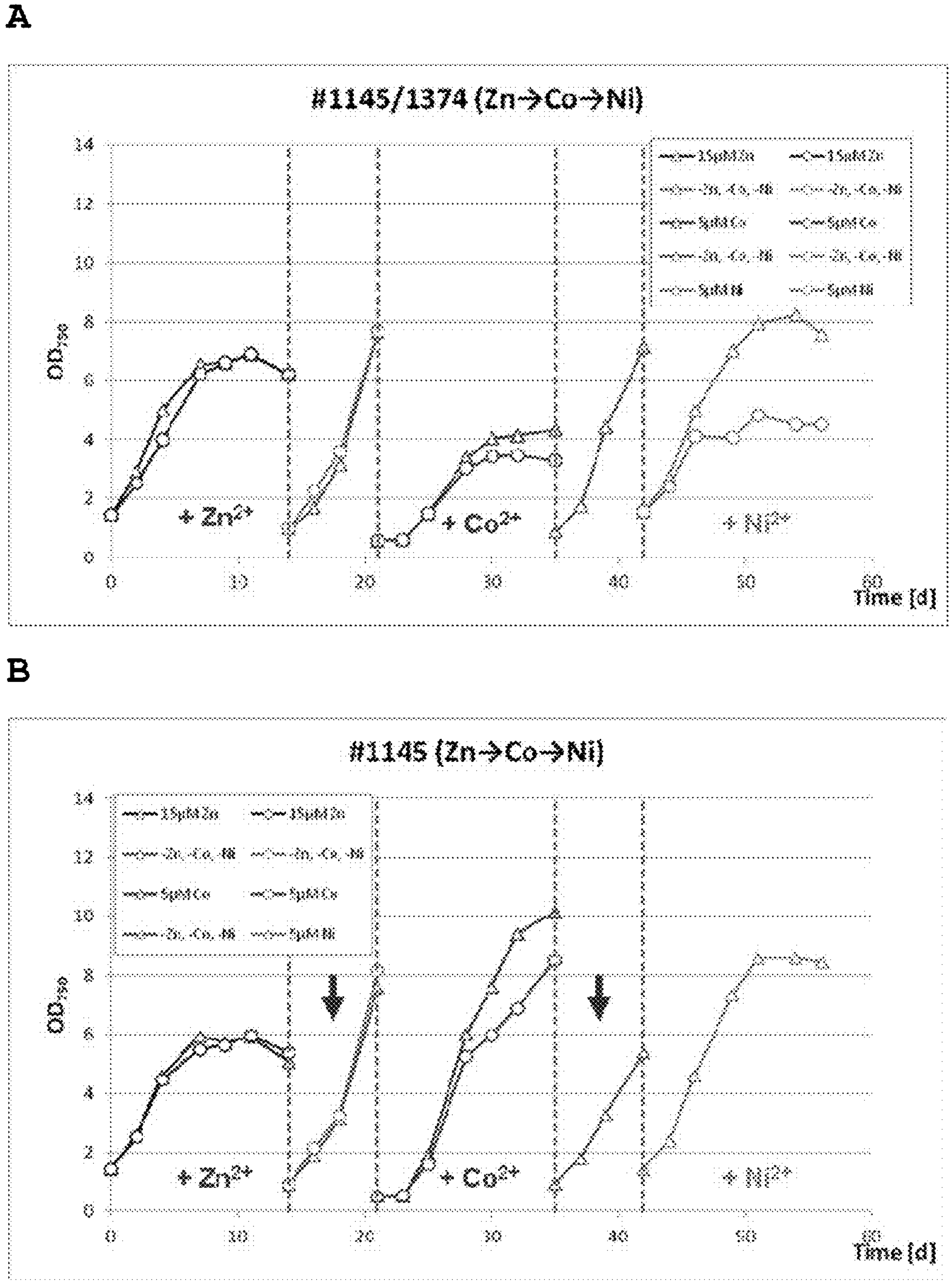

FIG. 28A shows the results of culture growth monitoring of *Synechocystis* PCC 6803 strain #1145/#1374 in 0.5 L photobioreactor scale in terms of culture OD at 750 nm as a function of cultivation time in days during sequential selective induction with $Zn^{2+}$, $Co^{2+}$ and $Ni^{2+}$ of the corresponding Pdc genes.

FIG. 28B shows the results of culture growth monitoring of *Synechocystis* PCC 6803 strain #1145 in 0.5 L photobioreactor scale in terms of culture OD at 750 nm as a function of cultivation time in days during sequential selective addition of $Zn^{2+}$, $Co^{2+}$ and $Ni^{2+}$ to the culture medium.

Figure 29:
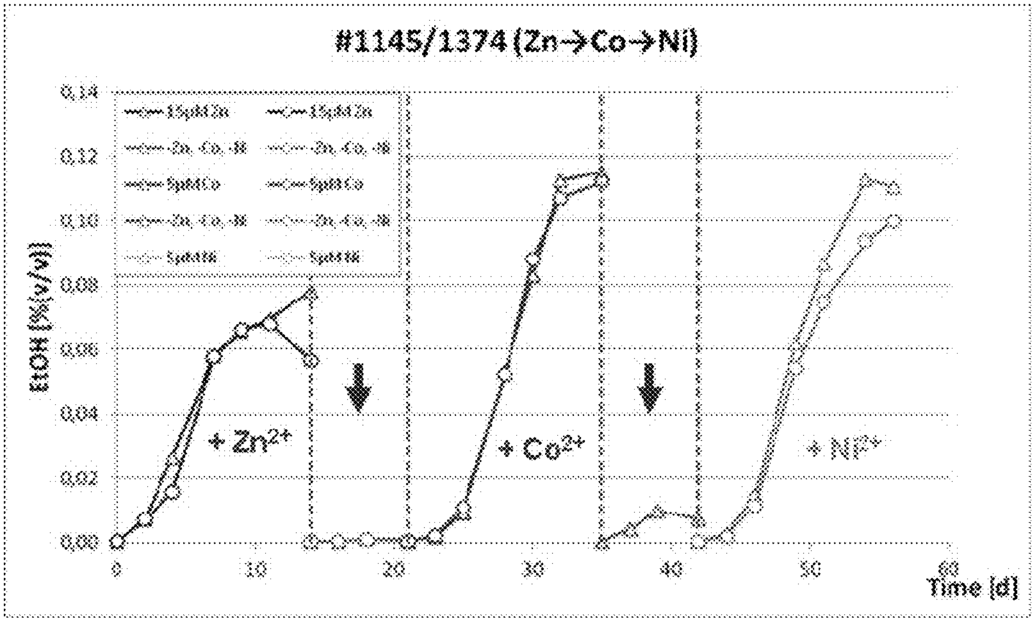
Figure 29:
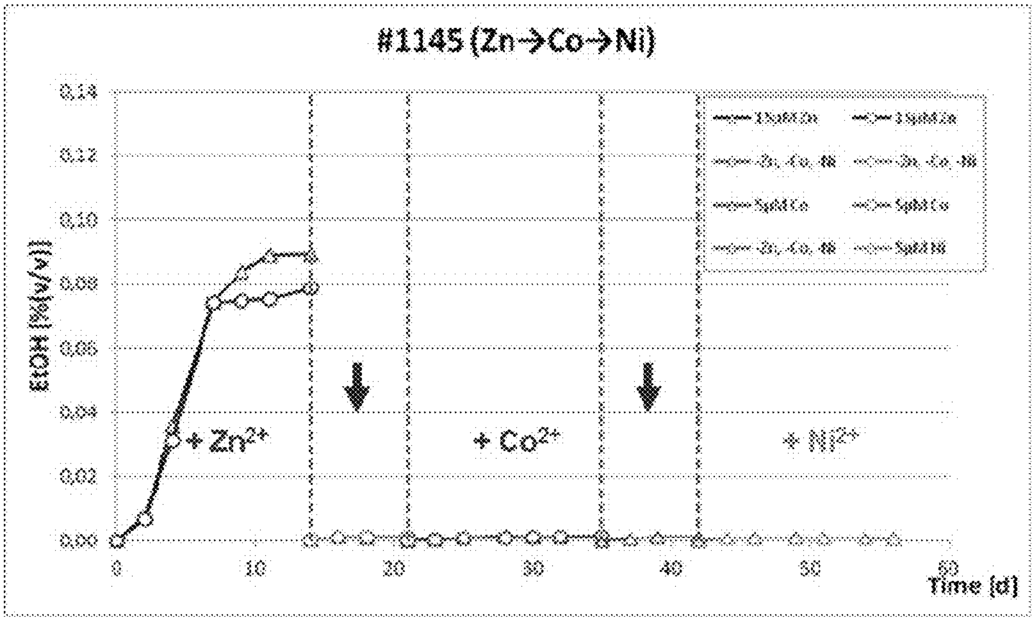

FIG. 29A shows the results of ethanol production of *Synechocystis* PCC 6803 strain #1145/#1374 in 0.5 L photobioreactor scale in %(v/v) as a function of cultivation time in days during sequential selective induction with $Zn^{2+}$, $Co^{2+}$ and $Ni^{2+}$ of the corresponding Pdc genes.

FIG. 29B shows the results of ethanol production of *Synechocystis* PCC 6803 strain #1145 in 0.5 L photobioreactor scale in %(v/v) as a function of cultivation time in days during sequential selective addition of $Zn^{2+}$, $Co^{2+}$ and $Ni^{2+}$ to the culture medium.

Figure 30:
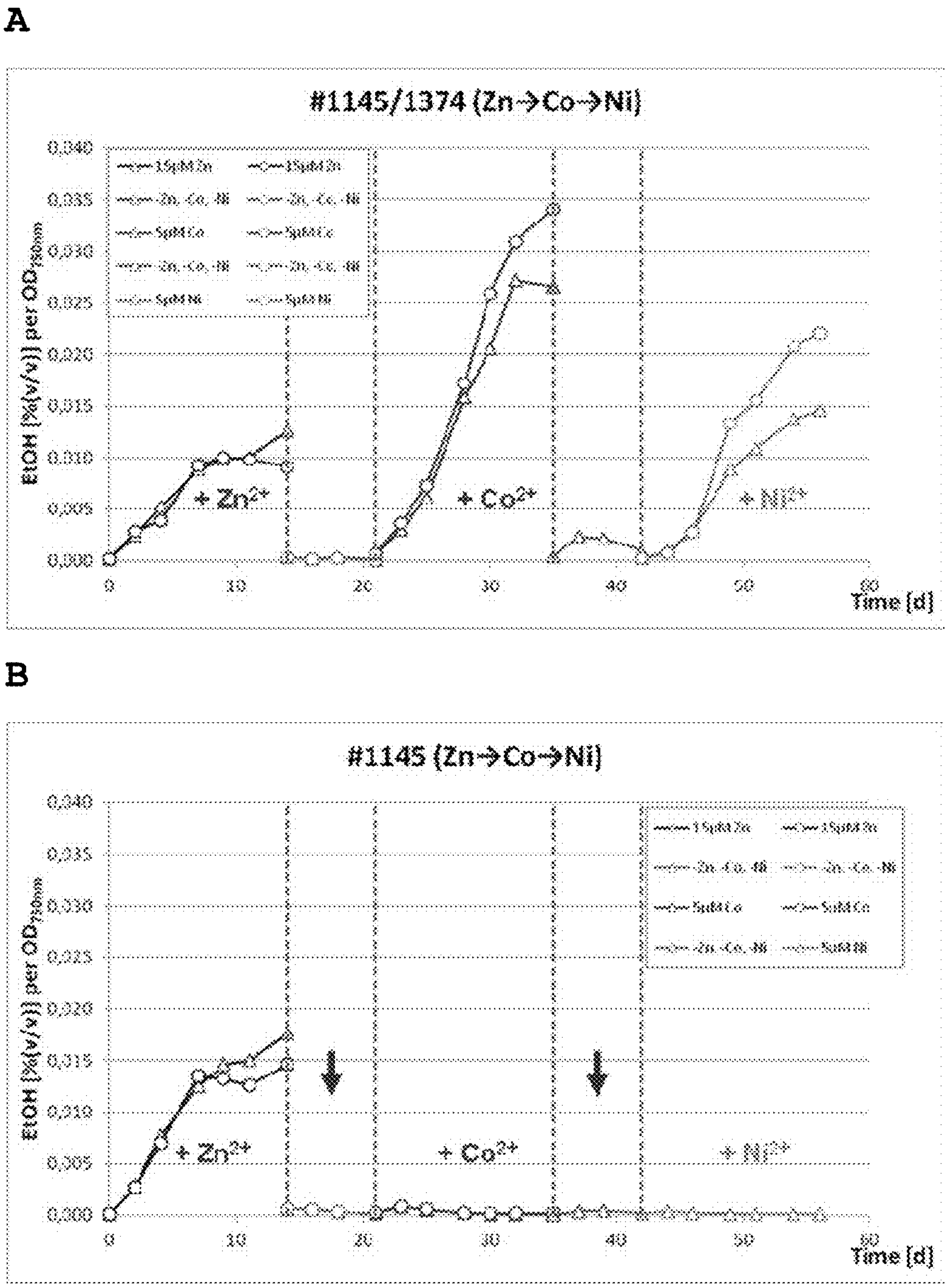

FIG. 30A shows the results of ethanol production of *Synechocystis* PCC 6803 strain #1145/#1374 in 0.5 L photobioreactor scale in %(v/v) normalised per culture OD at 750 nm as a function of cultivation time in days during sequential selective induction with $Zn^{2+}$, $Co^{2+}$ and $Ni^{2+}$ of the corresponding Pdc genes.

FIG. 30B shows the results of ethanol production of *Synechocystis* PCC 6803 strain #1145 in 0.5 L photobioreactor scale in %(v/v) normalised per culture OD at 750 nm as a function of cultivation time in days during sequential selective addition of $Zn^{2+}$, $Co^{2+}$ and $Ni^{2+}$ to the culture medium.

Figure 31A:
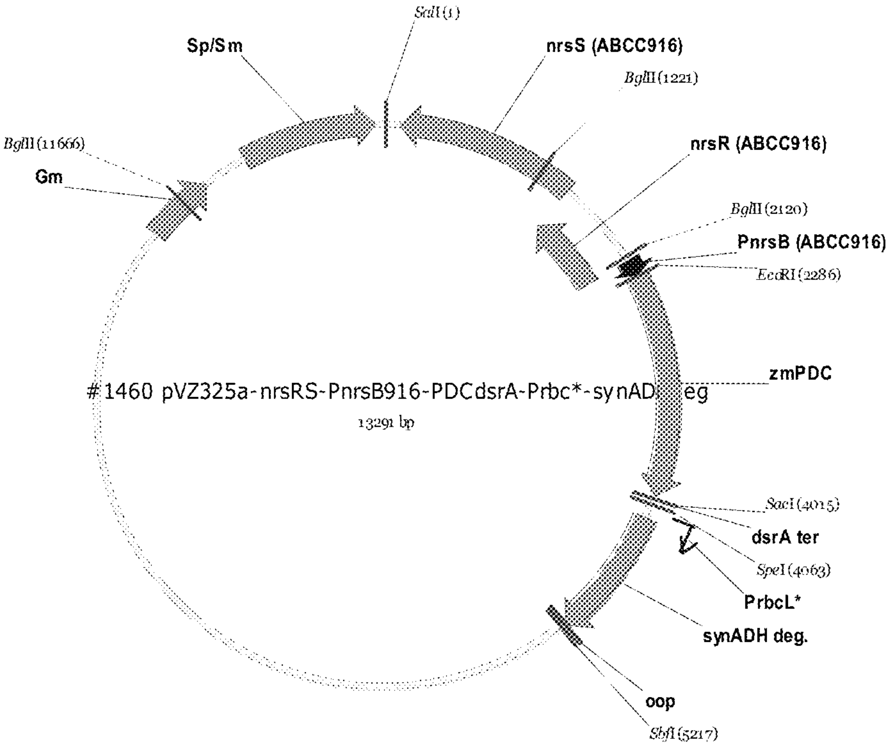

FIG. 31A depicts the map of self-replicating broad host range vector pVZ325a-based construct #1460 pVZ325a-nrsRS-PnrsB916-PDCdsrA-Prbc*-synADHdeg for transformation of *Synechococcus* sp. PCC7002 comprising a first production gene encoding a Pdc from *Zymomonas mobilis* under the transcriptional control of the $Ni^{2+}$-inducible promoter nrsRS-PnrsB916 and a degenerated adh-encoding gene from *Synechocystis* sp. PCC 6803 as second production gene under the transcriptional control of the constitutive promoter Prbc*.

Figure 31B:
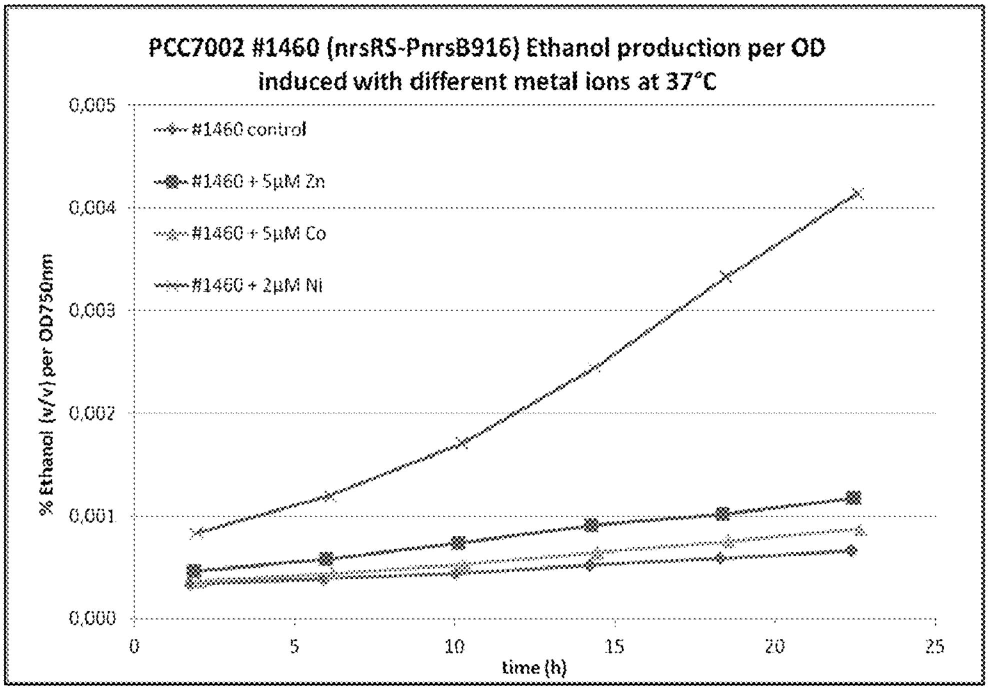

FIG. 31B shows the ethanol production in %(v/v) per OD of *Synechococcus* sp. PCC 7002 strain #1460 without induction and after selective induction with Zn, Co or Ni, respectively.

Figure 32:
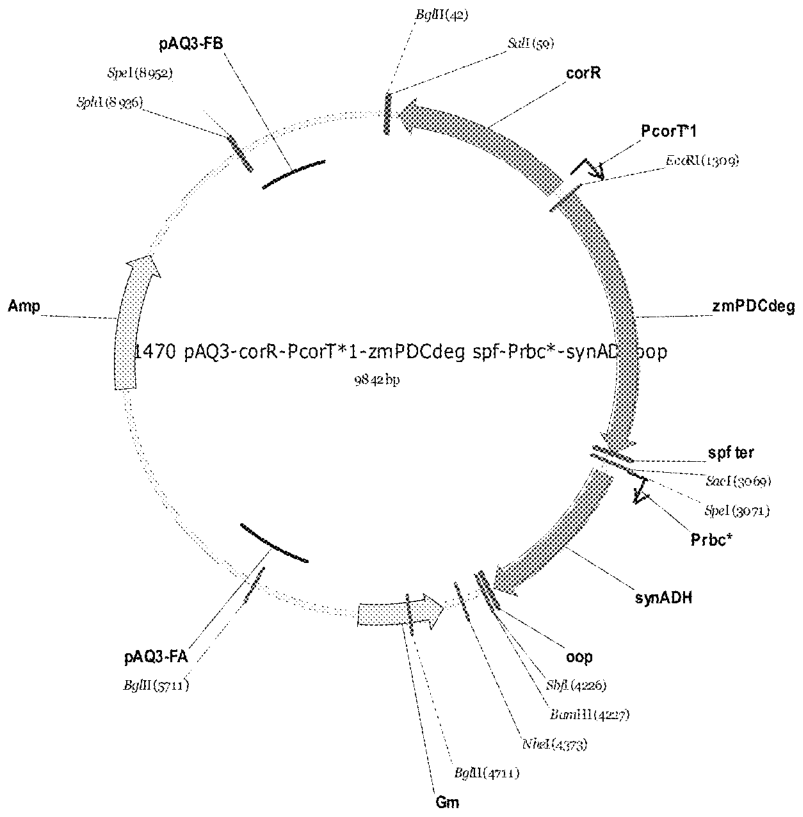

FIG. 32 depicts the vector map of construct #1470 pAQ3-corR-PcorT*1-zmPDCdeg_spf-Prbc*-synADHoop for integration into the endogenous pAQ3 plasmid of *Synechococcus* sp. PCC7002, comprising a codon-degenerated Pdc from *Zymomonas mobilis* as a first production gene under the transcriptional control of the $Co^{2+}$-inducible promoter corR-PcorT*1 and an adh-encoding gene from *Synechocystis* sp. PCC 6803 as second production gene under the transcriptional control of the constitutive promoter Prbc*.

Figure 33:
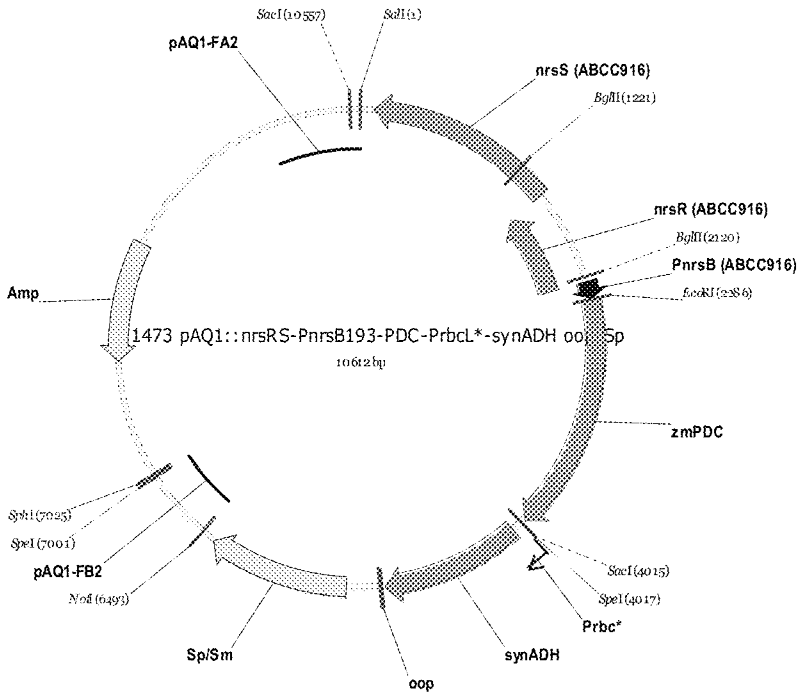

FIG. 33 depicts the vector map of construct #1473 pAQ1::nrsRS-PnrsB193-PDC-PrbcL*-synADH_oop-Sp for integration into the endogenous pAQ1 plasmid of *Synechococcus* sp. PCC7002, comprising a first production gene encoding Pdc from *Zymomonas mobilis* under the transcriptional control of the $Ni^{2+}$-inducible promoter nrsRS-PnrsB 193 and an adh-encoding gene from *Synechocystis* sp. PCC 6803 as second production gene under the transcriptional control of the constitutive Prbc* promoter.

Figure 34:
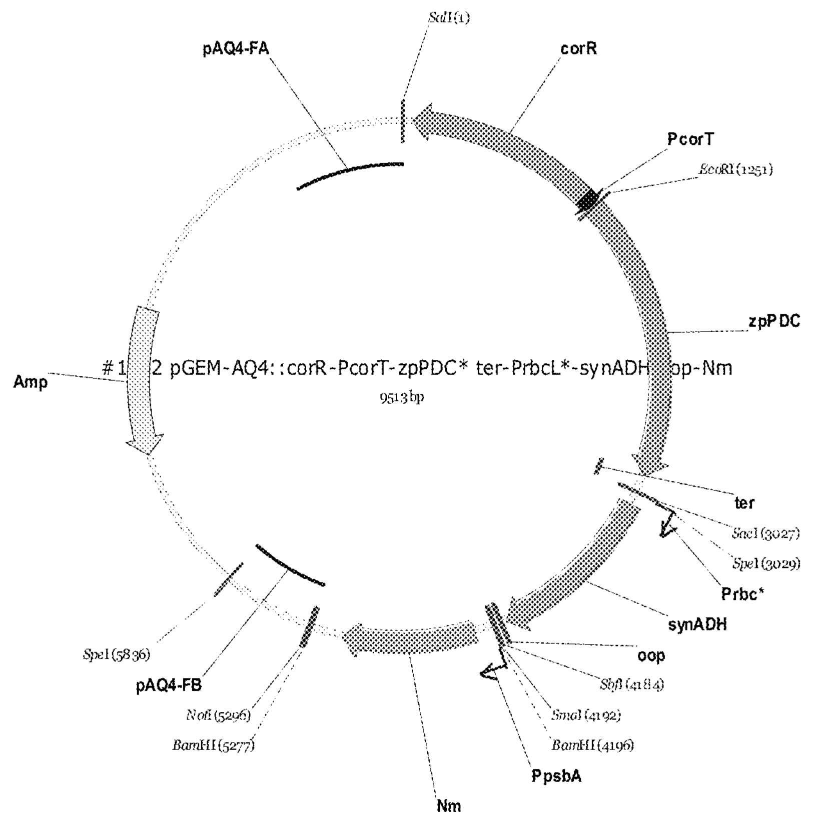

FIG. 34 depicts the vector map of construct #1332 pGEM-AQ4::corR-PcorT-zpPDC_ter-PrbcL*-synADH_oop-Nm for integration into the endogenous pAQ4 plasmid of *Synechococcus* sp. PCC7002, comprising a first production gene encoding Pdc from *Zymobacter palmae* under the transcriptional control of the $Co^{2+}$-inducible promoter corR-PcorT and an adh-encoding gene from *Synechocystis* sp. PCC 6803 as second production gene under the transcriptional control of the constitutive PrbcL* promoter.

Figure 35:
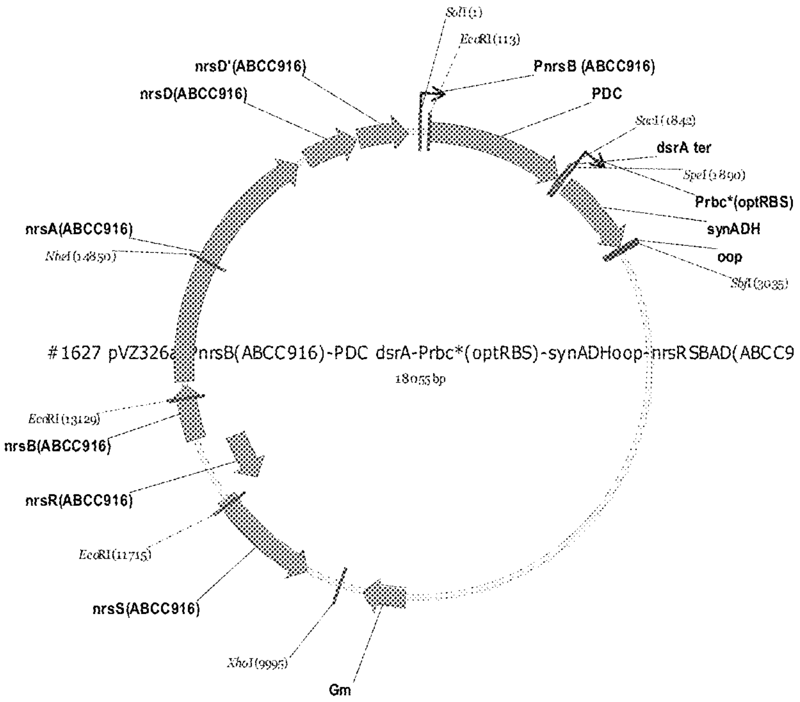

FIG. 35 depicts the vector map of self-replicating broad host range vector pVZ325-based construct #1627 pVZ326a-PnrsB(ABCC916)-PDC_dsrA-Prbc*(optRBS)-synADHoop-nrsRSBAD(ABCC916) for transformation of *Synechococcus* sp. PCC7002, comprising a first production gene encoding Pdc from *Zymomonas mobilis* under the transcriptional control of the $Ni^{2+}$-inducible promoter PnrsB (ABCC916) along with the nickel-resistance conferring nrsRSBAD gene cluster derived from a *Synechococcus* species closely related to *Synechococcus* PCC7002, an adh-encoding gene from *Synechocystis* sp. PCC 6803 as second production gene under the transcriptional control of the constitutive Prbc* promoter.

Figure 36A:
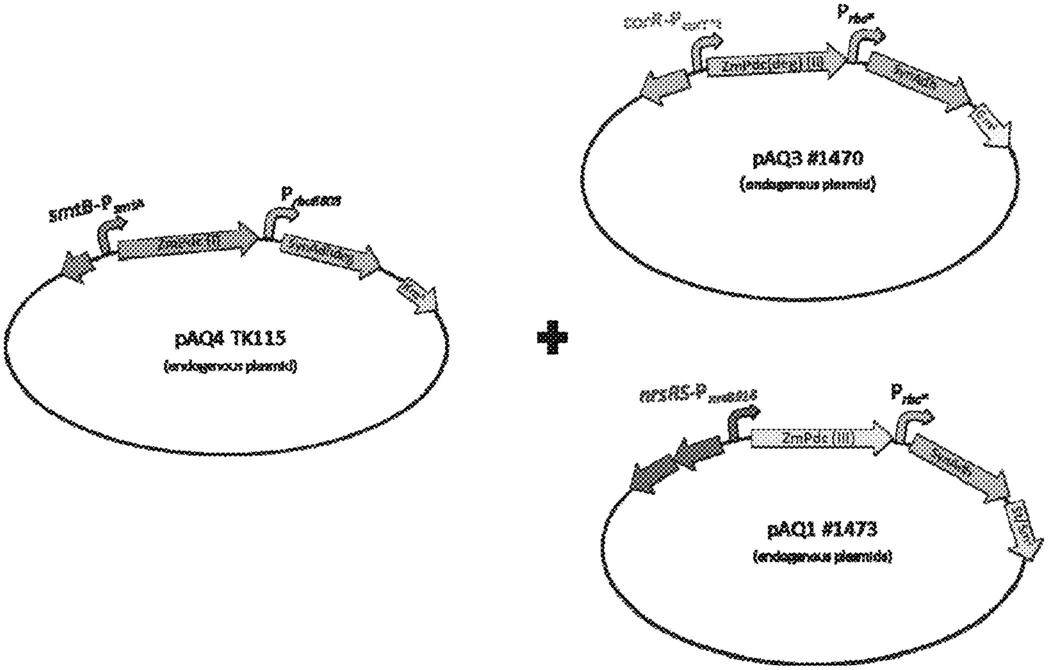

FIG. 36A schematically illustrates the metabolic enhancements incorporated in *Synechococcus* sp. PCC7002 strain TK115/#1470/#1473. The strain harbors a first production gene encoding Pdc from *Zymomonas mobilis* under the transcriptional control of the $Zn^{2+}$-inducible promoter smtB-PsmtA and a degenerated adh-gene from *Synechocystis* sp. PCC6803 under the transcriptional control of the constitutive Prbc promoter integrated into the endogenous plasmid pAQ4, a second first production gene encoding a degenerated pdc from *Zymomonas mobilis* under the transcriptional control of the $Co^{2+}$-inducible promoter corR-PcorT*1 and a second production gene which is an adh-gene from *Synechocystis* sp. PCC6803 under the transcriptional control of the constitutive Prbc* promoter integrated into the endogenous pAQ3 plasmid, and a pdc gene from *Zymomonas mobilis* as the third first production gene under the transcriptional control of the $Ni^{2+}$-inducible promoter nrsRS-PnrsB916 as well as an adh-gene from *Synechocystis* sp. PCC6803 under the transcriptional control of the constitutive Prbc* promoter integrated into the endogenous pAQ1 plasmid.

Figure 36B:
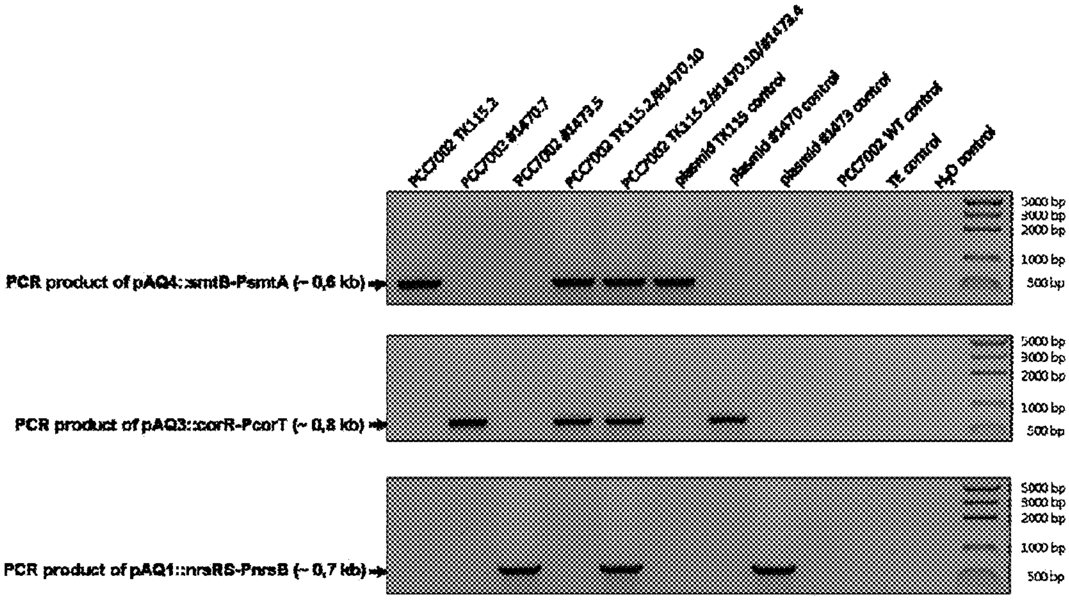

FIG. 36B shows digital images of agarose gels after electrophoretic analysis of PCR products from amplification of promoter constructs smtB-PsmtA integrated in pAQ4, corR-PcorT integrated in pAQ3 and nrsRS-PnrsB integrated in pAQ1, and combinations thereof, in metabolically enhanced *Synechococcus* sp. PCC7002 strain TK115/#1470/#1473 and controls.

Figure 36C:
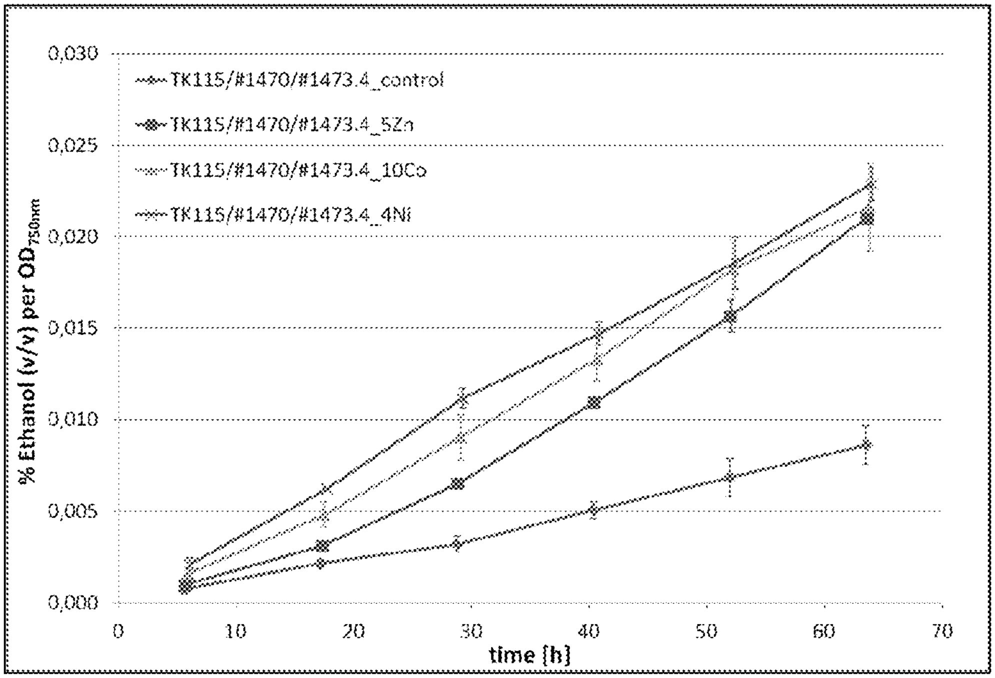

FIG. 36C shows the results of ethanol production of *Synechococcus* sp. PCC7002 strain TK115/#1470/#1473 in %(v/v) normalised per culture OD at 750 nm as a function of cultivation time in hours during selective induction with either $Zn^{2+}$, $Co^{2+}$ or $Ni^{2+}$, as well as a control without induction.

Figure 36D:
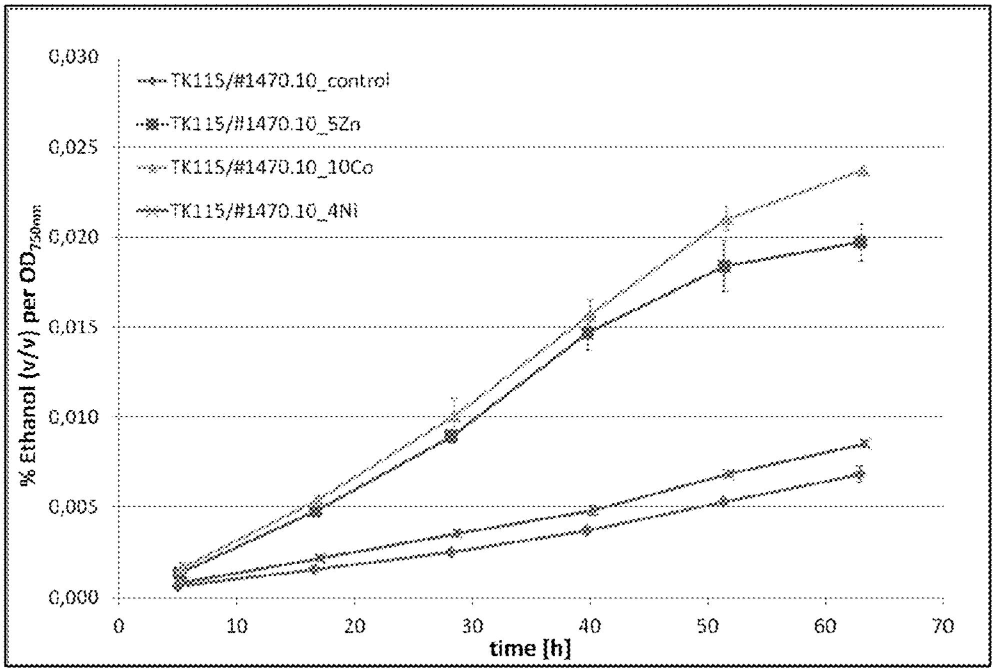

FIG. 36D shows the results of ethanol production of *Synechococcus* sp. PCC7002 strain TK115/#1470 in %(v/v) normalised per culture OD at 750 nm as a function of cultivation time in hours during selective induction with either $Zn^{2+}$, $Co^{2+}$ or $Ni^{2+}$, as well as a control without induction.

Figure 37A:
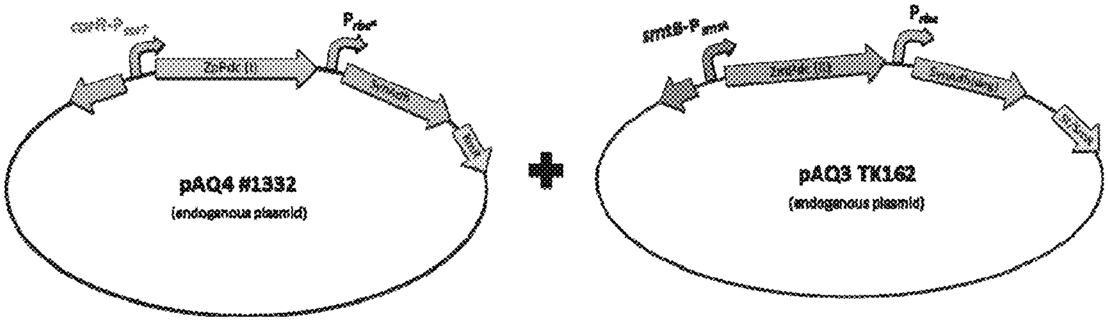

FIG. 37A schematically illustrates the metabolic enhancements incorporated in *Synechococcus* sp. PCC7002 strain #1332/TK162. The strain harbors a first production gene encoding Pdc from *Zymobacter palmae* under the transcriptional control of the $Co^{2+}$-inducible promoter corR-PcorT and a second production gene which is an adh-gene from *Synechocystis* sp. PCC6803 under the transcriptional control of the constitutive Prbc* promoter integrated into the endogenous pAQ4 plasmid, and a second first production gene encoding Pdc from *Zymomonas mobilis* under the transcriptional control of the $Zn^{2+}$-inducible promoter smtB-PsmtA and a degenerated adh-gene from *Synechocystis* sp. PCC6803 under the transcriptional control of the constitutive Prbc promoter integrated into the endogenous plasmid pAQ3.

Figure 37B:
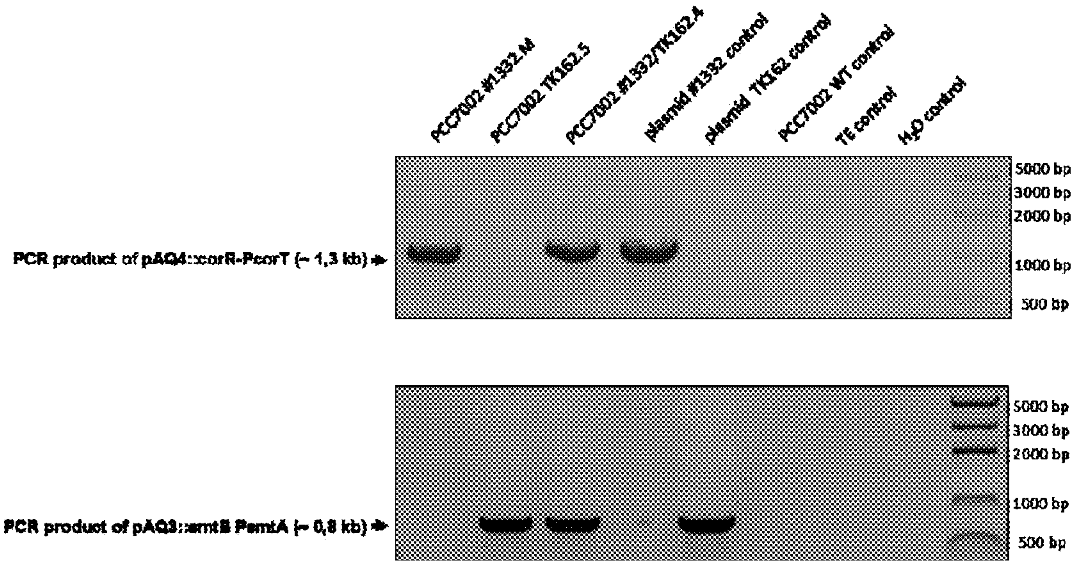

FIG. 37B shows DNA agarose gel images from PCR analysis for confirmation of successful transformation of *Synechococcus* sp. PCC7002 hybrid strain #1332/TK162.

Figure 37C:
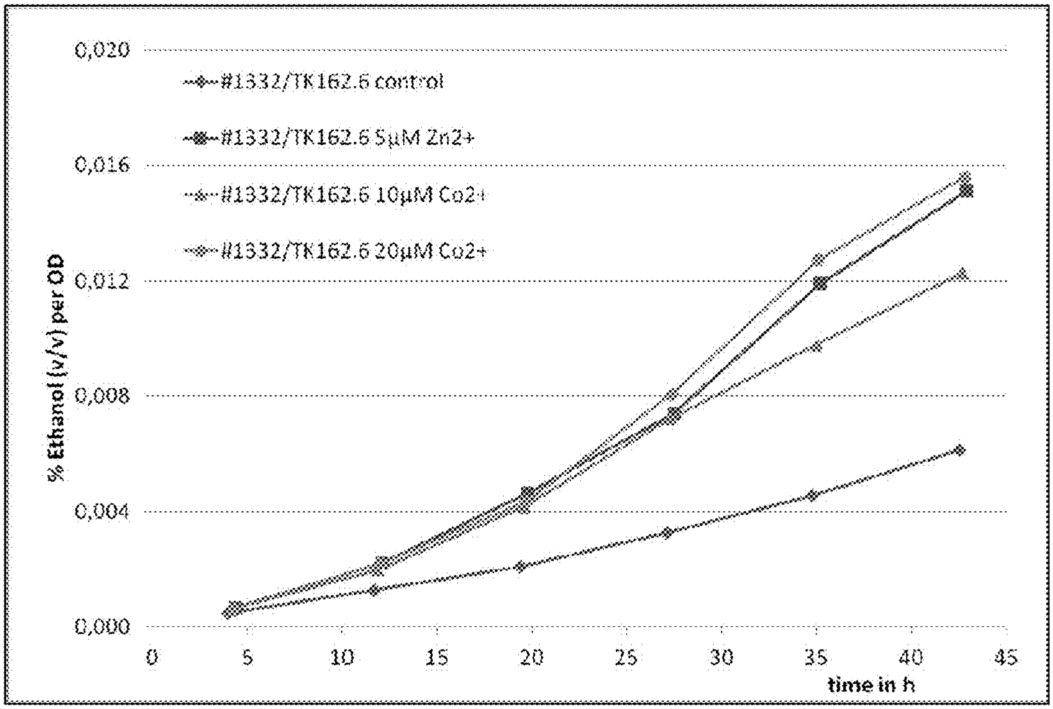

FIG. 37C shows the results of ethanol production in %(v/v) per OD of *Synechococcus* sp. PCC 7002 strain #1332/TK162 without induction and after selective induction with $Zn^{2+}$ and two different concentrations of $Co^{2+}$.

Figure 38A:
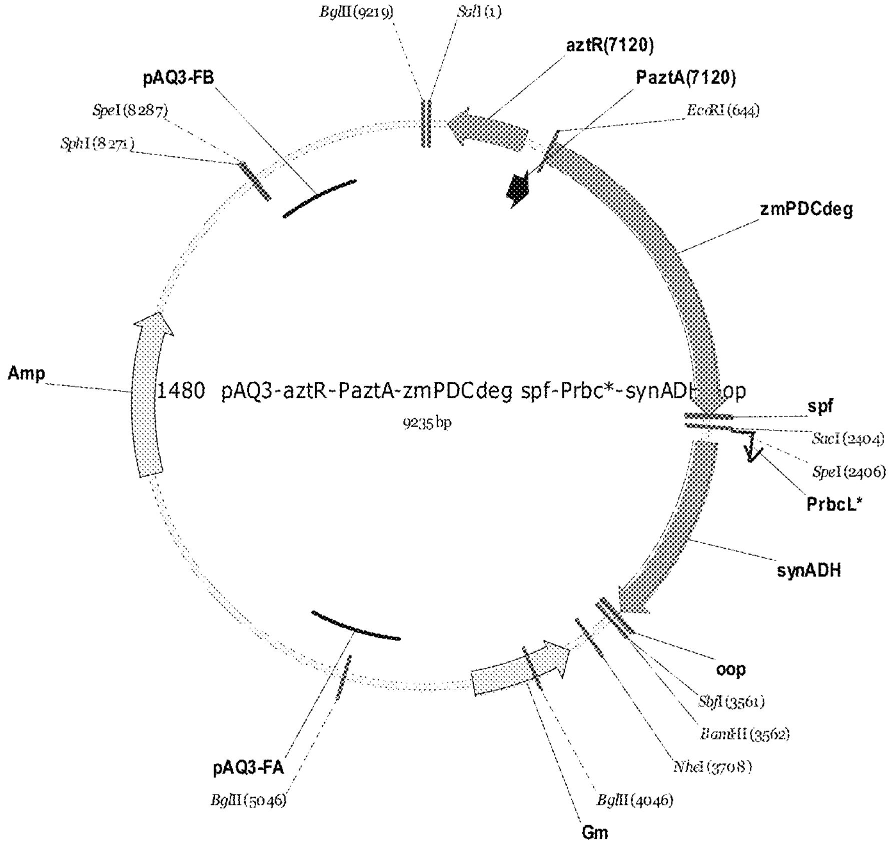

FIG. 38A depicts the vector map of construct #1480 pAQ3-aztR-PaztA-zmPDCdeg_spf-Prbc*-synADH_oop for integration into the endogenous pAQ3 plasmid of *Synechococcus* sp. PCC7002, comprising a degenerated version of the gene encoding Pdc from *Zymomonas mobilis* under the transcriptional control of the $Zn^{2+}$-inducible promoter aztR-PaztA (regulator gene/promoter) and an adh-encoding gene from *Synechocystis* sp. PCC6803 as second production gene under the transcriptional control of the constitutive PrbcL* promoter.

Figure 38B:
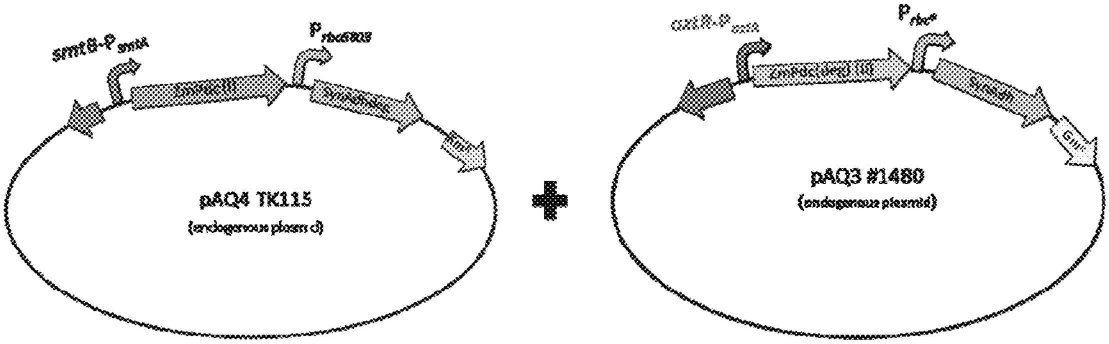

FIG. 38B schematically illustrates the metabolic enhancements incorporated in *Synechococcus* sp. PCC7002 strain TK115/#1480. The strain harbors a first production gene encoding Pdc from *Zymomonas mobilis* under the transcriptional control of the $Zn^{2+}$-inducible promoter smtB-PsmtA and a second production gene which is a degenerated adh-gene from *Synechocystis* sp. PCC6803 under the transcriptional control of the constitutive Prbc6803 promoter integrated into the endogenous pAQ4 plasmid. The strain further harbors a second first production gene which is a degenerated version of the gene encoding Pdc from *Zymomonas mobilis* under the transcriptional control of the $Zn^{2+}$-inducible promoter aztR-PaztA and an adh-gene from *Synechocystis* sp. PCC6803 under the transcriptional control of the constitutive Prbc* promoter integrated into the endogenous plasmid pAQ3.

Figure 38C:
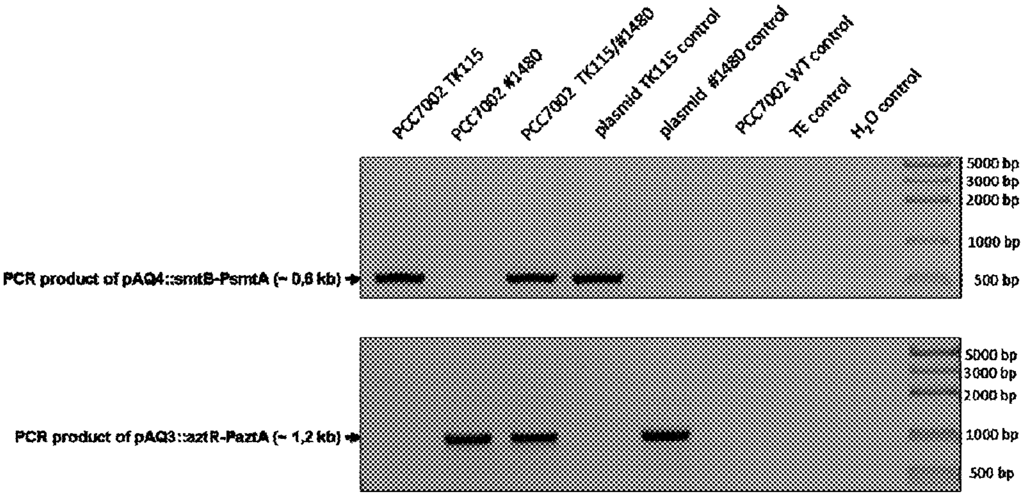

FIG. 38C shows DNA agarose gel images from PCR analysis for confirmation of successful transformation of *Synechococcus* sp. PCC7002 hybrid strain TK115/#1480.

Figure 38D:
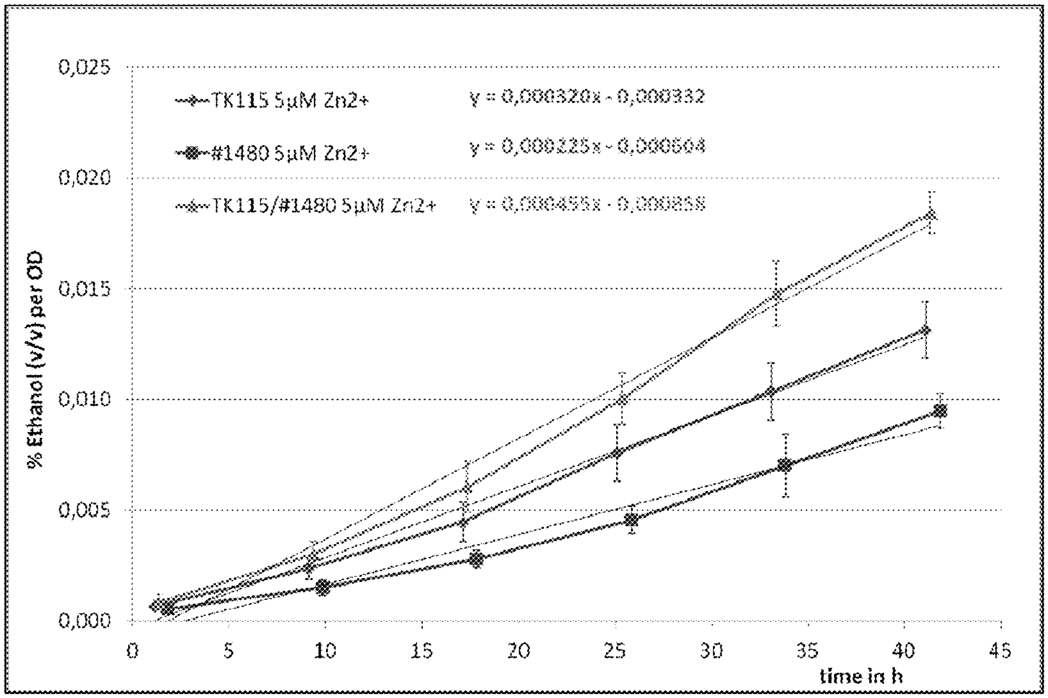

FIG. 38D shows the results of ethanol production in %(v/v) per OD over cultivation time in hours of *Synechococcus* sp. PCC 7002 strains TK115, #1480 and TK115/#1480 under selective induction with 5 μM $Zn^{2+}$.

Figure 38E:
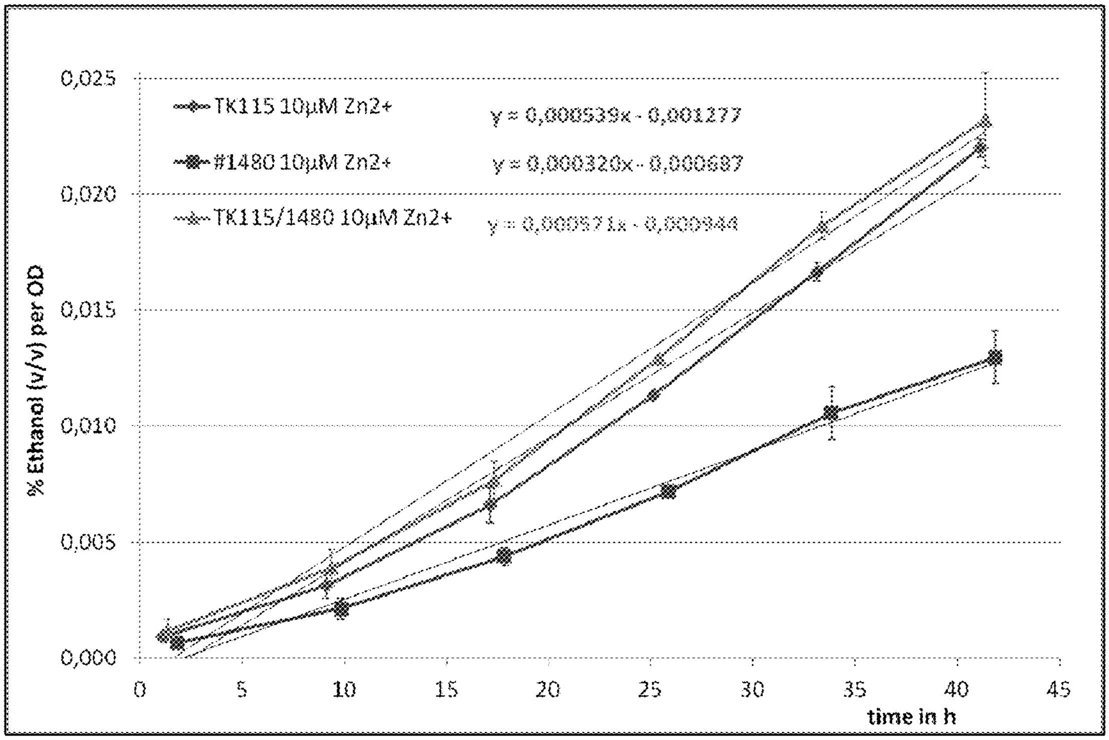

FIG. 38E shows the results of ethanol production in %(v/v) per OD over cultivation time in hours of *Synechococcus* sp. PCC 7002 strains TK115, #1480 and TK115/#1480 under selective induction with 10 μM $Zn^{2+}$.

Figure 39A:
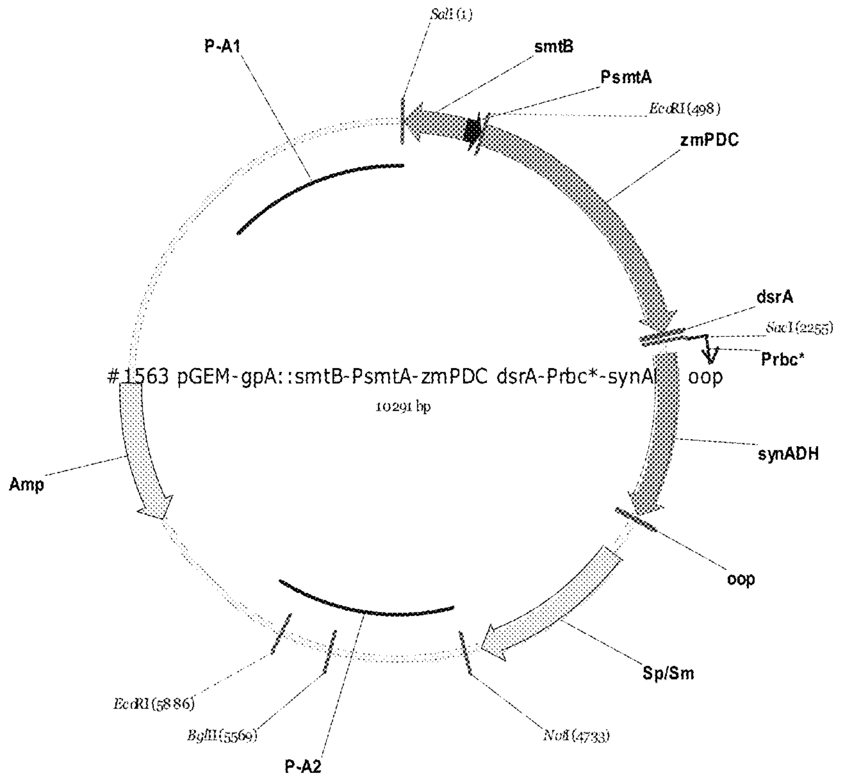

FIG. 39A depicts the vector map of construct #1563 pGEM-gpA::smtB-PsmtA-zmPDC_dsrA-Prbc*-synADH_oop for chromosomal integration in *Synechococcus* sp. PCC7002 between gene loci A0124 and A0125 (integration site A), comprising a first production gene encoding Pdc from *Zymomonas mobilis* under the transcriptional control of the $Zn^{2+}$-inducible promoter smtB-PsmtA (regulator gene/promoter) and an adh-encoding gene from *Synechocystis* sp. PCC6803 as second production gene under the transcriptional control of the constitutive Prbc* promoter.

Figure 39B:
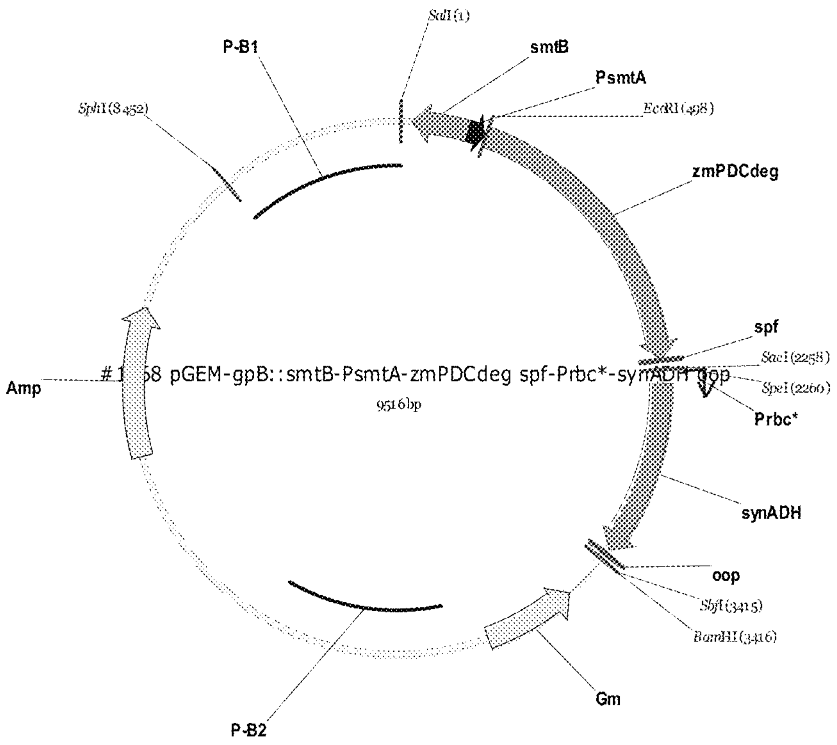

FIG. 39B depicts the vector map of construct #1568 pGEM-gpB::smtB-PsmtA-zmPDCdeg_spf-Prbc*-synADH_oop for chromosomal integration in *Synechococcus* sp. PCC7002 between gene loci A1330 and A1331 (integration site B), comprising a degenerated version of the gene encoding Pdc from *Zymomonas mobilis* as a first production gene under the transcriptional control of the $Zn^{2+}$-inducible promoter smtB-PsmtA (regulator gene/promoter) and an adh-encoding gene from *Synechocystis* sp. PCC6803 as second production gene under the transcriptional control of the constitutive Prbc* promoter.

Figure 39C:
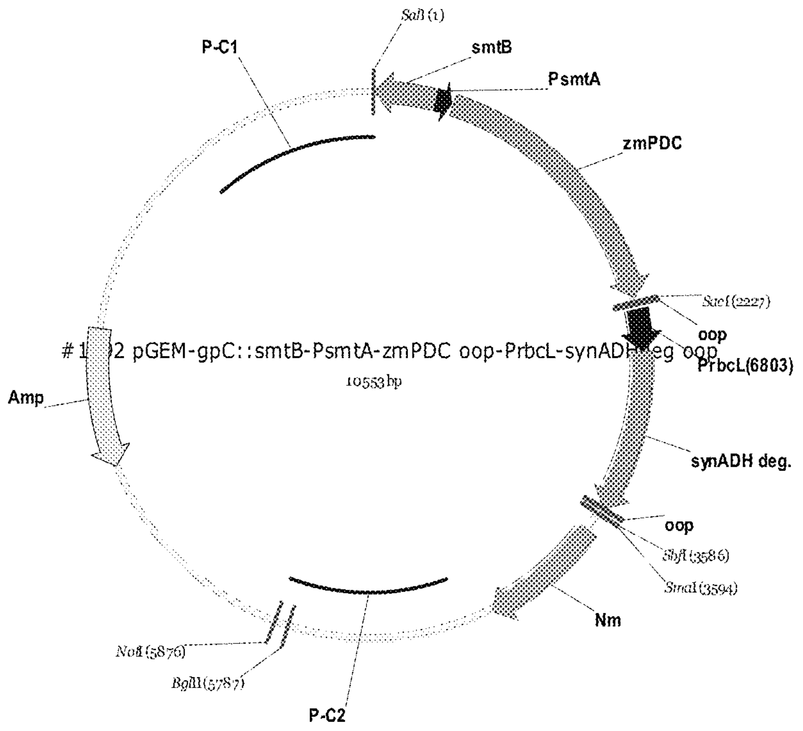

FIG. 39C depicts the vector map of construct #1692 pGEM-gpC::smtB-PsmtA-zmPDC_oop-PrbcL-synADHdeg_oop for chromosomal integration in *Synechococcus* sp. PCC7002 between gene loci A2578 and A2579 (integration site C), comprising a first production gene encoding Pdc from *Zymomonas mobilis* under the transcriptional control of the $Zn^{2+}$-inducible promoter smtB-PsmtA (regulator gene/promoter) and a degenerated version of the adh-encoding gene from *Synechocystis* sp. PCC6803 as second production gene under the transcriptional control of the constitutive PrbcL promoter.

Figure 40A:
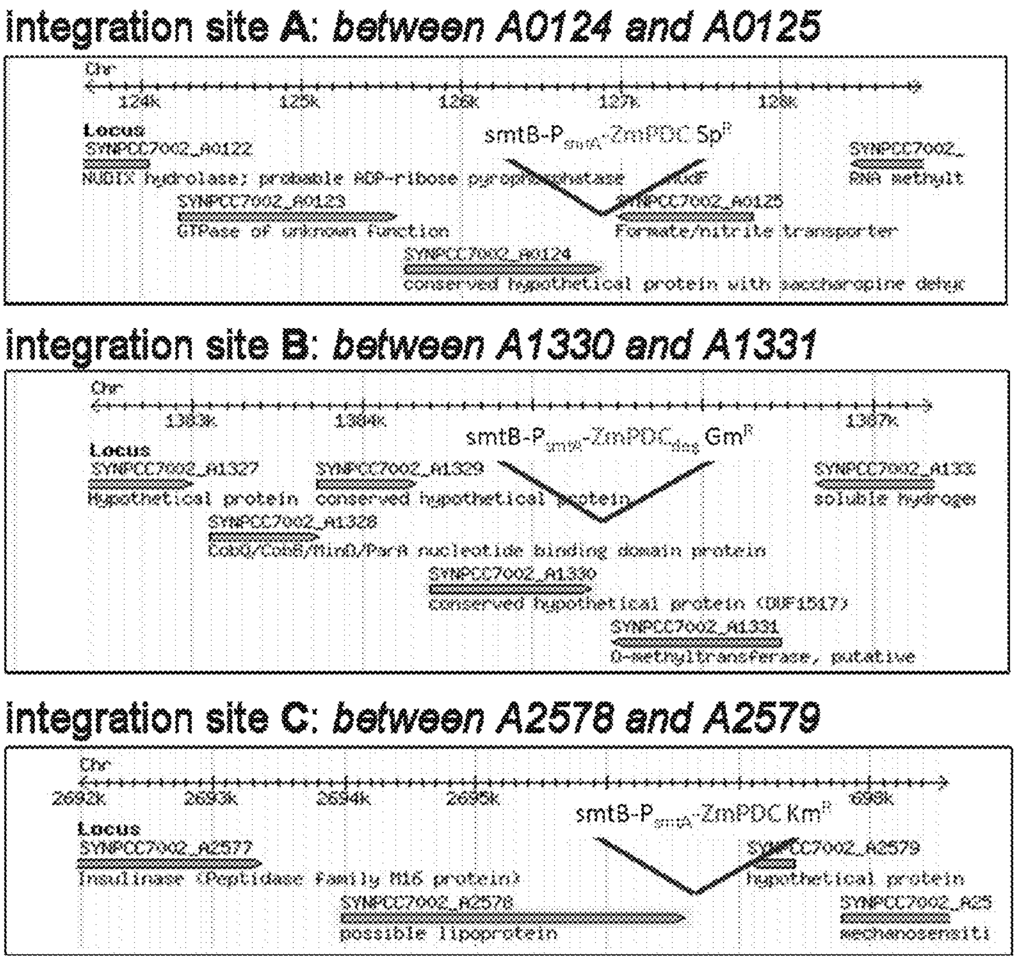

FIG. 40A schematically illustrates chromosomal integration sites A-C for constructs #1563, #1568 and #1692 in *Synechococcus* sp. PCC7002, each construct harbouring a Pdc gene under the transcriptional control of the same $Zn^{2+}$-inducible promoter smtB-PsmtA.

Figure 40B:
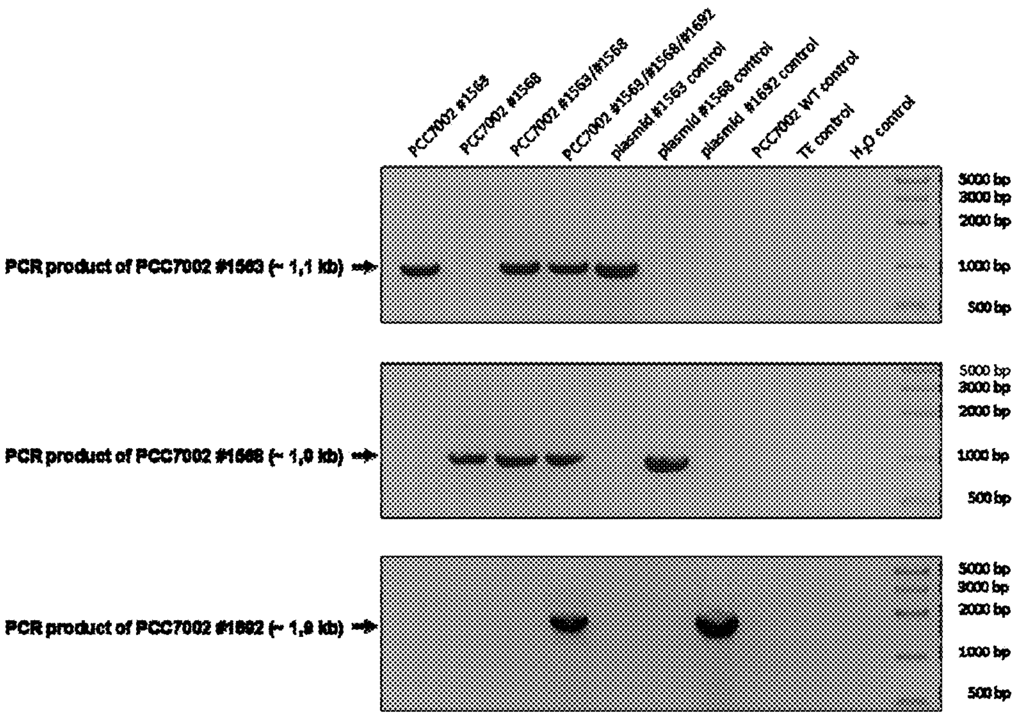

FIG. 40B shows DNA agarose gel images from PCR analysis for confirmation of successful transformation of *Synechococcus* sp. PCC7002 hybrid strain 1563/#1568/#1692.

Figure 40C:
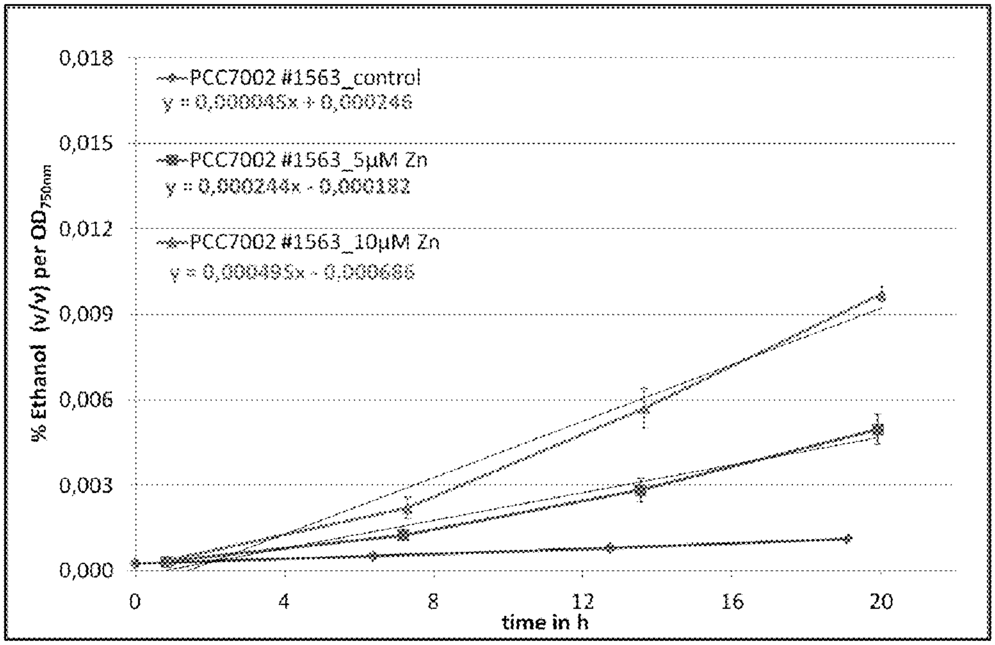

FIG. 40C shows the results of ethanol production in %(v/v) per OD over cultivation time in hours of *Synechococcus* sp. PCC 7002 strain #1563 under selective induction with 5 μM $Zn^{2+}$ and 10 μM $Zn^{2+}$.

Figure 40D:
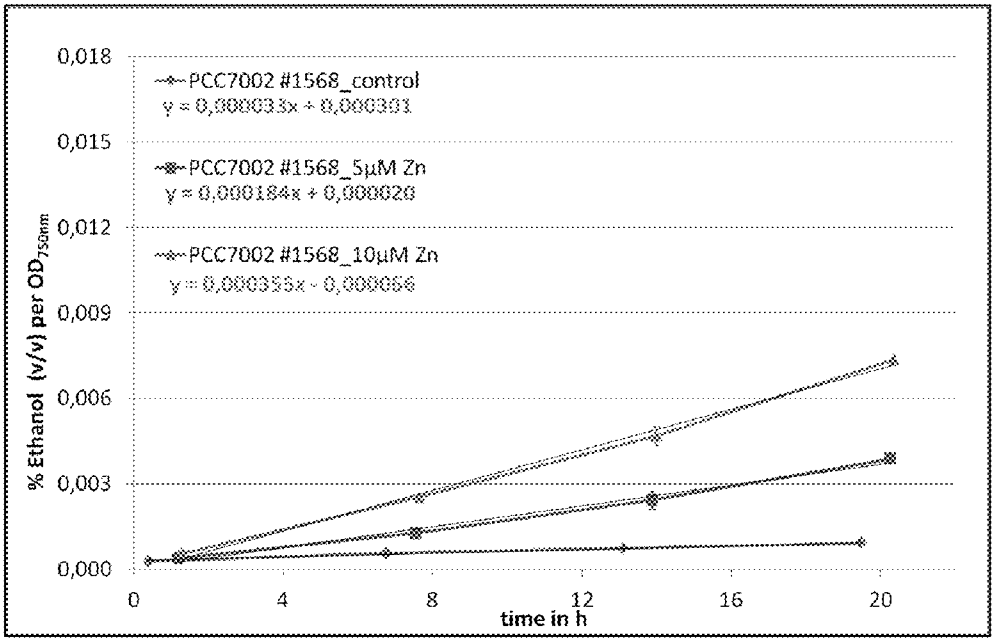

FIG. 40D shows the results of ethanol production in %(v/v) per OD over cultivation time in hours of *Synechococcus* sp. PCC 7002 strain #1568 under selective induction with 5 μM $Zn^{2+}$ and 10 μM $Zn^{2+}$.

Figure 40E:
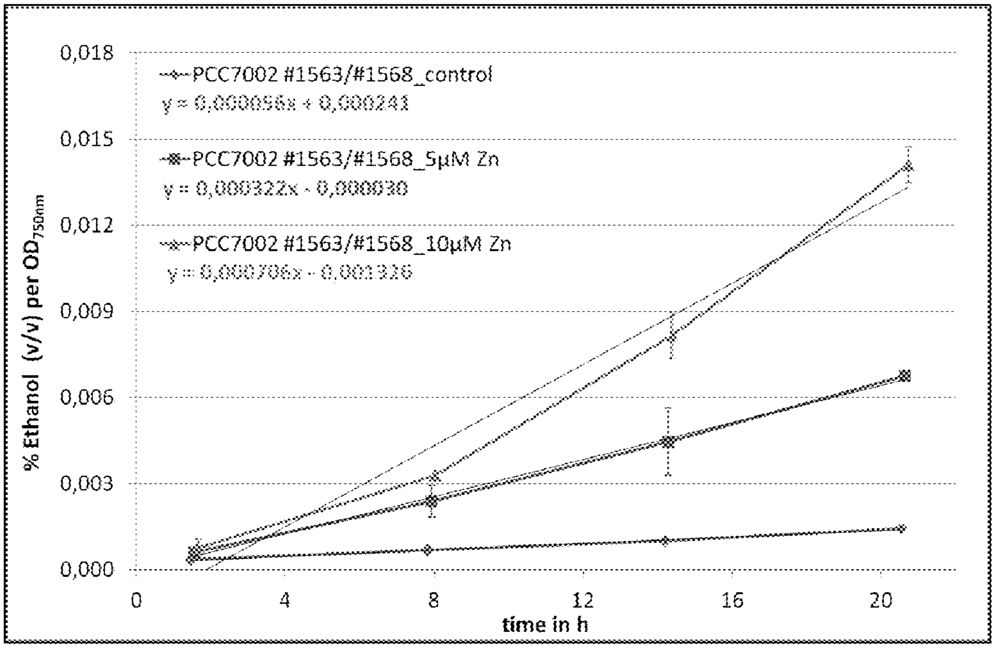

FIG. 40E shows the results of ethanol production in %(v/v) per OD over cultivation time in hours of *Synechococcus* sp. PCC 7002 strain #1563/#1568 under selective induction with 5 μM $Zn^{2+}$ and 10 μM $Zn^{2+}$.

Figure 40F:
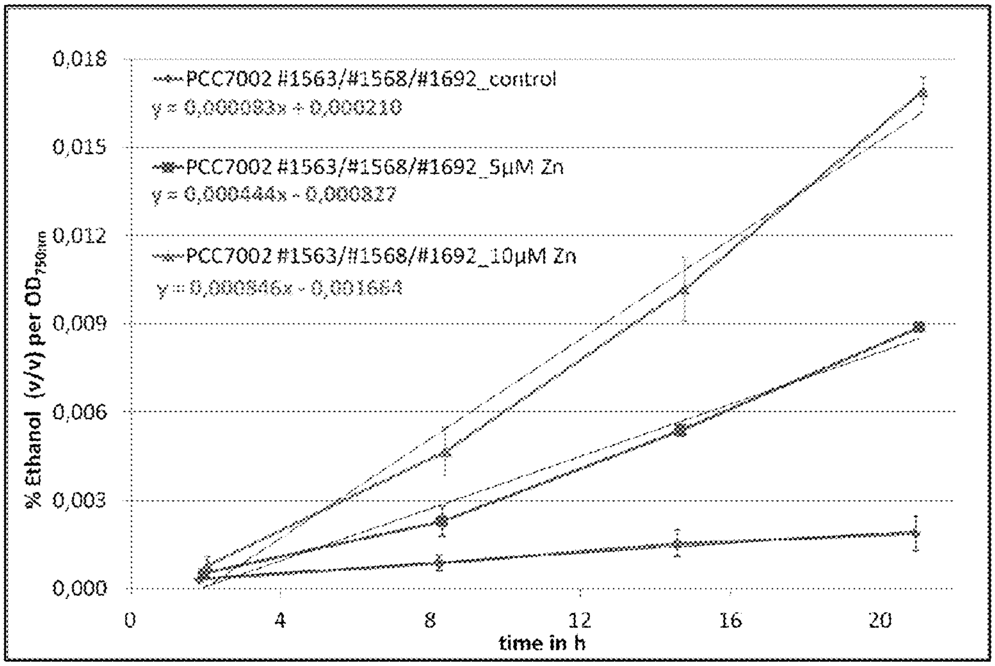

FIG. 40F shows the results of ethanol production in %(v/v) per OD over cultivation time in hours of *Synechococcus* sp. PCC 7002 strain #1563/#1568/#1692 under selective induction with 5 μM $Zn^{2+}$ and 10 μM $Zn^{2+}$.

Figure 41A:
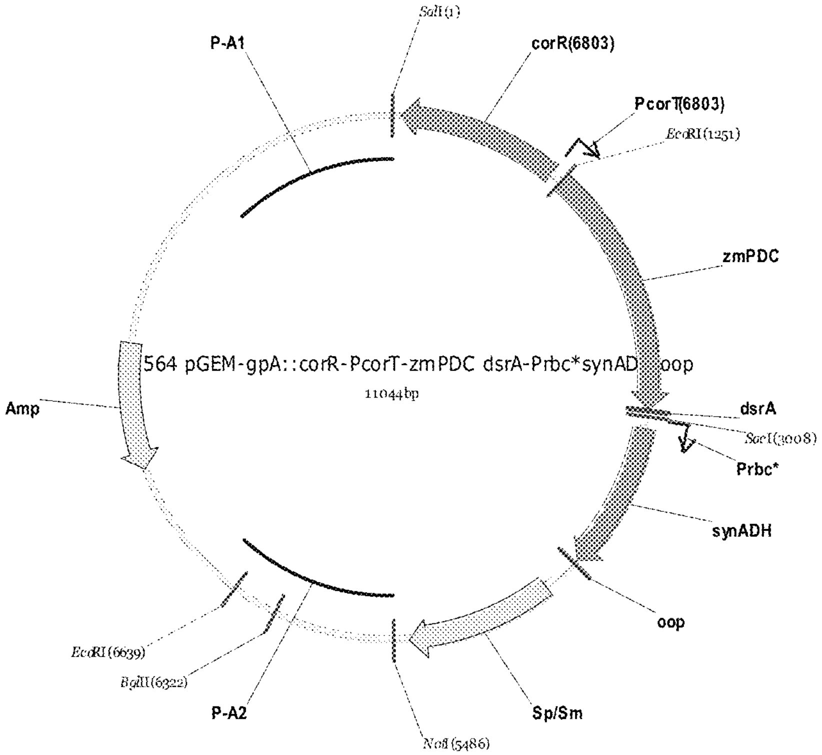

FIG. 41A shows the vector map of construct #1564 pGEM-gpA::corR-PcorT-zmPDC_dsrA-Prbc*synADH_oop for chromosomal integration in *Synechococcus* sp. PCC7002 between gene loci A0124 and A0125 (integration site A), comprising a first production gene encoding Pdc from *Zymomonas mobilis* under the transcriptional control of the $Co^{2+}$-inducible promoter corR-PcorT (regulator gene/promoter) and an adh-encoding gene from *Synechocystis* sp. PCC6803 as second production gene under the transcriptional control of the constitutive Prbc* promoter.

Figure 41B:
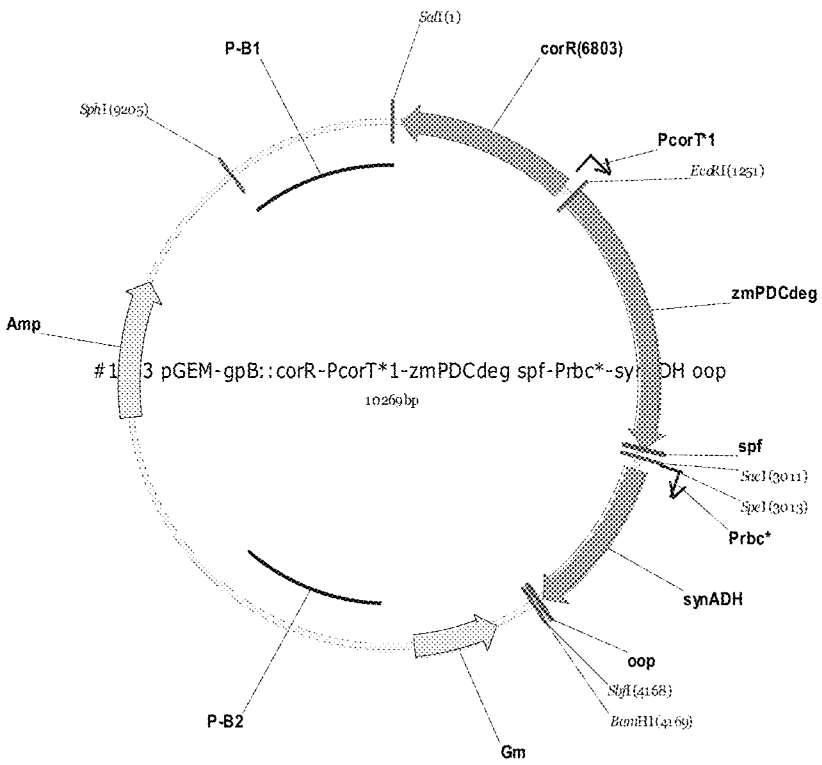

FIG. 41B shows the vector map of construct #1633 pGEM-gpB::corR-PcorT*1-zmPDCdeg_spf-Prbc*-synADH_oop for chromosomal integration in *Synechococcus* sp. PCC7002 between gene loci A1330 and A1331 (integration site B), comprising a degenerated version of the gene encoding Pdc from *Zymomonas mobilis* as a first production gene under the transcriptional control of the $Co^{2+}$-inducible promoter corR-PcorT (regulator gene/promoter) and an adh-encoding gene from *Synechocystis* sp. PCC6803 as second production gene under the transcriptional control of the constitutive Prbc* promoter.

Figure 41C:
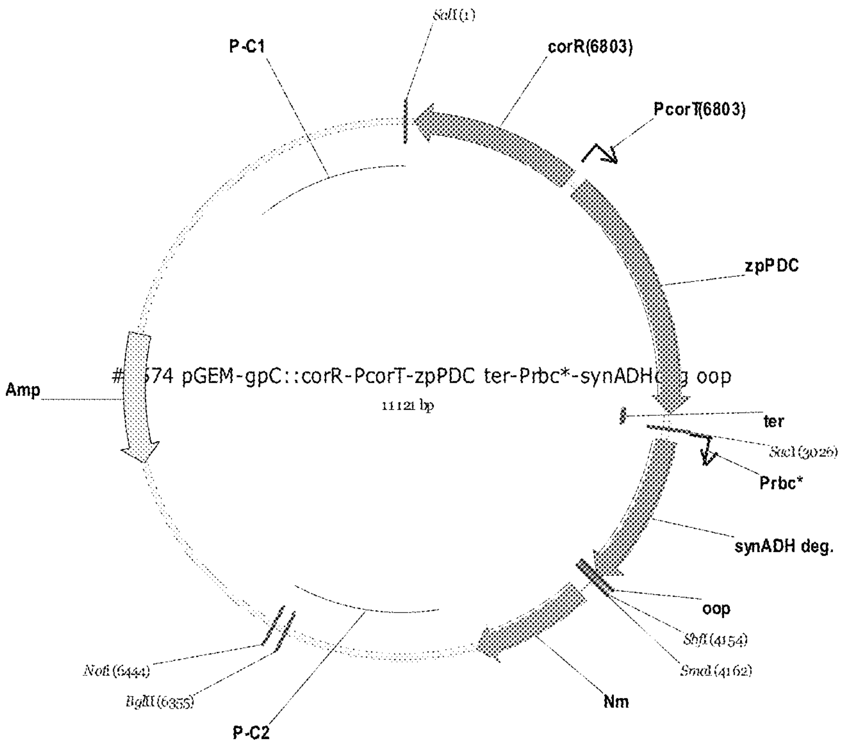

FIG. 41C shows the vector map of construct #1574 pGEM-gpC::corR-PcorT-zpPDC_ter-Prbc*-synADHdeg_oop for chromosomal integration in *Synechococcus* sp. PCC7002 between gene loci A2578 and A2579 (integration site C), comprising a first production gene encoding Pdc from *Zymobacter palmae* under the transcriptional control of the $Co^{2+}$-inducible promoter corR-PcorT (regulator gene/promoter) and a degenerated version of the adh-encoding gene from *Synechocystis* sp. PCC6803 as second production gene under the transcriptional control of the constitutive Prbc* promoter.

Figure 42A:
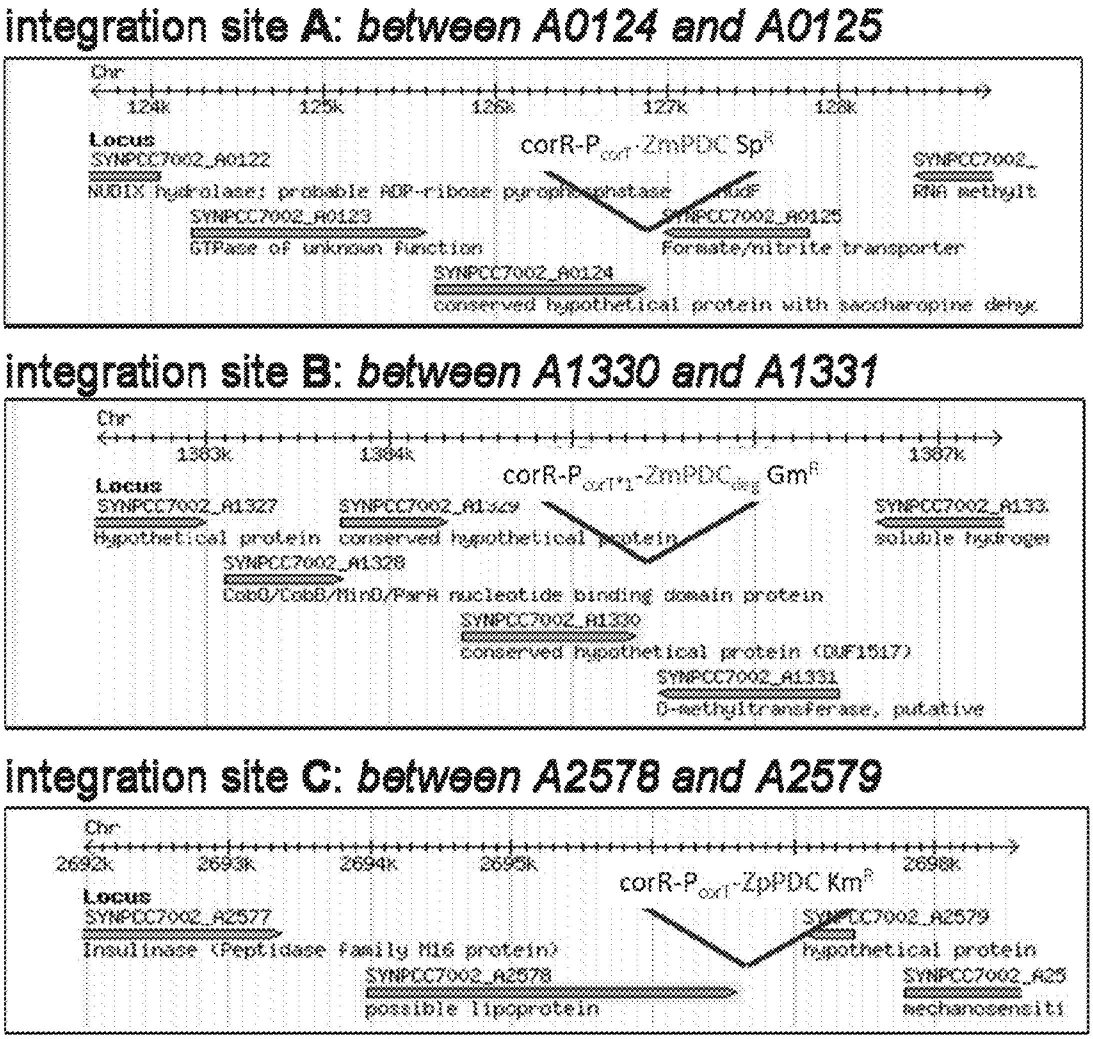

FIG. 42A schematically illustrates chromosomal integration sites A-C for constructs #1564, #1633 and #1574 in *Synechococcus* sp. PCC7002, each construct harbouring a different Pdc gene under the transcriptional control of the same $Co^{2+}$-inducible promoter corR-PcorT.

Figure 42B:
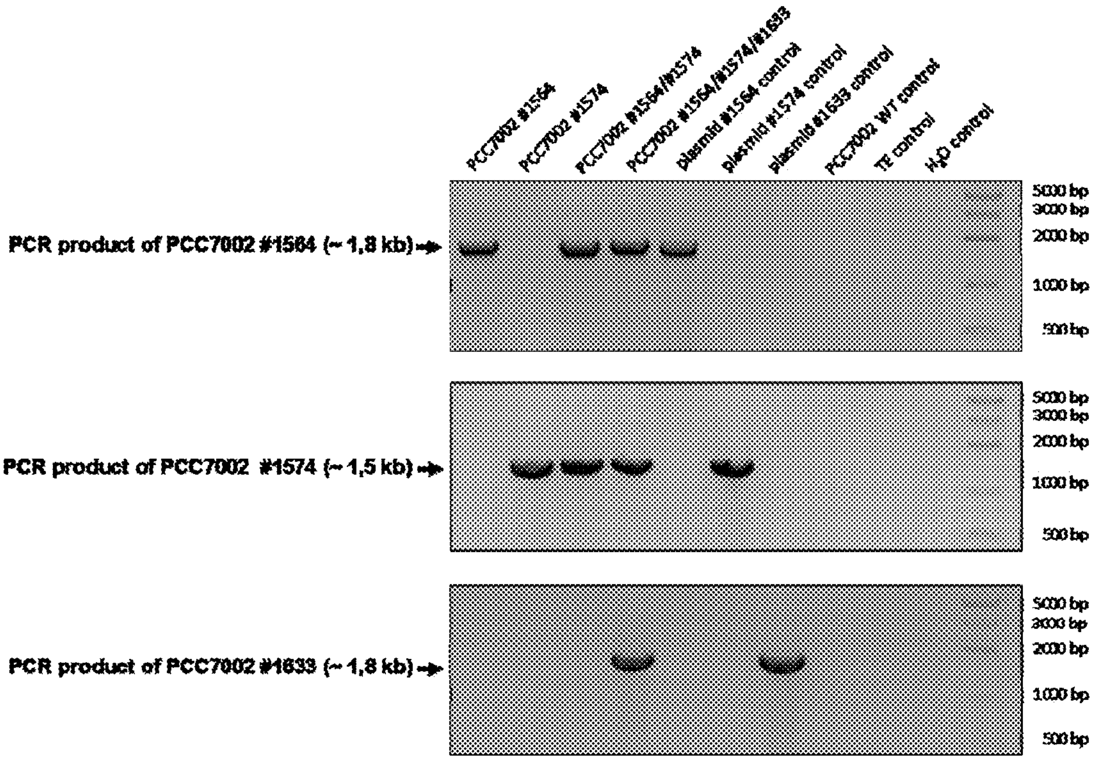

FIG. 42B shows DNA agarose gel images from PCR analysis for confirmation of successful transformation of *Synechococcus* sp. PCC7002 hybrid strain #1564/#1633/#1574.

DESCRIPTION OF THE INVENTION

The first aspect of the invention provides a metabolically enhanced cyanobacterium for the production of a first chemical compound, comprising:

at least two first production genes encoding first biocatalysts for the production of the first chemical compound;
wherein one of the two first production genes is under the transcriptional control of a first promoter for the first production gene;
wherein the other of the two first production genes is under the transcriptional control of a second promoter for the first production gene;
wherein the first promoter and second promoter are separately inducible under different conditions;
wherein the at least two first biocatalysts catalyze the same chemical reaction.

The use of a first and a second promoter for the first production gene allows for the first biocatalyst under the control of said first promoter to be expressed whereas at the same time the first biocatalyst under the control of the second promoter is not expressed, and vice versa. When the first promoter is induced, the first biocatalyst is expressed and the first chemical compound is produced, whereupon genetic alterations can occur in the corresponding first production gene. At the same time, the second promoter for the first production gene is maintained in an uninduced state and the corresponding second of the first biocatalysts is not expressed, thus better preserving the genetic integrity of the corresponding non-induced first production gene compared to the induced one.

DEFINITIONS AND GENERAL EXPLANATIONS

The following explanation of terms and methods are provided to better describe the present invention disclosure and to guide those of ordinary skill in the art in the understanding, interpretation and practice of the present invention. Unless explained otherwise, all technical and scientific terms used herein have the same meaning as commonly understood to one of ordinary skill in the art to which this disclosure belongs. The materials, methods and examples are illustrative only and not intended to be limiting. Other features and/or embodiments of the invention disclosure are apparent from the detailed description and the claims.

As used herein, the term “comprising” means “including”. The singular forms “a” or “an” or “the” expressly include the plural references unless the context clearly dictates otherwise. Referring to “at least one” or “at least two” object(s) expressly includes additional objects falling into the specification of said at least one or at least two objects according to the present invention. For example, “at least two first production genes” can also include a third or further additional first production gene used inventively according to the criteria of the present invention.

Database entry numbers given in the following are from the NCBI database (National Center for Biotechnology Information; available on the world wide web at ncbi.nlm.nih.gov) or from the CyanoBase, the genome database for cyanobacteria (available on the world wide web at bacteria.kazusa.or.jp/cyanobase/index.html); Yazukazu et al. “CyanoBase, the genome database for *Synechocystis* sp. Strain PCC6803: status for the year 2000”, Nucleic Acid Research, 2000, Vol. 18, page 72.)

The EC numbers cited throughout this patent application are enzyme commission numbers which is a numerical classification scheme for enzymes based on the chemical reactions which are catalyzed by the enzymes.

A promoter that is gradually inducible in a dose-dependent manner is a promoter that results in an inductor dose dependent expression of the corresponding promoter-controlled production gene.

As used herein, the term “metabolically enhanced” refers to any change in the endogenous genome of a wild type cyanobacterial cell or to the addition of endogenous and non-endogenous, exogenous genetic code to a wild type cyanobacterial cell, for example the introduction of a heterologous gene. More specifically, such changes are made by the hand of man through the use of recombinant DNA technology or mutagenesis. The changes can involve protein coding sequences or non-protein coding sequences in the genome such as regulatory sequences, non-coding RNA, antisense RNA, promoters or enhancers. Aspects of the invention utilize techniques and methods common to the fields of molecular biology, microbiology and cell culture. Useful laboratory references for these types of methodologies are readily available to those skilled in the art. See, for example, Molecular Cloning: A Laboratory Manual (Third Edition), Sambrook, J., et al. (2001) Cold Spring Harbor Laboratory Press; Current Protocols in Microbiology (2007) Edited by Coico, R., et al., John Wiley and Sons, Inc.; The Molecular Biology of Cyanobacteria (1994) Donald Bryant (Ed.), Springer Netherlands; Handbook Of Microalgal Culture: Biotechnology And Applied Phycology (2003) Richmond, A. (ed.), Blackwell Publishing; and “The cyanobacteria, Molecular Biology, Genomics and Evolution”, Edited by Antonia Herrero and Enrique Flores, Caister Academic Press, Norfolk, UK, 2008.

It is well known to a person of ordinary skill in the art that large plasmids can be produced using techniques such as the ones described in U.S. Pat. No. 6,472,184 B1 titled “method for producing nucleic acid polymers” and U.S. Pat. No. 5,750,380 titled “DNA polymerase mediated synthesis of double stranded nucleic acid molecules”, which are hereby incorporated in their entirety.

Denominations of genes are in the following presented in a three letter lower case name followed by a capitalized letter if more than one related gene exists, for example ziaA for the gene encoding a zinc transporting ATPase. The respective protein encoded by that gene is denominated by the same name with the first letter capitalized, such as ZiaA.

Denominations for promoter sequences, which control the transcription of a certain gene in their natural environment are given by a capitalized letter “P” followed by the gene name according to the above described nomenclature, for example “PziaA” for the promoter controlling the transcription of the ziaA gene.

Denominations for enzyme names can be given in a two or three letter code indicating the origin of the enzyme, followed by the above mentioned three letter code for the enzyme itself, such as SynAdh ($Zn^{2+}$ dependent alcohol dehydrogenase from *Synechocystis* PCC6803), ZmPdc (pyruvate decarboxylase from *Zymomonas mobilis*).

The term “nucleic acid” is intended to include nucleic acid molecules, such as polynucleotides which include an open reading frame encoding a polypeptide, and can further include non-coding regulatory sequences of genes, such as promoters and enhancers as well as non-coding RNAs. In addition, the terms are intended to include one or more genes that are part of a functional operon. In addition, the terms are intended to include a specific gene for a selected purpose. The gene can be endogenous to the host cell or can be recombinantly introduced into the host cell.

In a further embodiment, the invention also provides nucleic acids, which are at least 60%, 70%, 80%, 90% or 95% identical to the promoter nucleic acids or to the nucleic acids encoding either the first or second biocatalysts for the production of the first chemical compound disclosed therein. With regard to the promoters, truncated versions of the promoters including only a small portion of the native promoters upstream of the transcription start point, such as the region ranging from −35 to the transcription start can often be used. Furthermore, introducing nucleotide changes in the untranslated region into the promoter sequence, e.g. into the TATA box, the operator sequence and/or the ribosomal binding site (RBS) can be used to tailor or optimise the promoter for a certain purpose. The invention also provides amino acid sequences for enzymes for the production of the first chemical compounds, which are at least 60%, 70%, 80%, 90% or 95% identical to the amino acid sequences disclosed therein.

In yet a further embodiment, the invention also provides nucleic acids encoding first biocatalysts or second biocatalysts, wherein biocatalysts catalyzing the same chemical reaction are encoded by non-identical gene sequences. The invention provides nucleic acid sequences for biocatalysts catalyzing the same chemical reaction which are less than 80%, 70%, 60% or 50% identical to each other.

The percentage of identity of two nucleic acid sequences or two amino acid sequences can be determined using the algorithm of Thompson et al. (Clustal W, 1994 Nucleic Acid Research 22: pages 4673 to 4680). A nucleotide sequence or an amino acid sequence can also be used as a so-called "query sequence" to perform a nucleic acid or amino acid sequence search against public nucleic acid or protein sequence databases in order to, for example identify further unknown homologous promoters, or homologous protein sequences and nucleic acid sequences which can also be used in embodiments of this invention. In addition, any nucleic acid sequences or protein sequences disclosed in this patent application can also be used as a "query sequence" in order to identify yet unknown sequences in public databases, which can encode for example new enzymes which could be useful in this invention. Such searches can be performed using the algorithm of Karlin and Altschul (1990 Proceedings of the National Academy of Sciences USA 87: pages 2264 to 2268), modified as in Karlin and Altschul (1993 Proceedings of the National Academy of Sciences USA, 90: pages 5873 to 5877). Such an algorithm is incorporated in the Nblast and Xblast programs of Altschul et al. (1990 Journal of Molecular Biology 215, pages 403 to 410) Suitable parameters for these database searches with these programs are, for example, a score of 100 and a word length of 12 for blast nucleotide searches as performed with the Nblast program. Blast protein searches are performed with the Xblast program with a score of 50 and a word length of 3. Where gaps exist between two sequences, gapped blast is utilized as described in Altschul et al. (1997 Nucleic Acid Research, 25: pages 3389 to 3402).

The term "genome" refers to the chromosomal genome as well as to extrachromosomal plasmids which are normally present in the wild type cyanobacterium without having performed recombinant DNA technology. For example, cyanobacteria such as *Synechococcus* sp. PCC 7002 can include at least up to 6 extrachromosomal plasmids in their wild type form.

The term "biocatalysts" in the following refers to biomolecules which catalyse a chemical reaction. A biocatalyst can be a protein with catalytic activity, e.g. an enzyme, or a nucleic acid with catalytic activity, e.g. a ribozyme.

The use of the term "uninduced state" of a promoter in the following refers to a state where only less than or equal to 20%, preferably less than or equal to 15%, more preferably less than or equal to 10%, most preferred less than or equal to 5% of the first chemical compound per $OD_{750\ nm}$ (optical density of the cell suspension at 750 nm wavelength as a parameter of cell density) of the cyanobacteria are produced compared to the induced state of said promoter.

Likewise, referring to two or more promoters as being "different" or "separately inducible under different conditions" denotes promoters, wherein conditions for induction of one promoter maintain a second or further promoter in an uninduced state according to the criteria detailed above. The same rule applies to numerated promoters, e.g. first, second, third or further promoters are considered different promoters according the invention and fulfil the specifications detailed above.

The induction factor is defined as the quotient of the production rate of the first chemical compound per $OD_{750\ nm}$ in the induced state divided by the production rate of the first chemical compound per $OD_{750\ nm}$ in the uninduced state.

The use of the term "temporally separated" method steps throughout the patent application refers to method steps which are sequentially initiated during the method for producing the first chemical compound. According to the present invention, said sequential initiation requires a change of cultivation conditions, for example for the selective induction of the first, second or further promoter for the first production gene. Said change of cultivation conditions can be decidedly made, either directly or indirectly. Alternatively, said change of cultivation conditions can be inherent to the cultivation, for example due to the consumption of a compound. Said temporal separation of method steps thus stipulates the incorporation of inducible promoters to meet the criteria detailed above for each method step, as opposed for instance to the incorporation of constitutive promoters.

The inventors of the present invention surprisingly found that metabolically enhanced hybrid strains of cyanobacteria can be genetically stably maintained for much longer periods under non-inducing conditions than under induced cultivation conditions. The inventors discovered that under non-inducing conditions when the first biocatalysts, which divert fixed carbon-flux from the metabolic pathways for bacterial growth, are not expressed, the genes encoding these first biocatalysts do not accumulate mutations in contrast to their induced state.

Figure 1:
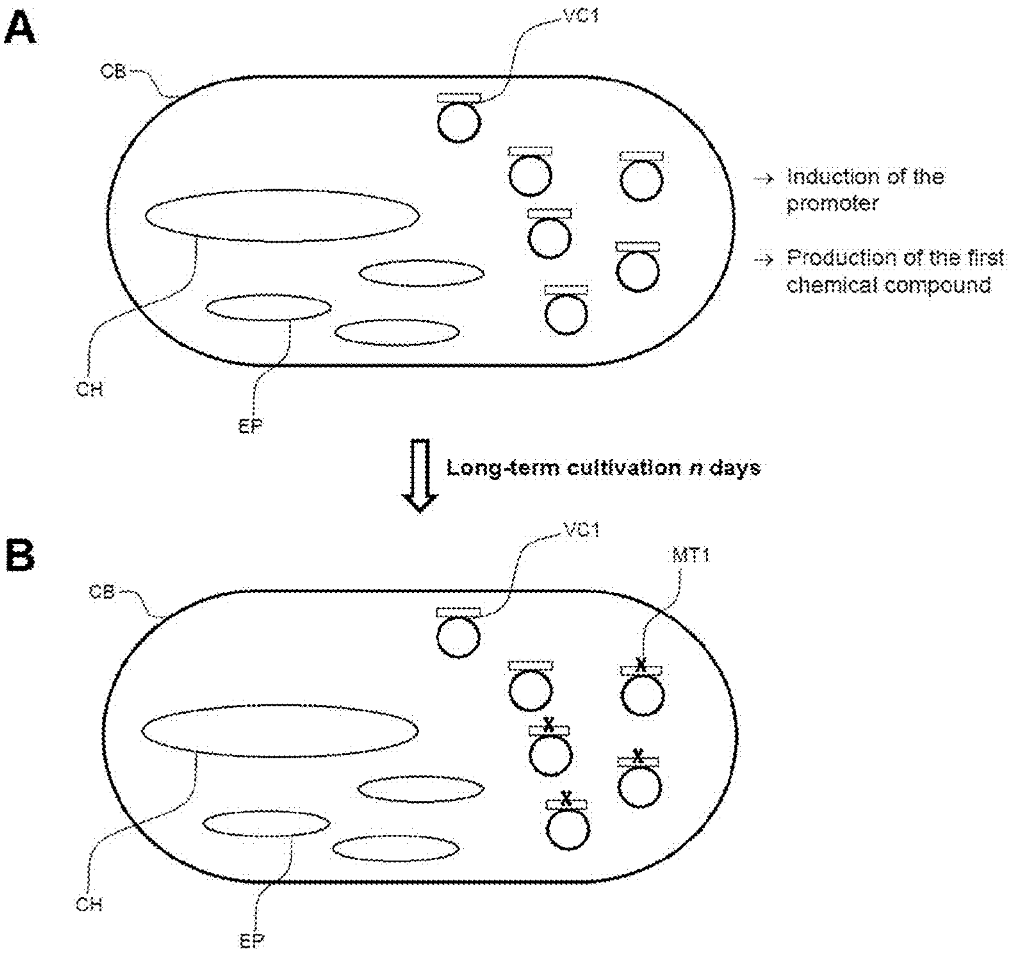

The recurrent problem of such genetic instability of cyanobacterial hybrid strains and the corresponding decrease of the production of the chemical compound is illustrated in FIG. 1. FIG. 1A schematically shows a cyanobacterial hybrid strain as conventionally used for the production of a first chemical compound. The cyanobacterial cell (CB) has been transformed with a vector (VC1), indicated by the circles, carrying a heterologous production gene which is under the transcriptional control of a first inducible promoter, indicated by the horizontal bars on top of the circles, and maintains multiple copies of the vector within one cyanobacterial cell. The large oval in the cyanobacterial cell indicates the bacterial chromosome (CH), whereas the smaller ovals indicate endogenous plasmids (EP). During cultivation, the promoter is induced, driving the expression of the corresponding heterologous production gene, the cyanobacterial cell producing the first chemical compound. In the course of long-term cultivation (FIG. 1B), mutations X (MT1) accumulate in copies of the heterologous production gene, resulting in a decreased expression of functional gene products (e.g. enzymes), thus leading to a decrease of the production of the first chemical compound. At the same time, the revertants grow faster than the metabolically enhanced cyanobacterial cells due to the disposal of the additional metabolic burden that the synthesis of the first chemical compound poses, eventually overgrowing the producing cells.

Due to these mutations in the production genes the metabolically enhanced production strain reverts to the metabolic wild type version, i.e. a strain which is no longer able to produce the first chemical compound. Importantly, these revertants can still carry the selection advantage of, for instance, antibiotic resistance or prototrophy in the case of auxotrophic host strains. For this reason, the revertants exhibit even under selection pressure a significant growth advantage over the first chemical compound-producing metabolically enhanced cyanobacterium strain, since their fixed carbon-flux does not longer bypass anabolic reactions and cell growth for synthesis of the first chemical compound. As soon as this metabolic wild type population overgrows the metabolically enhanced hybrid strain, the productivity in the culture decreases significantly.

The inventors consequently concluded that in order to overcome production decays for the first chemical compound and to prolong the synthesis of the first chemical compound, the solution is a metabolically enhanced cyanobacterial strain, which comprises two or more first production genes, each of which transcriptionally driven by different inducible promoters. Each inducible promoter controls the transcription of an operably linked first production gene and is separately inducible under different conditions. For instance, the metabolically enhanced cyanobacterial hybrid line comprises the first production genes encoding first biocatalysts for the production of the first chemical compound that are under the transcriptional control of a first promoter for the first production gene and a second promoter for the other first production gene, and wherein the first promoter and second promoter are separately inducible under different conditions.

Promoters that are separately inducible under different conditions can for example be promoters that require different inductors for induction. Such promoters can for instance be different metal-ion inducible promoters, e.g. $Zn^{2+}$, $Ni^{2+}$ or $Co^{2+}$ inducible promoters. Alternatively or in addition, such promoters can be inducible by the same inductor but require different concentrations of inductor compared to each other. For instance, the first and second promoter are both $Zn^{2+}$ inducible promoters, but the first promoter is induced in a concentration range of 1-10 μM $Zn^{2+}$, whereas the second promoter is induced in a concentration range of 10-20 μM $Zn^{2+}$, so that conditions for induction of the first promoter can be chosen which maintain the second promoter in an uninduced state according to the definition of the present invention.

Upon the specific induction of the first promoter for the first production gene, the corresponding first biocatalyst directs the metabolic carbon flux of the photoautotrophic cyanobacterium towards the production of the first chemical compound, for instance ethanol. At the same time, the first biocatalyst under the transcriptional control of the second promoter for the first production gene is not expressed and is better preserved from accumulating inactivating genetic alterations. Upon loss of activity of the first biocatalyst following the accumulation of mutations in the first production gene, the second promoter for the first production gene which has not yet accumulated inactivating alterations can be induced, so that the second of the first biocatalysts is expressed which catalyzes the same reaction as the first of the two first biocatalysts, thus leading to a recovery of the production of the first chemical compound and enabling the temporal extension of the production phase of the first chemical compound.

In a preferred embodiment of the invention, the metabolically enhanced cyanobacterium further comprises at least one second production gene encoding a second biocatalyst for the production of the first chemical compound. In such embodiments, the chemical reaction catalyzed by the first biocatalyst is different from the chemical reaction catalyzed by the second biocatalyst. In this case, the first biocatalysts can produce an intermediate, which is further converted by the second biocatalyst to the first chemical compound. In a variant of the metabolically enhanced cyanobacterium, the at least one second production gene is also under the transcriptional control of a first promoter for the second production gene. In some embodiments, said first promoter for the second production gene is inducible under the same conditions as the first promoter for the first production gene. In certain embodiments, the first promoter for the second production gene and the first promoter for the first production gene are the same single promoter.

Cyanobacteria according to certain embodiments of the invention can also comprise a whole sequence of recombinant genes coding for biocatalysts for the production of the first chemical compound in the case that a cascade, for example a series of different enzymes, is necessary to produce the first chemical compound. In particular, the first biocatalyst encoded by the first production gene can produce a first intermediate which is further converted by the second biocatalyst encoded by the second production gene into another second intermediate, which in turn is then further converted by a third biocatalyst encoded by a third production gene into a third intermediate, so that a sequence of consecutive recombinant biocatalysts, which provide intermediates for the next recombinant enzyme for the production of the first chemical compound can be introduced into the cyanobacteria.

In another preferred embodiment, the metabolically enhanced cyanobacterium comprises multiple first production genes, all encoding first biocatalysts catalysing the same chemical reaction, wherein each of the multiple first production genes is under the transcriptional control of a promoter for the first production gene which is separately inducible under different conditions in comparison to the other promoters for the first production gene. In one example, the metabolically enhanced cyanobacterium comprises a further third first production gene under the transcriptional control of a third promoter for the first production gene. In one example, the metabolically enhanced cyanobacterium comprises a fourth first production gene under the transcriptional control of a fourth promoter for the first production gene. In one example, the metabolically enhanced cyanobacterium comprises at least a further fifth first production gene under the transcriptional control of a fifth promoter for the first production gene.

In another preferred embodiment, the metabolically enhanced cyanobacterium comprises more than one second production gene, all encoding second biocatalysts catalysing the same chemical reaction. In one example, the metabolically enhanced cyanobacterium comprises two second production genes, wherein one of the two second production genes is under the transcriptional control of a first promoter for the second production gene and the other of the two second production genes is under the transcriptional control of a second promoter for the second production gene. In another example, the metabolically enhanced cyanobacterium comprises a further third second production gene under the transcriptional control of a third promoter for the second production gene. In another example, the metabolically enhanced cyanobacterium comprises a fourth second production gene under the transcriptional control of a fourth promoter for the second production gene. In another example, the metabolically enhanced cyanobacterium comprises at least a further fifth second production gene under the transcriptional control of a fifth promoter for the second production gene.

In some preferred embodiments, the promoters for the first production genes and the promoters for the second production genes are inducible under the same conditions, so that the first production gene and the second production gene are co-expressed under the same cultivation conditions. This ensures that the first chemical compound can be produced via the enzymatic action of the first and second biocatalyst. In one example, the first promoter for the first production gene and the first promoter for the second production gene are inducible under the same conditions. In another example, also the second promoter for the first production gene and the second promoter for the second production gene are inducible under the same conditions. In yet another example, at least a further third promoter for the first production gene and a further third promoter for the second production gene are inducible under the same conditions.

According to a preferred embodiment of the invention, provided is the metabolically enhanced cyanobacterium with a first production gene and a second production gene which are transcriptionally controlled by the same single promoter. For example, a single first promoter is operably linked with a first production gene and a second production gene to form a functional operon. An operon is a functional unit of DNA which contains a cluster of genes under the control of a single regulatory signal or promoter. Accordingly, both the first production gene and the second production gene of an operon are co-ordinately expressed upon induction of the corresponding promoter. In one example, the metabolically enhanced cyanobacterium comprises one single first promoter controlling the transcription of both the first production gene and the second production gene, thus forming the first operon. In another example, the metabolically enhanced cyanobacterium further comprises one single second promoter controlling the transcription of both a second first production gene and a second production gene, thus forming a second operon. In other examples, the metabolically enhanced cyanobacterium can comprise a third, fourth or further additional operon under the transcriptional control of a third, fourth or further promoter controlling the transcription of a first production gene and a second production gene.

In another preferred embodiment, the metabolically enhanced cyanobacterium comprises a second production gene that is endogenous. In some related examples, wherein the wild type cyanobacterium endogeneously expresses the second biocatalyst that is required and sufficient to convert the intermediate produced by the first biocatalysts into the first chemical compound, the endogenous second production gene can also be non-recombinant, i.e. not affected by any manipulation.

In a further variant, the metabolically enhanced cyanobacterium comprises a second production gene encoding a biocatalyst that catalyzes a chemical reaction that is also present in the wild type cyanobacterium. The inventors surprisingly discovered that under these conditions the genetic stability of the second production gene is much higher compared to the first production gene. Therefore, in some preferred embodiments, the second production gene encoding a biocatalyst that catalyzes a chemical reaction that is also present in the wild type cyanobacterium is under the transcriptional control of a constitutive promoter. The inventors found that the constitutive expression of a second biocatalyst, which catalyzes a chemical reaction also present in the wild type cyanobacterium thereby converting a first intermediate produced by the first biocatalyst into a second intermediate or into the first chemical compound, does not foster the accumulation of mutations in the second production gene.

In yet another preferred embodiment of the invention, the metabolically enhanced cyanobacterium comprises a second production gene that is recombinant. For example, the nucleotide sequence of an endogenous cyanobacterial gene can be altered to form a recombinant second production gene. Such alterations include for instance degenerated variants of a production gene in order to minimise the risk of homologous recombination with other closely related genes in the same strain, which might lead to the inactivation of the gene. In another example, an endogenous cyanobacterial gene is recombinantly put under the transcriptional control of a promoter that is different from the promoter transcriptionally controlling the gene in its native context to form a recombinant second production gene. In a preferred embodiment, a recombinant second production gene comprises an altered nucleotide sequence of an endogenous cyanobacterial gene under the transcriptional control of a promoter that is different from the promoter transcriptionally controlling the gene in its native context.

In some examples, this promoter is a constitutive promoter.

In yet other examples, an endogenous second production gene is operably linked to an inducible promoter to form a recombinant second production gene. In yet another example, an endogenous second production gene is operably linked with a first production gene and an inducible promoter to form part of an operon comprising a recombinant second production gene. In some of these examples, the second production can also be heterologous instead of endogenous. For example, a recombinant second production gene can comprises an altered nucleotide sequence of heterologous gene under the transcriptional control of a promoter, which can in some preferred instances be a constitutive promoter and in some other preferred instances an inducible promoter.

Some preferred embodiments comprise a combination of recombinant and non-recombinant second production genes. For example, additional copies of an endogenous second production gene can be recombinantly introduced into the cyanobacterium to increase the gene copy number. In another example, the cyanobacterial genome harboring an endogenous second production gene can be complemented with one or more additional heterologous second production genes. For instance, cyanobacteria known to endogenously harbor alcohol dehydrogenases could be complemented with a recombinant second production gene encoding an alcohol dehydrogenase enzyme derived from *Synechocystis* sp. PCC 6803. In preferred related embodiments, recombinant second production genes comprise degenerated versions if one or more endogenous second production gene is present in order to avoid the risk of inactivation by homologous recombination.

In preferred embodiments, the first biocatalyst catalyzes a chemical reaction which is not present in the wild type cyanobacteria. For instance, the introduction of the recombinant first production gene re-directs the metabolic flux of the photoautotrophic cyanobacterium towards the production of the first chemical compound. In preferred embodiments, the first biocatalyst is integrated with the natural metabolism of the cyanobacterium using primary or secondary metabolic products as substrate. In a preferred embodiment, the chemical reaction catalyzed by the first biocatalyst diverts carbon flux for the production of the first chemical compound via pyruvate as a naturally occurring metabolite towards the production of the first chemical compound. In another preferred embodiment, the first biocatalyst diverts carbon flux for the production of the first chemical compound via acetyl-CoA as a naturally occurring metabolite towards the production of the first chemical compound. In yet another preferred embodiment, the first biocatalyst utilizes secondary metabolites from valine biosynthesis and non-mevalonate pathways from valine and isoprenoid synthesis as precursors for the production of the first chemical compound, for example isoprene or isobutanol. In yet another preferred embodiment, the first biocatalyst catalyzes a chemical reaction which diverts acyl-ACP molecules from membrane biosynthesis to produce free fatty acids and alkanes.

In some embodiments, only the at least two first production genes encoding the first biocatalysts are under the transcriptional control of inducible promoters. This is based on the discovery by the inventors that in order to balance cell growth and production of the first chemical compound, and thus improve the genetic stability of the cyanobacterial strain, the control of the metabolic carbon flux of the genetically enhanced cyanobacterium requires only to put such production genes under the control of the inducible promoters that encode biocatalysts catalyzing a chemical reaction that separates the carbon flux from the cell growth and biomass accumulation, respectively, and is not present in the wild type cyanobacterium. If only the first production gene coding for a first biocatalyst catalysing a chemical reaction not present in the wild type cyanobacterium is put under the transcriptional control of a first inducible promoter, the cyanobacterial culture in the uninduced state can accumulate biomass without being prone to inactivating alterations in the first production gene. Only when sufficient biomass is reached, the first production gene will be induced so that a high level of production of the first chemical compound can be achieved.

In a related embodiment, the second biocatalyst catalyzes a chemical reaction which is present in the wild type cyanobacteria and has no influence on the carbon flux as it converts the intermediate produced by the first biocatalyst. In yet another related embodiment, the at least one second production gene encoding the second biocatalyst is under the transcriptional control of a constitutive promoter. The inventors found that a cyanobacterial hybrid strain which is metabolically enhanced according to the embodiments detailed above is less prone to accumulation of mutations in the first and second production genes and allows for a particularly prolonged production of the first chemical compound, for instance ethanol. The inventors concluded that the introduction of additional recombinant copies of biocatalysts which catalyze a chemical reaction present in the wild type cyanobacterium influences the metabolism of the cyanobacterium to a lower extent in the absence of catalytic activity of the first biocatalyst, however, it can also reduce the accumulation of toxic precursors/intermediates, e.g. as it is the case for acetaldehyde if ethanol is produced, in the presence of catalytic activity of the first biocatalyst. If ethanol is produced as the first chemical compound, the first biocatalyst could be a pyruvate decarboxylase, which is not present in wild type cyanobacteria. In contrast to that, most wild type cyanobacteria are known to harbor alcohol dehydrogenases, which could be the second biocatalyst. Accordingly, the at least one second production gene encoding an alcohol dehydrogenase could therefore be put under the transcriptional control of a constitutive promoter.

Figure 2:
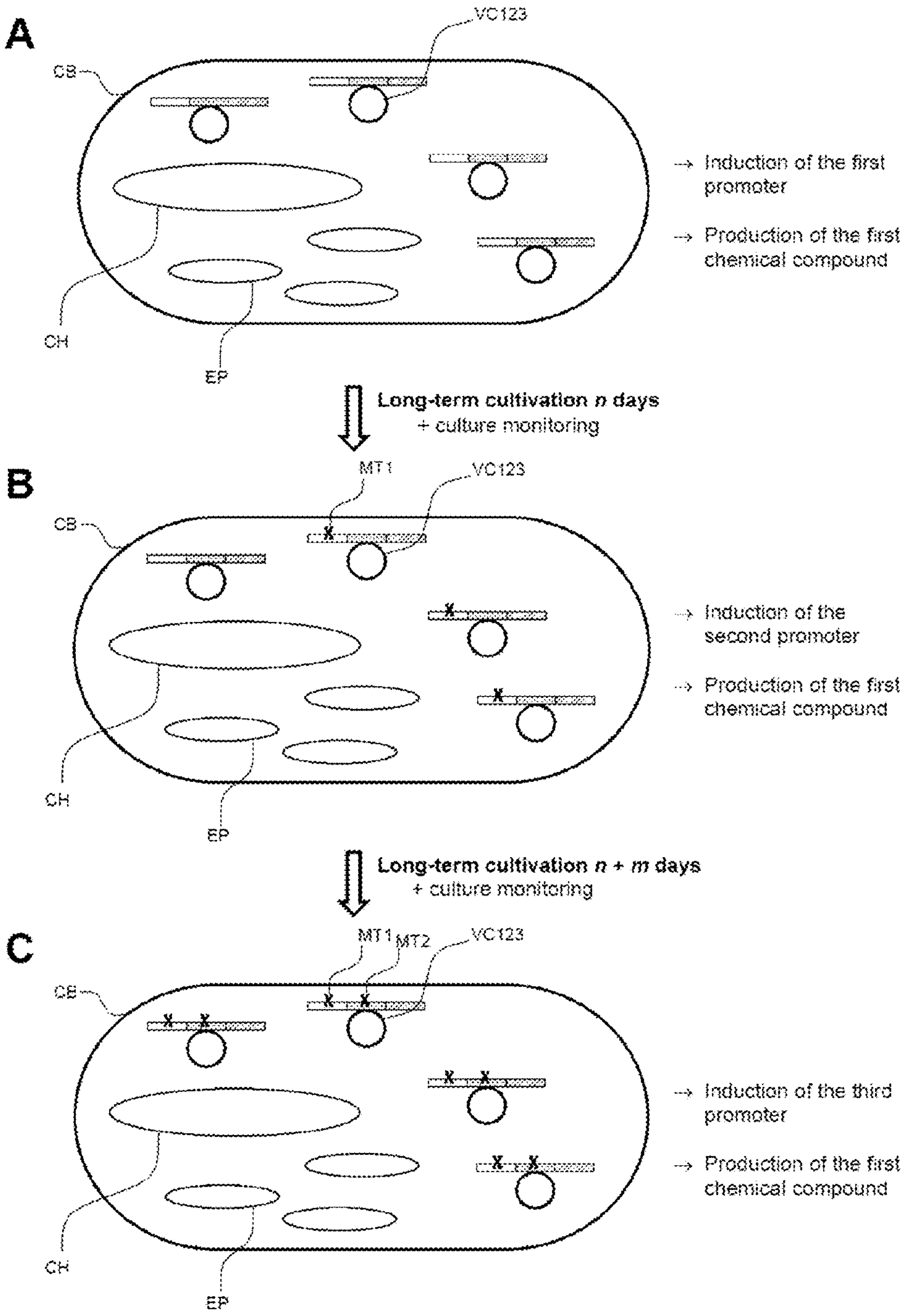

In some embodiments, the first production genes are co-located on the same genetic element. According to the invention, a genetic element is selected from a group comprising a vector, an endogenous plasmid, a chromosome and combinations thereof. For example, two first production genes, one of the two first production genes under the transcriptional control of a first promoter for a first production gene, the other first production gene under the transcriptional control of a second promoter for the first production gene, respectively, are co-located on the same genetic element. In another example, a third, fourth or further first production gene under the transcriptional control of a third, fourth or further promoter for the first production gene is co-located with said two first production genes on the same genetic element. FIG. 2 shows an exemplary embodiment wherein three first production genes are co-located on the same genetic element. In this example, the cyanobacterial cells (CB) have been transformed with self-replicating vectors (VC123), indicated by the circles, harboring three first production genes, indicated by the three interconnected horizontal bars with different hachures on top of the circles, each of which is under the control of a different inducible promoter. The cyanobacterial cell maintains multiple copies of the vector. The large oval in the cyanobacterial cell indicates the bacterial chromosome (CH), whereas the smaller ovals indicate endogenous plasmids EP). FIG. 2A shows the cyanobacterial cell prior to, or at the beginning of, the cultivation. Upon induction of the first inducible promoter for the first production gene, the corresponding first production genes are expressed and the cyanobacterial cell commences production of the first chemical compound. FIG. 2B shows the situation of the culture after long-term cultivation. Mutations (MT1) have accumulated in the first production genes that have been expressed, indicated by the X in the respective first small horizontal bar depicting the first production genes, consequently leading to a decrease of the productivity of the cyanobacterial culture, as revealed by culture monitoring. At this stage, the second inducible promoter for the second of the first production genes is induced, driving the expression of the second of the first production genes, thus leading to a recovery of the production of the first chemical compound. FIG. 2C depicts the final phase of this example. Mutations (MT2) have now also accumulated in the second of the first production genes, indicated by the X in the respective second small horizontal bar depicting the second first production genes, and the third inducible promoter of the first production gene is now induced in order to recover the production of the first chemical compound. Note that the figures serve illustrative purposes only. It is for example evident to those skilled in the art that the production genes of FIG. 2 could also be harbored by a bacterial chromosome (CH) or one or more endogenous plasmids (EP). Furthermore, said different versions of the first production genes of FIG. 2 could, for instance, be different operons instead, each comprising a first and a second production gene which are operably linked and under the transcriptional control of a single promoter driving the expression of the respective operon. In some embodiments, the at least one second production gene is located on a different genetic element, distinct from the genetic element harboring the first production genes. For instance, the first production genes are co-located on a vector, whereas the at least one second production gene is located on a bacterial chromosome. In another example, the first production genes are co-located on an endogenous plasmid. In yet another example, the first production genes are co-located on a bacterial chromosome. In a typical cyanobacterial cell, a plurality of said genetic elements is present. In certain preferred embodiments, the at least one second production gene is also co-located with the first production genes on the same genetic element. In a related embodiment, said genetic element comprises at least one first production gene which is operably linked with a second production gene and wherein the first and second production gene are under the transcriptional control of one single first promoter to form an operon. In another example, the genetic element comprises one first operon under the transcriptional control of a first promoter and at least one second operon under the transcriptional control of a second inducible promoter. In another embodiment, the genetic element comprises at least one further third operon under the transcriptional control of a third inducible promoter.

Figure 3:
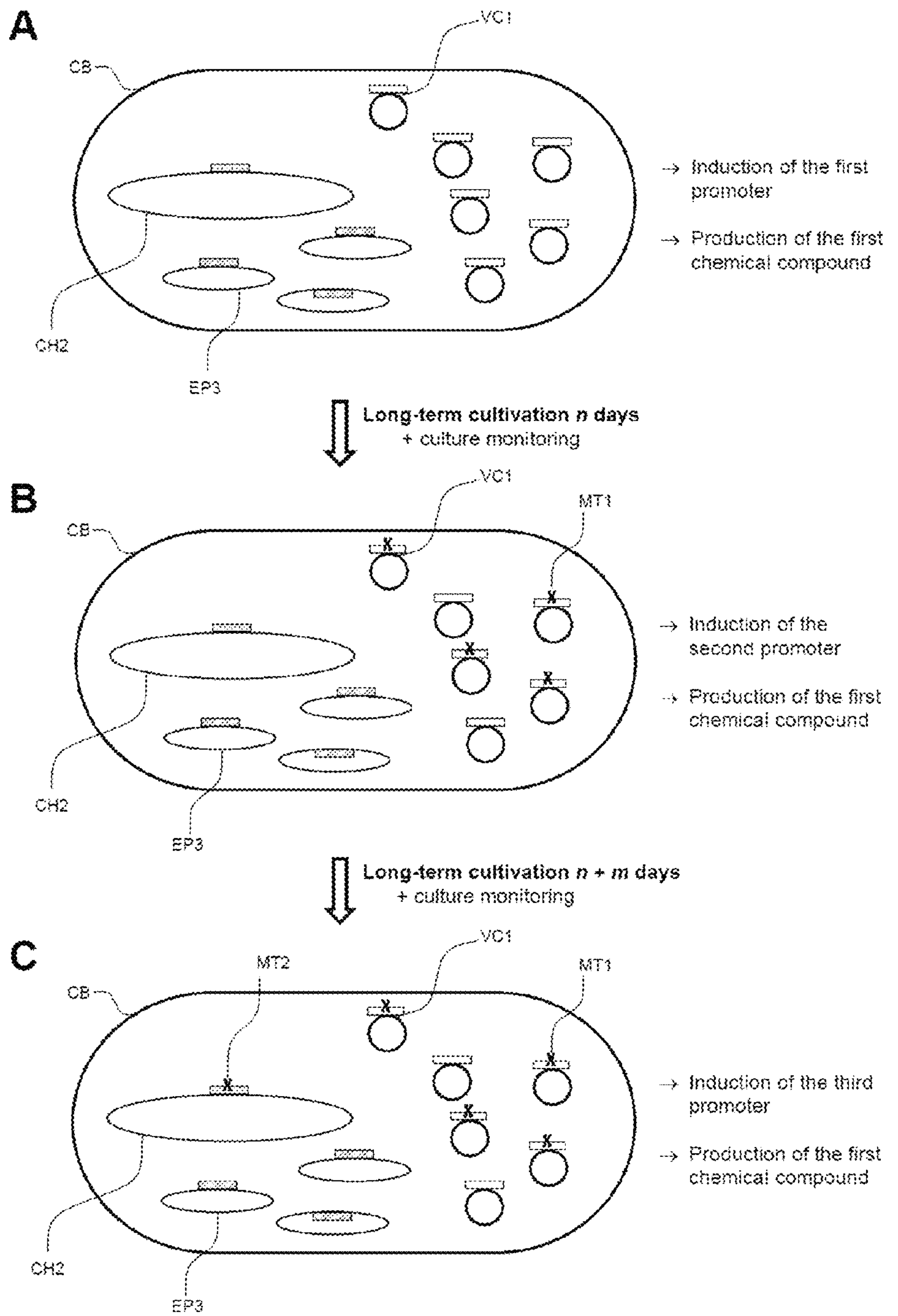

In other variants of the invention, said first production genes are located on different genetic elements (FIG. 3). For instance, a metabolically enhanced cyanobacterium (CB) comprises multiple identical copies of a self-replicating vector (VC1), indicated by the circles, harboring a first production gene under the control of the first inducible promoter for the first production gene, indicated by the horizontal bar on top of the circles. The cell has been further transformed with a second first production gene under the transcriptional control of the second inducible promoter for the first production which has been recombined into the bacterial chromosome (CH2), indicated by the horizontal bar on top of the large oval; and a third first production gene under the transcriptional control of the third inducible promoter for the first production gene which has been recombined into several copies of an endogenous plasmid (EP3), indicated by the horizontal bars on top of the small ovals. FIG. 3A shows the metabolically enhanced cyanobacterial strain prior to, or at the start of, the cultivation. Upon induction of the first promoter, the first production gene is expressed, which is in this case located on the vectors (VC1), and the bacterial culture commences production of the first chemical compound. After a certain period of time (FIG. 3B), mutations (MT1) have accumulated in the first production genes driven by the first promoter for the first production genes, indicated by the X, as determined by continuous culture monitoring, thus leading to a decrease of the production of the first chemical compound. In this phase, the second promoter is initiated, driving the expression of the alternative second first production gene on the bacterial chromosome (CH2), thus leading to a recovery of the production of the first chemical compound. In the course of further long-term cultivation (FIG. 3C), mutations (MT2) also accumulate in the second first production gene on the bacterial chromosome, indicated by the X, which is detected by continuous culture monitoring. A final cultivation phase is then initiated by inducing the third promoter for the third first production gene driving the expression of the first production genes located on the endogenous plasmids (EP3). In related embodiments, the at least one second production gene can be either co-located with one or more of the first production genes, or distinct from the first production genes on one or more different genetic element. Said genetic elements are selected from a group comprising a vector, an endogenous plasmid or a bacterial chromosome and combinations thereof. The metabolically enhanced cyanobacterium can comprise multiple copies of one or more of said genetic elements, thus increasing the gene dosage of the first and/or second production genes. In one example, at least one first production gene and one second production gene are operably linked and are under the transcriptional control of one single first inducible promoter to form a first operon. In certain preferred examples, the metabolically enhanced cyanobacterium comprises two or more of said operons, each of which is under the transcriptional control of a different inducible promoter, and wherein said operons are located on different genetic elements. For instance, a first operon is located on a vector, a second operon is located on an endogenous plasmid, and a third operon is located on the bacterial chromosome. In certain examples, the copy number of said operons is increased due to the presence of multiple copies of said genetic elements. The inventors discovered that the genetic stability of a metabolically enhanced cyanobacterium, comprising first production genes that are located on different genetic elements is improved so that cyanobacterial hybrid strains according to the embodiments above allow for a particularly prolonged production of the first chemical compound.

In yet another preferred embodiment, the metabolically enhanced cyanobacterium comprises combinations of first production genes that are co-located on the same genetic element as well as first production genes that located on different genetic elements. For example, the cyanobacterium can comprise two first production genes that are located on the same genetic element, e.g. multiple identical copies of a self-replicating plasmid, and at least a further third first production gene that is located on a different genetic element, e.g. integrated into endogenous plasmids or bacterial chromosomes, as well as combinations thereof if more than a third first production gene is present. As another example, the cyanobacterium comprises two first production genes that are co-located on endogenous plasmids and at least a further third first production gene that is located on the bacterial chromosomes or on a self-replicating plasmid, as well as combinations thereof if more than a third first production gene is present. Likewise, the at least one second production gene can be co-located with at least one of the first production genes, or be located on different genetic elements, as well as combinations thereof if more than one second production gene is present. The inventors found these embodiments are also particularly suitable to counteract genetic instability as well as intramolecular and intermolecular recombination of the production genes compared to the co-location of all first production genes, and thus aid prolonged production of the first chemical compound.

Preferred vectors for the transformation of cyanobacteria comprise for instance self-replicating broad-host range vectors based on RSF1010, such as pVZ and pDAG vectors. In some examples, vectors based on pDU1 can be advantageous. Preferred genetic elements for integration of first and second production genes are for instance the chromosome, and the endogenous cyanobacterial plasmids.

In some preferred embodiments, at least one first production gene is located on at least one type of endogenous plasmid present in cyanobacterial host cells. For instance, in *Synechococcus* sp. PCC 7002 the inventors found that particularly productive and genetically stable hybrid strains could be produced if at least one of the plasmids pAQ1, pAQ3, pAQ4, pAQ5, pAQ6 and/or pAQ7 was implemented as genetic element to harbor at least one first production gene and/or second production gene. In certain preferred examples, the endogenous plasmids comprise the pAQ4 plasmid, the pAQ3 plasmid and/or the pAQ1 plasmid. In some favourable embodiments, the endogenous plasmid comprises the pAQ4 plasmid. The inventors specifically created a novel integration site for homologous recombination of production genes into pAQ4 (FIG. 4 left). They designed two regions of homology, pAQ4-FA and pAQ4-FB, flanking the respective genetic construct, which recombine with homologous regions in pAQ4 between gene loci SYNPCC7002_D0017 (hypothetical protein, 237 nt, 78 aa) and SYNPCC7002_D0018 (CRISPR-associated protein Cas2, 294 nt, 97 aa). The inventors found particularly good production characteristics of *Synechococcus* sp. PCC 7002 strains which were metabolically enhanced in this way. In yet other favourable embodiments, the endogenous plasmid comprises the pAQ3 plasmid. The inventors implemented a method described by Xu and colleagues (2011) for homologous recombination of production genes into pAQ3 (FIG. 4 right) and found particularly good production characteristics of *Synechococcus* sp. PCC 7002 strains which were metabolically enhanced in this way. In yet other favourable embodiments, the endogenous plasmid comprises the pAQ1 plasmid. The inventors modified a method described by Xu and colleagues (2011), to accomplish an improved homologous recombination of production genes into pAQ1 between gene loci SYNPCC7002_B0001 and SYNPCC7002_B0002 (FIG. 5), which leads only to a minor deletion of 57 bp in the plasmid. *Synechococcus* sp. PCC 7002 strains metabolically enhanced in this way exhibited particularly good production characteristics. In certain related instances, the inventors discovered that the implementation of more than one type of these endogenous plasmids as a carrier for the production gene(s) in the same strain resulted metabolically enhanced hybrid strains with unexpectedly good production properties. For example, a combination comprising the pAQ4 plasmid harboring at least one first production gene with the pAQ3 plasmid harboring at least one further first production gene, in addition to at least one additional genetic element harboring at least one further first production gene, e.g. a self-replicating plasmid, pAQ1 plasmid and/or bacterial chromosome, resulted in *Synechococcus* sp. PCC 7002 hybrid strains with particularly good production characteristics.

Likewise, the inventors found for *Synechocystis* sp. PCC 6803 that particularly productive and genetically stable hybrid strains could be produced if at least one type of endogenous plasmid was implemented as genetic element to harbor at least one first production gene and/or second production gene. In certain preferred examples, the endogenous plasmids comprise the pSYSG plasmid endogenous to *Synechocystis* sp. PCC 6803. For example, the inventors found that metabolically enhanced *Synechocystis* sp. PCC 6803 comprising the pSYSG plasmid harboring at least one first production gene in addition to at least one additional genetic element harboring at least one further first production gene, e.g. a self-replicating plasmid and/or bacterial chromosome, resulted in hybrid strains with particularly good production characteristics.

In a preferred embodiment, the first biocatalysts and the second biocatalysts are ethanologenic enzymes. For instance, the first production genes encode a pyruvate decarboxylase enzyme catalyzing the reaction from pyruvate to acetaldehyde. In another example, the first production genes encode an AdhE enzyme (alcohol dehydrogenase E) which directly converts acetyl coenzyme A to ethanol. If the first production genes encode an AdhE enzyme, only the first production genes encoding first biocatalysts are required to produce ethanol. In another example, the second production gene encodes an Adh enzyme (alcohol dehydrogenase), catalyzing the reaction from acetaldehyde to ethanol. For instance, the pyruvate decarboxylase enzyme as first biocatalyst catalyzes the conversion of pyruvate to acetaldehyde, whereas the alcohol dehydrogenase Adh enzyme as second biocatalyst catalyzes the further conversion of acetaldehyde to the final first chemical compound ethanol.

Regarding the nucleic acid sequences, protein sequences and properties of these above-mentioned ethanologenic enzymes, reference is made to the PCT patent application WO 2009/098089 A2, which is incorporated for this purpose.

The pyruvate decarboxylase can, for example, be from *Zymomonas mobilis, Zymobacter palmae, Sarcina ventriculi* or the yeasts *Saccharomyces cerevisiae, Pichia pastoris* and *Klyveromyces lactis*. Moreover, pdc enzymes of plant origin like *Populus deltroides, Ipomea batatas* or *Zea mays* and pdc enzymes from other host species capable of expression in cyanobacteria can be used.

The Adh enzyme can, for example, be the Adh enzyme from *Synechocystis* sp. PCC 6803 (SynAdh), a $Zn^{2+}$ dependent alcohol dehydrogenase such as AdhI from *Zymomonas mobilis* (ZmAdh), or the Adh from other cyanobacteria. Alternatively or in addition, the enzyme can also be an iron-independent alcohol dehydrogenase (for example AdhII from *Zymomonas mobilis*). Both native and degenerated Adh enzymes can be used. Degenerated enzymes denote enzymes encoded by gene sequences which have been altered without changing the encoded amino acid sequence. Degenerated gene sequences include for instance changes in the wobble bases in the triplet codon which do not change the amino acid encoded by this triplet. The $Zn^{2+}$ dependent alcohol dehydrogenase can, for example, be an alcohol dehydrogenase enzyme having at least 60%, 70%, preferably 80% and most preferred 90% or even more than 90% sequence identity to the amino acid sequence of $Zn^{2+}$ dependent *Synechocystis* Adh.

Experiments have shown that in particular *Synechocystis* alcohol dehydrogenase (slr1192) is able to ensure a high ethanol production in metabolically enhanced cyanobacteria due to the fact that the forward reaction, the reduction of acetaldehyde to ethanol is much more preferred for *Synechocystis* alcohol dehydrogenase enzyme than the unwanted back reaction from ethanol to acetaldehyde. In certain other embodiments, other alcohol dehydrogenase enzymes from other host species can be used that are capable of expression in cyanobacteria.

The AdhE is an iron-dependent, bifunctional enzyme containing a CoA-depending aldehyde dehydrogenase and an alcohol dehydrogenase activity. One characteristic of iron-dependent alcohol dehydrogenases (for example AdhE and AdhII) is the sensitivity to oxygen. In the case of the AdhE from *E. coli* a mutant was described that shows in contrast to the wild type also Adh activity under aerobic conditions. The site of the mutation was determined in the coding region at the codon position 568. The G-to-A nucleotide transition in this codon results in an amino acid exchange from glutamic acid to lysine (E568K). The E568K derivative of the *E. coli* AdhE is active both aerobically and anaerobically (Holland-Staley et al., Aerobic Activity of *Escherichia coli* Alcohol Dehydrogenase is determined by a single amino acid, J Bacteriology 2000, 182, 6049-54). Adh enzymes directly converting acetyl coenzyme A to ethanol can preferably be from a thermophilic source thereby conferring an enhanced degree of stability. The AdhE can be from *Thermosynechococchus elongatus* BP-1 or also can be a non-thermophilic AdhE enzyme from *E. coli.*

The invention further provides biocatalysts catalyzing the same chemical reaction which are encoded by non-identical gene sequences. By this means, multiple versions of e.g. first production genes can be transformed into the cyanobacterial host cell, yet reducing the genes' risk of inactivation via homologous recombination after genetic alterations have occurred in some of these genes. In a related embodiment, such non-identical gene sequences share less than 80%, less than 70%, less than 60% or less than 50% sequence identity, or combinations thereof. Such non-identical sequences comprise, for instance, enzyme isoforms, gene sequences comprising conservative mutations, degenerated sequences comprising codon usage bias based on tRNA wobble bases, and combinations thereof. For example, enzyme isoforms of the first biocatalyst can comprise a pyruvate decarboxylase from *Zymomonas mobilis*, a second pyruvate decarboxylase from *Zymobacter palmae*, and a third pyruvate decarboxylase of the yeast *Saccharomyces cerevisiae*. Non-identical gene sequences comprising conservative mutations denote DNA or RNA sequences wherein a change in the nucleotide sequence leads to the replacement of one amino acid with a biochemically similar one, for instance a glutamic acid for an aspartic acid or an isoleucine for a valine. Gene sequences which are degenerated in order to reduce the risk of homologous recombination include in particular changes in the wobble bases in the triplet codon for the amino acids of the protein encoded by these genes which do not change the amino acid encoded by this triplet (Table 1). For instance, a specific nucleotide in the triplet can be replaced by another nucleotide so that the base triplet still codes for the same amino acid in the first or second biocatalysts. In this context, the term "SynADHdeg" denotes a degenerated DNA sequence having a sequence identity of 61% to the wild type *Synechocystis* adh gene coding for the *Synechocystis* sp. PCC 6803 alcohol dehydrogenase enzyme, the terms "zmPDCdeg" and "zpPDCdeg" denote degenerated DNA sequences having a sequence identity of 63.6% and 64.8% to the wild type *Zymomonas mobilis* pdc and *Zymobacter palmae* pdc, respectively. In other embodiments, the biocatalysts catalyzing the same chemical reaction can also be encoded by identical gene sequences.

TABLE 1

Codon usage of *Synechocystis* sp. PCC 6803 implemented to generate degenerated and/or codon-optimised gene sequences encoding the first or second production genes.

| UUU | Phe | .60 | 29 | UCU | Ser | .19 | 11 | UAU | Tyr | .45 | 12 | UGU | Cys | .57 | 5 |
|---|---|---|---|---|---|---|---|---|---|---|---|---|---|---|---|
| UUC | Phe | .40 | 19 | UCC | Ser | .37 | 22 | UAC | Tyr | .55 | 2 | UGC | Cys | .43 | 4 |
| UUA | Leu | .16 | 17 | UCA | Ser | .05 | 3 | UAA | END | .36 | 2 | UGA | END | .24 | 1 |
| UUG | Leu | .30 | 33 | UCG | Ser | .06 | 3 | UAG | END | .40 | 2 | UGG | Trp | 1.00 | 15 |
| CUU | Leu | .10 | 11 | CCU | Pro | .18 | 9 | CAU | His | .39 | 7 | CGU | Arg | .24 | 11 |
| CUC | Leu | .16 | 18 | CCC | Pro | .52 | 26 | CAC | His | .61 | 11 | CGC | Arg | .23 | 10 |
| CUA | Leu | .09 | 10 | CCA | Pro | .10 | 5 | CAA | Gln | .58 | 23 | CGA | Arg | .07 | 3 |
| CUG | Leu | .20 | 22 | CCG | Pro | .19 | 10 | CAG | Gln | .42 | 17 | CGG | Arg | .30 | 14 |
| AUU | Ile | .60 | 40 | ACU | Thr | .21 | 12 | AAU | Asn | .46 | 16 | AGU | Ser | .17 | 10 |
| AUC | Ile | .36 | 24 | ACC | Thr | .55 | 32 | AAC | Asn | .54 | 18 | AGC | Ser | .17 | 10 |
| AUA | Ile | .04 | 2 | ACA | Thr | .09 | 5 | AAA | Lys | .68 | 28 | AGA | Arg | .07 | 3 |
| AUG | Met | 1.00 | 27 | ACG | Thr | .14 | 8 | AAG | Lys | .32 | 13 | AGG | Arg | .09 | 4 |
| GUU | Val | .26 | 20 | GCU | Ala | .31 | 30 | GAU | Asp | .60 | 25 | GGU | Gly | .38 | 29 |
| GUC | Val | .18 | 14 | GCC | Ala | .44 | 43 | GAC | Asp | .40 | 17 | GGC | Gly | .28 | 21 |
| GUA | Val | .17 | 13 | GCA | Ala | .10 | 10 | GAA | Glu | .75 | 41 | GGA | Gly | .14 | 11 |
| GUG | Val | .39 | 30 | GCG | Ala | .15 | 15 | GAG | Glu | .25 | 14 | GGG | Gly | .20 | 15 |

A variety of suitable cyanobacterial host organisms can be metabolically enhanced to produce the first chemical compound according to the principles of the invention. In preferred embodiments, suitable cyanobacteria include but are not limited to genera of the group comprising *Synechocystis, Synechococcus, Anabaena, Chroococcidiopsis, Chlorogloeopsis, Cyanothece, Lyngbya, Phormidium, Nostoc, Spirulina, Arthrospira, Trichodesmium, Leptolyngbya, Plectonema, Myxosarcina, Pleurocapsa, Oscillatoria, Pseudanabaena. Cyanobacterium, Geitlerinema, Euhalothece, Calothrix, Scytonema*. In more preferred embodiments, the cyanobacterial host organisms comprise *Synechococcus* sp. PCC 7002 and other *Synechococcus* strains, *Synechocystis* sp. PCC 6803 strains, *Chlorogloeopsis* strains, and *Chroococcidiopsis* strains. In particularly preferred embodiments, the cyanobacterial host organisms comprise *Synechococcus* sp. PCC 7002 strains and *Synechocystis* sp. PCC 6803 strains.

A variety of suitable inducible promoters and promoter combinations are devised within the invention. Certain aspects and preferred embodiments of the invention require orthogonally inducible promoters in order to allow for the separate, sequential induction of the expression of the corresponding promoter-controlled first and/or second production genes by means of a change in the cultivation conditions. In some embodiments, rather than being orthogonally inducible, the different inducible promoters are inducible by the same inductor, but require inductor concentrations which are so different that the different promoters can be separately induced. Preferably, the induction conditions for different inducible promoters are so different from each other that a cross-induction is minimized or ideally eliminated. For instance, a first and second promoter that are separately inducible under different conditions means that whilst the first promoter is induced, the second promoter is maintained in an uninduced state, i.e. only less than or equal to 20%, preferably less than or equal to 15%, more preferably less than or equal to 10%, most preferred less than or equal to 5% of the first chemical compound per $OD_{750\ nm}$ of the cyanobacteria are produced via the corresponding uninduced gene compared to the induced state of the second promoter. The inventors discovered that with such a tight control of the expression of production genes which direct the metabolic flux away from the wild type cyanobacterial metabolism the genetic stability of the cyanobacterial hybrid strain can be greatly enhanced, thus enabling particularly long-termed production of the first chemical compound. The first and second promoters and/or further promoters can be inducible using different inductors such as different metal ions, different external stimuli such as heat, cold or light. In preferred embodiments, the inducible promoters are induced under conditions selected from a group comprising: by nutrient starvation, by stationary growth phase, by heat shock, by cold shock, by oxidative stress, by salt stress, by light, by darkness, by metal ions, by organic chemical compounds, and combinations thereof. For example, a particularly tight control of the expression of the first production genes can be achieved if these genes are under the transcriptional control of a Zn, Ni, or Co inducible promoter. In some preferred examples, the Co and Ni inducible promoters can be used for the transcriptional control of the first production genes if the cultivation of the cyanobacteria is done in mBG11 medium.

According to a further embodiment of the invention, the metabolically enhanced cyanobacteria can further comprise at least one recombinant regulator gene that is co-transformed with the corresponding inducible promoter, encoding a transcription factor such as a repressor or an activator binding to the inducible promoter in the case that the respective inducible promoter is heterologous to the metabolically enhanced cyanobacterium. For example, if a regulator gene codes for a repressor protein binding to the respective promoter in its uninduced state and said promoter is recombinantly introduced into a cyanobacterium as heterologous gene without the respective regulator gene, the promoter would be a constitutive promoter. Likewise, in the case that the recombinant regulator gene is an activator protein which binds to the respective promoter in the induced state and promotes binding of RNA polymerase to initiate transcription, these promoters would not be functional without the activator protein when they are heterologous to the metabolically enhanced cyanobacterium.

In certain preferred embodiments, the inducible promoters are selected from a group comprising: PntcA, PnblA, PisiA, PpetJ, PpetE, PggpS, PpsbA2, PpsaA, PsigB, PlrtA, PhtpG, PnirA, PnarB, PnrtA, PhspA, PclpB1, PhliB, PcrhC, PziaA, PsmtA, PcorT, PnrsB, PnrsB916, PaztA, PbmtA, Pbxa1, PzntA, PczrB, PnmtA. In certain other preferred embodiments, truncated or partially truncated versions of these promoters including only a small portion of the native promoters upstream of the transcription start point, such as the region ranging from −35 to the transcription start can often be used. Furthermore, introducing nucleotide changes into the promoter sequence, e.g. into the TATA box, the operator sequence, 5'-untranslated region and/or the ribosomal binding site (RBS) can be used to tailor or optimise the promoter strength and/or its induction conditions, e.g. the concentration of inductor required for induction. In some preferred variants, the different inducible promoters are inducible by different metal ions. For example, the first promoter for a first and/or second production gene can be the PpetE or PpetJ promoter, such that the induction occurs under copper-addition or copper-depletion. The second promoter for the first and/or second production gene can then be the $Zn^{2+}$-inducible promoter PziaA, PsmtA or PaztA. A further third promoter for the first and/or second production gene can be the $Co^{2+}$-inducible promoter PcorT. A further fourth promoter for the first and/or second production gene can be the $Ni^{2+}$-inducible promoter PnrsB.

In certain embodiments, the second production gene encodes a biocatalyst that does not affect the metabolic carbon flow of the cyanobacterial cell by its expression and therefore has no influence on the metabolic competition between cell growth and production of the chemical compound. Accordingly, genetic alterations in this gene do not provide a selection advantage and do not lead to overgrowing of the culture by corresponding revertants. For this reason, in some preferred embodiments, such second production genes can be put under the control of promoters different from the inducible promoters, for example constitutive promoters such as the Prbc promoter or an improved variant thereof. This promoter controls the transcription of the genes encoding the ribulose biphosphate carboxylase/oxygenase (rbcLXS genes: slr0009, slr0011 and slr0012), which is a constitutive and strong promoter. Similarly, also a third or further production gene encoding biocatalysts such as enzymes which catalyze metabolic reactions that do not affect the metabolic carbon flow of the cyanobacterial cell by their expression can be put under the control of a constitutive promoter. In some further examples, said second or further production gene can for instance encode a biocatalyst which catalyzes metabolic reactions already present in the wild type cyanobacterium.

Some preferred examples of metabolically enhanced cyanobacteria comprise a first production gene which is under the transcriptional control of the Zn-inducible promoter PziaA or the Zn-inducible promoter PsmtA, a second first production gene under the transcriptional control of the nickel-inducible promoter PnrsB and a third first production gene under the transcriptional control of the cobalt-inducible promoter PcorT, whereas the second production gene is under the transcriptional control of the constitutive Prbc promoter or an improved variant thereof.

In other preferred examples, the metabolically enhanced cyanobacterium can comprise two or more first production genes under the transcriptional control of a first, second or further promoter, wherein the promoters are inducible by the same inductor, but wherein the concentration of inductor required for induction of the first promoter is different from the concentration of inductor required for induction of the second or further promoter, and the concentration of inductor required for induction of the second promoter is different from the concentration of inductor required for the further promoter. In typical examples, the concentration of inductor required for the induction of the first promoter is lower compared to the concentration of inductor required for induction of the second promoter, and the concentration of inductor required for the induction of the second promoter is lower compared to the concentration of inductor required for induction of the third promoter. In some other examples, wherein the promoter responds to a depletion of the corresponding inductor, the concentration of inductor required for the induction of the first promoter is higher compared to the concentration of inductor required for induction of the second promoter and the concentration of inductor required for the induction of the second promoter is higher compared to the concentration of inductor required for induction of the third promoter. According criteria can be applied to a fourth or further promoter. For instance, the first, second and a further third promoter are all Zn-inducible promoters, but the first promoter requires a concentration of 1-5 $\mu M$ $Zn^{2+}$ for induction, the second promoter requires a concentration of 5-10 $\mu M$ $Zn^{2+}$ for induction, and the third promoter requires a concentration of >10 $\mu M$ $Zn^{2+}$ for induction, such that these promoters can be used inventively using distinct concentrations of the same inductor for sequential induction of the first production genes. Suitable different promoters which require different concentrations of inductor could be for instance the Zn-inducible promoters PziaA, PsmtA and PaztA. Alternatively, modified variants of the same promoter could be used, for instance recombinantly modified versions of the Zn-inducible PziaA promoter, which have been tailored to respond to different concentrations of the inductor.

The first chemical compound according to the present invention can be selected for example from the group of alcohols, alkanes, polyhydroxyalkanoates, e.g. PHB, fatty acids, fatty acid esters, carboxylic acids, such as amino acids, terpenes and terpenoids, peptides, polyketides, hydrogen, alkaloids, lactams, such as pyrrolidone, alkenes and ethers, such as THF and combinations thereof. In a preferred variant the first chemical compound comprises a biofuel. In a further variant of the genetically enhanced cyanobacteria provided by the invention, the first chemical compound comprises a hydrocarbon-based biofuel which is selected from the group comprising ethanol, isobutanol, fatty acid esters, alkanols, alkenes and alkanes. In another preferred variant, the first chemical compound comprises ethanol. The first chemical compound can also comprise ethylene or isoprene.

Depending on the first valuable chemical compound to be produced, the respective first production genes encoding enzymes for the production of these first chemical compounds have to be introduced into the cyanobacteria. For example, if the first chemical compound is ethanol, the first production gene encoding enzymes for ethanol production can be Pdc enzymes catalyzing the reaction from pyruvate to acetaldehyde or an AdhE enzyme which directly converts acetyl coenzyme A to ethanol. The second production gene can for instance be an Adh enzyme catalyzing the conversion of acetaldehyde to the first chemical compound ethanol.

Two other alcohols which are relatively widespread are propanol and butanol. Similar to ethanol, they can be produced by fermentation processes. The following enzymes are involved in isopropanol fermentation and can be encoded first and/or second production genes according to the present invention: acetyl-CoA acetyltransferase (EC:2.3.1.9), acetyl-CoA:acetoacetyl-CoA transferase (EC:2.8.3.8), acetoacetate decarboxylase (EC:4.1.1.4) and isopropanol dehydrogenase (EC:1.1.1.80).

The following enzymes are involved in isobutanol fermentation and can constitute first and/or second production genes according to the present invention: acetolactate synthase (EC: 2.2.1.6), acetolactate reductoisomerase (EC:1.1.1.86), 2,3-dihydroxy-3-methyl-butanoate dehydratase (EC:4.2.1.9), -ketoisovalerate decarboxylase (EC:4.1.1.74), and alcohol dehydrogenase (EC:1.1.1.1).

In the case that ethylene is to be produced as a first chemical compound, the first production gene encodes an enzyme for ethylene formation, in particular the ethylene-forming enzyme 1-aminocyclopropane-1-carboxylate oxidase (EC 1.14.17.4), which catalyzes the last step of ethylene formation, the oxidation of 1-aminocyclopropane-1-carboxylic acid to ethylene. The substrate for the ethylene-forming enzyme is synthesized by the enzyme 1-aminocyclopropane-1-carboxylic acid synthase (EC 4.4.1.14) from the amino acid methionine.

If the first chemical compound is an isoprenoid such as isoprene, the first production gene encodes an enzyme such as isoprene synthase. Isoprene synthase (EC 4.2.3.27) catalyzes the chemical reaction from dimethylallyl diphosphate to isoprene and diphosphate.

Terpenes are a large and very diverse class of organic compounds, produced primarily by a wide variety of plants, particularly conifers. Terpenes are derived biosynthetically from units of isoprene and are major biosynthetic building blocks in nearly every living organism. For example, steroids are derivatives of the triterpene squalene. When terpenes are chemically modified, for instance by oxidation or rearrangement of the carbon skeleton, the resulting compounds are generally referred to as terpenoids. Terpenes and terpenoids are the primary constituents of the essential oils for many types of plants and flowers. Examples of biosynthetic enzymes are farnesyl pyrophosphate synthase (EC 2.5.1.1), which catalyzes the reaction of dimethylallylpyrophosphate and isopentenyl pryrophosphate yielding farnesyl pyrophosphate. Another example is geranylgeranyl pyrophosphate synthase (EC 2.5.1.29), which catalyzes the reaction between transfarnesyl diphosphate and isopentenyl diphosphate yielding diphosphate and geranylgeranyl diphosphate.

In the case that the first chemical compound is hydrogen, the first production genes can for example code for hydrogenase, an enzyme catalyzing the following reaction:

$$12H^{+}+12X_{reduced}\rightarrow 6H_2+12X_{oxidized},$$

wherein X is an electron carrier such as ferredoxin.

Another example of first chemical compounds are the so-called non-ribosomal peptides (NRP) and the polyketides (PK). These compounds are synthesized by plants, fungi and only a few bacteria such as actinomycetes, myxobacteria and cyanobacteria. They are a group of structurally diverse secondary metabolites and often possess bioactivities of high pharmacological relevance. Hybrids of non-ribosomal peptides and polyketides also exist, exhibiting both a peptide and a polyketide part. First production genes for the production of non-ribosomal peptides as the first chemical compounds are for example gene clusters encoding for non-ribosomal peptide synthetases (NRPS). NRPS are characteristic modular multidomain enzyme complexes encoded by modular non-ribosomal peptide synthetases gene clusters. Examples for non-ribosomal peptide synthetases are actinomycin synthetase and gramicidin synthetase.

In general there are two distinct groups of polyketides (PK), the reduced polyketides of type I, the so-called macrolides and the aromatic polyketides of type II. Type I polyketides are synthesized by modular polyketide synthases (PKS), which are characteristic modular multidomain enzyme complexes encoded by modular PKS gene clusters. Examples for first production genes for the production of type I polyketides are the rapamycin synthase gene cluster and the oleandomycin synthase gene cluster. One example for a first production gene for type II polyketides is the actinorhodin polyketide synthase gene cluster.

Examples for first production genes for the production of hybrids of polyketides and non-ribosomal peptides are the microcystin synthetase gene cluster, microginin synthetase gene cluster, myxothiazole synthetase gene cluster.

Further examples of first chemical compounds are alkaloids. Alkaloids are a compound group which is synthesized by plants. Alkaloids have highly complex chemical structures and pronounced pharmacological activities. An example for biosynthetic enzymes for alkaloids which can be encoded by first production genes for the production of the chemical compound according to the present invention is strictosidine synthase, which catalyzes the stereoselective Pictet-Spengler reaction of tryptamine and secologanin to form 3a(S)-strictosidine. The primary importance of strictosidine is not only its precursor role for the biosynthetic pathway of ajmaline but also because it initiates all pathways leading to the entire monoterpene indol alkaloid family. Another example of an enzyme encoded by a first production gene is strictosidine glucosidase from the ajmaline biosynthetic pathway. This enzyme is able to activate strictosidine by deglycosylation thus generating an aglycon. This aglycon of strictosidine is the precursor for more than 2,000 monoterpenoid indol alkaloids.

Further examples of enzymes encoded by first production genes are:

(R,S)-3'-hydroxy-N-methylcoclaurine 4'-O-methyltransferase (4'OMT) central to the biosynthesis of most tetrahydrobenzylisoquinolin-derived alkaloids;

Berberine bridge enzyme (BBE) specific to the sanguinarine pathway;

(R,S)-reticuline 7-O-methyltransferase (7OMT) specific to laudanosine formation;

Salutaridinol 7-O-acetyltransferase (SalAT) and codeinone reductase that lead to morphine.

Vitamins, as yet further examples of first chemical compounds, are organic compounds that are essential nutrients for certain organisms and act mainly as cofactors in enzymatic reactions but can also have further importance, e.g. as anti oxidants in case of vitamin C. Vitamin C can be synthesized via the L-Ascorbic acid (L-AA) biosynthetic pathway from D-glucose in plants. The following enzymes are involved in vitamin C synthesis and can be encoded by first and/or second production genes according to the present invention: Hexokinase, Glucose-6-phosphate isomerase, Mannose-6-phosphate isomerase, Phosphomannomutase, Mannose-1-phosphate guanylyltransferase, GDP-mannose-3,5-epimerase, GDP-L-galactose phosphorylase, L-Galactose 1-phosphate phosphatase, L-galactose dehydrogenase, L-galactono-1,4-lactone dehydrogenase.

Lactams, as another example of first chemical compounds, are cyclic amides wherein the prefixes indicate how many carbon atoms (apart from the carbonyl moiety) are present in the ring: β-lactam (2 carbon atoms outside the carbonyl, 4 ring atoms in total), γ-lactam (3 and 5), δ-lactam (4 and 6).

One example for a γ-lactam is pyrrolidone, a colorless liquid which is used in industrial settings as a high-boiling, non-corrosive, polar solvent for a wide variety of applications. It is also an intermediate in the manufacture of polymers such as polyvinylpyrrolidone and polypyrrolidone.

Yet another example of first chemical compounds according to the present invention are ethers, a class of organic compounds that contain an ether group—an oxygen atom connected to two alkyl or aryl groups—of general formula R—O—R. A well-known example is tetrahydrofuran (THF), a colorless, water-miscible organic liquid. This heterocyclic compound is one of the most polar ethers with a wide liquid range, it is a useful solvent. Its main use, however, is as a precursor to polymers.

One example for the natural occurring ethers are the divinyl ether oxylipins. The main enzymes involved in their biosynthesis are the lipoxygenase and especially the divinyl ether synthase.

Alkanes, also known as saturated hydrocarbons, are chemical compounds that consist only of the elements carbon and hydrogen (i.e., hydrocarbons), wherein these atoms are linked together exclusively by single bonds (i.e., they are saturated compounds). Each carbon atom must have 4 bonds (either C—H or C—C bonds), and each hydrogen atom must be joined to a carbon atom (H—C bonds). The simplest possible alkane is methane, CH4. There is no limit to the number of carbon atoms that can be linked together. Alkanes, observed throughout nature, are produced directly from fatty acid metabolites. A two-gene pathway widespread in cyanobacteria is responsible for alkane biosynthesis and can be included in the first and/or second production genes. An acyl-ACP reductase (EC: 1.3.1.9) converts a fatty acyl-ACP into a fatty aldehyde that is subsequently converted into an alkane/alkene by an aldehyde decarbonylase (EC:4.1.99.5.).

Further examples of the first chemical compound include biopolymers such as polyhydroxyalkanoates or PHAs which are linear polyesters produced in nature by bacterial fermentation of sugar or lipids. They are produced by the bacteria to store carbon and energy. The simplest and most commonly occurring form of PHA is the fermentative production of poly-3-hydroxybutyrate (P3HB), but many other polymers of this class are produced by a variety of organisms: these include poly-4-hydroxybutyrate (P4HB), polyhydroxyvalerate (PHV), polyhydroxyhexanoate (PHH), polyhydroxyoctanoate (PHO) and their copolymers. The main enzymes involved in PHA synthesis are as follows: For P3HB synthesis two molecules of acetyl-CoA were condensed by a β-ketothiolase (EC:2.3.1.9) to synthesize acetoacetyl-CoA, which is converted to (R)-3-hydroxybutyryl-CoA (3HBCoA) by NADPH-dependent acetoacetyl-CoA reductase (EC: 1.1.1.36). The 3HBCoA is subsequently polymerized by poly (3-hydroxyalkanoate) synthase (EC:2.3.1.-) and converted to (P3HB). These can be included in the first and/or second production genes according to the present invention.

About 100,000 metric tons of the natural fatty acids are consumed in the preparation of various fatty acid esters. The simple esters with lower chain alcohols (methyl-, ethyl-, n-propyl-, isopropyl-, and butyl esters) are used as emollients in cosmetics and other personal care products and as lubricants. Esters of fatty acids with more complex alcohols, such as sorbitol, ethylene glycol, diethylene glycol and polyethylene glycol are consumed in foods, personal care, paper, water treatment, metal working fluids, rolling oils and synthetic lubricants. Fatty acids are typically present in the raw materials used for the production of biodiesel. A fatty acid ester (FAE) can be created by a transesterification reaction between fats or fatty acids and alcohols. The molecules in biodiesel are primarily fatty acid methyl esters FAMEs, usually obtained from vegetable oils by transesterification with methanol. The esterification of the ethanol with the acyl moieties of coenzyme A thioesters of fatty acids can be realized enzymatically by an unspecific long-chain-alcohol 0-fatty-acyltransferase (EC 2.3.1.75) from *Acinetobacter baylyi* strain ADP1.

In preferred embodiments, the metabolically enhanced cyanobacteria allow for a long-term production of the first chemical compound of at least or more than 60 days.

Metabolically enhanced cyanobacteria according to some other embodiments of the present invention can also include another production pathway for a second chemical compound so that these cyanobacteria produce the first and the second chemical compound. The second chemical compound differs from the first chemical compound and can also be selected from the above mentioned chemicals.

The second aspect of the present invention is directed to a method for producing metabolically enhanced cyanobacteria according to the first aspect of the invention, comprising the following method steps:

a) Providing the following at least two transformable nucleic acid sequences:
   - said first production gene under the transcriptional control of said first promoter for the first production gene;
   - said first production gene under the transcriptional control of said second promoter for the first production gene;
b) Transforming said at least two transformable nucleic acid sequences into the cyanobacteria cells.

In some embodiments, the at least two transformable nucleic acid sequences are provided on one genetic construct which is transformed into the cyanobacterial cell. In other embodiments, the at least two transformable nucleic acid sequences are provided on different genetic constructs which are separately transformed into the cyanobacterial cell. In yet other embodiments, a third or further transformable nucleic acid sequence is provided, either on one genetic construct with at least one of said at least two transformable nucleic acid sequences, or as one or more separate genetic constructs, and is transformed into the cyanobacterial cell.

The laboratory procedures in cell culture, molecular cloning and nucleic acid chemistry which are required to provide a transformable nucleic acid sequence according to method step a) are those well-known and commonly employed in the art. The techniques and procedures are generally performed according to conventional methods in the art and various general references, see, for example: Molecular Cloning: A Laboratory Manual (Third Edition), Sambrook, J., et al. (2001) Cold Spring Harbor Laboratory Press; Current Protocols in Microbiology (2007) Edited by Coico, R, et al., John Wiley and Sons, Inc.; The Molecular Biology of Cyanobacteria (1994) Donald Bryant (Ed.), Springer Netherlands; which are hereby incorporated in their entirety.

A transformable nucleic acid sequence as used herein means a nucleotide sequence (DNA sequence) capable of directing expression of a particular nucleotide sequence in the cyanobacterial host cell. Nucleic acid sequences of interest can, for instance, be obtained from the GenBank database or derived from protein databases. The sequence information may, for instance, be used to amplify the nucleic acid sequence of interest from a host organism using the polymerase chain reaction (PCR) technique. Suitable primer pairs for the PCR can be designed on the basis of the available sequence information using design algorithms or design rules which are known to those skilled in the art. The design of the primers can also accommodate non-coding flanking sequences which can facilitate the cloning and expression of the nucleic acid sequence. For example, restriction endonuclease recognition sites can be incorporated into the primers to enable the specific ligation of the nucleic acid sequence into a cloning and/or expression vector. In addition, the design can incorporate nucleic acid sequences which facilitate the insertion of the genetic construct into genetic elements via homologous recombination. Alternatively, the nucleic acid sequences can be synthetically produced. In providing the nucleic acid sequence for transformation, additional features can be considered, for instance incorporating an optimized codon-usage for cyanobacteria, introducing conservative mutations, elimination of restriction sites, or incorporating degenerated nucleic acid sequences. The nucleic acid sequence may further be inserted into a suitable cloning or expression vehicle to provide the transformable genetic construct of method step a). To this end, the restriction sites incorporated into the design of the nucleic acid sequence are preferably designed to match appropriate restriction sites of the vehicle of choice. Alternatively, the nucleic acid sequences can for example also be inserted into vehicles by recombination, if their design incorporates a suitable recombination site and the vehicle of choice contains a cognate recombination site as well. Vehicles of choice may, for instance, be vectors suitable for amplification and/or expression in cyanobacterial cells. Such vectors may also be used to facilitate further cloning steps, shuttling between vector systems, expression of the inserted product in cyanobacterial host cells, or integration of the inserted product into the genome of the cyanobacterial host cell.

Numerous methods can be used to transform the transformable nucleic acid sequence into the cyanobacterial cells in method step b). For instance, the insertion of the genetic construct into the host cell can be accomplished by methods of direct uptake, conjugation or electroporation. According to the present invention, transforming the cyanobacteria cells means that the genetic construct may be maintained as a non-integrated, self-replicating vector, for example a plasmid, or alternatively may be integrated into the host cell genome, for instance an endogenous plasmid or a bacterial chromosome. Transformation by direct uptake is possible for several cyanobacterial species that are naturally competent, i.e. capable of transporting DNA across the cell membrane. For instance, *Synechocystis* sp. PCC6803, *Synechococcus elongatus* PCC 7942, *Synechococcus* sp. PCC 7002 and *Thermosynechococcus elongatus* BP-1 are naturally transformable. Alternatively, transformation of cyanobacterial cells can be accomplished by conjugation. For instance, transformation by conjugation has been successfully for *Anabaena* sp. PCC 7120, *Anabaena variabilis* ATCC 29413, *Nostoc punctiforme* ATCC 290133, *Nostoc* sp. PCC 7422, *Synecococcus* sp. MA19, *Synechococcus* sp. NKBG15041c, *Synechococcus leopoliensis* UTCC 100 and *Synechocystis* sp. PCC 6803. Cyanobacterial transformation has also been accomplished by electroporation, for instance of *Synechocystis* sp. PCC 6803. For laboratory references for these types of methodologies see, for example, A. M. Ruffing, Bioengineered Bugs 2011, 2, 136-149, and references cited therein, which are hereby incorporated in their entirety.

A selection marker is required to screen for successful transformation events. In a preferred embodiment, the transformable genetic construct therefore further comprises an individual selection marker which allows selection of positive transformants carrying said transformable genetic construct. In addition, since according to the present invention the cyanobacterial cells can comprise different transformed genetic constructs located on the same as well as different genetic elements, these transformable genetic constructs have to carry different selective markers to accordingly select positive transformation events with each genetic construct and each genetic element. In a preferred embodiment, the transformable genetic construct further comprises a ubiquitous selection marker, i.e. a selection marker which is common to all the different transformable genetic constructs transformed into the cyanobacterium. The ubiquitous selection marker allows for selection of positive transformants carrying any of said transformable genetic constructs. In a preferred embodiment, the method comprises the use of selection markers that are based on antibiotic resistance, selection markers independent of antibiotic resistance, as well as combinations thereof. A variety of antibiotic resistance cassettes can be used as selective markers with cyanobacteria, for instance ABR cassettes for ampicillin, kanamycin, neomycin, gentamycin, streptomycin, spectinomycin, chloramphenicol, erythromycin, zeozin. Antibiotic resistance-free systems comprise, for example, selection markers that confer prototrophy to an auxotrophic cyanobacterial strain, or confer resistance against certain heavy metal ions as cobalt or zinc.

In a third aspect of the present invention, the invention provides a method for producing a first chemical compound using a metabolically enhanced cyanobacterium comprising the method steps of:

A) Culturing the metabolically enhanced cyanobacterium under conditions for induction of the first promoter for the first production gene, the cyanobacterium producing the first chemical compound;

B) Culturing the metabolically enhanced cyanobacterium under conditions for induction of the second promoter for the first production gene, the cyanobacterium producing the first chemical compound;

wherein method step A) and method step B) are temporally separated;

wherein the second promoter for the first production gene of method step B) is maintained in an uninduced state during method step A).

Suitable growth media for cyanobacteria comprise, for instance, the BG11 medium, which can be prepared with fresh water (BG11), sea water (mBG11) or brackish water.

The recipe for the cyanobacterial growth medium mBG11 is as follows:

$NaNO_3$: 1.5 g
$K_2HPO_4$: 0.04 g
$MgSO_4.7H_2O$: 0.075 g
$CaCl_2.2H_2O$: 0.036 g
Citric acid: 0.006 g
Ferric ammonium citrate: 0.006 g
EDTA (disodium salt): 0.001 g
$NaCO_3$: 0.02 g
Trace metal mix A5: 1.0 ml
Distilled water: 1.0 L
(pH 7.1 adjusted after sterilization)

Herein, the recipe for the trace metal mix A5 is:

$H_3BO_3$: 2.86 g
$MnCl_2.4H_2O$: 1.81 g
*$ZnSO_4.7H_2O$: 0.222 g
$NaMoO_4.2H_2O$: 0.39 g
$CuSO_4.5H_2O$: 0.079 g
*$Co(NO_3)_2.6H_2O$: 49.4 mg
Distilled water or seawater (35 practical salinity units=psu; see Unesco (1981a).
The Practical Salinity Scale 1978 and the International Equation of State of Seawater 1980. *Tech. Pap. Mar. Sci.,* 36: 25 pp.): 1.0 L The asterisk (*) denotes those metal supplements that can be either omitted or used in reduced amounts if these metals are also used as inductor for corresponding metal-inducible promoters in the metabolically enhanced cyanobacterial strain.

Due to the first production genes being under the control of inducible promoters, the cyanobacteria can be grown to a high density prior to method step A) in the uninduced state, since the flux of fixed-carbon is not diverted from the cells' natural metabolism, i.e. cell growth. According to the present invention, the conditions for induction of the first promoter for the first production gene in method step A) can be, for instance, the depletion of copper, copper addition, the addition of $Zn^{2+}$, $Co^{2+}$ or $Ni^{2+}$ to the culture medium, iron starvation, nitrogen starvation, selected nitrogen sources in the medium, or any other suitable induction condition. In method step A), the cyanobacteria can for example be induced by adding at least 2 μM $Zn^{2+}$, $Co^{2+}$ or $Ni^{2+}$ to the growth medium. The concentration of the inducing agent in the growth medium for an induction of the promoters can be for instance between 5 μM and 20 μM. The high cell density of the cyanobacterial culture together with the strength of the inducible promoter allows for a high production rate of the first chemical compound during method step A). If for example a drop in the production rate of the first chemical compound during method step A) is registered, method step B) is initiated by a change in the cultivation conditions, so that the second promoter for the first production gene is induced. Typically, induction of method step B) leads to a recovery of the production of the first chemical compound.

According to the teaching of the present invention, a fundamental feature of the method is that the method step A) and method step B) are temporally separated. This means that the method steps are sequentially initiated during the method for producing the first chemical compound by a change of cultivation conditions for selective induction of the first and second promoter for the first production gene. In this sense, method step B) is initiated after method step A). However, it is possible that during method step B) the conditions for induction of the first promoter for the first production gene of method step A) are maintained. For instance, if a $Zn^{2+}$ salt was added for induction of the first promoter for the first production gene in method step A), it is not required that this $Zn^{2+}$ salt is removed from the cultivation medium in method step B). The temporal separation of method steps A) and B) only requires that the second promoter for the first production gene of method step B) is maintained in an uninduced state during method step A). The inventors found that under these conditions the likelihood of reverted non-producing cells that can enrich and finally overgrow non-reverted producing cells is reduced, thereby enabling the long-term production of the first chemical compound according to the principle of the invention by a temporarily separated sequential induction of production genes encoding biocatalysts catalyzing the same reaction for the production of the first chemical compound.

In a preferred embodiment, the method comprises at least one further method step C) of culturing the metabolically enhanced cyanobacterium under conditions for induction of at least one further third promoter for the first production gene, the cyanobacterium producing the first chemical compound; wherein method step A), method step B) and method step C) are temporally separated from each other; wherein the third promoter for the first production gene of method step C) is maintained in an uninduced state during method steps A) and B). It is evident to those skilled in the art that the method provided by the invention can also comprise additional method steps which can be easily derived following the same principles as detailed for method steps A), B) and C).

In certain preferred embodiments, method steps A), B) and—if present—C) and further method steps comprise the expression of the at least one second production gene encoding the second biocatalyst for the production of the first chemical compound. The expression of the at least one second production gene in the respective method step can be controlled by an inducible promoter or can be constitutive. In preferred embodiments, the method steps comprise the constitutive expression of the at least one second production gene. For example, the inventors discovered that if the second biocatalyst catalyzes a reaction that does not affect the metabolic carbon flow of the cyanobacterial cell and therefore has no influence on the metabolic competition between cell growth and production of the chemical compound, the genetic pressure on the second production encoding the second biocatalyst is significantly lower compared to the genetic pressure on the first production gene encoding a biocatalyst that separates the carbon flux from the cell growth and biomass accumulation, respectively. Accordingly, genetic alterations in this gene do not provide a selection advantage and do not lead to overgrowing of the culture by corresponding revertants. According to this preferred embodiment, the second production gene can for instance encode an alcohol dehydrogenase, whereas the first production genes encode a pyruvate decarboxylase enzyme, in the case the first chemical compound is ethanol.

In certain embodiments, wherein the at least one second production gene is under the transcriptional control of the first, second or further promoter for the second production gene, also the first promoter for the second production gene is induced in method step A). In a related preferred embodiment, also the second promoter for the second production gene is induced in method step B). In yet another preferred embodiment, at least a further third promoter for the second production gene is induced in at least one further method step C). Herein, the second promoter for the second production gene of method step B) is maintained in an uninduced state during method step A), and the third promoter for the second production gene of method step C) is maintained in an uninduced state during method steps A) and B).

The simultaneous induction of the first, second and—if present—third or further promoters for the first and second production gene can be realized in different ways. For instance, the first, second and, if present, third promoter or further promoter for the first and second production gene, are either the same promoters or are promoters which are inducible under the same conditions. For instance, the first promoter for the first production gene is the zinc-inducible promoter PziaA, whereas the first promoter for the second production gene is the zinc-inducible promoter PsmtA, and the cultivation conditions in method step A) comprise a zinc concentration which is sufficient to induce both the first promoter for the first production gene and the first promoter for the second production gene. In yet another preferred embodiment, the promoters for the first and second production gene are the same promoters, for instance the first promoter for the first production gene and the first promoter for the second production gene are both the zinc-inducible promoter PziaA or the zinc-inducible promoter PsmtA. In certain preferred embodiments, both the first production genes and the second production genes of method step A) and/or method step B) and/or method step C) are transcriptionally controlled by the same single promoter. According to this embodiment, the first production gene and second production gene of the respective method step are operably linked and under the control of the same single promoter to form a functional operon. For example, a first production gene and a second production gene of a particular method step are operably linked in an operon and are co-ordinately expressed by induction of a single promoter which could be, for instance, a zinc-inducible promoter PziaA.

In a preferred embodiment of the method the metabolically enhanced cyanobacteria are subjected to sunlight and $CO_2$ during method steps A), B) and, if present, during method step C) and further method steps. Cyanobacteria are photoautotrophic prokaryotes that perform oxygen photosynthesis. The cyanobacteria interconnect atmospheric levels of carbon dioxide through photosynthesis according to the following generic equation:

$$CO_2+H_2O\rightarrow(CH_2O)_n+O_2.$$

Herein, (CH2O)n represents organic matter with fixed carbon that is fed into the metabolic pathways of the cyanobacteria and can subsequently be also converted into the first chemical compound.

In a preferred embodiment of the method, culture monitoring is applied during the method steps. For example, the culturing conditions of method step A) are maintained for a period of time and/or until monitoring indicates a threshold productivity decrease of the first chemical compound, before the next method step B) is initiated. In another preferred embodiment, the culturing conditions of method step B) are maintained for a period of time and/or until monitoring indicates a threshold productivity decrease of the first chemical compound, before the next method step C) is initiated. Furthermore, it is evident to those skilled in the art that the same procedural method can be applied to further additional method steps according to the same rules specified above. In a preferred embodiment, the monitoring of the cyanobacterial culture is selected from at least one method of the group comprising: biocatalyst activity tests, determining of the concentration of the first chemical compound in the growth medium and/or in the space above the growth medium, gene expression analysis on mRNA and/or protein level, detection of mutations e.g. by enzymatic mismatch detection using a mismatch-specific DNA endonuclease (CEL-I) from celery rods as described by Qiu et al. (Qiu P, Shandilya H, D'Alessio J M, O'Connor K, Durocher J, Gerard G F.: Mutation detection using Surveyor nuclease, Biotechniques 36 (2004), 702-7), or by real-time PCR in combination with melting curve analysis and/or by sequencing, and combinations thereof. For example, biocatalysts activity tests comprise testing the enzymatic activity of the pyruvate decarboxylase enzyme when the first chemical compound is ethanol. Alternatively, the concentration of ethanol can be determined in the growth medium or in the space above the growth medium using gas chromatography. Furthermore, real-time PCR assays have proven to be a powerful tool for rapid monitoring of the genetic condition of cyanobacterial hybrid strains. For instance, amplification of a core sequence within the production gene in question, followed by melt curve analysis of the amplificates can provide qualitative information about the genetic integrity of the production genes. Suitable real-time PCR routines can be devised by those skilled in the art. For additional laboratory references, see, for example, Real-Time PCR in Microbiology: From Diagnosis to Characterization, by Ian M. Mackay (ed.), Caister Academic Press 2007.

A threshold productivity decrease according to the present invention can for example be indicated by stagnation of the content of the first chemical compound during cultivation; i.e. even though the culture might be still growing, the total concentration of the first chemical compound (e.g. ethanol) in the culture does not increase anymore. Alternatively, if for instance the content of the first chemical compound for three subsequent days increases 0.05% (v/v) or less, 0.03% (v/v) or less, 0.01% (v/v) or less compared to the content of the previous day, a threshold productivity decrease has set in. These values are exemplary only, because they can vary depending on the produced chemical compound, the bioreactor design and culture conditions, the scale and the cell density. A threshold productivity decrease according to the present invention can also be defined by decrease of the content of the first chemical compound during cultivation. A threshold productivity decrease as determined by biocatalyst activity tests can for example be constituted by a decrease in PDC activity of at least or under 0.5 $\mu$mol $min^{-1}$ me protein, at least or under 0.4 $\mu$mol $min^{-1}$ me protein, at least or under 0.3 $\mu$mol $min^{-1}$ me protein or at least or under 0.2 $\mu$mol $min^{-1}$ me protein. In the case that nucleic acid mismatches are determined as the means of culture monitoring, the next method step is initiated if for instance if at least or more than 10%, at least or more than 20%, or at least or more than 40% of the cyanobacterial population are reverted.

In a preferred embodiment of the method, the cyanobacterium is selected from a group comprising *Synechocystis, Synechococcus, Anabaena, Chroococcidiopsis, Chlorogloeopsis, Cyanothece, Lyngbya, Phormidium, Nostoc, Spirulina, Arthrospira, Trichodesmium, Leptolyngbya, Plectonema, Myxosarcina, Pleurocapsa, Oscillatoria, Pseudanabaena, Cyanobacterium, Geitlerinema, Euhalothece, Calothrix*. In more preferred embodiments, the cyanobacterial host organisms comprise *Synechococcus* sp. PCC 7002 and other *Synechococcus* strains, *Synechocystis* sp. PCC 6803 and other *Synechocystis* strains, *Chlorogloeopsis* strains, *Chroococcidiopsis* strains, and Cyanobacterium strains. In particularly preferred embodiments, the cyanobacterial host organisms comprise *Synechococcus* sp. PCC 7002 strains and *Synechocystis* sp. PCC 6803 strains.

In a fourth aspect of the invention, the invention provides a metabolically enhanced cyanobacterium for the production of a first chemical compound, comprising:

at least a first and second first production gene encoding first biocatalysts for the production of the first chemical compound;

wherein both first production genes are under the transcriptional control of the same inducible promoter for the first production genes;

wherein the inducible promoter for the first production genes is gradually inducible in a dose-dependent manner;

wherein said first biocatalysts catalyze the same chemical reaction.

According to this aspect of the invention, the use of the same inducible promoter for the first production genes allows for the first biocatalysts under the control of said promoter to be cumulatively expressed under the same induction conditions. Moreover, since said promoter for the first production genes is gradually inducible in a dose-dependent manner, the choice of induction conditions allows modulating the expression level of the first biocatalysts in an incrementing way. For example, conditions for induction can be employed that do not induce the full activity of the promoter but still lead to a cumulative expression level of the first biocatalysts that is suitable to produce the first chemical compound. Thus, the overall expression of the first biocatalysts remains high because all corresponding first production genes are expressed and the higher gene copy number compensates for the lower induction level. Hereupon, genetic alterations can occur in the corresponding first production genes. However, the inventors found that after genetic alterations occurred in one or more copies of the first production genes, the optimal expression level can yet be assured by a subsequent higher induction of the promoter for the first production genes that then increasedly drives the remaining non-altered copies of the first production genes.

The inventors concluded that in order to overcome the problem of production decays for the first chemical compound and to prolong the synthesis of the first chemical compound, the solution is a metabolically enhanced cyanobacterial strain, which comprises two or more first production genes which are transcriptionally driven by the same promoter, and wherein this promoter allows for a stepwise induction depending on the concentration of the inductor, thereby enabling the systematic modulation of the expression level of the first biocatalysts. At the same time, increasing the dose of the first production genes in conjunction with the cumulative expression of said genes, allows compensating the shortfall of expression of the first biocatalysts even though each individual of the first production gene might not be fully induced.

For example, the metabolically enhanced cyanobacterial strain can comprise two first production genes encoding first biocatalysts for the production of the first chemical compound that are under the transcriptional control of the corresponding gradually inducible promoter for the first production genes. Upon induction of the promoter, for instance to an induction level of approximately 50% compared to the full induction, the bacterial culture commences producing the first chemical compound. Upon loss of activity of the first biocatalysts following the accumulation of alterations in a statistical proportion of the first production genes, a full induction of the promoter follows to now use the full capacity of the available first production genes, i.e. to increase the chance of transcription of those gene copies which have not accumulated inactivating alterations yet and thus maintain an optimal expression level for production of the first chemical compound. In this way, a temporal extension of the production phase of the first chemical compound can be accomplished.

In preferred embodiments of the fourth aspect of the invention, the metabolically enhanced cyanobacterium comprises at least one further first production gene under the transcriptional control of the same inducible promoter for the first production genes. In this way, the accumulated expression level of the first production genes can be maintained sufficiently high under even lower starting doses of induction of the promoter. Consequently, this allows including additional discrete induction steps to further prolong the productive phase of the bacterial culture according to the principles detailed above. For example, an induction level of approximately 33% compared to the full induction at the start of the production of the first chemical compound, followed by an induction level of approximately 66%, and finally a full induction level towards the end of the production. It will be obvious from these teachings to those skilled in the art that additional first production genes can be included according to the present invention in order to be able to further reduce the starting dose of induction and/or to be able to include additional doses of induction, i.e. to choose smaller increments between the doses of different induction steps.

In certain preferred embodiments, the same single inducible promoter controls the transcription of the first production genes. For example, the first production genes are operably linked to form an operon, which is transcriptionally controlled by a single gradually inducible promoter.

In preferred embodiments, the gradually inducible promoter is chosen from a group comprising dose-dependent metal-ion inducible promoters.

In further variants of the fourth aspect of the invention, the metabolically enhanced cyanobacterium can further comprise any metabolic enhancement according to the first aspect of the invention. Furthermore, all independent and dependent claims 1-38 of the first aspect of the invention can also be applied to the claims of the fourth aspect of the invention. For example, a cyanobacterium comprising a first set of at least two first production genes according to the fourth aspect of the invention can further comprise a second or further set of first production genes according to the first aspect of the invention, i.e. each of said first, second or further set of first production genes is under the transcriptional control of (a) different gradually inducible promoter, such that each set is separately inducible under different conditions.

In a fifth aspect of the present invention, the invention provides a method for producing a first chemical compound using a metabolically enhanced cyanobacterium comprising the method steps of:

A1) Culturing the metabolically enhanced cyanobacterium under a first condition for induction of the promoter for the first production genes, the cyanobacterium producing the first chemical compound;

A2) Culturing the metabolically enhanced cyanobacterium under a second condition for induction of the promoter for the first production genes, the cyanobacterium producing the first chemical compound;

wherein method step A1) and method step A2) are temporally separated;

wherein the first condition for induction results in a lower induction of the promoter for the first production genes than the second condition of induction.

According to the present invention, a first fundamental feature of the method is that in method step A1) the first production genes are simultaneously expressed, but under conditions that effect only partial induction of the promoter for the first production genes. Thus, the expression level of each of the first biocatalysts alone is lower compared to conditions for full induction of the respective first production gene, but is compensated by the cumulative expression of the first production genes, so that suitable amounts of the first biocatalysts are produced for the production of the first chemical compound. A second fundamental feature of the method is that method step A1) and method step A2) are temporally separated, meaning that the method steps are sequentially initiated during the method for producing the first chemical compound. In this sense, method step A2) is initiated after method step A1). This is realized by a change of cultivation conditions, which are characterized by an increased promoter induction in method step A2) relatively compared to the promoter induction in method step A1). For instance, for dose-dependent gradually inducible promoters, the concentration of the inductor in the culture is different in method step A2) compared to method step A1) to accomplish a higher induction level. The higher induction level of the promoter in method step A2) consequently increases the transcription level of all first production genes, therefore also increasing the expression level of functional biocatalysts. This enables to counteract the loss of part of the first production genes as a result of their genetic alteration, and therefore to extend the productive phase of a culture of metabolically enhanced cyanobacteria according to the principle of the invention by means of a temporarily separated and sequentially increased induction of the promoter controlling the first production genes.

In preferred embodiments, the method comprises at least one further method step A3) of culturing the metabolically enhanced cyanobacterium under a third condition for induction of the promoter for the first production genes, the cyanobacterium producing the first chemical compound; wherein method step A1), method step A2) and method step A3) are temporally separated from each other and wherein the second condition for induction results in a lower induction of the promoter for the first production genes than the third condition of induction. In preferred embodiments, the addition of a third or further method steps can be balanced with the number of first production genes being simultaneously induced, i.e. also involve a third or further first production gene. In this way, the starting dose of induction of the gradually inducible promoter for the first production genes in method step A1) can be further reduced because the corresponding loss of expression is compensated by the higher number of the first production genes. Correspondingly, additional levels of induction, i.e. smaller increments of induction levels between consecutive method steps can be chosen. It is evident to those skilled in the art that the method provided by the invention can also comprise additional method steps which can be easily derived following the same principles as detailed for method steps A1), A2) and A3).

In a variant of the fifth aspect of the invention, the method comprises additional method steps according to the features of the third aspect of the invention. In preferred embodiments, the method steps A1), A2) and, if present, A3) or further method steps of the fifth aspect of the invention form substeps of method step A) of the third aspect of the invention. In related preferred embodiments, the steps A1), A2) and, if present, A3) or further method steps of the fifth aspect of the invention can be used inventively as substeps B1), B2) and, if present, B3) or further substep of method step B) of the third aspect of the invention.

For instance, a first set of first production genes under the transcriptional control of a gradually inducible promoter according to the fifth aspect of the invention can be used inventively to form substeps A1) to A3) of method step A) of the third aspect of the invention. When said first set of first production genes eventually becomes unproductive, a second set of first production genes under the transcriptional control of a different gradually inducible promoter according to the fifth aspect of the invention can be used inventively to form substeps B1) to B3) of method step B) of the third aspect of the invention. For this purpose, the gradually inducible promoter of said second set of first production genes of method step B) is separately inducible under different conditions compared to the gradually inducible promoter of said first set of first production genes of method step A). This variant allows for a particularly prolonged production of the first chemical compound, and can be extended to even further method steps following the principles detailed above.

In further variants of the fifth aspect of the invention, all the examples and embodiments of the method of the third aspect of the invention can also be applied to the method of the fifth aspect of the invention. Furthermore, all independent and dependent claims of the third aspect of the invention can also be applied to the claims of the fifth aspect of the invention.

Brief Description of the Nucleotide Sequences

In the following sequence descriptions, inducible promoters are denominated as "regulator gene-promoter sequence", as for example in "ziaR-PziaA", wherein ziaR denotes the regulator gene and PziaA denotes the promoter sequence of the zinc inducible promoter. In gene names, the term "deg" denotes degenerated versions of the corresponding wild type genes, and the terms "deg" and "fco" denote codon-degenerated and full-codon optimised versions, respectively, of the corresponding wild type genes. The asterisk (*) in promoter names denotes promoters with optimised ribosome binding site.

SEQ ID NO:1: Construct comprising zinc-inducible promoter ziaR-PziaA from *Synechocystis* PCC6803 (ziaR-sll0792, ziaA-slr0798) and SalI/EcoRI restriction sites.

SEQ ID NO:2: Construct comprising cobalt-inducible promoter corR-PcorT from *Synechocystis* PCC6803 (corR-sll0794, corT-slr0797) and SalI/EcoRI restriction sites.

SEQ ID NO:3: Construct comprising nickel-inducible promoter nrsRS-PnrsB from *Synechocystis* PCC6803 (nrsS-sll0798, nrsR-sll0797, nrsB-slr0793) and SalI/EcoRI restriction sites.

SEQ ID NO:4: Construct comprising zinc-inducible promoter smtB-PsmtA from *Synechococcus* PCC7002 (smtB-SYNPCC7002_A2564, smtA-SYNPCC7002_A2563) and SalI/EcoRI restriction sites.

SEQ ID NO:5: Forward primer ziaR/PziaA-SalI-fw for the amplification of the construct comprising the ziaR-PziaA promoter sequence (SEQ ID NO:1).

SEQ ID NO:6: Forward primer PziaA-SalI-fw for the amplification of the construct comprising the PziaA promoter sequence, i.e. without the ziaR regulator gene.

SEQ ID NO:7: Reverse primer PziaA-EcoRI-rev for the amplification of the construct comprising the comprising the ziaR-PziaA promoter sequence.

SEQ ID NO:8: Forward primer corR/PcorT-SalI-fw for the amplification of the construct comprising the corR-PcorT promoter sequence (SEQ ID NO:2).

SEQ ID NO:9: Reverse primer PcorT-EcoRI-rev for the amplification of the construct comprising the corR-PcorT promoter sequence.

SEQ ID NO:10: Forward primer nrsRS/PnrsB-SalI-fw for the amplification of the construct comprising the nrsRS-PnrsB promoter sequence (SEQ ID NO:3).

SEQ ID NO:11: Forward primer nrsR/PnrsB-SalI-fw for the amplification of the construct comprising the nrsR-PnrsB promoter sequence, i.e. without the nrsS regulator gene.

SEQ ID NO:12: Reverse primer PnrsB-EcoRI-rev for the amplification of the construct comprising the nrsRS-PnrsB promoter sequence.

SEQ ID NO:13: Forward primer smtB/PsmtA-SalI-fw for the amplification of the construct comprising the smtB-PsmtA promoter sequence (SEQ ID NO:4).

SEQ ID NO:14: Forward primer PsmtA-SalI-fw for the amplification of the construct comprising the PsmtA promoter sequence, i.e. without the smtB regulator gene.

SEQ ID NO:15: Reverse primer PsmtA-EcoRI-rev for the amplification of the construct comprising the smtB-PsmtA promoter sequence.

SEQ ID NO:16: Native PDC gene from *Zymomonas mobilis* (ZmPDC).

SEQ ID NO:17: Native PDC gene from *Zymobacter palmae* (ZpPDC).

SEQ ID NO:18: Codon-degenerated PDC gene from *Zymomonas mobilis* (ZmPDCdeg).

SEQ ID NO:19: Codon-degenerated PDC gene from *Zymobacter palmae* (ZpPDCdeg).

SEQ ID NO:20: Self-replicating broad host range vector pVZ322a with aph (KanR2), GmR and CmR antibiotic resistance cassettes. CmR is eliminated in ethanologenic constructs due to insertion of ethanologenic genes via SalI/SbfI into this locus.

SEQ ID NO:21: Self-replicating broad host range vector pVZ325a with Sp/Sm, GmR and CmR antibiotic resistance cassettes. CmR is eliminated in ethanologenic constructs due to insertion of ethanologenic genes via SalI/SbfI into this locus.

SEQ ID NO:22: Nucleotide sequences of ethanologenic gene cassette from plasmid #1121 pVZ322a-smtB-PsmtA-ZmPDCoop-PrbcL-synADH(deg) integrated via SalI/SbfI into pVZ322a.

SEQ ID NO:23: Nucleotide sequences of ethanologenic gene cassette from plasmid #1217 pVZ325a-corR-PcorT-ZmPDCdsrA/oop-PrbcL*-synADH(deg) integrated via SalI/SbfI into pVZ325a.

SEQ ID NO:24: Nucleotide sequences of ethanologenic gene cassette from plasmid #1227 pVZ325a-nrsR-PnrsB-ZmPDCdsrA/oop-PrbcL*-synADH(deg) integrated via SalI/SbfI into pVZ325a.

SEQ ID NO:25: Nucleotide sequences of ethanologenic gene cassette from plasmid #1356 pVZ325a-nrsRS-PnrsB*-ZpPDCdsrA/oop-PrbcL*-synADH(deg) integrated via SalI/SbfI into pVZ325a.

SEQ ID NO:26: Nucleotide sequences of ethanologenic gene cassette from plasmid #1329 pVZ325a-nrsR-PnrsB-zpPDC-corR-PcorT-zmPDC(fco) integrated into pVZ325a.

SEQ ID NO:27: Nucleotide sequences of ethanologenic gene cassette from plasmid #1375 pVZ325a-nrsRS-PnrsB-zpPDC-corR-PcorT*-zmPDCdeg integrated into pVZ325a.

SEQ ID NO:28: Nucleotide sequences of ethanologenic gene cassette from plasmid #1376 pVZ325a-nrsRS-PnrsB*-zpPDC-corR-PcorT*-zmPDCdeg integrated into pVZ325a.

SEQ ID NO:29: Nucleotide sequences of ethanologenic gene cassette from plasmid #1379 pVZ325a-nrsR-PnrsB-zpPDC-corR-PcorT-zmPDCdeg integrated into pVZ325a.

SEQ ID NO:30: Nucleotide sequence of plasmid #1145 pJET-glgA::ziaR-PziaA-ZmPDC-PrbcL-synADH(deg)-Cm used for transformation of *Synechocystis* PCC6803 via integration into the glgA1 gene locus in the genome.

SEQ ID NO:31: Nucleotide sequence of plasmid TK115 pGEM-AQ4::smtB-PsmtA-ZmPDC-PrbcL-synADH(deg)-Nm used for transformation of *Synechococcus* PCC7002 via integration into the endogenous pAQ4 plasmid.

SEQ ID NO:32: Nucleotide sequence of flanking region pAQ4-FA with NsiI/SalI restriction sites for pAQ4 integration via homologous recombination.

SEQ ID NO:33: Forward primer #323 for amplification of flanking region pAQ4-FA.

SEQ ID NO:34: Reverse primer #324 for amplification of flanking region pAQ4-FA.

SEQ ID NO:35: Nucleotide sequence of flanking region pAQ4-FB with NotI/SpeI restriction sites for pAQ4 integration via homologous recombination.

SEQ ID NO:36: Forward primer #325 for amplification of flanking region pAQ4-FB.

SEQ ID NO:37: Reverse primer #326 for amplification of flanking region pAQ4-FB.

SEQ ID NO:38: Forward primer #327 for amplification of flanking region pAQ3-FA (as published by Xu et al, 2011) with NsiI/SalI restriction sites.

SEQ ID NO:39: Reverse primer #328 for amplification of flanking region pAQ3-FA (as published by Xu et al, 2011).

SEQ ID NO:40: Forward primer #329 for amplification of flanking region pAQ3-FB (as published by Xu et al, 2011).

SEQ ID NO:41: Reverse primer #330 for amplification of flanking region pAQ3-FB (as published by Xu et al, 2011) with NotI/SpeI restriction sites.

SEQ ID NO:42: Nucleotide sequence of flanking region pAQ1-FA2 with NsiI/SalI restriction sites for pAQ1 integration via homologous recombination.

SEQ ID NO:43: Forward primer #336 for amplification of flanking region pAQ1-FA2.

SEQ ID NO:44: Reverse primer #337 for amplification of flanking region pAQ1-FA2.

SEQ ID NO:45: Nucleotide sequence of flanking region pAQ1-FB2 with NotI/SpeI restriction sites for pAQ1 integration via homologous recombination.

SEQ ID NO:46: Forward primer #338 for amplification of flanking region pAQ1-FB2.

SEQ ID NO:47: Reverse primer #339 for amplification of flanking region pAQ1-FB2.

SEQ ID NO:48: Nucleotide sequences of ethanologenic gene cassette from #1381 pVZ325a-nrsRS-PnrsB-zpPDC-corR-PcorT-zmPDCdeg integrated into pVZ325a.

SEQ ID NO:49: Nucleotide sequences of ethanologenic gene cassette from #1383 pVZ325a-nrsRS-PnrsB*-zpPDC-corR-PcorT-zmPDCdeg integrated into pVZ325a.

SEQ ID NO:50: Nucleotide sequences of ethanologenic gene construct from #1389 pJet-pSYSG::nrsRS-PnrsB-zpPDC(deg)-Gm for homologous integration into *Synechocystis* PCC 6803 endogenous pSYSG plasmid.

SEQ ID NO:51: Nucleotide sequences of ethanologenic gene cassette from #1391 pVZ324a-corR-PcorT-ZpPDC integrated into pVZ325a.

SEQ ID NO:52: Nucleotide sequence of plasmid TK193 pGEM-AQ3::nrsRS-PnrsB-zpPDC(deg)-Gm used for transformation of *Synechococcus* PCC7002 via integration into the endogenous pAQ3 plasmid.

SEQ ID NO:53: Reverse primer PcorT*-EcoRI-rev for the amplification of the construct comprising the corR-PcorT promoter sequence (SEQ ID NO:2) incorporating an optimised RBS.

SEQ ID NO:54: Reverse primer PnrsB*-EcoRI-rev for the amplification of the construct comprising the nrsRS-PnrsB promoter sequence (SEQ ID NO:3) incorporating an optimised RBS.

SEQ ID NO:55: SynADH gene (slr1192) from *Synechocystis* sp. PCC 6803.

SEQ ID NO:56: Codon-degenerated SynADH gene (slr1192) from *Synechocystis* sp. PCC 6803.

SEQ ID NO:57: Nucleotide sequences of ethanologenic gene cassette from plasmid #1356 pVZ325a-nrsRS-PnrsB*-ZpPDC-PrbcL*-synADH(deg) integrated via SalI/SbfI into pVZ325a.

SEQ ID NO:58: Full codon-optimized pdc gene from *Zymomonas mobilis* (ZmPDCfco).

SEQ ID NO:59: Forward primer pSYSG-P1-XbaI-fw for amplification of pSYSG-P1 (SEQ ID NO:61).

SEQ ID NO:60: Reverse primer pSYSG-P1-XmaI-rev for amplification of pSYSG-P1 (SEQ ID NO:61).

SEQ ID NO:61: Nucleotide sequence of engineered flanking region pSYSG-P1 for pSYSG integration via homologous recombination.

SEQ ID NO:62: Forward primer pSYSG-P2-XhoI-fw for amplification of pSYSG-P2 (SEQ ID NO:64).

SEQ ID NO:63: Reverse primer pSYSG-P2-NotI-fw for amplification of pSYSG-P2 (SEQ ID NO:64).

SEQ ID NO:64: Nucleotide sequence of engineered flanking region pSYSG-P2 for pSYSG integration via homologous recombination.

SEQ ID NO:65: Nucleotide sequence of plasmid TK162 pGEM-AQ3::smtB-PsmtA-zmPDC_oop-PrbcL-synADH-deg_oop used for transformation of *Synechococcus* sp. PCC 7002 via integration into the endogenous pAQ3 plasmid.

SEQ ID NO:66: Nucleotide sequence of plasmid #1233 pGEM-AQ4::smtB-PsmtA-zpPDC-PrbcL*-synADHdeg for transformation of *Synechococcus* sp. PCC 7002 via integration into the endogenous pAQ4 plasmid.

SEQ ID NO:67: Nucleotide sequence of plasmid #1374 pVZ325a-nrsR-PnrsB-zpPDC_ter-corR-PcorT*1-zmPDC\deg_spf\ter for transformation of *Synechocystis* sp.PCC6803.

SEQ ID NO:68: Nucleotide sequence of plasmid #1460 pVZ325a-nrsRS-PnrsB916-PDC_dsrA-Prbc*-synADHdeg for transformation of *Synechococcus* sp. PCC7002.

SEQ ID NO:69: Nucleotide sequence of plasmid #1470 pAQ3-corR-PcorT*1-zmPDCdeg_spf-Prbc*-synADHoop for transformation of *Synechococcus* sp. PCC7002 via integration into the endogenous pAQ3 plasmid.

SEQ ID NO:70: Nucleotide sequence of plasmid #1473 pAQ1::nrsRS-PnrsB193-PDC-PrbcL*-synADH_oop-Sp for transformation of *Synechococcus* sp. PCC7002 via integration into the endogenous pAQ1 plasmid.

SEQ ID NO:71: Nucleotide sequence of plasmid #1332 pGEM-AQ4::corR-PcorT-zpPDC*_ter-PrbcL*-synADH_oop-Nm for integration into the endogenous pAQ4 plasmid of *Synechococcus* sp. PCC7002.

SEQ ID NO:72: Nucleotide sequence of plasmid #1627 pVZ326a-PnrsB(ABCC916)-PDC_dsrA-Prbc*(optRBS)-synADHoop-nrsRSBAD(ABCC916) for transformation of *Synechococcus* sp. PCC7002.

SEQ ID NO:73: Nucleotide sequence of plasmid #1329 pVZ325a-nrsR-PnrsB-zpPDC_ter-corR-PcorT-zmPDC(fco)_oop for transformation of *Synechocystis* sp. PCC6803.

SEQ ID NO:74: Nucleotide sequence of plasmid #1379 pVZ325a-nrsR-PnrsB-zpPDC_ter-corR-PcorT-zmPDCdeg_spf for transformation of *Synechocystis* sp. PCC6803.

SEQ ID NO:75: Nucleotide sequence of plasmid #1356 pVZ325a-nrsRS-PnrsB*-zpPDC_ter-Prbc*-synADHdeg_oop for transformation of *Synechococcus* sp. PCC7002.

SEQ ID NO:76: Nucleotide sequence of plasmid #1217 pVZ325a-corR-PcorT-zmPDC_dsrA-Prbc*-synADHdeg_oop for transformation of *Synechococcus* sp. PCC7002.

SEQ ID NO:77: Nucleotide sequence of plasmid #1227 pVZ325a-corR-PcorT-zmPDC_dsrA-Prbc*-synADHdeg_oop for transformation of *Synechocystis* sp. PCC6803.

SEQ ID NO:78: Nucleotide sequence of plasmid #1480 pAQ3-aztR-PaztA-zmPDCdeg_spf-Prbc*-synADH_oop for transformation of *Synechococcus* sp. PCC7002 via integration into the endogenous pAQ3 plasmid.

SEQ ID NO:79: Nucleotide sequence of plasmid #1563 pGEM-gpA::smtB-PsmtA-zmPDC_dsrA-Prbc*-synADH_oop for transformation of *Synechococcus* sp. PCC7002 by chromosomal integration between gene loci A0124 and A0125.

SEQ ID NO:80: Nucleotide sequence of plasmid #1568 pGEM-gpB::smtB-PsmtA-zmPDCdeg_spf-Prbc*-synADH_oop for transformation of *Synechococcus* sp. PCC7002 by chromosomal integration between gene loci A1330 and A1331.

SEQ ID NO:81: Nucleotide sequence of plasmid #1692 pGEM-gpC::smtB-PsmtA-zmPDC_oop-PrbcL-synADHdeg_oop for transformation of *Synechococcus* sp. PCC7002 by chromosomal integration between gene loci A2578 and A2579.

SEQ ID NO:82: Nucleotide sequence of plasmid #1564 pGEM-gpA::corR-PcorT-zmPDC_dsrA-Prbc*synADH_oop for transformation of *Synechococcus* sp. PCC7002 by chromosomal integration between gene loci A0124 and A0125.

SEQ ID NO:83: Nucleotide sequence of plasmid #1633 pGEM-gpB::corR-PcorT*1-zmPDCdeg_spf-Prbc*-synADH_oop for transformation of *Synechococcus* sp. PCC7002 by chromosomal integration between gene loci A1330 and A1331.

SEQ ID NO:84: Nucleotide sequence of plasmid #1574 pGEM-gpC::corR-PcorT-zpPDC_ter-Prbc*-synADHdeg_oop for transformation of *Synechococcus* sp. PCC7002 by chromosomal integration between gene loci A2578 and A2579.

REFERENCES

Hegemann, P., Method for producing nucleic acid polymers. U.S. Pat. No. 6,472,184 B1.

Altschul, S. F., Gish, W., Miller, W., Myers, E. W., Lipman, D. J., Basic local alignment search tool. J Mol Biol. 215 (1990), 403-10.

Altschul, S. F., Madden, T. L., Schïffer, A. A., Zhang, J., Zhang, Z., Miller, W., Lipman, D. J., Gapped BLAST and PSI-BLAST: a new generation of protein database search programs. Nucleic Acids Res. 25 (1997), 3389-402.

Bryant, D. (Ed.), The Molecular Biology of Cyanobacteria (1994), Kluwer Academic Publishers.

Coico, R., Emerging Technologies. Current Protocols in Microbiology. (2007) 17:1.0.1-1.0.4., John Wiley and Sons, Inc.

Herrero, A. and Flores, E. (Eds.), The Cyanobacteria, Molecular Biology, Genomics and Evolution (2008), Caister Academic Press, Norfolk, UK.

Holland-Staley, C. A., Lee, K., Clark, D. P., Cunningham, P. R., Aerobic Activity of *Escherichia Coli* Alcohol Dehydrogenase is determined by a single amino acid. J Bacteriology 182 (2000), 6049-54.

Hoppner, T. C. and Doelle, H. W., Purification and kinetic characteristics of pyruvate decarboxylase and ethanol dehydrogenase from *Zymomonas mobilis* in relation to ethanol production. Eur. J. Appl. Microbiol. Biotechnol. 17 (1983), 152-157.

Karlin, S., Altschul, S. F., Applications and statistics for multiple high-scoring segments in molecular sequences. Proc Natl Acad Sci USA 90 (1993), 5873-7.

Karlin, S., Altschul, S. F., Methods for assessing the statistical significance of molecular sequence features by using general scoring schemes. Proc Natl Acad Sci USA 87 (1990), 2264-8.

Keiichi, I., Rossi, J., DNA polymerase mediated synthesis of double stranded nucleic acids. U.S. Pat. No. 5,750,380 A.

Mackay I. M. (ed.), Real-Time PCR in Microbiology: From Diagnosis to Characterization, Caister Academic Press (2007).

Nakamura, Y., Kaneko, T. and Tabata, S., CyanoBase, the genome database for *Synechocystis* sp. Strain PCC6803: status for the year 2000. Nucleic Acid Research 28 (2000), 72.

Richmond, A. (Ed.), Handbook Of Microalgal Culture: Biotechnology And Applied Phycology (2003), Blackwell Publishing.

Ruffing, A. M., Engineered cyanobacteria. Teaching an old bug new tricks. Bioengineered Bugs 2 (2011), 136-149.

Sambrook, J., Russel, D., Molecular Cloning: A Laboratory Manual (Third Edition), (2001) Cold Spring Harbor Laboratory Press.

Takahama, K., Matsuoka, M., Nagahama, K., Ogawa, A., Construction and Analysis of a Recombinant Cyanobacterium Expressing a Chromosomally Inserted Gene for an Ethylene-Forming Enzyme at the psbAI Locus. J Bioscience Bioengineering 95 (2003), 302-305.

Thompson, J. D., Higgins, D. G., Gibson, T. J., CLUSTAL W: improving the sensitivity of progressive multiple sequence alignment through sequence weighting, position-specific gap penalties and weight matrix choice. Nucleic Acids Res. 22 (1994), 4673-80.

Ziegler, K., Woods, R. P., Kramer, D., Gründel, M., Dühring, U., Baier, K., Coleman, J., Smith C. R., Oesterheld, C., Lockau, W., Enke, H., Selection of ADH In Genetically Modified Cyanobacteria For The Production Of Ethanol. PCT patent application WO 2009/098089 A2.

EXAMPLES

In the following, certain embodiments of the invention will be explained in more detail with reference to figures and experimental data. The figures and examples are not intended to be limiting with respect to specific details. Individual features can be identified with a reference numeral. This does not exclude that more than one of such feature can be present.

Example 1

Plasmid Construction for *Synechocystis* sp. PCC 6803

NB: Asterisks (*) mark promoter variants with optimised ribosome binding site.

Construction of plasmid #1145: The pJET base plasmid was designed for genomic integration into *Synechocystis* sp. PCC 6803. Two regions of homology, glgA-P1 and glgA-P2, corresponding to adjacent upstream and downstream regions of glgA1 (sll1393) gene flank the genetic construct to allow for homologous integration into the glgA1 locus of the *Synechocystis* sp. PCC 6803 genome. The plasmid was designed with two antibiotic resistance cassettes, the Cm and Amp cassettes, to confer resistance against chloramphenicol and ampicillin, respectively. A genetic insert was generated, comprising the pyruvate decarboxylase gene from *Zymomonas mobilis* (zmPDC, SEQ ID NO:16) under the transcriptional control of the ziaR-PziaA promoter-regulator gene construct (ziaR-sll0792, ziaA-slr0798, SEQ ID NO:1), to give the first production gene under the transcriptional control of a zinc-inducible promoter. The insert further comprised the second production gene, which was the degenerated gene encoding the alcohol dehydrogenase from *Synechocystis* sp. PCC 6803 (synADHdeg, SEQ ID NO:56) under the transcriptional control of the constitutive Prbc promoter. The insert was ligated into the plasmid via SalI and SbfI restriction endonuclease sites. The map of plasmid #1145 is depicted in FIG. 7A, and the sequence is deposited under SEQ ID NO:30. Plasmid annotations are as follows: 3614 . . . 3644 terminator oop; 2603 . . . 3613 CDS synADH\deg; 2308 . . . 2340 terminator oop; 2341 . . . 2599 promoter PrbcL; 8465 . . . 9124 marker Gm; 6774 . . . 7565 recombination insert glgA-P1; 4830 . . . 5687 marker Amp; 567 . . . 2267 CDS zmPDC; 10 . . . 408 CDS ziaR; 416 . . . 559 promoter PziaA; 3651 . . . 4233 recombination insert glgA-P2.

Construction of plasmid #1217: The pVZ325a base plasmid (FIG. 20B, SEQ ID NO:21) was designed for self-replication in *Synechocystis* sp. PCC 6803. The plasmid was designed with two antibiotic resistance cassettes, the Sp/Sm and the Gm cassettes, to confer resistance against spectinomycin, streptomycin and gentamycin, respectively. A genetic insert was generated (SEQ ID NO:23), comprising the pyruvate decarboxylase gene from *Zymomonas mobilis* (zmPDC) under the transcriptional control of the corR-PcorT promoter-regulator gene construct (corR-sll0794, PcorT-slr0797, SEQ ID NO:2) as a first production gene under the transcriptional control of a cobalt-inducible promoter, and a second production gene, which was the degenerated gene encoding the alcohol dehydrogenase from *Synechocystis* sp. PCC 6803 (synADHdeg) under the transcriptional control of the constitutive Prbc* promoter. The insert was cloned into the plasmid via SalI and SbfI restriction endonuclease sites. The map of plasmid #1217 is depicted in FIG. 8A, and the plasmid sequence is deposited under SEQ ID NO:76. Plasmid annotations are as follows: 3068 . . . 3132 promoter Prbc*; 10317 . . . 10847 CDS Gm; 11185 . . . 12195 CDS Sp/Sm; 1255 . . . 2955 CDS zmPDC; 2981 . . . 3026 dsrA; 4145 . . . 4175 terminator oop; 3134 . . . 4144 CDS synADH\deg; 57 . . . 1166 CDS corR(6803); 1167 . . . 1249 promoter PcorT(6803).

Figure 9:
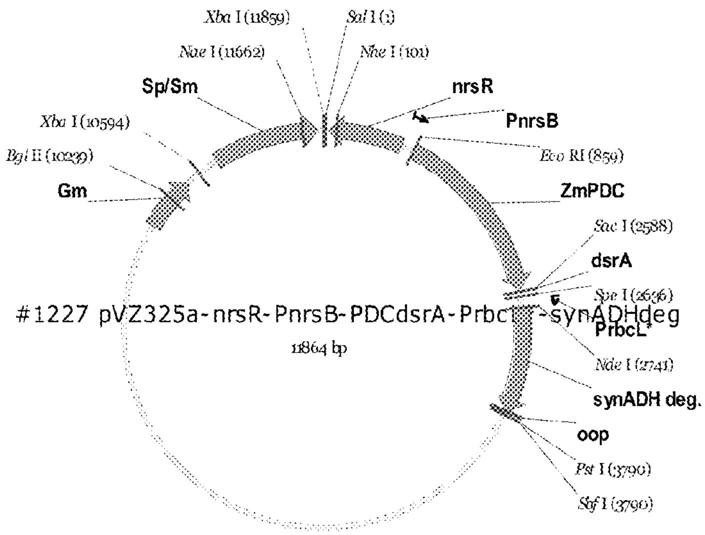
Figure 9:
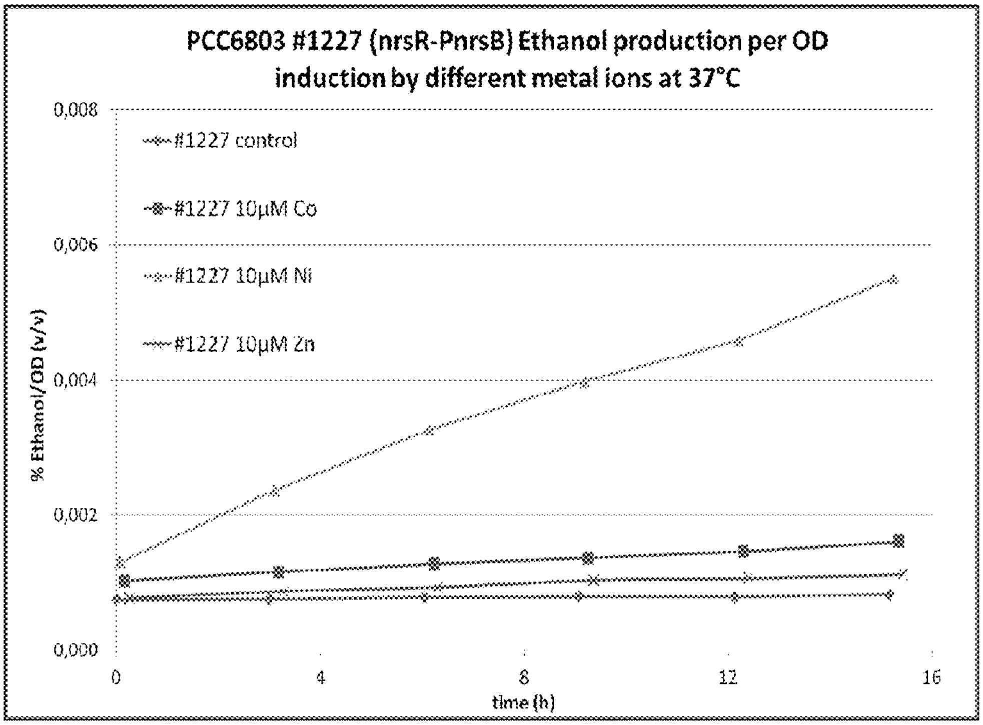

Construction of plasmid #1227: This construct is also based on the pVZ325a base plasmid. A genetic insert was generated (SEQ ID NO:24), comprising the pyruvate decarboxylase gene from *Zymomonas mobilis* (zmPDC) under the transcriptional control of the nrsR-PnrsB promoter-regulator gene construct (nrsS-sll0798, nrsR-sll0797, nrsB-sll0793, SEQ ID NO:3) as a first production gene under the transcriptional control of a nickel-inducible promoter, and a second production gene, which was the degenerated gene encoding the alcohol dehydrogenase from *Synechocystis* sp. PCC 6803 (SynADHdeg) under the transcriptional control of the constitutive Prbc* promoter. The insert was cloned into the plasmid via SalI and SbfI restriction endonuclease sites. The map of plasmid #1227 is depicted in FIG. 9. The plasmid sequence is deposited under SEQ ID NO:77. Plasmid annotations are as follows: 2676 . . . 2740 promoter Prbc*; 9925 . . . 10455 CDS Gm; 10793 . . . 11803 CDS Sp/Sm; 863 . . . 2563 CDS zmPDC; 2589 . . . 2634 dsrA; 3753 . . . 3783 terminator oop; 2742 . . . 3752 CDS synADHdeg; 33 . . . 734 CDS nrsR(6803); 736 . . . 855 promoter PnrsB(6803).

Construction of plasmid #1329: This construct is also based on the pVZ325a base plasmid. A genetic insert was generated (SEQ ID NO:26), comprising a first production gene encoding the pyruvate decarboxylase gene from *Zymobacter palmae* (zpPDC, SEQ ID NO:17) under the transcriptional control of the nickel-inducible nrsR-PnrsB promoter-regulator gene construct, and a second first production gene which was a codon-optimised (for cyanobacterial hosts) version of the gene encoding the pyruvate decarboxylase from *Zymomonas mobilis* (zmPDC(fco), SEQ ID NO:58) under the transcriptional control of the cobalt-inducible corR-PcorT promoter-regulator gene construct. The codon-optimised zmPDC shares approximately 80-90% sequence identity with the native zmPDC. The map of plasmid #1329 is depicted in FIG. 10A, and the sequence is deposited under SEQ ID NO:73. Plasmid annotations are as follows: 3852 . . . 5561 CDS zmPDC(fco); 5565 . . . 5593 terminator oop; 2661 . . . 3770 CDS corR; 3771 . . . 3853 promoter PcorT; 821 . . . 2500 CDS zpPDC; 11745 . . . 12275 CDS Gm; 12613 . . . 13623 CDS Sp/Sm; 1 . . . 702 CDS nrsR; 2501 . . . 2597 terminator ter; 703 . . . 831 promoter PnrsB. Plasmid #1329 is particularly designed to be transformed into cyanobacterial host cells which harbor at least one additional copy of a recombinant pdc gene in their genome.

Construction of plasmid #1379: This construct is also based on the pVZ325a base plasmid. A genetic insert was generated (SEQ ID NO:29), comprising a first production gene encoding the pyruvate decarboxylase gene from *Zymobacter palmae* (zpPDC) under the transcriptional control of the nickel-inducible nrsR-PnrsB promoter-regulator gene construct, and a second first production gene which was a degenerated version of the gene encoding the pyruvate decarboxylase from *Zymomonas mobilis* (zmPDCdeg, SEQ ID NO:18) under the transcriptional control of the corR-PcorT promoter-regulator gene construct. The codon-optimised zmPDC shares approximately 60-65% sequence identity with the native zmPDC. The map of plasmid #1379 is depicted in FIG. 10B, and the sequence is deposited under SEQ ID NO:74. Plasmid annotations are as follows: 5594 . . . 5641 terminator spf; 3887 . . . 5590 CDS zmPDCdeg; 2693 . . . 3802 CDS corR; 3803 . . . 3885 promoter PcorT; 735 . . . 858 promoter PnrsB; 853 . . . 2532 CDS zpPDC; 11788 . . . 12318 CDS Gm; 12656 . . . 13666 CDS Sp/Sm; 33 . . . 734 CDS nrsR; 2533 . . . 2629 terminator ter. Plasmid #1379 is particularly designed to be transformed into cyanobacterial host cells which harbor at least one additional copy of a recombinant pdc gene in their genome.

Construction of plasmid #1389: The plasmid is based on the pJET base vector and was designed as a cloning vector for amplification of constructs to be integrated into the endogenous pSYSG plasmid of *Synechocystis* sp. PCC 6803 by homologous recombination. A genetic insert was generated (SEQ ID NO:50), comprising a first production gene which was a degenerated version of the gene encoding the encoding the pyruvate decarboxylase gene from *Zymobacter palmae* (zpPDCdeg, SEQ ID NO:19) under the transcriptional control of the nickel-inducible nrsRS-PnrsB promoter-regulator gene construct. The insert was flanked by two regions of homology, pSYSG-P1 and pSYSG-P2, corresponding to positions slr1816 and sll1817 of pSYSG, to allow for homologous integration into the corresponding endogenous plasmid. The plasmid further harbored Amp and Gm antibiotic resistance cassettes. The map of plasmid #1389 is depicted in FIG. 19A.

Construction of plasmid #1391: The cloning vector for #1391 was generated by first removing the gentamycin resistance cassette Gm from the base vector pVZ325a by a MluI restriction endonuclease digestion/re-ligation, to give the pVZ324a plasmid with remaining Sp/Sm resistance cassette. A genetic insert was generated (SEQ ID NO:51), comprising a first production gene encoding the pyruvate decarboxylase gene from *Zymobacter palmae* (zpPDC) under the transcriptional control of the cobalt-inducible corR-PcorT promoter-regulator gene construct. The insert was cloned into the plasmid via SalI and SbfI restriction endonuclease sites. The map of plasmid #1391 is depicted in FIG. 19B.

Construction of plasmid #1374: This construct is also based on the pVZ325a base plasmid. A genetic insert was generated, comprising a first production gene encoding the pyruvate decarboxylase gene from *Zymobacter palmae* (zpPDC, SEQ ID NO:17) under the transcriptional control of the nickel-inducible nrsR-PnrsB promoter-regulator gene construct, and a second first production gene which was a degenerated version of the gene encoding the pyruvate decarboxylase from *Zymomonas mobilis* (zmPDCdeg, SEQ ID NO:18) under the transcriptional control of the corR-PcorT*1 promoter-regulator gene construct incorporating an optimised ribosome binding site for *Synechocystis* sp. PCC6803. The map of plasmid #1374 is depicted in FIG. 26. The sequence of plasmid #1374 is deposited under SEQ ID NO:67. Plasmid annotations are as follows: 3858 . . . 3937 promoter PcorT*1; 5648 . . . 5695 terminator spf\ter; 3938 . . . 5644 CDS zmPDCdeg; 2744 . . . 3856 CDS corR; 909 . . . 2582 CDS zpPDC; 785 . . . 908 promoter PnrsB; 11842 . . . 12372 CDS Gm; 12710 . . . 13720 CDS Sp/Sm; 2583 . . . 2679 terminator ter.

Example 2

Plasmid Construction for *Synechococcus* sp. PCC 7002

NB: Asterisks (*) mark promoter variants with optimised ribosome binding site.

Construction of plasmid TK115: The pGEM-TK base plasmid was tailored as a cloning vector for amplification of constructs to be homologously recombined into the endogenous plasmid pAQ4 of *Synechococcus* sp. PCC 7002 (see also FIG. 4 and FIG. 6). Two regions of homology, flanking region pAQ4-FA (751 nt) incorporating NsiI/SalI endonuclease restriction sites (SEQ ID NO:32) and flanking region pAQ4-FB (551 nt) incorporating NotI/SpeI endonuclease restriction sites (SEQ ID NO:35) were designed to integrate into pAQ4 between gene loci SYNPCC7002_D0017 (hypothetical protein, 237 nt, 78 aa) and SYNPCC7002_D0018 (CRISPR-associated protein Cas2, 294 nt, 97 aa). The flanking regions were amplified from pAQ4 by PCR using the primer pairs #323 and #324 (SEQ ID NOs:33 and 34) and #325 and #326 (SEQ ID NOs:36 and 37). The flanking regions pAQ4-FA and pAQ4-FB were then cloned into the pGEM-TK vector via the restriction endonuclease sites NsiI/SalI or NotI/SpeI, respectively. A genetic insert was generated, comprising a first production gene encoding the pyruvate decarboxylase from *Zymomonas mobilis* (zmPDC) under the transcriptional control of the zinc-inducible smtB-PsmtA promoter-regulator gene construct (SEQ ID NO:4), and a second production gene which was the degenerated gene encoding the alcohol dehydrogenase from *Synechocystis* sp. PCC 6803 (synADHdeg) under the transcriptional control of the constitutive Prbc promoter, as well as a neomycin (Nm) resistance cassette. The insert was cloned in between flanking regions pAQ4-FA and pAQ4-FB via restriction endonuclease sites SalI and NotI into the modified pGEM-TK plasmid. The map of plasmid TK115 is depicted in FIG. 14A, and the sequence is deposited under SEQ ID NO:31. Plasmid annotations are as follows: 393 . . . 492 promoter PsmtA; 6 . . . 392 CDS smtB; 4698 . . . 5237 intron pAQ4-FB; 3610 . . . 3670 promoter PpsbA; 3710 . . . 4491 marker Nm; 6105 . . . 6962 marker Amp; 8179 . . . 8915 intron pAQ4-FA; 2276 . . . 2534 promoter PrbcL(6803); 2243 . . . 2275 terminator oop; 2538 . . . 3548 CDS synADHdeg; 3549 . . . 3579 terminator oop; 502 . . . 2202 CDS zmPDC.

Construction of plasmid TK193: The pGEM-TK base plasmid was tailored as a cloning vector for amplification of constructs to be homologously recombined into the endogenous plasmid pAQ3 of *Synechococcus* sp. PCC 7002 (see also FIG. 4 and FIG. 6). Two regions of homology, flanking region pAQ3-FA incorporating NsiI/SalI endonuclease restriction sites and flanking region pAQ3-FB incorporating NotI/SpeI endonuclease restriction sites were designed to integrate into pAQ3 between gene loci SYNPCC7002_C0006 and SYNPCC7002_C0007 as previously described by Xu and colleagues (2011). The flanking regions were amplified from pAQ3 by PCR using the primer pairs #327 and #328 (SEQ ID NO:38 and SEQ ID NO:39) and #329 and #330 (SEQ ID NO:40 and SEQ ID NO:41). The flanking regions pAQ3-FA and pAQ3-FB were then cloned into the pGEM-TK vector via the restriction endonuclease sites NsiI/SalI or NotI/SpeI, respectively. A genetic insert was generated, comprising a first production gene which was the degenerated version of the gene encoding the pyruvate decarboxylase from *Zymobacter palmae* (zpPDC) under the transcriptional control of the nickel-inducible nrsRS-PnrsB promoter-regulator gene construct, as well as a gentamycin (Gm) resistance cassette. The insert was cloned in between flanking regions pAQ3-FA and pAQ3-FB via restriction endonuclease sites SalI and NotI into the modified pGEM-TK plasmid. The map of plasmid TK193 is shown in FIG. 23, and the sequence is deposited under SEQ ID NO:52.

Construction of plasmid TK162: The pGEM-TK base plasmid was tailored as a cloning vector for amplification of constructs to be homologously recombined into the endogenous plasmid pAQ3 of *Synechococcus* sp. PCC 7002 as described above. The plasmid was further furnished with a genetic insert comprising a Pdc gene from *Zymomonas mobilis* as a first production gene under the transcriptional control of the zinc-inducible smtB-PsmtA promoter-regulator gene construct, and a degenerated version of the gene encoding the alcohol dehydrogenase from *Synechocystis* sp. PCC 6803 (synADHdeg) as a second production gene under the transcriptional control of the constitutive PrbcL promoter. The insert was cloned in between flanking regions pAQ3-FA and pAQ3-FB into the modified pGEM-TK plasmid. The map of plasmid TK162 is shown in FIG. 24, and the sequence is deposited under SEQ ID NO:65. Plasmid annotations are as follows: 8408 . . . 8794 CDS smtB; 8795 . . . 8894 promoter PsmtA; 5 . . . 1705 CDS Pdc; 3052 . . . 3082 terminator oop; 2041 . . . 3051 CDS synADH\deg; 1746 . . . 1778 terminator oop; 1779 . . . 2037 promoter PrbcL\6803; 7834 . . . 8402 intron pAQ3-FA; 5760 . . . 6617 marker Amp; 3298 . . . 4306 marker Sp/Sm; 4406 . . . 4892 intron pAQ3-FB.

Construction of plasmids for pAQ1 integration: The pGEM-TK base plasmid was tailored as a cloning vector for amplification of constructs to be homologously recombined into the endogenous plasmid pAQ1 of *Synechococcus* sp. PCC 7002 (see also FIG. 5 and FIG. 6). Two regions of homology, flanking region pAQ1-FA (SEQ ID NO:42) incorporating NsiI/SalI endonuclease restriction sites and flanking region pAQ1-FB (SEQ ID NO:45) incorporating NotI/SpeI endonuclease restriction sites were designed to integrate into a so far unpublished site of pAQ1 between gene loci SYNPCC7002_B0001 and SYNPCC7002_B0002. The flanking regions were amplified from pAQ1 by PCR using the primer pairs #336 and #337 (SEQ ID NO:43 and SEQ ID NO:44) and #338 and #339 (SEQ ID NO:46 and SEQ ID NO:47). The flanking regions pAQ1-FA and pAQ1-FB were then cloned into the pGEM-TK vector via the restriction endonuclease sites NsiI/SalI or NotI/SpeI, respectively. Genetic inserts were cloned in between flanking regions pAQ1-FA and pAQ1-FB via restriction endonuclease sites SalI and NotI into the modified pGEM-TK plasmid.

Figure 15:
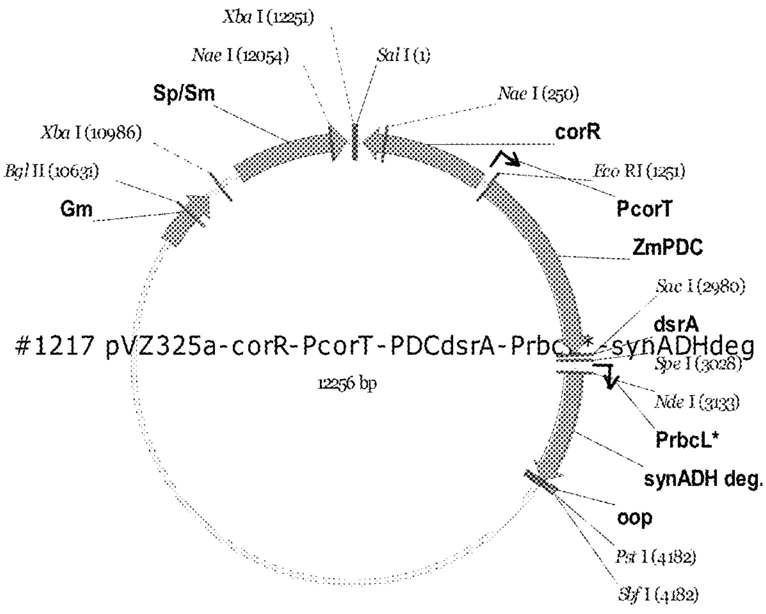
Figure 15:
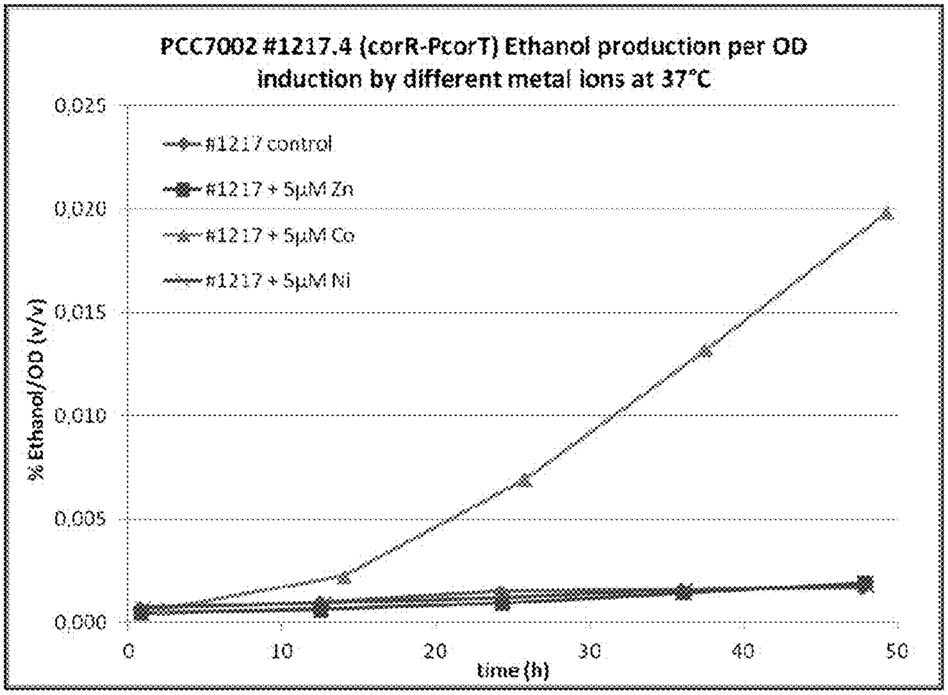

Construction of plasmid #1217: The plasmid is based on the pVZ325a plasmid and was designed for self-replication in *Synechococcus* sp. PCC 7002. It is produced as described for plasmid #1217 in Example 1 and carries two antibiotic resistance markers, a gentamycin (Gm) and a spectinomycin/streptomycin (Sp/Sm) cassette. The map of plasmid #1217 is depicted in FIG. 15.

Construction of plasmid #1356: The plasmid is based on the pVZ325a plasmid and was designed for self-replication in *Synechococcus* sp. PCC 7002. A genetic insert was generated (SEQ ID NO:57), comprising a first production gene encoding the pyruvate decarboxylase gene from *Zymobacter palmae* (zpPDC) under the transcriptional control of the nickel-inducible nrsRS-PnrsB* promoter-regulator gene construct, and a second production gene which was a degenerated version of the gene encoding the alcohol dehydrogenase from *Synechocystis* sp. PCC 6803 (synADHdeg) under the transcriptional control of the constitutive Prbc* promoter. The insert was cloned into the plasmid via SalI and SbfI restriction endonuclease sites. The plasmid further harbored Gm and Sp/Sm antibiotic resistance cassettes. The map of plasmid #1356 is depicted in FIG. 16A, and the plasmid sequence is deposited under SEQ ID NO:75. Plasmid annotations are as follows: 2304 . . . 3977 CDS zpPDC; 4116 . . . 4180 promoter Prbc*; 11365 . . . 11895 CDS Gm; 12233 . . . 13243 CDS Sp/Sm; 5193 . . . 5223 terminator oop; 4182 . . . 5192 CDS synADH\deg; 3978 . . . 4074 terminator ter; 1476 . . . 2179 CDS nrsR(6803); 2180 . . . 2300 promoter PnrsB*; 117 . . . 1478 CDS nrsS(6803).

Construction of plasmid #1375: The plasmid is based on the pVZ325a plasmid and was designed for self-replication in *Synechococcus* sp. PCC 7002. A genetic insert was generated (SEQ ID NO:27), comprising a first production gene encoding the pyruvate decarboxylase gene from *Zymobacter palmae* (zpPDC) under the transcriptional control of the nickel-inducible nrsRS-PnrsB promoter-regulator gene construct, and a second first production gene which was a degenerated version of the gene encoding the pyruvate decarboxylase from *Zymomonas mobilis* (zmPDCdeg) under the transcriptional control of the cobalt-inducible corR-PcorT* promoter-regulator gene construct. The plasmid further harbored Gm and Sp/Sm antibiotic resistance cassettes. The map of plasmid #1375 is depicted in FIG. 17A.

Construction of plasmid #1376: The plasmid is based on the pVZ325a plasmid and was designed for self-replication in *Synechococcus* sp. PCC 7002. A genetic insert was generated (SEQ ID NO:28), comprising a first production gene encoding the pyruvate decarboxylase gene from *Zymobacter palmae* (zpPDC) under the transcriptional control of the nickel-inducible nrsRS-PnrsB* promoter-regulator gene construct, and a second first production gene which was a degenerated version of the gene encoding the pyruvate decarboxylase from *Zymomonas mobilis* (zmPDCdeg) under the transcriptional control of the cobalt-inducible corR-PcorT* promoter-regulator gene construct. The plasmid further harbored Gm and Sp/Sm antibiotic resistance cassettes. The map of plasmid #1376 is depicted in FIG. 17B.

Construction of plasmid #1381: The plasmid is based on the pVZ325a plasmid and was designed for self-replication in *Synechococcus* sp. PCC 7002. A genetic insert was generated (SEQ ID NO:48), comprising a first production gene encoding the pyruvate decarboxylase gene from *Zymobacter palmae* (zpPDC) under the transcriptional control of the nickel-inducible nrsRS-PnrsB promoter-regulator gene construct, and a second first production gene which was a degenerated version of the gene encoding the pyruvate decarboxylase from *Zymomonas mobilis* (zmPDCdeg) under the transcriptional control of the cobalt-inducible corR-PcorT promoter-regulator gene construct promoter. The plasmid further harbored Gm and Sp/Sm antibiotic resistance cassettes. The map of plasmid #1381 is depicted in FIG. 18A.

Construction of plasmid #1383: The plasmid is based on the pVZ325a plasmid and was designed for self-replication in *Synechococcus* sp. PCC 7002. A genetic insert was generated (SEQ ID NO:49), comprising a first production gene encoding the pyruvate decarboxylase gene from *Zymobacter palmae* (zpPDC) under the transcriptional control of the nickel-inducible nrsRS-nrsB* promoter-regulator gene construct, and a second first production gene which was the degenerated version of the gene encoding the pyruvate decarboxylase from *Zymomonas mobilis* (zmPDCdeg) under the transcriptional control of the cobalt-inducible corR-PcorT promoter-regulator gene construct promoter. The plasmid further harbored Gm and Sp/Sm antibiotic resistance cassettes. The map of plasmid #1383 is depicted in FIG. 18B.

Construction of plasmid #1460: The plasmid is based on the pVZ325a plasmid and was designed for self-replication in *Synechococcus* sp. PCC 7002. A genetic insert was generated, comprising a first production gene encoding the pyruvate decarboxylase gene from *Zymomonas mobilis* (zmPDC) under the transcriptional control of the nickel-inducible nrsRS-PnrsB916 promoter-regulator gene construct, and a second production gene which was a degenerated version of the gene encoding the alcohol dehydrogenase from *Synechocystis* sp. PCC 6803 (synADHdeg) under the transcriptional control of the constitutive PrbcL* promoter. The insert was cloned into the plasmid via SalI and SbfI restriction endonuclease sites. The plasmid further harbored Gm and Sp/Sm antibiotic resistance cassettes. The map of plasmid #1460 is depicted in FIG. 31A, and the sequence is deposited under SEQ ID NO:68. Plasmid annotations are as follows: 100 . . . 1461 CDS nrsS\(ABCC916); 1458 . . . 2153 CDS nrsR\(ABCC916); 2154 . . . 2282 promoter PnrsB\(ABCC916); 4169 . . . 5179 CDS synADH\deg; 5180 . . . 5210 terminator oop; 4016 . . . 4061 insertion sequence dsrA\ter; 2290 . . . 3990 CDS zmPDC; 12220 . . . 13230 CDS Sp/Sm; 11352 . . . 11882 CDS Gm; 4103 . . . 4167 promoter PrbcL*.

Construction of plasmid #1470: The pGEM-TK base plasmid was tailored as a cloning vector for amplification of constructs to be homologously recombined into the endogenous plasmid pAQ3 of *Synechococcus* sp. PCC 7002 as already described above. A genetic insert was generated, comprising a first production gene which was the degenerated version of the gene encoding the pyruvate decarboxylase from *Zymomonas mobilis* (zmPDCdeg) under the transcriptional control of the cobalt-inducible corR-PcorT*1 promoter-regulator gene construct with optimised ribosome binding site, as well as the alcohol dehydrogenase from *Synechocystis* sp. PCC 6803 (synADH) as second production gene under the transcriptional control of the constitutive Prbc* promoter. The map of the plasmid is shown in FIG. 32, and the sequence is deposited under SEQ ID NO:69. Plasmid annotations are as follows: 1226 . . . 1305 promoter PcorT*1; 3016 . . . 3063 terminator spf\ter; 1306 . . . 3012 CDS zmPDCdeg; 112 . . . 1224 CDS corR; 3083 . . . 3147 promoter Prbc*; 3149 . . . 4159 CDS synADH; 4189 . . . 4220 terminator oop; 8956 . . . 9448 intron pAQ3-FB; 7231 . . . 8088 marker Amp; 5446 . . . 6014 intron pAQ3-FA; 4495 . . . 5028 marker Gm.

Construction of plasmid #1473: The pGEM-TK base plasmid was tailored as a cloning vector for amplification of constructs to be homologously recombined into the endogenous plasmid pAQ1 of *Synechococcus* sp. PCC 7002 as described above. A genetic insert was generated, comprising the pyruvate decarboxylase from *Zymomonas mobilis* (zmPDC) as a first production gene under the transcriptional control of the nickel-inducible nrsRS-PnrsB916 promoter-regulator gene construct, as well as the alcohol dehydrogenase from *Synechocystis* sp. PCC 6803 (synADH) as second production gene under the transcriptional control of the constitutive Prbc* promoter. The map of the plasmid is shown in FIG. 33, and the sequence is deposited under SEQ ID NO:70. Plasmid annotations are as follows: 100 . . . 1461 CDS nrsS\(ABCC916); 1458 . . . 2153 CDS nrsR\(ABCC916); 2154 . . . 2282 promoter PnrsB(ABCC916); 2290 . . . 3990 CDS zmPDC; 4029 . . . 4093 promoter Prbc*; 4095 . . . 5105 CDS synADH; 5135 . . . 5166 terminator oop; 6493 . . . 7000 intron pAQ1-FB2; 7868 . . . 8725 marker Amp; 9942 . . . 10612 intron pAQ1-FA2; 5381 . . . 6389 marker Sp/Sm.

Construction of plasmid #1332: The pGEM-TK base plasmid was tailored as a cloning vector for amplification of constructs to be homologously recombined into the endogenous plasmid pAQ4 of *Synechococcus* sp. PCC 7002 as described above. A genetic insert comprising a first production gene encoding the pyruvate decarboxylase gene from *Zymobacter palmae* (zpPDC) under the transcriptional control of the cobalt-inducible corR-PcorT promoter-regulator gene construct, as well as the alcohol dehydrogenase from *Synechocystis* sp. PCC 6803 (synADH) as second production gene under the transcriptional control of the constitutive Prbc* promoter with optimised ribosome binding site was inserted. The map of the plasmid is shown in FIG. 34, and the sequence is deposited under SEQ ID No:71. Plasmid annotations are as follows: 2925 . . . 3021 native terminator of zpPDC; 1251 . . . 2924 CDS zmPDC; 1167 . . . 1249 promoter PcorT; 57 . . . 1166 CDS corR; 4147 . . . 4178 terminator oop; 3107 . . . 4117 CDS synADH; 3041 . . . 3105 promoter Prbc*; 8777 . . . 9513 intron pAQ4-FA; 6703 . . . 7560 marker Amp; 4308 . . . 5089 Nm; 4208 . . . 4268 promoter PpsbA; 5296 . . . 5835 intron pAQ4-FB.

Construction of plasmid #1627: The plasmid is based on the pVZ325a plasmid and was designed for self-replication in *Synechococcus* sp. PCC 7002. The plasmid was furnished with genetic inserts comprising a first production gene encoding the pyruvate decarboxylase gene from *Zymomonas mobilis* under the transcriptional control of the nickel-inducible PnrsB(ABCC916) promoter and the alcohol dehydrogenase from *Synechocystis* sp. PCC 6803 (synADH) as second production gene under the transcriptional control of the constitutive Prbc* promoter with optimised ribosome binding site. The $Ni^{2+}$ resistance conferring gene cluster nrsRSBAD (ABCC916) that is derived from a *Synechococcus* species closely related *Synechococcus* PCC7002 was further inserted. The plasmid map is depicted in FIG. 35, and the sequence is deposited under SEQ ID NO:72. Plasmid annotations are as follows: 1889 . . . 1957 promoter Prbc*(optRBS); 1843 . . . 1888 insertion sequence dsrA_ter; 1958 . . . 2968 CDS synADH; 2998 . . . 3028 terminator oop; 117 . . . 1817 CDS PDC; 9170 . . . 9700 CDS Gm; 10428 . . . 11789 CDS nrsS(ABCC916); 11786 . . . 12481 CDS nrsR(ABCC916); 12611 . . . 13294 CDS nrsB(ABCC916); 13338 . . . 16505 CDS nrsA(ABCC916); 16628 . . . 17290 CDS nrsD(ABCC916); 17321 . . . 17941 CDS nrsD' (ABCC916); 6 . . . 109 promoter PnrsB\ABCC916.

Construction of plasmid #1480: The plasmid was tailored as a cloning vector for amplification of constructs to be homologously recombined into the endogenous plasmid pAQ3 of *Synechococcus* sp. PCC 7002 as described above. The plasmid was further furnished with a genetic insert comprising a degenerated version of the pyruvate decarboxylase gene from *Zymomonas mobilis* (zmPDCdeg) as a first production gene under the transcriptional control of the zinc-inducible aztR-PaztA promoter-regulator gene construct from *Anabaena* PCC7120, as well as the alcohol dehydrogenase from *Synechocystis* sp. PCC 6803 (synADH) as second production gene under the transcriptional control of the constitutive PrbcL* promoter. The map of the plasmid is shown in FIG. 38A, and the sequence is deposited under SEQ ID No:78. Plasmid annotations are as follows: 3830 . . . 4363 marker Gm; 4781 . . . 5349 intron pAQ3-FA; 6566 . . . 7423 marker Amp; 8291 . . . 8783 intron pAQ3-FB; 3524 . . . 3555 terminator oop; 2484 . . . 3494 CDS synADH; promoter 2418 . . . 2482 PrbcL*; 2351 . . . 2398 terminator spf; 97 . . . 507 CDS aztR(7120); 520 . . . 642 promoter PaztA(7120); 641 . . . 2347 CDS zmPDCdeg.

Construction of plasmid #1563: The plasmid pGEM was tailored as a cloning vector for amplification of constructs to be homologously recombined into the *Synechococcus* sp. PCC 7002 chromosome between gene loci A0124 and A0125. Two regions of homology, P-A1 and P-A2, flank the genetic construct to allow for chromosomal homologous integration. The plasmid was furnished with a genetic insert comprising a pyruvate decarboxylase gene from *Zymomonas mobilis* (zmPDC) as a first production gene under the transcriptional control of the zinc-inducible smtB-PsmtA promoter-regulator gene construct, as well as the alcohol dehydrogenase from *Synechocystis* sp. PCC 6803 (synADH) as second production gene under the transcriptional control of the constitutive Prbc* promoter. The map of the plasmid is shown in FIG. 39A, and the sequence is deposited under SEQ ID No:79. Plasmid annotations are as follows: 4739 . . . 6059 intron P-A2; 3621 . . . 4629 marker Sp/Sm; 6906 . . . 7763 marker Amp; 3375 . . . 3406 terminator oop; 2335 . . . 3345 CDS synADH; 2269 . . . 2333 promoter Prbc*, 6 . . . 392 CDS smtB; 393 . . . 492 promoter PsmtA; 2216 . . . 2240 terminator dsrA; 502 . . . 2204 CDS zmPDC; 8981 . . . 10291 intron P-A1.

Construction of plasmid #1568: The plasmid pGEM was tailored as a cloning vector for amplification of constructs to be homologously recombined into the *Synechococcus* sp. PCC 7002 chromosome between gene loci A1330 and A1331. Two regions of homology, P-B1 and P-B2, flank the genetic construct to allow for chromosomal homologous integration. The plasmid was furnished with a genetic insert comprising a degenerated pyruvate decarboxylase gene from *Zymomonas mobilis* (zmPDCdeg) as a first production gene under the transcriptional control of the zinc-inducible smtB-PsmtA promoter-regulator gene construct, as well as the alcohol dehydrogenase from *Synechocystis* sp. PCC 6803 (synADH) as second production gene under the transcriptional control of the constitutive Prbc* promoter. The map of the plasmid is shown in FIG. 39B, and the sequence is deposited under SEQ ID No:80. Plasmid annotations are as follows: 4447 . . . 5530 intron P-B2; 8452 . . . 9516 intron P-B1; 66 . . . 392 CDS smtB; 393 . . . 492 promoter PsmtA; 3684 . . . 4217 marker Gm; 6747 . . . 7604 marker Amp; 3378 . . . 3409 terminator oop; 2338 . . . 3348 CDS synADH; 2272 . . . 2336 promoter Prbc*; 2205 . . . 2252 terminator spf; 495 . . . 2201 CDS zmPDCdeg.

Construction of plasmid #1692: The plasmid pGEM was tailored as a cloning vector for amplification of constructs to be homologously recombined into the *Synechococcus* sp. PCC 7002 chromosome between gene loci A2578 and A2579. Two regions of homology, P-C1 and P-C2, flank the genetic construct to allow for chromosomal homologous integration. The plasmid was furnished with a genetic insert comprising a pyruvate decarboxylase gene from *Zymomonas mobilis* (zmPDC) as a first production gene under the transcriptional control of the zinc-inducible smtB-PsmtA promoter-regulator gene construct, as well as the degenerated alcohol dehydrogenase gene from *Synechocystis* sp. PCC 6803 (synADHdeg) as second production gene under the transcriptional control of the constitutive PrbcL promoter. The map of the plasmid is shown in FIG. 39C and the sequence is deposited under SEQ ID No:81. Plasmid annotations are as follows: 4691 . . . 5875 intron P-C2; 3710 . . . 4491 marker Nm; 7283 . . . 8140 marker Amp; 9357 . . . 10553 intron P-C1; 502 . . . 2202 CDS zmPDC; 3549 . . . 3579 terminator oop; 2538 . . . 3548 CDS synADHdeg; 2243 . . . 2275 terminator oop; 2276 . . . 2534 promoter PrbcL(6803); 6 . . . 392 CDS smtB; 393 . . . 492 promoter PsmtA.

Construction of plasmid #1564: The plasmid pGEM was tailored as a cloning vector for amplification of constructs to be homologously recombined into the *Synechococcus* sp. PCC 7002 chromosome between gene loci A0124 and A0125 as described above. A genetic insert comprising a pyruvate decarboxylase gene from *Zymomonas mobilis* (zmPDC) as a first production gene under the transcriptional control of the cobalt-inducible corR-PcorT promoter-regulator gene construct, as well as the alcohol dehydrogenase from *Synechocystis* sp. PCC 6803 (synADH) as second production gene under the transcriptional control of the constitutive Prbc* promoter were inserted between flanking regions P-A1 and P-A2. The map of the plasmid is shown in FIG. 41A, and the sequence is deposited under SEQ ID No:82. Plasmid annotations are as follows: 1167 . . . 1249 promoter PcorT (6803); 57 . . . 1166 CDS corR(6803); 2969 . . . 2993 terminator dsrA; 1255 . . . 2957 CDS zmPDC; 9734 . . . 11044 intron P-A1; 3022 . . . 3086 promoter Prbc*; 3088 . . . 4098 CDS synADH; 4128 . . . 4159 terminator oop; 7659 . . . 8516 marker Amp; 4374 . . . 5382 marker Sp/Sm; 5492 . . . 6812 intron P-A2.

Construction of plasmid #1633: The plasmid pGEM was tailored as a cloning vector for amplification of constructs to be homologously recombined into the *Synechococcus* sp. PCC 7002 chromosome between gene loci A1330 and A1331 as outlined above. The plasmid was further furnished with a genetic insert comprising a degenerated pyruvate decarboxylase gene from *Zymomonas mobilis* (zmPDCdeg) as a first production gene under the transcriptional control of the cobalt-inducible corR-PcorT*1 promoter-regulator gene construct with optimised ribosome binding site, as well as the alcohol dehydrogenase from *Synechocystis* sp. PCC 6803 (synADH) as second production gene under the transcriptional control of the constitutive Prbc* promoter. The map of the plasmid is shown in FIG. 41B, and the sequence is deposited under SEQ ID No:83. Plasmid annotations are as follows: 54 . . . 1166 CDS corR(6803); 1168 . . . 1247 promoter PcorT*1; 5200 . . . 6283 intron P-B2; 9205 . . . 10269 intron P-B1; 4437 . . . 4970 marker Gm; 7500 . . . 8357 marker Amp; 4131 . . . 4162 terminator oop; 3091 . . . 4101 CDS synADH; 3025 . . . 3089 promoter Prbc*; 2958 . . . 3005 terminator spf; 1248 . . . 2954 CDS zmPDCdeg.

Construction of plasmid #1574: The plasmid pGEM was tailored as a cloning vector for amplification of constructs to be homologously recombined into the *Synechococcus* sp. PCC 7002 chromosome between gene loci A2578 and A2579 as described above. A genetic insert comprising a pyruvate decarboxylase gene from *Zymobacter palmae* (zpPDC) as a first production gene under the transcriptional control of the cobalt-inducible corR-PcorT promoter-regulator gene construct, as well as the degenerated alcohol dehydrogenase gene from *Synechocystis* sp. PCC 6803 (synADHdeg) as second production gene under the transcriptional control of the constitutive Prbc* promoter were inserted between the flanking regions p-C1 and P-C2. The map of the plasmid is shown in FIG. 41C and the sequence is deposited under SEQ ID No:84. Plasmid annotations are as follows: 5259 . . . 6443 intron P-C2; 4117 . . . 4147 terminator oop; 3106 . . . 4116 CDS synADHdeg; 4278 . . . 5059 marker Nm; 7851 . . . 8708 marker Amp; 9925 . . . 11121 intron P-C1; 3040 . . . 3104 promoter Prbc*; 56 . . . 1165 CDS corR(6803); 1166 . . . 1248 promoter PcorT(6803); 1250 . . . 2923 CDS zpPDC; 2924 . . . 3020 terminator ter.

Example 3

Transformation of *Synechocystis* Sp. PCC 6803 by Spontaneous DNA Uptake

*Synechocystis* sp PCC 6803 is a naturally competent bacterium and is characterised by spontaneous uptake of free DNA without any pre-treatment. For transformation, 10 ml of the bacterial culture in a logarithmic growth phase ($OD_{750\,nm}$~0.8) were centrifuged for 10 min at 4000 rpm. The bulk of the supernatant was discarded and the bacterial pellet was resuspended in the remaining supernatant (approximately 100-200 µl). The resulting bacterial culture concentrate was then incubated with approximately 500-1000 ng of the respective transformable DNA for 1-2 hours under non-selective conditions, i.e. no shaking and low-light conditions (25-35 µmol $m^{-2}$ $sec^{-1}$), before being plated on BG11-1% cyanoagar without the addition of antibiotics. After 2 days of incubation at 28° C. (25-35 μmol $m^{-2}$ $sec^{-1}$ PPF), selection conditions were applied by adding the corresponding antibiotic(s) underneath the agar to form a gradient concentration of antibiotic(s). Colony growth on agar plates under selection conditions allowed for positive selection of transformants.

Example 4

Transformation of *Synechocystis* sp. PCC 6803 by Conjugation

The transformation of *Synechocystis* sp. PCC 6803 by conjugation followed the procedure described by Zinchenko et al. (1999). 3 ml overnight cultures were inoculated with *E. coli* strain XL-1 carrying the cargo plasmid (pVZ) and *E. coli* strain J53 [RP4]. The culture was supplemented with appropriate antibiotics (50 μg/ml ampicillin and 20 μg/ml kanamycin for *E. coli* J53 [RP4], and the construct-specific antibiotic for *E. coli* carrying the respective cargo plasmid pVZ). 250 μl of the overnight culture were mixed with about 10 ml LB medium without antibiotics and further cultured in 100 ml Erlenmeyer flasks for another 2.5 hours at 37° C. with shaking Bacteria were harvested by centrifugation in two 15 ml falcon tubes at 2500 rpm for 8 min at room temperature in a Hettich Rotina 240R centrifuge. The bacterial pellets were resuspended in 1 ml LB medium each, then mixed together in 2 ml Eppendorf tubes and centrifuged again (5 min, 2500 rpm in Hettich Mirco 200R centrifuge). The resulting pellet was resuspended in 100 μl LB medium and incubated without shaking 1 h at 30° C. Next, 1.9 ml *Synechocystis* culture of a mid-log growth phase (OD~0.8), was added, shaken slightly and centrifuged. The pellet was resuspended in approximately 50 μl BG-11 medium and dispensed dropwise on a HATF (nitrocellulose membrane) filter (Millipore Durapore Membrane Filter, 0.22 μm), which was located on a prepared culture plate (of 20 ml 2×BG-11 medium, 20 ml cyanoagar and 2 ml LB medium). Incubation for 2 days under low light conditions (25-35 μmol $m^{-2}$ $sec^{-1}$) at 28° C. was maintained. Afterwards, the cells were released from the membrane filter by in 200 μl BG-11 medium. Different dilutions of the cell suspension (1:10 or 1:100) were plated on 1%-cyano agar plate with antibiotic (for *Synechocystis* PCC 6803: Streptomycin 2 μg/ml, Gentamycin 2 μg/ml, Kanamycin 10 μg/ml). After approximately 10 days, first transconjugants became visible. A further week later, single colonies were transferred to plates with higher concentrations of antibiotics (e.g. Gentamycin and Streptomycin 5 μg/ml).

Example 5

Quantitative Determination of Acetaldehyde and/or Ethanol Content in Growth Media by Headspace Gas Chromatography (GC Online Measurement)

In a typical experiment for the quantitative determination of acetaldehyde and/or ethanol content in growth media by headspace gas chromatography (GC), the ethanol production of the respective cyanobacterial culture has to be induced 1-3 days prior to the GC measurement to trigger the overexpression of the pdc and Synadh production genes. For instance, the induction of the ziaA promoter occurred under zinc addition whereas the corT and the nrsB promoter were induced by cobalt and nickel addition, respectively. The induced hybrid cells were either scratched from BG11 plates or harvested from liquid cultures by centrifugation and then resuspended in appropriate fresh marine medium ensuring that the induction conditions were maintained (e.g. mBG11 with 10 μM zinc sulfate prepared with artificial seawater, or an instant ocean supplement for ziaA promoter). The medium was further supplemented with 50 mM TES, pH 7.3 and 20 mM NaHCO3. The sample was adjusted to an $OD_{750\ nm}$ of about 1.2 mL sample were then aliquoted per 20 mL GC vial loaded with 3 ml pure CO2. The tightly closed GC vials were placed onto the illuminated (150 μE $m^{-2}$ $s^{-1}$) headspace auto sampler and were analyzed on the same day on a Shimadzu GC-2010 gas chromatograph equipped with medium-bore capillary column (FS-CS-624, length 30 m; I.D. 0.32 mm; film 1.8 μm) and flame ionisation detector. After completion of the GC measurements, the final $OD_{750\ nm}$ was determined to normalise the ethanol production rate according to the average $OD_{750\ nm}$ of the bacterial sample. The average $OD_{750\ nm}$ was calculated as the arithmetic mean of the $OD_{750\ nm}$ at the time of sample preparation and the OD750 nm after completion of the GC measurement.

Example 6A

Validation of the ziaR-PziaA Promoter Specificity and Tightness in *Synechocystis* sp. PCC6803

A prerequisite for the inventively-used serial induction of different inducible promoters is a high specificity of each promoter to the respective inductor, as well as a tight repression of each promoter in its uninduced state. This prerequisite was tested for each of the metal-inducible promoters that were incorporated in the genetic constructs for the generation of metabolically enhanced *Synechocystis* sp. PCC 6803 set forth in Example 1. Particular focus was given to a potential cross-reactivity of different promoters upon addition of the respective alternative, i.e. unrelated, inductors. In FIG. 7B, the ethanol production of the ethanologenic, chromosome-integrative strain #1145 (for plasmid map refer to FIG. 7A, for nucleotide sequence see SEQ ID NO:30) is depicted that was analyzed by GC online measurements in the presence of either 10 μM $Co^{2+}$, 10 μM $Ni^{2+}$ or 10 μM $Zn^{2+}$, as well as without added metal-ions. The result shows that the ziaR-PziaA promoter regulating the recombinant pdc as first production gene in strain #1145 is very specific for zinc as the inductor, leading to a substantial ethanol production exclusively upon addition of zinc. Thus, the ziaR-PziaA promoter is well suited for use in metabolically enhanced cyanobacteria according to the present invention.

Example 6B

Validation of the corR-PcorT Promoter Specificity and Tightness in *Synechocystis* sp. PCC6803

FIG. 8B shows the ethanol production of the ethanologenic hybrid strain carrying the extrachromosomal plasmid #1217 (for plasmid map refer to FIG. 8A, for nucleotide sequence see SEQ ID NO:23) analyzed by GC online measurement in the presence of either 10 μM $Co^{2+}$, 10 μM $Ni^{2+}$ or 10 μM $Zn^{2+}$, as well as without added metal-ions. The results proof that the corR-PcorT promoter regulating the pdc gene on plasmid #1217 responds very specific to cobalt, leading to a substantial ethanol production exclusively upon addition of cobalt. Therefore, the corR-PcorT promoter tested in this experiment is particularly suitable for use in metabolically enhanced cyanobacteria according to the invention.

Example 6C

Validation of the nrsR-PnrsB Promoter Specificity and Tightness in *Synechocystis* sp. PCC6803

Finally, also the nrsR-PnrsB promoter was tested regarding its specificity and tightness. The ethanol production of the ethanologenic strain #1227 (for plasmid map refer to FIG. 9A, for nucleotide sequence see SEQ ID NO:24) is pictured in FIG. 9B. The ethanol production was analyzed by GC online measurements in the presence of either 10 μM $Co^{2+}$, 10 μM $Ni^{2+}$ or 10 μM $Zn^{2+}$, as well as without added metal-ions. The results demonstrate that the nrsR-PnrsB promoter is very tight as long as no nickel is present in the growth medium. Upon nickel addition, the ethanol production increases significantly. Since the nrsR-PnrsB promoter responds specifically to the presence of nickel, it is, too, well-suitable for use in metabolically enhanced cyanobacteria according to the present invention.

Example 7

Generation of Metabolically Enhanced *Synechocystis* sp. PCC 6803 Hybrid Strains with Multiple First Production Genes and a Second Production Gene

*Synechocystis* sp. PCC 6803 was transformed with constructs #1145 and #1329 to generate and test a metabolically enhanced cyanobacterium harboring three first production genes under the transcriptional control of different inducible promoters and a second production gene under the transcriptional control of a constitutive promoter. First, *Synechocystis* sp. PCC 6803 was transformed with the integrative construct #1145 (pJET-glgA::ziaR-PziaA-ZmPDC-PrbcL-synADH (deg)-Cm) via natural DNA uptake as described in Example 3. The plasmid map is shown in FIG. 7A, and the nucleotide sequence is deposited as SEQ ID NO:30. By homologous recombination with the genomic DNA the ΔglgA (sll1393) mutant containing the ethanologenic gene cassette under control of the zinc-inducible ziaR-PziaA promoter was generated (ΔglgA::ziaR-PziaA-ZmPDC-PrbcL-synADHdeg). After checking for correct replacement of the wild type version against the hybrid version and full segregation of the transformants by a specific polymerase chain reaction, the self-replicating plasmid #1329 (pVZ325a-nrsR-PnrsB-zpPDC-corR PcorT-zmPDC(fco)) was introduced into the ethanologenic ΔglgA mutant by conjugation as described in Example 4. The plasmid comprised two different pdc copies, namely the pdc from *Zymobacter palmae* and a codon optimized pdc from *Zymomonas mobilis*, under control of two different promoters, namely the nrsR-PnrsB and corR-PcorR. The map of plasmid #1329 is shown in FIG. 10A and corresponding DNA sequence is provided as SEQ ID NO:26. The presence of all the three different promoter-pdc constructs in the transformants was verified by PCR. The production gene assembly in the metabolically enhanced hybrid strain *Synechocystis* sp. PCC 6803 #1145/#1329 is schematically represented in FIG. 11A, i.e. one genomic integration of a pdc gene and an adh gene as well as two pdc genes on the pVZ vector #1329.

As a second variant of metabolically enhanced *Synechocystis* sp. PCC 6803 according to the present invention, a hybrid strain comprising the integrative construct #1389 for the endogenous plasmid pSYSG in addition to the ethanologenic chromosome-integrative construct #1145 and a self-replicating pVZ plasmid #1391 was generated. The map of construct #1389, an integrative vector for pSYSG is shown in FIG. 19A and the corresponding DNA sequence is provided as SEQ ID NO:50. The *Synechocystis* sp. PCC 6803 hybrid thus carried the chromosome-integrative construct #1145 with the *Zymomonas mobilis* pdc gene under the transcriptional control of the zinc-inducible ziaR-PziaA promoter as a first production gene, the replicative pVZ vector #1391 with the *Zymobacter palmae* pdc under the transcriptional control of the cobalt-inducible corR-PcorT promoter as the second first production gene and the pSYSG construct #1389 with the degenerated *Zymobacter palmae* pdc under the transcriptional control of the nickel-inducible nrsRS-PnrsB promoter as the third first production gene, as is schematically shown in FIG. 21.

As a third variant of metabolically enhanced *Synechocystis* sp. PCC 6803 according to the present invention, a hybrid strain comprising the ethanologenic chromosome-integrative construct #1145 and the self-replicating pVZ plasmid #1374 was generated. The map of plasmid #1374 is shown in FIG. 26 and the corresponding DNA sequence is provided as SEQ ID NO:67. As is schematically summarised in FIG. 27A, the *Synechocystis* sp. PCC 6803 hybrid #1145/1373 thus harboured three independently inducible pdc gene copies, namely the *Zymomonas mobilis* Pdc gene under the transcriptional control of the zinc-inducible ziaR-PziaA promoter as a first production gene, the *Zymobacter palmae* Pdc under the transcriptional control of the nickel-inducible nrsRS-PnrsB promoter as the second first production gene and the degenerated *Zymomonas mobilis* Pdc under the transcriptional control of the cobalt-inducible corR-PcorT*1 promoter as the third first production gene.

Example 8

Metabolic Characterisation of the Enhanced *Synechocystis* sp. PCC 6803 Hybrid Strains with Multiple First Production Genes and a Second Production Gene The transformant *Synechocystis* sp. PCC 6803 #1145/#1329 described in Example 7 was tested for EtOH production under specific induction conditions in GC online measurements (FIG. 11C). In a control experiment, the *Synechocystis* sp. PCC 6803 transconjugant carrying only plasmid #1329 was analysed as reference (FIG. 11B). The results show that ziaR-PziaA was repressed under non-induced conditions, i.e. in absence of Zn-salts, and induced in presence of Zn-salts. Accordingly, nrsR-PnrsB was repressed in the absence of Ni-salts and in the presence of Zn-salts, respectively, and was specifically induced by the presence of $Ni^{2+}$. CorR-PcorT was not induced in absence of Co-salts and upon addition of Zn-salts or Ni-salts, respectively, but was solely induced upon addition of $Co^{2+}$. As long as neither zinc nor cobalt or nickel were present in the growth medium, all three pdc genes remained silent, i.e. no significant EtOH production (<0.0005% v/v EtOH per $OD_{750\ nm}$) was detectable as a results of the very tight repression of the promoters used. As shown in FIG. 11B, the EtOH production of the reference strain comprising only the extrachromosomal pVZ plasmid #1329 is exclusively induced upon Ni and Co addition, respectively, whereas addition of Zn shows no effect. This results proofs that the additional pdc gene present in the genome of strain #1145/1329 but not in strain #1329 responds specifically to zinc addition. In conclusion, this example and the examples set forth above demonstrated the monospecificity of the three different metal-ion inducible promoters, and further demonstrated that cyanobacterial hybrid strains can be generated comprising at least three different first production genes which can be selectively and sequentially induced via their specific different promoters. FIGS. 12A and 12B show related GC online data from strain #1145/1329. In this experiment the strain #1145/1329 was not pre-induced on agar plates and the cells were accordingly not induced until the transfer to the GC vials that were supplemented with different combinations of zinc, cobalt and nickel. As evident from FIG. 12A, in the vial without added metal-ions almost no ethanol is produced, whereas in both vials with either nickel or cobalt supplementation, ethanol production is induced after a lag phase of about 30 hours. If nickel and cobalt were simultaneously supplemented, the ethanol production was significantly higher than in the vial with only one of both metal-ions added, indicating that two pdc genes were induced at the same time. FIG. 11B shows that similar behaviours were observed for the separate addition of zinc and cobalt in comparison to zinc plus cobalt: Simultaneous addition of zinc and cobalt resulted in a higher ethanol production rate than found for the separate addition of either one of the metal ions. In conclusion, also the data shown in FIGS. 12A and 12B indicate that each of the three pdc genes present in strain #1145/1329 can be selectively induced by the addition of the respective metal ion, thus providing the prerequisite of a selective sequential induction of the three first production genes according to the present invention to minimise genetic alteration and prolong the duration of ethanol production. FIG. 13 shows the results of an experiment investigating the accumulated Pdc activities upon simultaneous induction of different promoters of the three pdc production genes in strain #1145/1329. As expected, simultaneous addition of zinc, nickel and cobalt resulted in the highest Pdc activity, followed by the dual induction compared the sole addition of each metal ion. If none of the metal ions was added, the Pdc activity remained very low, demonstrating the tight repression of all three used inducible promoters.

Furthermore, the alternative transformant *Synechocystis* sp. PCC 6803 #1145/#1374 described in Example 7 was also tested for EtOH production under specific induction conditions in GC online measurements, following the general procedure described above. The results are shown in FIG. 27B and FIG. 27C. FIG. 27B shows the results of ethanol production in %(v/v) ethanol per culture OD over time of *Synechocystis* PCC6803 #1145/1374, as determined by GC online measurement under different induction conditions. It was found that addition of 15 μM Zn (crosshair markers), 5 μM Ni (triangle markers) and 5 μM Co (square markers), respectively, led to specific induction of the corresponding Pdc gene, so that ethanol production took place. In contrast, insignificant ethanol production was observed in the absence of these metals in the control experiment (diamond markers). These findings demonstrated that also in this alternative hybrid strain the Zn, Co, and Ni inducible promoters were selectively addressable by the respective metal ions, with no significant cross-induction detectable. Each of the three promoters specifically drove its operably linked production gene upon induction, as required according to the present invention and supports the specific response of each metal inducible promoter to its specific metal-ion in *Synechocystis* sp. PCC6803, as was already demonstrated in Example 6 above. FIG. 27C shows the Pdc activity in μmol per minute and milligram protein measured for *Synechocystis* PCC6803 #1145/1374 grown under selective induction conditions. In contrast to the control without addition of metal ions, which exhibits a very low Pdc activity, addition of $Ni^{2+}$, $Co^{2+}$ and $Zn^{2+}$, respectively, leads to specific induction of one of the three present Pdc copies.

Example 9

Culture Monitoring

The status of culture with respect to genetic integrity of the production genes and/or productivity of the first chemical compound is continuously or semi-continuously controlled by culture monitoring in order to track the productivity of the culture over the whole production period and to take timely measures upon productivity decrease. Amongst other techniques, culture monitoring included pdc enzyme activity tests as well as determination of ethanol content in the growth media by headspace gas chromatography. In addition, mutations in the pdc gene(s) were monitored by sequencing, enzymatic mismatches detection and/or melting point mismatch detection as well as combinations thereof.

Pdc activity test: The procedure investigates the activity of the overexpressed enzyme pyruvat decarboxylase (Pdc) in induced, ethanol producing cultures. The assay is an optical-enzymatic test wherein the kinetic reaction can be recorded using a spectrophotometer that measures absorbance of a sample over time. Pyruvate is enzymatically converted to acetaldehyde by Pdc, which is reduced to ethanol by ethanol dehydrogenase under NADH oxidation. The determined Pdc activity is related to the protein content, which is measured by Lowry protein assay for determining the total level of protein in solution. For further laboratory reference see for instance Hoppner et al. (1983).

Enzymatic mismatch detection: Enzymatic mismatch detection is performed according to Qiu et al. using the Surveyor Mutation Detection Kit (Transgenomic, NE, USA) according to the manufacturer's instructions. Briefly, the mismatch specific CEL-1 endonuclease from celery rods recognizes mismatches in fragments up to 2 kb. The amplification of two overlapping fragments of the pdc gene is necessary to cover the whole gene sequence. CEL-1 cleaves with high specificity at the 3'-end of any mismatch site in both DNA strands, i.e. base substitutions and insertions or deletions of nucleotides are recognized. To this end, whole DNA is prepared from the bacterial culture in regular intervals throughout the cultivation. Afterwards, the non-mutated and mutated pdc gene copies are amplified by conventional PCR. Next, both types of amplified products are denatured and then re-annealed under non-stringent conditions, leading to mismatched DNA-hybrids consisting of one strand of the original pdc gene and one strand of the mutant version. The DNA-hybrids are then digested with CEL-I endonuclease, leading to a degree of DNA fragmentation proportional to the extent of mutations accumulated in the pdc gene. The degree of DNA fragmentation is determined by DNA gel electrophoresis.

Example 10

Long-Term Cultivation of Metabolically Enhanced *Synechocystis* sp. PCC 6803 Strain #1145/#1374 with Sequential Induction of Multiple First Production Genes

*Synechocystis* sp. PCC 6803 strain #1145/#1374 as well as strain #1145 as a control were grown as pre-cultures in mBG11 liquid medium supplemented with gentamycin and chloramphenicol (strain #1145 only with chloramphenicol)

to apply selection pressure for constructs #1145 and #1374. Neither Zn, Ni or Co were added to the culture at this stage in order to avoid diverting fixed-carbon from cell growth, but to grow the uninduced culture to a high cell density. Upscale of the pre-culture in a main culture using mBG-11 medium (35 psu, artificial seawater salts) without addition of metal ions (Zn, Ni, Co) maintained repression of the three different promoters PziaA, PnrsB and PcorT*1. For plasmid maintenance and contamination control, chloramphenicol in a concentration of 100 mg $L^{-1}$ for #1145 and gentamycin in a concentration of 200 mg $L^{-1}$ for #1145/1374 was used.

Cells were cultivated in 0.5 L round bottles with a culture volume of 0.4 L. Mixing was achieved with a magnetic stir bar at 250 rpm, applied continuously. A light/dark photoperiod of 12 h/12 h was used. Illumination of the cultures was realized by fluorescence lamps (Sylvania Grolux FHO 39W/T5/GRO). The light intensity was dynamically adjusted according to the cell density, increasing from 140 μE m-2 $s^{-1}$ to up to 450 μE m-2 $s^{-1}$, whilst illumination was provided from two sides of the culture vessels. The temperature regime was set to 25-28° C. during the dark phase and 36-39° C. during the light phase. $CO_2$ enriched air was bubbled through the cultures by injection of 0.5% $CO_2$ at a flow rate of 20 mL $min^{-1}$.

The results of this long-term cultivation experiment are shown in FIGS. 28A and B, FIGS. 29A and B and FIGS. 30A and B. FIG. 28A shows the development of culture cell density as $OD_{750\ nm}$ over the cultivation time in days for the hybrid strain #1145/#1374, whereas FIG. 28B shows the same measurement for the control strain #1145. FIG. 29A shows the corresponding ethanol production in %(v/v) for the hybrid strain #1145/#1374 in this experiment, whereas FIG. 29B shows this measurement again for the control strain #1145. FIG. 30A additionally shows the corresponding ethanol production in %(v/v) normalised to the culture OD for the hybrid strain #1145/#1374 in this experiment, whereas FIG. 30B shows this measurement again for the control strain #1145. The graphs represent the results from double-experiments using biological replicates.

As can be seen in FIGS. 28A, 29A and 30A, the experiment was performed for a total cultivation period of about eight weeks. During the first 14 days of cultivation, the cells were induced by zinc addition. For this purpose, 5 μM zinc sulfate was added to the culture on the first cultivation day, and further 10 μM zinc sulfate on the second cultivation day, to give 15 μM zinc sulphate in total. Thenceforth the productivity of the culture was monitored. After about two weeks, a stagnation or decline of the cell density and/or ethanol productivity was detected. Hereupon, a medium exchange was performed by spinning the culture down at 6500 rpm for 10 minutes and replacing the supernatant using fresh mBG-11 medium, thereby adjusting the cell density to an $OD_{750\ nm}$ of about 1. A recovery phase of about one week, illustrated by the dashed vertical lines with the bold arrows in between, was maintained under repressed conditions, i.e. without addition of Zn, Co or Ni. Afterwards, the second induction was then realized by addition of 5 μM cobalt sulphate. After approximately two weeks of cultivation under induced conditions, a stagnation or decline of the cell density and/or ethanol productivity was again detected which was again followed by a medium exchange as outlined above, and one week cultivation under repressed condition for culture recovery. Finally, the third induction was subsequently accomplished with addition of 5 μM nickel sulfate. Accordingly, a third ethanol production phase was observed, until after about two weeks further cultivation time, corresponding to a total cultivation time of approximately 60 days, a stagnation or decline of the cell density and/or ethanol productivity was again detected and the experiment was terminated.

As can be derived from FIGS. 28B, 29B and 30B for the cultivation of the control strain #1145, which contains only one Pdc gene and was cultivated in parallel and treated in the same way as done with the ethanologenic strain #1145/1374, only one first ethanol production phase of about two weeks was observed with this strain.

In summary, the serial induction of the three inducible promoters controlling the recombinant first production genes in *Synechocystis* sp. PCC 6803 strain #1145/#1374 allowed to significantly prolong the production period with the metabolically enhanced cyanobacterium set forth by the present invention when compared to a hybrid strain harbouring only one production gene.

It should be noted that the medium exchange used in the present example may be omitted by directly adding the second or further inducing agent to the culture without the need to remove previously added inducing agent by change of medium.

Example 11

Generation of Metabolically Enhanced *Synechococcus* sp. PCC 7002

*Synechococcus* PCC 7002 was transformed with an ApaI/NsiI digested TK115 construct (pGEM-pAQ4::smtB-PsmtA-PDC-PrbcL-synADHdeg) via natural DNA uptake as set forth in Example 3 for *Synechocystis* sp. PCC 6803. The ApaI/NsiI part of TK115 contains regions of pAQ4 which flank the ethanologenic gene cassette and its promoter smtB-PsmtA (Zn inducible). By homologous recombination with the endogenous pAQ4 plasmid, a transformant comprising smtB-PsmtA-PDC-PrbcL-synADHdeg was generated. For further details refer to the plasmid map of TK115 (FIG. 14A) and the corresponding SEQ ID NO:31, as well as to the corresponding section for TK115 of Example 2. After checking for the correct replacement of the wild type version against the hybrid version, *Synechococcus* sp. PCC 7002 strain TK115 was tested for EtOH production under induction conditions (10 μM Zn) by GC online measurements. After addition of Zn, the *Synechococcus* sp. PCC 7002 strain TK115 strain produced EtOH with a rate of ~0.01% (v/v) $OD^{-1}$ $d^{-1}$. Without Zn and in the presence of Co and Ni the smtB-PsmtA promoter was tight (FIG. 14B).

Example 12

Generation of Metabolically Enhanced *Synechococcus* sp. PCC 7002 Hybrid Strains with Different Combinations of Multiple First Production Genes and at Least One Second Production Gene

*Synechococcus* sp. PCC 7002 strain TK115 was transformed by conjugation according to the method detailed in Example 4 for *Synechocystis* sp. PCC 6803, except that a specific medium for transformation of *Synechococcus* sp. PCC 7002 (according to Stevens et al. 1973) was used for growing *Synechococcus* sp. PCC 7002 prior to conjugation. A variety of different self-replicating ethanologenic pVZ plasmids harboring different combinations of pdc production genes and inducible promoters were used. The following plasmids were tested: #1375 (FIG. 17A, SEQ ID NO:27), #1376 (FIG. 17B, SEQ ID NO:28), #1381 (FIG. 18A, SEQ ID NO:48) and #1383 (FIG. 18B, SEQ ID NO:49). All plasmids contained two different pdc copies: the native version from

*Zymobacter palmae* and a degenerated version of the *Zymomonas mobilis* pdc under control of two different promoters, namely nrsRS-PnrsB and corR-PcorRT. Here, nrsRS-PnrsB was incorporated to provide the Ni inducible and corR-PcorRT was incorporated to provide the Co inducible promoter. The plasmids differed only in the incorporation of optimized ribosomal binding sites (RBS) in some of the promoters, upstream of the *Zymomonas mobilis* and/or *Zymobacter palmae* pdc, which are highlighted in the Figures and sequence denominations with an asterisk (*). The specific modifications of the RBS were incorporated by primer design, i.e. reverse primers PcorT*-EcoRI-rev (SEQ ID NO:53) and PnrsB*-EcoRI-rev (SEQ ID NO:54). The presence of the respective three different promoter-pdc versions in the corresponding *Synechococcus* sp. PCC 7002 hybrid strains, i.e. a first pdc production gene integrated into pAQ4 and two further pdc production genes on the respective pVZ vector, was verified by specific PCR. The transformants were then tested for EtOH production and promoter specificity under defined induction conditions in GC online measurements. The results demonstrate the hybrid strain *Synechococcus* sp. PCC 7002 TK115 responded specifically to Zn and produced EtOH (FIG. 14B). It was also shown that the corR-PcorT promoter in *Synechococcus* sp. PCC 7002 with plasmid #1217 (FIG. 15A) responds specifically to Co without any activation by Zn or Ni (FIG. 15B). In addition, tests with *Synechococcus* sp. PCC 7002 transformed with the self-replicating pVZ plasmid #1356 (FIG. 16A) showed that the nrsRS-PnrsB* promoter controlling the zmPDC gene responded specifically to Ni without detectable activation by Zn (FIG. 16B). However, a cross-induction of the nrsRS-PnrsB* promoter by Co was observed. To circumvent a corresponding problem of cross-induction during a production cultivation, a production gene transcriptionally controlled by the Ni-inducible promoter nrsRS-PnrsB would have to be induced first, i.e. prior to a production gene transcriptionally controlled by the Co-inducible promoter corR-PcorT. By doing that, the observed cross-induction would not be of relevance for the sequential induction of the production genes. The results further demonstrate the required mono-specifity of Zn and Ni, and, with certain limitations, also of Co for induction of smtB-PsmtA, nrsRS-PnrsB and corR-PcorT in the transformants *Synechococcus* sp. PCC 7002 TK115 #1375, *Synechococcus* sp. PCC 7002 TK115 #1376, *Synechococcus* sp. PCC 7002 TK115 #1381 and *Synechococcus* sp. PCC 7002 TK115 #1383, i.e. in these transformants Zn selectively induces smtB-PsmtA, Ni selectively induces nrsRS-PnrsB and Co selectively induces corR-PcorT but the least with slight cross-induction of nrsRS-PnrsB.

In addition, the pVZ325a based construct #1460 (FIG. 31, SEQ ID NO:68) comprising the Pdc gene from *Zymomonas mobilis* under control of a further nickel-inducible promoter was tested in *Synechococcus* sp. PCC7002. The promoter PnrsB(ABCC916) was identified in the genome of a *Synechococcus* species that is closely related to *Synechococcus* PCC7002. Construct #1460 also comprises the $Ni^{2+}$ dependent regulator genes nrsR and nrsS from said *Synechococcus* species, whose gene products act as transcriptional regulators of the nickel-inducible nrsB promoter. FIG. 31B shows the corresponding test of ethanol production of *Synechococcus* PCC7002 hybrid strain #1460 determined by GC online measurement under selective induction conditions. Addition of 2 μM nickel (crosshair markers) specifically induces ethanol production in PCC7002 hybrid strain #1460, whereas no significant ethanol production is observed in samples with 5 μM zinc (square markers), 5 μM cobalt (triangle markers) and with no metal-ions added (diamond markers), respectively. Notably, cobalt addition did not interfere with the action of the PnrsB(ABCC916) promoter from *Synechococcus*. Thus the nrsRS-PnrsB(ABCC916) promoter system derived from the *Synechococcus* species is a particular advantageous $Ni^{2+}$ inducible promoter when used for the purpose of sequential induction of multiple pdc copies in *Synechococcus* PCC7002.

In alternative variants of metabolically enhanced *Synechococcus* sp. PCC 7002 harboring different combinations of multiple first production genes to those detailed above, other integrative constructs for the endogenous *Synechococcus* plasmids pAQ1 and pAQ3 were tested, either in combination or in place of ethanologenic pAQ4 construct TK115. The sequence of TK193, an integrative vector for pAQ3 is provided as SEQ ID NO:52. An example for an alternative *Synechococcus* sp. PCC 7002 transformant, carrying the pAQ4 construct TK115, the replicative pVZ vector #1391 (FIG. 19B, SEQ ID NO:51) and the pAQ3 construct TK193, is schematically shown in FIG. 22.

FIG. 36A schematically shows a further variant of metabolic enhancements in *Synechococcus* sp. PCC7002 hybrid strain TK115/#1470/#1473. The strain comprises three independently inducible pdc gene copies due to integration of each specific pdc cassette in one of the three different endogenous plasmids pAQ4, pAQ3 and pAQ1. The respective plasmid maps and sequences of the constructs TK115, #1470 and #1473 that were used for transformation of *Synechococcus* sp. PCC7002 were already detailed above. FIG. 36B shows the corresponding PCR analysis for confirmation of the presence of the three Pdc gene copies introduced into the endogenous plasmids pAQ4, pAQ3 and pAQ1 of *Synechococcus* sp. PCC7002 hybrid strain TK115/#1470/#1473. The expected PCR products specific for successful integration of each Pdc cassette into the respective endogenous plasmid were only obtained for the desired hybrid strain, whereas the parental strains TK115 and TK115/#1470 were found to produce only one or two positive PCR products, respectively, as expected. The expected size of the PCR product is indicated by the arrow on the left hand side of the shown picture of the DNA agarose gels. FIG. 36C shows the ethanol production in %(v/v) per culture OD observed with *Synechococcus* sp. PCC7002 hybrid strain TK115/#1470/#1473, as determined by GC online measurements under selective induction conditions. Data represent the average of biological duplicates. In contrast to the control GC vial with no metal-ions added (diamond markers), addition of the metal-ions $Zn^{2+}$ (square markers), $Co^{2+}$ (triangle markers) and $Ni^{2+}$ (crosshair markers) specifically induce one of the three introduced Pdc genes, as is evident from the substantially elevated ethanol production. FIG. 36D shows the corresponding ethanol production in %(v/v) per culture OD observed with *Synechococcus* sp. PCC7002 hybrid strain TK115/#1470. Data represent the average of biological duplicates. In comparison to hybrid strain TK115/#1470/#1473, this strain yet lacks the pdc gene under transcriptional control of the nickel-inducible PnrsB916 promoter. The results show that in this case, in contrast to the results obtained from strain TK115/#1470/#1473 shown in FIG. 36C, the addition of $Ni^{2+}$ (crosshair markers) does not induce significant ethanol production, whereas the addition of the metal-ions $Zn^{2+}$ (square markers) and $Co^{2+}$ (triangle markers) again specifically induces substantially elevated ethanol production. Taken together, these results demonstrate that each of the three introduced Pdc copies can be controlled specifically by the choice of added metal-ion which allows a sequential and independent induction procedure that will extent the duration of ethanol production.

As an alternative hybrid strain variant, FIG. 37A schematically shows the two genetic manipulations realised in *Synechococcus* sp. PCC7002 hybrid strain #1332/TK162 harbouring two independently inducible pdc gene copies by integration of two distinct pdc/adh cassettes into the endogenous plasmids pAQ4 and pAQ3, respectively. FIG. 37B shows the results from PCR analysis for confirmation of the two pdc gene copies introduced into the endogenous plasmids pAQ4 and pAQ3 of *Synechococcus* PCC7002. The hybrid strain #1332/TK162 exhibits the expected PCR products confirming the successful integration of both pdc cassettes into the respective endogenous plasmid, whereas the parental hybrid strain #1332 exhibits only one positive PCR product, as expected. The predicted size of the PCR product is indicated by an arrow on the left hand side of the DNA agarose gel image. FIG. 37C shows the results from ethanol production in %(v/v) per OD of *Synechococcus* PCC7002 hybrid strain #1332/TK162, as determined by GC online measurement under selective induction conditions. Whilst in the control sample with no metal-ions added (diamond markers) insignificant ethanol production is observed, the addition 5 μM zinc (square markers), 10 μM cobalt (triangle markers) and 20 μM cobalt (round markers) specifically induce one of both introduced pdc genes and the ethanol production is substantially elevated. This demonstrates that each pdc gene copy can be transcriptionally controlled by addition of zinc and cobalt, respectively, allowing for a sequential and independent induction procedure for an extended duration of ethanol production.

Example 13

Long-Term Cultivation of Metabolically Enhanced *Synechococcus* sp. PCC7002 Hybrid Strain TK115/#1470/#1473 with Sequential Induction of Multiple First Production Genes

*Synechococcus* sp. PCC7002 hybrid strain TK115/#1470/#1473 is grown as pre-culture in mBG11 liquid medium supplemented with kanamycin, gentamycin and streptomycin to apply selection pressure for constructs TK115, #1470 and #1473. Neither Zn, Ni or Co will be added to the culture at this stage in order to avoid diverting fixed-carbon from cell growth, but to grow the uninduced culture to a high cell density. Upscale of the pre-culture into a main culture using mBG-11 medium (35 psu, artificial seawater salts) without addition of metal ions (Zn, Ni, Co) maintains repression of the three different promoters PsmtA, PcorT*1 and PnrsB916.

Cells will be cultivated in 0.5 L round bottles with a culture volume of 0.4 L. Mixing will be achieved with a magnetic stir bar at 250 rpm, applied continuously. For instance, a light/dark photoperiod of 12 h/12 h will be used. Illumination of the cultures will be realized by fluorescence lamps (Sylvania Grolux FHO 39W/T5/GRO). The light intensity will be dynamically adjusted according to the cell density, for instance increasing from 140 $\mu E\ m^{-2}\ s^{-1}$ to up to 450 $\mu E\ m^{-2}\ s^{-1}$, whilst illumination may be provided from two sides of the culture vessels. The temperature regime may be set to 25-28° C. during the dark phase and 36-39° C. during the light phase. $CO_2$ enriched air may be bubbled through the cultures by injection of 0.5% $CO_2$ at a flow rate of 20 mL $min^{-1}$.

At first, the cells may be induced by zinc addition. For this purpose, 5 μM zinc sulfate may be added to the culture on the first cultivation day, and further 5 μM zinc sulfate on the second cultivation day, to give 10 μM zinc sulphate in total. Thenceforth the productivity of the culture will be monitored. After a few weeks, a stagnation or decline of the cell density and/or ethanol productivity may be detected. Hereupon, a medium exchange can be performed, for instance by spinning the culture down at 6500 rpm for 10 minutes and replacing the supernatant using fresh mBG-11 medium, thereby adjusting the cell density to an $OD_{750\ nm}$ of about 1. A recovery phase of about one week may be maintained under repressed conditions, i.e. without addition of Zn, Co or Ni. Alternatively, the medium exchange and recovery phase may be omitted by directly entering the next induction step. Afterwards, the second induction may then realized by addition of 5 μM cobalt sulphate. After several weeks of cultivation under induced conditions, a stagnation or decline of the cell density and/or ethanol productivity may again be detected which may again be followed by a medium exchange as outlined above, and one week cultivation under repressed condition for culture recovery. Alternatively, the medium exchange and recovery phase may again be omitted by directly entering the next induction step. Finally, the third induction may subsequently be accomplished with addition of 2 μM nickel sulfate. Accordingly, a third ethanol production phase may be observed, until after several weeks further cultivation time a stagnation or decline of the cell density and/or ethanol productivity may again be detected and the experiment may be terminated.

In summary, the serial induction of the three inducible promoters controlling the recombinant first production genes in *Synechococcus* sp. PCC7002 hybrid strain TK115/#1470/#1473 may allow to significantly prolong the production period with the metabolically enhanced cyanobacterium set forth by the present invention when compared to a hybrid strain harbouring only one production gene.

Example 14

Generation of Metabolically Enhanced *Synechococcus* sp. PCC 7002 Strains with Multiple First Production Genes Under the Transcriptional Control of Different Promoters which Require Different Concentrations of the Same Inducing Agent for Induction

*Synechococcus* sp. PCC 7002 was transformed with constructs TK115 and #1480 to generate and test a metabolically enhanced cyanobacterium harboring two first production genes under the transcriptional control of different inducible promoters, as well as a second production gene under the transcriptional control of a constitutive promoter. In this example, the promoters controlling the two first production genes are chosen to be both inducible by zinc, but require different concentrations of zinc for full induction.

FIG. 38B is a schematic illustration of the two genetic manipulations realised in *Synechococcus* sp. PCC7002 hybrid strain #TK115/#1480, harbouring two inducible pdc gene copies both controlled by zinc inducible promoters smtB-PsmtA and aztR-PaztA, respectively, integrated into the endogenous plasmids pAQ4 and pAQ3.

FIG. 38C shows the corresponding results from PCR analysis for confirmation of the presence of the two pdc gene copies introduced in the endogenous plasmids pAQ4 and pAQ3 of *Synechococcus* PCC7002. The hybrid strain TK115/#1480 exhibits the expected PCR products which specifically confirm the successful integration of both pdc cassettes into the respective endogenous plasmid, whereas the parental hybrid strain TK115 exhibits only one positive PCR product, as expected. The predicted size of the expected PCR product is indicated by an arrow on the left hand side of the shown picture of the DNA agarose gel images.

FIG. 38D shows the results of the corresponding ethanol production achieved with *Synechococcus* sp. PCC7002 hybrid strain TK115/#1480 compared to the strains TK115 and #1480 harbouring a single pdc gene only, as determined by GC online measurement using a zinc concentration of 5 μM for induction. Data represent the arithmetic mean of biological duplicates. At 5 μM $Zn^{2+}$ addition, which leads to a moderate induction of smtB-PsmtA as well as the aztR-PaztA promoter system in *Synechococcus* PCC7002 the hybrid strain TK115/#1480 (triangle markers) exhibits a substantial higher ethanol production of approximately 0.0109% (v/v) per OD and day compared to both parental strains TK115 (triangle markers) and #1480 (square markers) harbouring only one pdc copy, which produce only 0.0077% and 0.0054% (v/v) per OD and day, respectively. This corresponds to approximately 200% higher ethanol production with hybrid strain TK115/#1480 in comparison to hybrid strain #1480, and approximately 142% higher ethanol production in comparison to hybrid strain TK115 at 5 μM $Zn^{2+}$ addition. This finding is attributed to the elevated gene dosage realized by integration of two different pdc gene copies into pAQ4 and pAQ3.

FIG. 38E shows the corresponding results from ethanol production when 10 μM $Zn^{2+}$ were used for induction of the promoters. It can be derived that under these inducing conditions hybrid strain TK115 exhibits an increased ethanol production compared to induction with 5 μM zinc. The ethanol production of TK115 is very similar to TK115/#1480. In contrast, only a minor increase in the ethanol production rate is observed for #1480 at 10 μM zinc induction.

The results demonstrate that the hybrid strain TK115/#1480 allows accomplishing a high ethanol production already at a moderate induction condition, e.g. 5 μM zinc, and that the ethanol production can be further increased by higher zinc concentrations, because the promoter PsmtA sustains a higher zinc concentration for full induction than the PaztA promoter.

This example illustrates how a metabolically enhanced cyanobacterium with multiple first production genes under control of inducible promoters requiring different concentrations of the same inducing agent can be used inventively for long-term ethanol production to accomplish an essentially constant level of ethanol production. For instance, two first production genes under the transcriptional control of inducible promoters which are inducible by the same inducing agent but require different concentrations of inducing agent for full induction, may be present in the cyanobacterium. During ethanol production, at first a low concentration of inducing agent may be established, leading to high expression of the first production gene under the transcriptional control of the inducible promoter requiring a low inducing agent concentration, whereas the other first production gene under the transcriptional control of the inducible promoter requiring a higher inducing agent concentration may be not expressed or only slightly expressed. Thus, the genetic selection pressure on the latter first production gene is kept low. When, for instance, stagnation or decrease in productivity is observed, for example due to the functional loss of some of the highly expressed first production genes by a "loss of function" mutation, a higher concentration of inducing agent may be added in order to increase the expression level of the first production gene under the transcriptional control of the inducible promoter requiring the higher inducing agent concentration. In this way, the functional loss of first production genes under transcriptional control of the promoter requiring a lower inducing concentration for full induction can be compensated, and the ethanol production can be maintained over a longer period of time by subsequent full induction of the remaining functional pdc gene copy under control of the promoter requiring the higher inducing concentration. Consequently, the ethanol production can be significantly prolonged in comparison to ethanol production with a conventional cyanobacterium harbouring only one first production gene.

As an alternative to the use of different promoters as above, also variants of the same promoter may be used, wherein these variants are engineered so as to require different concentrations of the same inducing agent for induction. As an example, *Synechococcus* sp. PCC 7002 may be transformed with constructs TK162 and a modified version of #1233, hereinafter named #1233*, to generate and test a metabolically enhanced cyanobacterium harboring two first production genes under the transcriptional control of modified variants of the same inducible promoter based on the smtB-PsmtA promoter, as well as a second production gene under the transcriptional control of a constitutive promoter. First, *Synechococcus* sp. PCC 7002 may be transformed with the integrative construct TK162 via natural DNA uptake as described before. The plasmid map is shown in FIG. 24, and the nucleotide sequence is deposited as SEQ ID NO:65. By homologous recombination with the endogenous plasmid pAQ3 the transformant *Synechococcus* sp. PCC 7002 strain TK162 containing the ethanologenic gene cassette under control of the zinc-inducible smtB-PsmtA promoter may be generated. After checking for correct replacement of the wild type version against the hybrid version and full segregation of the transformants by a specific polymerase chain reaction, the integrative plasmid #1233* may be introduced into the ethanologenic *Synechococcus* sp. PCC 7002 strain TK162 by natural uptake as described before. The plasmid #1233* may comprise a different pdc copy than TK162, namely the pdc from *Zymobacter palmae* while TK162 contains the pdc from *Zymomonas mobilis*. In contrast to the original plasmid #1233, the plasmid #1233* may comprise a modified variant of the smtB-PsmtA promoter (smtB-PsmtA*) in control of the pdc-encoding gene. Such a variant of the smtB-PsmtA promoter may comprise base pair substitutions and/or deletions in the operator region, the TATA box and/or ribosome binding sites, respectively, of PsmtA, which change the Zn concentration required for induction of the promoter smtB-PsmtA* compared to its wild-type version. Accordingly, the expression of the pdc from *Zymobacter palmae* on the variant of #1233* may require a different concentration of the inductor $Zn^{2+}$ than the expression of the pdc from *Zymomonas mobilis* on TK162 controlled by the unmodified smtB-PsmtA promoter.

A third and fourth pdc version under control of smtB-PsmtA promoter variants may be introduced on a replicative pVZ version, such as vector #1375 shown in FIG. 17A, after the promoters nrsRS-PnrsB and/or corR-PcorT* have been replaced by further promoter variants smtB-PsmtA and smtB-PsmtA* variants which may again differ from each other as well as from smtB-PsmtA* and the wild type promoter with respect to the Zn concentration required for induction.

Alternatively to variants of the smtB-PsmtA promoter other Zn inducible promoters, such as ziaR-PziaA (from *Synechocystis* sp. PCC6803) in combination with aztR-PaztA (from *Anabaena* sp. PCC7120) in combination with smtB-PsmtA, respectively, may be used to drive sequentially different pdc genes by increasing the concentration of the same inducing agent.

Furthermore, alternatively to the Zn inducible smtB-PsmtA promoter, other metal ion inducible promoters, such as corR-PcorT in combination with correspondingly modified variants, and/or nrsRS-PnrsB in combination with correspondingly modified variants, may be used inventively to selectively drive the expression of the corresponding different pdc genes by increasing the concentration of the same metal-ion inductor.

Example 15

Long-Term Cultivation of Metabolically Enhanced *Synechococcus* sp. PCC 7002 Strain TK162/#1233* with Sequential Induction of Multiple First Production Genes Under the Transcriptional Control of Variants of the Same Promoter Requiring Different Concentrations of the Same Inducing Agent for Induction

*Synechococcus* sp. PCC 7002 strain TK162/#1233* can be grown as a pre-culture in mBG11 liquid medium supplemented with kanamycin and streptomycin to apply selection pressure for constructs TK162 and #1233*. Zn is not added to the culture at this stage in order to avoid diverting fixed-carbon from cell growth, but to grow the uninduced culture to a high cell density. Upscale of the pre-culture into a main culture without addition of metal Zn, maintains repression of the smtB-PsmtA promoters driving the two pdc genes present on TK162 and #1233*. Here, 100 ml pre-culture can be used to inoculate the main culture in 500 ml Crison-PBRS. Upon reaching an $OD_{750\ nm}$ value of approximately 2, the culture may be induced with 5 μM Zn, leading to expression of the ethanologenic genes with *Zymomonas mobilis* pdc on the endogenous plasmid pAQ3 (TK162). Using 5 μM $Zn^{2+}$ the modified variant of the PsmtA promoter (smtB-PsmtA*) present on #1233* may remain essentially uninduced. Induction of smtB-PsmtA on TK162 leads to the production of ethanol. Thenceforth the productivity of the culture may be monitored. After a time period which may be several weeks or a few months, a decline of the productivity and the pdc enzyme activity may be detected. Hereupon the *Zymobacter palmae* pdc gene present on #1233* may be induced by addition of additional 5-10 μM $Zn^{2+}$ leading to expression of this second pdc gene and the recovery of ethanol productivity in the culture before the culture may later become unproductive.

In summary, the serial induction of the inducible promoters controlling the recombinant first production genes can allow to significantly prolong the production period with the metabolically enhanced cyanobacterium set forth by the present invention compared to a conventional hybrid strain.

If the modified construct #1375 with the ethanologenic genes under control of smtB-PsmtA and smtB-PsmtA* is also present in the strain to form *Synechococcus* sp. PCC 7002 strain TK162/#1233*/1375*, the production phase can be further extended by a third and further fourth selective induction of the expression of the corresponding third and fourth pdc gene using the required further increased $Zn^{2+}$ concentrations.

Example 16

Generation of Metabolically Enhanced *Synechococcus* sp. PCC 7002 Strain with Multiple First Production Genes Under the Transcriptional Control of the Same Gradually Inducible Promoter

*Synechococcus* sp. PCC7002 hybrid strain #1563/#1568/#1692 was generated by sequentially introducing three zinc-inducible pdc gene copies controlled by the smtB-PsmtA promoter into different locations of the *Synechococcus* PCC7002 chromosome as shown in FIG. 40A. For this purpose, the construct #1563 was used for integration of a first pdc gene from *Zymomonas mobilis* and an adh gene from *Synechocystis* sp. PCC6803 in between gene loci A0124 and A0125 (integration site A), construct #1568 was used for integration of a degenerated second pdc gene from *Zymomonas mobilis* and an adh gene from *Synechocystis* sp. PCC6803 in between gene loci 1330 and 1331 (integration site B), and construct #1692 was used for integration of a third pdc gene from *Zymomonas mobilis* and an adh gene from *Synechocystis* sp. PCC6803 in between gene loci A2578 and A2579 (integration site C). The successful integration of the three zinc-inducible pdc gene copies and the adh genes in the three different locations of the *Synechococcus* PCC7002 chromosome was verified by PCR analysis (FIG. 40B). PCR analysis of *Synechococcus* PCC7002 #1563/#1568/#1692 yielded all three expected PCR products specific for successful integration of each pdc/adh cassette into the different locations of the chromosome, whereas the parental precursor strains #1563 and #1563/#1568 yielded only one or two positive PCR product respectively, as was expected. The predicted product size of the PCR amplificate is indicated by an arrow on the left hand side of the DNA agarose gel images. Afterwards, the ethanol production with the metabolically enhanced hybrid strain *Synechococcus* sp. PCC7002 #1563/#1568/#1692 (FIG. 40F) was compared with the ethanol production of the precursor strains #1563 (FIG. 40C), #1568 (FIG. 40D) and #1563/#1568 FIG. 40F) harbouring a single pdc gene or two pdc genes only, respectively, by GC online measurement at a zinc concentrations of 0, 5 and 10 μM. Data represent arithmetic mean of biological duplicates for each data point in the graphs. The metabolically enhanced hybrid strain #1563/#1568/#1692 exhibits at both zinc induction concentrations of 5 μM and 10 μM a substantially higher ethanol production compared to the precursor strains with only one pdc gene. The production rate is approximately 171% higher compared to strain #1563, and approximately 239% higher compared to #1568. In addition, still an approximately 112% higher ethanol production rate is observed with hybrid strain #1563/#1568/#1692 in comparison to the precursor strain #1563/#1568 with two pdc genes at both zinc induction concentrations of 5 μM and 10 μM. These results are attributed to the elevated gene dosage realized by integration of three pdc gene copies into different locations of the chromosome.

Taken together, these results clearly show that the smtB-PsmtA promoter can be gradually induced by increasing the zinc-concentration and to correspondingly gradually increase the expression level of the PsmtA-controlled pdc genes, whilst at the same time achieving a relatively high ethanol production rate already at low inducing concentrations due to the elevated pdc gene copy number in the metabolically enhanced cyanobacterium.

As a second variant, a *Synechococcus* sp. PCC7002 hybrid strain #1564/#1633/#1574 was generated by sequentially introducing three cobalt-inducible pdc gene copies controlled by the corR-PcorT promoter into different locations of the *Synechococcus* PCC7002 chromosome as shown in FIG. 42A. For this purpose, the construct #1564 was used for integration of a first pdc gene from *Zymomonas mobilis* and an adh gene from *Synechocystis* sp. PCC6803 in between gene loci A0124 and A0125 (integration site A), construct #1633 was used for integration of a degenerated second pdc gene from *Zymomonas mobilis* and an adh gene from *Synechocystis* sp. PCC6803 in between gene loci 1330 and 1331

(integration site B), and construct #1574 was used for integration of a third pdc gene from *Zymomobacter palmae* and an adh gene from *Synechocystis* sp. PCC6803 in between gene loci A2578 and A2579 (integration site C). The successful integration of the three cobalt-inducible pdc gene copies and the adh genes in the three different locations of the *Synechococcus* PCC7002 chromosome was verified by PCR analysis (FIG. 42B). PCR analysis of *Synechococcus* PCC7002 #1564/#1633/#1574 yielded all three expected PCR products specific for successful integration of each pdc/adh cassette into the different locations of the chromosome, whereas the parental precursor strains #1564 and #1564/#1633 yielded only one or two positive PCR product respectively, as was expected. The predicted product size of the PCR amplificate is indicated by an arrow on the left hand side of the DNA agarose gel images.

Next, the ethanol production with the metabolically enhanced hybrid strain *Synechococcus* sp. PCC7002 #1564/#1633/#1574 will compared with the ethanol production of the precursor strains #1564, #1633 and #1564/#1633 harbouring a single pdc gene and two pdc genes only, respectively, by GC online measurement at cobalt concentrations of 0, 5 and 10 μM. The metabolically enhanced hybrid strain #1564/#1633/#1574 with the three pdc genes may exhibit a higher ethanol production compared to precursor strain #1564, #1633 and #1564/#1633 with one or two pdc gene copies only. This result may be attributed to the elevated gene dosage realized by integration of three pdc gene copies into different locations of the chromosome. These results will demonstrate that also the corR-PcorT promoter can be gradually induced by increasing the cobalt-concentration and to correspondingly gradually increase the expression level of the PcorT-controlled pdc genes, whilst at the same time achieving a relatively high ethanol production rate already at low inducing concentrations due to the elevated pdc gene copy number in the metabolically enhanced cyanobacterium.

In a further variant, *Synechococcus* sp. PCC 7002 can be transformed with constructs TK162 and #1233 to generate and test a metabolically enhanced cyanobacterium harboring two first production genes under the transcriptional control of the same inducible promoter, namely the Zn-inducible promoter smtB-PsmtA, and a second production gene under the transcriptional control of a constitutive promoter. First, *Synechococcus* sp. PCC 7002 can be transformed with the integrative construct TK162 (pGEM-AQ3::smtB-PsmtA-zmPDC-PrbcL-synADHdeg) via natural DNA uptake as described above. The plasmid map is shown in FIG. 24, and the nucleotide sequence is deposited as SEQ ID NO:65. By homologous recombination with the endogenous plasmid pAQ3 the transformant *Synechococcus* sp. PCC 7002 strain TK162 containing the ethanologenic gene cassette under control of the zinc-inducible smtB-PsmtA promoter is generated (pAQ3::smtB-PsmtA-zmPDC-PrbcL-synADHdeg). After checking for correct replacement of the wild type version against the hybrid version and full segregation of the transformants by a specific polymerase chain reaction, the integrative plasmid #1233 (pGEM-AQ4::smtB-PsmtA-zpPDC-PrbcL-synADHdeg.) can be introduced into the ethanologenic transformant strain TK162 by natural uptake as described previously. The plasmid #1233 comprises a different pdc copy than TK162, namely the pdc from *Zymobacter palmae* while TK162 contains the pdc from *Zymomonas mobilis*. By homologous recombination with the endogenous plasmid pAQ4 the transformant strain TK162/#1233 (pAQ3::smtB-zmPDC-PrbcL-synADHdeg, pAQ4::smtB-PsmtA-zpPDC-PrbcL-synADHdeg) is generated. Selection of transformant TK162 occurs via Sm/St and selection of TK162/#1233 via Km/Nm. The map of plasmid #1233 is shown in FIG. 25, the corresponding DNA sequence is provided as SEQ ID NO:66. The presence of both different pdc constructs in the transformant can be verified by PCR.

A third and fourth pdc version under control of smtB-PsmtA can be further introduced into hybrid strain TK162/#1233 on a self-replicative pVZ plasmid, such as plasmid #1375 shown in figure FIG. 17A, after the nrsRS-PnrsB and/or corR-PcorT* of #1375 have been replaced by smtB-PsmtA, to produce the *Synechococcus* sp. PCC 7002 strain TK162/#1233/#1375*. The selection of respective transformants can occur via Gentamycin resistance. Moreover, as alternative to the Zn-inducible smtB-PsmtA promoter of TK162/#1233 or TK162/#1233/#1375*, respectively, other metal ion inducible promoters, such as corR-PcorT or nrsRS-PnrsB can be also used to drive different pdc genes in a dose-dependent manner by increasing the concentration of corresponding inductor metal in subsequent method steps. Preferably, the different pdc genes are located on different genetic elements.

Example 17

Long-Term Cultivation of Metabolically Enhanced *Synechococcus* sp. PCC 7002 Hybrid Strains #1563/#1568/#1692 or #1564/#1633/#1574 with Sequential Gradual Induction of Multiple First Production Genes

*Synechococcus* sp. PCC 7002 #1563/#1568/#1692 or #1564/#1633/#1574 are grown as a pre-culture in mBG11 liquid medium supplemented with Sp, Gm and Km to apply selection pressure for constructs #1563, #1568 and #1692, or #1564, #1633 and #1574, respectively. Zn/Co are not added to the cultures at this stage in order to avoid diverting fixed-carbon from cell growth, but to grow the uninduced culture to a high cell density. Upscale of the #1563/#1568/#1692 pre-culture into a main culture without addition of metals Zn maintains repression of the smtB-PsmtA promoter driving the pdc genes present on #1563, #1568 and #1692, whereas the #1564/#1633/#1574 main culture without addition of Co likewise maintains repression of the corR-PcorT promoter driving the pdc genes present on #1564, #1633, #1574. Here, 100 ml pre-culture can be used to inoculate the main culture in 500 ml Crison-PBRs. Upon reaching an $OD_{750\ nm}$ value of approximately 2, the #1563/#1568/#1692 culture can be induced with 2.5-5 μM $Zn^{2+}$, leading to dose-dependent expression of the pdc genes under control of the smtB-PsmtA promoter. In similar manner, the #1564/#1633/#1574 culture can be induced with 2.5-5 μM $Co^{2+}$, leading to dose-dependent expression of the pdc genes under control of the corR-PcorT promoter. For both strains, due to the increased number of pdc genes under the transcriptional control of the same promoter, a relatively high ethanol production rate can be expected already at a low induction conditions, e.g. 2.5 μM zinc or 2.5 μM cobalt, respectively. After a time period which may be several weeks or a few months, a decline of the productivity and the pdc enzyme activity may be detected. Hereupon, the dose of the inductor $Zn^{2+}$ or $Co^{2+}$ may be increased to 5-10 μM to increase induction of the smtB-PsmtA or corR-PcorT promoter. This will cause elevated transcription of the pdc genes and lead to the recovery of pdc enzyme activity and ethanol productivity in the cultures. After another time period which may be several weeks or a few months, another decline of the productivity and the pdc enzyme activity may be detected. In this case, the production phase can be further extended by a third dose-dependent induction, which may occur at 10-15 μM $Zn^{2+}$ or $Co^{2+}$, respectively, to further increase induction of the smtB-PsmtA or corR-PcorT promoter.

In summary, the dose-dependent gradual induction of the smtB-PsmtA promoter by different levels of $Zn^{2+}$, e.g. a moderate prior to a complete induction, allows to significantly prolong the production period of the first chemical compound with the metabolically enhanced cyanobacterium set forth by the present invention compared to a conventional hybrid strain. The same principle applies to the dose-dependent gradual induction of the corR-PcorT promoter by different levels of $Co^{2+}$.

In this manner, metabolically enhanced cyanobacterial hybrid strains with multiple first production genes under the transcriptional control of the same gradually inducible promoter can be used inventively by stepwisely increasing induction of the promoters to compensate the loss of functional pdc genes, which may for instance happen due to occurrence of a "loss of function" mutation. Thereby ethanol production can be sustained at the same level by appropriate addition of inducing agent, for instance up to 15 μM zinc or 20 μM cobalt, when the number of remaining functional pdc copies is noticeably decreasing. By applying this strategy ethanol production can be maintained over a longer period of time compared to a conventional ethanologenic cell line with only on single pdc gene copy.

Example 18

Long-Term Cultivation of Metabolically Enhanced *Synechococcus* sp. PCC7002 Hybrid Strains TK162/#1233 with Sequential Gradual Induction of Multiple First Production Genes

*Synechococcus* sp. PCC 7002 strain TK162/#1233 is grown as a pre-culture in mBG11 liquid medium supplemented with kanamycin and streptomycin to apply selection pressure for constructs TK162 and #1233. Zn is not added to the culture at this stage in order to avoid diverting fixed-carbon from cell growth, but to grow the uninduced culture to a high cell density. Upscale of the pre-culture into a main culture without addition of Zn maintains repression of the smtB-PsmtA promoter driving the two pdc genes present on #1233 and TK162. Here, 100 ml pre-culture may be used to inoculate the main culture in 500 ml Crison-PBRS. Upon reaching an $OD_{750\ nm}$ value of approximately 2, the culture may be induced with 2.5-5 μM $Zn^{2+}$, leading to dose-dependent expression of the ethanologenic genes encoding the *Zymomonas mobilis* and *Zymobacter palmae* pdc under control of the smtB-PsmtA promoter on construct TK162 and #1233, and to the production of ethanol. Thenceforth the productivity of the culture may be monitored. After a time period which may be several weeks or a few months, a decline of the productivity and the pdc enzyme activity may be detected. Hereupon the dose of the inductor $Zn^{2+}$ may be increased to 10 μM to fully induce the smtB-PsmtA promoter. This may cause full transcription of the pdc genes and lead to the recovery of pdc enzyme activity and ethanol productivity in the culture before the culture may become unproductive. In summary, the dose-dependent gradual induction of the smtB-PsmtA promoter by different levels of $Zn^{2+}$, e.g. a moderate prior to a complete induction, can allow to significantly prolong the production period of the first chemical compound with the metabolically enhanced cyanobacterium set forth by the present invention compared to a conventional hybrid strain.

If the modified construct #1375* harboring the ethanologenic genes under control of the smtB-PsmtA promoter is also present in *Synechococcus* sp. PCC 7002 strain TK162/#1233/#1375*, production phase can be further extended by a third method step for gradual induction of the promoter. For example, the first dose-dependent induction may occur at 3.3 μM $Zn^{2+}$, the second dose-dependent induction may occur at 6.6 μM $Zn^{2+}$+ and the third dose-dependent induction may occur at 10 μM $Zn^{2+}$.

REFERENCE NUMERAL

CB: Cyanobacterial cell

CH: Bacterial chromosome

EP: Endogenous plasmid

VC1: Self-replicating plasmid vector with first production gene under the transcriptional control of a first inducible promoter for the first production gene MT1: Mutation in first production gene CH2: Bacterial chromosome with second first production gene under the transcriptional control of a second inducible promoter for the first production gene EP3: Endogenous plasmid with third first production gene under the transcriptional control of a third inducible promoter for the first production gene MT2: Mutation in the second first production gene VC123: Self-replicating plasmid vector with a first production gene under the transcriptional control of a first inducible promoter for the first production gene, a second first production gene under the transcriptional control of a second inducible promoter for the first production gene, and a third first production gene under the transcriptional control of a third inducible promoter for the first production gene

The invention claimed is:

1. A photoautotrophic cyanobacterium modified to produce ethanol comprising at least one recombinant alcohol dehydrogenase gene and multiple recombinant pyruvate decarboxylase genes wherein the copy number of said multiple recombinant pyruvate decarboxylase genes is greater than the copy number of said at least one recombinant alcohol dehydrogenase gene.

2. The photoautotrophic cyanobacterium of claim 1, wherein said recombinant alcohol dehydrogenase gene is operably linked to a promoter and wherein each of said multiple recombinant pyruvate decarboxylase genes are each operably linked to separate promoters.

3. The photoautotrophic cyanobacterium of claim 1, wherein said photoautotrophic cyanobacterium is capable of having greater expression of said multiple recombinant pyruvate decarboxylase genes than the expression of said recombinant alcohol dehydrogenase gene.

4. The photoautotrophic cyanobacterium of claim 1, wherein said alcohol dehydrogenase gene encodes for an alcohol dehydrogenase whose catalytic activity is NADPH dependent.

5. The photoautotrophic cyanobacterium of claim 4, wherein said alcohol dehydrogenase is derived from a *Synechocystis* sp., *Synechococcus* sp., or *Anabaena* sp. alcohol dehydrogenase.

6. The photoautotrophic cyanobacterium of claim 4, wherein said multiple recombinant pyruvate decarboxylase genes are derived from *Zymomonas* sp.

7. The photoautotrophic cyanobacterium of claim 2, wherein said promoter operably linked to said recombinant alcohol dehydrogenase is constitutive and wherein at least one of said separate promoters operably linked to said pyruvate decarboxylase genes is inducible.

8. The photoautotrophic cyanobacterium of claim 7, wherein one of said separate promoters operably linked to said pyruvate decarboxylase genes is inducible by $Zn^{2+}$.

9. The photoautotrophic cyanobacterium of claim 8, wherein said promoter that is inducible by $Zn^{2+}$has at least 70% identity to to the sequence of a ziaA promoter.

10. The photoautotrophic cyanobacterium of claim 7, wherein said constitutive promoter comprises Prbc.

11. The photoautotrophic cyanobacterium of claim 7, wherein said separate promoters are selected from the group consisting of PntcA, PnbIA, PisiA, PpetJ, PpetE, PggpS, PpsbA2, PpsaA, PsigB, PIrtA, PhtpG, PnirA, PnarB, PnrtA, PhspA, PcIpB1, PhliB, PcrhC, PziaA, PsmtA, PcorT, PnrsB, PnrsB916, PaztA, PbmtA, Pbxa1, PzntA, PczrB, and PnmtA.

12. The photoautotrophic cyanobacterium of claim 7, wherein said separate promoters are selected from the group consisting of PziaA, PsmtA, PcorT, and PnrsB.

13. The photoautotrophic cyanobacterium of claim 7, wherein said separate promoters are responsive to the concentration of nitrate and ammonium.

14. The photoautotrophic cyanobacterium of claim 1, wherein said at least one recombinant alcohol dehydrogenase gene and said multiple recombinant pyruvate decarboxylase genes are located on at least one extrachromosomal plasmid.

15. The photoautotrophic cyanobacterium of claim 14, wherein said at least one recombinant alcohol dehydrogenase gene and said multiple recombinant pyruvate decarboxylase genes are located on two or more extrachromosomal plasmids wherein said plasmids have different copy numbers.

16. The photoautotrophic cyanobacterium of claim 2, wherein said at least one recombinant alcohol dehydrogenase and at least one of said multiple recombinant pyruvate decarboxylase genes are located on the chromosome of said photoautotrophic cyanobacterium.

17. The photoautotrophic cyanobacterium of claim 16, wherein at least one recombinant pyruvate decarboxylase gene is located on at least one extrachromosomal plasmid.

18. The photoautotrophic cyanobacterium of claim 17, comprising two or more extrachromosomal plasmids each containing at least one recombinant pyruvate decarboxylase wherein said plasmids have different copy numbers relative to one another.

19. The photoautotrophic cyanobacterium of claim 7, wherein said inducible promoters are selected from promoters responsive to the concentration of metal ions selected from the group consisting of cobalt, zinc and nickel.

20. The photoautotrophic cyanobacterium of claim 7, wherein one of said inducible promoters is selected from promoters responsive to the concentration of cobalt ions.

21. The photoautotrophic cyanobacterium of claim 7, wherein one of said inducible promoters is selected from promoters responsive to the concentration of zinc ions.

22. The photoautotrophic cyanobacterium of claim 7, wherein one of said inducible promoters is selected from promoters responsive to the concentration of nickel ions.

23. The photoautotrophic cyanobacterium of claim 19, wherein said promoters are selected from different organisms and wherein said promoters have different promoter strengths relative to one another.

24. The photoautotrophic cyanobacterium of claim 1, wherein said cyanobacterium is selected from the group consisting of *Synechocystis, Synechococcus, Anabaena, Chroococcidiopsis, Chlorogloeopsis, Cyanothece, Lyngbya, Phormidium, Nostoc, Spirulina, Arthrospira, Trichodesmium, Leptolyngbya, Plectonema, Myxosarcina, Pleurocapsa, Oscillatoria, Pseudanabaena, Cyanobacterium, Geitlerinema, Euhalothece, Calothrix*, and *Scytonema.*

25. The photoautotrophic cyanobacterium of claim 24, wherein said cyanobacterium is selected from the group consisting of *Synechococcus* sp. strains and *Synechocystis* sp. strains.

* * * * *

UNITED STATES PATENT AND TRADEMARK OFFICE

CERTIFICATE OF CORRECTION

PATENT NO. : 9,315,820 B2
APPLICATION NO. : 14/320477
DATED : April 19, 2016
INVENTOR(S) : Ulf Dühring et al.

It is certified that error appears in the above-identified patent and that said Letters Patent is hereby corrected as shown below:

Title Page, Item 71; Applicant delete “GA” and insert --FL--.

Signed and Sealed this
Sixteenth Day of August, 2016

Michelle K. Lee
*Director of the United States Patent and Trademark Office*

SEQUENCE LISTING

```
<160> NUMBER OF SEQ ID NOS: 84

<210> SEQ ID NO 1
<211> LENGTH: 568
<212> TYPE: DNA
<213> ORGANISM: Artificial
<220> FEATURE:
<223> OTHER INFORMATION: Synthetic construct comprising zinc-inducible
      promoter ziaR-PziaA from Synechocystis PCC6803 (ziaR-sll0792,
      ziaA-slr0798) and SalI/EcoRI restriction sites

<400> SEQUENCE: 1

gtcgacctcc ttaatccgat tcctgcaaat ggtctgcaac ttcccgatac aaattcatca     60
```

-continued

```
catgattatc cgccaagctg tagtaaacat tacggccgac ccggcgatac tttaccaggc    120

gctgcgatcg taaaattcgt aattgatggg aaactgccga ttcactcact ttcatcgccg    180

ctgctaaatc acagacacag agttcttggc gggccaatgc cgacattaaa cgcaaccgac    240

tcggatcagc tagtgcactg aaaaactccg ccatttgctg ggcctggtcc aatgacatca    300

cctctggttg aacctgtcgt acctgctcaa gatgaacaag aggttgatca caaaggggca    360

tctcttcgtt ctggcaggat tgtgactttg acaacgagga cttactcata gaggttggcg    420

ttaggagcta gggaaaaatt taaactggat ttagaaaatg attttcatcc taacatcttt    480

aatatctgag catatcttca ggtgtttcaa gatttgtgct acggttcaag gaggtttttc    540

tttaaatcac gttggccgcc atgaattc                                      568


<210> SEQ ID NO 2
<211> LENGTH: 1256
<212> TYPE: DNA
<213> ORGANISM: Artificial
<220> FEATURE:
<223> OTHER INFORMATION: Synthetic construct comprising cobalt-inducible
      promoter corR-PcorT from Synechocystis PCC6803 (corR-sll0794,
      corT-slr0797) and SalI/EcoRI restriction sites

<400> SEQUENCE: 2

gtcgaccatg cgtccaaaac tttcaccatc ctttccctat caacctttac tgcactaaag     60

acaagtgaga tagcagtggc aatctggctt tgcaatcaat gtttccacta aagcgtttag    120

cgttactgcg gctagaagtc ctccaccgag gctcccctga atggtgatat ggggaatggg    180

actggtcatc agtcgtcgtt ttgcccccgg agcatgacta aaaccgatcg gcattccgat    240

cacaagagcc ggctgaatat gttgttgctc tatcagctta caggcagtga gtaaaacaga    300

aggggcatag ccgatcgcca gcacacatcc ttggggaatc tgttgtaacc gctgttgcca    360

atggtcatgg tgccaaaaag cttgctcggc ttccctaagc cctgtgatgt gagggtcgtc    420

aatcagcgtt ttaaccgtac atcctaaatg agctaaccga gtttgatcaa gagccgcagc    480

cacaaccgga acatcggtga cgactggaca ccctgctttc agtgcatctc gtgccgaggc    540

gatcgctccc tgactcaatc gaacggcgtt taccaagcta acatcaccac aggccagcac    600

taattgatgt agtaagtgaa tggtaatttc agagtaagcc gataaatccg gtagcaggtg    660

tttgagggat tcctgaaagg cttctggatg agttgttgtc tccgcatcta ggttcgtcca    720

caactgatcg agttttccta acccctcctg gacatccaca tcaagctgtt tcagttgggc    780

cagagcttcc gcttgggtaa tctggcaact ctggtcgcgt cccagtaatc cttctaaagc    840

agatgcggtt tggcggagtc gagtaatctg ctgaatcaca gcctgatatt gctgttgcaa    900

ctgcaccatt agggtgggat caaggctctc ttcagaatgg ctatccagca gttgccgaat    960

atgagacaac tgaaagccct gctgtttgag ggcaatgact cgttggagcc gttgtacgtc   1020

ctgctgagta taaaggcggt agttgccctc tgagcgttga acggggggaa gcaatcccag   1080

ggtgtggtaa tggcgcacca tgcgaggcgt aacgccacct cccactgcat ctgtgagttc   1140

tttaatcgtt aagtgattag tcttcatccc tttagtttac tcaaaacctt gacattgaca   1200

ctaatgttaa ggtttaggct gagaaggtaa aaatccaagt taaaaagcat gaattc       1256


<210> SEQ ID NO 3
<211> LENGTH: 2309
<212> TYPE: DNA
<213> ORGANISM: Artificial
<220> FEATURE:
<223> OTHER INFORMATION: Synthetic construct comprising nickel-inducible
```

-continued promoter nrsRS-PnrsB from Synechocystis PCC6803 (nrsS-sll0798, nrsR-sll0797, nrsB-slr0793) and SalI/EcoRI restriction sites

<400> SEQUENCE: 3

```
gtcgacccta tatcgggctt ttctcaataa aatctttatt ttttgaggtg ctttttagcc     60
ataaataatc actttagtat aaaattttga cggcgtaaag ttgataaaat agaattaaga    120
atggactatc ggtacagaaa aaatgggtaa ctggatggtg aataaacttc ccttacccaa    180
tgcactctcc accgttaaag accccctatg cttaacggtg atcacctggg caatggcgag    240
tcccaaccct gtcccccccg ttttgcgcga acgatctcga ttaactcggt aaaaacgctc    300
aaaaatgtgt tcctgttggt cgggggcaat gccgatgccg gtatcttgca cggtgatgat    360
agccatctgt tcatgggatg tcagggtaat atcaacacgt cccccagcag ttgtgtattg    420
aatggcgttg gcaattaggt ttgagaccag tcgatagagt tgggattcat taccccaggc    480
gtaaacttcc cctgaactca gatcactgct gagatcaatg tgggcggcga tcgctaattc    540
taaaaactct tcggtgaggt cactgactaa atcatttaaa caacaaagcc gccaatcttc    600
ggcggtggtt tcctgctcta agcgacttag tagcaataaa tccgtaatca attggcttaa    660
tcgccttccc tgtcgttcaa cggtatgtag catggtgtta atttctgggg aatggcttga    720
gtcgatgcgt aataccgctt ccaccgtggc caacagacta gccaatggcg atcgtaattc    780
atgggctgca ttcgcggtga attgttgttg ttgttggtag gactggtaaa tgggacgcat    840
ggctaacccc gctaagcccc aactggagaa ggcgaccaaa cccagggcaa tgggaaaact    900
aagccctaaa atccaaagaa tacgtttatt ttcggcatca aaggctgcca ggctccggcc    960
aatttgtaga tagccccagg aagatttgtc tgtattaccg gcgctatgca aaatggtggt   1020
gaattgtcga taccgatcgc cggttggggg gtgaatagtc tgccaagttt cctggttaaa   1080
aatggaggat agggaagccg gttgattagg cgaaaaagcc agcaggttgc cttgataatc   1140
aaataaacga atgtaatata aactgcgatc actaatgccc aacgtgtgac gttcaatcag   1200
ggtggggttg acctggcagg gttggttgac caaacacaga tcgggcaaca ttttttgtaa   1260
tactccggtg ggactagcat tactcggcaa catcggctct aaactgtcat gcaacgtccc   1320
ggcgatcgac tccacttctc gctccaacgc catccagttg gcctgcacaa tggcacgata   1380
aacccccaac cccaacaggg taagaatacc ccccattact agggcatacc agaaagccaa   1440
ttgcagacga ctacgggcaa agaggcgacg ggtattcatg gcgatagggt gaaccgatag   1500
ccttgaccgg gaactgtttt aattgggcaa ggacaatttt gttgagctag cttgcgtcgt   1560
atcaaacgca tttgggccgc caccacatta ctcatgggct cctcatcaag atcccacagt   1620
tgttgccgga tcttgctacc ggaaatgatc cgctctgggt tttgcatcag atattgaaaa   1680
atttgaaatt ctcttacggt taaagcaatt tcctgtcttt ctaggtttag tggctccgag   1740
atagttaccg ataacagatt attactggga tcaaggctga agttgcccaa agttaaaatt   1800
tgcggttgga attgtggcga tcgccgttgt agtgcccgca gtcttgctaa tagctctgcc   1860
atcacaaacg gttttgttag atagtcatct gccccggcat ctagtccttc gacacggttt   1920
tccggttctc ctaacgctgt taacatcaac accggcaagg aattaccctg ggttctcagt   1980
ttttgacaga gttccaaacc cgataatccc ggcagtaacc aatccacaat ggcaagggtg   2040
tattccgtcc attgattttc caaataatcc caagcttggg agccatccgt cacccaatcc   2100
accacatact tttcactaac tagcactttc ttaatagcca ttcccaaatc cgtctcatct   2160
tccaccagca aaattcgcat cgcctctgcc ttttttataa cggtctgatc ttagcggggg   2220
```

-continued aaggagattt tcacctgaat ttcataccccc ctttggcaga ctgggaaaat cttggacaaa 2280
ttcccaattt gaggtggtgt gatgaattc 2309

<210> SEQ ID NO 4
<211> LENGTH: 503
<212> TYPE: DNA
<213> ORGANISM: Artificial
<220> FEATURE:
<223> OTHER INFORMATION: Synthetic construct comprising zinc-inducible promoter smtB-PsmtA from Synechococcus PCC7002 (smtB-SYNPCC7002_A2564, smtA-SYNPCC7002_A2563) and SalI/EcoRI restriction sites

<400> SEQUENCE: 4
gtcgacgggc aaactttatg aagcagatca agcctatatc cgccaagcaa ccggcagccg 60
cgttgattag tgggtgtgtc catcctctgg ttcgtctagg tgctccgaag cgtcacgata 120
gagattaaga atgtggtgat ccttgaggcg ataaatcaca ttccgccctt ccttgcgata 180
gctcactaaa cgtgctgtgc gcagggttct tagttggtga gagacagccg attcactcat 240
ttcaacggcg gcggcgagtt cccccacccg catctctcca gtggccaggg ccgaaagaat 300
acgccagcgg ttggcatccc ccaagacacc aaaaaattcg gccatccgtt gggccttggc 360
ttggttcaag attttgccac tgtggtctgt cattgttcgc tgatctaaac aatacctgaa 420
taattgttca tgtgttaatc taaaaatgtg aacaatcgtt caactattta agacaatacc 480
ttggaggttt aaaccatgaa ttc 503

<210> SEQ ID NO 5
<211> LENGTH: 21
<212> TYPE: DNA
<213> ORGANISM: Artificial
<220> FEATURE:
<223> OTHER INFORMATION: Synthetically prepared primer sequence ziaR/PziaA-SalI-fw for the amplification of the construct comprising the ziaR-PziaA promoter sequence from Synechocystis sp. PCC6803 including SalI restriction site

<400> SEQUENCE: 5
atcgtcgacc tccttaatcc g 21

<210> SEQ ID NO 6
<211> LENGTH: 21
<212> TYPE: DNA
<213> ORGANISM: Artificial
<220> FEATURE:
<223> OTHER INFORMATION: Synthetically prepared forward primer PziaA-SalI-fw for the amplification of the construct comprising the PziaA promoter sequence without the ziaR regulator gene including SalI restriction site

<400> SEQUENCE: 6
aggtcgacgt taggagctag g 21

<210> SEQ ID NO 7
<211> LENGTH: 21
<212> TYPE: DNA
<213> ORGANISM: Artificial
<220> FEATURE:
<223> OTHER INFORMATION: Synthetically produced reverse primer PziaA-EcoRI-rev for the amplification of the construct comprising the comprising the ziaR-PziaA promoter sequence from Synechocystis sp. PCC6803 including EcoRI restriction site

<400> SEQUENCE: 7
aagaattcat ggcggccaac g 21

<210> SEQ ID NO 8
<211> LENGTH: 27
<212> TYPE: DNA
<213> ORGANISM: Artificial
<220> FEATURE:
<223> OTHER INFORMATION: Synthetically produced forward primer corR/PcorT-SalI-fw for the amplification of the construct comprising the corR-PcorT promoter sequence from Synechocystis sp. PCC6803 including SalI restriction site

<400> SEQUENCE: 8
gtcgaccatg cgtccaaaac tttcacc 27

<210> SEQ ID NO 9
<211> LENGTH: 31
<212> TYPE: DNA
<213> ORGANISM: Artificial
<220> FEATURE:
<223> OTHER INFORMATION: Synthetically produced reverse primer PcorT-EcoRI-rev for the amplification of the construct comprising the corR-PcorT promoter sequence from Synechocystis sp. PCC6803 including EcoRI restriction site

<400> SEQUENCE: 9
gaattcatgc tttttaactt ggatttttac c 31

<210> SEQ ID NO 10
<211> LENGTH: 25
<212> TYPE: DNA
<213> ORGANISM: Artificial
<220> FEATURE:
<223> OTHER INFORMATION: Synthetically produced forward primer nrsRS/PnrsB-SalI-fw for the amplification of the construct comprising the nrsRS-PnrsB promoter sequence from Synechocystis sp. PCC6803 including SalI restriction site

<400> SEQUENCE: 10
gtcgacccta tatcgggctt ttctc 25

<210> SEQ ID NO 11
<211> LENGTH: 26
<212> TYPE: DNA
<213> ORGANISM: Artificial
<220> FEATURE:
<223> OTHER INFORMATION: Synthetically produced forward primer nrsR/PnrsB-SalI-fw for the amplification of the construct comprising the nrsR-PnrsB promoter sequence from Synechocystis sp. PCC6803 without the nrsS regulator gene including SalI restriction site

<400> SEQUENCE: 11
gtcgacggga gtttgcaaac tccctc 26

<210> SEQ ID NO 12
<211> LENGTH: 27
<212> TYPE: DNA
<213> ORGANISM: Artificial
<220> FEATURE:
<223> OTHER INFORMATION: Synthetically produced reverse primer PnrsB-EcoRI-rev for the amplification of the construct comprising the nrsRS-PnrsB promoter sequence from Synechocystis sp. PCC6803 including EcoRI restriction site

<400> SEQUENCE: 12
gaattcatca caccacctca aattggg 27

<210> SEQ ID NO 13

-continued

<211> LENGTH: 29
<212> TYPE: DNA
<213> ORGANISM: Artificial
<220> FEATURE:
<223> OTHER INFORMATION: Synthetically produced forward primer smtB/PsmtA-SalI-fw for the amplification of the construct comprising the smtB-PsmtA promoter sequence from Synechococcus sp. PCC7002 including SalI restriction site

<400> SEQUENCE: 13
gtcgacgggc aaactttatg aagcagatc 29

<210> SEQ ID NO 14
<211> LENGTH: 28
<212> TYPE: DNA
<213> ORGANISM: Artificial
<220> FEATURE:
<223> OTHER INFORMATION: Synthetically produced forward primer PsmtA-SalI-fw for the amplification of the construct comprising the PsmtA promoter sequence from Synechococcus sp. PCC7002 without the smtB regulator gene including SalI restriction site

<400> SEQUENCE: 14
gtcgactgtg gtctgtcttt gttcgctg 28

<210> SEQ ID NO 15
<211> LENGTH: 32
<212> TYPE: DNA
<213> ORGANISM: Artificial
<220> FEATURE:
<223> OTHER INFORMATION: Synthetically produced reverse primer PsmtA-EcoRI-rev for the amplification of the construct comprising the smtB-PsmtA promoter sequence from Synechococcus sp. PCC7002 including EcoRI restriction site

<400> SEQUENCE: 15
gaattcatgg tttaaacctc caaggtattg tc 32

<210> SEQ ID NO 16
<211> LENGTH: 1710
<212> TYPE: DNA
<213> ORGANISM: Zymomonas mobilis

<400> SEQUENCE: 16
atgaattctt atactgtcgg tacctattta gcggagcggc ttgtccagat tggtctcaag 60
catcacttcg cagtcgcggg cgactacaac ctcgtccttc ttgacaacct gcttttgaac 120
aaaaacatgg agcaggttta ttgctgtaac gaactgaact gcggtttcag tgcagaaggt 180
tatgctcgtg ccaaaggcgc agcagcagcc gtcgttacct acagcgtcgg tgcgctttcc 240
gcatttgatg ctatcggtgg cgcctatgca gaaaaccttc cggttatcct gatctccggt 300
gctccgaaca acaatgatca cgctgctggt cacgtgttgc atcacgctct tggcaaaacc 360
gactatcact atcagttgga aatggccaag aacatcacgg ccgcagctga agcgatttac 420
accccagaag aagctccggc taaaatcgat cacgtgatta aaactgctct tcgtgagaag 480
aagccggttt atctcgaaat cgcttgcaac attgcttcca tgccctgcgc cgctcctgga 540
ccggcaagcg cattgttcaa tgacgaagcc agcgacgaag cttctttgaa tgcagcggtt 600
gaagaaaccc tgaaattcat cgccaaccgc gacaaagttg ccgtcctcgt cggcagcaag 660
ctgcgcgcag ctggtgctga agaagctgct gtcaaatttg ctgatgctct cggtggcgca 720
gttgctacca tggctgctgc aaaaagcttc ttcccagaag aaaacccgca ttacatcggt 780
acctcatggg gtgaagtcag ctatccgggc gttgaaaaga cgatgaaaga agccgatgcg 840

```
gttatcgctc tggctcctgt cttcaacgac tactccacca ctggttggac ggatattcct     900

gatcctaaga aactggttct cgctgaaccg cgttctgtcg tcgttaacgg cgttcgcttc     960

cccagcgttc atctgaaaga ctatctgacc cgtttggctc agaaagtttc caagaaaacc    1020

ggtgctttgg acttcttcaa atccctcaat gcaggtgaac tgaagaaagc cgctccggct    1080

gatccgagtg ctccgttggt caacgcagaa atcgcccgtc aggtcgaagc tcttctgacc    1140

ccgaacacga cggttattgc tgaaaccggt gactcttggt tcaatgctca gcgcatgaag    1200

ctcccgaacg gtgctcgcgt tgaatatgaa atgcagtggg gtcacatcgg ttggtccgtt    1260

cctgccgcct tcggttatgc cgtcggtgct ccggaacgtc gcaacatcct catggttggt    1320

gatggttcct tccagctgac ggctcaggaa gtcgctcaga tggttcgcct gaaactgccg    1380

gttatcatct tcttgatcaa taactatggt tacaccatcg aagttatgat ccatgatggt    1440

ccgtacaaca acatcaagaa ctgggattat gccggtctga tggaagtgtt caacggtaac    1500

ggtggttatg acagcggtgc tggtaaaggc ctgaaggcta aaaccggtgg cgaactggca    1560

gaagctatca aggttgctct ggcaaacacc gacggcccaa ccctgatcga atgcttcatc    1620

ggtcgtgaag actgcactga agaattggtc aaatggggta agcgcgttgc tgccgccaac    1680

agccgtaagc ctgttaacaa gctcctctag                                     1710


<210> SEQ ID NO 17
<211> LENGTH: 1677
<212> TYPE: DNA
<213> ORGANISM: Zymomobacter palmae

<400> SEQUENCE: 17

atgaattcct ataccgttgg tatgtacttg gcagaacgcc tagcccagat cggcctgaaa      60

caccactttg ccgtggccgg tgactacaac ctggtgttgc ttgatcagct cctgctgaac     120

aaagacatgg agcaggtcta ctgctgtaac gaacttaact gcggctttag cgccgaaggt     180

tacgctcgtg cacgtggtgc cgccgctgcc atcgtcacgt tcagcgtagg tgctatctct     240

gcaatgaacg ccatcggtgg cgcctatgca gaaaacctgc cggtcatcct gatctctggc     300

tcaccgaaca ccaatgacta cggcacaggc cacatcctgc accacaccat tggtactact     360

gactataact atcagctgga aatggtaaaa cacgttacct gcgcagctga aagcatcgtt     420

tctgccgaag aagcaccggc aaaaatcgac cacgtcatcc gtacggctct acgtgaacgc     480

aaaccggctt atctggaaat cgcatgcaac gtcgctggcg ctgaatgtgt tcgtccgggc     540

ccgatcaata gcctgctgcg tgaactcgaa gttgaccaga ccagtgtcac tgccgctgta     600

gatgccgccg tagaatggct gcaggaccgc cagaacgtcg tcatgctggt cggtagcaaa     660

ctgcgtgccg ctgccgctga aaaacaggct gttgccctag cggaccgcct gggctgcgct     720

gtcacgatca tggctgccga aaaaggcttc ttcccggaag atcatccgaa cttccgcggc     780

ctgtactggg gtgaagtcag ctccgaaggt gcacaggaac tggttgaaaa cgccgatgcc     840

atcctgtgtc tggcaccggt attcaacgac tatgctaccg ttggctggaa ctcctggccg     900

aaaggcgaca atgtcatggt catggacacc gaccgcgtca ctttcgcagg acagtccttc     960

gaaggtctgt cattgagcac cttcgccgca gcactggctg agaaagcacc ttctcgcccg    1020

gcaacgactc aaggcactca agcaccggta ctgggtattg aggccgcaga gcccaatgca    1080

ccgctgacca atgacgaaat gacgcgtcag atccagtcgc tgatcacttc cgacactact    1140

ctgacagcag aaacaggtga ctcttggttc aacgcttctc gcatgccgat tcctggcggt    1200

gctcgtgtcg aactggaaat gcaatggggt catatcggtt ggtccgtacc ttctgcattc    1260
```

ggtaacgccg ttggttctcc ggagcgtcgc cacatcatga tggtcggtga tggctctttc 1320
cagctgactg ctcaagaagt tgctcagatg atccgctatg aaatcccggt catcatcttc 1380
ctgatcaaca accgcggtta cgtcatcgaa atcgctatcc atgacggccc ttacaactac 1440
atcaaaaact ggaactacgc tggcctgatc gacgtcttca atgacgaaga tggtcatggc 1500
ctgggtctga aagcttctac tggtgcagaa ctagaaggcg ctatcaagaa agcactcgac 1560
aatcgtcgcg gtccgacgct gatcgaatgt aacatcgctc aggacgactg cactgaaacc 1620
ctgattgctt ggggtaaacg tgtagcagct accaactctc gcaaaccaca agcgtaa 1677

<210> SEQ ID NO 18
<211> LENGTH: 1710
<212> TYPE: DNA
<213> ORGANISM: Artificial
<220> FEATURE:
<223> OTHER INFORMATION: Synthetically produced codon-degenerated Pdc
gene from Zymomonas mobilis (ZmPDCdeg)

<400> SEQUENCE: 18
atgaattcct acaccgttgg cacttacctg gctgaacgct tggttcagat cggcttaaaa 60
caccattttg ctgttgctgg tgattataat ttggttttgt tagataattt attgctcaat 120
aagaatatgg aacaggtgta ctgttgcaat gagttaaatt gtggcttttc cgctgagggc 180
tacgcccgtg ctaagggtgc tgctgctgct gttgtgactt attctgttgg cgctttgagt 240
gcttttgacg ccattggcgg tgcttacgct gagaatttgc cagtgatttt aattagtggc 300
gccccaaata ataacgacca tgccgccggc catgtcctcc accatgcctt gggtaagact 360
gattaccatt accaactgga gatggctaaa aatattaccg ctgctgccga agctatctat 420
actcctgagg aagccccagc caagattgac catgtcatca agaccgcctt gcgggaaaaa 480
aaaccagtgt acttagagat tgcctgtaat atcgccagta tgccttgtgc tgccccccggt 540 ccagcttctg ctctctttaa cgatgaagct tctgatgagg ccagtctcaa cgctgctgtg 600
gaggaaactt taaagtttat tgctaatcgt gataaggtgg ctgttttagt tggttctaaa 660
ttacgtgctg ccggcgccga ggaagccgcc gttaagtttg ccgacgcctt aggcggtgct 720
gtggccacta tggccgccgc taagtctttt tttcctgaag agaatccaca ctatattggc 780
actagctggg gcgaggtttc ttacccaggt gtggagaaaa ccatgaagga ggctgacgct 840
gtgattgcct tagccccggt ttttaatgat tatagtacta ccggctggac cgacatcccg 900
gacccgaaaa agttagtgtt agccgaacca cggagtgttg ttgtgaatgg tgtgcgtttt 960
ccttctgtgc acttaaagga ttacttaact cggctcgccc agaaggtgag taaaaagact 1020
ggcgccctcg atttttttaa gagtttaaac gctggcgagt taaaaaaggc tgccccagcc 1080
gacccatccg ccccactcgt taatgctgaa attgctcggc aggttgaggc cttgttaact 1140
ccaaatacca ccgtgatcgc cgaaactggc gatagttggt ttaacgccca acgtatgaaa 1200
ttaccaaatg gcgcccgtgt ggagtacgag atgcaatggg gccatattgg ctggagtgtg 1260
ccggctgctt ttggctacgc tgttggcgcc ccagagcggc gtaatatttt aatggtgggc 1320
gacggcagtt ttcagttaac cgcccaagag gttgcccaaa tggtgcgttt aaagttacca 1380
gtgattattt ttctcattaa caattacggc tatactattg aggtgatgat tcacgacggc 1440
ccatataata atattaaaaa ttgggactac gctggcttaa tggaggtctt taatggcaat 1500
ggcggctacg attctggcgc cggcaagggt ttaaaagcca agactggcgg tgagttagct 1560
gaagccatta aagtggcctt agctaatact gatggtccta ctttaattga gtgttttatt 1620
ggccgggaag attgtaccga ggaactcgtt aagtggggca aacgtgtggc cgctgctaat 1680
tctcggaaac ccgtgaataa attattatga 1710

<210> SEQ ID NO 19
<211> LENGTH: 1677
<212> TYPE: DNA
<213> ORGANISM: Artificial
<220> FEATURE:
<223> OTHER INFORMATION: Synthetically produced codon-degenerated Pdc
gene from Zymobacter palmae (ZpPDCdeg)

<400> SEQUENCE: 19
atgaattctt acactgtggg catgtatctc gcggagcggt tggctcaaat tggtttaaag 60
catcatttcg ctgtcgctgg cgattataat ttagtcctct tagaccaatt gttgttaaat 120
aaggatatgg aacaagttta ttgttgcaat gaattgaatt gtggtttctc tgctgagggc 180
tatgcccgcg cgcgcggcgc tgctgccgct attgttacct tttctgtggg cgccatttcc 240
gcgatgaatg ctattggcgg tgcttacgcg gaaaatttac ccgttatttt aatttccggt 300
agtcccaata ctaacgatta tgggaccggg catattttac atcatactat cggcaccacc 360
gattacaatt accaattaga gatggtgaag catgtgactt gtgctgccga atctattgtg 420
tccgctgagg aagcgcccgc gaagattgat catgttattc gcaccgcctt gcgcgagcgg 480
aagcccgcct acttagaaat tgcgtgtaat gttgccggtg ccgagtgcgt gcgccccggt 540
cccattaact ctttattacg cgaattggag gtggatcaaa cttccgttac cgctgccgtg 600
gacgctgctg tggagtggtt acaagatcgg caaaatgttg ttatgttagt tggctctaag 660
ttacgcgctg ccgctgccga gaagcaagct gtggctttgg ccgatcggtt aggttgtgcc 720
gttaccatta tggccgctga gaagggtttt tttcctgagg accaccccaa ttttcggggt 780
ttatattggg gcgaagtttc tagtgagggc gcgcaagaat tagtggagaa tgctgacgct 840
attttatgct tggcgcccgt gtttaatgat tacgccactg tgggttggaa tagttggccc 900
aagggtgata acgttatggt tatggatact gatcgggtta cctttgcggg tcaaagtttt 960
gaaggcttaa gtctctctac ttttgctgcg gcgttagccg aaaaggcgcc ctcgcggccc 1020
gcgaccaccc aggggaccca ggcgcccgtg ttaggcatcg aagctgcgga acctaacgcg 1080
cccttaacta acgatgagat gacccgccaa attcaatctt taattaccag tgataccacc 1140
ttaaccgcgg aaaccggcga ttcctggttt aatgcctccc ggatgcccat ccccggtggc 1200
gcccgcgttg agttagagat gcagtggggc cacattggct ggagtgtgcc gtccgcgttt 1260
ggcaatgctg tgggctcccc cgaacgccgt catattatga tggttggcga cggtagtttt 1320
caattaaccg cccaggaggt ggcccaaatg attcggtacg aaattcccgt tattatcttt 1380
ttgattaata atcggggcta tgttattgag attgccattc acgatggtcc gtataattat 1440
attaagaatt ggaattatgc cggtttaatt gatgttttta acgatgaaga cggccacggt 1500
ttaggcttaa aggcctccac cggcgcggag ttggaaggtg ccattaaaaa ggcgttggat 1560
aaccgccggg gccccacctt aattgagtgc aatattgccc aagatgattg taccgaaact 1620
ttaatcgcct ggggcaagcg cgtggcggcc actaattccc ggaagcccca ggcctga 1677

<210> SEQ ID NO 20
<211> LENGTH: 9803
<212> TYPE: DNA
<213> ORGANISM: Artificial
<220> FEATURE:
<223> OTHER INFORMATION: Self-replicating broad host range vector -continued pVZ322a with aph (KanR2), GmR and CmR antibiotic resistance
cassettes

<400> SEQUENCE: 20

```
tcgacgaatt tctgccattc atccgcttat tatcacttat tcaggcgtag caccaggcgt     60
ttaagggcac caataactgc cttaaaaaaa ttacgccccg ccctgccact catcgcagta    120
ctgttgtaat tcattaagca ttctgccgac atggaagcca tcacagacgg catgatgaac    180
ctgaatcgcc agcggcatca gcaccttgtc gccttgcgta taatatttgc ccatggtgaa    240
aacgggggcg aagaagttgt ccatattggc cacgtttaaa tcaaaactgg tgaaactcac    300
ccagggattg gctgagacga aaaacatatt ctcaataaac cctttaggga aataggccag    360
gttttcaccg taacacgcca catcttgcga atatatgtgt agaaactgcc ggaaatcgtc    420
gtggtattca ctccagagcg atgaaaacgt ttcagtttgc tcatggaaaa cggtgtaaca    480
agggtgaaca ctatcccata tcaccagctc accgtctttc attgccatac ggaattccgg    540
atgagcattc atcaggcggg caagaatgtg aataaaggcc ggataaaact tgtgcttatt    600
tttctttacg gtctttaaaa aggccgtaat atccagctga acggtctggt tataggtaca    660
ttgagcaact gactgaaatg cctcaaaatg ttctttacga tgccattggg atatatcaac    720
ggtggtatat ccagtgattt ttttctccat tttagcttcc ttagctcctg aaaatctcga    780
taactcaaaa aatacgcccg gtagtgatct tatttcatta tggtgaaagt tggaacctct    840
tacgtgccga tcaacgtctc attttcgcca aaagttggcc cagggcttcc cggtatcaac    900
agggacacca ggatttattt attctgcgaa gtgatcttcc gtcacaggta tttattcgaa    960
gacgaaaggg cctcgtgata cgcctatttt tataggttaa tgtcatgata ataatggttt   1020
cttagacgtc aggtggcact tttcggggaa atgtgcgcgg aacccctatt tgtttatttt   1080
tctaaataca ttcaaatatg tatccgctca tgagacaata accctgataa atgcttcaat   1140
aatattgaaa aaggaagagt atgagtattc aacatttccg tgtcgccctt attccctttt   1200
ttgcggcatt ttgccttcct gtttttgctc acccagaaac gctggtgaaa gtaaaagatg   1260
ctgaagatca gttgggtgca cgagtgggtt acatcgaact ggatctcaac agcggtaaga   1320
tccttgagag ttttcgcccc gaagaacgtt ttccaatgat gagcactttt aaagttctgc   1380
tatgtggcgc ggtattatcc cgtgttgacg ccgggcaaga gcaactcggt cgccgcatac   1440
actattctca gaatgacttg gttgagtact caccagtcac agaaaagcat cttacggatg   1500
gcatgacagt aagagaatta tgcagtgctg ccataaccat gagtgataac actgcggcca   1560
acttacttct gacaacgatc ggaggaccga aggagctaac cgcttttttg cacaacatgg   1620
gggatcatgt aactcgcctt gatcgttggg aaccggagct gaatgaagcc ataccaaacg   1680
acgagcgtga caccacgatg cctgcaggag cagaagagca tacatctgga agcaaagcca   1740
ggaaagcggc ctatggagct gtgcggcagc gctcagtagg caatttttca aaatattgtt   1800
aagccttttc tgagcatggt atttttcatg gtattaccaa ttagcaggaa aataagccat   1860
tgaatataaa agataaaaat gtcttgttta caatagagtg gggggggtca gcctgccgcc   1920
ttgggccggg tgatgtcgta cttgcccgcc gcgaactcgg ttaccgtcca gcccagcgcg   1980
accagctccg gcaacgcctc gcgcacccgc tggcggcgct tgcgcatggt cgaaccactg   2040
gcctctgacg gccagacata gccgcacaag gtatctatgg aagccttgcc ggttttgccg   2100
gggtcgatcc agccacacag ccgctggtgc agcaggcggg cggtttcgct gtccagcgcc   2160
cgcacctcgt ccatgctgat gcgcacatgc tggccgccac ccatgacggc ctgcgcgatc   2220
```

-continued

```
aaggggttca gggccacgta caggcgcccg tccgcctcgt cgctggcgta ctccgacagc   2280
agccgaaacc cctgccgctt gcggccattc tgggcgatga tggatacctt ccaaaggcgc   2340
tcgatgcagt cctgtatgtg cttgagcgcc ccaccactat cgacctctgc cccgatttcc   2400
tttgccagcg cccgatagct acctttgacc acatggcatt cagcggtgac ggcctcccac   2460
ttgggttcca ggaacagccg gagctgccgt ccgccttcgg tcttgggttc cgggccaagc   2520
actaggccat taggcccagc catggccacc agcccttgca ggatgcgcag atcatcagcg   2580
cccagcggct ccgggccgct gaactcgatc cgcttgccgt cgccgtagtc atacgtcacg   2640
tccagcttgc tgcgcttgcg ctcgccccgc ttgagggcac ggaacaggcc gggggccaga   2700
cagtgcgccg ggtcgtgccg gacgtggctg aggctgtgct tgttcttagg cttcaccacg   2760
gggcaccccc ttgctcttgc gctgcctctc cagcacggcg ggcttgagca ccccgccgtc   2820
atgccgcctg aaccaccgat cagcgaacgg tgcgccatag ttggccttgc tcacaccgaa   2880
gcggacgaag aaccggcgct ggtcgtcgtc cacaccccat tcctcggcct cggcgctggt   2940
catgctcgac aggtaggact gccagcggat gttatcgacc agtaccgagc tgccccggct   3000
ggcctgctgc tggtcgcctg cgcccatcat ggccgcgccc ttgctggcat ggtgcaggaa   3060
cacgatagag cacccggtat cggcggcgat ggcctccatg cgaccgatga cctgggccat   3120
ggggccgctg gcgttttctt cctcgatgtg gaaccggcgc agcgtgtcca gcaccatcag   3180
gcggcggccc tcggcggcgc gcttgaggcc gtcgaaccac tccggggcca tgatgttggg   3240
caggctgccg atcagcggct ggatcagcag gccgtcagcc acggcttgcc gttcctcggc   3300
gctgaggtgc gccccaaggg cgtgcaggcg gtgatgaatg gcggtgggcg ggtcttcggc   3360
gggcaggtag atcaccgggc cggtgggcag ttcgcccacc tccagcagat ccggcccgcc   3420
tgcaatctgt gcggccagtt gcagggccag catggattta ccggcaccac cgggcgacac   3480
cagcgccccg accgtaccgg ccaccatgtt gggcaaaacg tagtccagcg gtggcggcgc   3540
tgctgcgaac gcctccagaa tattgatagg cttatgggta gccattgatt gcctcctttg   3600
caggcagttg gtggttaggc gctggcgggg tcactacccc cgccctgcgc cgctctgagt   3660
tcttccaggc actcgcgcag cgcctcgtat tcgtcgtcgg tcagccagaa cttgcgctga   3720
cgcatccctt tggccttcat gcgctcggca tatcgcgctt ggcgtacagc gtcagggctg   3780
gccagcaggt cgccggtctg cttgtccttt tggtctttca tatcagtcac cgagaaactt   3840
gccggggccg aaaggcttgt cttcgcggaa caaggacaag gtgcagccgt caaggttaag   3900
gctggccata tcagcgactg aaaagcggcc agcctcggcc ttgtttgacg tataaccaaa   3960
gccaccgggc aaccaatagc ccttgtcact tttgatcagg tagaccgacc ctgaagcgct   4020
tttttcgtat tccataaaac cccccttctgt gcgtgagtac tcatagtata acaggcgtga   4080
gtaccaacgc aagcactaca tgctgaaatc tggcccgccc ctgtccatgc ctcgctggcg   4140
gggtgccggt gcccgtgcca gctcggcccg cgcaagctgg acgctgggca gacccatgac   4200
cttgctgacg gtgcgctcga tgtaatccgc ttcgtggccg ggcttgcgct ctgccagcgc   4260
tgggctggcc tcggccatgg ccttgccgat ttcctcggca ctgcggcccc ggctggccag   4320
cttctgcgcg gcgataaagt cgcacttgct gaggtcatca ccgaagcgct tgaccagccc   4380
ggccatctcg ctgcggtact cgtccagcgc cgtgcgccgg tggcggctaa gctgccgctc   4440
gggcagttcg aggctggcca gcctgcgggc cttctcctgc tgccgctggg cctgctcgat   4500
ctgctggcca gcctgctgca ccagcgccgg gccagcggtg gcggtcttgc ccttggattc   4560
acgcagcagc acccacggct gataaccggc gcgggtggtg tgcttgtcct tgcggttggt   4620
```

gaagcccgcc aagcggccat agtggcggct gtcggcgctg gccgggtcgg cgtcgtactc 4680
gctggccagc gtccgggcaa tctgccccg aagttcaccg cctgcggcgt cggccacctt 4740
gacccatgcc tgatagttct tcgggctggt ttccactacc agggcaggct cccggccctc 4800
ggctttcatg tcatccaggt caaactcgct gaggtcgtcc accagcacca gaccatgccg 4860
ctcctgctcg gcgggcctga tatacacgtc attgccctgg gcattcatcc gcttgagcca 4920
tggcgtgttc tggagcactt cggcggctga ccattcccgg ttcatcatct ggccggtggt 4980
ggcgtccctg acgccgatat cgaagcgctc acagcccatg gccttgagct gtcggcctat 5040
ggcctgcaaa gtcctgtcgt tcttcatcgg gccaccaagc gcagccagat cgagccgtcc 5100
tcggttgtca gtggcgtcag gtcgagcaag agcaacgatg cgatcagcag caccaccgta 5160
ggcatcatgg aagccagcat cacggttagc catagcttcc agtgccaccc ccgcgacgcg 5220
ctccgggcgc tctgcgcggc gctgctcacc tcggcggcta cctcccgcaa ctctttggcc 5280
agctccaccc atgccgcccc tgtctggcgc tgggctttca gccactccgc cgcctgcgcc 5340
tcgctggcct gctgggtctg gctcatgacc tgccgggctt cgtcggccag tgtcgccatg 5400
ctctgggcca gcggttcgat ctgctccgct aactcgttga tgcctctgga tttcttcact 5460
ctgtcgattg cgttcatggt ctattgcctc ccggtattcc tgtaagtcga tgatctgggc 5520
gttggcggtg tcgatgttca gggccacgtc tgcccggtcg gtgcggatgc cccggccttc 5580
catctccacc acgttcggcc ccaggtgaac accgggcagg cgctcgatgc cctgcgcctc 5640
aagtgttctg tggtcaatgc gggcgtcgtg gccagcccgc tctaatgccc ggttggcatg 5700
gtcggcccat gcctcgcggg tctgctcaag ccatgccttg ggcttgagcg cttcggtctt 5760
ctgtgccccg cccttctccg ggtcttgcc gttgtaccgc ttgaaccact gagcggcggg 5820
ccgctcgatg ccgtcattga tccgctcgga gatcatcagg tggcagtgcg ggttctcgcc 5880
gccaccggca tggatggcca gcgtatacgg caggcgctcg gcaccggtca ggtgctgggc 5940
gaactcggac gccagcgcct tctgctggtc gagggtcagc tcgaccggca gggcaaattc 6000
gacctccttg aacagccgcc cattggcgcg ttcatacagg tcggcagcat cccagtagtc 6060
ggcgggccgc tcgacgaact ccggcatgtg cccggattcg gcgtgcaaga cttcatccat 6120
gtcgcgggca tacttgcctt cgcgctggat gtagtcggcc ttggccctgg ccgattggcc 6180
gcccgacctg ctgccggttt tcgccgtaag gtgataaatc gccatgctgc ctcgctgttg 6240
cttttgcttt tcggctccat gcaatggccc tcggagagcg caccgcccga agggtggccg 6300
ttaggccagt ttctcgaaga gaaaccggta agtgcgccct cccctacaaa gtagggtcgg 6360
gattgccgcc gctgtgcctc catgatagcc tacgagacag cacattaaca atggggtgtc 6420
aagatggtta aggggagcaa caaggcggcg gatcggctgg ccaagctcga agaacaacga 6480
gcgcgaatca atgccgaaat tcagcgggtg cgggcaaggg aacagcagca agagcgcaag 6540
aacgaaacaa ggcgcaaggt gctggtgggg gccatgattt tggccaaggt gaacagcagc 6600
gagtggccgg aggatcggct catggcggca atggatgcgt accttgaacg cgaccacgac 6660
cgcgccttgt tcggtctgcc gccacgccag aaggatgagc cgggctgaat gatcgaccga 6720
gacaggccct gcggggctgc acacgcgccc ccacccttcg ggtaggggga aaggccgcta 6780
aagcggctaa aagcgctcca gcgtatttct gcggggtttg gtgtggggtt tagcgggctt 6840
tgcccgcctt tccccctgcc gcgcagcggt ggggcggtgt gtagcctagc gcagcgaata 6900
gaccagctat ccggcctctg gccgggcata ttgggcaagg gcagcagcgc cccacaaggg 6960

-continued

```
cgctgataac cgcgcctagt ggattattct tagataatca tggatggatt tttccaacac   7020
cccgccagcc cccgcccctg ctgggtttgc aggtttgggg gcgtgacagt tattgcaggg   7080
gttcgtgaca gttattgcag gggggcgtga cagttattgc aggggttcgt gacagttagt   7140
acgggagtga cgggcactgg ctggcaatgt ctagcaacgg caggcatttc ggctgagggt   7200
aaaagaactt tccgctaagc gatagactgt atgtaaacac agtattgcaa ggacgcggaa   7260
catgcctcat gtggcggcca ggacggccag ccgggatcgg gatactggtc gttaccagag   7320
ccaccgaccc gagcaaaccc ttctctatca gatcgttgac gagtattacc cggcattcgc   7380
tgcgcttatg gcagagcagg gaaaggaatt gccgggctat gtgcaacggg aatttgaaga   7440
atttctccaa tgcgggcggc tggagcatgg ctttctacgg gttcgctgcg agtcttgcca   7500
cgccgagcac ctggtcgctt tcagctgtaa tccgggcagc gcaacggaac attcatcagt   7560
gtaaaaatgg aatcaataaa gccctgcgca gcgcgcaggg tcagcctgaa tacgcgtgct   7620
cgaattgaca taagcctgtt cggttcgtaa actgtaatgc aagtagcgta tgcgctcacg   7680
caactggtcc agaaccttga ccgaacgcag cggtggtaac ggcgcagtgg cggttttcat   7740
ggcttgttat gactgttttt ttgtacagtc tatgcctcgg gcatccaagc agcaagcgcg   7800
ttacgccgtg ggtcgatgtt tgatgttatg gagcagcaac gatgttacgc agcagcaacg   7860
atgttacgca gcagggcagt cgccctaaaa caaagttagg tggctcaagt atgggcatca   7920
ttcgcacatg taggctcggc cctgaccaag tcaaatccat gcgggctgct cttgatcttt   7980
tcggtcgtga gttcggagac gtagccacct actcccaaca tcagccggac tccgattacc   8040
tcgggaactt gctccgtagt aagacattca tcgcgcttgc tgccttcgac caagaagcgg   8100
ttgttggcgc tctcgcggct tacgttctgc ccaggtttga gcagccgcgt agtgagatct   8160
atatctatga tctcgcagtc tccggcgagc accggaggca gggcattgcc accgcgctca   8220
tcaatctcct caagcatgag gccaacgcgc ttggtgctta tgtgatctac gtgcaagcag   8280
attacggtga cgatcccgca gtggctctct atacaaagtt gggcatacgg gaagaagtga   8340
tgcactttga tatcgaccca agtaccgcca cctaacaatt cgttcaagcc gagatcggct   8400
tcccggccct agacgcgtat tcaggctgac cctgcgcgct gcgcagggct ttattgattc   8460
catttttaca ctgatgaatg ttccgttgcg ctgcccggat tacagatcct ctagaactag   8520
tggatccccc gggctgcagg gggggggggg aaagccacgt tgtgtctcaa aatctctgat   8580
gttacattgc acaagataaa aatatatcat catgaacaat aaaactgtct gcttacataa   8640
acagtaatac aaggggtgtt atgagccata ttcaacggga aacgtcttgc tcgaggccgc   8700
gattaaattc caacatggat gctgatttat atgggtataa atgggctcgc gataatgtcg   8760
ggcaatcagg tgcgacaatc tatcgattgt atgggaagcc cgatgcgcca gagttgtttc   8820
tgaaacatgg caaaggtagc gttgccaatg atgttacaga tgagatggtc agactaaact   8880
ggctgacgga atttatgcct cttccgacca tcaagcattt tatccgtact cctgatgatg   8940
catggttact caccactgcg atccccggga aaacagcatt ccaggtatta gaagaatatc   9000
ctgattcagg tgaaaatatt gttgatgcgc tggcagtgtt cctgcgccgg ttgcattcga   9060
ttcctgtttg taattgtcct tttaacagcg atcgcgtatt tcgtctcgct caggcgcaat   9120
cacgaatgaa taacggtttg gttgatgcga gtgattttga tgacgagcgt aatggctggc   9180
ctgttgaaca agtctggaaa gaaatgcata agcttttgcc attctcaccg gattcagtcg   9240
tcactcatgg tgatttctca cttgataacc ttatttttga cgaggggaaa ttaataggtt   9300
gtattgatgt tggacgagtc ggaatcgcag accgatacca ggatcttgcc atcctatgga   9360
```

```
actgcctcgg tgagttttct ccttcattac agaaacggct tttcaaaaa tatggtattg   9420
ataatcctga tatgaataaa ttgcagtttc atttgatgct cgatgagttt ttctaatcag   9480
aattggttaa ttggttgtaa cactggcaga gcattacgct gacttgacgg gacggcggct   9540
ttgttgaata aatcgaactt ttgctgagtt gaaggatcag atcacgcatc ttcccgacaa   9600
cgcagaccgt tccgtggcaa agcaaaagtt caaaatcacc aactggtcca cctacaacaa   9660
agctctcatc aaccgtggct ccctcacttt ctggctggat gatggggcga ttcaggcctg   9720
gtatgagtca gcaacacctt cttcacgagg cagacctcag cgcccccccc ccccggaatt   9780
cgatatcaag cttatcgata ccg                                           9803
```

<210> SEQ ID NO 21
<211> LENGTH: 9781
<212> TYPE: DNA
<213> ORGANISM: Artificial
<220> FEATURE:
<223> OTHER INFORMATION: Self-replicating broad host range vector pVZ325a with Sp/Sm, GmR and CmR antibiotic resistance cassettes

<400> SEQUENCE: 21

```
tcgacgaatt tctgccattc atccgcttat tatcacttat tcaggcgtag caccaggcgt     60
ttaagggcac caataactgc cttaaaaaaa ttacgccccg ccctgccact catcgcagta    120
ctgttgtaat tcattaagca ttctgccgac atggaagcca tcacagacgg catgatgaac    180
ctgaatcgcc agcggcatca gcaccttgtc gccttgcgta taatatttgc ccatggtgaa    240
aacgggggcg aagaagttgt ccatattggc cacgtttaaa tcaaaactgg tgaaactcac    300
ccagggattg gctgagacga aaaacatatt ctcaataaac cctttaggga aataggccag    360
gttttcaccg taacacgcca catcttgcga atatatgtgt agaaactgcc ggaaatcgtc    420
gtggtattca ctccagagcg atgaaaacgt ttcagtttgc tcatggaaaa cggtgtaaca    480
agggtgaaca ctatcccata tcaccagctc accgtctttc attgccatac ggaattccgg    540
atgagcattc atcaggcggg caagaatgtg aataaaggcc ggataaaact tgtgcttatt    600
tttctttacg gtctttaaaa aggccgtaat atccagctga acggtctggt tataggtaca    660
ttgagcaact gactgaaatg cctcaaaatg ttctttacga tgccattggg atatatcaac    720
ggtggtatat ccagtgattt ttttctccat tttagcttcc ttagctcctg aaaatctcga    780
taactcaaaa aatacgcccg gtagtgatct tatttcatta tggtgaaagt tggaacctct    840
tacgtgccga tcaacgtctc attttcgcca aaagttggcc cagggcttcc cggtatcaac    900
agggacacca ggatttattt attctgcgaa gtgatcttcc gtcacaggta tttattcgaa    960
gacgaaaggg cctcgtgata cgcctatttt tataggttaa tgtcatgata ataatggttt   1020
cttagacgtc aggtggcact tttcggggaa atgtgcgcgg aacccctatt tgtttatttt   1080
tctaaataca ttcaaatatg tatccgctca tgagacaata accctgataa atgcttcaat   1140
aatattgaaa aaggaagagt atgagtattc aacatttccg tgtcgccctt attccctttt   1200
ttgcggcatt ttgccttcct gtttttgctc acccagaaac gctggtgaaa gtaaaagatg   1260
ctgaagatca gttgggtgca cgagtgggtt acatcgaact ggatctcaac agcggtaaga   1320
tccttgagag ttttcgcccc gaagaacgtt ttccaatgat gagcactttt aaagttctgc   1380
tatgtggcgc ggtattatcc cgtgttgacg ccgggcaaga gcaactcggt cgccgcatac   1440
actattctca gaatgacttg gttgagtact caccagtcac agaaaagcat cttacggatg   1500
gcatgacagt aagagaatta tgcagtgctg ccataaccat gagtgataac actgcggcca   1560
```

-continued

```
acttacttct gacaacgatc ggaggaccga aggagctaac cgcttttttg cacaacatgg   1620
gggatcatgt aactcgcctt gatcgttggg aaccggagct gaatgaagcc ataccaaacg   1680
acgagcgtga caccacgatg cctgcaggag cagaagagca tacatctgga agcaaagcca   1740
ggaaagcggc ctatggagct gtgcggcagc gctcagtagg caatttttca aaatattgtt   1800
aagccttttc tgagcatggt atttttcatg gtattaccaa ttagcaggaa aataagccat   1860
tgaatataaa agataaaaat gtcttgttta caatagagtg gggggggtca gcctgccgcc   1920
ttgggccggg tgatgtcgta cttgcccgcc gcgaactcgg ttaccgtcca gcccagcgcg   1980
accagctccg gcaacgcctc gcgcacccgc tggcggcgct tgcgcatggt cgaaccactg   2040
gcctctgacg gccagacata gccgcacaag gtatctatgg aagccttgcc ggttttgccg   2100
gggtcgatcc agccacacag ccgctggtgc agcaggcggg cggtttcgct gtccagcgcc   2160
cgcacctcgt ccatgctgat gcgcacatgc tggccgccac ccatgacggc ctgcgcgatc   2220
aaggggttca gggccacgta caggcgcccg tccgcctcgt cgctggcgta ctccgacagc   2280
agccgaaacc cctgccgctt gcggccattc tgggcgatga tggatacctt ccaaaggcgc   2340
tcgatgcagt cctgtatgtg cttgagcgcc ccaccactat cgacctctgc cccgatttcc   2400
tttgccagcg cccgatagct acctttgacc acatggcatt cagcggtgac ggcctcccac   2460
ttgggttcca ggaacagccg gagctgccgt ccgccttcgg tcttgggttc cgggccaagc   2520
actaggccat taggcccagc catggccacc agcccttgca ggatgcgcag atcatcagcg   2580
cccagcggct ccgggccgct gaactcgatc cgcttgccgt cgccgtagtc atacgtcacg   2640
tccagcttgc tgcgcttgcg ctcgccccgc ttgagggcac ggaacaggcc gggggccaga   2700
cagtgcgccg ggtcgtgccg gacgtggctg aggctgtgct tgttcttagg cttcaccacg   2760
gggcaccccc ttgctcttgc gctgcctctc cagcacggcg ggcttgagca ccccgccgtc   2820
atgccgcctg aaccaccgat cagcgaacgg tgcgccatag ttggccttgc tcacaccgaa   2880
gcggacgaag aaccggcgct ggtcgtcgtc cacaccccat tcctcggcct cggcgctggt   2940
catgctcgac aggtaggact gccagcggat gttatcgacc agtaccgagc tgccccggct   3000
ggcctgctgc tggtcgcctg cgcccatcat ggccgcgccc ttgctggcat ggtgcaggaa   3060
cacgatagag cacccggtat cggcggcgat ggcctccatg cgaccgatga cctgggccat   3120
ggggccgctg gcgttttctt cctcgatgtg gaaccggcgc agcgtgtcca gcaccatcag   3180
gcggcggccc tcggcggcgc gcttgaggcc gtcgaaccac tccggggcca tgatgttggg   3240
caggctgccg atcagcggct ggatcagcag gccgtcagcc acggcttgcc gttcctcggc   3300
gctgaggtgc gccccaaggg cgtgcaggcg gtgatgaatg gcggtgggcg ggtcttcggc   3360
gggcaggtag atcaccgggc cggtgggcag ttcgcccacc tccagcagat ccggcccgcc   3420
tgcaatctgt gcggccagtt gcagggccag catggattta ccggcaccac cgggcgacac   3480
cagcgccccg accgtaccgg ccaccatgtt gggcaaaacg tagtccagcg gtggcggcgc   3540
tgctgcgaac gcctccagaa tattgatagg cttatgggta gccattgatt gcctcctttg   3600
caggcagttg gtggttaggc gctggcgggg tcactacccc cgccctgcgc cgctctgagt   3660
tcttccaggc actcgcgcag cgcctcgtat tcgtcgtcgg tcagccagaa cttgcgctga   3720
cgcatccctt tggccttcat gcgctcggca tatcgcgctt ggcgtacagc gtcagggctg   3780
gccagcaggt cgccggtctg cttgtccttt tggtctttca tatcagtcac cgagaaactt   3840
gccggggccg aaaggcttgt cttcgcggaa caaggacaag gtgcagccgt caaggttaag   3900
```

-continued

```
gctggccata tcagcgactg aaaagcggcc agcctcggcc ttgtttgacg tataaccaaa   3960
gccaccgggc aaccaatagc ccttgtcact tttgatcagg tagaccgacc ctgaagcgct   4020
tttttcgtat tccataaaac cccccttctgt gcgtgagtac tcatagtata acaggcgtga   4080
gtaccaacgc aagcactaca tgctgaaatc tggcccgccc ctgtccatgc ctcgctggcg   4140
gggtgccggt gcccgtgcca gctcggcccg cgcaagctgg acgctgggca gacccatgac   4200
cttgctgacg gtgcgctcga tgtaatccgc ttcgtggccg ggcttgcgct ctgccagcgc   4260
tgggctggcc tcggccatgg ccttgccgat ttcctcggca ctgcggcccc ggctggccag   4320
cttctgcgcg gcgataaagt cgcacttgct gaggtcatca ccgaagcgct tgaccagccc   4380
ggccatctcg ctgcggtact cgtccagcgc cgtgcgccgg tggcggctaa gctgccgctc   4440
gggcagttcg aggctggcca gcctgcgggc cttctcctgc tgccgctggg cctgctcgat   4500
ctgctggcca gcctgctgca ccagcgccgg gccagcggtg gcggtcttgc ccttggattc   4560
acgcagcagc acccacggct gataaccggc gcgggtggtg tgcttgtcct tgcggttggt   4620
gaagcccgcc aagcggccat agtggcggct gtcggcgctg gccgggtcgg cgtcgtactc   4680
gctggccagc gtccgggcaa tctgccccg aagttcaccg cctgcggcgt cggccacctt   4740
gacccatgcc tgatagttct tcgggctggt ttccactacc agggcaggct cccggccctc   4800
ggctttcatg tcatccaggt caaactcgct gaggtcgtcc accagcacca gaccatgccg   4860
ctcctgctcg gcgggcctga tatacacgtc attgccctgg gcattcatcc gcttgagcca   4920
tggcgtgttc tggagcactt cggcggctga ccattcccgg ttcatcatct ggccggtggt   4980
ggcgtccctg acgccgatat cgaagcgctc acagcccatg gccttgagct gtcggcctat   5040
ggcctgcaaa gtcctgtcgt tcttcatcgg gccaccaagc gcagccagat cgagccgtcc   5100
tcggttgtca gtggcgtcag gtcgagcaag agcaacgatg cgatcagcag caccaccgta   5160
ggcatcatgg aagccagcat cacggttagc catagcttcc agtgccaccc ccgcgacgcg   5220
ctccgggcgc tctgcgcggc gctgctcacc tcggcggcta cctcccgcaa ctctttggcc   5280
agctccaccc atgccgcccc tgtctggcgc tgggctttca gccactccgc cgcctgcgcc   5340
tcgctggcct gctgggtctg gctcatgacc tgccgggctt cgtcggccag tgtcgccatg   5400
ctctgggcca gcggttcgat ctgctccgct aactcgttga tgcctctgga tttcttcact   5460
ctgtcgattg cgttcatggt ctattgcctc ccggtattcc tgtaagtcga tgatctgggc   5520
gttggcggtg tcgatgttca gggccacgtc tgcccggtcg gtgcggatgc cccggccttc   5580
catctccacc acgttcggcc ccaggtgaac accgggcagg cgctcgatgc cctgcgcctc   5640
aagtgttctg tggtcaatgc gggcgtcgtg gccagcccgc tctaatgccc ggttggcatg   5700
gtcggcccat gcctcgcggg tctgctcaag ccatgccttg ggcttgagcg cttcggtctt   5760
ctgtgccccg cccttctccg gggtcttgcc gttgtaccgc ttgaaccact gagcggcggg   5820
ccgctcgatg ccgtcattga tccgctcgga gatcatcagg tggcagtgcg ggttctcgcc   5880
gccaccggca tggatggcca gcgtatacgg caggcgctcg gcaccggtca ggtgctgggc   5940
gaactcggac gccagcgcct tctgctggtc gagggtcagc tcgaccggca gggcaaattc   6000
gacctccttg aacagccgcc cattggcgcg ttcatacagg tcggcagcat cccagtagtc   6060
ggcgggccgc tcgacgaact ccggcatgtg cccggattcg gcgtgcaaga cttcatccat   6120
gtcgcgggca tacttgcctt cgcgctggat gtagtcggcc ttggccctgg ccgattggcc   6180
gcccgacctg ctgccggttt tcgccgtaag gtgataaatc gccatgctgc ctcgctgttg   6240
cttttgcttt tcggctccat gcaatggccc tcggagagcg caccgcccga agggtggccg   6300
```

-continued

```
ttaggccagt ttctcgaaga gaaaccggta agtgcgccct cccctacaaa gtagggtcgg   6360
gattgccgcc gctgtgcctc catgatagcc tacgagacag cacattaaca atggggtgtc   6420
aagatggtta aggggagcaa caaggcggcg gatcggctgg ccaagctcga agaacaacga   6480
gcgcgaatca atgccgaaat tcagcgggtg cgggcaaggg aacagcagca agagcgcaag   6540
aacgaaacaa ggcgcaaggt gctggtgggg gccatgattt tggccaaggt gaacagcagc   6600
gagtggccgg aggatcggct catggcggca atggatgcgt accttgaacg cgaccacgac   6660
cgcgccttgt tcggtctgcc gccacgccag aaggatgagc cgggctgaat gatcgaccga   6720
gacaggccct gcggggctgc acacgcgccc ccacccttcg ggtaggggga aaggccgcta   6780
aagcggctaa aagcgctcca gcgtatttct gcggggtttg gtgtggggtt tagcgggctt   6840
tgcccgcctt tccccctgcc gcgcagcggt ggggcggtgt gtagcctagc gcagcgaata   6900
gaccagctat ccggcctctg gccgggcata ttgggcaagg gcagcagcgc cccacaaggg   6960
cgctgataac cgcgcctagt ggattattct tagataatca tggatggatt tttccaacac   7020
cccgccagcc cccgcccctg ctgggtttgc aggtttgggg gcgtgacagt tattgcaggg   7080
gttcgtgaca gttattgcag gggggcgtga cagttattgc aggggttcgt gacagttagt   7140
acgggagtga cgggcactgg ctggcaatgt ctagcaacgg caggcatttc ggctgagggt   7200
aaaagaactt tccgctaagc gatagactgt atgtaaacac agtattgcaa ggacgcggaa   7260
catgcctcat gtggcggcca ggacggccag ccgggatcgg gatactggtc gttaccagag   7320
ccaccgaccc gagcaaaccc ttctctatca gatcgttgac gagtattacc cggcattcgc   7380
tgcgcttatg gcagagcagg gaaaggaatt gccgggctat gtgcaacggg aatttgaaga   7440
atttctccaa tgcgggcggc tggagcatgg ctttctacgg gttcgctgcg agtcttgcca   7500
cgccgagcac ctggtcgctt tcagctgtaa tccgggcagc gcaacggaac attcatcagt   7560
gtaaaaatgg aatcaataaa gccctgcgca gcgcgcaggg tcagcctgaa tacgcgtgct   7620
cgaattgaca taagcctgtt cggttcgtaa actgtaatgc aagtagcgta tgcgctcacg   7680
caactggtcc agaaccttga ccgaacgcag cggtggtaac ggcgcagtgg cggttttcat   7740
ggcttgttat gactgttttt ttgtacagtc tatgcctcgg gcatccaagc agcaagcgcg   7800
ttacgccgtg ggtcgatgtt tgatgttatg gagcagcaac gatgttacgc agcagcaacg   7860
atgttacgca gcagggcagt cgccctaaaa caaagttagg tggctcaagt atgggcatca   7920
ttcgcacatg taggctcggc cctgaccaag tcaaatccat gcgggctgct cttgatcttt   7980
tcggtcgtga gttcggagac gtagccacct actcccaaca tcagccggac tccgattacc   8040
tcgggaactt gctccgtagt aagacattca tcgcgcttgc tgccttcgac caagaagcgg   8100
ttgttggcgc tctcgcggct tacgttctgc ccaggtttga gcagccgcgt agtgagatct   8160
atatctatga tctcgcagtc tccggcgagc accggaggca gggcattgcc accgcgctca   8220
tcaatctcct caagcatgag gccaacgcgc ttggtgctta tgtgatctac gtgcaagcag   8280
attacggtga cgatcccgca gtggctctct atacaaagtt gggcatacgg gaagaagtga   8340
tgcactttga tatcgaccca agtaccgcca cctaacaatt cgttcaagcc gagatcggct   8400
tcccggccct agacgcgtat tcaggctgac cctgcgcgct gcgcagggct ttattgattc   8460
catttttaca ctgatgaatg ttccgttgcg ctgcccggat tacagatcct ctagaagaac   8520
agcaaggccg ccaatgcctg acgatgcgtg gagaccgaaa ccttgcgctc gttcgccagc   8580
caggacagaa atgcctcgac ttcgctgctg cccaaggttg ccgggtgacg cacaccgtgg   8640
```

aaacggatga aggcacgaac ccagtggaca taagcctgtt cggttcgtaa gctgtaatgc 8700
aagtagcgta tgcgctcacg caactggtcc agaaccttga ccgaacgcag cggtggtaac 8760
ggcgcagtgg cggttttcat ggcttgttat gactgttttt ttggggtaca gtctatgcct 8820
cgggcatcca agcagcaagc gcgttacgcc gtgggtcgat gtttgatgtt atggagcagc 8880
aacgatgtta cgcagcaggg cagtcgccct aaaacaaagt taaacatcat gagggaagcg 8940
gtgatcgccg aagtatcgac tcaactatca gaggtagttg gcgtcatcga gcgccatctc 9000
gaaccgacgt tgctggccgt acatttgtac ggctccgcag tggatggcgg cctgaagcca 9060
cacagtgata ttgatttgct ggttacggtg accgtaaggc ttgatgaaac aacgcggcga 9120
gctttgatca acgacctttt ggaaacttcg gcttcccctg gagagagcga gattctccgc 9180
gctgtagaag tcaccattgt tgtgcacgac gacatcattc cgtggcgtta tccagctaag 9240
cgcgaactgc aatttggaga atggcagcgc aatgacattc ttgcaggtat cttcgagcca 9300
gccacgatcg acattgatct ggctatcttg ctgacaaaag caagagaaca tagcgttgcc 9360
ttggtaggtc cagcggcgga ggaactcttt gatccggttc ctgaacagga tctatttgag 9420
gcgctaaatg aaaccttaac gctatggaac tcgccgcccg actgggctgg cgatgagcga 9480
aatgtagtgc ttacgttgtc ccgcatttgg tacagcgcag taaccggcaa aatcgcgccg 9540
aaggatgtcg ctgccgactg ggcaatggag cgcctgccgg cccagtatca gcccgtcata 9600
cttgaagcta gacaggctta tcttggacaa gaagaagatc gcttggcctc gcgcgcagat 9660
cagttggaag aatttgtcca ctacgtgaaa ggcgagatca ccaaggtagt cggcaaataa 9720
tgtctaacaa ttcgttcaag ccgacgccgc ttcgcggcgc ggcttaactc aagctctaga 9780
g 9781

<210> SEQ ID NO 22
<211> LENGTH: 3588
<212> TYPE: DNA
<213> ORGANISM: Artificial
<220> FEATURE:
<223> OTHER INFORMATION: Synthetically produced ethanologenic gene cassette from plasmid #1121 pVZ322a-smtB-PsmtA-ZmPDCoop-PrbcL-synADH(deg) integrated via SalI/SbfI into pVZ322a

<400> SEQUENCE: 22
gtcgacgggc aaactttatg aagcagatca agcctatatc cgccaagcaa ccggcagccg 60
cgttgattag tgggtgtgtc catcctctgg ttcgtctagg tgctccgaag cgtcacgata 120
gagattaaga atgtggtgat ccttgaggcg ataaatcaca ttccgccctt ccttgcgata 180
gctcactaaa cgtgctgtgc gcagggttct tagttggtga gagacagccg attcactcat 240
ttcaacggcg gcggcgagtt cccccacccg catctctcca gtggccaggg ccgaaagaat 300
acgccagcgg ttggcatccc ccaagacacc aaaaaattcg gccatccgtt gggccttggc 360
ttggttcaag attttgccac tgtggtctgt cattgttcgc tgatctaaac aatacctgaa 420
taattgttca tgtgttaatc taaaaatgtg aacaatcgtt caactattta agacaatacc 480
ttggaggttt aaaccatgaa ttcttatact gtcggtacct atttagcgga gcggcttgtc 540
cagattggtc tcaagcatca cttcgcagtc gcgggcgact acaacctcgt ccttcttgac 600
aacctgcttt tgaacaaaaa catggagcag gtttattgct gtaacgaact gaactgcggt 660
ttcagtgcag aaggttatgc tcgtgccaaa ggcgcagcag cagccgtcgt tacctacagc 720
gtcggtgcgc tttccgcatt tgatgctatc ggtggcgcct atgcagaaaa ccttccggtt 780
atcctgatct ccggtgctcc gaacaacaat gatcacgctg ctggtcacgt gttgcatcac 840

-continued

```
gctcttggca aaaccgacta tcactatcag ttggaaatgg ccaagaacat cacggccgca    900
gctgaagcga tttacacccc agaagaagct ccggctaaaa tcgatcacgt gattaaaact    960
gctcttcgtg agaagaagcc ggtttatctc gaaatcgctt gcaacattgc ttccatgccc   1020
tgcgccgctc ctggaccggc aagcgcattg ttcaatgacg aagccagcga cgaagcttct   1080
ttgaatgcag cggttgaaga aaccctgaaa ttcatcgcca accgcgacaa agttgccgtc   1140
ctcgtcggca gcaagctgcg cgcagctggt gctgaagaag ctgctgtcaa atttgctgat   1200
gctctcggtg gcgcagttgc taccatggct gctgcaaaaa gcttcttccc agaagaaaac   1260
ccgcattaca tcggtacctc atggggtgaa gtcagctatc cgggcgttga aaagacgatg   1320
aaagaagccg atgcggttat cgctctggct cctgtcttca acgactactc caccactggt   1380
tggacggata ttcctgatcc taagaaactg gttctcgctg aaccgcgttc tgtcgtcgtt   1440
aacggcgttc gcttccccag cgttcatctg aaagactatc tgacccgttt ggctcagaaa   1500
gtttccaaga aaaccggtgc tttggacttc ttcaaatccc tcaatgcagg tgaactgaag   1560
aaagccgctc cggctgatcc gagtgctccg ttggtcaacg cagaaatcgc ccgtcaggtc   1620
gaagctcttc tgaccccgaa cacgacggtt attgctgaaa ccggtgactc ttggttcaat   1680
gctcagcgca tgaagctccc gaacggtgct cgcgttgaat atgaaatgca gtggggtcac   1740
atcggttggt ccgttcctgc cgccttcggt tatgccgtcg gtgctccgga acgtcgcaac   1800
atcctcatgg ttggtgatgg ttccttccag ctgacggctc aggaagtcgc tcagatggtt   1860
cgcctgaaac tgccggttat catcttcttg atcaataact atggttacac catcgaagtt   1920
atgatccatg atggtccgta caacaacatc aagaactggg attatgccgg tctgatggaa   1980
gtgttcaacg gtaacggtgg ttatgacagc ggtgctggta aaggcctgaa ggctaaaacc   2040
ggtggcgaac tggcagaagc tatcaaggtt gctctggcaa acaccgacgg cccaaccctg   2100
atcgaatgct tcatcggtcg tgaagactgc actgaagaat tggtcaaatg ggggtaagcgc   2160
gttgctgccg ccaacagccg taagcctgtt aacaagctcc tctagttttt ggggatcaat   2220
tcgagctcgg tacccaaact agtaacgctc ggttgccgcc gggcgttttt tattccgaca   2280
tcaggaattg taattagaaa gtccaaaaat tgtaatttaa aaaacagtca atggagagca   2340
ttgccataag taaaggcatc ccctgcgtga taagattacc ttcagaaaac agatagttgc   2400
tgggttatcg cagatttttc tcgcaaccaa ataactgtaa ataataactg tctctggggc   2460
gacggtaggc tttatattgc caaatttcgc ccgtgggaga aagctaggct attcaatgtt   2520
tatggaggac tgacccatat gatcaaggct tatgccgctt tagaggctaa tggcaagttg   2580
cagccgttcg agtatgatcc gggcgcttta ggcgccaacg aagttgaaat cgaagttcaa   2640
tactgcggtg tttgtcattc cgacctcagt atgatcaaca atgagtgggg tatcagtaac   2700
tatccgttgg ttcccggcca cgaagttgtt ggcaccgttg ctgctatggg tgagggtgtt   2760
aatcacgtgg aagttggtga cctggttggt ttaggctggc acagtggtta ttgtatgact   2820
tgtcactcct gcctgagcgg ttatcataat ttgtgcgcta ccgccgagag tactatcgtt   2880
ggtcattatg gcggtttcgg tgaccgtgtg cgtgctaaag gtgtgtccgt tgttaagctg   2940
cccaagggta tcgatttggc ttccgctggt ccgttgtttt gcggtggtat cactgtgttt   3000
tcccccatgg ttgagttatc cctgaaaccg accgccaagg ttgccgttat tggtatcggt   3060
ggtctcggtc acctggccgt tcagttcttg cgtgcttggg gttgcgaggt taccgctttc   3120
actagctccg ctcgtaaaca gaccgaggtt ctggagctgg gtgcccatca tattttggac   3180
```

-continued

```
agtactaacc ccgaagccat tgcttccgcc gagggtaagt tcgattacat cattagtacc   3240

gttaatttaa aattggattg gaatctgtat atttccactt tagccccgca aggtcacttt   3300

catttcgtgg gtgttgttct cgaacccctc gacttgaact tgttcccgtt gctcatgggt   3360

cagcggagtg tgtccgctag tccggttggc tccccggcta ctatcgctac tatgctcgat   3420

ttcgccgttc ggcacgatat caagccggtt gttgagcagt tctccttcga ccaaattaat   3480

gaagccattg ctcacttgga gtccggtaag gctcactacc gtgtggtttt gagtcactcc   3540

aagaactgaa acgctcggtt gccgccgggc gttttttatt cctgcagg                3588
```

<210> SEQ ID NO 23
<211> LENGTH: 4184
<212> TYPE: DNA
<213> ORGANISM: Artificial
<220> FEATURE:
<223> OTHER INFORMATION: Synthetically produced ethanologenic gene cassette from plasmid #1217 pVZ325a-corR-PcorT-ZmPDCdsrA/oop-PrbcL*-synADH(deg) integrated via SalI/SbfI into pVZ325a

<400> SEQUENCE: 23

```
gtcgaccatg cgtccaaaac tttcaccatc ctttccctat caacctttac tgcactaaag     60

acaagtgaga tagcagtggc aatctggctt tgcaatcaat gtttccacta aagcgtttag    120

cgttactgcg gctagaagtc ctccaccgag gctcccctga atggtgatat ggggaatggg    180

actggtcatc agtcgtcgtt ttgcccccgg agcatgacta aaaccgatcg gcattccgat    240

cacaagagcc ggctgaatat gttgttgctc tatcagctta caggcagtga gtaaaacaga    300

aggggcatag ccgatcgcca gcacacatcc ttggggaatc tgttgtaacc gctgttgcca    360

atggtcatgg tgccaaaaag cttgctcggc ttccctaagc cctgtgatgt gagggtcgtc    420

aatcagcgtt ttaaccgtac atcctaaatg agctaaccga gtttgatcaa gagccgcagc    480

cacaaccgga acatcggtga cgactggaca ccctgctttc agtgcatctc gtgccgaggc    540

gatcgctccc tgactcaatc gaacggcgtt taccaagcta acatcaccac aggccagcac    600

taattgatgt agtaagtgaa tggtaatttc agagtaagcc gataaatccg gtagcaggtg    660

tttgagggat tcctgaaagg cttctggatg agttgttgtc tccgcatcta ggttcgtcca    720

caactgatcg agttttccta acccctcctg gacatccaca tcaagctgtt tcagttgggc    780

cagagcttcc gcttgggtaa tctggcaact ctggtcgcgt cccagtaatc cttctaaagc    840

agatgcggtt tggcggagtc gagtaatctg ctgaatcaca gcctgatatt gctgttgcaa    900

ctgcaccatt agggtgggat caaggctctc ttcagaatgg ctatccagca gttgccgaat    960

atgagacaac tgaaagccct gctgtttgag ggcaatgact cgttggagcc gttgtacgtc   1020

ctgctgagta taaaggcggt agttgccctc tgagcgttga acgggggga gcaatcccag   1080

ggtgtggtaa tggcgcacca tgcgaggcgt aacgccacct cccactgcat ctgtgagttc   1140

tttaatcgtt aagtgattag tcttcatccc tttagtttac tcaaaacctt gacattgaca   1200

ctaatgttaa ggtttaggct gagaaggtaa aaatccaagt taaaaagcat gaattcttat   1260

actgtcggta cctatttagc ggagcggctt gtccagattg gtctcaagca tcacttcgca   1320

gtcgcgggcg actacaacct cgtccttctt gacaacctgc ttttgaacaa aaacatggag   1380

caggtttatt gctgtaacga actgaactgc ggtttcagtg cagaaggtta tgctcgtgcc   1440

aaaggcgcag cagcagccgt cgttacctac agcgtcggtg cgctttccgc atttgatgct   1500

atcggtggcg cctatgcaga aaaccttccg gttatcctga tctccggtgc tccgaacaac   1560

aatgatcacg ctgctggtca cgtgttgcat cacgctcttg gcaaaaccga ctatcactat   1620
```

cagttggaaa tggccaagaa catcacggcc gcagctgaag cgatttacac cccagaagaa 1680
gctccggcta aaatcgatca cgtgattaaa actgctcttc gtgagaagaa gccggtttat 1740
ctcgaaatcg cttgcaacat tgcttccatg ccctgcgccg ctcctggacc ggcaagcgca 1800
ttgttcaatg acgaagccag cgacgaagct tctttgaatg cagcggttga agaaaccctg 1860
aaattcatcg ccaaccgcga caaagttgcc gtcctcgtcg gcagcaagct gcgcgcagct 1920
ggtgctgaag aagctgctgt caaatttgct gatgctctcg gtggcgcagt tgctaccatg 1980
gctgctgcaa aaagcttctt cccagaagaa aacccgcatt acatcggtac ctcatggggt 2040
gaagtcagct atccgggcgt tgaaaagacg atgaaagaag ccgatgcggt tatcgctctg 2100
gctcctgtct tcaacgacta ctccaccact ggttggacgg atattcctga tcctaagaaa 2160
ctggttctcg ctgaaccgcg ttctgtcgtc gttaacggcg ttcgcttccc cagcgttcat 2220
ctgaaagact atctgacccg tttggctcag aaagtttcca agaaaaccgg tgctttggac 2280
ttcttcaaat ccctcaatgc aggtgaactg aagaaagccg ctccggctga tccgagtgct 2340
ccgttggtca acgcagaaat cgcccgtcag gtcgaagctc ttctgacccc gaacacgacg 2400
gttattgctg aaaccggtga ctcttggttc aatgctcagc gcatgaagct cccgaacggt 2460
gctcgcgttg aatatgaaat gcagtggggt cacatcggtt ggtccgttcc tgccgccttc 2520
ggttatgccg tcggtgctcc ggaacgtcgc aacatcctca tggttggtga tggttccttc 2580
cagctgacgg ctcaggaagt cgctcagatg gttcgcctga aactgccggt tatcatcttc 2640
ttgatcaata actatggtta caccatcgaa gttatgatcc atgatggtcc gtacaacaac 2700
atcaagaact gggattatgc cggtctgatg gaagtgttca acggtaacgg tggttatgac 2760
agcggtgctg gtaaaggcct gaaggctaaa accggtggcg aactggcaga agctatcaag 2820
gttgctctgg caaacaccga cggcccaacc ctgatcgaat gcttcatcgg tcgtgaagac 2880
tgcactgaag aattggtcaa atggggtaag cgcgttgctg ccgccaacag ccgtaagcct 2940
gttaacaagc tcctctagtt tttggggatc aattcgagct cagcaagttt catcccgacc 3000
ccctcagggt cgggattttt ttattgtact agtaacgccc ggttgccacc gggcgttttt 3060
tattccgaca ttgccataag taaaggcatc ccctgcgtga taagattacc ttcagtttat 3120
ggaggactga ccatatgatc aaggcttatg ccgctttaga ggctaatggc aagttgcagc 3180
cgttcgagta tgatccgggc gctttaggcg ccaacgaagt tgaaatcgaa gttcaatact 3240
gcggtgtttg tcattccgac ctcagtatga tcaacaatga gtggggtatc agtaactatc 3300
cgttggttcc cggccacgaa gttgttggca ccgttgctgc tatgggtgag ggtgttaatc 3360
acgtggaagt tggtgacctg gttggtttag gctggcacag tggttattgt atgacttgtc 3420
actcctgcct gagcggttat cataatttgt gcgctaccgc cgagagtact atcgttggtc 3480
attatggcgg tttcggtgac cgtgtgcgtg ctaaaggtgt gtccgttgtt aagctgccca 3540
agggtatcga tttggcttcc gctggtccgt tgttttgcgg tggtatcact gtgttttccc 3600
ccatggttga gttatccctg aaaccgaccg ccaaggttgc cgttattggt atcggtggtc 3660
tcggtcacct ggccgttcag ttcttgcgtg cttggggttg cgaggttacc gctttcacta 3720
gctccgctcg taaacagacc gaggttctgg agctgggtgc ccatcatatt ttggacagta 3780
ctaaccccga agccattgct tccgccgagg gtaagttcga ttacatcatt agtaccgtta 3840
atttaaaatt ggattggaat ctgtatattt ccactttagc ccgcaaggt cactttcatt 3900
tcgtgggtgt tgttctcgaa cccctcgact tgaacttgtt cccgttgctc atgggtcagc 3960

```
ggagtgtgtc cgctagtccg gttggctccc cggctactat cgctactatg ctcgatttcg   4020

ccgttcggca cgatatcaag ccggttgttg agcagttctc cttcgaccaa attaatgaag   4080

ccattgctca cttggagtcc ggtaaggctc actaccgtgt ggttttgagt cactccaaga   4140

actgaaacgc tcggttgccg ccgggcgttt tttattcctg cagg                    4184
```

<210> SEQ ID NO 24
<211> LENGTH: 3792
<212> TYPE: DNA
<213> ORGANISM: Artificial
<220> FEATURE:
<223> OTHER INFORMATION: Synthetically produced ethanologenic gene cassette from plasmid #1227 pVZ325a-nrsR-PnrsB-ZmPDCdsrA/oop-PrbcL*-synADH(deg) integrated via SalI/SbfI into pVZ325a

<400> SEQUENCE: 24

```
gtcgacggga gtttgcaaac tccctcatat tcatggcgat agggtgaacc gatagccttg     60

accgggaact gttttaattg ggcaaggaca attttgttga gctagcttgc gtcgtatcaa    120

acgcatttgg gccgccacca cattactcat gggctcctca tcaagatccc acagttgttg    180

ccggatcttg ctaccggaaa tgatccgctc tgggttttgc atcagatatt gaaaaatttg    240

aaattctctt acggttaaag caatttcctg tctttctagg tttagtggct ccgagatagt    300

taccgataac agattattac tgggatcaag gctgaagttg cccaaagtta aaatttgcgg    360

ttggaattgt ggcgatcgcc gttgtagtgc ccgcagtctt gctaatagct ctgccatcac    420

aaacggtttt gttagatagt catctgcccc ggcatctagt ccttcgacac ggtttttccgg   480

ttctcctaac gctgttaaca tcaacaccgg caaggaatta ccctgggttc tcagtttttg    540

acagagttcc aaacccgata atcccggcag taaccaatcc acaatggcaa gggtgtattc    600

cgtccattga ttttccaaat aatcccaagc ttgggagcca tccgtcaccc aatccaccac    660

atacttttca ctaactagca ctttcttaat agccattccc aaatccgtct catcttccac    720

cagcaaaatt cgcatcgcct ctgccttttt tataacggtc tgatcttagc gggggaagga    780

gattttcacc tgaatttcat accccctttg gcagactggg aaaatcttgg acaaattccc    840

aatttgaggt ggtgtgatga attcttatac tgtcggtacc tatttagcgg agcggcttgt    900

ccagattggt ctcaagcatc acttcgcagt cgcgggcgac tacaacctcg tccttcttga    960

caacctgctt ttgaacaaaa acatggagca ggtttattgc tgtaacgaac tgaactgcgg   1020

tttcagtgca gaaggttatg ctcgtgccaa aggcgcagca gcagccgtcg ttacctacag   1080

cgtcggtgcg ctttccgcat ttgatgctat cggtggcgcc tatgcagaaa accttccggt   1140

tatcctgatc tccggtgctc cgaacaacaa tgatcacgct gctggtcacg tgttgcatca   1200

cgctcttggc aaaaccgact atcactatca gttggaaatg gccaagaaca tcacggccgc   1260

agctgaagcg atttacaccc cagaagaagc tccggctaaa atcgatcacg tgattaaaac   1320

tgctcttcgt gagaagaagc cggtttatct cgaaatcgct tgcaacattg cttccatgcc   1380

ctgcgccgct cctggaccgg caagcgcatt gttcaatgac gaagccagcg acgaagcttc   1440

tttgaatgca gcggttgaag aaaccctgaa attcatcgcc aaccgcgaca aagttgccgt   1500

cctcgtcggc agcaagctgc gcgcagctgg tgctgaagaa gctgctgtca aatttgctga   1560

tgctctcggt ggcgcagttg ctaccatggc tgctgcaaaa agcttcttcc cagaagaaaa   1620

cccgcattac atcggtacct catggggtga agtcagctat ccgggcgttg aaaagacgat   1680

gaaagaagcc gatgcggtta tcgctctggc tcctgtcttc aacgactact ccaccactgg   1740

ttggacggat attcctgatc ctaagaaact ggttctcgct gaaccgcgtt ctgtcgtcgt   1800
```

-continued

```
taacggcgtt cgcttcccca gcgttcatct gaaagactat ctgacccgtt tggctcagaa   1860
agtttccaag aaaaccggtg ctttggactt cttcaaatcc ctcaatgcag gtgaactgaa   1920
gaaagccgct ccggctgatc cgagtgctcc gttggtcaac gcagaaatcg cccgtcaggt   1980
cgaagctctt ctgaccccga acacgacggt tattgctgaa accggtgact cttggttcaa   2040
tgctcagcgc atgaagctcc cgaacggtgc tcgcgttgaa tatgaaatgc agtggggtca   2100
catcggttgg tccgttcctg ccgccttcgg ttatgccgtc ggtgctccgg aacgtcgcaa   2160
catcctcatg gttggtgatg gttccttcca gctgacggct caggaagtcg ctcagatggt   2220
tcgcctgaaa ctgccggtta tcatcttctt gatcaataac tatggttaca ccatcgaagt   2280
tatgatccat gatggtccgt acaacaacat caagaactgg gattatgccg gtctgatgga   2340
agtgttcaac ggtaacggtg gttatgacag cggtgctggt aaaggcctga aggctaaaac   2400
cggtggcgaa ctggcagaag ctatcaaggt tgctctggca aacaccgacg gcccaaccct   2460
gatcgaatgc ttcatcggtc gtgaagactg cactgaagaa ttggtcaaat ggggtaagcg   2520
cgttgctgcc gccaacagcc gtaagcctgt taacaagctc ctctagtttt tggggatcaa   2580
ttcgagctca gcaagtttca tcccgacccc ctcagggtcg ggattttttt attgtactag   2640
taacgcccgg ttgccaccgg gcgtttttta ttccgacatt gccataagta aaggcatccc   2700
ctgcgtgata agattacctt cagtttatgg aggactgacc atatgatcaa ggcttatgcc   2760
gctttagagg ctaatggcaa gttgcagccg ttcgagtatg atccgggcgc tttaggcgcc   2820
aacgaagttg aaatcgaagt tcaatactgc ggtgtttgtc attccgacct cagtatgatc   2880
aacaatgagt ggggtatcag taactatccg ttggttcccg gccacgaagt tgttggcacc   2940
gttgctgcta tgggtgaggg tgttaatcac gtggaagttg gtgacctggt tggtttaggc   3000
tggcacagtg gttattgtat gacttgtcac tcctgcctga gcggttatca taatttgtgc   3060
gctaccgccg agagtactat cgttggtcat tatggcggtt tcggtgaccg tgtgcgtgct   3120
aaaggtgtgt ccgttgttaa gctgcccaag ggtatcgatt tggcttccgc tggtccgttg   3180
ttttgcggtg gtatcactgt gttttccccc atggttgagt tatccctgaa accgaccgcc   3240
aaggttgccg ttattggtat cggtggtctc ggtcacctgg ccgttcagtt cttgcgtgct   3300
tggggttgcg aggttaccgc tttcactagc tccgctcgta aacagaccga ggttctggag   3360
ctgggtgccc atcatatttt ggacagtact aaccccgaag ccattgcttc cgccgagggt   3420
aagttcgatt acatcattag taccgttaat ttaaaattgg attggaatct gtatatttcc   3480
actttagccc cgcaaggtca ctttcatttc gtgggtgttg ttctcgaacc cctcgacttg   3540
aacttgttcc cgttgctcat gggtcagcgg agtgtgtccg ctagtccggt tggctccccg   3600
gctactatcg ctactatgct cgatttcgcc gttcggcacg atatcaagcc ggttgttgag   3660
cagttctcct tcgaccaaat taatgaagcc attgctcact tggagtccgg taaggctcac   3720
taccgtgtgg ttttgagtca ctccaagaac tgaaacgctc ggttgccgcc gggcgttttt   3780
tattcctgca gg                                                       3792
```

<210> SEQ ID NO 25
<211> LENGTH: 5232
<212> TYPE: DNA
<213> ORGANISM: Artificial
<220> FEATURE:
<223> OTHER INFORMATION: Synthetically produced ethanologenic gene cassette from plasmid #1356 pVZ325a-nrsRS-PnrsB*-ZpPDCdsrA/oop-PrbcL*-synADH(deg) integrated via SalI/SbfI into pVZ325a

<400> SEQUENCE: 25

```
gtcgacccta tatcgggctt ttctcaataa aatctttatt ttttgaggtg ctttttagcc     60
ataaataatc actttagtat aaaattttga cggcgtaaag ttgataaaat agaattaaga    120
atggactatc ggtacagaaa aaatgggtaa ctggatggtg aataaacttc ccttacccaa    180
tgcactctcc accgttaaag acccccctatg cttaacggtg atcacctggg caatggcgag    240
tcccaaccct gtcccccccg ttttgcgcga acgatctcga ttaactcggt aaaaacgctc    300
aaaaatgtgt tcctgttggt cgggggcaat gccgatgccg gtatcttgca cggtgatgat    360
agccatctgt tcatgggatg tcagggtaat atcaacacgt cccccagcag ttgtgtattg    420
aatggcgttg gcaattaggt ttgagaccag tcgatagagt tgggattcat taccccaggc    480
gtaaacttcc cctgaactca gatcactgct gagatcaatg tgggcggcga tcgctaattc    540
taaaaactct tcggtgaggt cactgactaa atcatttaaa caacaaagcc gccaatcttc    600
ggcggtggtt tcctgctcta agcgacttag tagcaataaa tccgtaatca attggcttaa    660
tcgccttccc tgtcgttcaa cggtatgtag catggtgtta atttctgggg aatggcttga    720
gtcgatgcgt aataccgctt ccaccgtggc caacagacta gccaatggcg atcgtaattc    780
atgggctgca ttcgcggtga attgttgttg ttgttggtag gactggtaaa tgggacgcat    840
ggctaacccc gctaagcccc aactggagaa ggcgaccaaa cccagggcaa tgggaaaact    900
aagccctaaa atccaaagaa tacgtttatt ttcggcatca aaggctgcca ggctccggcc    960
aatttgtaga tagccccagg aagatttgtc tgtattaccg gcgctatgca aaatggtggt   1020
gaattgtcga taccgatcgc cggttggggg gtgaatagtc tgccaagttt cctggttaaa   1080
aatggaggat agggaagccg gttgattagg cgaaaaagcc agcaggttgc cttgataatc   1140
aaataaacga atgtaatata aactgcgatc actaatgccc aacgtgtgac gttcaatcag   1200
ggtggggttg acctggcagg gttggttgac caaacacaga tcgggcaaca ttttttgtaa   1260
tactccggtg ggactagcat tactcggcaa catcggctct aaactgtcat gcaacgtccc   1320
ggcgatcgac tccacttctc gctccaacgc catccagttg gcctgcacaa tggcacgata   1380
aacccccaac cccaacaggg taagaatacc ccccattact agggcatacc agaaagccaa   1440
ttgcagacga ctacgggcaa agaggcgacg ggtattcatg gcgatagggt gaaccgatag   1500
ccttgaccgg gaactgtttt aattgggcaa ggacaatttt gttgagctag cttgcgtcgt   1560
atcaaacgca tttgggccgc caccacatta ctcatgggct cctcatcaag atcccacagt   1620
tgttgccgga tcttgctacc ggaaatgatc cgctctgggt tttgcatcag atattgaaaa   1680
atttgaaatt ctcttacggt taaagcaatt tcctgtcttt ctaggtttag tggctccgag   1740
atagttaccg ataacagatt attactggga tcaaggctga agttgcccaa agttaaaatt   1800
tgcggttgga attgtggcga tcgccgttgt agtgcccgca gtcttgctaa tagctctgcc   1860
atcacaaacg gttttgttag atagtcatct gccccggcat ctagtccttc gacacggttt   1920
tccggttctc ctaacgctgt taacatcaac accggcaagg aattaccctg ggttctcagt   1980
ttttgacaga gttccaaacc cgataatccc ggcagtaacc aatccacaat ggcaagggtg   2040
tattccgtcc attgattttc caaataatcc caagcttggg agccatccgt cacccaatcc   2100
accacatact tttcactaac tagcactttc ttaatagcca ttcccaaatc cgtctcatct   2160
tccaccagca aaattcgcat cgcctctgcc ttttttataa cggtctgatc ttagcggggg   2220
aaggagattt tcacctgaat ttcatacccc ctttggcaga ctgggaaaat cttggacaaa   2280
ttcccaattg gaggaggtgt gatgaattcc tataccgttg gtatgtactt ggcagaacgc   2340
```

-continued

```
ctagcccaga tcggcctgaa acaccacttt gccgtggccg gtgactacaa cctggtgttg   2400
cttgatcagc tcctgctgaa caaagacatg gagcaggtct actgctgtaa cgaacttaac   2460
tgcggcttta gcgccgaagg ttacgctcgt gcacgtggtg ccgccgctgc catcgtcacg   2520
ttcagcgtag gtgctatctc tgcaatgaac gccatcggtg gcgcctatgc agaaaacctg   2580
ccggtcatcc tgatctctgg ctcaccgaac accaatgact acggcacagg ccacatcctg   2640
caccacacca ttggtactac tgactataac tatcagctgg aaatggtaaa acacgttacc   2700
tgcgcacgtg aaagcatcgt ttctgccgaa gaagcaccgg caaaaatcga ccacgtcatc   2760
cgtacggctc tacgtgaacg caaaccggct tatctggaaa tcgcatgcaa cgtcgctggc   2820
gctgaatgtg ttcgtccggg cccgatcaat agcctgctgc gtgaactcga agttgaccag   2880
accagtgtca ctgccgctgt agatgccgcc gtagaatggc tgcaggaccg ccagaacgtc   2940
gtcatgctgg tcggtagcaa actgcgtgcc gctgccgctg aaaaacaggc tgttgcccta   3000
gcggaccgcc tgggctgcgc tgtcacgatc atggctgccg aaaaaggctt cttcccggaa   3060
gatcatccga acttccgcgg cctgtactgg ggtgaagtca gctccgaagg tgcacaggaa   3120
ctggttgaaa acgccgatgc catcctgtgt ctggcaccgg tattcaacga ctatgctacc   3180
gttggctgga actcctggcc gaaaggcgac aatgtcatgg tcatggacac cgaccgcgtc   3240
actttcgcag gacagtcctt cgaaggtctg tcattgagca ccttcgccgc agcactggct   3300
gagaaagcac cttctcgccc ggcaacgact caaggcactc aagcaccggt actgggtatt   3360
gaggccgcag agcccaatgc accgctgacc aatgacgaaa tgacgcgtca gatccagtcg   3420
ctgatcactt ccgacactac tctgacagca gaaacaggtg actcttggtt caacgcttct   3480
cgcatgccga ttcctggcgg tgctcgtgtc gaactggaaa tgcaatgggg tcatatcggt   3540
tggtccgtac cttctgcatt cggtaacgcc gttggttctc cggagcgtcg ccacatcatg   3600
atggtcggtg atggctcttt ccagctgact gctcaagaag ttgctcagat gatccgctat   3660
gaaatcccgg tcatcatctt cctgatcaac aaccgcggtt acgtcatcga aatcgctatc   3720
catgacggcc cttacaacta catcaaaaac tggaactacg ctggcctgat cgacgtcttc   3780
aatgacgaag atggtcatgg cctgggtctg aaagcttcta ctggtgcaga actagaaggc   3840
gctatcaaga aagcactcga caatcgtcgc ggtccgacgc tgatcgaatg taacatcgct   3900
caggacgact gcactgaaac cctgattgct tggggtaaac gtgtagcagc taccaactct   3960
cgcaaaccac aagcgtaagt tgatgtagtg aattaggcgg ggcctattag ggccccacca   4020
catagcccct cttacggcgc aatacccgta agaggggctg ttttatataa ttaaaactag   4080
taacgcccgg ttgccaccgg gcgtttttta ttccgacatt gccataagta aaggcatccc   4140
ctgcgtgata agattacctt cagtttatgg aggactgacc atatgatcaa ggcttatgcc   4200
gctttagagg ctaatggcaa gttgcagccg ttcgagtatg atccgggcgc tttaggcgcc   4260
aacgaagttg aaatcgaagt tcaatactgc ggtgtttgtc attccgacct cagtatgatc   4320
aacaatgagt ggggtatcag taactatccg ttggttcccg gccacgaagt tgttggcacc   4380
gttgctgcta tgggtgaggg tgttaatcac gtggaagttg gtgacctggt tggtttaggc   4440
tggcacagtg gttattgtat gacttgtcac tcctgcctga gcggttatca taatttgtgc   4500
gctaccgccg agagtactat cgttggtcat tatggcggtt tcggtgaccg tgtgcgtgct   4560
aaaggtgtgt ccgttgttaa gctgcccaag ggtatcgatt tggcttccgc tggtccgttg   4620
ttttgcggtg gtatcactgt gttttccccc atggttgagt tatccctgaa accgaccgcc   4680
```

aaggttgccg ttattggtat cggtggtctc ggtcacctgg ccgttcagtt cttgcgtgct 4740
tggggttgcg aggttaccgc tttcactagc tccgctcgta aacagaccga ggttctggag 4800
ctgggtgccc atcatatttt ggacagtact aaccccgaag ccattgcttc cgccgagggt 4860
aagttcgatt acatcattag taccgttaat ttaaaattgg attggaatct gtatatttcc 4920
actttagccc cgcaaggtca ctttcatttc gtgggtgttg ttctcgaacc cctcgacttg 4980
aacttgttcc cgttgctcat gggtcagcgg agtgtgtccg ctagtccggt tggctccccg 5040
gctactatcg ctactatgct cgatttcgcc gttcggcacg atatcaagcc ggttgttgag 5100
cagttctcct tcgaccaaat taatgaagcc attgctcact tggagtccgg taaggctcac 5160
taccgtgtgg ttttgagtca ctccaagaac tgaaacgctc ggttgccgcc gggcgttttt 5220
tattcctgca gg 5232

<210> SEQ ID NO 26
<211> LENGTH: 5643
<212> TYPE: DNA
<213> ORGANISM: Artificial
<220> FEATURE:
<223> OTHER INFORMATION: Synthetically produced ethanologenic gene cassette from plasmid #1329 pVZ325a-nrsR-PnrsB-zpPDC-corR-PcorT-zmPDC(fco) integrated into pVZ325a

<400> SEQUENCE: 26
gtcgacggga gtttgcaaac tccctcatat tcatggcgat agggtgaacc gatagccttg 60
accgggaact gttttaattg ggcaaggaca attttgttga gctagcttgc gtcgtatcaa 120
acgcatttgg gccgccacca cattactcat gggctcctca tcaagatccc acagttgttg 180
ccggatcttg ctaccggaaa tgatccgctc tgggttttgc atcagatatt gaaaaatttg 240
aaattctctt acggttaaag caatttcctg tctttctagg tttagtggct ccgagatagt 300
taccgataac agattattac tgggatcaag gctgaagttg cccaaagtta aaatttgcgg 360
ttggaattgt ggcgatcgcc gttgtagtgc ccgcagtctt gctaatagct ctgccatcac 420
aaacggtttt gttagatagt catctgcccc ggcatctagt ccttcgacac ggttttccgg 480
ttctcctaac gctgttaaca tcaacaccgg caaggaatta ccctgggttc tcagtttttg 540
acagagttcc aaacccgata atcccggcag taaccaatcc acaatggcaa gggtgtattc 600
cgtccattga ttttccaaat aatcccaagc ttgggagcca tccgtcaccc aatccaccac 660
atacttttca ctaactagca ctttcttaat agccattccc aaatccgtct catcttccac 720
cagcaaaatt cgcatcgcct ctgccttttt tataacggtc tgatcttagc gggggaagga 780
gattttcacc tgaatttcat accccctttg gcagactggg aaaatcttgg acaaattccc 840
aatttgaggt ggtgtgatga attcctatac cgttggtatg tacttggcag aacgcctagc 900
ccagatcggc ctgaaacacc actttgccgt ggccggtgac tacaacctgg tgttgcttga 960
tcagctcctg ctgaacaaag acatggagca ggtctactgc tgtaacgaac ttaactgcgg 1020
ctttagcgcc gaaggttacg ctcgtgcacg tggtgccgcc gctgccatcg tcacgttcag 1080
cgtaggtgct atctctgcaa tgaacgccat cggtggcgcc tatgcagaaa acctgccggt 1140
catcctgatc tctggctcac cgaacaccaa tgactacggc acaggccaca tcctgcacca 1200
caccattggt actactgact ataactatca gctggaaatg gtaaaacacg ttacctgcgc 1260
acgtgaaagc atcgtttctg ccgaagaagc accggcaaaa atcgaccacg tcatccgtac 1320
ggctctacgt gaacgcaaac cggcttatct ggaaatcgca tgcaacgtcg ctggcgctga 1380
atgtgttcgt ccgggcccga tcaatagcct gctgcgtgaa ctcgaagttg accagaccag 1440

```
tgtcactgcc gctgtagatg ccgccgtaga atggctgcag gaccgccaga acgtcgtcat   1500
gctggtcggt agcaaactgc gtgccgctgc cgctgaaaaa caggctgttg ccctagcgga   1560
ccgcctgggc tgcgctgtca cgatcatggc tgccgaaaaa ggcttcttcc cggaagatca   1620
tccgaacttc cgcggcctgt actggggtga agtcagctcc gaaggtgcac aggaactggt   1680
tgaaaacgcc gatgccatcc tgtgtctggc accggtattc aacgactatg ctaccgttgg   1740
ctggaactcc tggccgaaag gcgacaatgt catggtcatg gacaccgacc gcgtcacttt   1800
cgcaggacag tccttcgaag gtctgtcatt gagcaccttc gccgcagcac tggctgagaa   1860
agcaccttct cgcccggcaa cgactcaagg cactcaagca ccggtactgg gtattgaggc   1920
cgcagagccc aatgcaccgc tgaccaatga cgaaatgacg cgtcagatcc agtcgctgat   1980
cacttccgac actactctga cagcagaaac aggtgactct tggttcaacg cttctcgcat   2040
gccgattcct ggcggtgctc gtgtcgaact ggaaatgcaa tggggtcata tcggttggtc   2100
cgtaccttct gcattcggta acgccgttgg ttctccggag cgtcgccaca tcatgatggt   2160
cggtgatggc tctttccagc tgactgctca agaagttgct cagatgatcc gctatgaaat   2220
cccggtcatc atcttcctga tcaacaaccg cggttacgtc atcgaaatcg ctatccatga   2280
cggcccttac aactacatca aaaactggaa ctacgctggc ctgatcgacg tcttcaatga   2340
cgaagatggt catggcctgg gtctgaaagc ttctactggt gcagaactag aaggcgctat   2400
caagaaagca ctcgacaatc gtcgcggtcc gacgctgatc gaatgtaaca tcgctcagga   2460
cgactgcact gaaaccctga ttgcttgggg taaacgtgta gcagctacca actctcgcaa   2520
accacaagcg taagttgatg tagtgaatta ggcggggcct attagggccc caccacatag   2580
cccctcttac ggcgcaatac ccgtaagagg ggctgtttta tataattaaa actagagtcg   2640
accatgcgtc caaaactttc accatccttt ccctatcaac ctttactgca ctaaagacaa   2700
gtgagatagc agtggcaatc tggctttgca atcaatgttt ccactaaagc gtttagcgtt   2760
actgcggcta gaagtcctcc accgaggctc ccctgaatgg tgatatgggg aatgggactg   2820
gtcatcagtc gtcgttttgc cccggagca tgactaaaac cgatcggcat tccgatcaca   2880
agagccggct gaatatgttg ttgctctatc agcttacagg cagtgagtaa aacagaaggg   2940
gcatagccga tcgccagcac acatccttgg ggaatctgtt gtaaccgctg ttgccaatgg   3000
tcatggtgcc aaaaagcttg ctcggcttcc ctaagccctg tgatgtgagg gtcgtcaatc   3060
agcgttttaa ccgtacatcc taaatgagct aaccgagttt gatcaagagc cgcagccaca   3120
accggaacat cggtgacgac tggacaccct gctttcagtg catctcgtgc cgaggcgatc   3180
gctccctgac tcaatcgaac ggcgtttacc aagctaacat caccacaggc cagcactaat   3240
tgatgtagta agtgaatggt aatttcagag taagccgata aatccggtag caggtgtttg   3300
agggattcct gaaaggcttc tggatgagtt gttgtctccg catctaggtt cgtccacaac   3360
tgatcgagtt ttcctaaccc ctcctggaca tccacatcaa gctgtttcag ttgggccaga   3420
gcttccgctt gggtaatctg gcaactctgg tcgcgtccca gtaatccttc taaagcagat   3480
gcggtttggc ggagtcgagt aatctgctga atcacagcct gatattgctg ttgcaactgc   3540
accattaggg tgggatcaag gctctcttca gaatggctat ccagcagttg ccgaatatga   3600
gacaactgaa agccctgctg tttgagggca atgactcgtt ggagccgttg tacgtcctgc   3660
tgagtataaa ggcggtagtt gccctctgag cgttgaacgg ggggaagcaa tcccagggtg   3720
tggtaatggc gcaccatgcg aggcgtaacg ccacctccca ctgcatctgt gagttcttta   3780
```

-continued atcgttaagt gattagtctt catcccttta gtttactcaa aaccttgaca ttgacactaa 3840
tgttaaggtt taggctgaga aggtaaaaat ccaagttaaa aagcatgaat tcctataccg 3900
tgggtaccta tttggccgaa cggttggtgc aaattggttt gaaacaccac tttgccgtgg 3960
ccggtgacta caacttggtg ttgttggaca acttgttgtt gaacaaaaac atggaacaag 4020
tgtattgttg taacgaattg aactgtggtt tttccgccga aggttatgct cgggccaaag 4080
gtgccgccgc cgccgtggtg acctactccg tgggtgcctt gtccgccttt gatgctattg 4140
gtggtgccta tgccgaaaac ttgcccgtga ttttgatttc cggtgctccc aacaacaatg 4200
atcacgctgc tggtcacgtg ttgcaccacg ctttgggtaa aaccgactat cactatcaat 4260
tggaaatggc caaaaacatt accgccgccg ctgaagccat ttacaccccc gaagaagctc 4320
ccgctaaaat tgatcacgtg attaaaaccg ctttgcggga aaaaaaaccc gtgtatttgg 4380
aaattgcttg taacattgct tccatgccct gtgccgctcc cggtcccgcc tccgccttgt 4440
ttaatgacga agcctccgac gaagcttcct tgaatgccgc cgtggaagaa accttgaaat 4500
ttattgccaa ccgggacaaa gtggccgtgt tggtgggttc caaattgcgg gccgctggtg 4560
ctgaagaagc tgctgtgaaa tttgctgatg ctttgggtgg tgccgtggct accatggctg 4620
ctgccaaatc ctttttttccc gaagaaaacc cccactacat tggtacctcc tggggtgaag 4680
tgtcctatcc cggtgtggaa aaaaccatga aagaagccga tgccgtgatt gctttggctc 4740
ccgtgtttaa cgactactcc accaccggtt ggaccgatat tcccgatccc aaaaaattgg 4800
tgttggctga accccggtcc gtggtggtga acggtgtgcg gtttccctcc gtgcacttga 4860
aagactattt gacccggttg gctcaaaaag tgtccaaaaa aaccggtgct ttggactttt 4920
ttaaatcctt gaatgccggt gaattgaaaa aagccgctcc cgctgatccc tccgctccct 4980
tggtgaacgc cgaaattgcc cggcaagtgg aagctttgtt gacccccaac accaccgtga 5040
ttgctgaaac cggtgactcc tggtttaatg ctcaacggat gaaattgccc aacggtgctc 5100
gggtggaata tgaaatgcaa tggggtcaca ttggttggtc cgtgcccgcc gcctttggtt 5160
atgccgtggg tgctcccgaa cggcggaaca ttttgatggt gggtgatggt tcctttcaat 5220
tgaccgctca agaagtggct caaatggtgc ggttgaaatt gcccgtgatt attttttttga 5280 ttaataacta tggttacacc attgaagtga tgattcacga tggtccctac aacaacatta 5340
aaaactggga ttatgccggt ttgatggaag tgtttaacgg taacggtggt tatgactccg 5400
gtgctggtaa aggtttgaaa gctaaaaccg gtggtgaatt ggccgaagct attaaagtgg 5460
ctttggccaa caccgacggt cccaccttga ttgaatgttt tattggtcgg gaagactgta 5520
ccgaagaatt ggtgaaatgg ggtaaacggg tggctgccgc caactcccgg aaacccgtga 5580
acaaattgtt gtagttaaac gctcggttgc cgccgggcgt tttttactag tctcgagctg 5640
cag 5643

<210> SEQ ID NO 27
<211> LENGTH: 7104
<212> TYPE: DNA
<213> ORGANISM: Artificial
<220> FEATURE:
<223> OTHER INFORMATION: Synthetically produced ethanologenic gene cassette from plasmid #1375 pVZ325a-nrsRS-PnrsB-zpPDC-corR-PcorT*-zmPDCdeg integrated into pVZ325a

<400> SEQUENCE: 27
gtcgacccta tatcgggctt ttctcaataa aatctttatt ttttgaggtg ctttttagcc 60
ataaataatc actttagtat aaaattttga cggcgtaaag ttgataaaat agaattaaga 120

-continued

```
atggactatc ggtacagaaa aaatgggtaa ctggatggtg aataaacttc ccttacccaa    180
tgcactctcc accgttaaag acccccctatg cttaacggtg atcacctggg caatggcgag    240
tcccaaccct gtcccccccg ttttgcgcga acgatctcga ttaactcggt aaaaacgctc    300
aaaaatgtgt tcctgttggt cgggggcaat gccgatgccg gtatcttgca cggtgatgat    360
agccatctgt tcatgggatg tcagggtaat atcaacacgt cccccagcag ttgtgtattg    420
aatggcgttg gcaattaggt ttgagaccag tcgatagagt tgggattcat taccccaggc    480
gtaaacttcc cctgaactca gatcactgct gagatcaatg tgggcggcga tcgctaattc    540
taaaaactct tcggtgaggt cactgactaa atcatttaaa caacaaagcc gccaatcttc    600
ggcggtggtt tcctgctcta agcgacttag tagcaataaa tccgtaatca attggcttaa    660
tcgccttccc tgtcgttcaa cggtatgtag catggtgtta atttctgggg aatggcttga    720
gtcgatgcgt aataccgctt ccaccgtggc caacagacta gccaatggcg atcgtaattc    780
atgggctgca ttcgcggtga attgttgttg ttgttggtag gactggtaaa tgggacgcat    840
ggctaacccc gctaagcccc aactggagaa ggcgaccaaa cccagggcaa tgggaaaact    900
aagccctaaa atccaaagaa tacgtttatt ttcggcatca aaggctgcca ggctccggcc    960
aatttgtaga tagccccagg aagatttgtc tgtattaccg gcgctatgca aaatggtggt   1020
gaattgtcga taccgatcgc cggttggggg gtgaatagtc tgccaagttt cctggttaaa   1080
aatggaggat agggaagccg gttgattagg cgaaaaagcc agcaggttgc cttgataatc   1140
aaataaacga atgtaatata aactgcgatc actaatgccc aacgtgtgac gttcaatcag   1200
ggtggggttg acctggcagg gttggttgac caaacacaga tcgggcaaca ttttttgtaa   1260
tactccggtg ggactagcat tactcggcaa catcggctct aaactgtcat gcaacgtccc   1320
ggcgatcgac tccacttctc gctccaacgc catccagttg gcctgcacaa tggcacgata   1380
aacccccaac cccaacaggg taagaatacc ccccattact agggcatacc agaaagccaa   1440
ttgcagacga ctacgggcaa agaggcgacg ggtattcatg gcgatagggt gaaccgatag   1500
ccttgaccgg gaactgtttt aattgggcaa ggacaatttt gttgagctag cttgcgtcgt   1560
atcaaacgca tttgggccgc caccacatta ctcatgggct cctcatcaag atcccacagt   1620
tgttgccgga tcttgctacc ggaaatgatc cgctctgggt tttgcatcag atattgaaaa   1680
atttgaaatt ctcttacggt taaagcaatt tcctgtcttt ctaggtttag tggctccgag   1740
atagttaccg ataacagatt attactggga tcaaggctga agttgcccaa agttaaaatt   1800
tgcggttgga attgtggcga tcgccgttgt agtgcccgca gtcttgctaa tagctctgcc   1860
atcacaaacg gttttgttag atagtcatct gccccggcat ctagtccttc gacacggttt   1920
tccggttctc ctaacgctgt taacatcaac accggcaagg aattaccctg ggttctcagt   1980
ttttgacaga gttccaaacc cgataatccc ggcagtaacc aatccacaat ggcaagggtg   2040
tattccgtcc attgattttc caaataatcc caagcttggg agccatccgt cacccaatcc   2100
accacatact tttcactaac tagcactttc ttaatagcca ttcccaaatc cgtctcatct   2160
tccaccagca aaattcgcat cgcctctgcc ttttttataa cggtctgatc ttagcggggg   2220
aaggagattt tcacctgaat ttcatacccc ctttggcaga ctgggaaaat cttggacaaa   2280
ttcccaattt gaggtggtgt gatgaattcc tataccgttg gtatgtactt ggcagaacgc   2340
ctagcccaga tcggcctgaa acaccacttt gccgtggccg gtgactacaa cctggtgttg   2400
cttgatcagc tcctgctgaa caaagacatg gagcaggtct actgctgtaa cgaacttaac   2460
```

-continued

```
tgcggcttta gcgccgaagg ttacgctcgt gcacgtggtg ccgccgctgc catcgtcacg   2520
ttcagcgtag gtgctatctc tgcaatgaac gccatcggtg gcgcctatgc agaaaacctg   2580
ccggtcatcc tgatctctgg ctcaccgaac accaatgact acggcacagg ccacatcctg   2640
caccacacca ttggtactac tgactataac tatcagctgg aaatggtaaa acacgttacc   2700
tgcgcacgtg aaagcatcgt ttctgccgaa gaagcaccgg caaaaatcga ccacgtcatc   2760
cgtacggctc tacgtgaacg caaaccggct tatctggaaa tcgcatgcaa cgtcgctggc   2820
gctgaatgtg ttcgtccggg cccgatcaat agcctgctgc gtgaactcga agttgaccag   2880
accagtgtca ctgccgctgt agatgccgcc gtagaatggc tgcaggaccg ccagaacgtc   2940
gtcatgctgg tcggtagcaa actgcgtgcc gctgccgctg aaaaacaggc tgttgcccta   3000
gcggaccgcc tgggctgcgc tgtcacgatc atggctgccg aaaaaggctt cttcccggaa   3060
gatcatccga acttccgcgg cctgtactgg ggtgaagtca gctccgaagg tgcacaggaa   3120
ctggttgaaa acgccgatgc catcctgtgt ctggcaccgg tattcaacga ctatgctacc   3180
gttggctgga actcctggcc gaaaggcgac aatgtcatgg tcatggacac cgaccgcgtc   3240
actttcgcag gacagtcctt cgaaggtctg tcattgagca ccttcgccgc agcactggct   3300
gagaaagcac cttctcgccc ggcaacgact caaggcactc aagcaccggt actgggtatt   3360
gaggccgcag agcccaatgc accgctgacc aatgacgaaa tgacgcgtca gatccagtcg   3420
ctgatcactt ccgacactac tctgacagca gaaacaggtg actcttggtt caacgcttct   3480
cgcatgccga ttcctggcgg tgctcgtgtc gaactggaaa tgcaatgggg tcatatcggt   3540
tggtccgtac cttctgcatt cggtaacgcc gttggttctc cggagcgtcg ccacatcatg   3600
atggtcggtg atggctcttt ccagctgact gctcaagaag ttgctcagat gatccgctat   3660
gaaatcccgg tcatcatctt cctgatcaac aaccgcggtt acgtcatcga aatcgctatc   3720
catgacggcc cttacaacta catcaaaaac tggaactacg ctggcctgat cgacgtcttc   3780
aatgacgaag atggtcatgg cctgggtctg aaagcttcta ctggtgcaga actagaaggc   3840
gctatcaaga aagcactcga caatcgtcgc ggtccgacgc tgatcgaatg taacatcgct   3900
caggacgact gcactgaaac cctgattgct tggggtaaac gtgtagcagc taccaactct   3960
cgcaaaccac aagcgtaagt tgatgtagtg aattaggcgg ggcctattag ggccccacca   4020
catagcccct cttacggcgc aatacccgta agaggggctg ttttatataa ttaaaactag   4080
aaagattcga ccatgcgtcc aaaactttca ccatcctttc cctatcaacc tttactgcac   4140
taaagacaag tgagatagca gtggcaatct ggctttgcaa tcaatgtttc cactaaagcg   4200
tttagcgtta ctgcggctag aagtcctcca ccgaggctcc cctgaatggt gatatgggga   4260
atgggactgg tcatcagtcg tcgttttgcc cccggagcat gactaaaacc gatcggcatt   4320
ccgatcacaa gagccggctg aatatgttgt tgctctatca gcttacaggc agtgagtaaa   4380
acagaagggg catagccgat cgccagcaca catccttggg gaatctgttg taaccgctgt   4440
tgccaatggt catggtgcca aaaagcttgc tcggcttccc taagccctgt gatgtgaggg   4500
tcgtcaatca gcgttttaac cgtacatcct aaatgagcta accgagtttg atcaagagcc   4560
gcagccacaa ccggaacatc ggtgacgact ggacaccctg ctttcagtgc atctcgtgcc   4620
gaggcgatcg ctccctgact caatcgaacg gcgtttacca agctaacatc accacaggcc   4680
agcactaatt gatgtagtaa gtgaatggta atttcagagt aagccgataa atccggtagc   4740
aggtgtttga gggattcctg aaaggcttct ggatgagttg ttgtctccgc atctaggttc   4800
gtccacaact gatcgagttt tcctaacccc tcctggacat ccacatcaag ctgtttcagt   4860
```

-continued

```
tgggccagag cttccgcttg ggtaatctgg caactctggt cgcgtcccag taatccttct   4920
aaagcagatg cggtttggcg gagtcgagta atctgctgaa tcacagcctg atattgctgt   4980
tgcaactgca ccattagggt gggatcaagg ctctcttcag aatggctatc cagcagttgc   5040
cgaatatgag acaactgaaa gccctgctgt ttgagggcaa tgactcgttg gagccgttgt   5100
acgtcctgct gagtataaag gcggtagttg ccctctgagc gttgaacggg gggaagcaat   5160
cccagggtgt ggtaatggcg caccatgcga ggcgtaacgc cacctcccac tgcatctgtg   5220
agttctttaa tcgttaagtg attagtcttc atgactttag tttactcaaa accttgacat   5280
tgacactaat gttaaggttt aggctgagaa ggtaaaaatc gaggataaaa agcatgaatt   5340
cctacaccgt tggcacttac ctggctgaac gcttggttca gatcggctta aaacaccatt   5400
ttgctgttgc tggtgattat aatttggttt tgttagataa tttattgctc aataagaata   5460
tggaacaggt gtactgttgc aatgagttaa attgtggctt ttccgctgag ggctacgccc   5520
gtgctaaggg tgctgctgct gctgttgtga cttattctgt tggcgctttg agtgcttttg   5580
acgccattgg cggtgcttac gctgagaatt tgccagtgat tttaattagt ggcgccccaa   5640
ataataacga ccatgccgcc ggccatgtcc tccaccatgc cttgggtaag actgattacc   5700
attaccaact ggagatggct aaaaatatta ccgctgctgc cgaagctatc tatactcctg   5760
aggaagcccc agccaagatt gaccatgtca tcaagaccgc cttgcgggaa aaaaaaccag   5820
tgtacttaga gattgcctgt aatatcgcca gtatgccttg tgctgccccc ggtccagctt   5880
ctgctctctt taacgatgaa gcttctgatg aggccagtct caacgctgct gtggaggaaa   5940
ctttaaagtt tattgctaat cgtgataagg tggctgtttt agttggttct aaattacgtg   6000
ctgccggcgc cgaggaagcc gccgttaagt ttgccgacgc cttaggcggt gctgtggcca   6060
ctatggccgc cgctaagtct ttttttcctg aagagaatcc acactatatt ggcactagct   6120
ggggcgaggt ttcttaccca ggtgtggaga aaaccatgaa ggaggctgac gctgtgattg   6180
ccttagcccc ggtttttaat gattatagta ctaccggctg gaccgacatc ccggacccga   6240
aaaagttagt gttagccgaa ccacggagtg ttgttgtgaa tggtgtgcgt tttccttctg   6300
tgcacttaaa ggattactta actcggctcg cccagaaggt gagtaaaaag actggcgccc   6360
tcgatttttt taagagttta aacgctggcg agttaaaaaa ggctgcccca gccgacccat   6420
ccgccccact cgttaatgct gaaattgctc ggcaggttga ggccttgtta actccaaata   6480
ccaccgtgat cgccgaaact ggcgatagtt ggtttaacgc ccaacgtatg aaattaccaa   6540
atggcgcccg tgtggagtac gagatgcaat ggggccatat tggctggagt gtgccggctg   6600
cttttggcta cgctgttggc gccccagagc ggcgtaatat tttaatggtg ggcgacggca   6660
gttttcagtt aaccgcccaa gaggttgccc aaatggtgcg tttaaagtta ccagtgatta   6720
tttttctcat taacaattac ggctatacta ttgaggtgat gattcacgac ggcccatata   6780
ataatattaa aaattgggac tacgctggct taatggaggt ctttaatggc aatggcggct   6840
acgattctgg cgccggcaag ggtttaaaag ccaagactgg cggtgagtta gctgaagcca   6900
ttaaagtggc cttagctaat actgatggtc ctactttaat tgagtgtttt attggccggg   6960
aagattgtac cgaggaactc gttaagtggg gcaaacgtgt ggccgctgct aattctcgga   7020
aacccgtgaa taaattatta tgaaatattt tagccgcccc agtcagtaat gactggggcg   7080
tttttattg ggagctcctg cagg                                            7104
```

<210> SEQ ID NO 28

<211> LENGTH: 7104
<212> TYPE: DNA
<213> ORGANISM: Artificial
<220> FEATURE:
<223> OTHER INFORMATION: Synthetically produced ethanologenic gene cassette from plasmid #1376 pVZ325a-nrsRS-PnrsB*-zpPDC-corR-PcorT*-zmPDCdeg integrated into pVZ325a

<400> SEQUENCE: 28
gtcgacccta tatcgggctt ttctcaataa aatctttatt ttttgaggtg ctttttagcc 60
ataaataatc actttagtat aaaattttga cggcgtaaag ttgataaaat agaattaaga 120
atggactatc ggtacagaaa aaatgggtaa ctggatggtg aataaacttc ccttacccaa 180
tgcactctcc accgttaaag accccctatg cttaacggtg atcacctggg caatggcgag 240
tcccaaccct gtcccccccg ttttgcgcga acgatctcga ttaactcggt aaaaacgctc 300
aaaaatgtgt tcctgttggt cgggggcaat gccgatgccg gtatcttgca cggtgatgat 360
agccatctgt tcatgggatg tcagggtaat atcaacacgt cccccagcag ttgtgtattg 420
aatggcgttg gcaattaggt ttgagaccag tcgatagagt tgggattcat taccccaggc 480
gtaaacttcc cctgaactca gatcactgct gagatcaatg tgggcggcga tcgctaattc 540
taaaaactct tcggtgaggt cactgactaa atcatttaaa caacaaagcc gccaatcttc 600
ggcggtggtt tcctgctcta agcgacttag tagcaataaa tccgtaatca attggcttaa 660
tcgccttccc tgtcgttcaa cggtatgtag catggtgtta atttctgggg aatggcttga 720
gtcgatgcgt aataccgctt ccaccgtggc caacagacta gccaatggcg atcgtaattc 780
atgggctgca ttcgcggtga attgttgttg ttgttggtag gactggtaaa tgggacgcat 840
ggctaacccc gctaagcccc aactggagaa ggcgaccaaa cccagggcaa tgggaaaact 900
aagccctaaa atccaaagaa tacgtttatt ttcggcatca aaggctgcca ggctccggcc 960
aatttgtaga tagccccagg aagatttgtc tgtattaccg gcgctatgca aaatggtggt 1020
gaattgtcga taccgatcgc cggttggggg gtgaatagtc tgccaagttt cctggttaaa 1080
aatggaggat agggaagccg gttgattagg cgaaaaagcc agcaggttgc cttgataatc 1140
aaataaacga atgtaatata aactgcgatc actaatgccc aacgtgtgac gttcaatcag 1200
ggtggggttg acctggcagg gttggttgac caaacacaga tcgggcaaca ttttttgtaa 1260
tactccggtg ggactagcat tactcggcaa catcggctct aaactgtcat gcaacgtccc 1320
ggcgatcgac tccacttctc gctccaacgc catccagttg gcctgcacaa tggcacgata 1380
aacccccaac cccaacaggg taagaatacc ccccattact agggcatacc agaaagccaa 1440
ttgcagacga ctacgggcaa agaggcgacg ggtattcatg gcgatagggt gaaccgatag 1500
ccttgaccgg gaactgtttt aattgggcaa ggacaatttt gttgagctag cttgcgtcgt 1560
atcaaacgca tttgggccgc caccacatta ctcatgggct cctcatcaag atcccacagt 1620
tgttgccgga tcttgctacc ggaaatgatc cgctctgggt tttgcatcag atattgaaaa 1680
atttgaaatt ctcttacggt taaagcaatt tcctgtcttt ctaggtttag tggctccgag 1740
atagttaccg ataacagatt attactggga tcaaggctga agttgcccaa agttaaaatt 1800
tgcggttgga attgtggcga tcgccgttgt agtgcccgca gtcttgctaa tagctctgcc 1860
atcacaaacg gttttgttag atagtcatct gccccggcat ctagtccttc gacacggttt 1920
tccggttctc ctaacgctgt taacatcaac accggcaagg aattaccctg ggttctcagt 1980
ttttgacaga gttccaaacc cgataatccc ggcagtaacc aatccacaat ggcaagggtg 2040
tattccgtcc attgattttc caaataatcc caagcttggg agccatccgt cacccaatcc 2100

-continued

```
accacatact tttcactaac tagcactttc ttaatagcca ttcccaaatc cgtctcatct   2160
tccaccagca aaattcgcat cgcctctgcc ttttttataa cggtctgatc ttagcggggg   2220
aaggagattt tcacctgaat ttcatacccc ctttggcaga ctgggaaaat cttggacaaa   2280
ttcccaattg gaggaggtgt gatgaattcc tataccgttg gtatgtactt ggcagaacgc   2340
ctagcccaga tcggcctgaa acaccacttt gccgtggccg gtgactacaa cctggtgttg   2400
cttgatcagc tcctgctgaa caaagacatg gagcaggtct actgctgtaa cgaacttaac   2460
tgcggcttta gcgccgaagg ttacgctcgt gcacgtggtg ccgccgctgc catcgtcacg   2520
ttcagcgtag gtgctatctc tgcaatgaac gccatcggtg gcgcctatgc agaaaacctg   2580
ccggtcatcc tgatctctgg ctcaccgaac accaatgact acggcacagg ccacatcctg   2640
caccacacca ttggtactac tgactataac tatcagctgg aaatggtaaa acacgttacc   2700
tgcgcacgtg aaagcatcgt ttctgccgaa gaagcaccgg caaaaatcga ccacgtcatc   2760
cgtacggctc tacgtgaacg caaaccggct tatctggaaa tcgcatgcaa cgtcgctggc   2820
gctgaatgtg ttcgtccggg cccgatcaat agcctgctgc gtgaactcga agttgaccag   2880
accagtgtca ctgccgctgt agatgccgcc gtagaatggc tgcaggaccg ccagaacgtc   2940
gtcatgctgg tcggtagcaa actgcgtgcc gctgccgctg aaaaacaggc tgttgcccta   3000
gcggaccgcc tgggctgcgc tgtcacgatc atggctgccg aaaaaggctt cttcccggaa   3060
gatcatccga acttccgcgg cctgtactgg ggtgaagtca gctccgaagg tgcacaggaa   3120
ctggttgaaa acgccgatgc catcctgtgt ctggcaccgg tattcaacga ctatgctacc   3180
gttggctgga actcctggcc gaaaggcgac aatgtcatgg tcatggacac cgaccgcgtc   3240
actttcgcag gacagtcctt cgaaggtctg tcattgagca ccttcgccgc agcactggct   3300
gagaaagcac cttctcgccc ggcaacgact caaggcactc aagcaccggt actgggtatt   3360
gaggccgcag agcccaatgc accgctgacc aatgacgaaa tgacgcgtca gatccagtcg   3420
ctgatcactt ccgacactac tctgacagca gaaacaggtg actcttggtt caacgcttct   3480
cgcatgccga ttcctggcgg tgctcgtgtc gaactggaaa tgcaatgggg tcatatcggt   3540
tggtccgtac cttctgcatt cggtaacgcc gttggttctc cggagcgtcg ccacatcatg   3600
atggtcggtg atggctcttt ccagctgact gctcaagaag ttgctcagat gatccgctat   3660
gaaatcccgg tcatcatctt cctgatcaac aaccgcggtt acgtcatcga aatcgctatc   3720
catgacggcc cttacaacta catcaaaaac tggaactacg ctggcctgat cgacgtcttc   3780
aatgacgaag atggtcatgg cctgggtctg aaagcttcta ctggtgcaga actagaaggc   3840
gctatcaaga aagcactcga caatcgtcgc ggtccgacgc tgatcgaatg taacatcgct   3900
caggacgact gcactgaaac cctgattgct tggggtaaac gtgtagcagc taccaactct   3960
cgcaaaccac aagcgtaagt tgatgtagtg aattaggcgg ggcctattag ggccccacca   4020
catagcccct cttacggcgc aatacccgta agaggggctg ttttatataa ttaaaactag   4080
aaagattcga ccatgcgtcc aaaactttca ccatcctttc cctatcaacc tttactgcac   4140
taaagacaag tgagatagca gtggcaatct ggctttgcaa tcaatgtttc cactaaagcg   4200
tttagcgtta ctgcggctag aagtcctcca ccgaggctcc cctgaatggt gatatgggga   4260
atgggactgg tcatcagtcg tcgttttgcc cccggagcat gactaaaacc gatcggcatt   4320
ccgatcacaa gagccggctg aatatgttgt tgctctatca gcttacaggc agtgagtaaa   4380
acagaagggg catagccgat cgccagcaca catccttggg gaatctgttg taaccgctgt   4440
```

-continued tgccaatggt catggtgcca aaaagcttgc tcggcttccc taagccctgt gatgtgaggg 4500
tcgtcaatca gcgttttaac cgtacatcct aaatgagcta accgagtttg atcaagagcc 4560
gcagccacaa ccggaacatc ggtgacgact ggacaccctg ctttcagtgc atctcgtgcc 4620
gaggcgatcg ctccctgact caatcgaacg gcgtttacca agctaacatc accacaggcc 4680
agcactaatt gatgtagtaa gtgaatggta atttcagagt aagccgataa atccggtagc 4740
aggtgtttga gggattcctg aaaggcttct ggatgagttg ttgtctccgc atctaggttc 4800
gtccacaact gatcgagttt tcctaacccc tcctggacat ccacatcaag ctgtttcagt 4860
tgggccagag cttccgcttg ggtaatctgg caactctggt cgcgtcccag taatccttct 4920
aaagcagatg cggtttggcg gagtcgagta atctgctgaa tcacagcctg atattgctgt 4980
tgcaactgca ccattagggt gggatcaagg ctctcttcag aatggctatc cagcagttgc 5040
cgaatatgag acaactgaaa gccctgctgt ttgagggcaa tgactcgttg gagccgttgt 5100
acgtcctgct gagtataaag gcggtagttg ccctctgagc gttgaacggg gggaagcaat 5160
cccagggtgt ggtaatggcg caccatgcga ggcgtaacgc cacctcccac tgcatctgtg 5220
agttctttaa tcgttaagtg attagtcttc atgactttag tttactcaaa accttgacat 5280
tgacactaat gttaaggttt aggctgagaa ggtaaaaatc gaggataaaa agcatgaatt 5340
cctacaccgt tggcacttac ctggctgaac gcttggttca gatcggctta aaacaccatt 5400
ttgctgttgc tggtgattat aatttggttt tgttagataa tttattgctc aataagaata 5460
tggaacaggt gtactgttgc aatgagttaa attgtggctt ttccgctgag ggctacgccc 5520
gtgctaaggg tgctgctgct gctgttgtga cttattctgt tggcgctttg agtgcttttg 5580
acgccattgg cggtgcttac gctgagaatt tgccagtgat tttaattagt ggcgccccaa 5640
ataataacga ccatgccgcc ggccatgtcc tccaccatgc cttgggtaag actgattacc 5700
attaccaact ggagatggct aaaaatatta ccgctgctgc cgaagctatc tatactcctg 5760
aggaagcccc agccaagatt gaccatgtca tcaagaccgc cttgcgggaa aaaaaaccag 5820
tgtacttaga gattgcctgt aatatcgcca gtatgccttg tgctgccccc ggtccagctt 5880
ctgctctctt taacgatgaa gcttctgatg aggccagtct caacgctgct gtggaggaaa 5940
ctttaaagtt tattgctaat cgtgataagg tggctgtttt agttggttct aaattacgtg 6000
ctgccggcgc cgaggaagcc gccgttaagt ttgccgacgc cttaggcggt gctgtggcca 6060
ctatggccgc cgctaagtct ttttttcctg aagagaatcc acactatatt ggcactagct 6120
ggggcgaggt ttcttaccca ggtgtggaga aaaccatgaa ggaggctgac gctgtgattg 6180
ccttagcccc ggtttttaat gattatagta ctaccggctg gaccgacatc ccggacccga 6240
aaaagttagt gttagccgaa ccacggagtg ttgttgtgaa tggtgtgcgt tttccttctg 6300
tgcacttaaa ggattactta actcggctcg cccagaaggt gagtaaaaag actggcgccc 6360
tcgatttttt taagagttta aacgctggcg agttaaaaaa ggctgcccca gccgacccat 6420
ccgcccccact cgttaatgct gaaattgctc ggcaggttga ggccttgtta actccaaata 6480
ccaccgtgat cgccgaaact ggcgatagtt ggtttaacgc ccaacgtatg aaattaccaa 6540
atggcgcccg tgtggagtac gagatgcaat ggggccatat tggctggagt gtgccggctg 6600
cttttggcta cgctgttggc gccccagagc ggcgtaatat tttaatggtg ggcgacggca 6660
gttttcagtt aaccgcccaa gaggttgccc aaatggtgcg tttaaagtta ccagtgatta 6720
tttttctcat taacaattac ggctatacta ttgaggtgat gattcacgac ggcccatata 6780
ataatattaa aaattgggac tacgctggct taatggaggt ctttaatggc aatggcggct 6840
acgattctgg cgccggcaag ggtttaaaag ccaagactgg cggtgagtta gctgaagcca 6900
ttaaagtggc cttagctaat actgatggtc ctactttaat tgagtgtttt attggccggg 6960
aagattgtac cgaggaactc gttaagtggg gcaaacgtgt ggccgctgct aattctcgga 7020
aacccgtgaa taaattatta tgaaatattt tagccgcccc agtcagtaat gactggggcg 7080
ttttttattg ggagctcctg cagg 7104

<210> SEQ ID NO 29
<211> LENGTH: 5655
<212> TYPE: DNA
<213> ORGANISM: Artificial
<220> FEATURE:
<223> OTHER INFORMATION: Synthetically produced ethanologenic gene cassette from plasmid #1379 pVZ325a-nrsR-PnrsB-zpPDC-corR-PcorT-zmPDCdeg integrated into pVZ325a

<400> SEQUENCE: 29
gtcgacggga gtttgcaaac tccctcatat tcatggcgat agggtgaacc gatagccttg 60
accgggaact gttttaattg ggcaaggaca attttgttga gctagcttgc gtcgtatcaa 120
acgcatttgg gccgccacca cattactcat gggctcctca tcaagatccc acagttgttg 180
ccggatcttg ctaccggaaa tgatccgctc tgggttttgc atcagatatt gaaaaatttg 240
aaattctctt acggttaaag caatttcctg tctttctagg tttagtggct ccgagatagt 300
taccgataac agattattac tgggatcaag gctgaagttg cccaaagtta aaatttgcgg 360
ttggaattgt ggcgatcgcc gttgtagtgc ccgcagtctt gctaatagct ctgccatcac 420
aaacggtttt gttagatagt catctgcccc ggcatctagt ccttcgacac ggttttccgg 480
ttctcctaac gctgttaaca tcaacaccgg caaggaatta ccctgggttc tcagtttttg 540
acagagttcc aaacccgata atcccggcag taaccaatcc acaatggcaa gggtgtattc 600
cgtccattga ttttccaaat aatcccaagc ttgggagcca tccgtcaccc aatccaccac 660
atacttttca ctaactagca ctttcttaat agccattccc aaatccgtct catcttccac 720
cagcaaaatt cgcatcgcct ctgccttttt tataacggtc tgatcttagc gggggaagga 780
gattttcacc tgaatttcat accccctttg gcagactggg aaaatcttgg acaaattccc 840
aatttgaggt ggtgtgatga attcctatac cgttggtatg tacttggcag aacgcctagc 900
ccagatcggc ctgaaacacc actttgccgt ggccggtgac tacaacctgg tgttgcttga 960
tcagctcctg ctgaacaaag acatggagca ggtctactgc tgtaacgaac ttaactgcgg 1020
ctttagcgcc gaaggttacg ctcgtgcacg tggtgccgcc gctgccatcg tcacgttcag 1080
cgtaggtgct atctctgcaa tgaacgccat cggtggcgcc tatgcagaaa acctgccggt 1140
catcctgatc tctggctcac cgaacaccaa tgactacggc acaggccaca tcctgcacca 1200
caccattggt actactgact ataactatca gctggaaatg gtaaaacacg ttacctgcgc 1260
acgtgaaagc atcgtttctg ccgaagaagc accggcaaaa atcgaccacg tcatccgtac 1320
ggctctacgt gaacgcaaac cggcttatct ggaaatcgca tgcaacgtcg ctggcgctga 1380
atgtgttcgt ccgggcccga tcaatagcct gctgcgtgaa ctcgaagttg accagaccag 1440
tgtcactgcc gctgtagatg ccgccgtaga atggctgcag gaccgccaga acgtcgtcat 1500
gctggtcggt agcaaactgc gtgccgctgc cgctgaaaaa caggctgttg ccctagcgga 1560
ccgcctgggc tgcgctgtca cgatcatggc tgccgaaaaa ggcttcttcc cggaagatca 1620
tccgaacttc cgcggcctgt actggggtga agtcagctcc gaaggtgcac aggaactggt 1680

-continued

```
tgaaaacgcc gatgccatcc tgtgtctggc accggtattc aacgactatg ctaccgttgg   1740
ctggaactcc tggccgaaag gcgacaatgt catggtcatg gacaccgacc gcgtcacttt   1800
cgcaggacag tccttcgaag gtctgtcatt gagcaccttc gccgcagcac tggctgagaa   1860
agcaccttct cgcccggcaa cgactcaagg cactcaagca ccggtactgg gtattgaggc   1920
cgcagagccc aatgcaccgc tgaccaatga cgaaatgacg cgtcagatcc agtcgctgat   1980
cacttccgac actactctga cagcagaaac aggtgactct tggttcaacg cttctcgcat   2040
gccgattcct ggcggtgctc gtgtcgaact ggaaatgcaa tggggtcata tcggttggtc   2100
cgtaccttct gcattcggta acgccgttgg ttctccggag cgtcgccaca tcatgatggt   2160
cggtgatggc tctttccagc tgactgctca agaagttgct cagatgatcc gctatgaaat   2220
cccggtcatc atcttcctga tcaacaaccg cggttacgtc atcgaaatcg ctatccatga   2280
cggcccttac aactacatca aaaactggaa ctacgctggc ctgatcgacg tcttcaatga   2340
cgaagatggt catggcctgg gtctgaaagc ttctactggt gcagaactag aaggcgctat   2400
caagaaagca ctcgacaatc gtcgcggtcc gacgctgatc gaatgtaaca tcgctcagga   2460
cgactgcact gaaaccctga ttgcttgggg taaacgtgta gcagctacca actctcgcaa   2520
accacaagcg taagttgatg tagtgaatta ggcggggcct attagggccc caccacatag   2580
cccctcttac ggcgcaatac ccgtaagagg ggctgtttta tataattaaa actagagtcg   2640
accatgcgtc caaaactttc accatccttt ccctatcaac ctttactgca ctaaagacaa   2700
gtgagatagc agtggcaatc tggctttgca atcaatgttt ccactaaagc gtttagcgtt   2760
actgcggcta gaagtcctcc accgaggctc ccctgaatgg tgatatgggg aatgggactg   2820
gtcatcagtc gtcgttttgc ccccggagca tgactaaaac cgatcggcat tccgatcaca   2880
agagccggct gaatatgttg ttgctctatc agcttacagg cagtgagtaa aacagaaggg   2940
gcatagccga tcgccagcac acatccttgg ggaatctgtt gtaaccgctg ttgccaatgg   3000
tcatggtgcc aaaaagcttg ctcggcttcc ctaagccctg tgatgtgagg gtcgtcaatc   3060
agcgttttaa ccgtacatcc taaatgagct aaccgagttt gatcaagagc cgcagccaca   3120
accggaacat cggtgacgac tggacaccct gctttcagtg catctcgtgc cgaggcgatc   3180
gctccctgac tcaatcgaac ggcgtttacc aagctaacat caccacaggc cagcactaat   3240
tgatgtagta agtgaatggt aatttcagag taagccgata aatccggtag caggtgtttg   3300
agggattcct gaaaggcttc tggatgagtt gttgtctccg catctaggtt cgtccacaac   3360
tgatcgagtt ttcctaaccc ctcctggaca tccacatcaa gctgtttcag ttgggccaga   3420
gcttccgctt gggtaatctg gcaactctgg tcgcgtccca gtaatccttc taaagcagat   3480
gcggtttggc ggagtcgagt aatctgctga atcacagcct gatattgctg ttgcaactgc   3540
accattaggg tgggatcaag gctctcttca gaatggctat ccagcagttg ccgaatatga   3600
gacaactgaa agccctgctg tttgagggca atgactcgtt ggagccgttg tacgtcctgc   3660
tgagtataaa ggcggtagtt gccctctgag cgttgaacgg ggggaagcaa tcccagggtg   3720
tggtaatggc gcaccatgcg aggcgtaacg ccacctccca ctgcatctgt gagttcttta   3780
atcgttaagt gattagtctt catcccttta gtttactcaa aaccttgaca ttgacactaa   3840
tgttaaggtt taggctgaga aggtaaaaat ccaagttaaa aagcatgaat tcctacaccg   3900
ttggcactta cctggctgaa cgcttggttc agatcggctt aaaacaccat tttgctgttg   3960
ctggtgatta taatttggtt ttgttagata atttattgct caataagaat atggaacagg   4020
tgtactgttg caatgagtta aattgtggct tttccgctga gggctacgcc cgtgctaagg   4080
```

-continued gtgctgctgc tgctgttgtg acttattctg ttggcgcttt gagtgctttt gacgccattg 4140
gcggtgctta cgctgagaat ttgccagtga ttttaattag tggcgcccca aataataacg 4200
accatgccgc cggccatgtc ctccaccatg ccttgggtaa gactgattac cattaccaac 4260
tggagatggc taaaaatatt accgctgctg ccgaagctat ctatactcct gaggaagccc 4320
cagccaagat tgaccatgtc atcaagaccg ccttgcggga aaaaaaacca gtgtacttag 4380
agattgcctg taatatcgcc agtatgcctt gtgctgcccc cggtccagct tctgctctct 4440
ttaacgatga agcttctgat gaggccagtc tcaacgctgc tgtggaggaa actttaaagt 4500
ttattgctaa tcgtgataag gtggctgttt tagttggttc taaattacgt gctgccggcg 4560
ccgaggaagc cgccgttaag tttgccgacg ccttaggcgg tgctgtggcc actatggccg 4620
ccgctaagtc tttttttcct gaagagaatc cacactatat tggcactagc tggggcgagg 4680
tttcttaccc aggtgtggag aaaaccatga aggaggctga cgctgtgatt gccttagccc 4740
cggtttttaa tgattatagt actaccggct ggaccgacat cccggacccg aaaaagttag 4800
tgttagccga accacggagt gttgttgtga atggtgtgcg ttttccttct gtgcacttaa 4860
aggattactt aactcggctc gcccagaagg tgagtaaaaa gactggcgcc ctcgattttt 4920
ttaagagttt aaacgctggc gagttaaaaa aggctgcccc agccgaccca tccgccccac 4980
tcgttaatgc tgaaattgct cggcaggttg aggccttgtt aactccaaat accaccgtga 5040
tcgccgaaac tggcgatagt tggtttaacg cccaacgtat gaaattacca aatggcgccc 5100
gtgtggagta cgagatgcaa tggggccata ttggctggag tgtgccggct gcttttggct 5160
acgctgttgg cgccccagag cggcgtaata ttttaatggt gggcgacggc agttttcagt 5220
taaccgccca agaggttgcc caaatggtgc gtttaaagtt accagtgatt atttttctca 5280
ttaacaatta cggctatact attgaggtga tgattcacga cggcccatat aataatatta 5340
aaaattggga ctacgctggc ttaatggagg tctttaatgg caatggcggc tacgattctg 5400
gcgccggcaa gggtttaaaa gccaagactg gcggtgagtt agctgaagcc attaaagtgg 5460
ccttagctaa tactgatggt cctactttaa ttgagtgttt tattggccgg gaagattgta 5520
ccgaggaact cgttaagtgg ggcaaacgtg tggccgctgc taattctcgg aaacccgtga 5580
ataaattatt atgaaatatt ttagccgccc cagtcagtaa tgactggggc gtttttttatt 5640 gggagctcct gcagg 5655

<210> SEQ ID NO 30
<211> LENGTH: 9221
<212> TYPE: DNA
<213> ORGANISM: Artificial
<220> FEATURE:
<223> OTHER INFORMATION: Synthetically produced plasmid #1145
pJET-glgA::ziaR-PziaA-ZmPDC-PrbcL-synADH(deg)-Cm for
transformation of Synechocystis sp. PCC6803 via integration into
the glgA1 gene locus in the genome

<400> SEQUENCE: 30
tcgacctcct taatccgatt cctgcaaatg gtctgcaact tcccgataca aattcatcac 60
atgattatcc gccaagctgt agtaaacatt acggccgacc cggcgatact ttaccaggcg 120
ctgcgatcgt aaaattcgta attgatggga aactgccgat tcactcactt tcatcgccgc 180
tgctaaatca cagacacaga gttcttggcg ggccaatgcc gacattaaac gcaaccgact 240
cggatcagct agtgcactga aaaactccgc catttgctgg gcctggtcca atgacatcac 300
ctctggttga acctgtcgta cctgctcaag atgaacaaga ggttgatcac aaaggggcat 360
ctcttcgttc tggcaggatt gtgactttga caacgaggac ttactcatag aggttggcgt 420
taggagctag ggaaaaattt aaactggatt tagaaaatga ttttcatcct aacatcttta 480
atatctgagc atatcttcag gtgtttcaag atttgtgcta cggttcaagg aggtttttct 540
ttaaatcacg ttggccgcca tgaattctta tactgtcggt acctatttag cggagcggct 600
tgtccagatt ggtctcaagc atcacttcgc agtcgcgggc gactacaacc tcgtccttct 660
tgacaacctg cttttgaaca aaaacatgga gcaggtttat tgctgtaacg aactgaactg 720
cggtttcagt gcagaaggtt atgctcgtgc caaaggcgca gcagcagccg tcgttaccta 780
cagcgtcggt gcgctttccg catttgatgc tatcggtggc gcctatgcag aaaaccttcc 840
ggttatcctg atctccggtg ctccgaacaa caatgatcac gctgctggtc acgtgttgca 900
tcacgctctt ggcaaaaccg actatcacta tcagttggaa atggccaaga acatcacggc 960
cgcagctgaa gcgatttaca ccccagaaga agctccggct aaaatcgatc acgtgattaa 1020
aactgctctt cgtgagaaga agccggttta tctcgaaatc gcttgcaaca ttgcttccat 1080
gccctgcgcc gctcctggac cggcaagcgc attgttcaat gacgaagcca gcgacgaagc 1140
ttctttgaat gcagcggttg aagaaaccct gaaattcatc gccaaccgcg acaaagttgc 1200
cgtcctcgtc ggcagcaagc tgcgcgcagc tggtgctgaa gaagctgctg tcaaatttgc 1260
tgatgctctc ggtggcgcag ttgctaccat ggctgctgca aaaagcttct tcccagaaga 1320
aaacccgcat tacatcggta cctcatgggg tgaagtcagc tatccgggcg ttgaaaagac 1380
gatgaaagaa gccgatgcgg ttatcgctct ggctcctgtc ttcaacgact actccaccac 1440
tggttggacg gatattcctg atcctaagaa actggttctc gctgaaccgc gttctgtcgt 1500
cgttaacggc gttcgcttcc ccagcgttca tctgaaagac tatctgaccc gtttggctca 1560
gaaagtttcc aagaaaaccg gtgctttgga cttcttcaaa tccctcaatg caggtgaact 1620
gaagaaagcc gctccggctg atccgagtgc tccgttggtc aacgcagaaa tcgcccgtca 1680
ggtcgaagct cttctgaccc cgaacacgac ggttattgct gaaaccggtg actcttggtt 1740
caatgctcag cgcatgaagc tcccgaacgg tgctcgcgtt gaatatgaaa tgcagtgggg 1800
tcacatcggt tggtccgttc ctgccgcctt cggttatgcc gtcggtgctc cggaacgtcg 1860
caacatcctc atggttggtg atggttcctt ccagctgacg gctcaggaag tcgctcagat 1920
ggttcgcctg aaactgccgg ttatcatctt cttgatcaat aactatggtt acaccatcga 1980
agttatgatc catgatggtc cgtacaacaa catcaagaac tgggattatg ccggtctgat 2040
ggaagtgttc aacggtaacg gtggttatga cagcggtgct ggtaaaggcc tgaaggctaa 2100
aaccggtggc gaactggcag aagctatcaa ggttgctctg gcaaacaccg acggcccaac 2160
cctgatcgaa tgcttcatcg gtcgtgaaga ctgcactgaa gaattggtca aatggggtaa 2220
gcgcgttgct gccgccaaca gccgtaagcc tgttaacaag ctcctctagt tttggggat 2280 caattcgagc tcggtaccca aactagtaac gctcggttgc cgccgggcgt tttttattcc 2340
gacatcagga attgtaatta gaaagtccaa aaattgtaat ttaaaaaaca gtcaatggag 2400
agcattgcca taagtaaagg catcccctgc gtgataagat taccttcaga aaacagatag 2460
ttgctgggtt atcgcagatt tttctcgcaa ccaaataact gtaaataata actgtctctg 2520
gggcgacggt aggctttata ttgccaaatt tcgcccgtgg gagaaagcta ggctattcaa 2580
tgtttatgga ggactgaccc atatgatcaa ggcttatgcc gctttagagg ctaatggcaa 2640
gttgcagccg ttcgagtatg atccgggcgc tttaggcgcc aacgaagttg aaatcgaagt 2700

-continued

```
tcaatactgc ggtgtttgtc attccgacct cagtatgatc aacaatgagt ggggtatcag   2760
taactatccg ttggttcccg gccacgaagt tgttggcacc gttgctgcta tgggtgaggg   2820
tgttaatcac gtggaagttg gtgacctggt tggtttaggc tggcacagtg gttattgtat   2880
gacttgtcac tcctgcctga gcggttatca taatttgtgc gctaccgccg agagtactat   2940
cgttggtcat tatggcggtt tcggtgaccg tgtgcgtgct aaaggtgtgt ccgttgttaa   3000
gctgcccaag ggtatcgatt tggcttccgc tggtccgttg ttttgcggtg gtatcactgt   3060
gttttccccc atggttgagt tatccctgaa accgaccgcc aaggttgccg ttattggtat   3120
cggtggtctc ggtcacctgg ccgttcagtt cttgcgtgct tggggttgcg aggttaccgc   3180
tttcactagc tccgctcgta aacagaccga ggttctggag ctgggtgccc atcatatttt   3240
ggacagtact aaccccgaag ccattgcttc cgccgagggt aagttcgatt acatcattag   3300
taccgttaat ttaaaattgg attggaatct gtatatttcc actttagccc cgcaaggtca   3360
ctttcatttc gtgggtgttg ttctcgaacc cctcgacttg aacttgttcc cgttgctcat   3420
gggtcagcgg agtgtgtccg ctagtccggt tggctccccg gctactatcg ctactatgct   3480
cgatttcgcc gttcggcacg atatcaagcc ggttgttgag cagttctcct tcgaccaaat   3540
taatgaagcc attgctcact tggagtccgg taaggctcac taccgtgtgg ttttgagtca   3600
ctccaagaac tgaaacgctc ggttgccgcc gggcgttttt tattcctgca ggcgatcgta   3660
gctgaaataa taactgtcat tattgagccc agtggcgtgg agaatattgg ctccagcaat   3720
accctggtgt ttgaaattgt ggatggtgta acaaacccgt tgatggtcca tgccatggaa   3780
acggtaaatt tcatacaaca acaccggcac cagtcccgtt tgccaatcgt ggcagtggat   3840
aatgtctggg cgtttgttac tgcgtagcaa aaactccatg gccgccttgg agaaaaaggc   3900
aaagcgcata tggtcgtcta gagcgccata ataatgaccc cgattgaaaa agttatcaga   3960
agatttgggc tgaatgaaga agcagagcct accgtgaacc cagccacaaa aaacatcaca   4020
gaagattgag cttccatacc agggcacctc taggttgcgg taagcatcgt gtaaacccca   4080
gatgtggtca tagcgcatgc aatcgtacat gggtaggatt agctcgacgc aatggccccg   4140
cagttccaat tcacggctta ggccgtaaat aacatccccc aatcccccag ccttaatgac   4200
gggggcgcat tctgaggcaa tttgaacgga attcactggc cgtcgtttta caacgtcgtg   4260
actgggaaaa ccctggcgtt acccaactta atcgccttgc agcacatccc cctttcgcca   4320
gctggcgtaa tagcgaagag gcccgcaccg atcgcccttc ccaacagttg cgcagcctga   4380
atggcgaatg gcgcctgatg cggtattttc tccttacgca tctgtgcggt atttcacacc   4440
gcatatggtg cactctcagt acaatctgct ctgatgccgc atagttaagc cagccccgac   4500
acccgccaac acccgctgac gcgccctgac gggcttgtct gctcccggca tccgcttaca   4560
gacaagctgt gaccgtctcc gggagctgca tgtgtcagag gttttcaccg tcatcaccga   4620
aacgcgcgag acgaaagggc ctcgtgatac gcctattttt ataggttaat gtcatgataa   4680
taatggtttc ttagacgtca ggtggcactt ttcggggaaa tgtgcgcgga acccctattt   4740
gtttattttt ctaaatacat tcaaatatgt atccgctcat gagacaataa ccctgataaa   4800
tgcttcaata atattgaaaa aggaagagta tgagtattca acatttccgt gtcgccctta   4860
ttcccttttt tgcggcattt tgccttcctg tttttgctca cccagaaacg ctggtgaaag   4920
taaaagatgc tgaagatcag ttgggtgcac gagtgggtta catcgaactg gatctcaaca   4980
gcggtaagat ccttgagagt tttcgccccg aagaacgttt tccaatgatg agcactttta   5040
aagttctgct atgtggcgcg gtattatccc gtattgacgc cgggcaagag caactcggtc   5100
```

gccgcataca ctattctcag aatgacttgg ttgagtactc accagtcaca gaaaagcatc 5160
ttacggatgg catgacagta agagaattat gcagtgctgc cataaccatg agtgataaca 5220
ctgcggccaa cttacttctg acaacgatcg gaggaccgaa ggagctaacc gcttttttgc 5280
acaacatggg ggatcatgta actcgccttg atcgttggga accggagctg aatgaagcca 5340
taccaaacga cgagcgtgac accacgatgc ctgtagcaat ggcaacaacg ttgcgcaaac 5400
tattaactgg cgaactactt actctagctt cccggcaaca attaatagac tggatggagg 5460
cggataaagt tgcaggacca cttctgcgct cggcccttcc ggctggctgg tttattgctg 5520
ataaatctgg agccggtgag cgtgggtctc gcggtatcat tgcagcactg gggccagatg 5580
gtaagccctc ccgtatcgta gttatctaca cgacggggag tcaggcaact atggatgaac 5640
gaaatagaca gatcgctgag ataggtgcct cactgattaa gcattggtaa ctgtcagacc 5700
aagtttactc atatatactt tagattgatt taaaacttca tttttaattt aaaaggatct 5760
aggtgaagat cctttttgat aatctcatga ccaaaatccc ttaacgtgag ttttcgttcc 5820
actgagcgtc agaccccgta gaaaagatca aaggatcttc ttgagatcct ttttttctgc 5880
gcgtaatctg ctgcttgcaa acaaaaaaac caccgctacc agcggtggtt tgtttgccgg 5940
atcaagagct accaactctt tttccgaagg taactggctt cagcagagcg cagataccaa 6000
atactgttct tctagtgtag ccgtagttag gccaccactt caagaactct gtagcaccgc 6060
ctacatacct cgctctgcta atcctgttac cagtggctgc tgccagtggc gataagtcgt 6120
gtcttaccgg gttggactca agacgatagt taccggataa ggcgcagcgg tcgggctgaa 6180
cggggggttc gtgcacacag cccagcttgg agcgaacgac ctacaccgaa ctgagatacc 6240
tacagcgtga gctatgagaa agcgccacgc ttcccgaagg gagaaaggcg gacaggtatc 6300
cggtaagcgg cagggtcgga acaggagagc gcacgaggga gcttccaggg ggaaacgcct 6360
ggtatcttta tagtcctgtc gggtttcgcc acctctgact tgagcgtcga tttttgtgat 6420
gctcgtcagg ggggcggagc ctatggaaaa acgccagcaa cgcggccttt ttacggttcc 6480
tggccttttg ctggcctttt gctcacatgt tctttcctgc gttatcccct gattctgtgg 6540
ataaccgtat taccgccttt gagtgagctg ataccgctcg ccgcagccga acgaccgagc 6600
gcagcgagtc agtgagcgag gaagcggaag agcgcccaat acgcaaaccg cctctccccg 6660
cgcgttggcc gattcattaa tgcagctggc acgacaggtt tcccgactgg aaagcgggca 6720
gtgagcgcaa cgcaattaat gtgagttagc tcactcatta ggcaccccag gctttacact 6780
ttatgcttcc ggctcgtatg ttgtgtggaa ttgtgagcgg ataacaattt cacacaggaa 6840
acagctatga ccatgattac gccaagctta gcccggatgt attcgtaggc ttccacatat 6900
tggagccctg gtttattcca agagtagtcg taggccatgc cctgcaaggc caaggtttta 6960
aaagccacgg gatcatcctt atacaaggcg atcgcccgac tgagggccgt ttccagggca 7020
tactcatccg gttgatagaa aacaaaacca ttacgtttct ccgggggatg gttctggtca 7080
taatcccggt cgaaaacagt atttaccaaa ccgcctactc cccgcaccac cggaacggcc 7140
ccataacgca gaccaatcat ttgggtcaaa ccacagggtt cgtagttact gggcaccaca 7200
ataatgtccg ccgctccgta aattaagtgg gccagctcct cgtcaaagcc caactctaga 7260
tggacattgg ggttatcgtt gagatgttgt ttttcatgcc agaaccattt gctcagattg 7320
ggttcggtgg cggagccgag caggacaaat tgcgctccct ggctgagggc gtagtagatg 7380
gagtgatgca ccaagtgcac acctttttgt ccatccaagc ggccaataaa gcagagcatg 7440

```
ggttttttat catccgtttc taacagtaat ctttcccgta acgcttgctt atttttttgcc   7500
ttatcgccaa aggttttgac actgaagtta ctcgccagta aaggatcaat ttctgggttc   7560
cacacttcgt aatccaaacc gttcaaaata ccgccgaatt tttgctgatg gatttccagg   7620
gtatggccca agccacagga aatatcggaa aaacgggctt cccaagcatg gtggggggaa   7680
acggtgttgc atcgccacgt tgtgtctcaa aatctctgat gttacattgc acaagataaa   7740
aatatatcat catgaacaat aaaactgtct gcttacataa acagtaatac aaggggtgtt   7800
atgagccata ttcaacggga aacgtcttgc tcgaggccgc gattaaattc caacatggat   7860
gctgatttat atgggtataa atgggctcgc gataatgtcg ggcaatcagg tgcgacaatc   7920
tatcgattgt atgggaagcc cgatgcgcca gagttgtttc tgaaacatgg caaaggtagc   7980
gttgccaatg atgttacaga tgagatggtc agactaaact ggctgacgga atttatgcct   8040
cttccgacca tcaagcattt tatccgtact cctgatgatg catggttact caccactgcg   8100
atccccgcat cgcaggatgc tgctggctac cctgtggaac acctacatct gtattaacga   8160
agcgctaacc gtttttatca ggctctggga ggcagaataa atgatcatat cgtcaattat   8220
tacctccacg gggagagcct gagcaaactg gcctcaggca tttgagaagc acacggtcac   8280
actgcttccg gtagtcaata aaccggtaaa ccagcaatag acataagcgg ctatttaacg   8340
accctgccct gaaccgacga ccgggtcgaa tttgctttcg aatttctgcc attcatccgc   8400
ttattatcac ttattcaggc gtagcaccag gcgtttaagg gcaccaataa ctgccttaaa   8460
aaaattacgc cccgccctgc cactcatcgc agtactgttg taattcatta agcattctgc   8520
cgacatggaa gccatcacag acggcatgat gaacctgaat cgccagcggc atcagcacct   8580
tgtcgccttg cgtataatat ttgcccatgg tgaaaacggg ggcgaagaag ttgtccatat   8640
tggccacgtt taaatcaaaa ctggtgaaac tcacccaggg attggctgag acgaaaaaca   8700
tattctcaat aaacccttta gggaaatagg ccaggttttc accgtaacac gccacatctt   8760
gcgaatatat gtgtagaaac tgccggaaat cgtcgtggta ttcactccag agcgatgaaa   8820
acgtttcagt ttgctcatgg aaaacggtgt aacaagggtg aacactatcc catatcacca   8880
gctcaccgtc tttcattgcc atacggaatt ccggatgagc attcatcagg cgggcaagaa   8940
tgtgaataaa ggccggataa aacttgtgct tatttttctt tacggtcttt aaaaaggccg   9000
taatatccag ctgaacggtc tggttatagg tacattgagc aactgactga aatgcctcaa   9060
aatgttcttt acgatgccat tgggatatat caacggtggt atatccagtg atttttttct   9120
ccattttagc ttccttagct cctgaaaatc tcgataactc aaaaaatacg cccggtagtg   9180
atcttatttc attatggtga aagttggaac ctcttacgta g                        9221
```

<210> SEQ ID NO 31
<211> LENGTH: 8915
<212> TYPE: DNA
<213> ORGANISM: Artificial
<220> FEATURE:
<223> OTHER INFORMATION: Synthetically produced plasmid TK115 pGEM-AQ4::smtB-PsmtA-ZmPDC-PrbcL-synADH(deg)-Nm for transformation of Synechococcus sp. PCC7002 via integration into the endogenous pAQ4 plasmid

<400> SEQUENCE: 31

```
tcgacgggca aactttatga agcagatcaa gcctatatcc gccaagcaac cggcagccgc     60
gttgattagt gggtgtgtcc atcctctggt tcgtctaggt gctccgaagc gtcacgatag    120
agattaagaa tgtggtgatc cttgaggcga taaatcacat tccgcccttc cttgcgatag    180
```

-continued

```
ctcactaaac gtgctgtgcg cagggttctt agttggtgag agacagccga ttcactcatt    240
tcaacggcgg cggcgagttc ccccacccgc atctctccag tggccagggc cgaaagaata    300
cgccagcggt tggcatcccc caagacacca aaaaattcgg ccatccgttg ggccttggct    360
tggttcaaga ttttgccact gtggtctgtc attgttcgct gatctaaaca atacctgaat    420
aattgttcat gtgttaatct aaaaatgtga acaatcgttc aactatttaa gacaatacct    480
tggaggttta aaccatgaat tcttatactg tcggtaccta tttagcggag cggcttgtcc    540
agattggtct caagcatcac ttcgcagtcg cgggcgacta caacctcgtc cttcttgaca    600
acctgctttt gaacaaaaac atggagcagg tttattgctg taacgaactg aactgcggtt    660
tcagtgcaga aggttatgct cgtgccaaag gcgcagcagc agccgtcgtt acctacagcg    720
tcggtgcgct ttccgcattt gatgctatcg gtggcgccta tgcagaaaac cttccggtta    780
tcctgatctc cggtgctccg aacaacaatg atcacgctgc tggtcacgtg ttgcatcacg    840
ctcttggcaa aaccgactat cactatcagt tggaaatggc caagaacatc acggccgcag    900
ctgaagcgat ttacacccca gaagaagctc cggctaaaat cgatcacgtg attaaaactg    960
ctcttcgtga gaagaagccg gtttatctcg aaatcgcttg caacattgct tccatgccct   1020
gcgccgctcc tggaccggca agcgcattgt tcaatgacga agccagcgac gaagcttctt   1080
tgaatgcagc ggttgaagaa accctgaaat tcatcgccaa ccgcgacaaa gttgccgtcc   1140
tcgtcggcag caagctgcgc gcagctggtg ctgaagaagc tgctgtcaaa tttgctgatg   1200
ctctcggtgg cgcagttgct accatggctg ctgcaaaaag cttcttccca gaagaaaacc   1260
cgcattacat cggtacctca tggggtgaag tcagctatcc gggcgttgaa aagacgatga   1320
aagaagccga tgcggttatc gctctggctc ctgtcttcaa cgactactcc accactggtt   1380
ggacggatat tcctgatcct aagaaactgg ttctcgctga accgcgttct gtcgtcgtta   1440
acggcgttcg cttccccagc gttcatctga aagactatct gacccgtttg gctcagaaag   1500
tttccaagaa aaccggtgct ttggacttct tcaaatccct caatgcaggt gaactgaaga   1560
aagccgctcc ggctgatccg agtgctccgt tggtcaacgc agaaatcgcc cgtcaggtcg   1620
aagctcttct gaccccgaac acgacggtta ttgctgaaac cggtgactct tggttcaatg   1680
ctcagcgcat gaagctcccg aacggtgctc gcgttgaata tgaaatgcag tggggtcaca   1740
tcggttggtc cgttcctgcc gccttcggtt atgccgtcgg tgctccggaa cgtcgcaaca   1800
tcctcatggt tggtgatggt tccttccagc tgacggctca ggaagtcgct cagatggttc   1860
gcctgaaact gccggttatc atcttcttga tcaataacta tggttacacc atcgaagtta   1920
tgatccatga tggtccgtac aacaacatca agaactggga ttatgccggt ctgatggaag   1980
tgttcaacgg taacggtggt tatgacagcg gtgctggtaa aggcctgaag gctaaaaccg   2040
gtggcgaact ggcagaagct atcaaggttg ctctggcaaa caccgacggc ccaaccctga   2100
tcgaatgctt catcggtcgt gaagactgca ctgaagaatt ggtcaaatgg ggtaagcgcg   2160
ttgctgccgc caacagccgt aagcctgtta acaagctcct ctagtttttg gggatcaatt   2220
cgagctcggt acccaaacta gtaacgctcg gttgccgccg ggcgtttttt attccgacat   2280
caggaattgt aattagaaag tccaaaaatt gtaatttaaa aaacagtcaa tggagagcat   2340
tgccataagt aaaggcatcc cctgcgtgat aagattacct tcagaaaaca gatagttgct   2400
gggttatcgc agatttttct cgcaaccaaa taactgtaaa taataactgt ctctggggcg   2460
acggtaggct ttatattgcc aaatttcgcc cgtgggagaa agctaggcta ttcaatgttt   2520
atggaggact gacccatatg atcaaggctt atgccgcttt agaggctaat ggcaagttgc   2580
```

```
agccgttcga gtatgatccg ggcgctttag gcgccaacga agttgaaatc gaagttcaat   2640
actgcggtgt ttgtcattcc gacctcagta tgatcaacaa tgagtggggt atcagtaact   2700
atccgttggt tcccggccac gaagttgttg gcaccgttgc tgctatgggt gagggtgtta   2760
atcacgtgga agttggtgac ctggttggtt taggctggca cagtggttat tgtatgactt   2820
gtcactcctg cctgagcggt tatcataatt tgtgcgctac cgccgagagt actatcgttg   2880
gtcattatgg cggtttcggt gaccgtgtgc gtgctaaagg tgtgtccgtt gttaagctgc   2940
ccaagggtat cgatttggct tccgctggtc cgttgttttg cggtggtatc actgtgtttt   3000
cccccatggt tgagttatcc ctgaaaccga ccgccaaggt tgccgttatt ggtatcggtg   3060
gtctcggtca cctggccgtt cagttcttgc gtgcttgggg ttgcgaggtt accgctttca   3120
ctagctccgc tcgtaaacag accgaggttc tggagctggg tgcccatcat attttggaca   3180
gtactaaccc cgaagccatt gcttccgccg agggtaagtt cgattacatc attagtaccg   3240
ttaatttaaa attggattgg aatctgtata tttccacttt agccccgcaa ggtcactttc   3300
atttcgtggg tgttgttctc gaacccctcg acttgaactt gttcccgttg ctcatgggtc   3360
agcggagtgt gtccgctagt ccggttggct ccccggctac tatcgctact atgctcgatt   3420
tcgccgttcg gcacgatatc aagccggttg ttgagcagtt ctccttcgac caaattaatg   3480
aagccattgc tcacttggag tccggtaagg ctcactaccg tgtggttttg agtcactcca   3540
agaactgaaa cgctcggttg ccgccgggcg ttttttattc ctgcaggccc cccgggggat   3600
ccactagagg atctcaatga atattggttg acacgggcgt ataagacatg ttatactgtt   3660
gaataacaag gacggatctg atcaagagac aggatgagga tcgtttcgca tgattgaaca   3720
agatggattg cacgcaggtt ctccggccgc ttgggtggag aggctattcg gctatgactg   3780
ggcacaacag acaatcggct gctctgatgc cgccgtgttc cggctgtcag cgcaggggcg   3840
cccggttctt tttgtcaaga ccgacctgtc cggtgccctg aatgaactgc aggacgaggc   3900
agcgcggcta tcgtggctgg ccacgacggg cgttccttgc gcagctgtgc tcgacgttgt   3960
cactgaagcg ggaagggact ggctgctatt gggcgaagtg ccggggcagg atctcctgtc   4020
atctcacctt gctcctgccg agaaagtatc catcatggct gatgcaatgc ggcggctgca   4080
tacgcttgat ccggctacct gcccattcga ccaccaagcg aaacatcgca tcgagcgagc   4140
acgtactcgg atggaagccg gtcttgtcga tcaggatgat ctggacgaag agcatcaggg   4200
gctcgcgcca gccgaactgt tcgccaggct caaggcgcgc atgcccgacg gcgaggatct   4260
cgtcgtgacc catggcgatg cctgcttgcc gaatatcatg gtggaaaatg gccgcttttc   4320
tggattcatc gactgtggcc ggctgggtgt ggcggaccgc tatcaggaca tagcgttggc   4380
tacccgtgat attgctgaag agcttggcgg cgaatgggct gaccgcttcc tcgtgcttta   4440
cggtatcgcc gctcccgatt cgcagcgcat cgccttctat cgccttcttg acgagttctt   4500
ctgagcggga ctctggggtt cgaaatgacc gaccaagcga cgcccaacct gccatcacga   4560
gatttcgatt ccaccgccgc cttctatgaa aggttgggct tcggaatcgt tttccgggac   4620
gccggctgga tgatcctcca gcgcggggat ctcatgctgg agttcttcgc ccaccgggga   4680
tcctctagtt ctagagcggc cgcatcatca atccccgtga tgtttcagtc ccgtagtcgg   4740
gatttagtgg ttggaaagcg gaacgtcgcg ccgaaaccat cgccaggacg ggtttcagtc   4800
ccgtagtcgg gatttagtgg ttggaaagtg attatgttca agaaatcaca acgcaaaaga   4860
aaaagtttca gtcccgtagt cgggatttag tggttggaaa gtcaagcgag atacccacca   4920
```

-continued

```
gaaagccttt gacctggttt cagtcccgag tcgggattta gtggttggaa aggcggcggc   4980
tgatgtcgcc aatgcggtta tcgatggcca gtttcagtcc cgtagtcggg atttagtggt   5040
tggaaagtcc caagggggac agggcggtga tcctcgatgt tgcgtgtttc agtcccgtag   5100
tcgggattta gtggttggaa agactcgtct atatatacag agattactac agagatgttt   5160
cagtcccgta gtcgggattt agtggttgga aagcgggaaa gtagcctgtt ttgtggagaa   5220
ttgcaggcgt ttcagtacta gtgatggcgg ccgggagcat gcgacgtcgg gcccaattcg   5280
ccctatagtg agtcgtatta caattcactg gccgtcgttt tacaacgtcg tgactgggaa   5340
aaccctggcg ttacccaact taatcgcctt gcagcacatc cccctttcgc cagctggcgt   5400
aatagcgaag aggcccgcac cgatcgccct tcccaacagt tgcgcagcct gaatggcgaa   5460
tggacgcgcc ctgtagcggc gcattaagcg cggcgggtgt ggtggttacg cgcagcgtga   5520
ccgctacact tgccagcgcc ctagcgcccg ctcctttcgc tttcttccct tcctttctcg   5580
ccacgttcgc cggctttccc cgtcaagctc taaatcgggg gctcccttta gggttccgat   5640
ttagagcttt acggcacctc gaccgcaaaa aacttgattt gggtgatggt tcacgtagtg   5700
ggccatcgcc ctgatagacg gtttttcgcc ctttgacgtt ggagtccacg ttctttaata   5760
gtggactctt gttccaaact ggaacaacac tcaaccctat ctcggtctat tcttttgatt   5820
tataagggat tttgccgatt tcggcctatt ggttaaaaaa tgagctgatt taacaaatat   5880
ttaacgcgaa ttttaacaaa atattaacgt ttacaatttc gcctgatgcg gtattttctc   5940
cttacgcatc tgtgcggtat ttcacaccgc atacaggtgg cacttttcgg ggaaatgtgc   6000
gcggaacccc tatttgttta tttttctaaa tacattcaaa tatgtatccg ctcatgagac   6060
aataaccctg ataaatgctt caataatatt gaaaaaggaa gagtatgagt attcaacatt   6120
tccgtgtcgc ccttattccc ttttttgcgg cattttgcct tcctgttttt gctcacccag   6180
aaacgctggt gaaagtaaaa gatgctgaag atcagttggg tgcacgagtg ggttacatcg   6240
aactggatct caacagcggt aagatccttg agagttttcg ccccgaagaa cgttttccaa   6300
tgatgagcac ttttaaagtt ctgctatgtg gcgcggtatt atcccgtatt gacgccgggc   6360
aagagcaact cggtcgccgc atacactatt ctcagaatga cttggttgag tactcaccag   6420
tcacagaaaa gcatcttacg gatggcatga cagtaagaga attatgcagt gctgccataa   6480
ccatgagtga taacactgcg gccaacttac ttctgacaac gatcggagga ccgaaggagc   6540
taaccgcttt tttgcacaac atgggggatc atgtaactcg ccttgatcgt tgggaaccgg   6600
agctgaatga agccatacca aacgacgagc gtgacaccac gatgcctgta gcaatgccaa   6660
caacgttgcg caaactatta actggcgaac tacttactct agcttcccgg caacaattaa   6720
tagactggat ggaggcggat aaagttgcag gaccacttct gcgctcggcc cttccggctg   6780
gctggtttat tgctgataaa tctggagccg gtgagcgtgg gtctcgcggt atcattgcag   6840
cactggggcc agatggtaag ccctcccgta tcgtagttat ctacacgacg gggagtcagg   6900
caactatgga tgaacgaaat agacagatcg ctgagatagg tgcctcactg attaagcatt   6960
ggtaactgtc agaccaagtt tactcatata tactttagat tgatttaaaa cttcattttt   7020
aatttaaaag gatctaggtg aagatccttt ttgataatct catgaccaaa atcccttaac   7080
gtgagttttc gttccactga gcgtcagacc ccgtagaaaa gatcaaagga tcttcttgag   7140
atcctttttt tctgcgcgta atctgctgct tgcaaacaaa aaaaccaccg ctaccagcgg   7200
tggtttgttt gccggatcaa gagctaccaa ctctttttcc gaaggtaact ggcttcagca   7260
gagcgcagat accaaatact gtccttctag tgtagccgta gttaggccac cacttcaaga   7320
```

actctgtagc accgcctaca tacctcgctc tgctaatcct gttaccagtg gctgctgcca 7380
gtggcgataa gtcgtgtctt accgggttgg actcaagacg atagttaccg gataaggcgc 7440
agcggtcggg ctgaacgggg ggttcgtgca cacagcccag cttggagcga acgacctaca 7500
ccgaactgag atacctacag cgtgagctat gagaaagcgc cacgcttccc gaagggagaa 7560
aggcggacag gtatccggta agcggcaggg tcggaacagg agagcgcacg agggagcttc 7620 caggggggaaa cgcctggtat ctttatagtc ctgtcgggtt tcgccacctc tgacttgagc 7680
gtcgattttt gtgatgctcg tcaggggggc ggagcctatg gaaaaacgcc agcaacgcgg 7740
cctttttacg gttcctggcc ttttgctggc cttttgctca catgttcttt cctgcgttat 7800
cccctgattc tgtggataac cgtattaccg cctttgagtg agctgatacc gctcgccgca 7860
gccgaacgac cgagcgcagc gagtcagtga gcgaggaagc ggaagagcgc ccaatacgca 7920
aaccgcctct ccccgcgcgt tggccgattc attaatgcag ctggcacgac aggtttcccg 7980
actggaaagc gggcagtgag cgcaacgcaa ttaatgtgag ttagctcact cattaggcac 8040
cccaggcttt acactttatg cttccggctc gtatgttgtg tggaattgtg agcggataac 8100
aatttcacac aggaaacagc tatgaccatg attacgccaa gctatttagg tgacactata 8160
gaatactcaa gctatgcatg agggtgcaat ttgagtggtt tcagtcccgt aatcgggatt 8220
tagtggttgg aaagaacgac aaggcttaca agggggtaat tcgtgatttg tttcagtccc 8280
gtaatcggga tttagtggtt ggaaagtagg caggggagtg aaatggtttc atgttgggct 8340
catgtttcag tcccgtaatc gggatttagt ggttggaaag cagtaagatg aaggaggtgg 8400
tgcatatcac ttgcgtttca gtcccgtaat cgggatttag tggttggaaa gctagatttg 8460
cttatagagt tgactgttat cgggacttgt ttcagtcccg taatcgggat ttagtggttg 8520
gaaagatgat ggcgttgcca gcgttctcgg attggagaat ttaacgtttc agtcccgtaa 8580
tcgggattta gtggttggaa agccctgaga agtttggctg ttttgctgac tgcgatctgg 8640
tttcagtccc gtaatcggga tttagtggtt ggaaagcatc gaggcagtag agcaaatcgc 8700
aggccacctc atagtttcag tcccgtaatc gggatttagt ggttggaaag tcattggggt 8760
ctgcattggg gccatcgcta tcgtcctgtt tcagtcccgt aatcgggatt tagtggttgg 8820
aaagtgggac gctccgtaag gtttggagaa tagggtctag tgtttcagtc ccgtaatcgg 8880
gatttagtgg ttggaaagca cttcgtcgct gattg 8915

<210> SEQ ID NO 32
<211> LENGTH: 751
<212> TYPE: DNA
<213> ORGANISM: Artificial
<220> FEATURE:
<223> OTHER INFORMATION: Engineered flanking region pAQ4-FA of Synechococcus sp. PCC7002 with additional NsiI/SalI restriction sites for pAQ4 integration via homologous recombination

<400> SEQUENCE: 32
atatgcatga gggtgcaatt tgagtggttt cagtcccgta atcgggattt agtggttgga 60
aagaacgaca aggcttacaa gggggtaatt cgtgatttgt ttcagtcccg taatcgggat 120
ttagtggttg gaaagtaggc aggggagtga aatggtttca tgttgggctc atgtttcagt 180
cccgtaatcg ggatttagtg gttggaaagc agtaagatga aggaggtggt gcatatcact 240
tgcgtttcag tcccgtaatc gggatttagt ggttggaaag ctagatttgc ttatagagtt 300
gactgttatc gggacttgtt tcagtcccgt aatcgggatt tagtggttgg aaagatgatg 360

-continued gcgttgccag cgttctcgga ttggagaatt taacgtttca gtcccgtaat cgggatttag 420
tggttggaaa gccctgagaa gtttggctgt tttgctgact gcgatctggt ttcagtcccg 480
taatcgggat ttagtggttg gaaagcatcg aggcagtaga gcaaatcgca ggccacctca 540
tagtttcagt cccgtaatcg ggatttagtg gttggaaagt cattggggtc tgcattgggg 600
ccatcgctat cgtcctgttt cagtcccgta atcgggattt agtggttgga aagtgggacg 660
ctccgtaagg tttggagaat agggtctagt gtttcagtcc cgtaatcggg atttagtggt 720
tggaaagcac ttcgtcgctg attgtcgaca t 751

<210> SEQ ID NO 33
<211> LENGTH: 28
<212> TYPE: DNA
<213> ORGANISM: Artificial
<220> FEATURE:
<223> OTHER INFORMATION: Synthetically produced forward primer #323 for amplification of engineered flanking region pAQ4-FA of Synechococcus sp. PCC7002

<400> SEQUENCE: 33
atatgcatga gggtgcaatt tgagtggt 28

<210> SEQ ID NO 34
<211> LENGTH: 28
<212> TYPE: DNA
<213> ORGANISM: Artificial
<220> FEATURE:
<223> OTHER INFORMATION: Synthetically produced reverse primer #324 for amplification of engineered flanking region pAQ4-FA of Synechococcus sp. PCC7002

<400> SEQUENCE: 34
atgtcgacaa tcagcgacga agtgcttt 28

<210> SEQ ID NO 35
<211> LENGTH: 551
<212> TYPE: DNA
<213> ORGANISM: Artificial
<220> FEATURE:
<223> OTHER INFORMATION: Engineered flanking region pAQ4-FB of Synechococcus sp. PCC7002 with additional NotI/SpeI restriction sites for pAQ4 integration via homologous recombination

<400> SEQUENCE: 35
tagcggccgc atcatcaatc cccgtgatgt ttcagtcccg tagtcgggat ttagtggttg 60
gaaagcggaa cgtcgcgccg aaaccatcgc caggacgggt ttcagtcccg tagtcgggat 120
ttagtggttg gaaagtgatt atgttcaaga aatcacaacg caaaagaaaa agtttcagtc 180
ccgtagtcgg gatttagtgg ttggaaagtc aagcgagata cccaccagaa agcctttgac 240
ctggtttcag tcccgagtcg ggatttagtg gttggaaagg cggcggctga tgtcgccaat 300
gcggttatcg atggccagtt tcagtcccgt agtcgggatt tagtggttgg aaagtcccaa 360
gggggacagg gcggtgatcc tcgatgttgc gtgtttcagt cccgtagtcg ggatttagtg 420
gttggaaaga ctcgtctata tatacagaga ttactacaga gatgtttcag tcccgtagtc 480
gggatttagt ggttggaaag cgggaaagta gcctgttttg tggagaattg caggcgtttc 540
agtactagtt a 551

<210> SEQ ID NO 36
<211> LENGTH: 30
<212> TYPE: DNA
<213> ORGANISM: Artificial

<220> FEATURE:
<223> OTHER INFORMATION: Synthetically produced forward primer #325 for amplification of engineered flanking region pAQ4-FB of Synechococcus sp. PCC7002

<400> SEQUENCE: 36
tagcggccgc atcatcaatc cccgtgatgt 30

<210> SEQ ID NO 37
<211> LENGTH: 28
<212> TYPE: DNA
<213> ORGANISM: Artificial
<220> FEATURE:
<223> OTHER INFORMATION: Synthetically produced reverse primer #326 for amplification of engineered flanking region pAQ4-FB of Synechococcus sp. PCC7002

<400> SEQUENCE: 37
taactagtac tgaaacgcct gcaattct 28

<210> SEQ ID NO 38
<211> LENGTH: 28
<212> TYPE: DNA
<213> ORGANISM: Artificial
<220> FEATURE:
<223> OTHER INFORMATION: Synthetically produced forward primer #327 for amplification of flanking region pAQ3-FA of Synechococcus sp. PCC7002 including NsiI/SalI restriction sites

<400> SEQUENCE: 38
atatgcatcc acaacttttt gggatgct 28

<210> SEQ ID NO 39
<211> LENGTH: 27
<212> TYPE: DNA
<213> ORGANISM: Artificial
<220> FEATURE:
<223> OTHER INFORMATION: Synthetically produced reverse primer #328 for amplification of flanking region pAQ3-FA of Synechococcus sp. PCC7002

<400> SEQUENCE: 39
atgtcgacct cgttcaaggc aggcaac 27

<210> SEQ ID NO 40
<211> LENGTH: 30
<212> TYPE: DNA
<213> ORGANISM: Artificial
<220> FEATURE:
<223> OTHER INFORMATION: Synthetically produced forward primer #329 for amplification of flanking region pAQ3-FB of Synechococcus sp. PCC7002

<400> SEQUENCE: 40
tagcggccgc cctgccttga acgagaaaga 30

<210> SEQ ID NO 41
<211> LENGTH: 28
<212> TYPE: DNA
<213> ORGANISM: Artificial
<220> FEATURE:
<223> OTHER INFORMATION: Synthetically produced reverse primer #330 for amplification of flanking region pAQ3-FB of Synechococcus sp. PCC7002 including NotI/SpeI restriction sites

<400> SEQUENCE: 41
taactagttt ggagataatc gcctttgg 28

<210> SEQ ID NO 42
<211> LENGTH: 685
<212> TYPE: DNA
<213> ORGANISM: Artificial
<220> FEATURE:
<223> OTHER INFORMATION: Engineered flanking region pAQ1-FA2 of Synechococcus sp. PCC7002 including NsiI/SalI restriction sites for pAQ1 integration via homologous recombination

<400> SEQUENCE: 42
atatgcatct ccaacatgag ggctttgtat ttaagccgga tatcaacagg cgatcgctct 60
caccaaagat tcacctgtta gagctactca acatccatca gttcttaaaa ccaggggtga 120
cattcaccgg ggcgagcctt gaagggttca aggaaaattg tttgcggtat gccaagccga 180
tcaagtggat tcttggcaga acgatcaccg acaaaatgag cccgctcgaa attgctcagg 240
cgctcctagg caagcttgac cggaaattgg aatacaaggg gcgctttgga tcgcgggata 300
accgtcagcg ggtctatgag gcgatcgccc ctaacgatca gcgcgaaaag gtctttgctc 360
attggttaca gcgtgaccaa gcaaaattag gggccgtgtc caacccctgt ataaatagat 420
ttattcagga ggcttagacc cgtgatcgaa atactcgttg tgcagctctc ccttggcaat 480
cccaaacaat ctcaagattt gctctgcggt atcgggacgt tttatgccct tgcggaaagc 540
gcctttgctc ttctggtagc ccctagactg tgccagatca taagcctcac tgagggtgag 600
ggcactaccg gggcatgag ctcgcccaag agattcagcg accggggcga tcgcccttgg 660
taattctctc aggcgctgtc gacat 685

<210> SEQ ID NO 43
<211> LENGTH: 28
<212> TYPE: DNA
<213> ORGANISM: Artificial
<220> FEATURE:
<223> OTHER INFORMATION: Synthetically produced forward primer #336 for amplification of engineered flanking region pAQ1-FA2 of Synechococcus sp. PCC7002

<400> SEQUENCE: 43
atatgcatct ccaacatgag ggctttgt 28

<210> SEQ ID NO 44
<211> LENGTH: 28
<212> TYPE: DNA
<213> ORGANISM: Artificial
<220> FEATURE:
<223> OTHER INFORMATION: Synthetically produced reverse primer #337 for amplification of engineered flanking region pAQ1-FA2 of Synechococcus sp. PCC7002

<400> SEQUENCE: 44
atgtcgacag cgcctgagag aattacca 28

<210> SEQ ID NO 45
<211> LENGTH: 519
<212> TYPE: DNA
<213> ORGANISM: Artificial
<220> FEATURE:
<223> OTHER INFORMATION: Engineered flanking region pAQ1-FB2 of Synechococcus sp. PCC7002 including NotI/SpeI restriction sites for pAQ1 integration via homologous recombination

<400> SEQUENCE: 45
tagcggccgc tggaatttcc cgattctctg atgggagatc caaaaattct cgcagtccct 60
caatcacgat atcggtcttg gatcgccctg tagcttccga caactgctca attttttcga 120

-continued gcatctctac cgggcatcgg aatgaaatta acggtgtttt agccatgtgt tatacagtgt 180
ttacaacttg actaacaaat acctgctagt gtatacatat tgtattgcaa tgtatacgct 240
attttcactg ctgtctttaa tggggattat cgcaagcaag taaaaaagcc tgaaaacccc 300
aataggtaag ggattccgag cttactcgat aattatcacc tttgagcgcc cctaggagga 360
ggcgaaaagc tatgtctgac aaggggtttg acccctgaag tcgttgcgcg agcattaagg 420
tctgcggata gcccataaca tacttttgtt gaacttgtgc gcttttatca accccttaag 480
ggcttgggag cgttttatac gagtgcgggg aactagtta 519

<210> SEQ ID NO 46
<211> LENGTH: 30
<212> TYPE: DNA
<213> ORGANISM: Artificial
<220> FEATURE:
<223> OTHER INFORMATION: Synthetically produced forward primer #338 for amplification of engineered flanking region pAQ1-FB2 of Synechococcus sp. PCC7002

<400> SEQUENCE: 46
tagcggccgc tggaatttcc cgattctctg 30

<210> SEQ ID NO 47
<211> LENGTH: 28
<212> TYPE: DNA
<213> ORGANISM: Artificial
<220> FEATURE:
<223> OTHER INFORMATION: Synthetically produced reverse primer #339 for amplification of engineered flanking region pAQ1-FB2 of Synechococcus sp. PCC7002

<400> SEQUENCE: 47
taactagttc cccgcactcg tataaaac 28

<210> SEQ ID NO 48
<211> LENGTH: 7100
<212> TYPE: DNA
<213> ORGANISM: Artificial
<220> FEATURE:
<223> OTHER INFORMATION: Synthetically produced ethanologenic gene cassette from plasmid #1381 pVZ325a-nrsRS-PnrsB-zpPDC-corR-PcorT-zmPDCdeg integrated into pVZ325a

<400> SEQUENCE: 48
gtcgacccta tatcgggctt ttctcaataa aatctttatt ttttgaggtg ctttttagcc 60
ataaataatc actttagtat aaaattttga cggcgtaaag ttgataaaat agaattaaga 120
atggactatc ggtacagaaa aaatgggtaa ctggatggtg aataaacttc ccttacccaa 180
tgcactctcc accgttaaag accccctatg cttaacggtg atcacctggg caatggcgag 240
tcccaaccct gtcccccccg ttttgcgcga acgatctcga ttaactcggt aaaaacgctc 300
aaaaatgtgt tcctgttggt cgggggcaat gccgatgccg gtatcttgca cggtgatgat 360
agccatctgt tcatgggatg tcagggtaat atcaacacgt cccccagcag ttgtgtattg 420
aatggcgttg gcaattaggt ttgagaccag tcgatagagt tgggattcat taccccaggc 480
gtaaacttcc cctgaactca gatcactgct gagatcaatg tgggcggcga tcgctaattc 540
taaaaactct tcggtgaggt cactgactaa atcatttaaa caacaaagcc gccaatcttc 600
ggcggtggtt tcctgctcta agcgacttag tagcaataaa tccgtaatca attggcttaa 660
tcgccttccc tgtcgttcaa cggtatgtag catggtgtta atttctgggg aatggcttga 720

-continued

```
gtcgatgcgt aataccgctt ccaccgtggc caacagacta gccaatggcg atcgtaattc    780
atgggctgca ttcgcggtga attgttgttg ttgttggtag gactggtaaa tgggacgcat    840
ggctaacccc gctaagcccc aactggagaa ggcgaccaaa cccagggcaa tgggaaaact    900
aagccctaaa atccaaagaa tacgtttatt ttcggcatca aaggctgcca ggctccggcc    960
aatttgtaga tagccccagg aagatttgtc tgtattaccg gcgctatgca aaatggtggt   1020
gaattgtcga taccgatcgc cggttggggg gtgaatagtc tgccaagttt cctggttaaa   1080
aatggaggat agggaagccg gttgattagg cgaaaaagcc agcaggttgc cttgataatc   1140
aaataaacga atgtaatata aactgcgatc actaatgccc aacgtgtgac gttcaatcag   1200
ggtggggttg acctggcagg gttggttgac caaacacaga tcgggcaaca tttttgtaa    1260
tactccggtg ggactagcat tactcggcaa catcggctct aaactgtcat gcaacgtccc   1320
ggcgatcgac tccacttctc gctccaacgc catccagttg gcctgcacaa tggcacgata   1380
aacccccaac cccaacaggg taagaatacc ccccattact agggcatacc agaaagccaa   1440
ttgcagacga ctacgggcaa agaggcgacg ggtattcatg gcgatagggt gaaccgatag   1500
ccttgaccgg gaactgtttt aattgggcaa ggacaatttt gttgagctag cttgcgtcgt   1560
atcaaacgca tttgggccgc caccacatta ctcatgggct cctcatcaag atcccacagt   1620
tgttgccgga tcttgctacc ggaaatgatc cgctctgggt tttgcatcag atattgaaaa   1680
atttgaaatt ctcttacggt taaagcaatt tcctgtcttt ctaggtttag tggctccgag   1740
atagttaccg ataacagatt attactggga tcaaggctga agttgcccaa agttaaaatt   1800
tgcggttgga attgtggcga tcgccgttgt agtgcccgca gtcttgctaa tagctctgcc   1860
atcacaaacg gttttgttag atagtcatct gccccggcat ctagtccttc gacacggttt   1920
tccggttctc ctaacgctgt taacatcaac accggcaagg aattaccctg ggttctcagt   1980
ttttgacaga gttccaaacc cgataatccc ggcagtaacc aatccacaat ggcaagggtg   2040
tattccgtcc attgattttc caaataatcc caagcttggg agccatccgt cacccaatcc   2100
accacatact tttcactaac tagcactttc ttaatagcca ttcccaaatc cgtctcatct   2160
tccaccagca aaattcgcat cgcctctgcc tttttataa cggtctgatc ttagcggggg    2220
aaggagattt tcacctgaat ttcatacccc ctttggcaga ctgggaaaat cttggacaaa   2280
ttcccaattt gaggtggtgt gatgaattcc tataccgttg gtatgtactt ggcagaacgc   2340
ctagcccaga tcggcctgaa acaccacttt gccgtggccg gtgactacaa cctggtgttg   2400
cttgatcagc tcctgctgaa caaagacatg gagcaggtct actgctgtaa cgaacttaac   2460
tgcggcttta gcgccgaagg ttacgctcgt gcacgtggtg ccgccgctgc catcgtcacg   2520
ttcagcgtag gtgctatctc tgcaatgaac gccatcggtg gcgcctatgc agaaaacctg   2580
ccggtcatcc tgatctctgg ctcaccgaac accaatgact acggcacagg ccacatcctg   2640
caccacacca ttggtactac tgactataac tatcagctgg aaatggtaaa acacgttacc   2700
tgcgcacgtg aaagcatcgt ttctgccgaa gaagcaccgg caaaaatcga ccacgtcatc   2760
cgtacggctc tacgtgaacg caaaccggct tatctggaaa tcgcatgcaa cgtcgctggc   2820
gctgaatgtg ttcgtccggg cccgatcaat agcctgctgc gtgaactcga agttgaccag   2880
accagtgtca ctgccgctgt agatgccgcc gtagaatggc tgcaggaccg ccagaacgtc   2940
gtcatgctgg tcggtagcaa actgcgtgcc gctgccgctg aaaaacaggc tgttgcccta   3000
gcggaccgcc tgggctgcgc tgtcacgatc atggctgccg aaaaaggctt cttcccggaa   3060
gatcatccga acttccgcgg cctgtactgg ggtgaagtca gctccgaagg tgcacaggaa   3120
```

-continued

```
ctggttgaaa acgccgatgc catcctgtgt ctggcaccgg tattcaacga ctatgctacc   3180
gttggctgga actcctggcc gaaaggcgac aatgtcatgg tcatggacac cgaccgcgtc   3240
actttcgcag gacagtcctt cgaaggtctg tcattgagca ccttcgccgc agcactggct   3300
gagaaagcac cttctcgccc ggcaacgact caaggcactc aagcaccggt actgggtatt   3360
gaggccgcag agcccaatgc accgctgacc aatgacgaaa tgacgcgtca gatccagtcg   3420
ctgatcactt ccgacactac tctgacagca gaaacaggtg actcttggtt caacgcttct   3480
cgcatgccga ttcctggcgg tgctcgtgtc gaactggaaa tgcaatgggg tcatatcggt   3540
tggtccgtac cttctgcatt cggtaacgcc gttggttctc cggagcgtcg ccacatcatg   3600
atggtcggtg atggctcttt ccagctgact gctcaagaag ttgctcagat gatccgctat   3660
gaaatcccgg tcatcatctt cctgatcaac aaccgcggtt acgtcatcga aatcgctatc   3720
catgacggcc cttacaacta catcaaaaac tggaactacg ctggcctgat cgacgtcttc   3780
aatgacgaag atggtcatgg cctgggtctg aaagcttcta ctggtgcaga actagaaggc   3840
gctatcaaga aagcactcga caatcgtcgc ggtccgacgc tgatcgaatg taacatcgct   3900
caggacgact gcactgaaac cctgattgct tggggtaaac gtgtagcagc taccaactct   3960
cgcaaaccac aagcgtaagt tgatgtagtg aattaggcgg ggcctattag ggccccacca   4020
catagcccct cttacggcgc aatacccgta agaggggctg ttttatataa ttaaaactag   4080
agtcgaccat gcgtccaaaa ctttcaccat cctttcccta tcaaccttta ctgcactaaa   4140
gacaagtgag atagcagtgg caatctggct ttgcaatcaa tgtttccact aaagcgttta   4200
gcgttactgc ggctagaagt cctccaccga ggctcccctg aatggtgata tggggaatgg   4260
gactggtcat cagtcgtcgt tttgcccccg gagcatgact aaaaccgatc ggcattccga   4320
tcacaagagc cggctgaata tgttgttgct ctatcagctt acaggcagtg agtaaaacag   4380
aaggggcata gccgatcgcc agcacacatc cttggggaat ctgttgtaac cgctgttgcc   4440
aatggtcatg gtgccaaaaa gcttgctcgg cttccctaag ccctgtgatg tgagggtcgt   4500
caatcagcgt tttaaccgta catcctaaat gagctaaccg agtttgatca agagccgcag   4560
ccacaaccgg aacatcggtg acgactggac accctgcttt cagtgcatct cgtgccgagg   4620
cgatcgctcc ctgactcaat cgaacggcgt ttaccaagct aacatcacca caggccagca   4680
ctaattgatg tagtaagtga atggtaattt cagagtaagc cgataaatcc ggtagcaggt   4740
gtttgaggga ttcctgaaag gcttctggat gagttgttgt ctccgcatct aggttcgtcc   4800
acaactgatc gagttttcct aacccctcct ggacatccac atcaagctgt ttcagttggg   4860
ccagagcttc cgcttgggta atctggcaac tctggtcgcg tcccagtaat ccttctaaag   4920
cagatgcggt ttggcggagt cgagtaatct gctgaatcac agcctgatat tgctgttgca   4980
actgcaccat tagggtggga tcaaggctct cttcagaatg gctatccagc agttgccgaa   5040
tatgagacaa ctgaaagccc tgctgtttga gggcaatgac tcgttggagc cgttgtacgt   5100
cctgctgagt ataaaggcgg tagttgccct ctgagcgttg aacgggggga agcaatccca   5160
gggtgtggta atggcgcacc atgcgaggcg taacgccacc tcccactgca tctgtgagtt   5220
ctttaatcgt taagtgatta gtcttcatcc ctttagttta ctcaaaacct tgacattgac   5280
actaatgtta aggtttaggc tgagaaggta aaaatccaag ttaaaaagca tgaattccta   5340
caccgttggc acttacctgg ctgaacgctt ggttcagatc ggcttaaaac accattttgc   5400
tgttgctggt gattataatt tggttttgtt agataattta ttgctcaata agaatatgga   5460
```

acaggtgtac tgttgcaatg agttaaattg tggcttttcc gctgagggct acgcccgtgc 5520
taagggtgct gctgctgctg ttgtgactta ttctgttggc gctttgagtg cttttgacgc 5580
cattggcggt gcttacgctg agaatttgcc agtgatttta attagtggcg ccccaaataa 5640
taacgaccat gccgccggcc atgtcctcca ccatgccttg ggtaagactg attaccatta 5700
ccaactggag atggctaaaa atattaccgc tgctgccgaa gctatctata ctcctgagga 5760
agccccagcc aagattgacc atgtcatcaa gaccgccttg cgggaaaaaa aaccagtgta 5820
cttagagatt gcctgtaata tcgccagtat gccttgtgct gcccccggtc cagcttctgc 5880
tctctttaac gatgaagctt ctgatgaggc cagtctcaac gctgctgtgg aggaaacttt 5940
aaagtttatt gctaatcgtg ataaggtggc tgttttagtt ggttctaaat tacgtgctgc 6000
cggcgccgag gaagccgccg ttaagtttgc cgacgcctta ggcggtgctg tggccactat 6060
ggccgccgct aagtcttttt ttcctgaaga gaatccacac tatattggca ctagctgggg 6120
cgaggtttct tacccaggtg tggagaaaac catgaaggag gctgacgctg tgattgcctt 6180
agccccggtt tttaatgatt atagtactac cggctggacc gacatcccgg acccgaaaaa 6240
gttagtgtta gccgaaccac ggagtgttgt tgtgaatggt gtgcgttttc cttctgtgca 6300
cttaaaggat tacttaactc ggctcgccca gaaggtgagt aaaaagactg gcgccctcga 6360 ttttttaag agtttaaacg ctggcgagtt aaaaaaggct gccccagccg acccatccgc 6420
cccactcgtt aatgctgaaa ttgctcggca ggttgaggcc ttgttaactc caaataccac 6480
cgtgatcgcc gaaactggcg atagttggtt taacgcccaa cgtatgaaat taccaaatgg 6540
cgcccgtgtg gagtacgaga tgcaatgggg ccatattggc tggagtgtgc cggctgcttt 6600
tggctacgct gttggcgccc cagagcggcg taatatttta atggtgggcg acggcagttt 6660
tcagttaacc gcccaagagg ttgcccaaat ggtgcgttta aagttaccag tgattatttt 6720
tctcattaac aattacggct atactattga ggtgatgatt cacgacggcc catataataa 6780
tattaaaaat tgggactacg ctggcttaat ggaggtcttt aatggcaatg gcggctacga 6840
ttctggcgcc ggcaagggtt taaaagccaa gactggcggt gagttagctg aagccattaa 6900
agtggcctta gctaatactg atggtcctac tttaattgag tgttttattg gccgggaaga 6960
ttgtaccgag gaactcgtta agtggggcaa acgtgtggcc gctgctaatt ctcggaaacc 7020
cgtgaataaa ttattatgaa atattttagc cgccccagtc agtaatgact ggggcgtttt 7080
ttattgggag ctcctgcagg 7100

<210> SEQ ID NO 49
<211> LENGTH: 7100
<212> TYPE: DNA
<213> ORGANISM: Artificial
<220> FEATURE:
<223> OTHER INFORMATION: Synthetically produced ethanologenic gene cassette from plasmid #1383 pVZ325a-nrsRS-PnrsB*-zpPDC-corR-PcorT-zmPDCdeg integrated into pVZ325a

<400> SEQUENCE: 49
gtcgacccta tatcgggctt ttctcaataa aatctttatt ttttgaggtg ctttttagcc 60
ataaataatc actttagtat aaaattttga cggcgtaaag ttgataaaat agaattaaga 120
atggactatc ggtacagaaa aaatgggtaa ctggatggtg aataaacttc ccttacccaa 180
tgcactctcc accgttaaag accccctatg cttaacggtg atcacctggg caatggcgag 240
tcccaaccct gtcccccccg ttttgcgcga acgatctcga ttaactcggt aaaaacgctc 300
aaaaatgtgt tcctgttggt cgggggcaat gccgatgccg gtatcttgca cggtgatgat 360

```
agccatctgt tcatgggatg tcagggtaat atcaacacgt cccccagcag ttgtgtattg    420
aatggcgttg gcaattaggt ttgagaccag tcgatagagt tgggattcat taccccaggc    480
gtaaacttcc cctgaactca gatcactgct gagatcaatg tgggcggcga tcgctaattc    540
taaaaactct tcggtgaggt cactgactaa atcatttaaa caacaaagcc gccaatcttc    600
ggcggtggtt tcctgctcta agcgacttag tagcaataaa tccgtaatca attggcttaa    660
tcgccttccc tgtcgttcaa cggtatgtag catggtgtta atttctgggg aatggcttga    720
gtcgatgcgt aataccgctt ccaccgtggc caacagacta gccaatggcg atcgtaattc    780
atgggctgca ttcgcggtga attgttgttg ttgttggtag gactggtaaa tgggacgcat    840
ggctaacccc gctaagcccc aactggagaa ggcgaccaaa cccagggcaa tgggaaaact    900
aagccctaaa atccaaagaa tacgtttatt ttcggcatca aaggctgcca ggctccggcc    960
aatttgtaga tagccccagg aagatttgtc tgtattaccg gcgctatgca aaatggtggt   1020
gaattgtcga taccgatcgc cggttggggg gtgaatagtc tgccaagttt cctggttaaa   1080
aatggaggat agggaagccg gttgattagg cgaaaaagcc agcaggttgc cttgataatc   1140
aaataaacga atgtaatata aactgcgatc actaatgccc aacgtgtgac gttcaatcag   1200
ggtggggttg acctggcagg gttggttgac caaacacaga tcgggcaaca ttttttgtaa   1260
tactccggtg ggactagcat tactcggcaa catcggctct aaactgtcat gcaacgtccc   1320
ggcgatcgac tccacttctc gctccaacgc catccagttg gcctgcacaa tggcacgata   1380
aacccccaac cccaacaggg taagaatacc ccccattact agggcatacc agaaagccaa   1440
ttgcagacga ctacgggcaa agaggcgacg ggtattcatg gcgatagggt gaaccgatag   1500
ccttgaccgg gaactgtttt aattgggcaa ggacaatttt gttgagctag cttgcgtcgt   1560
atcaaacgca tttgggccgc caccacatta ctcatgggct cctcatcaag atcccacagt   1620
tgttgccgga tcttgctacc ggaaatgatc cgctctgggt tttgcatcag atattgaaaa   1680
atttgaaatt ctcttacggt taaagcaatt tcctgtcttt ctaggtttag tggctccgag   1740
atagttaccg ataacagatt attactggga tcaaggctga agttgcccaa agttaaaatt   1800
tgcggttgga attgtggcga tcgccgttgt agtgcccgca gtcttgctaa tagctctgcc   1860
atcacaaacg gttttgttag atagtcatct gccccggcat ctagtccttc gacacggttt   1920
tccggttctc ctaacgctgt taacatcaac accggcaagg aattaccctg ggttctcagt   1980
ttttgacaga gttccaaacc cgataatccc ggcagtaacc aatccacaat ggcaagggtg   2040
tattccgtcc attgattttc caaataatcc caagcttggg agccatccgt cacccaatcc   2100
accacatact tttcactaac tagcactttc ttaatagcca ttcccaaatc cgtctcatct   2160
tccaccagca aaattcgcat cgcctctgcc ttttttataa cggtctgatc ttagcggggg   2220
aaggagattt tcacctgaat ttcatacccc ctttggcaga ctgggaaaat cttggacaaa   2280
ttcccaattg gaggaggtgt gatgaattcc tataccgttg gtatgtactt ggcagaacgc   2340
ctagcccaga tcggcctgaa acaccacttt gccgtggccg gtgactacaa cctggtgttg   2400
cttgatcagc tcctgctgaa caaagacatg gagcaggtct actgctgtaa cgaacttaac   2460
tgcggcttta gcgccgaagg ttacgctcgt gcacgtggtg ccgccgctgc catcgtcacg   2520
ttcagcgtag gtgctatctc tgcaatgaac gccatcggtg gcgcctatgc agaaaacctg   2580
ccggtcatcc tgatctctgg ctcaccgaac accaatgact acggcacagg ccacatcctg   2640
caccacacca ttggtactac tgactataac tatcagctgg aaatggtaaa acacgttacc   2700
```

```
tgcgcacgtg aaagcatcgt ttctgccgaa gaagcaccgg caaaaatcga ccacgtcatc   2760
cgtacggctc tacgtgaacg caaaccggct tatctggaaa tcgcatgcaa cgtcgctggc   2820
gctgaatgtg ttcgtccggg cccgatcaat agcctgctgc gtgaactcga agttgaccag   2880
accagtgtca ctgccgctgt agatgccgcc gtagaatggc tgcaggaccg ccagaacgtc   2940
gtcatgctgg tcggtagcaa actgcgtgcc gctgccgctg aaaaacaggc tgttgcccta   3000
gcggaccgcc tgggctgcgc tgtcacgatc atggctgccg aaaaaggctt cttcccggaa   3060
gatcatccga acttccgcgg cctgtactgg ggtgaagtca gctccgaagg tgcacaggaa   3120
ctggttgaaa acgccgatgc catcctgtgt ctggcaccgg tattcaacga ctatgctacc   3180
gttggctgga actcctggcc gaaaggcgac aatgtcatgg tcatggacac cgaccgcgtc   3240
actttcgcag gacagtcctt cgaaggtctg tcattgagca ccttcgccgc agcactggct   3300
gagaaagcac cttctcgccc ggcaacgact caaggcactc aagcaccggt actgggtatt   3360
gaggccgcag agcccaatgc accgctgacc aatgacgaaa tgacgcgtca gatccagtcg   3420
ctgatcactt ccgacactac tctgacagca gaaacaggtg actcttggtt caacgcttct   3480
cgcatgccga ttcctggcgg tgctcgtgtc gaactggaaa tgcaatgggg tcatatcggt   3540
tggtccgtac cttctgcatt cggtaacgcc gttggttctc cggagcgtcg ccacatcatg   3600
atggtcggtg atggctcttt ccagctgact gctcaagaag ttgctcagat gatccgctat   3660
gaaatcccgg tcatcatctt cctgatcaac aaccgcggtt acgtcatcga aatcgctatc   3720
catgacggcc cttacaacta catcaaaaac tggaactacg ctggcctgat cgacgtcttc   3780
aatgacgaag atggtcatgg cctgggtctg aaagcttcta ctggtgcaga actagaaggc   3840
gctatcaaga aagcactcga caatcgtcgc ggtccgacgc tgatcgaatg taacatcgct   3900
caggacgact gcactgaaac cctgattgct tggggtaaac gtgtagcagc taccaactct   3960
cgcaaaccac aagcgtaagt tgatgtagtg aattaggcgg ggcctattag ggccccacca   4020
catagcccct cttacggcgc aatacccgta agaggggctg ttttatataa ttaaaactag   4080
agtcgaccat gcgtccaaaa ctttcaccat cctttcccta tcaaccttta ctgcactaaa   4140
gacaagtgag atagcagtgg caatctggct ttgcaatcaa tgtttccact aaagcgttta   4200
gcgttactgc ggctagaagt cctccaccga ggctcccctg aatggtgata tggggaatgg   4260
gactggtcat cagtcgtcgt tttgcccccg gagcatgact aaaaccgatc ggcattccga   4320
tcacaagagc cggctgaata tgttgttgct ctatcagctt acaggcagtg agtaaaacag   4380
aaggggcata gccgatcgcc agcacacatc cttggggaat ctgttgtaac cgctgttgcc   4440
aatggtcatg gtgccaaaaa gcttgctcgg cttccctaag ccctgtgatg tgagggtcgt   4500
caatcagcgt tttaaccgta catcctaaat gagctaaccg agtttgatca agagccgcag   4560
ccacaaccgg aacatcggtg acgactggac accctgcttt cagtgcatct cgtgccgagg   4620
cgatcgctcc ctgactcaat cgaacggcgt ttaccaagct aacatcacca caggccagca   4680
ctaattgatg tagtaagtga atggtaattt cagagtaagc cgataaatcc ggtagcaggt   4740
gtttgaggga ttcctgaaag gcttctggat gagttgttgt ctccgcatct aggttcgtcc   4800
acaactgatc gagttttcct aacccctcct ggacatccac atcaagctgt ttcagttggg   4860
ccagagcttc cgcttgggta atctggcaac tctggtcgcg tcccagtaat ccttctaaag   4920
cagatgcggt ttggcggagt cgagtaatct gctgaatcac agcctgatat tgctgttgca   4980
actgcaccat tagggtggga tcaaggctct cttcagaatg gctatccagc agttgccgaa   5040
tatgagacaa ctgaaagccc tgctgtttga gggcaatgac tcgttggagc cgttgtacgt   5100
```

```
cctgctgagt ataaaggcgg tagttgccct ctgagcgttg aacgggggga agcaatccca   5160
gggtgtggta atggcgcacc atgcgaggcg taacgccacc tcccactgca tctgtgagtt   5220
ctttaatcgt taagtgatta gtcttcatcc ctttagttta ctcaaaacct tgacattgac   5280
actaatgtta aggtttaggc tgagaaggta aaaatccaag ttaaaaagca tgaattccta   5340
caccgttggc acttacctgg ctgaacgctt ggttcagatc ggcttaaaac accattttgc   5400
tgttgctggt gattataatt tggttttgtt agataattta ttgctcaata agaatatgga   5460
acaggtgtac tgttgcaatg agttaaattg tggcttttcc gctgagggct acgcccgtgc   5520
taagggtgct gctgctgctg ttgtgactta ttctgttggc gctttgagtg cttttgacgc   5580
cattggcggt gcttacgctg agaatttgcc agtgatttta attagtggcg ccccaaataa   5640
taacgaccat gccgccggcc atgtcctcca ccatgccttg ggtaagactg attaccatta   5700
ccaactggag atggctaaaa atattaccgc tgctgccgaa gctatctata ctcctgagga   5760
agccccagcc aagattgacc atgtcatcaa gaccgccttg cgggaaaaaa aaccagtgta   5820
cttagagatt gcctgtaata tcgccagtat gccttgtgct gccccccggtc cagcttctgc   5880
tctctttaac gatgaagctt ctgatgaggc cagtctcaac gctgctgtgg aggaaacttt   5940
aaagtttatt gctaatcgtg ataaggtggc tgttttagtt ggttctaaat tacgtgctgc   6000
cggcgccgag gaagccgccg ttaagtttgc cgacgcctta ggcggtgctg tggccactat   6060
ggccgccgct aagtcttttt ttcctgaaga gaatccacac tatattggca ctagctgggg   6120
cgaggtttct tacccaggtg tggagaaaac catgaaggag gctgacgctg tgattgcctt   6180
agccccggtt tttaatgatt atagtactac cggctggacc gacatcccgg acccgaaaaa   6240
gttagtgtta gccgaaccac ggagtgttgt tgtgaatggt gtgcgttttc cttctgtgca   6300
cttaaaggat tacttaactc ggctcgccca gaaggtgagt aaaaagactg gcgccctcga   6360
ttttttaag agtttaaacg ctggcgagtt aaaaaaggct gccccagccg acccatccgc   6420
cccactcgtt aatgctgaaa ttgctcggca ggttgaggcc ttgttaactc caaataccac   6480
cgtgatcgcc gaaactggcg atagttggtt taacgcccaa cgtatgaaat taccaaatgg   6540
cgcccgtgtg gagtacgaga tgcaatgggg ccatattggc tggagtgtgc cggctgcttt   6600
tggctacgct gttggcgccc cagagcggcg taatatttta atggtgggcg acggcagttt   6660
tcagttaacc gcccaagagg ttgcccaaat ggtgcgttta aagttaccag tgattatttt   6720
tctcattaac aattacggct atactattga ggtgatgatt cacgacggcc catataataa   6780
tattaaaaat tgggactacg ctggcttaat ggaggtcttt aatggcaatg gcggctacga   6840
ttctggcgcc ggcaagggtt taaaagccaa gactggcggt gagttagctg aagccattaa   6900
agtggcctta gctaatactg atggtcctac tttaattgag tgttttattg gccgggaaga   6960
ttgtaccgag gaactcgtta agtggggcaa acgtgtggcc gctgctaatt ctcggaaacc   7020
cgtgaataaa ttattatgaa atattttagc cgccccagtc agtaatgact ggggcgtttt   7080
ttattgggag ctcctgcagg                                               7100
```

<210> SEQ ID NO 50
<211> LENGTH: 10530
<212> TYPE: DNA
<213> ORGANISM: Artificial
<220> FEATURE:
<223> OTHER INFORMATION: Synthetically produced ethanologenic gene construct from plasmid #1389 pJet-pSYSG::nrsRS-PnrsB-zpPDC(deg)-Gm for homologous integration into Synechocystis sp. PCC6803 endogenous pSYSG plasmid

<400> SEQUENCE: 50
tgctttttag ccataaataa tcactttagt ataaaatttt gacggcgtaa agttgataaa 60
atagaattaa gaatggacta tcggtacaga aaaaatgggt aactggatgg tgaataaact 120
tcccttaccc aatgcactct ccaccgttaa agacccccta tgcttaacgg tgatcacctg 180
ggcaatggcg agtcccaacc ctgtcccccc cgttttgcgc gaacgatctc gattaactcg 240
gtaaaaacgc tcaaaaatgt gttcctgttg gtcgggggca atgccgatgc cggtatcttg 300
cacggtgatg atagccatct gttcatggga tgtcagggta atatcaacac gtcccccagc 360
agttgtgtat tgaatggcgt tggcaattag gtttgagacc agtcgataga gttgggattc 420
attaccccag gcgtaaactt cccctgaact cagatcactg ctgagatcaa tgtgggcggc 480
gatcgctaat tctaaaaact cttcggtgag gtcactgact aaatcattta aacaacaaag 540
ccgccaatct tcggcggtgg tttcctgctc taagcgactt agtagcaata aatccgtaat 600
caattggctt aatcgccttc cctgtcgttc aacggtatgt agcatggtgt taatttctgg 660
ggaatggctt gagtcgatgc gtaataccgc ttccaccgtg gccaacagac tagccaatgg 720
cgatcgtaat tcatgggctg cattcgcggt gaattgttgt tgttgttggt aggactggta 780
aatgggacgc atggctaacc ccgctaagcc ccaactggag aaggcgacca aacccagggc 840
aatgggaaaa ctaagcccta aaatccaaag aatacgttta ttttcggcat caaaggctgc 900
caggctccgg ccaatttgta gatagcccca ggaagatttg tctgtattac cggcgctatg 960
caaaatggtg gtgaattgtc gataccgatc gccggttggg gggtgaatag tctgccaagt 1020
ttcctggtta aaaatggagg atagggaagc cggttgatta ggcgaaaaag ccagcaggtt 1080
gccttgataa tcaaataaac gaatgtaata taaactgcga tcactaatgc ccaacgtgtg 1140
acgttcaatc agggtggggt tgacctggca gggttggttg accaaacaca gatcgggcaa 1200
catttttgt aatactccgg tgggactagc attactcggc aacatcggct ctaaactgtc 1260
atgcaacgtc ccggcgatcg actccacttc tcgctccaac gccatccagt tggcctgcac 1320
aatggcacga taaaccccca accccaacag ggtaagaata ccccccatta ctagggcata 1380
ccagaaagcc aattgcagac gactacgggc aaagaggcga cgggtattca tggcgatagg 1440
gtgaaccgat agccttgacc gggaactgtt ttaattgggc aaggacaatt ttgttgagct 1500
agcttgcgtc gtatcaaacg catttgggcc gccaccacat tactcatggg ctcctcatca 1560
agatcccaca gttgttgccg gatcttgcta ccggaaatga tccgctctgg gttttgcatc 1620
agatattgaa aaatttgaaa ttctcttacg gttaaagcaa tttcctgtct ttctaggttt 1680
agtggctccg agatagttac cgataacaga ttattactgg gatcaaggct gaagttgccc 1740
aaagttaaaa tttgcggttg gaattgtggc gatcgccgtt gtagtgcccg cagtcttgct 1800
aatagctctg ccatcacaaa cggttttgtt agatagtcat ctgccccggc atctagtcct 1860
tcgacacggt tttccggttc tcctaacgct gttaacatca acaccggcaa ggaattaccc 1920
tgggttctca gtttttgaca gagttccaaa cccgataatc ccggcagtaa ccaatccaca 1980
atggcaaggg tgtattccgt ccattgattt tccaaataat cccaagcttg ggagccatcc 2040
gtcacccaat ccaccacata cttttcacta actagcactt tcttaatagc cattcccaaa 2100
tccgtctcat cttccaccag caaaattcgc atcgcctctg cctttttat aacggtctga 2160
tcttagcggg ggaaggagat tttcacctga atttcatacc ccctttggca gactgggaaa 2220
atcttggaca aattcccaat ttgaggtggt gtgatgaatt cttacactgt gggcatgtat 2280

```
ctcgcggagc ggttggctca aattggttta aagcatcatt tcgctgtcgc tggcgattat   2340
aatttagtcc tcttagacca attgttgtta aataaggata tggaacaagt ttattgttgc   2400
aatgaattga attgtggttt ctctgctgag ggctatgccc gcgcgcgcgg cgctgctgcc   2460
gctattgtta ccttttctgt gggcgccatt tccgcgatga atgctattgg cggtgcttac   2520
gcggaaaatt tacccgttat tttaatttcc ggtagtccca atactaacga ttatgggacc   2580
gggcatattt tacatcatac tatcggcacc accgattaca attaccaatt agagatggtg   2640
aagcatgtga cttgtgctgc cgaatctatt gtgtccgctg aggaagcgcc cgcgaagatt   2700
gatcatgtta ttcgcaccgc cttgcgcgag cggaagcccg cctacttaga aattgcgtgt   2760
aatgttgccg gtgccgagtg cgtgcgcccc ggtcccatta actctttatt acgcgaattg   2820
gaggtggatc aaacttccgt taccgctgcc gtggacgctg ctgtggagtg gttacaagat   2880
cggcaaaatg ttgttatgtt agttggctct aagttacgcg ctgccgctgc cgagaagcaa   2940
gctgtggctt tggccgatcg gttaggttgt gccgttacca ttatggccgc tgagaagggt   3000
ttttttcctg aggaccaccc caattttcgg ggtttatatt ggggcgaagt ttctagtgag   3060
ggcgcgcaag aattagtgga gaatgctgac gctattttat gcttggcgcc cgtgtttaat   3120
gattacgcca ctgtgggttg gaatagttgg cccaagggtg ataacgttat ggttatggat   3180
actgatcggg ttacctttgc gggtcaaagt tttgaaggct taagtctctc tacttttgct   3240
gcggcgttag ccgaaaaggc gccctcgcgg cccgcgacca cccaggggac ccaggcgccc   3300
gtgttaggca tcgaagctgc ggaacctaac gcgcccttaa ctaacgatga gatgacccgc   3360
caaattcaat ctttaattac cagtgatacc accttaaccg cggaaaccgg cgattcctgg   3420
tttaatgcct cccggatgcc catccccggt ggcgcccgcg ttgagttaga gatgcagtgg   3480
ggccacattg gctggagtgt gccgtccgcg tttggcaatg ctgtgggctc cccccgaacgc   3540
cgtcatatta tgatggttgg cgacggtagt tttcaattaa ccgcccagga ggtggcccaa   3600
atgattcggt acgaaattcc cgttattatc tttttgatta ataatcgggg ctatgttatt   3660
gagattgcca ttcacgatgg tccgtataat tatattaaga attggaatta tgccggttta   3720
attgatgttt ttaacgatga agacggccac ggtttaggct taaaggcctc caccggcgcg   3780
gagttggaag gtgccattaa aaaggcgttg gataaccgcc ggggccccac cttaattgag   3840
tgcaatattg cccaagatga ttgtaccgaa actttaatcg cctggggcaa gcgcgtggcg   3900
gccactaatt cccggaagcc ccaggcctga aagtcctaag agcccgcacg gcgcaagccc   3960
gtgcgggctt ttttgtggag ctcgaattgg ccgcggcgtt gtgacaattt accgaacaac   4020
tccgcggccg ggaagccgat ctcggcttga acgaattgtt aggtggcggt acttgggtcg   4080
atatcaaagt gcatcacttc ttcccgtatg cccaactttg tatagagagc cactgcggga   4140
tcgtcaccgt aatctgcttg cacgtagatc acataagcac caagcgcgtt ggcctcatgc   4200
ttgaggagat tgatgagcgc ggtggcaatg ccctgcctcc ggtgctcgcc ggagactgcg   4260
agatcataga tatagatctc actacgcggc tgctcaaacc tgggcagaac gtaagccgcg   4320
agagcgccaa caaccgcttc ttggtcgaag gcagcaagcg cgatgaatgt cttactacgg   4380
agcaagttcc cgaggtaatc ggagtccggc tgatgttggg agtaggtggc tacgtctccg   4440
aactcacgac cgaaaagatc aagagcagcc cgcatggatt tgacttggtc agggccgagc   4500
ctacatgtgc gaatgatgcc catacttgag ccacctaact ttgttttagg gcgactgccc   4560
tgctgcgtaa catcgttgct gctgcgtaac atcgttgctg ctccataaca tcaaacatcg   4620
acccacggcg taacgcgctt gctgcttgga tgcccgaggc atagactgta caaaaaaaca   4680
```

gtcataacaa gccatgaaaa ccgccactgc gccgttacca ccgctgcgtt cggtcaaggt 4740
tctggaccag ttgcgtgagc gcatacgcta cttgcattac agtttacgaa ccgaacaggc 4800
ttatgtcaat tcgagcatcg attgtatggg aagcccgatg cgccagagtt gtttctgaaa 4860
catggcaaag gtagcgttgc caatgatgtt acagatgaga tggtcagact aaactggctg 4920
acggaattta tgcctcttcc gaccatcaag cattttatcc gtactcctga tgatgcatgg 4980
ttactcacca ctgcgatccc cgggtcttgc cagaagattt actctagttc taccctggac 5040
ctgtctgtgt aactgtactt ttccatctct gagtgcatga tgaagaacga gcagtagaga 5100
tgccatgctt tgatgtatag cggtctaacg gatagctcgt agtagccaaa gtctaaaccc 5160
cttgccctat ctcgaaggat cttctgcttg agggtagacc tagtggtctc taagttgatg 5220
aattttctgt cgagaatgtc gctcatagtt tgaagaattg gcataaccaa ttcgtgaaac 5280
tattaagggc tgagttcttc ccaaccctgt tctgttcttt gtctctctgg acctgggtta 5340
tgtttaaact tccaattttt cctcttgtgt tgagtggttc tccccagcta tggatgggct 5400
tgtcgcctta gtctgtaact gctcaacgat gtggagccct tccaacagtg cttgggtttc 5460
cttaagcttc tctattaggc ttagtctgat tacgtttaat tctggattta tagcatcttt 5520
gggcgaattt ttactgatgt aatctttaaa agcttccgtt tgctcgtgat atcgcttaat 5580
tttagaaaaa agtgcgcaca tgtgcgcact tttctgcttc tgctgttcat cttctgggtc 5640
attgaggatt ttggtgatat atctacgact tgccccaaat acagacatta actctcggtt 5700
gatagacttt tgtcctttgc tggggcgacc tttaagcttt tcatagccag cctcctttag 5760
cttacgggcc gcttctcgaa tttcactagg ggtgtagttt ttgcgttggg tattttcttc 5820
aacttcaact tgtaatgccg tgagggttgc tgtttctgca tcaatgtcca taatgttcac 5880
cggcactcct tcgccaaaga atgccgtaaa tgtttctggg gattctgccg ctaatttctc 5940
tagggctgct ttacgatgtc ctccggctaa tagcctgtag tgtctgtcca ctgttaacgg 6000
ggtaatcagt cccaggactt gaatactttc cactaactct ttgacatgct tagcgttaat 6060
ttgacgggta tctccctctg gccgatcgcc gattttgtcc aggggcacca gtccttcctt 6120
catctgttgt cgttgcaagg tttcttcggc tgcttccgaa gtagcggagc gtgcttgagc 6180
tttgcttatg tctagaagat ctcctacaat attctcagct gccatggaaa atcgatgttc 6240
ttcttttatt ctctcaagat tttcaggctg tatattaaaa cttatattaa gaactatgct 6300
aaccacctca tcaggaaccg ttgtaggtgg cgtgggtttt cttggcaatc gactctcatg 6360
aaaactacga gctaaatatt caatatgttc ctcttgacca actttattct gcattttttt 6420
tgaacgaggt ttagagcaag cttcaggaaa ctgagacagg aattttatta aaaatttaaa 6480
ttttgaagaa agttcagggt taatagcatc cattttttgc tttgcaagtt cctcagcatt 6540
cttaacaaaa gacgtctctt ttgacatgtt taaagtttaa acctcctgtg tgaaattgtt 6600
atccgctcac aattccacac attatacgag ccggaagcat aaagtgtaaa gcctggggtg 6660
cctaatgagt gagctaactc acattaattg cgttgcgctc actgccaatt gctttccagt 6720
cgggaaacct gtcgtgccag ctgcattaat gaatcggcca acgcgcgggg agaggcggtt 6780
tgcgtattgg gcgctcttcc gcttcctcgc tcactgactc gctgcgctcg gtcgttcggc 6840
tgcggcgagc ggtatcagct cactcaaagg cggtaatacg gttatccaca gaatcagggg 6900
ataacgcagg aaagaacatg tgagcaaaag gccagcaaaa ggccaggaac cgtaaaaagg 6960
ccgcgttgct ggcgtttttc cataggctcc gcccccctga cgagcatcac aaaaatcgac 7020

-continued

```
gctcaagtca gaggtggcga aacccgacag gactataaag ataccaggcg tttccccctg   7080
gaagctccct cgtgcgctct cctgttccga ccctgccgct taccggatac ctgtccgcct   7140
ttctcccttc gggaagcgtg gcgctttctc atagctcacg ctgtaggtat ctcagttcgg   7200
tgtaggtcgt tcgctccaag ctgggctgtg tgcacgaacc ccccgttcag cccgaccgct   7260
gcgccttatc cggtaactat cgtcttgagt ccaacccggt aagacacgac ttatcgccac   7320
tggcagcagc cactggtaac aggattagca gagcgaggta tgtaggcggt gctacagagt   7380
tcttgaagtg gtggcctaac tacggctaca ctagaaggac agtatttggt atctgcgctc   7440
tgctgaagcc agttaccttc ggaaaaagag ttggtagctc ttgatccggc aaacaaacca   7500
ccgctggtag cggtggtttt tttgtttgca agcagcagat tacgcgcaga aaaaaaggat   7560
ctcaagaaga tcctttgatc ttttctacgg ggtctgacgc tcagtggaac gaaaactcac   7620
gttaagggat tttggtcatg agattatcaa aaaggatctt cacctagatc cttttaaatt   7680
aaaaatgaag ttttaaatca atctaaagta tatatgagta aacttggtct gacagttacc   7740
aatgcttaat cagtgaggca cctatctcag cgatctgtct atttcgttca tccatagttg   7800
cctgactccc cgtcgtgtag ataactacga tacgggaggg cttaccatct ggccccagtg   7860
ctgcaatgat accgcgagac ccacgctcac cggctccaga tttatcagca ataaaccagc   7920
cagccggaag ggccgagcgc agaagtggtc ctgcaacttt atccgcctcc atccagtcta   7980
ttaattgttg ccgggaagct agagtaagta gttcgccagt taatagtttg cgcaacgttg   8040
ttgccattgc tacaggcatc gtggtgtcac gctcgtcgtt tggtatggct tcattcagct   8100
ccggttccca acgatcaagg cgagttacat gatcccccat gttgtgcaaa aaagcggtta   8160
gctccttcgg tcctccgatc gttgtcagaa gtaagttggc cgcagtgtta tcactcatgg   8220
ttatggcagc actgcataat tctcttactg tcatgccatc cgtaagatgc ttttctgtga   8280
ctggtgagta ctcaaccaag tcattctgag aatagtgtat gcggcgaccg agttgctctt   8340
gcccggcgtc aatacgggat aataccgcgc cacatagcag aactttaaaa gtgctcatca   8400
ttggaaaacg ttcttcgggg cgaaaactct caaggatctt accgctgttg agatccagtt   8460
cgatgtaacc cactcgtgca cccaactgat cttcagcatc ttttactttc accagcgttt   8520
ctgggtgagc aaaaacagga aggcaaaatg ccgcaaaaaa gggaataagg gcgacacgga   8580
aatgttgaat actcatactc ttcctttttc aatattattg aagcatttat cagggttatt   8640
gtctcatgag cggatacata tttgaatgta tttagaaaaa taaacaaata ggggttccgc   8700
gcacatttcc ccgaaaagtg ccacctgacg tctaagaaac cattattatc atgacattaa   8760
cctataaaaa taggcgtatc acgaggcctg cccctgcagc cgaattatat tatttttgcc   8820
aaataatttt taacaaaagc tctgaagtct tcttcattta aattcttaga tgatacttca   8880
tctggaaaat tgtcccaatt agtagcatca cgctgtgagt aagttctaaa ccattttttt   8940
attgttgtat tatctctaat cttactactc gatgagtttt cggtattatc tctattttta   9000
acttggagca ggttccattc attgtttttt tcatcatagt gaataaaatc aactgcttta   9060
acacttgtgc ctgaacacca tatccatccg gcgtaatacg actcactata gggagagcgg   9120
ccgctccgta gttgctctta caccaatcac tctaggtatg gcccgtatgt ccctgcttac   9180
ttttcgttgg agccggagct tgaccccctc ggatttttat gtccgcgatg gaagggttat   9240
tcttcttttc cttaccttgc tggggttagt gctgtcccac agtgggggaa ctatgccccg   9300
acaaacccac tcttgtccct gccatgctta aggctgcgcc cagagcctca ttatccttgg   9360
tttgtcagta atccactaca gatgtgacgt ttgtggtctc tatcgggact taggttgctc   9420
```

tcttgtttgt gtgattttgc tgttgcttgg tcttcgtcgt cgttccttaa ctttccttct 9480
tctctgggta tgcttcctgg tagtgccccc cctttgctcc tatgtcctct accccttctt 9540
tatttgtttc tgtgacagaa ttggcccagg aagccggtgt gagcgttcgc actgtccaga 9600
cctgggctaa ggctggttac ttctctaagc aaggctccaa cgcctatgac atccttggtt 9660
actaccgttg gtacactcgc agcctgcggc aggatctgga tgaacataag gctaaagttg 9720
ctcgttctga ctgggatacc aagtggcgtg aaggtcgtgc gaggaagtct ctcgccgaag 9780
cttctcttgt tgagttacaa atgcagagta aggttaagca ggtagttccc atcgatcttg 9840
ttatctcaga aattgacaag gttttgtcct cttccattcg tttgttccgg gatctacctt 9900
cttacttttc cgcccccac tgctatcagt cttcctctga agttgccgct gccctagagc 9960
aagctgtgag tctggcttta aaagattttc agtcccagct tgtgagtctt tctttaggtg 10020
ctgaattagt ggagaagtca aaggtcttcc atgactcatt ctcctcctct gatacctcgt 10080
cttgaccttc tgttgtttct gtcaacgctg tgatagatgg attgctcagt ctctacccag 10140
cttgttgtga tgttcacatc tgcatctcta tgtcagagac catttctcta actttttcta 10200
tcgttagggt cgggtctttc atgttgacgt gcacatactg ggaagcatat tcttcgatgc 10260
gcttaaagtt ttgccgtggt agtttagctt gatgctcttc cacgttgaaa cctgctaagt 10320
agttacatac ggctgacagc ggcaaaaaat gtttgagtat aaggccatag ttgatgcttg 10380
ttggaattcg ctgctttgtc gcgtcactgt ttagttcctt ccagttctca aacttgtctt 10440
catctttgat gactaaccat gagtagggtg ccccgtagaa tactcgaccc tatatcgggc 10500
ttttctcaat aaaatcttta ttttttgagg 10530

<210> SEQ ID NO 51
<211> LENGTH: 3035
<212> TYPE: DNA
<213> ORGANISM: Artificial
<220> FEATURE:
<223> OTHER INFORMATION: Synthetically produced ethanologenic gene cassette from plasmid #1391 pVZ324a-corR-PcorT-ZpPDC integrated into pVZ325a

<400> SEQUENCE: 51
gtcgaccatg cgtccaaaac tttcaccatc ctttccctat caacctttac tgcactaaag 60
acaagtgaga tagcagtggc aatctggctt tgcaatcaat gtttccacta aagcgtttag 120
cgttactgcg gctagaagtc ctccaccgag gctcccctga atggtgatat ggggaatggg 180
actggtcatc agtcgtcgtt ttgcccccgg agcatgacta aaaccgatcg gcattccgat 240
cacaagagcc ggctgaatat gttgttgctc tatcagctta caggcagtga gtaaaacaga 300
aggggcatag ccgatcgcca gcacacatcc ttggggaatc tgttgtaacc gctgttgcca 360
atggtcatgg tgccaaaaag cttgctcggc ttccctaagc cctgtgatgt gagggtcgtc 420
aatcagcgtt ttaaccgtac atcctaaatg agctaaccga gtttgatcaa gagccgcagc 480
cacaaccgga acatcggtga cgactggaca ccctgctttc agtgcatctc gtgccgaggc 540
gatcgctccc tgactcaatc gaacggcgtt taccaagcta acatcaccac aggccagcac 600
taattgatgt agtaagtgaa tggtaatttc agagtaagcc gataaatccg gtagcaggtg 660
tttgagggat tcctgaaagg cttctggatg agttgttgtc tccgcatcta ggttcgtcca 720
caactgatcg agttttccta acccctcctg gacatccaca tcaagctgtt tcagttgggc 780
cagagcttcc gcttgggtaa tctggcaact ctggtcgcgt cccagtaatc cttctaaagc 840

-continued agatgcggtt tggcggagtc gagtaatctg ctgaatcaca gcctgatatt gctgttgcaa 900
ctgcaccatt agggtgggat caaggctctc ttcagaatgg ctatccagca gttgccgaat 960
atgagacaac tgaaagccct gctgtttgag ggcaatgact cgttggagcc gttgtacgtc 1020
ctgctgagta taaaggcggt agttgccctc tgagcgttga acggggggaa gcaatcccag 1080
ggtgtggtaa tggcgcacca tgcgaggcgt aacgccacct cccactgcat ctgtgagttc 1140
tttaatcgtt aagtgattag tcttcatccc tttagtttac tcaaaacctt gacattgaca 1200
ctaatgttaa ggtttaggct gagaaggtaa aaatccaagt taaaaagcat gaattcctat 1260
accgttggta tgtacttggc agaacgccta gcccagatcg gcctgaaaca ccactttgcc 1320
gtggccggtg actacaacct ggtgttgctt gatcagctcc tgctgaacaa agacatggag 1380
caggtctact gctgtaacga acttaactgc ggctttagcg ccgaaggtta cgctcgtgca 1440
cgtggtgccg ccgctgccat cgtcacgttc agcgtaggtg ctatctctgc aatgaacgcc 1500
atcggtggcg cctatgcaga aaacctgccg gtcatcctga tctctggctc accgaacacc 1560
aatgactacg gcacaggcca catcctgcac cacaccattg gtactactga ctataactat 1620
cagctggaaa tggtaaaaca cgttacctgc gcagctgaaa gcatcgtttc tgccgaagaa 1680
gcaccggcaa aaatcgacca cgtcatccgt acggctctac gtgaacgcaa accggcttat 1740
ctggaaatcg catgcaacgt cgctggcgct gaatgtgttc gtccgggccc gatcaatagc 1800
ctgctgcgtg aactcgaagt tgaccagacc agtgtcactg ccgctgtaga tgccgccgta 1860
gaatggctgc aggaccgcca gaacgtcgtc atgctggtcg gtagcaaact gcgtgccgct 1920
gccgctgaaa aacaggctgt tgccctagcg gaccgcctgg gctgcgctgt cacgatcatg 1980
gctgccgaaa aaggcttctt cccggaagat catccgaact tccgcggcct gtactggggt 2040
gaagtcagct ccgaaggtgc acaggaactg gttgaaaacg ccgatgccat cctgtgtctg 2100
gcaccggtat tcaacgacta tgctaccgtt ggctggaact cctggccgaa aggcgacaat 2160
gtcatggtca tggacaccga ccgcgtcact ttcgcaggac agtccttcga aggtctgtca 2220
ttgagcacct tcgccgcagc actggctgag aaagcacctt ctcgcccggc aacgactcaa 2280
ggcactcaag caccggtact gggtattgag gccgcagagc ccaatgcacc gctgaccaat 2340
gacgaaatga cgcgtcagat ccagtcgctg atcacttccg acactactct gacagcagaa 2400
acaggtgact cttggttcaa cgcttctcgc atgccgattc ctggcggtgc tcgtgtcgaa 2460
ctggaaatgc aatggggtca tatcggttgg tccgtacctt ctgcattcgg taacgccgtt 2520
ggttctccgg agcgtcgcca catcatgatg gtcggtgatg gctctttcca gctgactgct 2580
caagaagttg ctcagatgat ccgctatgaa atcccggtca tcatcttcct gatcaacaac 2640
cgcggttacg tcatcgaaat cgctatccat gacggccctt acaactacat caaaaactgg 2700
aactacgctg gcctgatcga cgtcttcaat gacgaagatg gtcatggcct gggtctgaaa 2760
gcttctactg gtgcagaact agaaggcgct atcaagaaag cactcgacaa tcgtcgcggt 2820
ccgacgctga tcgaatgtaa catcgctcag gacgactgca ctgaaaccct gattgcttgg 2880
ggtaaacgtg tagcagctac caactctcgc aaaccacaag cgtaagttga tgtagtgaat 2940
taggcggggc ctattagggc cccaccacat agcccctctt acggcgcaat acccgtaaga 3000
ggggctgttt tatataatta aagagctcct gcagg 3035

<210> SEQ ID NO 52
<211> LENGTH: 9297
<212> TYPE: DNA
<213> ORGANISM: Artificial -continued
<220> FEATURE:
<223> OTHER INFORMATION: Synthetically produced plasmid TK193
pGEM-AQ3::nrsRS-PnrsB-zpPDC(deg)-Gm for transformation of
Synechococcus sp. PCC7002 via integration into the endogenous
pAQ3 plasmid

<400> SEQUENCE: 52

```
aattcgctgc tttgtcgcgt cactgtttag ttccttccag ttctcaaact tgtcttcatc     60
tttgatgact aaccatgagt agggtgcccc gtagaatact cgaccctata tcgggctttt    120
ctcaataaaa tctttatttt ttgaggtgct ttttagccat aaataatcac tttagtataa    180
aattttgacg gcgtaaagtt gataaaatag aattaagaat ggactatcgg tacagaaaaa    240
atgggtaact ggatggtgaa taaacttccc ttacccaatg cactctccac cgttaaagac    300
cccctatgct taacggtgat cacctgggca atggcgagtc ccaaccctgt cccccccgtt    360
ttgcgcgaac gatctcgatt aactcggtaa aaacgctcaa aaatgtgttc ctgttggtcg    420
ggggcaatgc cgatgccggt atcttgcacg gtgatgatag ccatctgttc atgggatgtc    480
agggtaatat caacacgtcc cccagcagtt gtgtattgaa tggcgttggc aattaggttt    540
gagaccagtc gatagagttg ggattcatta ccccaggcgt aaacttcccc tgaactcaga    600
tcactgctga gatcaatgtg ggcggcgatc gctaattcta aaaactcttc ggtgaggtca    660
ctgactaaat catttaaaca acaaagccgc caatcttcgg cggtggtttc ctgctctaag    720
cgacttagta gcaataaatc cgtaatcaat tggcttaatc gccttccctg tcgttcaacg    780
gtatgtagca tggtgttaat ttctggggaa tggcttgagt cgatgcgtaa taccgcttcc    840
accgtggcca acagactagc caatggcgat cgtaattcat gggctgcatt cgcggtgaat    900
tgttgttgtt gttggtagga ctggtaaatg ggacgcatgg ctaaccccgc taagccccaa    960
ctggagaagg cgaccaaacc cagggcaatg ggaaaactaa gccctaaaat ccaaagaata   1020
cgtttatttt cggcatcaaa ggctgccagg ctccggccaa tttgtagata gccccaggaa   1080
gatttgtctg tattaccggc gctatgcaaa atggtggtga attgtcgata ccgatcgccg   1140
gttggggggt gaatagtctg ccaagtttcc tggttaaaaa tggaggatag ggaagccggt   1200
tgattaggcg aaaaagccag caggttgcct tgataatcaa ataaacgaat gtaatataaa   1260
ctgcgatcac taatgcccaa cgtgtgacgt tcaatcaggg tggggttgac ctggcagggt   1320
tggttgacca aacacagatc gggcaacatt ttttgtaata ctccggtggg actagcatta   1380
ctcggcaaca tcggctctaa actgtcatgc aacgtcccgg cgatcgactc cacttctcgc   1440
tccaacgcca tccagttggc ctgcacaatg gcacgataaa cccccaaccc caacagggta   1500
agaatacccc ccattactag ggcataccag aaagccaatt gcagacgact acgggcaaag   1560
aggcgacggg tattcatggc gatagggtga accgatagcc ttgaccggga actgttttaa   1620
ttgggcaagg acaattttgt tgagctagct tgcgtcgtat caaacgcatt tgggccgcca   1680
ccacattact catgggctcc tcatcaagat cccacagttg ttgccggatc ttgctaccgg   1740
aaatgatccg ctctgggttt tgcatcagat attgaaaaat ttgaaattct cttacggtta   1800
aagcaatttc ctgtctttct aggtttagtg gctccgagat agttaccgat aacagattat   1860
tactgggatc aaggctgaag ttgcccaaag ttaaaatttg cggttggaat tgtggcgatc   1920
gccgttgtag tgcccgcagt cttgctaata gctctgccat cacaaacggt tttgttagat   1980
agtcatctgc cccggcatct agtccttcga cacggttttc cggttctcct aacgctgtta   2040
acatcaacac cggcaaggaa ttaccctggg ttctcagttt ttgacagagt tccaaacccg   2100
ataatcccgg cagtaaccaa tccacaatgg caagggtgta ttccgtccat tgattttcca   2160
```

-continued

```
aataatccca agcttgggag ccatccgtca cccaatccac cacatacttt tcactaacta   2220
gcactttctt aatagccatt cccaaatccg tctcatcttc caccagcaaa attcgcatcg   2280
cctctgcctt ttttataacg gtctgatctt agcgggggaa ggagattttc acctgaattt   2340
catacccct ttggcagact gggaaaatct tggacaaatt cccaatttga ggtggtgtga   2400
tgaattctta cactgtgggc atgtatctcg cggagcggtt ggctcaaatt ggtttaaagc   2460
atcatttcgc tgtcgctggc gattataatt tagtcctctt agaccaattg ttgttaaata   2520
aggatatgga acaagtttat tgttgcaatg aattgaattg tggtttctct gctgagggct   2580
atgcccgcgc gcgcggcgct gctgccgcta ttgttacctt ttctgtgggc gccatttccg   2640
cgatgaatgc tattggcggt gcttacgcgg aaaatttacc cgttatttta atttccggta   2700
gtcccaatac taacgattat gggaccgggc atattttaca tcatactatc ggcaccaccg   2760
attacaatta ccaattagag atggtgaagc atgtgacttg tgctgccgaa tctattgtgt   2820
ccgctgagga agcgcccgcg aagattgatc atgttattcg caccgccttg cgcgagcgga   2880
agcccgccta cttagaaatt gcgtgtaatg ttgccggtgc cgagtgcgtg cgccccggtc   2940
ccattaactc tttattacgc gaattggagg tggatcaaac ttccgttacc gctgccgtgg   3000
acgctgctgt ggagtggtta caagatcggc aaaatgttgt tatgttagtt ggctctaagt   3060
tacgcgctgc cgctgccgag aagcaagctg tggctttggc cgatcggtta ggttgtgccg   3120
ttaccattat ggccgctgag aagggttttt ttcctgagga ccacccccaat tttcggggtt   3180
tatattgggg cgaagtttct agtgagggcg cgcaagaatt agtggagaat gctgacgcta   3240
ttttatgctt ggcgcccgtg tttaatgatt acgccactgt gggttggaat agttggccca   3300
agggtgataa cgttatggtt atggatactg atcgggttac ctttgcgggt caaagttttg   3360
aaggcttaag tctctctact tttgctgcgg cgttagccga aaaggcgccc tcgcggcccg   3420
cgaccaccca ggggacccag gcgcccgtgt taggcatcga agctgcggaa cctaacgcgc   3480
ccttaactaa cgatgagatg acccgccaaa ttcaatcttt aattaccagt gataccacct   3540
taaccgcgga aaccggcgat tcctggttta atgcctcccg gatgcccatc cccggtggcg   3600
cccgcgttga gttagagatg cagtggggcc acattggctg gagtgtgccg tccgcgtttg   3660
gcaatgctgt gggctccccc gaacgccgtc atattatgat ggttggcgac ggtagttttc   3720
aattaaccgc ccaggaggtg gcccaaatga ttcggtacga aattcccgtt attatctttt   3780
tgattaataa tcggggctat gttattgaga ttgccattca cgatggtccg tataattata   3840
ttaagaattg gaattatgcc ggtttaattg atgtttttaa cgatgaagac ggccacggtt   3900
taggcttaaa ggcctccacc ggcgcggagt tggaaggtgc cattaaaaag gcgttggata   3960
accgccgggg ccccaccttta attgagtgca atattgccca agatgattgt accgaaactt   4020
taatcgcctg ggcaagcgc gtggcggcca ctaattcccg gaagccccag gcctgaaagt   4080
cctaagagcc cgcacggcgc aagcccgtgc gggctttttt gtggagctcg aattggccgc   4140
ggcgttgtga caatttaccg aacaactccg cggccgggaa gccgatctcg gcttgaacga   4200
attgttaggt ggcggtactt gggtcgatat caaagtgcat cacttcttcc cgtatgccca   4260
actttgtata gagagccact gcgggatcgt caccgtaatc tgcttgcacg tagatcacat   4320
aagcaccaag cgcgttggcc tcatgcttga ggagattgat gagcgcggtg gcaatgccct   4380
gcctccggtg ctcgccggag actgcgagat catagatata gatctcacta cgcggctgct   4440
caaacctggg cagaacgtaa gccgcgagag cgccaacaac cgcttcttgg tcgaaggcag   4500
```

-continued

```
caagcgcgat gaatgtctta ctacggagca agttcccgag gtaatcggag tccggctgat   4560
gttgggagta ggtggctacg tctccgaact cacgaccgaa aagatcaaga gcagcccgca   4620
tggatttgac ttggtcaggg ccgagcctac atgtgcgaat gatgcccata cttgagccac   4680
ctaactttgt tttagggcga ctgccctgct gcgtaacatc gttgctgctg cgtaacatcg   4740
ttgctgctcc ataacatcaa acatcgaccc acggcgtaac gcgcttgctg cttggatgcc   4800
cgaggcatag actgtacaaa aaaacagtca taacaagcca tgaaaaccgc cactgcgccg   4860
ttaccaccgc tgcgttcggt caaggttctg gaccagttgc gtgagcgcat acgctacttg   4920
cattacagtt tacgaaccga acaggcttat gtcaattcga gcatcgattg tatgggaagc   4980
ccgatgcgcc agagttgttt ctgaaacatg gcaaaggtag cgttgccaat gatgttacag   5040
atgagatggt cagactaaac tggctgacgg aatttatgcc tcttccgacc atcaagcatt   5100
ttatccgtac tcctgatgat gcatggttac tcaccactgc gatccccgcc ctgccttgaa   5160
cgagaaagag ttatgacaaa ttaaaattct gactcttaga ttatttccag agaggctgat   5220
tttcccaatc tttgggaaag cctaagtttt tagattctat ttctggatac atctcaaaag   5280
ttctttttaa atgctgtgca aaattatgct ctggtttaat tctgtctaag agatactgaa   5340
tacaacataa gccagtgaaa attttacggc tgtttctttg attaatatcc tccaatactt   5400
ctctagagag ccattttcct tttaacctat caggcaattt aggtgattct cctagctgta   5460
tattccagag ccttgaatga tgagcgcaaa tatttctaat atgcgacaaa gaccgtaacc   5520
aagatataaa aaacttgtta ggtaattgga aatgagtatg tattttttgt cgtgtcttag   5580
atggtaataa atttgtgtac attctagata actgcccaaa ggcgattatc tccaaactag   5640
tgatggcggc cgggagcatg cgacgtcggg cccaattcgc cctatagtga gtcgtattac   5700
aattcactgg ccgtcgtttt acaacgtcgt gactgggaaa accctggcgt tacccaactt   5760
aatcgccttg cagcacatcc ccctttcgcc agctggcgta atagcgaaga ggcccgcacc   5820
gatcgccctt cccaacagtt gcgcagcctg aatggcgaat ggacgcgccc tgtagcggcg   5880
cattaagcgc ggcgggtgtg gtggttacgc gcagcgtgac cgctacactt gccagcgccc   5940
tagcgcccgc tcctttcgct ttcttccctt cctttctcgc cacgttcgcc ggctttcccc   6000
gtcaagctct aaatcggggg ctccctttag ggttccgatt tagagcttta cggcacctcg   6060
accgcaaaaa acttgatttg ggtgatggtt cacgtagtgg gccatcgccc tgatagacgg   6120
tttttcgccc tttgacgttg gagtccacgt tctttaatag tggactcttg ttccaaactg   6180
gaacaacact caaccctatc tcggtctatt cttttgattt ataagggatt ttgccgattt   6240
cggcctattg gttaaaaaat gagctgattt aacaaatatt taacgcgaat tttaacaaaa   6300
tattaacgtt tacaatttcg cctgatgcgg tattttctcc ttacgcatct gtgcggtatt   6360
tcacaccgca tacaggtggc acttttcggg gaaatgtgcg cggaacccct atttgtttat   6420
ttttctaaat acattcaaat atgtatccgc tcatgagaca ataaccctga taaatgcttc   6480
aataatattg aaaaaggaag agtatgagta ttcaacattt ccgtgtcgcc cttattccct   6540
tttttgcggc attttgcctt cctgtttttg ctcacccaga aacgctggtg aaagtaaaag   6600
atgctgaaga tcagttgggt gcacgagtgg gttacatcga actggatctc aacagcggta   6660
agatccttga gagttttcgc cccgaagaac gttttccaat gatgagcact tttaaagttc   6720
tgctatgtgg cgcggtatta tcccgtattg acgccgggca agagcaactc ggtcgccgca   6780
tacactattc tcagaatgac ttggttgagt actcaccagt cacagaaaag catcttacgg   6840
atggcatgac agtaagagaa ttatgcagtg ctgccataac catgagtgat aacactgcgg   6900
```

ccaacttact tctgacaacg atcggaggac cgaaggagct aaccgctttt ttgcacaaca 6960
tgggggatca tgtaactcgc cttgatcgtt gggaaccgga gctgaatgaa gccataccaa 7020
acgacgagcg tgacaccacg atgcctgtag caatgccaac aacgttgcgc aaactattaa 7080
ctggcgaact acttactcta gcttcccggc aacaattaat agactggatg gaggcggata 7140
aagttgcagg accacttctg cgctcggccc ttccggctgg ctggtttatt gctgataaat 7200
ctggagccgg tgagcgtggg tctcgcggta tcattgcagc actggggcca gatggtaagc 7260
cctcccgtat cgtagttatc tacacgacgg ggagtcaggc aactatggat gaacgaaata 7320
gacagatcgc tgagataggt gcctcactga ttaagcattg gtaactgtca gaccaagttt 7380
actcatatat actttagatt gatttaaaac ttcattttta atttaaaagg atctaggtga 7440
agatcctttt tgataatctc atgaccaaaa tcccttaacg tgagttttcg ttccactgag 7500
cgtcagaccc cgtagaaaag atcaaaggat cttcttgaga tccttttttt ctgcgcgtaa 7560
tctgctgctt gcaaacaaaa aaaccaccgc taccagcggt ggtttgtttg ccggatcaag 7620
agctaccaac tctttttccg aaggtaactg gcttcagcag agcgcagata ccaaatactg 7680
tccttctagt gtagccgtag ttaggccacc acttcaagaa ctctgtagca ccgcctacat 7740
acctcgctct gctaatcctg ttaccagtgg ctgctgccag tggcgataag tcgtgtctta 7800
ccgggttgga ctcaagacga tagttaccgg ataaggcgca gcggtcgggc tgaacggggg 7860
gttcgtgcac acagcccagc ttggagcgaa cgacctacac cgaactgaga tacctacagc 7920
gtgagctatg agaaagcgcc acgcttcccg aagggagaaa ggcggacagg tatccggtaa 7980
gcggcagggt cggaacagga gagcgcacga gggagcttcc agggggaaac gcctggtatc 8040
tttatagtcc tgtcgggttt cgccacctct gacttgagcg tcgatttttg tgatgctcgt 8100
caggggggcg gagcctatgg aaaaacgcca gcaacgcggc ctttttacgg ttcctggcct 8160
tttgctggcc ttttgctcac atgttctttc ctgcgttatc ccctgattct gtggataacc 8220
gtattaccgc ctttgagtga gctgataccg ctcgccgcag ccgaacgacc gagcgcagcg 8280
agtcagtgag cgaggaagcg gaagagcgcc caatacgcaa accgcctctc cccgcgcgtt 8340
ggccgattca ttaatgcagc tggcacgaca ggtttcccga ctggaaagcg ggcagtgagc 8400
gcaacgcaat taatgtgagt tagctcactc attaggcacc ccaggcttta cactttatgc 8460
ttccggctcg tatgttgtgt ggaattgtga gcggataaca atttcacaca ggaaacagct 8520
atgaccatga ttacgccaag ctatttaggt gacactatag aatactcaag ctatgcatcc 8580
acaacttttt gggatgctga tggtaaaccc atttccgccc aagaatttat cgaaaagcta 8640
tttggcgacc tgcccgacct cttcaaggat gaagccgaac tacgcaccat ctgggggaaa 8700
cccgataccc gtaaatcgtt cctgaccgga ctcgcggaaa aaggctacgg tgacacccaa 8760
ctgaaggcga tcgcacgcat tgccgaagcg gaaaaaagtg atgtctatga tgtcctgact 8820
tgggttgcct acaacaccaa acccattagc agagaagagc gagtaattaa gcatcgagat 8880
ctgattttct cgaagtacac cggaaagcag caagaatttt tagattttgt cctagaccaa 8940
tacattcgag aaggagtgga ggaacttgat cgggggaaac tgcctaccct catcgaaatc 9000
aaataccaaa ccgttaatga aggtttagtg atcttgggtc aggatatcgg tcaagtattc 9060
gcagattttc aggcggattt atataccgaa gatgtggcat aaaaaaggac ggcgatcgcc 9120
gggggcgttg cctgccttga acgaggcata ctgggaagca tattcttcga tgcgcttaaa 9180
gttttgccgt ggtagtttag cttgatgctc ttccacgttg aaacctgcta agtagttaca 9240

-continued tacggctgac agcggcaaaa aatgtttgag tataaggcca tagttgatgc ttgttgg 9297

<210> SEQ ID NO 53
<211> LENGTH: 36
<212> TYPE: DNA
<213> ORGANISM: Artificial
<220> FEATURE:
<223> OTHER INFORMATION: Synthetically produced reverse primer PcorT*-EcoRI-rev for the amplification of the construct comprising the corR-PcorT promoter sequence from Synechocystis sp. PCC6803 incorporating an optimised ribosome binding site

<400> SEQUENCE: 53
gaattcatgc tttttatcct cgatttttac cttctc 36

<210> SEQ ID NO 54
<211> LENGTH: 27
<212> TYPE: DNA
<213> ORGANISM: Artificial
<220> FEATURE:
<223> OTHER INFORMATION: Synthetically produced reverse primer PnrsB*-EcoRI-rev for the amplification of the construct comprising the nrsRS-PnrsB promoter sequence from Synechocystis sp. PCC6803 incorporating an optimised ribosome binding site

<400> SEQUENCE: 54
gaattcatca cacctcctcc aattggg 27

<210> SEQ ID NO 55
<211> LENGTH: 1011
<212> TYPE: DNA
<213> ORGANISM: Synechocystis sp. PCC 6803

<400> SEQUENCE: 55
atgattaaag cctacgctgc cctggaagcc aacggaaaac tccaaccctt tgaatacgac 60
cccggtgccc tgggtgctaa tgaggtggag attgaggtgc agtattgtgg ggtgtgccac 120
agtgatttgt ccatgattaa taacgaatgg ggcatttcca attacccccct agtgccgggt 180 catgaggtgg tgggtactgt ggccgccatg ggcgaagggg tgaaccatgt tgaggtgggg 240
gatttagtgg ggctgggttg gcattcgggc tactgcatga cctgccatag ttgtttatct 300
ggctaccaca acctttgtgc cacggcggaa tcgaccattg tgggccacta cggtggcttt 360
ggcgatcggg ttcgggccaa gggagtcagc gtggtgaaat tacctaaagg cattgaccta 420
gccagtgccg ggcccctttt ctgtggagga attaccgttt tcagtcctat ggtggaactg 480
agtttaaagc ccactgcaaa agtggcagtg atcggcattg gggcttggg ccatttagcg 540 gtgcaatttc tccgggcctg ggctgtgaa gtgactgcct ttacctccag tgccaggaag 600
caaacggaag tgttggaatt gggcgctcac cacatactag attccaccaa tccagaggcg 660
atcgccagtg cggaaggcaa atttgactat attatctcca ctgtgaacct gaagcttgac 720
tggaacttat acatcagcac cctggcgccc cagggacatt tccactttgt tggggtggtg 780
ttggagcctt tggatctaaa tctttttccc cttttgatgg gacaacgctc cgtttctgcc 840
tccccagtgg gtagtcccgc caccattgcc accatgttgg actttgctgt gcgccatgac 900
attaaacccg tggtggaaca atttagcttt gatcagatca acgaggcgat cgcccatcta 960
gaaagcggca aagcccatta tcgggtagtg ctcagccata gtaaaaatta g 1011

<210> SEQ ID NO 56
<211> LENGTH: 1011
<212> TYPE: DNA
<213> ORGANISM: Artificial
<220> FEATURE:
<223> OTHER INFORMATION: Synthetically produced codon-degenerated SynADH gene (slr1192) from Synechocystis sp. PCC6803

<400> SEQUENCE: 56
atgatcaagg cttatgccgc tttagaggct aatggcaagt tgcagccgtt cgagtatgat 60
ccgggcgctt taggcgccaa cgaagttgaa atcgaagttc aatactgcgg tgtttgtcat 120
tccgacctca gtatgatcaa caatgagtgg ggtatcagta actatccgtt ggttcccggc 180
cacgaagttg ttggcaccgt tgctgctatg ggtgagggtg ttaatcacgt ggaagttggt 240
gacctggttg gtttaggctg gcacagtggt tattgtatga cttgtcactc ctgcctgagc 300
ggttatcata atttgtgcgc taccgccgag agtactatcg ttggtcatta tggcggtttc 360
ggtgaccgtg tgcgtgctaa aggtgtgtcc gttgttaagc tgcccaaggg tatcgatttg 420
gcttccgctg gtccgttgtt ttgcggtggt atcactgtgt tttcccccat ggttgagtta 480
tccctgaaac cgaccgccaa ggttgccgtt attggtatcg gtggtctcgg tcacctggcc 540
gttcagttct tgcgtgcttg ggttgcgag gttaccgctt tcactagctc cgctcgtaaa 600
cagaccgagg ttctggagct gggtgcccat catattttgg acagtactaa ccccgaagcc 660
attgcttccg ccgagggtaa gttcgattac atcattagta ccgttaattt aaaattggat 720
tggaatctgt atatttccac tttagccccg caaggtcact ttcatttcgt gggtgttgtt 780
ctcgaacccc tcgacttgaa cttgttcccg ttgctcatgg gtcagcggag tgtgtccgct 840
agtccggttg gctccccggc tactatcgct actatgctcg atttcgccgt tcggcacgat 900
atcaagccgg ttgttgagca gttctccttc gaccaaatta atgaagccat tgctcacttg 960
gagtccggta aggctcacta ccgtgtggtt ttgagtcact ccaagaactg a 1011

<210> SEQ ID NO 57
<211> LENGTH: 5232
<212> TYPE: DNA
<213> ORGANISM: Artificial
<220> FEATURE:
<223> OTHER INFORMATION: Synthetically produced ethanologenic gene cassette from plasmid #1356 pVZ325a-nrsRS-PnrsB*-ZpPDC-PrbcL*-synADH(deg) integrated via SalI/SbfI into pVZ325a

<400> SEQUENCE: 57
gtcgacccta tatcgggctt ttctcaataa aatctttatt ttttgaggtg ctttttagcc 60
ataaataatc actttagtat aaaattttga cggcgtaaag ttgataaaat agaattaaga 120
atggactatc ggtacagaaa aaatgggtaa ctggatggtg aataaacttc ccttacccaa 180
tgcactctcc accgttaaag accccctatg cttaacggtg atcacctggg caatggcgag 240
tcccaaccct gtcccccccg ttttgcgcga acgatctcga ttaactcggt aaaaacgctc 300
aaaaatgtgt tcctgttggt cgggggcaat gccgatgccg gtatcttgca cggtgatgat 360
agccatctgt tcatgggatg tcagggtaat atcaacacgt cccccagcag ttgtgtattg 420
aatggcgttg gcaattaggt ttgagaccag tcgatagagt tgggattcat taccccaggc 480
gtaaacttcc cctgaactca gatcactgct gagatcaatg tgggcggcga tcgctaattc 540
taaaaactct tcggtgaggt cactgactaa atcatttaaa caacaaagcc gccaatcttc 600
ggcggtggtt tcctgctcta agcgacttag tagcaataaa tccgtaatca attggcttaa 660
tcgccttccc tgtcgttcaa cggtatgtag catggtgtta atttctgggg aatggcttga 720
gtcgatgcgt aataccgctt ccaccgtggc caacagacta gccaatggcg atcgtaattc 780
atgggctgca ttcgcggtga attgttgttg ttgttggtag gactggtaaa tgggacgcat 840
ggctaacccc gctaagcccc aactggagaa ggcgaccaaa cccagggcaa tgggaaaact 900
aagccctaaa atccaaagaa tacgtttatt ttcggcatca aaggctgcca ggctccggcc 960
aatttgtaga tagccccagg aagatttgtc tgtattaccg gcgctatgca aaatggtggt 1020
gaattgtcga taccgatcgc cggttggggg gtgaatagtc tgccaagttt cctggttaaa 1080
aatggaggat agggaagccg gttgattagg cgaaaaagcc agcaggttgc cttgataatc 1140
aaataaacga atgtaatata aactgcgatc actaatgccc aacgtgtgac gttcaatcag 1200
ggtggggttg acctggcagg gttggttgac caaacacaga tcgggcaaca ttttttgtaa 1260
tactccggtg ggactagcat tactcggcaa catcggctct aaactgtcat gcaacgtccc 1320
ggcgatcgac tccacttctc gctccaacgc catccagttg gcctgcacaa tggcacgata 1380
aacccccaac cccaacaggg taagaatacc ccccattact agggcatacc agaaagccaa 1440
ttgcagacga ctacgggcaa agaggcgacg ggtattcatg gcgatagggt gaaccgatag 1500
ccttgaccgg gaactgtttt aattgggcaa ggacaatttt gttgagctag cttgcgtcgt 1560
atcaaacgca tttgggccgc caccacatta ctcatgggct cctcatcaag atcccacagt 1620
tgttgccgga tcttgctacc ggaaatgatc cgctctgggt tttgcatcag atattgaaaa 1680
atttgaaatt ctcttacggt taaagcaatt tcctgtcttt ctaggtttag tggctccgag 1740
atagttaccg ataacagatt attactggga tcaaggctga agttgcccaa agttaaaatt 1800
tgcggttgga attgtggcga tcgccgttgt agtgcccgca gtcttgctaa tagctctgcc 1860
atcacaaacg gttttgttag atagtcatct gccccggcat ctagtccttc gacacggttt 1920
tccggttctc ctaacgctgt taacatcaac accggcaagg aattaccctg ggttctcagt 1980
ttttgacaga gttccaaacc cgataatccc ggcagtaacc aatccacaat ggcaagggtg 2040
tattccgtcc attgattttc caaataatcc caagcttggg agccatccgt cacccaatcc 2100
accacatact tttcactaac tagcactttc ttaatagcca ttcccaaatc cgtctcatct 2160
tccaccagca aaattcgcat cgcctctgcc tttttttataa cggtctgatc ttagcggggg 2220
aaggagattt tcacctgaat ttcatacccc ctttggcaga ctgggaaaat cttggacaaa 2280
ttcccaattg gaggaggtgt gatgaattcc tataccgttg gtatgtactt ggcagaacgc 2340
ctagcccaga tcggcctgaa acaccacttt gccgtggccg gtgactacaa cctggtgttg 2400
cttgatcagc tcctgctgaa caaagacatg gagcaggtct actgctgtaa cgaacttaac 2460
tgcggcttta gcgccgaagg ttacgctcgt gcacgtggtg ccgccgctgc catcgtcacg 2520
ttcagcgtag gtgctatctc tgcaatgaac gccatcggtg gcgcctatgc agaaaacctg 2580
ccggtcatcc tgatctctgg ctcaccgaac accaatgact acggcacagg ccacatcctg 2640
caccacacca ttggtactac tgactataac tatcagctgg aaatggtaaa acacgttacc 2700
tgcgcacgtg aaagcatcgt ttctgccgaa gaagcaccgg caaaaatcga ccacgtcatc 2760
cgtacggctc tacgtgaacg caaaccggct tatctggaaa tcgcatgcaa cgtcgctggc 2820
gctgaatgtg ttcgtccggg cccgatcaat agcctgctgc gtgaactcga agttgaccag 2880
accagtgtca ctgccgctgt agatgccgcc gtagaatggc tgcaggaccg ccagaacgtc 2940
gtcatgctgg tcggtagcaa actgcgtgcc gctgccgctg aaaaacaggc tgttgcccta 3000
gcggaccgcc tgggctgcgc tgtcacgatc atggctgccg aaaaaggctt cttcccggaa 3060
gatcatccga acttccgcgg cctgtactgg ggtgaagtca gctccgaagg tgcacaggaa 3120
ctggttgaaa acgccgatgc catcctgtgt ctggcaccgg tattcaacga ctatgctacc 3180

-continued gttggctgga actcctggcc gaaaggcgac aatgtcatgg tcatggacac cgaccgcgtc 3240
actttcgcag gacagtcctt cgaaggtctg tcattgagca ccttcgccgc agcactggct 3300
gagaaagcac cttctcgccc ggcaacgact caaggcactc aagcaccggt actgggtatt 3360
gaggccgcag agcccaatgc accgctgacc aatgacgaaa tgacgcgtca gatccagtcg 3420
ctgatcactt ccgacactac tctgacagca gaaacaggtg actcttggtt caacgcttct 3480
cgcatgccga ttcctggcgg tgctcgtgtc gaactggaaa tgcaatgggg tcatatcggt 3540
tggtccgtac cttctgcatt cggtaacgcc gttggttctc cggagcgtcg ccacatcatg 3600
atggtcggtg atggctcttt ccagctgact gctcaagaag ttgctcagat gatccgctat 3660
gaaatcccgg tcatcatctt cctgatcaac aaccgcggtt acgtcatcga aatcgctatc 3720
catgacggcc cttacaacta catcaaaaac tggaactacg ctggcctgat cgacgtcttc 3780
aatgacgaag atggtcatgg cctgggtctg aaagcttcta ctggtgcaga actagaaggc 3840
gctatcaaga aagcactcga caatcgtcgc ggtccgacgc tgatcgaatg taacatcgct 3900
caggacgact gcactgaaac cctgattgct tggggtaaac gtgtagcagc taccaactct 3960
cgcaaaccac aagcgtaagt tgatgtagtg aattaggcgg ggcctattag ggccccacca 4020
catagcccct cttacggcgc aatacccgta agaggggctg ttttatataa ttaaaactag 4080
taacgcccgg ttgccaccgg gcgtttttta ttccgacatt gccataagta aaggcatccc 4140
ctgcgtgata agattacctt cagtttatgg aggactgacc atatgatcaa ggcttatgcc 4200
gctttagagg ctaatggcaa gttgcagccg ttcgagtatg atccgggcgc tttaggcgcc 4260
aacgaagttg aaatcgaagt tcaatactgc ggtgtttgtc attccgacct cagtatgatc 4320
aacaatgagt ggggtatcag taactatccg ttggttcccg gccacgaagt tgttggcacc 4380
gttgctgcta tgggtgaggg tgttaatcac gtggaagttg gtgacctggt tggtttaggc 4440
tggcacagtg gttattgtat gacttgtcac tcctgcctga gcggttatca taatttgtgc 4500
gctaccgccg agagtactat cgttggtcat tatggcggtt tcggtgaccg tgtgcgtgct 4560
aaaggtgtgt ccgttgttaa gctgcccaag ggtatcgatt tggcttccgc tggtccgttg 4620
ttttgcggtg gtatcactgt gttttccccc atggttgagt tatccctgaa accgaccgcc 4680
aaggttgccg ttattggtat cggtggtctc ggtcacctgg ccgttcagtt cttgcgtgct 4740
tggggttgcg aggttaccgc tttcactagc tccgctcgta aacagaccga ggttctggag 4800
ctgggtgccc atcatatttt ggacagtact aaccccgaag ccattgcttc cgccgagggt 4860
aagttcgatt acatcattag taccgttaat ttaaaattgg attggaatct gtatatttcc 4920
actttagccc cgcaaggtca ctttcatttc gtgggtgttg ttctcgaacc cctcgacttg 4980
aacttgttcc cgttgctcat gggtcagcgg agtgtgtccg ctagtccggt tggctccccg 5040
gctactatcg ctactatgct cgatttcgcc gttcggcacg atatcaagcc ggttgttgag 5100
cagttctcct tcgaccaaat taatgaagcc attgctcact tggagtccgg taaggctcac 5160
taccgtgtgg ttttgagtca ctccaagaac tgaaacgctc ggttgccgcc gggcgttttt 5220
tattcctgca gg 5232

<210> SEQ ID NO 58
<211> LENGTH: 1710
<212> TYPE: DNA
<213> ORGANISM: Artificial
<220> FEATURE:
<223> OTHER INFORMATION: Synthetically produced full codon-optimized Pdc
gene from Zymomonas mobilis (ZmPDCfco)

<400> SEQUENCE: 58
atgaattcct ataccgtggg tacctatttg gccgaacggt tggtgcaaat tggtttgaaa 60
caccactttg ccgtggccgg tgactacaac ttggtgttgt tggacaactt gttgttgaac 120
aaaaacatgg aacaagtgta ttgttgtaac gaattgaact gtggtttttc cgccgaaggt 180
tatgctcggg ccaaaggtgc cgccgccgcc gtggtgacct actccgtggg tgccttgtcc 240
gcctttgatg ctattggtgg tgcctatgcc gaaaacttgc ccgtgatttt gatttccggt 300
gctcccaaca acaatgatca cgctgctggt cacgtgttgc accacgcttt gggtaaaacc 360
gactatcact atcaattgga aatggccaaa aacattaccg ccgccgctga agccatttac 420
acccccgaag aagctcccgc taaaattgat cacgtgatta aaaccgcttt gcgggaaaaa 480
aaacccgtgt atttggaaat tgcttgtaac attgcttcca tgccctgtgc cgctcccggt 540
cccgcctccg ccttgtttaa tgacgaagcc tccgacgaag cttccttgaa tgccgccgtg 600
gaagaaacct tgaaatttat tgccaaccgg gacaaagtgg ccgtgttggt gggttccaaa 660
ttgcgggccg ctggtgctga agaagctgct gtgaaatttg ctgatgcttt gggtggtgcc 720
gtggctacca tggctgctgc caaatccttt tttcccgaag aaaacccccca ctacattggt 780 acctcctggg gtgaagtgtc ctatcccggt gtggaaaaaa ccatgaaaga agccgatgcc 840
gtgattgctt tggctcccgt gtttaacgac tactccacca ccggttggac cgatattccc 900
gatcccaaaa aattggtgtt ggctgaaccc cggtccgtgg tggtgaacgg tgtgcggttt 960
ccctccgtgc acttgaaaga ctatttgacc cggttggctc aaaaagtgtc caaaaaaacc 1020
ggtgctttgg actttttttaa atccttgaat gccggtgaat tgaaaaaagc cgctcccgct 1080
gatccctccg ctcccttggt gaacgccgaa attgcccggc aagtggaagc tttgttgacc 1140
cccaacacca ccgtgattgc tgaaaccggt gactcctggt ttaatgctca acggatgaaa 1200
ttgcccaacg gtgctcgggt ggaatatgaa atgcaatggg gtcacattgg ttggtccgtg 1260
cccgccgcct ttggttatgc cgtgggtgct cccgaacggc ggaacatttt gatggtgggt 1320
gatggttcct ttcaattgac cgctcaagaa gtggctcaaa tggtgcggtt gaaattgccc 1380
gtgattattt ttttgattaa taactatggt tacaccattg aagtgatgat tcacgatggt 1440
ccctacaaca acattaaaaa ctgggattat gccggtttga tggaagtgtt taacggtaac 1500
ggtggttatg actccggtgc tggtaaaggt ttgaaagcta aaaccggtgg tgaattggcc 1560
gaagctatta aagtggcttt ggccaacacc gacggtccca ccttgattga atgttttatt 1620
ggtcgggaag actgtaccga agaattggtg aaatggggta aacgggtggc tgccgccaac 1680
tcccggaaac ccgtgaacaa attgttgtag 1710

<210> SEQ ID NO 59
<211> LENGTH: 27
<212> TYPE: DNA
<213> ORGANISM: Artificial
<220> FEATURE:
<223> OTHER INFORMATION: Synthetically produced forward primer pSYSG-P1-XbaI-fw for amplification of engineered pSYSG-P1 from Synechocystis sp. PCC6803 including XbaI restriction site

<400> SEQUENCE: 59
tctagacata agcaaagctc aagcacg 27

<210> SEQ ID NO 60
<211> LENGTH: 29
<212> TYPE: DNA
<213> ORGANISM: Artificial

<220> FEATURE:
<223> OTHER INFORMATION: Synthetically produced reverse primer pSYSG-P1-XmaI-rev for amplification of engineered pSYSG-P1 from Synechocystis sp. PCC6803 including XmaI restriction site

<400> SEQUENCE: 60
cccgggtctt gccagaagat ttactctag 29

<210> SEQ ID NO 61
<211> LENGTH: 1198
<212> TYPE: DNA
<213> ORGANISM: Artificial
<220> FEATURE:
<223> OTHER INFORMATION: Engineered flanking region pSYSG-P1 of Synechocystis sp. PCC6803 for pSYSG integration via homologous recombination

<400> SEQUENCE: 61
tctagacata agcaaagctc aagcacgctc cgctacttcg gaagcagccg aagaaacctt 60
gcaacgacaa cagatgaagg aaggactggt gcccctggac aaaatcggcg atcggccaga 120
gggagatacc cgtcaaatta acgctaagca tgtcaaagag ttagtggaaa gtattcaagt 180
cctgggactg attaccccgt taacagtgga cagacactac aggctattag ccggaggaca 240
tcgtaaagca gccctagaga aattagcggc agaatcccca gaaacattta cggcattctt 300
tggcgaagga gtgccggtga acattatgga cattgatgca gaaacagcaa ccctcacggc 360
attacaagtt gaagttgaag aaaataccca acgcaaaaac tacacccccta gtgaaattcg 420 agaagcggcc cgtaagctaa aggaggctgg ctatgaaaag cttaaaggtc gccccagcaa 480
aggacaaaag tctatcaacc gagagttaat gtctgtattt ggggcaagtc gtagatatat 540
caccaaaatc ctcaatgacc cagaagatga acagcagaag cagaaaagtg cgcacatgtg 600
cgcacttttt tctaaaatta agcgatatca cgagcaaacg gaagctttta aagattacat 660
cagtaaaaat tcgcccaaag atgctataaa tccagaatta aacgtaatca gactaagcct 720
aatagagaag cttaaggaaa cccaagcact gttggaaggg ctccacatcg ttgagcagtt 780
acagactaag gcgacaagcc catccatagc tggggagaac cactcaacac aagaggaaaa 840
attggaagtt taaacataac ccaggtccag agagacaaag aacagaacag ggttgggaag 900
aactcagccc ttaatagttt cacgaattgg ttatgccaat tcttcaaact atgagcgaca 960
ttctcgacag aaaattcatc aacttagaga ccactaggtc taccctcaag cagaagatcc 1020
ttcgagatag ggcaaggggt ttagactttg gctactacga gctatccgtt agaccgctat 1080
acatcaaagc atggcatctc tactgctcgt tcttcatcat gcactcagag atggaaaagt 1140
acagttacac agacaggtcc agggtagaac tagagtaaat cttctggcaa gacccggg 1198

<210> SEQ ID NO 62
<211> LENGTH: 28
<212> TYPE: DNA
<213> ORGANISM: Artificial
<220> FEATURE:
<223> OTHER INFORMATION: Synthetically produced forward primer pSYSG-P2-XhoI-fw for amplification of engineered pSYSG-P2 from Synechocystis sp. PCC6803 including XhoI restriction site

<400> SEQUENCE: 62
ctcgagtatt ctacggggca ccctactc 28

<210> SEQ ID NO 63
<211> LENGTH: 28
<212> TYPE: DNA

<213> ORGANISM: Artificial
<220> FEATURE:
<223> OTHER INFORMATION: Synthetically produced reverse primer pSYSG-P2-NotI-fw for amplification of engineered pSYSG-P2 from Synechocystis sp. PCC6803 including NotI restriction site

<400> SEQUENCE: 63
gcggccgctc cgtagttgct cttacacc 28

<210> SEQ ID NO 64
<211> LENGTH: 1372
<212> TYPE: DNA
<213> ORGANISM: Artificial
<220> FEATURE:
<223> OTHER INFORMATION: Engineered flanking region pSYSG-P2 of Synechocystis sp. PCC6803 for pSYSG integration via homologous recombination

<400> SEQUENCE: 64
ctcgagtatt ctacggggca ccctactcat ggttagtcat caaagatgaa gacaagtttg 60
agaactggaa ggaactaaac agtgacgcga caaagcagcg aattccaaca agcatcaact 120
atggccttat actcaaacat tttttgccgc tgtcagccgt atgtaactac ttagcaggtt 180
tcaacgtgga agagcatcaa gctaaactac cacggcaaaa ctttaagcgc atcgaagaat 240
atgcttccca gtatgtgcac gtcaacatga aagacccgac cctaacgata gaaaaagtta 300
gagaaatggt ctctgacata gagatgcaga tgtgaacatc acaacaagct gggtagagac 360
tgagcaatcc atctatcaca gcgttgacag aaacaacaga aggtcaagac gaggtatcag 420
aggaggagaa tgagtcatgg aagacctttg acttctccac taattcagca cctaaagaaa 480
gactcacaag ctgggactga aaatctttta aagccagact cacagcttgc tctagggcag 540
cggcaacttc agaggaagac tgatagcagt ggggggcgga aaagtaagaa ggtagatccc 600
ggaacaaacg aatggaagag gacaaaacct tgtcaatttc tgagataaca agatcgatgg 660
gaactacctg cttaacctta ctctgcattt gtaactcaac aagagaagct tcggcgagag 720
acttcctcgc acgaccttca cgccacttgg tatcccagtc agaacgagca actttagcct 780
tatgttcatc cagatcctgc cgcaggctgc gagtgtacca acggtagtaa ccaaggatgt 840
cataggcgtt ggagccttgc ttagagaagt aaccagcctt agcccaggtc tggacagtgc 900
gaacgctcac accggcttcc tgggccaatt ctgtcacaga aacaaataaa gaaggggtag 960
aggacatagg agcaaagggg gggcactacc aggaagcata cccagagaag aaggaaagtt 1020
aaggaacgac gacgaagacc aagcaacagc aaaatcacac aaacaagaga gcaacctaag 1080
tcccgataga gaccacaaac gtcacatctg tagtggatta ctgacaaacc aaggataatg 1140
aggctctggg cgcagcctta agcatggcag ggacaagagt gggtttgtcg gggcatagtt 1200
cccccactgt gggacagcac taaccccagc aaggtaagga aaagaagaat aacccttcca 1260
tcgcggacat aaaaatccga gggggtcaag ctccggctcc aacgaaaagt aagcagggac 1320
atacgggcca tacctagagt gattggtgta agagcaacta cggagcggcc gc 1372

<210> SEQ ID NO 65
<211> LENGTH: 8899
<212> TYPE: DNA
<213> ORGANISM: Artificial
<220> FEATURE:
<223> OTHER INFORMATION: Synthetically produced plasmid TK162 pGEM-AQ3::smtB-PsmtA-zmPDC_oop-PrbcL-synADHdeg_oop for transformation of Synechococcus sp. PCC7002 via integration into the endogenous pAQ3 plasmid

<400> SEQUENCE: 65
aattcttata ctgtcggtac ctatttagcg gagcggcttg tccagattgg tctcaagcat 60
cacttcgcag tcgcgggcga ctacaacctc gtccttcttg acaacctgct tttgaacaaa 120
aacatggagc aggtttattg ctgtaacgaa ctgaactgcg gtttcagtgc agaaggttat 180
gctcgtgcca aaggcgcagc agcagccgtc gttacctaca gcgtcggtgc gctttccgca 240
tttgatgcta tcggtggcgc ctatgcagaa aaccttccgg ttatcctgat ctccggtgct 300
ccgaacaaca atgatcacgc tgctggtcac gtgttgcatc acgctcttgg caaaaccgac 360
tatcactatc agttggaaat ggccaagaac atcacggccg cagctgaagc gatttacacc 420
ccagaagaag ctccggctaa aatcgatcac gtgattaaaa ctgctcttcg tgagaagaag 480
ccggtttatc tcgaaatcgc ttgcaacatt gcttccatgc cctgcgccgc tcctggaccg 540
gcaagcgcat tgttcaatga cgaagccagc gacgaagctt ctttgaatgc agcggttgaa 600
gaaaccctga aattcatcgc caaccgcgac aaagttgccg tcctcgtcgg cagcaagctg 660
cgcgcagctg gtgctgaaga agctgctgtc aaatttgctg atgctctcgg tggcgcagtt 720
gctaccatgg ctgctgcaaa aagcttcttc ccagaagaaa acccgcatta catcggtacc 780
tcatggggtg aagtcagcta tccgggcgtt gaaaagacga tgaaagaagc cgatgcggtt 840
atcgctctgg ctcctgtctt caacgactac tccaccactg gttggacgga tattcctgat 900
cctaagaaac tggttctcgc tgaaccgcgt tctgtcgtcg ttaacggcgt tcgcttcccc 960
agcgttcatc tgaaagacta tctgacccgt ttggctcaga aagtttccaa gaaaaccggt 1020
gctttggact tcttcaaatc cctcaatgca ggtgaactga agaaagccgc tccggctgat 1080
ccgagtgctc cgttggtcaa cgcagaaatc gcccgtcagg tcgaagctct tctgaccccg 1140
aacacgacgg ttattgctga aaccggtgac tcttggttca atgctcagcg catgaagctc 1200
ccgaacggtg ctcgcgttga atatgaaatg cagtggggtc acatcggttg gtccgttcct 1260
gccgccttcg gttatgccgt cggtgctccg gaacgtcgca acatcctcat ggttggtgat 1320
ggttccttcc agctgacggc tcaggaagtc gctcagatgg ttcgcctgaa actgccggtt 1380
atcatcttct tgatcaataa ctatggttac accatcgaag ttatgatcca tgatggtccg 1440
tacaacaaca tcaagaactg ggattatgcc ggtctgatgg aagtgttcaa cggtaacggt 1500
ggttatgaca gcggtgctgg taaaggcctg aaggctaaaa ccggtggcga actggcagaa 1560
gctatcaagg ttgctctggc aaacaccgac ggcccaaccc tgatcgaatg cttcatcggt 1620
cgtgaagact gcactgaaga attggtcaaa tggggtaagc gcgttgctgc cgccaacagc 1680
cgtaagcctg ttaacaagct cctctagttt ttggggatca attcgagctc ggtacccaaa 1740
ctagtaacgc tcggttgccg ccgggcgttt tttattccga catcaggaat tgtaattaga 1800
aagtccaaaa attgtaattt aaaaaacagt caatggagag cattgccata agtaaaggca 1860
tcccctgcgt gataagatta ccttcagaaa acagatagtt gctgggttat cgcagatttt 1920
tctcgcaacc aaataactgt aaataataac tgtctctggg gcgacggtag gctttatatt 1980
gccaaatttc gcccgtggga gaaagctagg ctattcaatg tttatggagg actgacccat 2040
atgatcaagg cttatgccgc tttagaggct aatggcaagt tgcagccgtt cgagtatgat 2100
ccgggcgctt taggcgccaa cgaagttgaa atcgaagttc aatactgcgg tgtttgtcat 2160
tccgacctca gtatgatcaa caatgagtgg ggtatcagta actatccgtt ggttcccggc 2220
cacgaagttg ttggcaccgt tgctgctatg ggtgagggtg ttaatcacgt ggaagttggt 2280
gacctggttg gtttaggctg gcacagtggt tattgtatga cttgtcactc ctgcctgagc 2340

-continued

```
ggttatcata atttgtgcgc taccgccgag agtactatcg ttggtcatta tggcggtttc   2400
ggtgaccgtg tgcgtgctaa aggtgtgtcc gttgttaagc tgcccaaggg tatcgatttg   2460
gcttccgctg gtccgttgtt ttgcggtggt atcactgtgt tttcccccat ggttgagtta   2520
tccctgaaac cgaccgccaa ggttgccgtt attggtatcg gtggtctcgg tcacctggcc   2580
gttcagttct tgcgtgcttg ggttgcgag gttaccgctt tcactagctc cgctcgtaaa   2640
cagaccgagg ttctggagct gggtgcccat catattttgg acagtactaa ccccgaagcc   2700
attgcttccg ccgagggtaa gttcgattac atcattagta ccgttaattt aaaattggat   2760
tggaatctgt atatttccac tttagccccg caaggtcact ttcatttcgt gggtgttgtt   2820
ctcgaacccc tcgacttgaa cttgttcccg ttgctcatgg gtcagcggag tgtgtccgct   2880
agtccggttg gctccccggc tactatcgct actatgctcg atttcgccgt tcggcacgat   2940
atcaagccgg ttgttgagca gttctccttc gaccaaatta atgaagccat tgctcacttg   3000
gagtccggta aggctcacta ccgtgtggtt ttgagtcact ccaagaactg aaacgctcgg   3060
ttgccgccgg gcgtttttta ttcctgcagc cttgctctag aagaacagca aggccgccaa   3120
tgcctgacga tgcgtggaga ccgaaacctt gcgctcgttc gccagccagg acagaaatgc   3180
ctcgacttcg ctgctgccca aggttgccgg gtgacgcaca ccgtggaaac ggatgaaggc   3240
acgaacccag tggacataag cctgttcggt tcgtaagctg taatgcaagt agcgtatgcg   3300
ctcacgcaac tggtccagaa ccttgaccga acgcagcggt ggtaacggcg cagtggcggt   3360
tttcatggct tgttatgact gtttttttgg ggtacagtct atgcctcggg catccaagca   3420
gcaagcgcgt tacgccgtgg gtcgatgttt gatgttatgg agcagcaacg atgttacgca   3480
gcagggcagt cgccctaaaa caaagttaaa catcatgagg gaagcggtga tcgccgaagt   3540
atcgactcaa ctatcagagg tagttggcgt catcgagcgc catctcgaac cgacgttgct   3600
ggccgtacat ttgtacggct ccgcagtgga tggcggcctg aagccacaca gtgatattga   3660
tttgctggtt acggtgaccg taaggcttga tgaaacaacg cggcgagctt tgatcaacga   3720
ccttttggaa acttcggctt cccctggaga gagcgagatt ctccgcgctg tagaagtcac   3780
cattgttgtg cacgacgaca tcattccgtg gcgttatcca gctaagcgcg aactgcaatt   3840
tggagaatgg cagcgcaatg acattcttgc aggtatcttc gagccagcca cgatcgacat   3900
tgatctggct atcttgctga caaaagcaag agaacatagc gttgccttgg taggtccagc   3960
ggcggaggaa ctctttgatc cggttcctga acaggatcta tttgaggcgc taaatgaaac   4020
cttaacgcta tggaactcgc cgcccgactg ggctggcgat gagcgaaatg tagtgcttac   4080
gttgtcccgc atttggtaca gcgcagtaac cggcaaaatc gcgccgaagg atgtcgctgc   4140
cgactgggca atggagcgcc tgccggccca gtatcagccc gtcatacttg aagctagaca   4200
ggcttatctt ggacaagaag aagatcgctt ggcctcgcgc gcagatcagt tggaagaatt   4260
tgtccactac gtgaaaggcg agatcaccaa ggtagtcggc aaataatgtc taacaattcg   4320
ttcaagccga cgccgcttcg cggcgcggct taactcaagc gttagatgca ctaccggtat   4380
ctttctagaa gatctcctac aatgccctgc cttgaacgag aaagagttat gacaaattaa   4440
aattctgact cttagattat ttccagagag gctgattttc ccaatctttg ggaaagccta   4500
agtttttaga ttctatttct ggatacatct caaaagttct ttttaaatgc tgtgcaaaat   4560
tatgctctgg tttaattctg tctaagagat actgaataca acataagcca gtgaaaattt   4620
tacggctgtt tctttgatta atatcctcca atacttctct agagagccat tttcctttta   4680
```

-continued

```
acctatcagg caatttaggt gattctccta gctgtatatt ccagagcctt gaatgatgag   4740
cgcaaatatt tctaatatgc gacaaagacc gtaaccaaga tataaaaaac ttgttaggta   4800
attggaaatg agtatgtatt ttttgtcgtg tcttagatgg taataaattt gtgtacattc   4860
tagataactg cccaaaggcg attatctcca aactagtgat ggcggccggg agcatgcgac   4920
gtcgggccca attcgcccta tagtgagtcg tattacaatt cactggccgt cgttttacaa   4980
cgtcgtgact gggaaaaccc tggcgttacc caacttaatc gccttgcagc acatccccct   5040
ttcgccagct ggcgtaatag cgaagaggcc cgcaccgatc gcccttccca acagttgcgc   5100
agcctgaatg gcgaatggac gcgccctgta gcggcgcatt aagcgcggcg ggtgtggtgg   5160
ttacgcgcag cgtgaccgct acacttgcca gcgccctagc gcccgctcct ttcgctttct   5220
tcccttcctt tctcgccacg ttcgccggct ttccccgtca agctctaaat cgggggctcc   5280
ctttagggtt ccgatttaga gctttacggc acctcgaccg caaaaaactt gatttgggtg   5340
atggttcacg tagtgggcca tcgccctgat agacggtttt tcgccctttg acgttggagt   5400
ccacgttctt taatagtgga ctcttgttcc aaactggaac aacactcaac cctatctcgg   5460
tctattcttt tgatttataa gggattttgc cgatttcggc ctattggtta aaaaatgagc   5520
tgatttaaca aatatttaac gcgaatttta acaaaatatt aacgtttaca atttcgcctg   5580
atgcggtatt ttctccttac gcatctgtgc ggtatttcac accgcataca ggtggcactt   5640
ttcggggaaa tgtgcgcgga acccctattt gtttattttt ctaaatacat tcaaatatgt   5700
atccgctcat gagacaataa ccctgataaa tgcttcaata atattgaaaa aggaagagta   5760
tgagtattca acatttccgt gtcgccctta ttcccttttt tgcggcattt tgccttcctg   5820
tttttgctca cccagaaacg ctggtgaaag taaaagatgc tgaagatcag ttgggtgcac   5880
gagtgggtta catcgaactg gatctcaaca gcggtaagat ccttgagagt tttcgccccg   5940
aagaacgttt tccaatgatg agcactttta aagttctgct atgtggcgcg gtattatccc   6000
gtattgacgc cgggcaagag caactcggtc gccgcataca ctattctcag aatgacttgg   6060
ttgagtactc accagtcaca gaaaagcatc ttacggatgg catgacagta agagaattat   6120
gcagtgctgc cataaccatg agtgataaca ctgcggccaa cttacttctg acaacgatcg   6180
gaggaccgaa ggagctaacc gcttttttgc acaacatggg ggatcatgta actcgccttg   6240
atcgttggga accggagctg aatgaagcca taccaaacga cgagcgtgac accacgatgc   6300
ctgtagcaat gccaacaacg ttgcgcaaac tattaactgg cgaactactt actctagctt   6360
cccggcaaca attaatagac tggatggagg cggataaagt tgcaggacca cttctgcgct   6420
cggcccttcc ggctggctgg tttattgctg ataaatctgg agccggtgag cgtgggtctc   6480
gcggtatcat tgcagcactg gggccagatg gtaagccctc ccgtatcgta gttatctaca   6540
cgacggggag tcaggcaact atggatgaac gaaatagaca gatcgctgag ataggtgcct   6600
cactgattaa gcattggtaa ctgtcagacc aagtttactc atatatactt tagattgatt   6660
taaaacttca tttttaattt aaaaggatct aggtgaagat cctttttgat aatctcatga   6720
ccaaaatccc ttaacgtgag ttttcgttcc actgagcgtc agaccccgta gaaaagatca   6780
aaggatcttc ttgagatcct ttttttctgc gcgtaatctg ctgcttgcaa acaaaaaaac   6840
caccgctacc agcggtggtt tgtttgccgg atcaagagct accaactctt tttccgaagg   6900
taactggctt cagcagagcg cagataccaa atactgtcct tctagtgtag ccgtagttag   6960
gccaccactt caagaactct gtagcaccgc ctacatacct cgctctgcta atcctgttac   7020
cagtggctgc tgccagtggc gataagtcgt gtcttaccgg gttggactca agacgatagt   7080
```

tacccggataa ggcgcagcgg tcgggctgaa cggggggttc gtgcacacag cccagcttgg 7140
agcgaacgac ctacaccgaa ctgagatacc tacagcgtga gctatgagaa agcgccacgc 7200
ttcccgaagg gagaaaggcg gacaggtatc cggtaagcgg cagggtcgga acaggagagc 7260
gcacgaggga gcttccaggg ggaaacgcct ggtatcttta tagtcctgtc gggtttcgcc 7320
acctctgact tgagcgtcga tttttgtgat gctcgtcagg ggggcggagc ctatggaaaa 7380
acgccagcaa cgcggccttt ttacggttcc tggccttttg ctggcctttt gctcacatgt 7440
tctttcctgc gttatcccct gattctgtgg ataaccgtat taccgccttt gagtgagctg 7500
ataccgctcg ccgcagccga acgaccgagc gcagcgagtc agtgagcgag gaagcggaag 7560
agcgcccaat acgcaaaccg cctctccccg cgcgttggcc gattcattaa tgcagctggc 7620
acgacaggtt tcccgactgg aaagcgggca gtgagcgcaa cgcaattaat gtgagttagc 7680
tcactcatta ggcaccccag gctttacact ttatgcttcc ggctcgtatg ttgtgtggaa 7740
ttgtgagcgg ataacaattt cacacaggaa acagctatga ccatgattac gccaagctat 7800
ttaggtgaca ctatagaata ctcaagctat gcatccacaa ctttttggga tgctgatggt 7860
aaacccattt ccgcccaaga atttatcgaa aagctatttg gcgacctgcc cgacctcttc 7920
aaggatgaag ccgaactacg caccatctgg gggaaacccg atacccgtaa atcgttcctg 7980
accggactcg cggaaaaagg ctacggtgac acccaactga aggcgatcgc acgcattgcc 8040
gaagcggaaa aaagtgatgt ctatgatgtc ctgacttggg ttgcctacaa caccaaaccc 8100
attagcagag aagagcgagt aattaagcat cgagatctga ttttctcgaa gtacaccgga 8160
aagcagcaag aatttttaga ttttgtccta gaccaataca ttcgagaagg agtggaggaa 8220
cttgatcggg ggaaactgcc taccctcatc gaaatcaaat accaaaccgt taatgaaggt 8280
ttagtgatct tgggtcagga tatcggtcaa gtattcgcag attttcaggc ggatttatat 8340
accgaagatg tggcataaaa aaggacggcg atcgccgggg gcgttgcctg ccttgaacga 8400
ggtcgacggg caaactttat gaagcagatc aagcctatat ccgccaagca accggcagcc 8460
gcgttgatta gtgggtgtgt ccatcctctg gttcgtctag gtgctccgaa gcgtcacgat 8520
agagattaag aatgtggtga tccttgaggc gataaatcac attccgccct tccttgcgat 8580
agctcactaa acgtgctgtg cgcagggttc ttagttggtg agagacagcc gattcactca 8640
tttcaacggc ggcggcgagt tcccccaccc gcatctctcc agtggccagg gccgaaagaa 8700
tacgccagcg gttggcatcc cccaagacac caaaaaattc ggccatccgt tgggccttgg 8760
cttggttcaa gattttgcca ctgtggtctg tcattgttcg ctgatctaaa caatacctga 8820
ataattgttc atgtgttaat ctaaaaatgt gaacaatcgt tcaactattt aagacaatac 8880
cttggaggtt taaaccatg 8899

<210> SEQ ID NO 66
<211> LENGTH: 8725
<212> TYPE: DNA
<213> ORGANISM: Artificial
<220> FEATURE:
<223> OTHER INFORMATION: Synthetically produced plasmid #1233
pGEM-AQ4::smtB-PsmtA-zpPDC-PrbcL*-synADHdeg for transformation of
Synechococcus sp. PCC7002 via integration into the endogenous
pAQ4 plasmid

<400> SEQUENCE: 66
tcgacgggca aactttatga agcagatcaa gcctatatcc gccaagcaac cggcagccgc 60
gttgattagt gggtgtgtcc atcctctggt tcgtctaggt gctccgaagc gtcacgatag 120

-continued

```
agattaagaa tgtggtgatc cttgaggcga taaatcacat tccgcccttc cttgcgatag    180
ctcactaaac gtgctgtgcg cagggttctt agttggtgag agacagccga ttcactcatt    240
tcaacggcgg cggcgagttc ccccacccgc atctctccag tggccagggc cgaaagaata    300
cgccagcggt tggcatcccc caagacacca aaaaattcgg ccatccgttg ggccttggct    360
tggttcaaga ttttgccact gtggtctgtc attgttcgct gatctaaaca atacctgaat    420
aattgttcat gtgttaatct aaaaatgtga acaatcgttc aactatttaa gacaatacct    480
tggaggttta aaccatgaat tcctataccg ttggtatgta cttggcagaa cgcctagccc    540
agatcggcct gaaacaccac tttgccgtgg ccggtgacta caacctggtg ttgcttgatc    600
agctcctgct gaacaaagac atggagcagg tctactgctg taacgaactt aactgcggct    660
ttagcgccga aggttacgct cgtgcacgtg gtgccgccgc tgccatcgtc acgttcagcg    720
taggtgctat ctctgcaatg aacgccatcg gtggcgccta tgcagaaaac ctgccggtca    780
tcctgatctc tggctcaccg aacaccaatg actacggcac aggccacatc ctgcaccaca    840
ccattggtac tactgactat aactatcagc tggaaatggt aaaacacgtt acctgcgcag    900
ctgaaagcat cgtttctgcc gaagaagcac cggcaaaaat cgaccacgtc atccgtacgg    960
ctctacgtga acgcaaaccg gcttatctgg aaatcgcatg caacgtcgct ggcgctgaat   1020
gtgttcgtcc gggcccgatc aatagcctgc tgcgtgaact cgaagttgac cagaccagtg   1080
tcactgccgc tgtagatgcc gccgtagaat ggctgcagga ccgccagaac gtcgtcatgc   1140
tggtcggtag caaactgcgt gccgctgccg ctgaaaaaca ggctgttgcc ctagcggacc   1200
gcctgggctg cgctgtcacg atcatggctg ccgaaaaagg cttcttcccg gaagatcatc   1260
cgaacttccg cggcctgtac tggggtgaag tcagctccga aggtgcacag gaactggttg   1320
aaaacgccga tgccatcctg tgtctggcac cggtattcaa cgactatgct accgttggct   1380
ggaactcctg gccgaaaggc gacaatgtca tggtcatgga caccgaccgc gtcactttcg   1440
caggacagtc cttcgaaggt ctgtcattga gcaccttcgc cgcagcactg gctgagaaag   1500
caccttctcg cccggcaacg actcaaggca ctcaagcacc ggtactgggt attgaggccg   1560
cagagcccaa tgcaccgctg accaatgacg aaatgacgcg tcagatccag tcgctgatca   1620
cttccgacac tactctgaca gcagaaacag gtgactcttg gttcaacgct tctcgcatgc   1680
cgattcctgg cggtgctcgt gtcgaactgg aaatgcaatg gggtcatatc ggttggtccg   1740
taccttctgc attcggtaac gccgttggtt ctccggagcg tcgccacatc atgatggtcg   1800
gtgatggctc tttccagctg actgctcaag aagttgctca gatgatccgc tatgaaatcc   1860
cggtcatcat cttcctgatc aacaaccgcg gttacgtcat cgaaatcgct atccatgacg   1920
gcccttacaa ctacatcaaa aactggaact acgctggcct gatcgacgtc ttcaatgacg   1980
aagatggtca tggcctgggt ctgaaagctt ctactggtgc agaactagaa ggcgctatca   2040
agaaagcact cgacaatcgt cgcggtccga cgctgatcga atgtaacatc gctcaggacg   2100
actgcactga aaccctgatt gcttggggta aacgtgtagc agctaccaac tctcgcaaac   2160
cacaagcgta agttgatgta gtgaattagg cggggcctat tagggcccca ccacatagcc   2220
cctcttacgg cgcaataccc gtaagagggg ctgttttata taattaaaac tagtcgatcg   2280
acattgccat aagtaaaggc atcccctgcg tgataagatt accttcagtt tatggaggac   2340
tgaccatatg atcaaggctt atgccgcttt agaggctaat ggcaagttgc agccgttcga   2400
gtatgatccg ggcgctttag gcgccaacga agttgaaatc gaagttcaat actgcggtgt   2460
```

-continued

```
ttgtcattcc gacctcagta tgatcaacaa tgagtggggt atcagtaact atccgttggt   2520
tcccggccac gaagttgttg gcaccgttgc tgctatgggt gagggtgtta atcacgtgga   2580
agttggtgac ctggttggtt taggctggca cagtggttat tgtatgactt gtcactcctg   2640
cctgagcggt tatcataatt tgtgcgctac cgccgagagt actatcgttg gtcattatgg   2700
cggtttcggt gaccgtgtgc gtgctaaagg tgtgtccgtt gttaagctgc ccaagggtat   2760
cgatttggct tccgctggtc cgttgttttg cggtggtatc actgtgtttt cccccatggt   2820
tgagttatcc ctgaaaccga ccgccaaggt tgccgttatt ggtatcggtg gtctcggtca   2880
cctggccgtt cagttcttgc gtgcttgggg ttgcgaggtt accgctttca ctagctccgc   2940
tcgtaaacag accgaggttc tggagctggg tgcccatcat attttggaca gtactaaccc   3000
cgaagccatt gcttccgccg agggtaagtt cgattacatc attagtaccg ttaatttaaa   3060
attggattgg aatctgtata tttccacttt agccccgcaa ggtcactttc atttcgtggg   3120
tgttgttctc gaacccctcg acttgaactt gttcccgttg ctcatgggtc agcggagtgt   3180
gtccgctagt ccggttggct ccccggctac tatcgctact atgctcgatt tcgccgttcg   3240
gcacgatatc aagccggttg ttgagcagtt ctccttcgac caaattaatg aagccattgc   3300
tcacttggag tccggtaagg ctcactaccg tgtggttttg agtcactcca agaactgaaa   3360
cgctcggttg ccgccgggcg ttttttattc ctgcaggccc cccgggggat ccactagagg   3420
atctcaatga atattggttg acacgggcgt ataagacatg ttatactgtt gaataacaag   3480
gacggatctg atcaagagac aggatgagga tcgtttcgca tgattgaaca agatggattg   3540
cacgcaggtt ctccggccgc ttgggtggag aggctattcg gctatgactg ggcacaacag   3600
acaatcggct gctctgatgc cgccgtgttc cggctgtcag cgcaggggcg cccggttctt   3660
tttgtcaaga ccgacctgtc cggtgccctg aatgaactgc aggacgaggc agcgcggcta   3720
tcgtggctgg ccacgacggg cgttccttgc gcagctgtgc tcgacgttgt cactgaagcg   3780
ggaagggact ggctgctatt gggcgaagtg ccggggcagg atctcctgtc atctcacctt   3840
gctcctgccg agaaagtatc catcatggct gatgcaatgc ggcggctgca tacgcttgat   3900
ccggctacct gcccattcga ccaccaagcg aaacatcgca tcgagcgagc acgtactcgg   3960
atggaagccg gtcttgtcga tcaggatgat ctggacgaag agcatcaggg gctcgcgcca   4020
gccgaactgt tcgccaggct caaggcgcgc atgcccgacg gcgaggatct cgtcgtgacc   4080
catggcgatg cctgcttgcc gaatatcatg gtggaaaatg gccgcttttc tggattcatc   4140
gactgtggcc ggctgggtgt ggcggaccgc tatcaggaca tagcgttggc tacccgtgat   4200
attgctgaag agcttggcgg cgaatgggct gaccgcttcc tcgtgcttta cggtatcgcc   4260
gctcccgatt cgcagcgcat cgccttctat cgccttcttg acgagttctt ctgagcggga   4320
ctctggggtt cgaaatgacc gaccaagcga cgcccaacct gccatcacga gatttcgatt   4380
ccaccgccgc cttctatgaa aggttgggct tcggaatcgt tttccgggac gccggctgga   4440
tgatcctcca gcgcggggat ctcatgctgg agttcttcgc ccaccgggga tcctctagtt   4500
ctagagcggc cgcatcatca atccccgtga tgtttcagtc ccgtagtcgg gatttagtgg   4560
ttggaaagcg gaacgtcgcg ccgaaaccat cgccaggacg ggtttcagtc ccgtagtcgg   4620
gatttagtgg ttggaaagtg attatgttca agaaatcaca acgcaaaaga aaaagtttca   4680
gtcccgtagt cgggatttag tggttggaaa gtcaagcgag atacccacca gaaagccttt   4740
gacctggttt cagtcccgag tcgggattta gtggttggaa aggcggcggc tgatgtcgcc   4800
aatgcggtta tcgatggcca gtttcagtcc cgtagtcggg atttagtggt tggaaagtcc   4860
```

-continued

```
caagggggac agggcggtga tcctcgatgt tgcgtgtttc agtcccgtag tcgggattta   4920
gtggttggaa agactcgtct atatatacag agattactac agagatgttt cagtcccgta   4980
gtcgggattt agtggttgga aagcgggaaa gtagcctgtt ttgtggagaa ttgcaggcgt   5040
ttcagtacta gtgatggcgg ccgggagcat gcgacgtcgg gcccaattcg ccctatagtg   5100
agtcgtatta caattcactg gccgtcgttt tacaacgtcg tgactgggaa aaccctggcg   5160
ttacccaact taatcgcctt gcagcacatc ccccttttcgc cagctggcgt aatagcgaag   5220
aggcccgcac cgatcgccct tcccaacagt tgcgcagcct gaatggcgaa tggacgcgcc   5280
ctgtagcggc gcattaagcg cggcgggtgt ggtggttacg cgcagcgtga ccgctacact   5340
tgccagcgcc ctagcgcccg ctcctttcgc tttcttccct tcctttctcg ccacgttcgc   5400
cggctttccc cgtcaagctc taaatcgggg gctcccttta gggttccgat ttagagcttt   5460
acggcacctc gaccgcaaaa aacttgattt gggtgatggt tcacgtagtg ggccatcgcc   5520
ctgatagacg gtttttcgcc ctttgacgtt ggagtccacg ttctttaata gtggactctt   5580
gttccaaact ggaacaacac tcaaccctat ctcggtctat tcttttgatt tataagggat   5640
tttgccgatt tcggcctatt ggttaaaaaa tgagctgatt taacaaatat ttaacgcgaa   5700
ttttaacaaa atattaacgt ttacaatttc gcctgatgcg gtattttctc cttacgcatc   5760
tgtgcggtat ttcacaccgc atacaggtgg cacttttcgg ggaaatgtgc gcggaacccc   5820
tatttgttta tttttctaaa tacattcaaa tatgtatccg ctcatgagac aataaccctg   5880
ataaatgctt caataatatt gaaaaaggaa gagtatgagt attcaacatt tccgtgtcgc   5940
ccttattccc ttttttgcgg cattttgcct tcctgttttt gctcacccag aaacgctggt   6000
gaaagtaaaa gatgctgaag atcagttggg tgcacgagtg ggttacatcg aactggatct   6060
caacagcggt aagatccttg agagttttcg ccccgaagaa cgttttccaa tgatgagcac   6120
ttttaaagtt ctgctatgtg gcgcggtatt atcccgtatt gacgccgggc aagagcaact   6180
cggtcgccgc atacactatt ctcagaatga cttggttgag tactcaccag tcacagaaaa   6240
gcatcttacg gatggcatga cagtaagaga attatgcagt gctgccataa ccatgagtga   6300
taacactgcg gccaacttac ttctgacaac gatcggagga ccgaaggagc taaccgcttt   6360
tttgcacaac atgggggatc atgtaactcg ccttgatcgt tgggaaccgg agctgaatga   6420
agccatacca aacgacgagc gtgacaccac gatgcctgta gcaatgccaa caacgttgcg   6480
caaactatta actggcgaac tacttactct agcttcccgg caacaattaa tagactggat   6540
ggaggcggat aaagttgcag gaccacttct gcgctcggcc cttccggctg gctggtttat   6600
tgctgataaa tctggagccg gtgagcgtgg gtctcgcggt atcattgcag cactggggcc   6660
agatggtaag ccctcccgta tcgtagttat ctacacgacg gggagtcagg caactatgga   6720
tgaacgaaat agacagatcg ctgagatagg tgcctcactg attaagcatt ggtaactgtc   6780
agaccaagtt tactcatata tactttagat tgatttaaaa cttcattttt aatttaaaag   6840
gatctaggtg aagatccttt ttgataatct catgaccaaa atcccttaac gtgagttttc   6900
gttccactga gcgtcagacc ccgtagaaaa gatcaaagga tcttcttgag atcctttttt   6960
tctgcgcgta atctgctgct tgcaaacaaa aaaaccaccg ctaccagcgg tggtttgttt   7020
gccggatcaa gagctaccaa ctctttttcc gaaggtaact ggcttcagca gagcgcagat   7080
accaaatact gtccttctag tgtagccgta gttaggccac cacttcaaga actctgtagc   7140
accgcctaca tacctcgctc tgctaatcct gttaccagtg gctgctgcca gtggcgataa   7200
```

gtcgtgtctt accgggttgg actcaagacg atagttaccg gataaggcgc agcggtcggg 7260
ctgaacgggg ggttcgtgca cacagcccag cttggagcga acgacctaca ccgaactgag 7320
atacctacag cgtgagctat gagaaagcgc cacgcttccc gaagggagaa aggcggacag 7380
gtatccggta agcggcaggg tcggaacagg agagcgcacg agggagcttc caggggggaaa 7440 cgcctggtat ctttatagtc ctgtcgggtt tcgccacctc tgacttgagc gtcgattttt 7500
gtgatgctcg tcaggggggc ggagcctatg gaaaaacgcc agcaacgcgg cctttttacg 7560
gttcctggcc ttttgctggc cttttgctca catgttcttt cctgcgttat cccctgattc 7620
tgtggataac cgtattaccg cctttgagtg agctgatacc gctcgccgca gccgaacgac 7680
cgagcgcagc gagtcagtga gcgaggaagc ggaagagcgc ccaatacgca aaccgcctct 7740
ccccgcgcgt tggccgattc attaatgcag ctggcacgac aggtttcccg actggaaagc 7800
gggcagtgag cgcaacgcaa ttaatgtgag ttagctcact cattaggcac cccaggcttt 7860
acactttatg cttccggctc gtatgttgtg tggaattgtg agcggataac aatttcacac 7920
aggaaacagc tatgaccatg attacgccaa gctatttagg tgacactata gaatactcaa 7980
gctatgcatg agggtgcaat ttgagtggtt tcagtcccgt aatcgggatt tagtggttgg 8040
aaagaacgac aaggcttaca aggggggtaat tcgtgatttg tttcagtccc gtaatcggga 8100
tttagtggtt ggaaagtagg caggggagtg aaatggtttc atgttgggct catgtttcag 8160
tcccgtaatc gggatttagt ggttggaaag cagtaagatg aaggaggtgg tgcatatcac 8220
ttgcgtttca gtcccgtaat cgggatttag tggttggaaa gctagatttg cttatagagt 8280
tgactgttat cgggacttgt ttcagtcccg taatcgggat ttagtggttg gaaagatgat 8340
ggcgttgcca gcgttctcgg attggagaat ttaacgtttc agtcccgtaa tcgggattta 8400
gtggttggaa agccctgaga agtttggctg ttttgctgac tgcgatctgg tttcagtccc 8460
gtaatcggga tttagtggtt ggaaagcatc gaggcagtag agcaaatcgc aggccacctc 8520
atagtttcag tcccgtaatc gggatttagt ggttggaaag tcattggggt ctgcattggg 8580
gccatcgcta tcgtcctgtt tcagtcccgt aatcgggatt tagtggttgg aaagtgggac 8640
gctccgtaag gtttggagaa tagggtctag tgtttcagtc ccgtaatcgg gatttagtgg 8700
ttggaaagca cttcgtcgct gattg 8725

<210> SEQ ID NO 67
<211> LENGTH: 13731
<212> TYPE: DNA
<213> ORGANISM: Artificial
<220> FEATURE:
<223> OTHER INFORMATION: Synthetic vector construct #1374
pVZ325a-nrsR-PnrsB-zpPDC_ter-corR-PcorT*1-zmPDC+eg_spf er for
transformation of Synechocystis sp. PCC6803

<400> SEQUENCE: 67
tcgttcaagc cgacgccgct tcgcggcgcg gcttaactca agctctagag tcgacgggag 60
tttgcaaact ccctcatatt catggcgata gggtgaaccg atagccttga ccgggaactg 120
ttttaattgg gcaaggacaa ttttgttgag ctagcttgcg tcgtatcaaa cgcatttggg 180
ccgccaccac attactcatg ggctcctcat caagatccca cagttgttgc cggatcttgc 240
taccggaaat gatccgctct gggttttgca tcagatattg aaaaatttga aattctctta 300
cggttaaagc aatttcctgt ctttctaggt ttagtggctc cgagatagtt accgataaca 360
gattattact gggatcaagg ctgaagttgc ccaaagttaa aatttgcggt tggaattgtg 420
gcgatcgccg ttgtagtgcc cgcagtcttg ctaatagctc tgccatcaca aacggttttg 480

```
ttagatagtc atctgccccg gcatctagtc cttcgacacg gttttccggt tctcctaacg    540
ctgttaacat caacaccggc aaggaattac cctgggttct cagtttttga cagagttcca    600
aacccgataa tcccggcagt aaccaatcca caatggcaag ggtgtattcc gtccattgat    660
tttccaaata atcccaagct tgggagccat ccgtcaccca atccaccaca tacttttcac    720
taactagcac tttcttaata gccattccca aatccgtctc atcttccacc agcaaaattc    780
gcatcgcctc tgcctttttt ataacggtct gatcttagcg ggggaaggag attttcacct    840
gaatttcata ccccctttgg cagactggga aaatcttgga caaattccca atttgaggtg    900
gtgtgatgaa ttcctatacc gttggtatgt acttggcaga acgcctagcc cagatcggcc    960
tgaaacacca ctttgccgtg gccggtgact acaacctggt gttgcttgat cagctcctgc   1020
tgaacaaaga catggagcag gtctactgct gtaacgaact taactgcggc tttagcgccg   1080
aaggttacgc tcgtgcacgt ggtgccgccg ctgccatcgt cacgttcagc gtaggtgcta   1140
tctctgcaat gaacgccatc ggtggcgcct atgcagaaaa cctgccggtc atcctgatct   1200
ctggctcacc gaacaccaat gactacggca caggccacat cctgcaccac accattggta   1260
ctactgacta taactatcag ctggaaatgg taaaacacgt tacctgcgca cgtgaaagca   1320
tcgtttctgc cgaagaagca ccggcaaaaa tcgaccacgt catccgtacg gctctacgtg   1380
aacgcaaacc ggcttatctg gaaatcgcat gcaacgtcgc tggcgctgaa tgtgttcgtc   1440
cgggcccgat caatagcctg ctgcgtgaac tcgaagttga ccagaccagt gtcactgccg   1500
ctgtagatgc cgccgtagaa tggctgcagg accgccagaa cgtcgtcatg ctggtcggta   1560
gcaaactgcg tgccgctgcc gctgaaaaac aggctgttgc cctagcggac cgcctgggct   1620
gcgctgtcac gatcatggct gccgaaaaag gcttcttccc ggaagatcat ccgaacttcc   1680
gcggcctgta ctggggtgaa gtcagctccg aaggtgcaca ggaactggtt gaaaacgccg   1740
atgccatcct gtgtctggca ccggtattca acgactatgc taccgttggc tggaactcct   1800
ggccgaaagg cgacaatgtc atggtcatgg acaccgaccg cgtcactttc gcaggacagt   1860
ccttcgaagg tctgtcattg agcaccttcg ccgcagcact ggctgagaaa gcaccttctc   1920
gcccggcaac gactcaaggc actcaagcac cggtactggg tattgaggcc gcagagccca   1980
atgcaccgct gaccaatgac gaaatgacgc gtcagatcca gtcgctgatc acttccgaca   2040
ctactctgac agcagaaaca ggtgactctt ggttcaacgc ttctcgcatg ccgattcctg   2100
gcggtgctcg tgtcgaactg gaaatgcaat ggggtcatat cggttggtcc gtaccttctg   2160
cattcggtaa cgccgttggt tctccggagc gtcgccacat catgatggtc ggtgatggct   2220
ctttccagct gactgctcaa gaagttgctc agatgatccg ctatgaaatc ccggtcatca   2280
tcttcctgat caacaaccgc ggttacgtca tcgaaatcgc tatccatgac ggcccttaca   2340
actacatcaa aaactggaac tacgctggcc tgatcgacgt cttcaatgac gaagatggtc   2400
atggcctggg tctgaaagct tctactggtg cagaactaga aggcgctatc aagaaagcac   2460
tcgacaatcg tcgcggtccg acgctgatcg aatgtaacat cgctcaggac gactgcactg   2520
aaaccctgat tgcttggggt aaacgtgtag cagctaccaa ctctcgcaaa ccacaagcgt   2580
aagttgatgt agtgaattag gcggggccta ttagggcccc accacatagc cctcttacg   2640
gcgcaatacc cgtaagaggg gctgttttat ataattaaaa ctagaaagat tcgaccatgc   2700
gtccaaaact ttcaccatcc tttccctatc aacctttact gcactaaaga caagtgagat   2760
agcagtggca atctggcttt gcaatcaatg tttccactaa agcgtttagc gttactgcgg   2820
```

ctagaagtcc tccaccgagg ctcccctgaa tggtgatatg gggaatggga ctggtcatca 2880
gtcgtcgttt tgcccccgga gcatgactaa aaccgatcgg cattccgatc acaagagccg 2940
gctgaatatg ttgttgctct atcagcttac aggcagtgag taaaacagaa ggggcatagc 3000
cgatcgccag cacacatcct tggggaatct gttgtaaccg ctgttgccaa tggtcatggt 3060
gccaaaaagc ttgctcggct tccctaagcc ctgtgatgtg agggtcgtca atcagcgttt 3120
taaccgtaca tcctaaatga gctaaccgag tttgatcaag agccgcagcc acaaccggaa 3180
catcggtgac gactggacac cctgctttca gtgcatctcg tgccgaggcg atcgctccct 3240
gactcaatcg aacggcgttt accaagctaa catcaccaca ggccagcact aattgatgta 3300
gtaagtgaat ggtaatttca gagtaagccg ataaatccgg tagcaggtgt ttgagggatt 3360
cctgaaaggc ttctggatga gttgttgtct ccgcatctag gttcgtccac aactgatcga 3420
gttttcctaa cccctcctgg acatccacat caagctgttt cagttgggcc agagcttccg 3480
cttgggtaat ctggcaactc tggtcgcgtc ccagtaatcc ttctaaagca gatgcggttt 3540
ggcggagtcg agtaatctgc tgaatcacag cctgatattg ctgttgcaac tgcaccatta 3600
gggtgggatc aaggctctct tcagaatggc tatccagcag ttgccgaata tgagacaact 3660
gaaagccctg ctgtttgagg gcaatgactc gttggagccg ttgtacgtcc tgctgagtat 3720
aaaggcggta gttgccctct gagcgttgaa cggggggaag caatcccagg gtgtggtaat 3780
ggcgcaccat gcgaggcgta acgccacctc ccactgcatc tgtgagttct ttaatcgtta 3840
agtgattagt cttcatgact ttagtttact caaaaccttg acattgacac taatgttaag 3900
gtttaggctg agaaggtaaa aatcgaggat aaaaagcatg aattcctaca ccgttggcac 3960
ttacctggct gaacgcttgg ttcagatcgg cttaaaacac cattttgctg ttgctggtga 4020
ttataatttg gttttgttag ataatttatt gctcaataag aatatggaac aggtgtactg 4080
ttgcaatgag ttaaattgtg gcttttccgc tgagggctac gcccgtgcta agggtgctgc 4140
tgctgctgtt gtgacttatt ctgttggcgc tttgagtgct tttgacgcca ttggcggtgc 4200
ttacgctgag aatttgccag tgattttaat tagtggcgcc ccaaataata acgaccatgc 4260
cgccggccat gtcctccacc atgccttggg taagactgat taccattacc aactggagat 4320
ggctaaaaat attaccgctg ctgccgaagc tatctatact cctgaggaag ccccagccaa 4380
gattgaccat gtcatcaaga ccgccttgcg ggaaaaaaaa ccagtgtact tagagattgc 4440
ctgtaatatc gccagtatgc cttgtgctgc cccccggtcca gcttctgctc tctttaacga 4500
tgaagcttct gatgaggcca gtctcaacgc tgctgtggag gaaactttaa agtttattgc 4560
taatcgtgat aaggtggctg ttttagttgg ttctaaatta cgtgctgccg gcgccgagga 4620
agccgccgtt aagtttgccg acgccttagg cggtgctgtg gccactatgg ccgccgctaa 4680
gtcttttttt cctgaagaga atccacacta tattggcact agctggggcg aggtttctta 4740
cccaggtgtg gagaaaacca tgaaggaggc tgacgctgtg attgccttag ccccggtttt 4800
taatgattat agtactaccg gctggaccga catcccggac ccgaaaaagt tagtgttagc 4860
cgaaccacgg agtgttgttg tgaatggtgt gcgttttcct tctgtgcact taaaggatta 4920
cttaactcgg ctcgcccaga aggtgagtaa aaagactggc gccctcgatt tttttaagag 4980
tttaaacgct ggcgagttaa aaaaggctgc cccagccgac ccatccgccc cactcgttaa 5040
tgctgaaatt gctcggcagg ttgaggcctt gttaactcca aataccaccg tgatcgccga 5100
aactggcgat agttggttta acgcccaacg tatgaaatta ccaaatggcg cccgtgtgga 5160
gtacgagatg caatggggcc atattggctg gagtgtgccg gctgcttttg gctacgctgt 5220

-continued

```
tggcgcccca gagcggcgta atattttaat ggtgggcgac ggcagttttc agttaaccgc   5280
ccaagaggtt gcccaaatgg tgcgtttaaa gttaccagtg attatttttc tcattaacaa   5340
ttacggctat actattgagg tgatgattca cgacggccca tataataata ttaaaaattg   5400
ggactacgct ggcttaatgg aggtctttaa tggcaatggc ggctacgatt ctggcgccgg   5460
caagggttta aaagccaaga ctggcggtga gttagctgaa gccattaaag tggccttagc   5520
taatactgat ggtcctactt taattgagtg ttttattggc cgggaagatt gtaccgagga   5580
actcgttaag tggggcaaac gtgtggccgc tgctaattct cggaaacccg tgaataaatt   5640
attatgaaat attttagccg ccccagtcag taatgactgg ggcgtttttt attgggagct   5700
cctgcaggag cagaagagca tacatctgga agcaaagcca ggaaagcggc ctatggagct   5760
gtgcggcagc gctcagtagg caatttttca aaatattgtt aagccttttc tgagcatggt   5820
atttttcatg gtattaccaa ttagcaggaa aataagccat tgaatataaa agataaaaat   5880
gtcttgttta caatagagtg gggggggtca gcctgccgcc ttgggccggg tgatgtcgta   5940
cttgcccgcc gcgaactcgg ttaccgtcca gcccagcgcg accagctccg gcaacgcctc   6000
gcgcacccgc tggcggcgct tgcgcatggt cgaaccactg gcctctgacg gccagacata   6060
gccgcacaag gtatctatgg aagccttgcc ggttttgccg gggtcgatcc agccacacag   6120
ccgctggtgc agcaggcggg cggtttcgct gtccagcgcc cgcacctcgt ccatgctgat   6180
gcgcacatgc tggccgccac ccatgacggc ctgcgcgatc aaggggttca gggccacgta   6240
caggcgcccg tccgcctcgt cgctggcgta ctccgacagc agccgaaacc cctgccgctt   6300
gcggccattc tgggcgatga tggatacctt ccaaaggcgc tcgatgcagt cctgtatgtg   6360
cttgagcgcc ccaccactat cgacctctgc cccgatttcc tttgccagcg cccgatagct   6420
acctttgacc acatggcatt cagcggtgac ggcctcccac ttgggttcca ggaacagccg   6480
gagctgccgt ccgccttcgg tcttgggttc cgggccaagc actaggccat taggcccagc   6540
catggccacc agcccttgca ggatgcgcag atcatcagcg cccagcggct ccgggccgct   6600
gaactcgatc cgcttgccgt cgccgtagtc atacgtcacg tccagcttgc tgcgcttgcg   6660
ctcgccccgc ttgagggcac ggaacaggcc gggggccaga cagtgcgccg ggtcgtgccg   6720
gacgtggctg aggctgtgct tgttcttagg cttcaccacg gggcaccccc ttgctcttgc   6780
gctgcctctc cagcacggcg ggcttgagca ccccgccgtc atgccgcctg aaccaccgat   6840
cagcgaacgg tgcgccatag ttggccttgc tcacaccgaa gcggacgaag aaccggcgct   6900
ggtcgtcgtc cacaccccat tcctcggcct cggcgctggt catgctcgac aggtaggact   6960
gccagcggat gttatcgacc agtaccgagc tgccccggct ggcctgctgc tggtcgcctg   7020
cgcccatcat ggccgcgccc ttgctggcat ggtgcaggaa cacgatagag cacccggtat   7080
cggcggcgat ggcctccatg cgaccgatga cctgggccat ggggccgctg gcgttttctt   7140
cctcgatgtg gaaccggcgc agcgtgtcca gcaccatcag gcggcggccc tcggcggcgc   7200
gcttgaggcc gtcgaaccac tccggggcca tgatgttggg caggctgccg atcagcggct   7260
ggatcagcag gccgtcagcc acggcttgcc gttcctcggc gctgaggtgc gccccaaggg   7320
cgtgcaggcg gtgatgaatg gcggtgggcg ggtcttcggc gggcaggtag atcaccgggc   7380
cggtgggcag ttcgcccacc tccagcagat ccggcccgcc tgcaatctgt gcggccagtt   7440
gcagggccag catggattta ccggcaccac cgggcgacac cagcgccccg accgtaccgg   7500
ccaccatgtt gggcaaaacg tagtccagcg gtggcggcgc tgctgcgaac gcctccagaa   7560
```

```
tattgatagg cttatgggta gccattgatt gcctcctttg caggcagttg gtggttaggc   7620
gctggcgggg tcactacccc cgccctgcgc cgctctgagt tcttccaggc actcgcgcag   7680
cgcctcgtat tcgtcgtcgg tcagccagaa cttgcgctga cgcatccctt tggccttcat   7740
gcgctcggca tatcgcgctt ggcgtacagc gtcagggctg gccagcaggt cgccggtctg   7800
cttgtccttt tggtctttca tatcagtcac cgagaaactt gccggggccg aaaggcttgt   7860
cttcgcggaa caaggacaag gtgcagccgt caaggttaag gctggccata tcagcgactg   7920
aaaagcggcc agcctcggcc ttgtttgacg tataaccaaa gccaccgggc aaccaatagc   7980
ccttgtcact tttgatcagg tagaccgacc ctgaagcgct tttttcgtat tccataaaac   8040
ccccttctgt gcgtgagtac tcatagtata acaggcgtga gtaccaacgc aagcactaca   8100
tgctgaaatc tggcccgccc ctgtccatgc ctcgctggcg gggtgccggt gcccgtgcca   8160
gctcggcccg cgcaagctgg acgctgggca gacccatgac cttgctgacg gtgcgctcga   8220
tgtaatccgc ttcgtggccg ggcttgcgct ctgccagcgc tgggctggcc tcggccatgg   8280
ccttgccgat ttcctcggca ctgcggcccc ggctggccag cttctgcgcg gcgataaagt   8340
cgcacttgct gaggtcatca ccgaagcgct tgaccagccc ggccatctcg ctgcggtact   8400
cgtccagcgc cgtgcgccgg tggcggctaa gctgccgctc gggcagttcg aggctggcca   8460
gcctgcgggc cttctcctgc tgccgctggg cctgctcgat ctgctggcca gcctgctgca   8520
ccagcgccgg gccagcggtg gcggtcttgc ccttggattc acgcagcagc acccacggct   8580
gataaccggc gcgggtggtg tgcttgtcct tgcggttggt gaagcccgcc aagcggccat   8640
agtggcggct gtcggcgctg gccgggtcgg cgtcgtactc gctggccagc gtccgggcaa   8700
tctgcccccg aagttcaccg cctgcggcgt cggccacctt gacccatgcc tgatagttct   8760
tcgggctggt ttccactacc agggcaggct cccggccctc ggctttcatg tcatccaggt   8820
caaactcgct gaggtcgtcc accagcacca gaccatgccg ctcctgctcg gcgggcctga   8880
tatacacgtc attgccctgg gcattcatcc gcttgagcca tggcgtgttc tggagcactt   8940
cggcggctga ccattcccgg ttcatcatct ggccggtggt ggcgtccctg acgccgatat   9000
cgaagcgctc acagcccatg gccttgagct gtcggcctat ggcctgcaaa gtcctgtcgt   9060
tcttcatcgg gccaccaagc gcagccagat cgagccgtcc tcggttgtca gtggcgtcag   9120
gtcgagcaag agcaacgatg cgatcagcag caccaccgta ggcatcatgg aagccagcat   9180
cacggttagc catagcttcc agtgccaccc ccgcgacgcg ctccgggcgc tctgcgcggc   9240
gctgctcacc tcggcggcta cctcccgcaa ctctttggcc agctccaccc atgccgcccc   9300
tgtctggcgc tgggctttca gccactccgc cgcctgcgcc tcgctggcct gctgggtctg   9360
gctcatgacc tgccgggctt cgtcggccag tgtcgccatg ctctgggcca gcggttcgat   9420
ctgctccgct aactcgttga tgcctctgga tttcttcact ctgtcgattg cgttcatggt   9480
ctattgcctc ccggtattcc tgtaagtcga tgatctgggc gttggcggtg tcgatgttca   9540
gggccacgtc tgcccggtcg gtgcggatgc ccccggcctt catctccacc acgttcggcc   9600
ccaggtgaac accgggcagg cgctcgatgc cctgcgcctc aagtgttctg tggtcaatgc   9660
gggcgtcgtg gccagcccgc tctaatgccc ggttggcatg gtcggcccat gcctcgcggg   9720
tctgctcaag ccatgccttg ggcttgagcg cttcggtctt ctgtgccccg cccttctccg   9780
gggtcttgcc gttgtaccgc ttgaaccact gagcggcggg ccgctcgatg ccgtcattga   9840
tccgctcgga gatcatcagg tggcagtgcg ggttctcgcc gccaccggca tggatggcca   9900
gcgtatacgg caggcgctcg gcaccggtca ggtgctgggc gaactcggac gccagcgcct   9960
```

```
tctgctggtc gagggtcagc tcgaccggca gggcaaattc gacctccttg aacagccgcc  10020
cattggcgcg ttcatacagg tcggcagcat cccagtagtc ggcgggccgc tcgacgaact  10080
ccggcatgtg cccggattcg gcgtgcaaga cttcatccat gtcgcgggca tacttgcctt  10140
cgcgctggat gtagtcggcc ttggccctgg ccgattggcc gcccgacctg ctgccggttt  10200
tcgccgtaag gtgataaatc gccatgctgc ctcgctgttg cttttgcttt tcggctccat  10260
gcaatggccc tcggagagcg caccgcccga agggtggccg ttaggccagt ttctcgaaga  10320
gaaaccggta agtgcgccct cccctacaaa gtagggtcgg gattgccgcc gctgtgcctc  10380
catgatagcc tacgagacag cacattaaca atggggtgtc aagatggtta aggggagcaa  10440
caaggcggcg gatcggctgg ccaagctcga agaacaacga gcgcgaatca atgccgaaat  10500
tcagcgggtg cgggcaaggg aacagcagca agagcgcaag aacgaaacaa ggcgcaaggt  10560
gctggtgggg gccatgattt tggccaaggt gaacagcagc gagtggccgg aggatcggct  10620
catggcggca atggatgcgt accttgaacg cgaccacgac cgcgccttgt tcggtctgcc  10680
gccacgccag aaggatgagc cgggctgaat gatcgaccga gacaggccct gcggggctgc  10740
acacgcgccc ccacccttcg ggtaggggga aaggccgcta aagcggctaa aagcgctcca  10800
gcgtatttct gcggggtttg gtgtggggtt tagcgggctt tgcccgcctt tccccctgcc  10860
gcgcagcggt ggggcggtgt gtagcctagc gcagcgaata gaccagctat ccggcctctg  10920
gccgggcata ttgggcaagg gcagcagcgc cccacaaggg cgctgataac cgcgcctagt  10980
ggattattct tagataatca tggatggatt tttccaacac cccgccagcc cccgcccctg  11040
ctgggtttgc aggtttgggg gcgtgacagt tattgcaggg gttcgtgaca gttattgcag  11100
gggggcgtga cagttattgc aggggttcgt gacagttagt acgggagtga cgggcactgg  11160
ctggcaatgt ctagcaacgg caggcatttc ggctgagggt aaaagaactt tccgctaagc  11220
gatagactgt atgtaaacac agtattgcaa ggacgcggaa catgcctcat gtggcggcca  11280
ggacggccag ccgggatcgg gatactggtc gttaccagag ccaccgaccc gagcaaaccc  11340
ttctctatca gatcgttgac gagtattacc cggcattcgc tgcgcttatg gcagagcagg  11400
gaaaggaatt gccgggctat gtgcaacggg aatttgaaga atttctccaa tgcgggcggc  11460
tggagcatgg ctttctacgg gttcgctgcg agtcttgcca cgccgagcac ctggtcgctt  11520
tcagctgtaa tccgggcagc gcaacggaac attcatcagt gtaaaaatgg aatcaataaa  11580
gccctgcgca gcgcgcaggg tcagcctgaa tacgcgtgct cgaattgaca taagcctgtt  11640
cggttcgtaa actgtaatgc aagtagcgta tgcgctcacg caactggtcc agaaccttga  11700
ccgaacgcag cggtggtaac ggcgcagtgg cggttttcat ggcttgttat gactgttttt  11760
ttgtacagtc tatgcctcgg gcatccaagc agcaagcgcg ttacgccgtg ggtcgatgtt  11820
tgatgttatg gagcagcaac gatgttacgc agcagcaacg atgttacgca gcagggcagt  11880
cgccctaaaa caaagttagg tggctcaagt atgggcatca ttcgcacatg taggctcggc  11940
cctgaccaag tcaaatccat gcgggctgct cttgatcttt tcggtcgtga gttcggagac  12000
gtagccacct actcccaaca tcagccggac tccgattacc tcgggaactt gctccgtagt  12060
aagacattca tcgcgcttgc tgccttcgac caagaagcgg ttgttggcgc tctcgcggct  12120
tacgttctgc ccaggtttga gcagccgcgt agtgagatct atatctatga tctcgcagtc  12180
tccggcgagc accggaggca gggcattgcc accgcgctca tcaatctcct caagcatgag  12240
gccaacgcgc ttggtgctta tgtgatctac gtgcaagcag attacggtga cgatcccgca  12300
```

```
gtggctctct atacaaagtt gggcatacgg gaagaagtga tgcactttga tatcgaccca  12360
agtaccgcca cctaacaatt cgttcaagcc gagatcggct tcccggccct agacgcgtat  12420
tcaggctgac cctgcgcgct gcgcagggct ttattgattc catttttaca ctgatgaatg  12480
ttccgttgcg ctgcccggat tacagatcct ctagaagaac agcaaggccg ccaatgcctg  12540
acgatgcgtg gagaccgaaa ccttgcgctc gttcgccagc caggacagaa atgcctcgac  12600
ttcgctgctg cccaaggttg ccgggtgacg cacaccgtgg aaacggatga aggcacgaac  12660
ccagtggaca taagcctgtt cggttcgtaa gctgtaatgc aagtagcgta tgcgctcacg  12720
caactggtcc agaaccttga ccgaacgcag cggtggtaac ggcgcagtgg cggttttcat  12780
ggcttgttat gactgttttt ttggggtaca gtctatgcct cgggcatcca agcagcaagc  12840
gcgttacgcc gtgggtcgat gtttgatgtt atggagcagc aacgatgtta cgcagcaggg  12900
cagtcgccct aaaacaaagt taaacatcat gagggaagcg gtgatcgccg aagtatcgac  12960
tcaactatca gaggtagttg gcgtcatcga gcgccatctc gaaccgacgt tgctggccgt  13020
acatttgtac ggctccgcag tggatggcgg cctgaagcca cacagtgata ttgatttgct  13080
ggttacggtg accgtaaggc ttgatgaaac aacgcggcga gctttgatca acgacctttt  13140
ggaaacttcg gcttcccctg gagagagcga gattctccgc gctgtagaag tcaccattgt  13200
tgtgcacgac gacatcattc cgtggcgtta tccagctaag cgcgaactgc aatttggaga  13260
atggcagcgc aatgacattc ttgcaggtat cttcgagcca gccacgatcg acattgatct  13320
ggctatcttg ctgacaaaag caagagaaca tagcgttgcc ttggtaggtc cagcggcgga  13380
ggaactcttt gatccggttc ctgaacagga tctatttgag gcgctaaatg aaaccttaac  13440
gctatggaac tcgccgcccg actgggctgg cgatgagcga aatgtagtgc ttacgttgtc  13500
ccgcatttgg tacagcgcag taaccggcaa aatcgcgccg aaggatgtcg ctgccgactg  13560
ggcaatggag cgcctgccgg cccagtatca gcccgtcata cttgaagcta gacaggctta  13620
tcttggacaa gaagaagatc gcttggcctc gcgcgcagat cagttggaag aatttgtcca  13680
ctacgtgaaa ggcgagatca ccaaggtagt cggcaaataa tgtctaacaa t           13731
```

<210> SEQ ID NO 68
<211> LENGTH: 13291
<212> TYPE: DNA
<213> ORGANISM: Artificial
<220> FEATURE:
<223> OTHER INFORMATION: Synthetic vector construct #1460 pVZ325a-nrsRS-PnrsB916-PDCdsrA-Prbc*-synADHdeg for transformation of Synechococcus sp. PCC7002

<400> SEQUENCE: 68

```
tcgacaaaat gaagtaccga agacaaccat cattggggtt gtcttttta ttggttaatt     60
ggcgaaagac tccaagggcg atcgcctttt aattaagttc tattcacctt ttctgagggg    120
taaacgcaga gtgaattggc taccttgatc cgcatcactc tggatttgga tagatccgtg    180
ataagcaagg gcgatcgcct gggcaatggc aagccctaaa cctgtccccc cggttttacg    240
ggaacggtca tcattaactc ggtaaaaccg tttaaaaatc tgttgttgtt gctctgggga    300
aatgcccata cctgtatccg taacggtaat tttggcatgg cgatcatccg tttttaaatt    360
tacattcacg ctgccacctt tgggggtata acgcagggca ttgtcgagga gattggacac    420
tagacgatag agttgggatt cgttcccttg cacataaatt tcctgtttgg ggagttcgtt    480
cgtgagggta ataccgacgg cgatcgccat ctctaaaaat tcttcggtga ggtcactgac    540
cagatcattc agacaacaat ccctccagtt ttctgaagtt tggggttgct ccaaacgact    600
```

gagcaacagc agatcattaa ttaattgact gagccgccgc ccctgccgtt cgacggtctg 660
gagcatggtt tggatgtcct gttgatcccc accattgagg cgcaaaatca cttcgacggt 720
tgccagcaaa ctcgcgaggg gcgatcgcag ttcgtgggcg gcatcagcgg taaattgttg 780
ctgctgttgg taagcgtcgt agatagggcg catggctaaa cctgctaacc accaactaga 840
gagggtaact acgccgagag caagaggtaa actgacccct aaaacccagc gaatccgttg 900
attttcctga tcaaaggcca tgaggctccg accaatctgg agataacccc atgaatcttg 960
aatatttgca gcgtcgtggg tgtaggcact atgaagaatc gtcgtaaatt gtcggtaacg 1020
gtcatcctcc tgtctaatgg tttgccatgt ctccggttgt aggttctggg ataagctctg 1080
cggttgattg ggggaaaagg caactaattg accttgatgg ttaaataggc ggatgtaata 1140
aaggcggcga tcgctaatgc ccatcgtgtg ccgttcaatt aaagttggtg tagtgtcaca 1200
gggctgatta acaaggcata gatctggaaa aatttgctgt aaagttcctg tggggttcgc 1260
attctccggc agtattggtt ctaggctatc gtgcagcgtt ccggcgattg actccacttc 1320
ccgttcaagg gcaacccaat tcgcttgcac aatggaacga taaaccccca gccctaaagc 1380
actcaaaatt ccccccatta cgagggcata ccagagagca agacggaggc gactgcgagc 1440
aaacagacga taactgttca tggttctacc gtaaaccgat aaccttggcc ggggacagtt 1500
tctatcgggc aaaaacaagc atatttcgct aattttcgcc gaattaaccg catttgcgcc 1560
gctacaacat tactaacggg ttcctcctcc aaatcccaaa gctgttgccg aattttactg 1620
ccggagagaa tgcgatctgg gttttgcatg aggtattgca gaatctgaaa ttccttgacc 1680
gtgagggtaa tggcttgggg ggcttgccct gtctgtctca ctactaattc ggtattgctg 1740
gggtcaaggc taaaattgcc cacccgaaga atttggggct gaaattgggg cgatcgccgt 1800
tggagagcgc gaacccgtgc gagtaattcc gccatcacaa aaggtttgac caaataatca 1860
tccgcccccg catccaagcc tctcactcga ttttctggtt ctcccaaggc agtcaacatc 1920
aatactggga gaggattatg ctgcgatcgc agtttttgac aaagctccaa gcctgacagt 1980
cctggcaaca accaatctag aattgccaca ccgtaatcag tccattgatt ttccagataa 2040
tgccaagcct gctgcccatc cgtcacccaa tccactacat acttctcgct gataagcacc 2100
ttcttaatca ccaagcctag atcttcttcg tcttctacca ataaaattcg catggtttaa 2160
gccagaatta ccacgaactt tatcctaatc acaaacagcc tatttcactt agatttcata 2220
ccccctctgg caaactggaa aaaattttcg tgccattttg tctctaaatg tgaggtgctg 2280
tgatgaattc ttatactgtc ggtacctatt tagcggagcg gcttgtccag attggtctca 2340
agcatcactt cgcagtcgcg ggcgactaca acctcgtcct tcttgacaac ctgcttttga 2400
acaaaaacat ggagcaggtt tattgctgta acgaactgaa ctgcggtttc agtgcagaag 2460
gttatgctcg tgccaaaggc gcagcagcag ccgtcgttac ctacagcgtc ggtgcgcttt 2520
ccgcatttga tgctatcggt ggcgcctatg cagaaaacct tccggttatc ctgatctccg 2580
gtgctccgaa caacaatgat cacgctgctg gtcacgtgtt gcatcacgct cttggcaaaa 2640
ccgactatca ctatcagttg gaaatggcca agaacatcac ggccgcagct gaagcgattt 2700
acaccccaga agaagctccg gctaaaatcg atcacgtgat taaaactgct cttcgtgaga 2760
agaagccggt ttatctcgaa atcgcttgca acattgcttc catgccctgc gccgctcctg 2820
gaccggcaag cgcattgttc aatgacgaag ccagcgacga agcttctttg aatgcagcgg 2880
ttgaagaaac cctgaaattc atcgccaacc gcgacaaagt tgccgtcctc gtcggcagca 2940

-continued

```
agctgcgcgc agctggtgct gaagaagctg ctgtcaaatt tgctgatgct ctcggtggcg   3000
cagttgctac catggctgct gcaaaaagct tcttcccaga agaaaacccg cattacatcg   3060
gtacctcatg ggtgaagtc agctatccgg gcgttgaaaa gacgatgaaa gaagccgatg   3120
cggttatcgc tctggctcct gtcttcaacg actactccac cactggttgg acggatattc   3180
ctgatcctaa gaaactggtt ctcgctgaac cgcgttctgt cgtcgttaac ggcgttcgct   3240
tccccagcgt tcatctgaaa gactatctga cccgtttggc tcagaaagtt tccaagaaaa   3300
ccggtgcttt ggacttcttc aaatccctca atgcaggtga actgaagaaa gccgctccgg   3360
ctgatccgag tgctccgttg gtcaacgcag aaatcgcccg tcaggtcgaa gctcttctga   3420
ccccgaacac gacggttatt gctgaaaccg gtgactcttg gttcaatgct cagcgcatga   3480
agctcccgaa cggtgctcgc gttgaatatg aaatgcagtg gggtcacatc ggttggtccg   3540
ttcctgccgc cttcggttat gccgtcggtg ctccggaacg tcgcaacatc ctcatggttg   3600
gtgatggttc cttccagctg acggctcagg aagtcgctca gatggttcgc ctgaaactgc   3660
cggttatcat cttcttgatc aataactatg gttacaccat cgaagttatg atccatgatg   3720
gtccgtacaa caacatcaag aactgggatt atgccggtct gatggaagtg ttcaacggta   3780
acggtggtta tgacagcggt gctggtaaag gcctgaaggc taaaaccggt ggcgaactgg   3840
cagaagctat caaggttgct ctggcaaaca ccgacggccc aaccctgatc gaatgcttca   3900
tcggtcgtga agactgcact gaagaattgg tcaaatgggg taagcgcgtt gctgccgcca   3960
acagccgtaa gcctgttaac aagctcctct agtttttggg gatcaattcg agctcagcaa   4020
gtttcatccc gacccccctca gggtcgggat ttttttattg tactagtaac gcccggttgc   4080
caccgggcgt tttttattcc gacattgcca taagtaaagg catcccctgc gtgataagat   4140
taccttcagt ttatggagga ctgaccatat gatcaaggct tatgccgctt tagaggctaa   4200
tggcaagttg cagccgttcg agtatgatcc gggcgcttta ggcgccaacg aagttgaaat   4260
cgaagttcaa tactgcggtg tttgtcattc cgacctcagt atgatcaaca atgagtgggg   4320
tatcagtaac tatccgttgg ttcccggcca cgaagttgtt ggcaccgttg ctgctatggg   4380
tgagggtgtt aatcacgtgg aagttggtga cctggttggt ttaggctggc acagtggtta   4440
ttgtatgact tgtcactcct gcctgagcgg ttatcataat ttgtgcgcta ccgccgagag   4500
tactatcgtt ggtcattatg gcggtttcgg tgaccgtgtg cgtgctaaag gtgtgtccgt   4560
tgttaagctg cccaagggta tcgatttggc ttccgctggt ccgttgtttt gcggtggtat   4620
cactgtgttt tcccccatgg ttgagttatc cctgaaaccg accgccaagg ttgccgttat   4680
tggtatcggt ggtctcggtc acctggccgt tcagttcttg cgtgcttggg gttgcgaggt   4740
taccgctttc actagctccg ctcgtaaaca gaccgaggtt ctggagctgg gtgcccatca   4800
tattttggac agtactaacc ccgaagccat tgcttccgcc gagggtaagt tcgattacat   4860
cattagtacc gttaatttaa aattggattg gaatctgtat atttccactt tagccccgca   4920
aggtcacttt catttcgtgg gtgttgttct cgaacccctc gacttgaact tgttcccgtt   4980
gctcatgggt cagcggagtg tgtccgctag tccggttggc tccccggcta ctatcgctac   5040
tatgctcgat ttcgccgttc ggcacgatat caagccggtt gttgagcagt tctccttcga   5100
ccaaattaat gaagccattg ctcacttgga gtccggtaag gctcactacc gtgtggtttt   5160
gagtcactcc aagaactgaa acgctcggtt gccgccgggc gtttttttatt cctgcaggag   5220
cagaagagca tacatctgga agcaaagcca ggaaagcggc ctatggagct gtgcggcagc   5280
gctcagtagg caatttttca aaatattgtt aagccttttc tgagcatggt atttttcatg   5340
```

```
gtattaccaa ttagcaggaa aataagccat tgaatataaa agataaaaat gtcttgttta   5400
caatagagtg ggggggtca gcctgccgcc ttgggccggg tgatgtcgta cttgcccgcc   5460
gcgaactcgg ttaccgtcca gcccagcgcg accagctccg gcaacgcctc gcgcacccgc   5520
tggcggcgct tgcgcatggt cgaaccactg gcctctgacg gccagacata gccgcacaag   5580
gtatctatgg aagccttgcc ggttttgccg gggtcgatcc agccacacag ccgctggtgc   5640
agcaggcggg cggtttcgct gtccagcgcc cgcacctcgt ccatgctgat gcgcacatgc   5700
tggccgccac ccatgacggc ctgcgcgatc aaggggttca gggccacgta caggcgcccg   5760
tccgcctcgt cgctggcgta ctccgacagc agccgaaacc cctgccgctt gcggccattc   5820
tgggcgatga tggatacctt ccaaaggcgc tcgatgcagt cctgtatgtg cttgagcgcc   5880
ccaccactat cgacctctgc cccgatttcc tttgccagcg cccgatagct acctttgacc   5940
acatggcatt cagcggtgac ggcctcccac ttgggttcca ggaacagccg gagctgccgt   6000
ccgccttcgg tcttgggttc cgggccaagc actaggccat taggcccagc catggccacc   6060
agcccttgca ggatgcgcag atcatcagcg cccagcggct ccgggccgct gaactcgatc   6120
cgcttgccgt cgccgtagtc atacgtcacg tccagcttgc tgcgcttgcg ctcgccccgc   6180
ttgagggcac ggaacaggcc gggggccaga cagtgcgccg ggtcgtgccg gacgtggctg   6240
aggctgtgct tgttcttagg cttcaccacg gggcaccccc ttgctcttgc gctgcctctc   6300
cagcacggcg ggcttgagca ccccgccgtc atgccgcctg aaccaccgat cagcgaacgg   6360
tgcgccatag ttggccttgc tcacaccgaa gcggacgaag aaccggcgct ggtcgtcgtc   6420
cacaccccat tcctcggcct cggcgctggt catgctcgac aggtaggact gccagcggat   6480
gttatcgacc agtaccgagc tgccccggct ggcctgctgc tggtcgcctg cgcccatcat   6540
ggccgcgccc ttgctggcat ggtgcaggaa cacgatagag cacccggtat cggcggcgat   6600
ggcctccatg cgaccgatga cctgggccat ggggccgctg gcgttttctt cctcgatgtg   6660
gaaccggcgc agcgtgtcca gcaccatcag gcggcggccc tcggcggcgc gcttgaggcc   6720
gtcgaaccac tccggggcca tgatgttggg caggctgccg atcagcggct ggatcagcag   6780
gccgtcagcc acggcttgcc gttcctcggc gctgaggtgc gccccaaggg cgtgcaggcg   6840
gtgatgaatg gcggtgggcg ggtcttcggc gggcaggtag atcaccgggc cggtgggcag   6900
ttcgcccacc tccagcagat ccggcccgcc tgcaatctgt gcggccagtt gcagggccag   6960
catggattta ccggcaccac cgggcgacac cagcgccccg accgtaccgg ccaccatgtt   7020
gggcaaaacg tagtccagcg gtggcggcgc tgctgcgaac gcctccagaa tattgatagg   7080
cttatgggta gccattgatt gcctcctttg caggcagttg gtggttaggc gctggcgggg   7140
tcactacccc cgccctgcgc cgctctgagt tcttccaggc actcgcgcag cgcctcgtat   7200
tcgtcgtcgg tcagccagaa cttgcgctga cgcatccctt tggccttcat gcgctcggca   7260
tatcgcgctt ggcgtacagc gtcagggctg gccagcaggt cgccggtctg cttgtccttt   7320
tggtctttca tatcagtcac cgagaaactt gccggggccg aaaggcttgt cttcgcggaa   7380
caaggacaag gtgcagccgt caaggttaag gctggccata tcagcgactg aaaagcggcc   7440
agcctcggcc ttgtttgacg tataaccaaa gccaccgggc aaccaatagc ccttgtcact   7500
tttgatcagg tagaccgacc ctgaagcgct tttttcgtat tccataaaac cccccttctgt   7560
gcgtgagtac tcatagtata acaggcgtga gtaccaacgc aagcactaca tgctgaaatc   7620
tggcccgccc ctgtccatgc ctcgctggcg gggtgccggt gcccgtgcca gctcggcccg   7680
```

-continued

```
cgcaagctgg acgctgggca gacccatgac cttgctgacg gtgcgctcga tgtaatccgc   7740
ttcgtggccg ggcttgcgct ctgccagcgc tgggctggcc tcggccatgg ccttgccgat   7800
ttcctcggca ctgcggcccc ggctggccag cttctgcgcg gcgataaagt cgcacttgct   7860
gaggtcatca ccgaagcgct tgaccagccc ggccatctcg ctgcggtact cgtccagcgc   7920
cgtgcgccgg tggcggctaa gctgccgctc gggcagttcg aggctggcca gcctgcgggc   7980
cttctcctgc tgccgctggg cctgctcgat ctgctggcca gcctgctgca ccagcgccgg   8040
gccagcggtg gcggtcttgc ccttggattc acgcagcagc acccacggct gataaccggc   8100
gcgggtggtg tgcttgtcct tgcggttggt gaagcccgcc aagcggccat agtggcggct   8160
gtcggcgctg gccgggtcgg cgtcgtactc gctggccagc gtccgggcaa tctgcccccg   8220
aagttcaccg cctgcggcgt cggccacctt gacccatgcc tgatagttct tcgggctggt   8280
ttccactacc agggcaggct cccggccctc ggctttcatg tcatccaggt caaactcgct   8340
gaggtcgtcc accagcacca gaccatgccg ctcctgctcg gcgggcctga tatacacgtc   8400
attgccctgg gcattcatcc gcttgagcca tggcgtgttc tggagcactt cggcggctga   8460
ccattcccgg ttcatcatct ggccggtggt ggcgtccctg acgccgatat cgaagcgctc   8520
acagcccatg gccttgagct gtcggcctat ggcctgcaaa gtcctgtcgt tcttcatcgg   8580
gccaccaagc gcagccagat cgagccgtcc tcggttgtca gtggcgtcag gtcgagcaag   8640
agcaacgatg cgatcagcag caccaccgta ggcatcatgg aagccagcat cacggttagc   8700
catagcttcc agtgccaccc ccgcgacgcg ctccgggcgc tctgcgcggc gctgctcacc   8760
tcggcggcta cctcccgcaa ctctttggcc agctccaccc atgccgcccc tgtctggcgc   8820
tgggctttca gccactccgc cgcctgcgcc tcgctggcct gctgggtctg gctcatgacc   8880
tgccgggctt cgtcggccag tgtcgccatg ctctgggcca gcggttcgat ctgctccgct   8940
aactcgttga tgcctctgga tttcttcact ctgtcgattg cgttcatggt ctattgcctc   9000
ccggtattcc tgtaagtcga tgatctgggc gttggcggtg tcgatgttca gggccacgtc   9060
tgcccggtcg gtgcggatgc cccggccttc catctccacc acgttcggcc ccaggtgaac   9120
accgggcagg cgctcgatgc cctgcgcctc aagtgttctg tggtcaatgc gggcgtcgtg   9180
gccagcccgc tctaatgccc ggttggcatg gtcggcccat gcctcgcggg tctgctcaag   9240
ccatgccttg ggcttgagcg cttcggtctt ctgtgccccg cccttctccg ggtcttgcc    9300
gttgtaccgc ttgaaccact gagcggcggg ccgctcgatg ccgtcattga tccgctcgga   9360
gatcatcagg tggcagtgcg ggttctcgcc gccaccggca tggatggcca gcgtatacgg   9420
caggcgctcg gcaccggtca ggtgctgggc gaactcggac gccagcgcct tctgctggtc   9480
gagggtcagc tcgaccggca gggcaaattc gacctccttg aacagccgcc cattggcgcg   9540
ttcatacagg tcggcagcat cccagtagtc ggcgggccgc tcgacgaact ccggcatgtg   9600
cccggattcg gcgtgcaaga cttcatccat gtcgcgggca tacttgcctt cgcgctggat   9660
gtagtcggcc ttggccctgg ccgattggcc gcccgacctg ctgccggttt tcgccgtaag   9720
gtgataaatc gccatgctgc ctcgctgttg cttttgcttt tcggctccat gcaatggccc   9780
tcggagagcg caccgcccga agggtggccg ttaggccagt ttctcgaaga gaaaccggta   9840
agtgcgccct cccctacaaa gtagggtcgg gattgccgcc gctgtgcctc catgatagcc   9900
tacgagacag cacattaaca atggggtgtc aagatggtta aggggagcaa caaggcggcg   9960
gatcggctgg ccaagctcga agaacaacga gcgcgaatca atgccgaaat tcagcgggtg  10020
cgggcaaggg aacagcagca agagcgcaag aacgaaacaa ggcgcaaggt gctggtgggg  10080
```

gccatgattt tggccaaggt gaacagcagc gagtggccgg aggatcggct catggcggca 10140
atggatgcgt accttgaacg cgaccacgac cgcgccttgt tcggtctgcc gccacgccag 10200
aaggatgagc cgggctgaat gatcgaccga gacaggccct gcggggctgc acacgcgccc 10260
ccacccttcg ggtaggggga aaggccgcta aagcggctaa aagcgctcca gcgtatttct 10320
gcggggtttg gtgtggggtt tagcgggctt tgcccgcctt tccccctgcc gcgcagcggt 10380
ggggcggtgt gtagcctagc gcagcgaata gaccagctat ccggcctctg gccgggcata 10440
ttgggcaagg gcagcagcgc cccacaaggg cgctgataac cgcgcctagt ggattattct 10500
tagataatca tggatggatt tttccaacac cccgccagcc cccgccccctg ctgggtttgc 10560 aggtttgggg gcgtgacagt tattgcaggg gttcgtgaca gttattgcag gggggcgtga 10620
cagttattgc aggggttcgt gacagttagt acgggagtga cgggcactgg ctggcaatgt 10680
ctagcaacgg caggcatttc ggctgagggt aaaagaactt tccgctaagc gatagactgt 10740
atgtaaacac agtattgcaa ggacgcggaa catgcctcat gtggcggcca ggacggccag 10800
ccgggatcgg gatactggtc gttaccagag ccaccgaccc gagcaaaccc ttctctatca 10860
gatcgttgac gagtattacc cggcattcgc tgcgcttatg gcagagcagg gaaaggaatt 10920
gccgggctat gtgcaacggg aatttgaaga atttctccaa tgcgggcggc tggagcatgg 10980
ctttctacgg gttcgctgcg agtcttgcca cgccgagcac ctggtcgctt tcagctgtaa 11040
tccgggcagc gcaacggaac attcatcagt gtaaaaatgg aatcaataaa gccctgcgca 11100
gcgcgcaggg tcagcctgaa tacgcgtgct cgaattgaca taagcctgtt cggttcgtaa 11160
actgtaatgc aagtagcgta tgcgctcacg caactggtcc agaaccttga ccgaacgcag 11220
cggtggtaac ggcgcagtgg cggttttcat ggcttgttat gactgttttt ttgtacagtc 11280
tatgcctcgg gcatccaagc agcaagcgcg ttacgccgtg ggtcgatgtt tgatgttatg 11340
gagcagcaac gatgttacgc agcagcaacg atgttacgca gcagggcagt cgccctaaaa 11400
caaagttagg tggctcaagt atgggcatca ttcgcacatg taggctcggc cctgaccaag 11460
tcaaatccat gcgggctgct cttgatcttt tcggtcgtga gttcggagac gtagccacct 11520
actcccaaca tcagccggac tccgattacc tcgggaactt gctccgtagt aagacattca 11580
tcgcgcttgc tgccttcgac caagaagcgg ttgttggcgc tctcgcggct tacgttctgc 11640
ccaggtttga gcagccgcgt agtgagatct atatctatga tctcgcagtc tccggcgagc 11700
accggaggca gggcattgcc accgcgctca tcaatctcct caagcatgag gccaacgcgc 11760
ttggtgctta tgtgatctac gtgcaagcag attacggtga cgatcccgca gtggctctct 11820
atacaaagtt gggcatacgg gaagaagtga tgcactttga tatcgaccca agtaccgcca 11880
cctaacaatt cgttcaagcc gagatcggct tcccggccct agacgcgtat tcaggctgac 11940
cctgcgcgct gcgcagggct ttattgattc catttttaca ctgatgaatg ttccgttgcg 12000
ctgcccggat tacagatcct ctagaagaac agcaaggccg ccaatgcctg acgatgcgtg 12060
gagaccgaaa ccttgcgctc gttcgccagc caggacagaa atgcctcgac ttcgctgctg 12120
cccaaggttg ccgggtgacg cacaccgtgg aaacggatga aggcacgaac ccagtggaca 12180
taagcctgtt cggttcgtaa gctgtaatgc aagtagcgta tgcgctcacg caactggtcc 12240
agaaccttga ccgaacgcag cggtggtaac ggcgcagtgg cggttttcat ggcttgttat 12300
gactgttttt ttggggtaca gtctatgcct cgggcatcca agcagcaagc gcgttacgcc 12360
gtgggtcgat gtttgatgtt atggagcagc aacgatgtta cgcagcaggg cagtcgccct 12420
aaaacaaagt taaacatcat gagggaagcg gtgatcgccg aagtatcgac tcaactatca 12480
gaggtagttg gcgtcatcga gcgccatctc gaaccgacgt tgctggccgt acatttgtac 12540
ggctccgcag tggatggcgg cctgaagcca cacagtgata ttgatttgct ggttacggtg 12600
accgtaaggc ttgatgaaac aacgcggcga gctttgatca acgacctttt ggaaacttcg 12660
gcttcccctg gagagagcga gattctccgc gctgtagaag tcaccattgt tgtgcacgac 12720
gacatcattc cgtggcgtta tccagctaag cgcgaactgc aatttggaga atggcagcgc 12780
aatgacattc ttgcaggtat cttcgagcca gccacgatcg acattgatct ggctatcttg 12840
ctgacaaaag caagagaaca tagcgttgcc ttggtaggtc cagcggcgga ggaactcttt 12900
gatccggttc ctgaacagga tctatttgag gcgctaaatg aaaccttaac gctatggaac 12960
tcgccgcccg actgggctgg cgatgagcga aatgtagtgc ttacgttgtc ccgcatttgg 13020
tacagcgcag taaccggcaa aatcgcgccg aaggatgtcg ctgccgactg ggcaatggag 13080
cgcctgccgg cccagtatca gcccgtcata cttgaagcta gacaggctta tcttggacaa 13140
gaagaagatc gcttggcctc gcgcgcagat cagttggaag aatttgtcca ctacgtgaaa 13200
ggcgagatca ccaaggtagt cggcaaataa tgtctaacaa ttcgttcaag ccgacgccgc 13260
ttcgcggcgc ggcttaactc aagctctaga g 13291

<210> SEQ ID NO 69
<211> LENGTH: 9842
<212> TYPE: DNA
<213> ORGANISM: Artificial
<220> FEATURE:
<223> OTHER INFORMATION: Synthetic vector construct #1470 pAQ3-corR-PcorT*1-zmPDCdeg_spf-Prbc*-synADHoop for transformation of Synechococcus sp. PCC7002 via integration into the endogenous pAQ3 plasmid

<400> SEQUENCE: 69
aagaacatcg attttccatg gcagctgaga atattgtagg agatcttcta gaaagatgtc 60
gaccatgcgt ccaaaacttt caccatcctt tccctatcaa cctttactgc actaaagaca 120
agtgagatag cagtggcaat ctggctttgc aatcaatgtt tccactaaag cgtttagcgt 180
tactgcggct agaagtcctc caccgaggct cccctgaatg gtgatatggg gaatgggact 240
ggtcatcagt cgtcgttttg cccccggagc atgactaaaa ccgatcggca ttccgatcac 300
aagagccggc tgaatatgtt gttgctctat cagcttacag gcagtgagta aaacagaagg 360
ggcatagccg atcgccagca cacatccttg gggaatctgt tgtaaccgct gttgccaatg 420
gtcatggtgc caaaaagctt gctcggcttc cctaagccct gtgatgtgag ggtcgtcaat 480
cagcgtttta accgtacatc ctaaatgagc taaccgagtt tgatcaagag ccgcagccac 540
aaccggaaca tcggtgacga ctggacaccc tgctttcagt gcatctcgtg ccgaggcgat 600
cgctccctga ctcaatcgaa cggcgtttac caagctaaca tcaccacagg ccagcactaa 660
ttgatgtagt aagtgaatgg taatttcaga gtaagccgat aaatccggta gcaggtgttt 720
gagggattcc tgaaaggctt ctggatgagt tgttgtctcc gcatctaggt tcgtccacaa 780
ctgatcgagt tttcctaacc cctcctggac atccacatca agctgtttca gttgggccag 840
agcttccgct tgggtaatct ggcaactctg gtcgcgtccc agtaatcctt ctaaagcaga 900
tgcggtttgg cggagtcgag taatctgctg aatcacagcc tgatattgct gttgcaactg 960
caccattagg gtgggatcaa ggctctcttc agaatggcta tccagcagtt gccgaatatg 1020
agacaactga aagccctgct gtttgagggc aatgactcgt tggagccgtt gtacgtcctg 1080
ctgagtataa aggcggtagt tgccctctga gcgttgaacg gggggaagca atcccagggt 1140
gtggtaatgg cgcaccatgc gaggcgtaac gccacctccc actgcatctg tgagttcttt 1200
aatcgttaag tgattagtct tcatgacttt agtttactca aaaccttgac attgacacta 1260
atgttaaggt ttaggctgag aaggtaaaaa tcgaggataa aaagcatgaa ttcctacacc 1320
gttggcactt acctggctga acgcttggtt cagatcggct taaaacacca ttttgctgtt 1380
gctggtgatt ataatttggt tttgttagat aatttattgc tcaataagaa tatggaacag 1440
gtgtactgtt gcaatgagtt aaattgtggc ttttccgctg agggctacgc ccgtgctaag 1500
ggtgctgctg ctgctgttgt gacttattct gttggcgctt tgagtgcttt tgacgccatt 1560
ggcggtgctt acgctgagaa tttgccagtg attttaatta gtggcgcccc aaataataac 1620
gaccatgccg ccggccatgt cctccaccat gccttgggta agactgatta ccattaccaa 1680
ctggagatgg ctaaaaatat taccgctgct gccgaagcta tctatactcc tgaggaagcc 1740
ccagccaaga ttgaccatgt catcaagacc gccttgcggg aaaaaaaacc agtgtactta 1800
gagattgcct gtaatatcgc cagtatgcct tgtgctgccc ccggtccagc ttctgctctc 1860
tttaacgatg aagcttctga tgaggccagt ctcaacgctg ctgtggagga aactttaaag 1920
tttattgcta atcgtgataa ggtggctgtt ttagttggtt ctaaattacg tgctgccggc 1980
gccgaggaag ccgccgttaa gtttgccgac gccttaggcg gtgctgtggc cactatggcc 2040
gccgctaagt ctttttttcc tgaagagaat ccacactata ttggcactag ctggggcgag 2100
gtttcttacc caggtgtgga gaaaaccatg aaggaggctg acgctgtgat tgccttagcc 2160
ccggttttta atgattatag tactaccggc tggaccgaca tcccggaccc gaaaaagtta 2220
gtgttagccg aaccacggag tgttgttgtg aatggtgtgc gttttccttc tgtgcactta 2280
aaggattact taactcggct cgcccagaag gtgagtaaaa agactggcgc cctcgatttt 2340
tttaagagtt taaacgctgg cgagttaaaa aaggctgccc cagccgaccc atccgcccca 2400
ctcgttaatg ctgaaattgc tcggcaggtt gaggccttgt taactccaaa taccaccgtg 2460
atcgccgaaa ctggcgatag ttggtttaac gcccaacgta tgaaattacc aaatggcgcc 2520
cgtgtggagt acgagatgca atggggccat attggctgga gtgtgccggc tgcttttggc 2580
tacgctgttg gcgccccaga gcggcgtaat attttaatgg tgggcgacgg cagttttcag 2640
ttaaccgccc aagaggttgc ccaaatggtg cgtttaaagt taccagtgat tatttttctc 2700
attaacaatt acggctatac tattgaggtg atgattcacg acggcccata taataatatt 2760
aaaaattggg actacgctgg cttaatggag gtctttaatg gcaatggcgg ctacgattct 2820
ggcgccggca agggtttaaa agccaagact ggcggtgagt tagctgaagc cattaaagtg 2880
gccttagcta atactgatgg tcctacttta attgagtgtt ttattggccg gggaagattgt 2940 accgaggaac tcgttaagtg gggcaaacgt gtggccgctg ctaattctcg gaaacccgtg 3000
aataaattat tatgaaatat tttagccgcc ccagtcagta atgactgggg cgtttttttat 3060 tgggagctca ctagtcgatc gacattgcca taagtaaagg catcccctgc gtgataagat 3120
taccttcagt ttatggagga ctgaccatat gattaaagcc tacgctgccc tggaagccaa 3180
cggaaaactc caaccctttg aatacgaccc cggtgccctg ggtgctaatg aggtggagat 3240
tgaggtgcag tattgtgggg tgtgccacag tgatttgtcc atgattaata acgaatgggg 3300
catttccaat tacccccctag tgccgggtca tgaggtggtg ggtactgtgg ccgccatggg 3360
cgaaggggtg aaccatgttg aggtggggga tttagtgggg ctgggttggc attcgggcta 3420
ctgcatgacc tgccatagtt gtttatctgg ctaccacaac ctttgtgcca cggcggaatc 3480
gaccattgtg ggccactacg gtggctttgg cgatcgggtt cgggccaagg gagtcagcgt 3540
ggtgaaatta cctaaaggca ttgacctagc cagtgccggg ccccttttct gtggaggaat 3600
taccgttttc agtcctatgg tggaactgag tttaaagccc actgcaaaag tggcagtgat 3660
cggcattggg ggcttgggcc atttagcggt gcaatttctc cgggcctggg gctgtgaagt 3720
gactgccttt acctccagtg ccaggaagca aacggaagtg ttggaattgg gcgctcacca 3780
catactagat tccaccaatc cagaggcgat cgccagtgcg gaaggcaaat ttgactatat 3840
tatctccact gtgaacctga agcttgactg gaacttatac atcagcaccc tggcgcccca 3900
gggacatttc cactttgttg ggtggtgtt ggagcctttg gatctaaatc tttttcccct 3960
tttgatggga caacgctccg tttctgcctc cccagtgggt agtcccgcca ccattgccac 4020
catgttggac tttgctgtgc gccatgacat taaacccgtg gtggaacaat ttagctttga 4080
tcagatcaac gaggcgatcg cccatctaga aagcggcaaa gcccattatc gggtagtgct 4140
cagccatagt aaaaattagc tctgcaaagg ttgcttctgg gtccgtggaa cgctcggttg 4200
ccgccgggcg ttttttattc ctgcaggatc cacaggacgg gtgtggtcgc catgatcgcg 4260
tagtcgatag tggctccaag tagcgaagcg agcaggactg ggcggcggcc aaagcggtcg 4320
gacagtgctc cgagaacggg tgcgcataga aattgcatca acgcatatag cgctagcagc 4380
acgccatagt gactggcgat gctgtcggaa tggacgatcg aattggccgc ggcgttgtga 4440
caatttaccg aacaactccg cggccgggaa gccgatctcg gcttgaacga attgttaggt 4500
ggcggtactt gggtcgatat caaagtgcat cacttcttcc cgtatgccca actttgtata 4560
gagagccact gcgggatcgt caccgtaatc tgcttgcacg tagatcacat aagcaccaag 4620
cgcgttggcc tcatgcttga ggagattgat gagcgcggtg gcaatgccct gcctccggtg 4680
ctcgccggag actgcgagat catagatata gatctcacta cgcggctgct caaacttggg 4740
cagaacgtaa gccgcgagag cgccaacaac cgcttcttgg tcgaaggcag caagcgcgat 4800
gaatgtctta ctacggagca agttcccgag gtaatcggag tccggctgat gttgggagta 4860
ggtggctacg tctccgaact cacgaccgaa aagatcaaga gcagcccgca tggatttgac 4920
ttggtcaggg ccgagcctac atgtgcgaat gatgcccata cttgagccac ctaactttgt 4980
tttagggcga ctgccctgct gcgtaacatc gttgctgctg cgtaacatcg ttgctgctcc 5040
ataacatcaa acatcgaccc acggcgtaac gcgcttgctg cttggatgcc cgaggcatag 5100
actgtacaaa aaaacagtca taacaagcca tgaaaaccgc cactgcgccg ttaccaccgc 5160
tgcgttcggt caaggttctg gaccagttgc gtgagcgcat acgctacttg cattacagtt 5220
tacgaaccga acaggcttat gtcaattcga gcatcgattg tatgggaagc ccgatgcgcc 5280
agagttgttt ctgaaacatg gcaaaggtag cgttgccaat gatgttacag atgagatggt 5340
cagactaaac tggctgacgg aatttatgcc tcttccgacc atcaagcatt ttatccgtac 5400
tcctgatgat gcatggttac tcaccactgc gatccccgat cccccccctcg atcaaggcag 5460
gcaacgcccc cggcgatcgc cgtccttttt tatgccacat cttcggtata taaatccgcc 5520
tgaaaatctg cgaatacttg accgatatcc tgacccaaga tcactaaacc ttcattaacg 5580
gtttggtatt tgatttcgat gagggtaggc agtttccccc gatcaagttc ctccactcct 5640
tctcgaatgt attggtctag gacaaaatct aaaaattctt gctgctttcc ggtgtacttc 5700
gagaaaatca gatctcgatg cttaattact cgctcttctc tgctaatggg tttggtgttg 5760
taggcaaccc aagtcaggac atcatagaca tcactttttt ccgcttcggc aatgcgtgcg 5820

-continued atcgccttca gttgggtgtc accgtagcct ttttccgcga gtccggtcag gaacgattta 5880
cgggtatcgg gtttccccca gatggtgcgt agttcggctt catccttgaa gaggtcgggc 5940
aggtcgccaa atagcttttc gataaattct tgggcggaaa tgggtttacc atcagcatcc 6000
caaaaagttg tggatgcata gcttgagtat tctatagtgt cacctaaata gcttggcgta 6060
atcatggtca tagctgtttc ctgtgtgaaa ttgttatccg ctcacaattc cacacaacat 6120
acgagccgga agcataaagt gtaaagcctg gggtgcctaa tgagtgagct aactcacatt 6180
aattgcgttg cgctcactgc ccgctttcca gtcgggaaac ctgtcgtgcc agctgcatta 6240
atgaatcggc caacgcgcgg ggagaggcgg tttgcgtatt gggcgctctt ccgcttcctc 6300
gctcactgac tcgctgcgct cggtcgttcg gctgcggcga gcggtatcag ctcactcaaa 6360
ggcggtaata cggttatcca cagaatcagg ggataacgca ggaaagaaca tgtgagcaaa 6420
aggccagcaa aaggccagga accgtaaaaa ggccgcgttg ctggcgtttt tccataggct 6480
ccgcccccct gacgagcatc acaaaaatcg acgctcaagt cagaggtggc gaaacccgac 6540
aggactataa agataccagg cgtttccccc tggaagctcc ctcgtgcgct ctcctgttcc 6600
gaccctgccg cttaccggat acctgtccgc ctttctccct tcgggaagcg tggcgctttc 6660
tcatagctca cgctgtaggt atctcagttc ggtgtaggtc gttcgctcca agctgggctg 6720
tgtgcacgaa ccccccgttc agcccgaccg ctgcgcctta tccggtaact atcgtcttga 6780
gtccaacccg gtaagacacg acttatcgcc actggcagca gccactggta acaggattag 6840
cagagcgagg tatgtaggcg gtgctacaga gttcttgaag tggtggccta actacggcta 6900
cactagaagg acagtatttg gtatctgcgc tctgctgaag ccagttacct tcggaaaaag 6960
agttggtagc tcttgatccg gcaaacaaac caccgctggt agcggtggtt tttttgtttg 7020
caagcagcag attacgcgca gaaaaaaagg atctcaagaa gatcctttga tcttttctac 7080
ggggtctgac gctcagtgga acgaaaactc acgttaaggg attttggtca tgagattatc 7140
aaaaaggatc ttcacctaga tccttttaaa ttaaaaatga agttttaaat caatctaaag 7200
tatatatgag taaacttggt ctgacagtta ccaatgctta atcagtgagg cacctatctc 7260
agcgatctgt ctatttcgtt catccatagt tgcctgactc cccgtcgtgt agataactac 7320
gatacgggag ggcttaccat ctggccccag tgctgcaatg ataccgcgag acccacgctc 7380
accggctcca gatttatcag caataaacca gccagccgga agggccgagc gcagaagtgg 7440
tcctgcaact ttatccgcct ccatccagtc tattaattgt tgccgggaag ctagagtaag 7500
tagttcgcca gttaatagtt tgcgcaacgt tgttggcatt gctacaggca tcgtggtgtc 7560
acgctcgtcg tttggtatgg cttcattcag ctccggttcc caacgatcaa ggcgagttac 7620
atgatccccc atgttgtgca aaaaagcggt tagctccttc ggtcctccga tcgttgtcag 7680
aagtaagttg gccgcagtgt tatcactcat ggttatggca gcactgcata attctcttac 7740
tgtcatgcca tccgtaagat gcttttctgt gactggtgag tactcaacca agtcattctg 7800
agaatagtgt atgcggcgac cgagttgctc ttgcccggcg tcaatacggg ataataccgc 7860
gccacatagc agaactttaa aagtgctcat cattggaaaa cgttcttcgg ggcgaaaact 7920
ctcaaggatc ttaccgctgt tgagatccag ttcgatgtaa cccactcgtg cacccaactg 7980
atcttcagca tcttttactt tcaccagcgt ttctgggtga gcaaaaacag gaaggcaaaa 8040
tgccgcaaaa aagggaataa gggcgacacg gaaatgttga atactcatac tcttcctttt 8100
tcaatattat tgaagcattt atcagggtta ttgtctcatg agcggataca tatttgaatg 8160
tatttagaaa aataaacaaa taggggttcc gcgcacattt ccccgaaaag tgccacctgt 8220

```
atgcggtgtg aaataccgca cagatgcgta aggagaaaat accgcatcag gcgaaattgt   8280

aaacgttaat attttgttaa aattcgcgtt aaatatttgt taaatcagct cattttttaa   8340

ccaataggcc gaaatcggca aaatccctta taaatcaaaa gaatagaccg agatagggtt   8400

gagtgttgtt ccagtttgga acaagagtcc actattaaag aacgtggact ccaacgtcaa   8460

agggcgaaaa accgtctatc agggcgatgg cccactacgt gaaccatcac ccaaatcaag   8520

ttttttgcgg tcgaggtgcc gtaaagctct aaatcggaac cctaaaggga gcccccgatt   8580

tagagcttga cggggaaagc cggcgaacgt ggcgagaaag gaagggaaga aagcgaaagg   8640

agcgggcgct agggcgctgg caagtgtagc ggtcacgctg cgcgtaacca ccacacccgc   8700

cgcgcttaat gcgccgctac agggcgcgtc cattcgccat tcaggctgcg caactgttgg   8760

gaagggcgat cggtgcgggc ctcttcgcta ttacgccagc tggcgaaagg gggatgtgct   8820

gcaaggcgat taagttgggt aacgccaggg ttttcccagt cacgacgttg taaaacgacg   8880

gccagtgaat tgtaatacga ctcactatag ggcgaattgg gcccgacgtc gcatgctccc   8940

ggccgccatc actagtttgg agataatcgc ctttgggcag ttatctagaa tgtacacaaa   9000

tttattacca tctaagacac gacaaaaaat acatactcat ttccaattac ctaacaagtt   9060

ttttatatct tggttacggt ctttgtcgca tattagaaat atttgcgctc atcattcaag   9120

gctctggaat atacagctag gagaatcacc taaattgcct gataggttaa aaggaaaatg   9180

gctctctaga gaagtattgg aggatattaa tcaaagaaac agccgtaaaa ttttcactgg   9240

cttatgttgt attcagtatc tcttagacag aattaaacca gagcataatt ttgcacagca   9300

tttaaaaaga acttttgaga tgtatccaga aatagaatct aaaaacttag gctttcccaa   9360

agattgggaa aatcagcctc tctggaaata atctaagagt cagaatttta atttgtcata   9420

actctttctc gttcaaggca gggcggcctg cacatactgg gaagcatatt cttcgatgcg   9480

cttaaagttt tgccgtggta gtttagcttg atgctcttcc acgttgaaac ctgctaagta   9540

gttacatacg gctgacagcg gcaaaaaatg tttgagtata aggccatagt tgatgcttgt   9600

tggaattaaa tttttaataa aattcctgtc tcagtttcct gaagcttgct ctaaacctcg   9660

ttcaaaaaaa atgcagaata aagttggtca agaggaacat attgaatatt tagctcgtag   9720

ttttcatgag agtcgattgc caagaaaacc cacgccacct acaacggttc ctgatgaggt   9780

ggttagcata gttcttaata taagttttaa tatacagcct gaaaatcttg agagaataaa   9840

ag                                                                  9842
```

<210> SEQ ID NO 70
<211> LENGTH: 10612
<212> TYPE: DNA
<213> ORGANISM: Artificial
<220> FEATURE:
<223> OTHER INFORMATION: Synthetic vector construct #1473
pAQ1::nrsRS-PnrsB193-PDC-PrbcL*-synADH_oop-Sp for transformation
of Synechococcus sp. PCC7002 via integration into the endogenous
pAQ1 plasmid

<400> SEQUENCE: 70

```
tcgacaaaat gaagtaccga agacaaccat cattggggtt gtctttttta ttggttaatt     60

ggcgaaagac tccaagggcg atcgcctttt aattaagttc tattcacctt ttctgagggg    120

taaacgcaga gtgaattggc taccttgatc cgcatcactc tggatttgga tagatccgtg    180

ataagcaagg gcgatcgcct gggcaatggc aagccctaaa cctgtccccc cggttttacg    240

ggaacggtca tcattaactc ggtaaaaccg tttaaaaatc tgttgttgtt gctctgggga    300
```

-continued

```
aatgcccata cctgtatccg taacggtaat tttggcatgg cgatcatccg tttttaaatt    360
tacattcacg ctgccacctt tgggggtata acgcagggca ttgtcgagga gattggacac    420
tagacgatag agttgggatt cgttcccttg cacataaatt tcctgtttgg ggagttcgtt    480
cgtgagggta ataccgacgg cgatcgccat ctctaaaaat tcttcggtga ggtcactgac    540
cagatcattc agacaacaat ccctccagtt ttctgaagtt tggggttgct ccaaacgact    600
gagcaacagc agatcattaa ttaattgact gagccgccgc ccctgccgtt cgacggtctg    660
gagcatggtt tggatgtcct gttgatcccc accattgagg cgcaaaatca cttcgacggt    720
tgccagcaaa ctcgcgaggg gcgatcgcag ttcgtgggcg gcatcagcgg taaattgttg    780
ctgctgttgg taagcgtcgt agatagggcg catggctaaa cctgctaacc accaactaga    840
gagggtaact acgccgagag caagaggtaa actgacccct aaaacccagc gaatccgttg    900
attttcctga tcaaaggcca tgaggctccg accaatctgg agataacccc atgaatcttg    960
aatatttgca gcgtcgtggg tgtaggcact atgaagaatc gtcgtaaatt gtcggtaacg   1020
gtcatcctcc tgtctaatgg tttgccatgt ctccggttgt aggttctggg ataagctctg   1080
cggttgattg ggggaaaagg caactaattg accttgatgg ttaaataggc ggatgtaata   1140
aaggcggcga tcgctaatgc ccatcgtgtg ccgttcaatt aaagttggtg tagtgtcaca   1200
gggctgatta acaaggcata gatctggaaa aatttgctgt aaagttcctg tggggttcgc   1260
attctccggc agtattggtt ctaggctatc gtgcagcgtt ccggcgattg actccacttc   1320
ccgttcaagg gcaacccaat tcgcttgcac aatggaacga taaacccccca gccctaaagc   1380
actcaaaatt ccccccatta cgagggcata ccagagagca agacggaggc gactgcgagc   1440
aaacagacga taactgttca tggttctacc gtaaaccgat aaccttggcc ggggacagtt   1500
tctatcgggc aaaaacaagc atatttcgct aattttcgcc gaattaaccg catttgcgcc   1560
gctacaacat tactaacggg ttcctcctcc aaatcccaaa gctgttgccg aattttactg   1620
ccggagagaa tgcgatctgg gttttgcatg aggtattgca gaatctgaaa ttccttgacc   1680
gtgagggtaa tggcttgggg ggcttgccct gtctgtctca ctactaattc ggtattgctg   1740
gggtcaaggc taaaattgcc cacccgaaga atttggggct gaaattgggg cgatcgccgt   1800
tggagagcgc gaacccgtgc gagtaattcc gccatcacaa aaggtttgac caaataatca   1860
tccgcccccg catccaagcc tctcactcga ttttctggtt ctcccaaggc agtcaacatc   1920
aatactggga gaggattatg ctgcgatcgc agtttttgac aaagctccaa gcctgacagt   1980
cctggcaaca accaatctag aattgccaca ccgtaatcag tccattgatt ttccagataa   2040
tgccaagcct gctgcccatc cgtcacccaa tccactacat acttctcgct gataagcacc   2100
ttcttaatca ccaagcctag atcttcttcg tcttctacca ataaaattcg catggtttaa   2160
gccagaatta ccacgaactt tatcctaatc acaaacagcc tatttcactt agatttcata   2220
ccccctctgg caaactggaa aaaattttcg tgccattttg tctctaaatg tgaggtgctg   2280
tgatgaattc ttatactgtc ggtacctatt tagcggagcg gcttgtccag attggtctca   2340
agcatcactt cgcagtcgcg ggcgactaca acctcgtcct tcttgacaac ctgcttttga   2400
acaaaaacat ggagcaggtt tattgctgta acgaactgaa ctgcggtttc agtgcagaag   2460
gttatgctcg tgccaaaggc gcagcagcag ccgtcgttac ctacagcgtc ggtgcgcttt   2520
ccgcatttga tgctatcggt ggcgcctatg cagaaaacct tccggttatc ctgatctccg   2580
gtgctccgaa caacaatgat cacgctgctg gtcacgtgtt gcatcacgct cttggcaaaa   2640
```

-continued

```
ccgactatca ctatcagttg gaaatggcca agaacatcac ggccgcagct gaagcgattt   2700
acaccccaga agaagctccg gctaaaatcg atcacgtgat taaaactgct cttcgtgaga   2760
agaagccggt ttatctcgaa atcgcttgca acattgcttc catgccctgc gccgctcctg   2820
gaccggcaag cgcattgttc aatgacgaag ccagcgacga agcttctttg aatgcagcgg   2880
ttgaagaaac cctgaaattc atcgccaacc gcgacaaagt tgccgtcctc gtcggcagca   2940
agctgcgcgc agctggtgct gaagaagctg ctgtcaaatt tgctgatgct ctcggtggcg   3000
cagttgctac catggctgct gcaaaaagct tcttcccaga agaaaacccg cattacatcg   3060
gtacctcatg gggtgaagtc agctatccgg gcgttgaaaa gacgatgaaa gaagccgatg   3120
cggttatcgc tctggctcct gtcttcaacg actactccac cactggttgg acggatattc   3180
ctgatcctaa gaaactggtt ctcgctgaac cgcgttctgt cgtcgttaac ggcgttcgct   3240
tccccagcgt tcatctgaaa gactatctga cccgtttggc tcagaaagtt tccaagaaaa   3300
ccggtgcttt ggacttcttc aaatccctca atgcaggtga actgaagaaa gccgctccgg   3360
ctgatccgag tgctccgttg gtcaacgcag aaatcgcccg tcaggtcgaa gctcttctga   3420
ccccgaacac gacggttatt gctgaaaccg gtgactcttg gttcaatgct cagcgcatga   3480
agctcccgaa cggtgctcgc gttgaatatg aaatgcagtg gggtcacatc ggttggtccg   3540
ttcctgccgc cttcggttat gccgtcggtg ctccggaacg tcgcaacatc ctcatggttg   3600
gtgatggttc cttccagctg acggctcagg aagtcgctca gatggttcgc ctgaaactgc   3660
cggttatcat cttcttgatc aataactatg gttacaccat cgaagttatg atccatgatg   3720
gtccgtacaa caacatcaag aactgggatt atgccggtct gatggaagtg ttcaacggta   3780
acggtggtta tgacagcggt gctggtaaag gcctgaaggc taaaaccggt ggcgaactgg   3840
cagaagctat caaggttgct ctggcaaaca ccgacggccc aaccctgatc gaatgcttca   3900
tcggtcgtga agactgcact gaagaattgg tcaaatgggg taagcgcgtt gctgccgcca   3960
acagccgtaa gcctgttaac aagctcctct agtttttggg gatcaattcg agctcactag   4020
tcgatcgaca ttgccataag taaaggcatc ccctgcgtga taagattacc ttcagtttat   4080
ggaggactga ccatatgatt aaagcctacg ctgccctgga agccaacgga aaactccaac   4140
cctttgaata cgaccccggt gccctgggtg ctaatgaggt ggagattgag gtgcagtatt   4200
gtggggtgtg ccacagtgat ttgtccatga ttaataacga atggggcatt tccaattacc   4260
ccctagtgcc gggtcatgag gtggtgggta ctgtggccgc catgggcgaa ggggtgaacc   4320
atgttgaggt gggggattta gtggggctgg gttggcattc gggctactgc atgacctgcc   4380
atagttgttt atctggctac cacaaccttt gtgccacggc ggaatcgacc attgtgggcc   4440
actacggtgg ctttggcgat cgggttcggg ccaagggagt cagcgtggtg aaattaccta   4500
aaggcattga cctagccagt gccgggcccc ttttctgtgg aggaattacc gttttcagtc   4560
ctatggtgga actgagttta aagcccactg caaaagtggc agtgatcggc attgggggct   4620
tgggccattt agcggtgcaa tttctccggg cctggggctg tgaagtgact gcctttacct   4680
ccagtgccag gaagcaaacg gaagtgttgg aattgggcgc tcaccacata ctagattcca   4740
ccaatccaga ggcgatcgcc agtgcggaag gcaaatttga ctatattatc tccactgtga   4800
acctgaagct tgactggaac ttatacatca gcaccctggc gccccaggga catttccact   4860
ttgttggggt ggtgttggag cctttggatc taaatctttt tccccttttg atgggacaac   4920
gctccgtttc tgcctcccca gtgggtagtc ccgccaccat tgccaccatg ttggactttg   4980
ctgtgcgcca tgacattaaa cccgtggtgg aacaatttag ctttgatcag atcaacgagg   5040
```

-continued

```
cgatcgccca tctagaaagc ggcaaagccc attatcgggt agtgctcagc catagtaaaa   5100
attagctctg caaaggttgc ttctgggtcc gtggaacgct cggttgccgc cgggcgtttt   5160
ttattcctgc agccttgctc tagaagaaca gcaaggccgc caatgcctga cgatgcgtgg   5220
agaccgaaac cttgcgctcg ttcgccagcc aggacagaaa tgcctcgact tcgctgctgc   5280
ccaaggttgc cgggtgacgc acaccgtgga aacggatgaa ggcacgaacc cagtggacat   5340
aagcctgttc ggttcgtaag ctgtaatgca agtagcgtat gcgctcacgc aactggtcca   5400
gaaccttgac cgaacgcagc ggtggtaacg gcgcagtggc ggttttcatg gcttgttatg   5460
actgtttttt tggggtacag tctatgcctc gggcatccaa gcagcaagcg cgttacgccg   5520
tgggtcgatg tttgatgtta tggagcagca acgatgttac gcagcagggc agtcgcccta   5580
aaacaaagtt aaacatcatg agggaagcgg tgatcgccga agtatcgact caactatcag   5640
aggtagttgg cgtcatcgag cgccatctcg aaccgacgtt gctggccgta catttgtacg   5700
gctccgcagt ggatggcggc ctgaagccac acagtgatat tgatttgctg gttacggtga   5760
ccgtaaggct tgatgaaaca acgcggcgag ctttgatcaa cgaccttttg gaaacttcgg   5820
cttcccctgg agagagcgag attctccgcg ctgtagaagt caccattgtt gtgcacgacg   5880
acatcattcc gtggcgttat ccagctaagc gcgaactgca atttggagaa tggcagcgca   5940
atgacattct tgcaggtatc ttcgagccag ccacgatcga cattgatctg gctatcttgc   6000
tgacaaaagc aagagaacat agcgttgcct tggtaggtcc agcggcggag gaactctttg   6060
atccggttcc tgaacaggat ctatttgagg cgctaaatga aaccttaacg ctatggaact   6120
cgccgcccga ctgggctggc gatgagcgaa atgtagtgct tacgttgtcc cgcatttggt   6180
acagcgcagt aaccggcaaa atcgcgccga aggatgtcgc tgccgactgg gcaatggagc   6240
gcctgccggc ccagtatcag cccgtcatac ttgaagctag acaggcttat cttggacaag   6300
aagaagatcg cttggcctcg cgcgcagatc agttggaaga atttgtccac tacgtgaaag   6360
gcgagatcac caaggtagtc ggcaaataat gtctaacaat tcgttcaagc cgacgccgct   6420
tcgcggcgcg gcttaactca agcgttagat gcactaccgg tatctttcta gaagatcctc   6480
tagttctaga gcggccgctg gaatttcccg attctctgat gggagatcca aaaattctcg   6540
cagtccctca atcacgatat cggtcttgga tcgccctgta gcttccgaca actgctcaat   6600
tttttcgagc atctctaccg ggcatcggaa tgaaattaac ggtgttttag ccatgtgtta   6660
tacagtgttt acaacttgac taacaaatac ctgctagtgt atacatattg tattgcaatg   6720
tatacgctat tttcactgct gtctttaatg gggattatcg caagcaagta aaaaagcctg   6780
aaaaccccaa taggtaaggg attccgagct tactcgataa ttatcacctt tgagcgcccc   6840
taggaggagg cgaaaagcta tgtctgacaa ggggtttgac ccctgaagtc gttgcgcgag   6900
cattaaggtc tgcggatagc ccataacata cttttgttga acttgtgcgc ttttatcaac   6960
cccttaaggg cttgggagcg ttttatacga gtgcggggaa ctagtgatgg cggccgggag   7020
catgcgacgt cgggcccaat tcgccctata gtgagtcgta ttacaattca ctggccgtcg   7080
ttttacaacg tcgtgactgg gaaaaccctg gcgttaccca acttaatcgc cttgcagcac   7140
atcccccttt cgccagctgg cgtaatagcg aagaggcccg caccgatcgc ccttcccaac   7200
agttgcgcag cctgaatggc gaatggacgc gccctgtagc ggcgcattaa gcgcggcggg   7260
tgtggtggtt acgcgcagcg tgaccgctac acttgccagc gccctagcgc ccgctccttt   7320
cgctttcttc ccttcctttc tcgccacgtt cgccggcttt ccccgtcaag ctctaaatcg   7380
```

ggggctccct ttagggttcc gatttagagc tttacggcac ctcgaccgca aaaaacttga 7440
tttgggtgat ggttcacgta gtgggccatc gccctgatag acggtttttc gccctttgac 7500
gttggagtcc acgttcttta atagtggact cttgttccaa actggaacaa cactcaaccc 7560
tatctcggtc tattcttttg atttataagg gattttgccg atttcggcct attggttaaa 7620
aaatgagctg atttaacaaa tatttaacgc gaattttaac aaaatattaa cgtttacaat 7680
ttcgcctgat gcggtatttt ctccttacgc atctgtgcgg tatttcacac cgcatacagg 7740
tggcactttt cggggaaatg tgcgcggaac ccctatttgt ttatttttct aaatacattc 7800
aaatatgtat ccgctcatga gacaataacc ctgataaatg cttcaataat attgaaaaag 7860
gaagagtatg agtattcaac atttccgtgt cgcccttatt cccttttttg cggcattttg 7920
ccttcctgtt tttgctcacc cagaaacgct ggtgaaagta aaagatgctg aagatcagtt 7980
gggtgcacga gtgggttaca tcgaactgga tctcaacagc ggtaagatcc ttgagagttt 8040
tcgccccgaa gaacgttttc caatgatgag cacttttaaa gttctgctat gtggcgcggt 8100
attatcccgt attgacgccg ggcaagagca actcggtcgc cgcatacact attctcagaa 8160
tgacttggtt gagtactcac cagtcacaga aaagcatctt acggatggca tgacagtaag 8220
agaattatgc agtgctgcca taaccatgag tgataacact gcggccaact tacttctgac 8280
aacgatcgga ggaccgaagg agctaaccgc ttttttgcac aacatggggg atcatgtaac 8340
tcgccttgat cgttgggaac cggagctgaa tgaagccata ccaaacgacg agcgtgacac 8400
cacgatgcct gtagcaatgc caacaacgtt gcgcaaacta ttaactggcg aactacttac 8460
tctagcttcc cggcaacaat taatagactg gatggaggcg gataaagttg caggaccact 8520
tctgcgctcg gcccttccgg ctggctggtt tattgctgat aaatctggag ccggtgagcg 8580
tgggtctcgc ggtatcattg cagcactggg gccagatggt aagccctccc gtatcgtagt 8640
tatctacacg acggggagtc aggcaactat ggatgaacga aatagacaga tcgctgagat 8700
aggtgcctca ctgattaagc attggtaact gtcagaccaa gtttactcat atatacttta 8760
gattgattta aaacttcatt tttaatttaa aaggatctag gtgaagatcc tttttgataa 8820
tctcatgacc aaaatccctt aacgtgagtt ttcgttccac tgagcgtcag accccgtaga 8880
aaagatcaaa ggatcttctt gagatccttt ttttctgcgc gtaatctgct gcttgcaaac 8940
aaaaaaacca ccgctaccag cggtggtttg tttgccggat caagagctac caactctttt 9000
tccgaaggta actggcttca gcagagcgca gataccaaat actgtccttc tagtgtagcc 9060
gtagttaggc caccacttca agaactctgt agcaccgcct acatacctcg ctctgctaat 9120
cctgttacca gtggctgctg ccagtggcga taagtcgtgt cttaccgggt tggactcaag 9180
acgatagtta ccggataagg cgcagcggtc gggctgaacg gggggttcgt gcacacagcc 9240
cagcttggag cgaacgacct acaccgaact gagataccta cagcgtgagc tatgagaaag 9300
cgccacgctt cccgaaggga gaaaggcgga caggtatccg gtaagcggca gggtcggaac 9360
aggagagcgc acgagggagc ttccaggggg aaacgcctgg tatctttata gtcctgtcgg 9420
gtttcgccac ctctgacttg agcgtcgatt tttgtgatgc tcgtcagggg ggcggagcct 9480
atggaaaaac gccagcaacg cggccttttt acggttcctg gccttttgct ggccttttgc 9540
tcacatgttc tttcctgcgt tatcccctga ttctgtggat aaccgtatta ccgcctttga 9600
gtgagctgat accgctcgcc gcagccgaac gaccgagcgc agcgagtcag tgagcgagga 9660
agcggaagag cgcccaatac gcaaaccgcc tctccccgcg cgttggccga ttcattaatg 9720
cagctggcac gacaggtttc ccgactggaa agcgggcagt gagcgcaacg caattaatgt 9780
gagttagctc actcattagg caccccaggc tttacacttt atgcttccgg ctcgtatgtt 9840
gtgtggaatt gtgagcggat aacaatttca cacaggaaac agctatgacc atgattacgc 9900
caagctattt aggtgacact atagaatact caagctatgc atctccaaca tgagggcttt 9960
gtatttaagc cggatatcaa caggcgatcg ctctcaccaa agattcacct gttagagcta 10020
ctcaacatcc atcagttctt aaaaccaggg gtgacattca ccggggcgag ccttgaaggg 10080
ttcaaggaaa attgtttgcg gtatgccaag ccgatcaagt ggattcttgg cagaacgatc 10140
accgacaaaa tgagcccgct cgaaattgct caggcgctcc taggcaagct tgaccggaaa 10200
ttggaataca aggggcgctt tggatcgcgg gataaccgtc agcgggtcta tgaggcgatc 10260
gcccctaacg atcagcgcga aaaggtcttt gctcattggt tacagcgtga ccaagcaaaa 10320
ttaggggccg tgtccaaccc ctgtataaat agatttattc aggaggctta gacccgtgat 10380
cgaaatactc gttgtgcagc tctcccttgg caatcccaaa caatctcaag atttgctctg 10440
cggtatcggg acgttttatg cccttgcgga aagcgccttt gctcttctgg tagcccctag 10500
actgtgccag atcataagcc tcactgaggg tgagggcact accgggggca tgagctcgcc 10560
caagagattc agcgaccggg gcgatcgccc ttggtaattc tctcaggcgc tg 10612

<210> SEQ ID NO 71
<211> LENGTH: 9513
<212> TYPE: DNA
<213> ORGANISM: Artificial
<220> FEATURE:
<223> OTHER INFORMATION: Synthetic vector construct #1332
pGEM-AQ4::corR-PcorT-zpPDC*_ter-PrbcL*-synADH_oop-Nm for
integration into the endogenous pAQ4 plasmid of Synechococcus sp.
PCC7002

<400> SEQUENCE: 71
tcgaccatgc gtccaaaact ttcaccatcc tttccctatc aacctttact gcactaaaga 60
caagtgagat agcagtggca atctggcttt gcaatcaatg tttccactaa agcgtttagc 120
gttactgcgg ctagaagtcc tccaccgagg ctcccctgaa tggtgatatg gggaatggga 180
ctggtcatca gtcgtcgttt tgcccccgga gcatgactaa aaccgatcgg cattccgatc 240
acaagagccg gctgaatatg ttgttgctct atcagcttac aggcagtgag taaaacagaa 300
ggggcatagc cgatcgccag cacacatcct tggggaatct gttgtaaccg ctgttgccaa 360
tggtcatggt gccaaaaagc ttgctcggct tccctaagcc ctgtgatgtg agggtcgtca 420
atcagcgttt taaccgtaca tcctaaatga gctaaccgag tttgatcaag agccgcagcc 480
acaaccggaa catcggtgac gactggacac cctgctttca gtgcatctcg tgccgaggcg 540
atcgctccct gactcaatcg aacggcgttt accaagctaa catcaccaca ggccagcact 600
aattgatgta gtaagtgaat ggtaatttca gagtaagccg ataaatccgg tagcaggtgt 660
ttgagggatt cctgaaaggc ttctggatga gttgttgtct ccgcatctag gttcgtccac 720
aactgatcga gttttcctaa cccctcctgg acatccacat caagctgttt cagttgggcc 780
agagcttccg cttgggtaat ctggcaactc tggtcgcgtc ccagtaatcc ttctaaagca 840
gatgcggttt ggcggagtcg agtaatctgc tgaatcacag cctgatattg ctgttgcaac 900
tgcaccatta gggtgggatc aaggctctct tcagaatggc tatccagcag ttgccgaata 960
tgagacaact gaaagccctg ctgtttgagg gcaatgactc gttggagccg ttgtacgtcc 1020
tgctgagtat aaaggcggta gttgccctct gagcgttgaa cggggggaag caatcccagg 1080
gtgtggtaat ggcgcaccat gcgaggcgta acgccacctc ccactgcatc tgtgagttct 1140
ttaatcgtta agtgattagt cttcatccct ttagtttact caaaaccttg acattgacac 1200
taatgttaag gtttaggctg agaaggtaaa aatccaagtt aaaaagcatg aattcctata 1260
ccgttggtat gtacttggca gaacgcctag cccagatcgg cctgaaacac cactttgccg 1320
tggccggtga ctacaacctg gtgttgcttg atcagctcct gctgaacaaa gacatggagc 1380
aggtctactg ctgtaacgaa cttaactgcg gctttagcgc cgaaggttac gctcgtgcac 1440
gtggtgccgc cgctgccatc gtcacgttca gcgtaggtgc tatctctgca atgaacgcca 1500
tcggtggcgc ctatgcagaa aacctgccgg tcatcctgat ctctggctca ccgaacacca 1560
atgactacgg cacaggccac atcctgcacc acaccattgg tactactgac tataactatc 1620
agctggaaat ggtaaaacac gttacctgcg cagctgaaag catcgtttct gccgaagaag 1680
caccggcaaa aatcgaccac gtcatccgta cggctctacg tgaacgcaaa ccggcttatc 1740
tggaaatcgc atgcaacgtc gctggcgctg aatgtgttcg tccgggcccg atcaatagcc 1800
tgctgcgtga actcgaagtt gaccagacca gtgtcactgc cgctgtagat gccgccgtag 1860
aatggctgca ggaccgccag aacgtcgtca tgctggtcgg tagcaaactg cgtgccgctg 1920
ccgctgaaaa acaggctgtt gccctagcgg accgcctggg ctgcgctgtc acgatcatgg 1980
ctgccgcaaa aggcttcttc ccggaagatc atccgaactt ccgcggcctg tactggggtg 2040
aagtcagctc cgaaggtgca caggaactgg ttgaaaacgc cgatgccatc ctgtgtctgg 2100
caccggtatt caacgactat gctaccgttg gctggaactc ctggccgaaa ggcgacaatg 2160
tcatggtcat ggacaccgac cgcgtcactt tcgcaggaca gtccttcgaa ggtctgtcat 2220
tgagcacctt cgccgcagca ctggctgaga aagcaccttc tcgcccggca acgactcaag 2280
gcactcaagc accggtactg ggtattgagg ccgcagagcc caatgcaccg ctgaccaatg 2340
acgaaatgac gcgtcagatc cagtcgctga tcacttccga cactactctg acagcagaaa 2400
caggtgactc ttggttcaac gcttctcgca tgccgattcc tggcggtgct cgtgtcgaac 2460
tggaaatgca atggggtcat atcggttggt ccgtaccttc tgcattcggt aacgccgttg 2520
gttctccgga gcgtcgccac atcatgatgg tcggtgatgg ctctttccag ctgactgctc 2580
aagaagttgc tcagatgatc cgctatgaaa tcccggtcat catcttcctg atcaacaacc 2640
gcggttacgt catcgaaatc gctatccatg acggccctta caactacatc aaaaactgga 2700
actacgctgg cctgatcgac gtcttcaatg acgaagatgg tcatggcctg ggtctgaaag 2760
cttctactgg tgcagaacta gaaggcgcta tcaagaaagc actcgacaat cgtcgcggtc 2820
cgacgctgat cgaatgtaac atcgctcagg acgactgcac tgaaaccctg attgcttggg 2880
gtaaacgtgt agcagctacc aactctcgca aaccacaagc gtaagttgat gtagtgaatt 2940
aggcggggcc tattagggcc ccaccacata gcccctctta cggcgcaata cccgtaagag 3000
gggctgtttt atataattaa agagctcact agtcgatcga cattgccata agtaaaggca 3060
tcccctgcgt gataagatta ccttcagttt atggaggact gaccatatga ttaaagccta 3120
cgctgccctg gaagccaacg gaaaactcca accctttgaa tacgaccccg gtgccctggg 3180
tgctaatgag gtggagattg aggtgcagta ttgtggggtg tgccacagtg atttgtccat 3240
gattaataac gaatggggca tttccaatta ccccctagtg ccgggtcatg aggtggtggg 3300
tactgtggcc gccatgggcg aaggggtgaa ccatgttgag gtgggggatt tagtggggct 3360
gggttggcat tcgggctact gcatgacctg ccatagttgt ttatctggct accacaacct 3420
ttgtgccacg gcggaatcga ccattgtggg ccactacggt ggctttggcg atcgggttcg 3480

```
ggccaaggga gtcagcgtgg tgaaattacc taaaggcatt gacctagcca gtgccgggcc   3540
ccttttctgt ggaggaatta ccgttttcag tcctatggtg gaactgagtt taaagcccac   3600
tgcaaaagtg gcagtgatcg gcattggggg cttgggccat ttagcggtgc aatttctccg   3660
ggcctggggc tgtgaagtga ctgcctttac ctccagtgcc aggaagcaaa cggaagtgtt   3720
ggaattgggc gctcaccaca tactagattc caccaatcca gaggcgatcg ccagtgcgga   3780
aggcaaattt gactatatta tctccactgt gaacctgaag cttgactgga acttatacat   3840
cagcaccctg gcgccccagg gacatttcca ctttgttggg gtggtgttgg agcctttgga   3900
tctaaatctt tttccccttt tgatgggaca acgctccgtt tctgcctccc cagtgggtag   3960
tcccgccacc attgccacca tgttggactt tgctgtgcgc catgacatta aacccgtggt   4020
ggaacaattt agctttgatc agatcaacga ggcgatcgcc catctagaaa gcggcaaagc   4080
ccattatcgg gtagtgctca gccatagtaa aaattagctc tgcaaaggtt gcttctgggt   4140
ccgtggaacg ctcggttgcc gccgggcgtt ttttattcct gcaggccccc cgggggatcc   4200
actagaggat ctcaatgaat attggttgac acgggcgtat aagacatgtt atactgttga   4260
ataacaagga cggatctgat caagagacag gatgaggatc gtttcgcatg attgaacaag   4320
atggattgca cgcaggttct ccggccgctt gggtggagag gctattcggc tatgactggg   4380
cacaacagac aatcggctgc tctgatgccg ccgtgttccg gctgtcagcg caggggcgcc   4440
cggttctttt tgtcaagacc gacctgtccg gtgccctgaa tgaactgcag gacgaggcag   4500
cgcggctatc gtggctggcc acgacgggcg ttccttgcgc agctgtgctc gacgttgtca   4560
ctgaagcggg aagggactgg ctgctattgg gcgaagtgcc ggggcaggat ctcctgtcat   4620
ctcaccttgc tcctgccgag aaagtatcca tcatggctga tgcaatgcgg cggctgcata   4680
cgcttgatcc ggctacctgc ccattcgacc accaagcgaa acatcgcatc gagcgagcac   4740
gtactcggat ggaagccggt cttgtcgatc aggatgatct ggacgaagag catcaggggc   4800
tcgcgccagc cgaactgttc gccaggctca aggcgcgcat gcccgacggc gaggatctcg   4860
tcgtgaccca tggcgatgcc tgcttgccga atatcatggt ggaaaatggc cgcttttctg   4920
gattcatcga ctgtggccgg ctgggtgtgg cggaccgcta tcaggacata gcgttggcta   4980
cccgtgatat tgctgaagag cttggcggcg aatgggctga ccgcttcctc gtgctttacg   5040
gtatcgccgc tcccgattcg cagcgcatcg ccttctatcg ccttcttgac gagttcttct   5100
gagcgggact ctggggttcg aaatgaccga ccaagcgacg cccaacctgc catcacgaga   5160
tttcgattcc accgccgcct tctatgaaag gttgggcttc ggaatcgttt tccgggacgc   5220
cggctggatg atcctccagc gcggggatct catgctggag ttcttcgccc accggggatc   5280
ctctagttct agagcggccg catcatcaat ccccgtgatg tttcagtccc gtagtcggga   5340
tttagtggtt ggaaagcgga acgtcgcgcc gaaaccatcg ccaggacggg tttcagtccc   5400
gtagtcggga tttagtggtt ggaaagtgat tatgttcaag aaatcacaac gcaaaagaaa   5460
aagtttcagt cccgtagtcg ggatttagtg gttggaaagt caagcgagat acccaccaga   5520
aagcctttga cctggtttca gtcccgagtc gggatttagt ggttggaaag gcggcggctg   5580
atgtcgccaa tgcggttatc gatggccagt ttcagtcccg tagtcgggat ttagtggttg   5640
gaaagtccca agggggacag ggcggtgatc ctcgatgttg cgtgtttcag tcccgtagtc   5700
gggatttagt ggttggaaag actcgtctat atatacagag attactacag agatgtttca   5760
gtcccgtagt cgggatttag tggttggaaa gcgggaaagt agcctgtttt gtggagaatt   5820
gcaggcgttt cagtactagt gatggcggcc gggagcatgc gacgtcgggc ccaattcgcc   5880
```

ctatagtgag tcgtattaca attcactggc cgtcgtttta caacgtcgtg actgggaaaa 5940
ccctggcgtt acccaactta atcgccttgc agcacatccc cctttcgcca gctggcgtaa 6000
tagcgaagag gcccgcaccg atcgcccttc ccaacagttg cgcagcctga atggcgaatg 6060
gacgcgccct gtagcggcgc attaagcgcg gcgggtgtgg tggttacgcg cagcgtgacc 6120
gctacacttg ccagcgccct agcgcccgct cctttcgctt tcttcccttc ctttctcgcc 6180
acgttcgccg gctttccccg tcaagctcta aatcgggggc tccctttagg gttccgattt 6240
agagctttac ggcacctcga ccgcaaaaaa cttgatttgg gtgatggttc acgtagtggg 6300
ccatcgccct gatagacggt ttttcgccct ttgacgttgg agtccacgtt ctttaatagt 6360
ggactcttgt tccaaactgg aacaacactc aaccctatct cggtctattc ttttgattta 6420
taagggattt tgccgatttc ggcctattgg ttaaaaaatg agctgattta acaaatattt 6480
aacgcgaatt ttaacaaaat attaacgttt acaatttcgc ctgatgcggt attttctcct 6540
tacgcatctg tgcggtattt cacaccgcat acaggtggca cttttcgggg aaatgtgcgc 6600
ggaaccccta tttgtttatt tttctaaata cattcaaata tgtatccgct catgagacaa 6660
taaccctgat aaatgcttca ataatattga aaaaggaaga gtatgagtat tcaacatttc 6720
cgtgtcgccc ttattccctt ttttgcggca ttttgccttc ctgtttttgc tcacccagaa 6780
acgctggtga aagtaaaaga tgctgaagat cagttgggtg cacgagtggg ttacatcgaa 6840
ctggatctca acagcggtaa gatccttgag agttttcgcc ccgaagaacg ttttccaatg 6900
atgagcactt ttaaagttct gctatgtggc gcggtattat cccgtattga cgccgggcaa 6960
gagcaactcg gtcgccgcat acactattct cagaatgact tggttgagta ctcaccagtc 7020
acagaaaagc atcttacgga tggcatgaca gtaagagaat tatgcagtgc tgccataacc 7080
atgagtgata acactgcggc caacttactt ctgacaacga tcggaggacc gaaggagcta 7140
accgcttttt tgcacaacat gggggatcat gtaactcgcc ttgatcgttg ggaaccggag 7200
ctgaatgaag ccataccaaa cgacgagcgt gacaccacga tgcctgtagc aatgccaaca 7260
acgttgcgca aactattaac tggcgaacta cttactctag cttcccggca acaattaata 7320
gactggatgg aggcggataa agttgcagga ccacttctgc gctcggccct tccggctggc 7380
tggtttattg ctgataaatc tggagccggt gagcgtgggt ctcgcggtat cattgcagca 7440
ctggggccag atggtaagcc ctcccgtatc gtagttatct acacgacggg gagtcaggca 7500
actatggatg aacgaaatag acagatcgct gagataggtg cctcactgat taagcattgg 7560
taactgtcag accaagttta ctcatatata ctttagattg atttaaaact tcatttttaa 7620
tttaaaagga tctaggtgaa gatccttttt gataatctca tgaccaaaat cccttaacgt 7680
gagttttcgt tccactgagc gtcagacccc gtagaaaaga tcaaaggatc ttcttgagat 7740
cctttttttc tgcgcgtaat ctgctgcttg caaacaaaaa aaccaccgct accagcggtg 7800
gtttgtttgc cggatcaaga gctaccaact ctttttccga aggtaactgg cttcagcaga 7860
gcgcagatac caaatactgt ccttctagtg tagccgtagt taggccacca cttcaagaac 7920
tctgtagcac cgcctacata cctcgctctg ctaatcctgt taccagtggc tgctgccagt 7980
ggcgataagt cgtgtcttac cgggttggac tcaagacgat agttaccgga taaggcgcag 8040
cggtcgggct gaacgggggg ttcgtgcaca cagcccagct tggagcgaac gacctacacc 8100
gaactgagat acctacagcg tgagctatga gaaagcgcca cgcttcccga agggagaaag 8160
gcggacaggt atccggtaag cggcagggtc ggaacaggag agcgcacgag ggagcttcca 8220
gggggaaacg cctggtatct ttatagtcct gtcgggtttc gccacctctg acttgagcgt 8280
cgatttttgt gatgctcgtc aggggggcgg agcctatgga aaaacgccag caacgcggcc 8340
tttttacggt tcctggcctt ttgctggcct tttgctcaca tgttctttcc tgcgttatcc 8400
cctgattctg tggataaccg tattaccgcc tttgagtgag ctgataccgc tcgccgcagc 8460
cgaacgaccg agcgcagcga gtcagtgagc gaggaagcgg aagagcgccc aatacgcaaa 8520
ccgcctctcc ccgcgcgttg gccgattcat taatgcagct ggcacgacag gtttcccgac 8580
tggaaagcgg gcagtgagcg caacgcaatt aatgtgagtt agctcactca ttaggcaccc 8640
caggctttac actttatgct tccggctcgt atgttgtgtg gaattgtgag cggataacaa 8700
tttcacacag gaaacagcta tgaccatgat tacgccaagc tatttaggtg acactataga 8760
atactcaagc tatgcatgag ggtgcaattt gagtggtttc agtcccgtaa tcgggattta 8820
gtggttggaa agaacgacaa ggcttacaag gggtaattc gtgatttgtt tcagtcccgt 8880
aatcgggatt tagtggttgg aaagtaggca ggggagtgaa atggtttcat gttgggctca 8940
tgtttcagtc ccgtaatcgg gatttagtgg ttggaaagca gtaagatgaa ggaggtggtg 9000
catatcactt gcgtttcagt cccgtaatcg ggatttagtg gttggaaagc tagatttgct 9060
tatagagttg actgttatcg ggacttgttt cagtcccgta atcgggattt agtggttgga 9120
aagatgatgg cgttgccagc gttctcggat tggagaattt aacgtttcag tcccgtaatc 9180
gggatttagt ggttggaaag ccctgagaag tttggctgtt ttgctgactg cgatctggtt 9240
tcagtcccgt aatcgggatt tagtggttgg aaagcatcga ggcagtagag caaatcgcag 9300
gccacctcat agtttcagtc ccgtaatcgg gatttagtgg ttggaaagtc attggggtct 9360
gcattggggc catcgctatc gtcctgtttc agtcccgtaa tcgggattta gtggttggaa 9420
agtgggacgc tccgtaaggt ttggagaata gggtctagtg tttcagtccc gtaatcggga 9480
tttagtggtt ggaaagcact tcgtcgctga ttg 9513

<210> SEQ ID NO 72
<211> LENGTH: 18055
<212> TYPE: DNA
<213> ORGANISM: Artificial
<220> FEATURE:
<223> OTHER INFORMATION: Synthetic vector construct #1627
pVZ326a-PnrsB(ABCC916)-PDC_dsrA-Prbc*(optRBS)-synADHoop-
nrsRSBAD(ABCC916) for transformation of of Synechococcus sp.
PCC7002

<400> SEQUENCE: 72
tcgactttat cctaatcaca aacagcctat ttcacttaga tttcataccc cctctggcaa 60
actggaaaaa attttcgtgc cattttgtct ctaaatgtga ggtgctgtga tgaattctta 120
tactgtcggt acctatttag cggagcggct tgtccagatt ggtctcaagc atcacttcgc 180
agtcgcgggc gactacaacc tcgtccttct tgacaacctg cttttgaaca aaaacatgga 240
gcaggtttat tgctgtaacg aactgaactg cggtttcagt gcagaaggtt atgctcgtgc 300
caaaggcgca gcagcagccg tcgttaccta cagcgtcggt gcgctttccg catttgatgc 360
tatcggtggc gcctatgcag aaaaccttcc ggttatcctg atctccggtg ctccgaacaa 420
caatgatcac gctgctggtc acgtgttgca tcacgctctt ggcaaaaccg actatcacta 480
tcagttggaa atggccaaga acatcacggc cgcagctgaa gcgatttaca ccccagaaga 540
agctccggct aaaatcgatc acgtgattaa aactgctctt cgtgagaaga agccggttta 600
tctcgaaatc gcttgcaaca ttgcttccat gccctgcgcc gctcctggac cggcaagcgc 660

-continued

```
attgttcaat gacgaagcca gcgacgaagc ttctttgaat gcagcggttg aagaaaccct    720
gaaattcatc gccaaccgcg acaaagttgc cgtcctcgtc ggcagcaagc tgcgcgcagc    780
tggtgctgaa gaagctgctg tcaaatttgc tgatgctctc ggtggcgcag ttgctaccat    840
ggctgctgca aaaagcttct tcccagaaga aaacccgcat tacatcggta cctcatgggg    900
tgaagtcagc tatccgggcg ttgaaaagac gatgaaagaa gccgatgcgg ttatcgctct    960
ggctcctgtc ttcaacgact actccaccac tggttggacg gatattcctg atcctaagaa   1020
actggttctc gctgaaccgc gttctgtcgt cgttaacggc gttcgcttcc ccagcgttca   1080
tctgaaagac tatctgaccc gtttggctca gaaagtttcc aagaaaaccg gtgctttgga   1140
cttcttcaaa tccctcaatg caggtgaact gaagaaagcc gctccggctg atccgagtgc   1200
tccgttggtc aacgcagaaa tcgcccgtca ggtcgaagct cttctgaccc cgaacacgac   1260
ggttattgct gaaaccggtg actcttggtt caatgctcag cgcatgaagc tcccgaacgg   1320
tgctcgcgtt gaatatgaaa tgcagtgggg tcacatcggt tggtccgttc ctgccgcctt   1380
cggttatgcc gtcggtgctc cggaacgtcg caacatcctc atggttggtg atggttcctt   1440
ccagctgacg gctcaggaag tcgctcagat ggttcgcctg aaactgccgg ttatcatctt   1500
cttgatcaat aactatggtt acaccatcga agttatgatc catgatggtc cgtacaacaa   1560
catcaagaac tgggattatg ccggtctgat ggaagtgttc aacggtaacg gtggttatga   1620
cagcggtgct ggtaaaggcc tgaaggctaa aaccggtggc gaactggcag aagctatcaa   1680
ggttgctctg gcaaacaccg acggcccaac cctgatcgaa tgcttcatcg gtcgtgaaga   1740
ctgcactgaa gaattggtca aatggggtaa gcgcgttgct gccgccaaca gccgtaagcc   1800
tgttaacaag ctcctctagt ttttggggat caattcgagc tcagcaagtt tcatcccgac   1860
cccctcaggg tcgggatttt tttattgtac tagttgacat aagtaaaggc atcccctgcg   1920
tgatataatt accttcagtt taaggaggta tacacatatg attaaagcct acgctgccct   1980
ggaagccaac ggaaaactcc aaccctttga atacgacccc ggtgccctgg gtgctaatga   2040
ggtggagatt gaggtgcagt attgtggggt gtgccacagt gatttgtcca tgattaataa   2100
cgaatggggc atttccaatt acccccctagt gccgggtcat gaggtggtgg gtactgtggc   2160
cgccatgggc gaaggggtga accatgttga ggtgggggat ttagtggggc tgggttggca   2220
ttcgggctac tgcatgacct gccatagttg tttatctggc taccacaacc tttgtgccac   2280
ggcggaatcg accattgtgg gccactacgg tggctttggc gatcgggttc gggccaaggg   2340
agtcagcgtg gtgaaattac ctaaaggcat tgacctagcc agtgccgggc ccctttttctg   2400
tggaggaatt accgttttca gtcctatggt ggaactgagt ttaaagccca ctgcaaaagt   2460
ggcagtgatc ggcattgggg gcttgggcca tttagcggtg caatttctcc gggcctgggg   2520
ctgtgaagtg actgccttta cctccagtgc caggaagcaa acggaagtgt tggaattggg   2580
cgctcaccac atactagatt ccaccaatcc agaggcgatc gccagtgcgg aaggcaaatt   2640
tgactatatt atctccactg tgaacctgaa gcttgactgg aacttataca tcagcaccct   2700
ggcgccccag ggacatttcc actttgttgg ggtggtgttg gagcctttgg atctaaatct   2760
ttttcccctt ttgatgggac aacgctccgt ttctgcctcc ccagtgggta gtcccgccac   2820
cattgccacc atgttggact ttgctgtgcg ccatgacatt aaacccgtgg tggaacaatt   2880
tagctttgat cagatcaacg aggcgatcgc ccatctagaa agcggcaaag cccattatcg   2940
ggtagtgctc agccatagta aaaattagct ctgcaaaggt tgcttctggg tccgtggaac   3000
gctcggttgc cgccgggcgt tttttattcc tgcaggagca gaagagcata catctggaag   3060
```

caaagccagg aaagcggcct atggagctgt gcggcagcgc tcagtaggca atttttcaaa 3120
atattgttaa gccttttctg agcatggtat ttttcatggt attaccaatt agcaggaaaa 3180
taagccattg aatataaaag ataaaaatgt cttgtttaca atagagtggg gggggtcagc 3240
ctgccgcctt gggccgggtg atgtcgtact tgcccgccgc gaactcggtt accgtccagc 3300
ccagcgcgac cagctccggc aacgcctcgc gcacccgctg gcggcgcttg cgcatggtcg 3360
aaccactggc ctctgacggc cagacatagc cgcacaaggt atctatggaa gccttgccgg 3420
ttttgccggg gtcgatccag ccacacagcc gctggtgcag caggcgggcg gtttcgctgt 3480
ccagcgcccg cacctcgtcc atgctgatgc gcacatgctg gccgccaccc atgacggcct 3540
gcgcgatcaa ggggttcagg gccacgtaca ggcgcccgtc cgcctcgtcg ctggcgtact 3600
ccgacagcag ccgaaacccc tgccgcttgc ggccattctg ggcgatgatg gataccttcc 3660
aaaggcgctc gatgcagtcc tgtatgtgct tgagcgcccc accactatcg acctctgccc 3720
cgatttcctt tgccagcgcc cgatagctac ctttgaccac atggcattca gcggtgacgg 3780
cctcccactt gggttccagg aacagccgga gctgccgtcc gccttcggtc ttgggttccg 3840
ggccaagcac taggccatta ggcccagcca tggccaccag cccttgcagg atgcgcagat 3900
catcagcgcc cagcggctcc gggccgctga actcgatccg cttgccgtcg ccgtagtcat 3960
acgtcacgtc cagcttgctg cgcttgcgct cgccccgctt gagggcacgg aacaggccgg 4020
gggccagaca gtgcgccggg tcgtgccgga cgtggctgag gctgtgcttg ttcttaggct 4080
tcaccacggg gcaccccctt gctcttgcgc tgcctctcca gcacggcggg cttgagcacc 4140
ccgccgtcat gccgcctgaa ccaccgatca gcgaacggtg cgccatagtt ggccttgctc 4200
acaccgaagc ggacgaagaa ccggcgctgg tcgtcgtcca caccccattc ctcggcctcg 4260
gcgctggtca tgctcgacag gtaggactgc cagcggatgt tatcgaccag taccgagctg 4320
ccccggctgg cctgctgctg gtcgcctgcg cccatcatgg ccgcgccctt gctggcatgg 4380
tgcaggaaca cgatagagca cccggtatcg gcggcgatgg cctccatgcg accgatgacc 4440
tgggccatgg ggccgctggc gttttcttcc tcgatgtgga accggcgcag cgtgtccagc 4500
accatcaggc ggcggccctc ggcggcgcgc ttgaggccgt cgaaccactc cggggccatg 4560
atgttgggca ggctgccgat cagcggctgg atcagcaggc cgtcagccac ggcttgccgt 4620
tcctcggcgc tgaggtgcgc cccaagggcg tgcaggcggt gatgaatggc ggtgggcggg 4680
tcttcggcgg gcaggtagat caccgggccg gtgggcagtt cgcccacctc cagcagatcc 4740
ggcccgcctg caatctgtgc ggccagttgc agggccagca tggatttacc ggcaccaccg 4800
ggcgacacca gcgccccgac cgtaccggcc accatgttgg gcaaaacgta gtccagcggt 4860
ggcggcgctg ctgcgaacgc ctccagaata ttgataggct tatgggtagc cattgattgc 4920
ctcctttgca ggcagttggt ggttaggcgc tggcggggtc actacccccg ccctgcgccg 4980
ctctgagttc ttccaggcac tcgcgcagcg cctcgtattc gtcgtcggtc agccagaact 5040
tgcgctgacg catccctttg gccttcatgc gctcggcata tcgcgcttgg cgtacagcgt 5100
cagggctggc cagcaggtcg ccggtctgct tgtccttttg gtctttcata tcagtcaccg 5160
agaaacttgc cggggccgaa aggcttgtct tcgcggaaca aggacaaggt gcagccgtca 5220
aggttaaggc tggccatatc agcgactgaa aagcggccag cctcggcctt gtttgacgta 5280
taaccaaagc caccgggcaa ccaatagccc ttgtcacttt tgatcaggta gaccgaccct 5340
gaagcgcttt tttcgtattc cataaaaccc ccttctgtgc gtgagtactc atagtataac 5400
aggcgtgagt accaacgcaa gcactacatg ctgaaatctg gcccgcccct gtccatgcct 5460
cgctggcggg gtgccggtgc ccgtgccagc tcggcccgcg caagctggac gctgggcaga 5520
cccatgacct tgctgacggt gcgctcgatg taatccgctt cgtggccggg cttgcgctct 5580
gccagcgctg ggctggcctc ggccatggcc ttgccgattt cctcggcact gcggccccgg 5640
ctggccagct tctgcgcggc gataaagtcg cacttgctga ggtcatcacc gaagcgcttg 5700
accagcccgg ccatctcgct gcggtactcg tccagcgccg tgcgccggtg gcggctaagc 5760
tgccgctcgg gcagttcgag gctggccagc ctgcgggcct tctcctgctg ccgctgggcc 5820
tgctcgatct gctggccagc ctgctgcacc agcgccgggc cagcggtggc ggtcttgccc 5880
ttggattcac gcagcagcac ccacggctga taaccggcgc gggtggtgtg cttgtccttg 5940
cggttggtga agcccgccaa gcggccatag tggcggctgt cggcgctggc cgggtcggcg 6000
tcgtactcgc tggccagcgt ccgggcaatc tgcccccgaa gttcaccgcc tgcggcgtcg 6060
gccaccttga cccatgcctg atagttcttc gggctggttt ccactaccag ggcaggctcc 6120
cggccctcgg ctttcatgtc atccaggtca aactcgctga ggtcgtccac cagcaccaga 6180
ccatgccgct cctgctcggc gggcctgata tacacgtcat tgccctgggc attcatccgc 6240
ttgagccatg gcgtgttctg gagcacttcg gcggctgacc attcccggtt catcatctgg 6300
ccggtggtgg cgtccctgac gccgatatcg aagcgctcac agcccatggc cttgagctgt 6360
cggcctatgg cctgcaaagt cctgtcgttc ttcatcgggc caccaagcgc agccagatcg 6420
agccgtcctc ggttgtcagt ggcgtcaggt cgagcaagag caacgatgcg atcagcagca 6480
ccaccgtagg catcatggaa gccagcatca cggttagcca tagcttccag tgccaccccc 6540
gcgacgcgct ccgggcgctc tgcgcggcgc tgctcacctc ggcggctacc tcccgcaact 6600
ctttggccag ctccacccat gccgcccctg tctggcgctg ggctttcagc cactccgccg 6660
cctgcgcctc gctggcctgc tgggtctggc tcatgacctg ccgggcttcg tcggccagtg 6720
tcgccatgct ctgggccagc ggttcgatct gctccgctaa ctcgttgatg cctctggatt 6780
tcttcactct gtcgattgcg ttcatggtct attgcctccc ggtattcctg taagtcgatg 6840
atctgggcgt tggcggtgtc gatgttcagg gccacgtctg cccggtcggt gcggatgccc 6900
cggccttcca tctccaccac gttcggcccc aggtgaacac cgggcaggcg ctcgatgccc 6960
tgcgcctcaa gtgttctgtg gtcaatgcgg gcgtcgtggc cagcccgctc taatgcccgg 7020
ttggcatggt cggcccatgc ctcgcgggtc tgctcaagcc atgccttggg cttgagcgct 7080
tcggtcttct gtgccccgcc cttctccggg gtcttgccgt tgtaccgctt gaaccactga 7140
gcggcgggcc gctcgatgcc gtcattgatc cgctcggaga tcatcaggtg gcagtgcggg 7200
ttctcgccgc caccggcatg gatggccagc gtatacggca ggcgctcggc accggtcagg 7260
tgctgggcga actcggacgc cagcgccttc tgctggtcga gggtcagctc gaccggcagg 7320
gcaaattcga cctccttgaa cagccgccca ttggcgcgtt catacaggtc ggcagcatcc 7380
cagtagtcgg cgggccgctc gacgaactcc ggcatgtgcc cggattcggc gtgcaagact 7440
tcatccatgt cgcgggcata cttgccttcg cgctggatgt agtcggcctt ggccctggcc 7500
gattggccgc ccgacctgct gccggttttc gccgtaaggt gataaatcgc catgctgcct 7560
cgctgttgct tttgcttttc ggctccatgc aatggccctc ggagagcgca ccgcccgaag 7620
ggtggccgtt aggccagttt ctcgaagaga aaccggtaag tgcgccctcc cctacaaagt 7680
agggtcggga ttgccgccgc tgtgcctcca tgatagccta cgagacagca cattaacaat 7740
ggggtgtcaa gatggttaag ggagcaacaa aggcggcgga tcggctggcc aagctcgaag 7800

-continued aacaacgagc gcgaatcaat gccgaaattc agcgggtgcg ggcaagggaa cagcagcaag 7860
agcgcaagaa cgaaacaagg cgcaaggtgc tggtgggggc catgattttg gccaaggtga 7920
acagcagcga gtggccggag gatcggctca tggcggcaat ggatgcgtac cttgaacgcg 7980
accacgaccg cgccttgttc ggtctgccgc cacgccagaa ggatgagccg ggctgaatga 8040
tcgaccgaga caggccctgc ggggctgcac acgcgccccc acccttcggg taggggggaaa 8100
ggccgctaaa gcggctaaaa gcgctccagc gtatttctgc ggggtttggt gtggggttta 8160
gcgggctttg cccgcctttc cccctgccgc gcagcggtgg ggcggtgtgt agcctagcgc 8220
agcgaataga ccagctatcc ggcctctggc cgggcatatt gggcaagggc agcagcgccc 8280
cacaagggcg ctgataaccg cgcctagtgg attattctta gataatcatg gatggatttt 8340
tccaacaccc cgccagcccc cgcccctgct gggtttgcag gtttgggggc gtgacagtta 8400
ttgcaggggt tcgtgacagt tattgcaggg gggcgtgaca gttattgcag gggttcgtga 8460
cagttagtac gggagtgacg ggcactggct ggcaatgtct agcaacggca ggcatttcgg 8520
ctgagggtaa aagaactttc cgctaagcga tagactgtat gtaaacacag tattgcaagg 8580
acgcggaaca tgcctcatgt ggcggccagg acggccagcc gggatcggga tactggtcgt 8640
taccagagcc accgacccga gcaaaccctt ctctatcaga tcgttgacga gtattacccg 8700
gcattcgctg cgcttatggc agagcaggga aaggaattgc cgggctatgt gcaacgggaa 8760
tttgaagaat ttctccaatg cgggcggctg gagcatggct ttctacgggt tcgctgcgag 8820
tcttgccacg ccgagcacct ggtcgctttc agctgtaatc cgggcagcgc aacggaacat 8880
tcatcagtgt aaaaatggaa tcaataaagc cctgcgcagc gcgcagggtc agcctgaata 8940
cgcgtgctcg aattgacata agcctgttcg gttcgtaaac tgtaatgcaa gtagcgtatg 9000
cgctcacgca actggtccag aaccttgacc gaacgcagcg gtggtaacgg cgcagtggcg 9060
gttttcatgg cttgttatga ctgttttttt gtacagtcta tgcctcgggc atccaagcag 9120
caagcgcgtt acgccgtggg tcgatgtttg atgttatgga gcagcaacga tgttacgcag 9180
cagcaacgat gttacgcagc agggcagtcg ccctaaaaca aagttaggtg gctcaagtat 9240
gggcatcatt cgcacatgta ggctcggccc tgaccaagtc aaatccatgc gggctgctct 9300
tgatcttttc ggtcgtgagt tcggagacgt agccacctac tcccaacatc agccggactc 9360
cgattacctc gggaacttgc tccgtagtaa gacattcatc gcgcttgctg ccttcgacca 9420
agaagcggtt gttggcgctc tcgcggctta cgttctgccc aggtttgagc agccgcgtag 9480
tgagatctat atctatgatc tcgcagtctc cggcgagcac cggaggcagg gcattgccac 9540
cgcgctcatc aatctcctca agcatgaggc caacgcgctt ggtgcttatg tgatctacgt 9600
gcaagcagat tacggtgacg atcccgcagt ggctctctat acaaagttgg gcatacggga 9660
agaagtgatg cactttgata tcgacccaag taccgccacc taacaattcg ttcaagccga 9720
gatcggcttc ccggccctag acgcgtattc aggctgaccc tgcgcgctgc gcagggcttt 9780
attgattcca tttttacact gatgaatgtt ccgttgcgct gcccggatta cagatcctct 9840
agaggggggg ggggaaagcc acgttgtgtc tcaaaatctc tgatgttaca ttgcacaaga 9900
taaaaatata tcatcatgaa caataaaact gtctgcttac ataaacagta atacaagggg 9960
tgttatgagc catattcaac gggaaacgtc ttgctcgagg ccgcgattaa attccaacat 10020
ggatgctgat ttatatgggt ataaatgggc tcgcgataat gtcgggcaat caggtgcgac 10080
aatctatcga ttgtatggga agcccgatgc gccagagttg tttctgaaac atggcaaagg 10140
tagcgttgcc aatgatgtta cagatgagat ggtcagacta aactggctga cggaatttat 10200
gcctcttccg accatcaagc attttatccg tactcctgat gatgcatggt gttgcttggg 10260
gtggtggtaa aaccgttaac taaaaaacaa ttgatcgact ttatttaaac cgtctttttt 10320
atctaaaatt cgcaaaatga agtaccgaag acaaccatca ttggggttgt ctttttttatt 10380 ggttaattgg cgaaagactc caagggcgat cgccttttaa ttaagttcta ttcacctttt 10440
ctgaggggta aacgcagagt gaattggcta ccttgatccg catcactctg gatttggata 10500
gatccgtgat aagcaagggc gatcgcctgg gcaatggcaa gccctaaacc tgtccccccg 10560
gttttacggg aacggtcatc attaactcgg taaaaccgtt taaaaatctg ttgttgttgc 10620
tctggggaaa tgcccatacc tgtatccgta acggtaattt tggcatggcg atcatccgtt 10680
tttaaattta cattcacgct gccacctttg ggggtataac gcagggcatt gtcgaggaga 10740
ttggacacta gacgatagag ttgggattcg ttcccttgca cataaatttc ctgtttgggg 10800
agttcgttcg tgagggtaat accgacggcg atcgccatct ctaaaaattc ttcggtgagg 10860
tcactgacca gatcattcag acaacaatcc ctccagtttt ctgaagtttg gggttgctcc 10920
aaacgactga gcaacagcag atcattaatt aattgactga gccgccgccc ctgccgttcg 10980
acggtctgga gcatggtttg gatgtcctgt tgatccccac cattgaggcg caaaatcact 11040
tcgacggttg ccagcaaact cgcgaggggc gatcgcagtt cgtgggcggc atcagcggta 11100
aattgttgct gctgttggta agcgtcgtag atagggcgca tggctaaacc tgctaaccac 11160
caactagaga gggtaactac gccgagagca agaggtaaac tgacccctaa aacccagcga 11220
atccgttgat tttcctgatc aaaggccatg aggctccgac caatctggag ataaccccat 11280
gaatcttgaa tatttgcagc gtcgtgggtg taggcactat gaagaatcgt cgtaaattgt 11340
cggtaacggt catcctcctg tctaatggtt tgccatgtct ccggttgtag gttctgggat 11400
aagctctgcg gttgattggg ggaaaaggca actaattgac cttgatggtt aaataggcgg 11460
atgtaataaa ggcggcgatc gctaatgccc atcgtgtgcc gttcaattaa agttggtgta 11520
gtgtcacagg gctgattaac aaggcataga tctggaaaaa tttgctgtaa agttcctgtg 11580
gggttcgcat tctccggcag tattggttct aggctatcgt gcagcgttcc ggcgattgac 11640
tccacttccc gttcaagggc aacccaattc gcttgcacaa tggaacgata aacccccagc 11700
cctaaagcac tcagaattcc ccccattacg agggcatacc agagagcaag acggaggcga 11760
ctgcgagcaa acagacgata actgttcatg gttctaccgt aaaccgataa ccttggccgg 11820
ggacagtttc tatcgggcaa aaacaagcat atttcgctaa ttttcgccga attaaccgca 11880
tttgcgccgc tacaacatta ctaacgggtt cctcctccaa atcccaaagc tgttgccgaa 11940
ttttactgcc ggagagaatg cgatctgggt tttgcatgag gtattgcaga atctgaaatt 12000
ccttgaccgt gagggtaatg gcttgggggg cttgccctgt ctgtctcact actaattcgg 12060
tattgctggg gtcaaggcta aaattgccca cccgaagaat ttggggctga aattggggcg 12120
atcgccgttg gagagcgcga acccgtgcga gtaattccgc catcacaaaa ggtttgacca 12180
aataatcatc cgcccccgca tccaagcctc tcactcgatt ttctggttct cccaaggcag 12240
tcaacatcaa tactgggaga ggattatgct gcgatcgcag tttttgacaa agctccaagc 12300
ctgacagtcc tggcaacaac caatctagaa ttgccacacc gtaatcagtc cattgatttt 12360
ccagataatg ccaagcctgc tgcccatccg tcacccaatc cactacatac ttctcgctga 12420
taagcacctt cttaatcacc aagcctagat cttcttcgtc ttctaccaat aaaattcgca 12480
tggtttaagc cagaattacc acgaacttta tcctaatcac aaacagccta tttcacttag 12540

```
atttcatacc ccctctggca aactggaaaa aattttcgtg ccattttgtc tctaaatgtg  12600
aggtgctgtg atgaaatcga ctcgcttagc cagttccgtt cttgccgtta gtttagcctt  12660
gggagccccc agcgttgtct ttgcccacgt gggtcatggt gatgaatttc aggcggaggg  12720
cggtatcaac cgcgtcaagg tcaatgcgga aacggattct cttttgggca ttgagatcaa  12780
agaaattgcg cctacaacag atggcagtgc tggagtctat atccccatga cggcgatcgt  12840
tgaggatggt gacaaaaaac tggtgtttgt ccactacggt gatttctatg agcctgtccc  12900
tgtgaccact ggcgcaaccc aaggggaatt ggtggaaatt acagatgggt tgtctattgg  12960
agaacattta gttattcaag gttcgctatc tctttacgct gaatcccgca agactcaaac  13020
tgcagaaact ggaacggaaa caacggcaga aaccgaacca atgccggcag attctgaatc  13080
tcctgtgaca atcacttccg aaaaccacgc ccaagccgat gcccagggaa ttccccacag  13140
ccatgatgag aatggtgatc ttgtggcgac ctctcaggcg agatttcctt tcataacaac  13200
aattatcggt gcggcggcga tcgccgtgct tggtggattg ggtattcgag ccttcaacat  13260
gagtcgcaaa ggcaaaaatt tctttggtga ataggtcggt tttatgacgg gacaaaccca  13320
tattcttttt gacttttatg ttcaattcct tactcaataa cattctcaaa aattcgatcg  13380
cccaacgttg gttgattgtg atcgcggcga tcggcgtaac gctgtgggga ttagtcagtc  13440
tcacccaaat gccgttggat gttttccccg aatttgcgcc gccccaagtg gatattcaca  13500
cggaggcaac aggtctagca ccagaggaag tcgaaaccca gattaccgtc cccatcgaaa  13560
gtgcggtaaa tggtttaccc ggtgtgacct tggtgcgatc gtcctcgaag gtcggcttgt  13620
cgatggtgca agtcgtcttt gaccaagatg ccgatatcta caaagcaagg caagcagtca  13680
ctgaacggtt gcaacagatc accagtcaat tgccggaggg aacccatgcc cccgaaattt  13740
cgccgctggt gtcacctttg ggaaccattc tgcaatattc cctcacccta aatggacagg  13800
gacaaacctc tctcatggat ttacgccgtt tcgtggaaac gaccctcaat aatcaggtgt  13860
tgtccgtgcc gggggtctcc caagtgacga tctatggagg tgaggaacgg gaagaacaaa  13920
ttctcgttga tccagcaagg ttagaagccc tcaatgtttc ccttgatgaa gtgaccgcag  13980
cagcggagtc agctagttct aatgctcctg gggggtttctt gattggtggg ggtcaagaat  14040
tgcttattcg tgggattggt caagtgcaat ccatcgaaga tttacagcaa tccgttgtga  14100
aagtgaacgc agcaggggaa ccaattttgt tggaggatgt tgcccaggtg cagacagggg  14160
ctgctcttaa acgggggggat gcaagcttta atggtcagcc tgcggtggta gtaatgatca  14220
ataaacagcc tgatgtggat acgccgacgg tcactaaagg ggtagaagcg atcatcgctg  14280
attttcaggc aaatcttccc gctgatgtgc agatcgcgcg gacgtttaga caggcaaatt  14340
tcatcgatat ggcgatcgcc aatgtgagtg catctttact ccaagggatc gtgattgtgt  14400
cgattattat gctgctgttt ttgatgaact ggcggacggc aatgattacc ctgagcgcga  14460
ttccgttatc cctgctgatc ggcttgatgt tcatgaaagc ctttggtttg gggattaata  14520
ccatgaccct cggtggtttg gtggtggcga tcggttccgt ggtggatgat tccattgtgg  14580
atatggaaaa ttgctatcgg gggttacgga aaaaccaagc ctcagataat cctaaacacc  14640
cgctgcaaat cgtttatgaa acctcgaaag aagtgcggtt agcggtgatt ttttccacgg  14700
tgattatcgt tgtggtcttt gcgccgatct ttagtttgac aggcgttgag ggacggattt  14760
ttgcgccgat gggtttggct tatctattgt cgatcgccgc ttcgacttta gtagcaatga  14820
ccctttctcc agcactctgt ggcattttgc tagcgaatca aacgttgccc cctgaaggta  14880
```

cttgggtgtc gcggtttgcc gaatggattt atcgtcccct cctgaatctt tctttaaaag 14940
caccccaatt aatcctaggg tttgccctcg caaccttagt cgcggcgatc gccattgtgc 15000
cgtccttagg tcgcgttttt ttgccagagt ttcaggaaaa atccatggtc aattctatgg 15060
tgctgttccc tggggtgtcc ttggatatga ccaaccgcgc agggatggca ttatcaaaat 15120
ctatcggcga aaatcctctc tatgagtgga ttcaagtccg tgcgggtcgt gcgccagggg 15180
atgctgatgg ggctggggtt agcatggctc acgtcgatgt ggaactcagt gatcttgccc 15240
tcaaggatcg agaagccagt gtgcaacaat tgcggcagga atttctcaat ttaccagggg 15300
ttgcgcccaa tattggcggt tttatttccc atcgcatgga tgaggtgcta tctggggtca 15360
gaagtgcgat cgctatcaag atctatggtt ctgatttaca ggaactgcgc agcattgggg 15420
aacaagtacg ggatgccatt gaaccgattg aaggtttggt ggatttgcaa ctcgaacccc 15480
aactcccaat ccgtcaagtg caaatccaat atgatcgcgc ggcggcggcc cgttatggcg 15540
taaccatggc aaccttgtct gagacggtgg aaaccgcgtt aaatggccgt gtggtgggtc 15600
aagtgcccga aaatcagcaa ttaattaata tcaccgttgc cctacaggaa tcggctcgta 15660
atagtttaga tgcgatccgc gcaattccct tgggtacgcc gactggggaa atgattaccc 15720
tcggtaatgt tgcccaagtg gattacggta tgggagcgaa tgttgttaat cgtgaggatg 15780
tgtcccggtt aattgtcgtt tctaccaatg tggcagggcg cgatcttggc agtgtggtcg 15840
ccgatattca aagcattatt cgtgatcaaa ttcaattacc ggaaggctat tttatccagt 15900
acggtgggca gtttgaagcg gaacaaaacg cgaccaataa tctgttgatc tacagtcttt 15960
tggcgatcgc cgtgattacg attttgatgt atttttccgt caaatccttc cctgccaccg 16020
tcgccatcat gctgaattta cccttggcat tagtgggggg cattgcatcc atcgccttaa 16080
cgggaggggt catttccatc gcctcattaa tcgggtttat taccttattc ggggtcgccg 16140
tgcggaatgg attattactg gtggataatt acaaccaaaa atttgccgct ggagttcctc 16200
tgaaacaggc tgtgatgcag ggttctctgg atcgggttaa tgccattctg atgaccgctt 16260
tgacctcggc tttggggatg ttacctttgg cgatcgcctc cggcgcaggg aacgaaattc 16320
ttcaaccttt ggcgatcgtg gtactgggtg gtttgtttac ttccactgcg ttaactttac 16380
tcgtcatccc agcactttat gccaaatttg gacggtggtt tatgcccaaa caaaccagat 16440
caaatgtcta tcaacctgtc gtactggaac cgcctttagt cggcagtaat gacattagaa 16500
actaactttt ttatatacca aaatttaggg cgtgacagat tttcttaaga gggaagaatc 16560
acgctttttt tgtttttcta atagatctaa atatctcttt tttttcataa aaattttgga 16620
acatcaaatg agtaaaatat tttcattatt tgcctgttta aaaaatacag tttttgcgag 16680
attatacttt gcccaaacca ttaatcttat cggggatgct ttgacatggt tgggattagc 16740
actcctcgcc tttgaaattg cgggggaaca atcgggtcag attctcgcag ggcattaac 16800
cttgcgggtg accgcctatg tgattttatc gcccattgct ggagtcattg cggatcgttt 16860
tgaccgtaaa aaaattatgg tcatgaccca tttaatgcgg atggcgatcg tttgtttctt 16920
tcccttcgtg aatcaggctt ggcaaatcta tggcatcgtg cttggactca atatttttgc 16980
tgcctttttt acgccaacct ataccgcaac tattccgtta gtaacaggtg agaaagaata 17040
tcctcaggcg atcgccctat ccagtgccac ctatcaactg ttgggtgtgt taggtcccgg 17100
tctagctggt agtgtggcgg cgtttgtggg aactcgttct atattttttc tggatggtgc 17160
aacctttttt attgcagcta ttttgttaat gacattgccg attcaactgt tagttaatca 17220
cgaaaaatca tcgtcaaaaa gtttatataa aaccctagaa gatatcaaag ctggtagttt 17280

```
ttgtctgtag gcagatcccc agattcgtta tgccttatta atgcaacttg tggcggcgat  17340
cgccggagca gaaattctgg taaataccgt cagttatgta caaggtagtt tagctcttgg  17400
caaagtggaa tacagttggg taatggcagc ctttggcatg ggcgcaaccc taacatccgt  17460
ttgcattaat tatcttcaaa actattttca aaaaatgact ctggtaacaa tcggagccag  17520
tttaattact ttggcattag tcccagccag tttcgttggt ttccaaagtt tattactatt  17580
gtggttattc gctggcattg gtcaaacctt ggtgaatgtt cccacccaaa ccctgattgc  17640
agatcgcgtt gcagtagaag tgcagggacg agtctatggc gcacatttcg catggagtca  17700
tttttggtgg gcatttgcct atcctttagc aggttggctt ggtctgcaat ttacgacagc  17760
atttcttgtc agtagtatcg ttggcagcat tgccttagtg agctttttct tgatggtcaa  17820
acccacaaac attacccaag gactttggca tgaacatgct catcaccatg atttaaccca  17880
caatcaccac accgagtccc gcgaactaaa ccatcggcat agtcatctac attttcacta  17940
gggcgatcgc ccccggtttc gccacaaaaa aactccccag gccggggagt catagatcac  18000
gctttattgc gtatctgagg aaaatcctaa ggagcaacga gatgaaccta aaggg       18055
```

<210> SEQ ID NO 73
<211> LENGTH: 13716
<212> TYPE: DNA
<213> ORGANISM: Artificial
<220> FEATURE:
<223> OTHER INFORMATION: Synthetic vector construct #1329
pVZ325a-nrsR-PnrsB-zpPDC_ter-corR-PcorT-zmPDC(fco)_oop for
transformation of Synechocystis sp. PCC6803

<400> SEQUENCE: 73

```
tggcgatagg gtgaaccgat agccttgacc gggaactgtt ttaattgggc aaggacaatt     60
ttgttgagct agcttgcgtc gtatcaaacg catttgggcc gccaccacat tactcatggg    120
ctcctcatca agatcccaca gttgttgccg gatcttgcta ccggaaatga tccgctctgg    180
gttttgcatc agatattgaa aaatttgaaa ttctcttacg gttaaagcaa tttcctgtct    240
ttctaggttt agtggctccg agatagttac cgataacaga ttattactgg gatcaaggct    300
gaagttgccc aaagttaaaa tttgcggttg gaattgtggc gatcgccgtt gtagtgcccg    360
cagtcttgct aatagctctg ccatcacaaa cggttttgtt agatagtcat ctgccccggc    420
atctagtcct tcgacacggt tttccggttc tcctaacgct gttaacatca acaccggcaa    480
ggaattaccc tgggttctca gtttttgaca gagttccaaa cccgataatc ccggcagtaa    540
ccaatccaca atggcaaggg tgtattccgt ccattgattt tccaaataat cccaagcttg    600
ggagccatcc gtcacccaat ccaccacata cttttcacta actagcactt tcttaatagc    660
cattcccaaa tccgtctcat cttccaccag caaaattcgc atcgcctctg ccttttttat    720
aacggtctga tcttagcggg ggaaggagat tttcacctga atttcatacc cccttttggca   780
gactgggaaa atcttggaca aattcccaat ttgaggtggt gtgatgaatt cctataccgt    840
tggtatgtac ttggcagaac gcctagccca gatcggcctg aaacaccact ttgccgtggc    900
cggtgactac aacctggtgt tgcttgatca gctcctgctg aacaaagaca tggagcaggt    960
ctactgctgt aacgaactta actgcggctt tagcgccgaa ggttacgctc gtgcacgtgg   1020
tgccgccgct gccatcgtca cgttcagcgt aggtgctatc tctgcaatga acgccatcgg   1080
tggcgcctat gcagaaaacc tgccggtcat cctgatctct ggctcaccga acaccaatga   1140
ctacggcaca ggccacatcc tgcaccacac cattggtact actgactata actatcagct   1200
```

-continued

```
ggaaatggta aaacacgtta cctgcgcacg tgaaagcatc gtttctgccg aagaagcacc   1260
ggcaaaaatc gaccacgtca tccgtacggc tctacgtgaa cgcaaaccgg cttatctgga   1320
aatcgcatgc aacgtcgctg gcgctgaatg tgttcgtccg ggcccgatca atagcctgct   1380
gcgtgaactc gaagttgacc agaccagtgt cactgccgct gtagatgccg ccgtagaatg   1440
gctgcaggac cgccagaacg tcgtcatgct ggtcggtagc aaactgcgtg ccgctgccgc   1500
tgaaaaacag gctgttgccc tagcggaccg cctgggctgc gctgtcacga tcatggctgc   1560
cgaaaaaggc ttcttcccgg aagatcatcc gaacttccgc ggcctgtact ggggtgaagt   1620
cagctccgaa ggtgcacagg aactggttga aaacgccgat gccatcctgt gtctggcacc   1680
ggtattcaac gactatgcta ccgttggctg gaactcctgg ccgaaaggcg acaatgtcat   1740
ggtcatggac accgaccgcg tcactttcgc aggacagtcc ttcgaaggtc tgtcattgag   1800
caccttcgcc gcagcactgg ctgagaaagc accttctcgc ccggcaacga ctcaaggcac   1860
tcaagcaccg gtactgggta ttgaggccgc agagcccaat gcaccgctga ccaatgacga   1920
aatgacgcgt cagatccagt cgctgatcac ttccgacact actctgacag cagaaacagg   1980
tgactcttgg ttcaacgctt ctcgcatgcc gattcctggc ggtgctcgtg tcgaactgga   2040
aatgcaatgg ggtcatatcg gttggtccgt accttctgca ttcggtaacg ccgttggttc   2100
tccggagcgt cgccacatca tgatggtcgg tgatggctct ttccagctga ctgctcaaga   2160
agttgctcag atgatccgct atgaaatccc ggtcatcatc ttcctgatca acaaccgcgg   2220
ttacgtcatc gaaatcgcta tccatgacgg ccccttacaac tacatcaaaa actggaacta   2280
cgctggcctg atcgacgtct tcaatgacga agatggtcat ggcctgggtc tgaaagcttc   2340
tactggtgca gaactagaag gcgctatcaa gaaagcactc gacaatcgtc gcggtccgac   2400
gctgatcgaa tgtaacatcg ctcaggacga ctgcactgaa accctgattg cttggggtaa   2460
acgtgtagca gctaccaact ctcgcaaacc acaagcgtaa gttgatgtag tgaattaggc   2520
ggggcctatt agggccccac cacatagccc ctcttacggc gcaatacccg taagaggggc   2580
tgttttatat aattaaaact agagtcgacc atgcgtccaa aactttcacc atcctttccc   2640
tatcaacctt tactgcacta aagacaagtg agatagcagt ggcaatctgg ctttgcaatc   2700
aatgtttcca ctaaagcgtt tagcgttact gcggctagaa gtcctccacc gaggctcccc   2760
tgaatggtga tatggggaat gggactggtc atcagtcgtc gttttgcccc cggagcatga   2820
ctaaaaccga tcggcattcc gatcacaaga gccggctgaa tatgttgttg ctctatcagc   2880
ttacaggcag tgagtaaaac agaaggggca tagccgatcg ccagcacaca tccttgggga   2940
atctgttgta accgctgttg ccaatggtca tggtgccaaa aagcttgctc ggcttcccta   3000
agccctgtga tgtgagggtc gtcaatcagc gttttaaccg tacatcctaa atgagctaac   3060
cgagtttgat caagagccgc agccacaacc ggaacatcgg tgacgactgg acaccctgct   3120
ttcagtgcat ctcgtgccga ggcgatcgct ccctgactca atcgaacggc gtttaccaag   3180
ctaacatcac cacaggccag cactaattga tgtagtaagt gaatggtaat ttcagagtaa   3240
gccgataaat ccggtagcag gtgtttgagg gattcctgaa aggcttctgg atgagttgtt   3300
gtctccgcat ctaggttcgt ccacaactga tcgagttttc ctaacccctc ctggacatcc   3360
acatcaagct gtttcagttg ggccagagct tccgcttggg taatctggca actctggtcg   3420
cgtcccagta atccttctaa agcagatgcg gtttggcgga gtcgagtaat ctgctgaatc   3480
acagcctgat attgctgttg caactgcacc attagggtgg gatcaaggct ctcttcagaa   3540
tggctatcca gcagttgccg aatatgagac aactgaaagc cctgctgttt gagggcaatg   3600
```

-continued

```
actcgttgga gccgttgtac gtcctgctga gtataaaggc ggtagttgcc ctctgagcgt   3660
tgaacggggg gaagcaatcc cagggtgtgg taatggcgca ccatgcgagg cgtaacgcca   3720
cctcccactg catctgtgag ttctttaatc gttaagtgat tagtcttcat ccctttagtt   3780
tactcaaaac cttgacattg acactaatgt taaggtttag gctgagaagg taaaaatcca   3840
agttaaaaag catgaattcc tataccgtgg gtacctattt ggccgaacgg ttggtgcaaa   3900
ttggtttgaa acaccacttt gccgtggccg gtgactacaa cttggtgttg ttggacaact   3960
tgttgttgaa caaaaacatg gaacaagtgt attgttgtaa cgaattgaac tgtggttttt   4020
ccgccgaagg ttatgctcgg gccaaaggtg ccgccgccgc cgtggtgacc tactccgtgg   4080
gtgccttgtc cgcctttgat gctattggtg gtgcctatgc cgaaaacttg cccgtgattt   4140
tgatttccgg tgctcccaac aacaatgatc acgctgctgg tcacgtgttg caccacgctt   4200
tgggtaaaac cgactatcac tatcaattgg aaatggccaa aaacattacc gccgccgctg   4260
aagccattta cacccccgaa gaagctcccg ctaaaattga tcacgtgatt aaaaccgctt   4320
tgcgggaaaa aaaacccgtg tatttggaaa ttgcttgtaa cattgcttcc atgccctgtg   4380
ccgctcccgg tcccgcctcc gccttgttta atgacgaagc ctccgacgaa gcttccttga   4440
atgccgccgt ggaagaaacc ttgaaattta ttgccaaccg ggacaaagtg gccgtgttgg   4500
tgggttccaa attgcgggcc gctggtgctg aagaagctgc tgtgaaattt gctgatgctt   4560
tgggtggtgc cgtggctacc atggctgctg ccaaatcctt ttttcccgaa gaaaaccccc   4620
actacattgg tacctcctgg ggtgaagtgt cctatcccgg tgtggaaaaa accatgaaag   4680
aagccgatgc cgtgattgct ttggctcccg tgtttaacga ctactccacc accggttgga   4740
ccgatattcc cgatcccaaa aaattggtgt tggctgaacc ccggtccgtg gtggtgaacg   4800
gtgtgcggtt tccctccgtg cacttgaaag actatttgac ccggttggct caaaaagtgt   4860
ccaaaaaaac cggtgctttg gactttttta aatccttgaa tgccggtgaa ttgaaaaaag   4920
ccgctcccgc tgatccctcc gctcccttgg tgaacgccga aattgcccgg caagtggaag   4980
ctttgttgac ccccaacacc accgtgattg ctgaaaccgg tgactcctgg tttaatgctc   5040
aacggatgaa attgcccaac ggtgctcggg tggaatatga aatgcaatgg ggtcacattg   5100
gttggtccgt gcccgccgcc tttggttatg ccgtgggtgc tcccgaacgg cggaacattt   5160
tgatggtggg tgatggttcc tttcaattga ccgctcaaga agtggctcaa atggtgcggt   5220
tgaaattgcc cgtgattatt tttttgatta ataactatgg ttacaccatt gaagtgatga   5280
ttcacgatgg tccctacaac aacattaaaa actgggatta tgccggtttg atggaagtgt   5340
ttaacggtaa cggtggttat gactccggtg ctggtaaagg tttgaaagct aaaaccggtg   5400
gtgaattggc cgaagctatt aaagtggctt tggccaacac cgacggtccc accttgattg   5460
aatgttttat tggtcgggaa gactgtaccg aagaattggt gaaatggggt aaacgggtgg   5520
ctgccgccaa ctcccggaaa cccgtgaaca aattgttgta gttaaacgct cggttgccgc   5580
cgggcgtttt ttactagtct cgagctgcag gagcagaaga gcatacatct ggaagcaaag   5640
ccaggaaagc ggcctatgga gctgtgcggc agcgctcagt aggcaatttt tcaaaatatt   5700
gttaagcctt ttctgagcat ggtatttttc atggtattac caattagcag gaaaataagc   5760
cattgaatat aaaagataaa aatgtcttgt ttacaataga gtgggggggg tcagcctgcc   5820
gccttgggcc gggtgatgtc gtacttgccc gccgcgaact cggttaccgt ccagcccagc   5880
gcgaccagct ccggcaacgc ctcgcgcacc cgctggcggc gcttgcgcat ggtcgaacca   5940
```

```
ctggcctctg acggccagac atagccgcac aaggtatcta tggaagcctt gccggttttg   6000
ccggggtcga tccagccaca cagccgctgg tgcagcaggc gggcggtttc gctgtccagc   6060
gcccgcacct cgtccatgct gatgcgcaca tgctggccgc cacccatgac ggcctgcgcg   6120
atcaaggggt tcagggccac gtacaggcgc ccgtccgcct cgtcgctggc gtactccgac   6180
agcagccgaa acccctgccg cttgcggcca ttctgggcga tgatggatac cttccaaagg   6240
cgctcgatgc agtcctgtat gtgcttgagc gccccaccac tatcgacctc tgccccgatt   6300
tcctttgcca gcgcccgata gctacctttg accacatggc attcagcggt gacggcctcc   6360
cacttgggtt ccaggaacag ccggagctgc cgtccgcctt cggtcttggg ttccgggcca   6420
agcactaggc cattaggccc agccatggcc accagccctt gcaggatgcg cagatcatca   6480
gcgcccagcg gctccgggcc gctgaactcg atccgcttgc cgtcgccgta gtcatacgtc   6540
acgtccagct tgctgcgctt gcgctcgccc cgcttgaggg cacggaacag gccgggggcc   6600
agacagtgcg ccgggtcgtg ccggacgtgg ctgaggctgt gcttgttctt aggcttcacc   6660
acggggcacc cccttgctct tgcgctgcct ctccagcacg gcgggcttga gcaccccgcc   6720
gtcatgccgc ctgaaccacc gatcagcgaa cggtgcgcca tagttggcct tgctcacacc   6780
gaagcggacg aagaaccggc gctggtcgtc gtccacaccc cattcctcgg cctcggcgct   6840
ggtcatgctc gacaggtagg actgccagcg gatgttatcg accagtaccg agctgccccg   6900
gctggcctgc tgctggtcgc ctgcgcccat catggccgcg cccttgctgg catggtgcag   6960
gaacacgata gagcacccgg tatcggcggc gatggcctcc atgcgaccga tgacctgggc   7020
catggggccg ctggcgtttt cttcctcgat gtggaaccgg cgcagcgtgt ccagcaccat   7080
caggcggcgg ccctcggcgg cgcgcttgag gccgtcgaac cactccgggg ccatgatgtt   7140
gggcaggctg ccgatcagcg gctggatcag caggccgtca gccacggctt gccgttcctc   7200
ggcgctgagg tgcgccccaa gggcgtgcag gcggtgatga atggcggtgg gcgggtcttc   7260
ggcgggcagg tagatcaccg ggccggtggg cagttcgccc acctccagca gatccggccc   7320
gcctgcaatc tgtgcggcca gttgcagggc cagcatggat ttaccggcac caccgggcga   7380
caccagcgcc ccgaccgtac cggccaccat gttgggcaaa acgtagtcca gcggtggcgg   7440
cgctgctgcg aacgcctcca gaatattgat aggcttatgg gtagccattg attgcctcct   7500
ttgcaggcag ttggtggtta ggcgctggcg gggtcactac ccccgccctg cgccgctctg   7560
agttcttcca ggcactcgcg cagcgcctcg tattcgtcgt cggtcagcca gaacttgcgc   7620
tgacgcatcc ctttggcctt catgcgctcg gcatatcgcg cttggcgtac agcgtcaggg   7680
ctggccagca ggtcgccggt ctgcttgtcc ttttggtctt tcatatcagt caccgagaaa   7740
cttgccgggg ccgaaaggct tgtcttcgcg gaacaaggac aaggtgcagc cgtcaaggtt   7800
aaggctggcc atatcagcga ctgaaaagcg gccagcctcg gccttgtttg acgtataacc   7860
aaagccaccg ggcaaccaat agcccttgtc acttttgatc aggtagaccg accctgaagc   7920
gcttttttcg tattccataa aacccccttc tgtgcgtgag tactcatagt ataacaggcg   7980
tgagtaccaa cgcaagcact acatgctgaa atctggcccg cccctgtcca tgcctcgctg   8040
gcggggtgcc ggtgcccgtg ccagctcggc ccgcgcaagc tggacgctgg gcagacccat   8100
gaccttgctg acggtgcgct cgatgtaatc cgcttcgtgg ccgggcttgc gctctgccag   8160
cgctgggctg gcctcggcca tggccttgcc gatttcctcg gcactgcggc cccggctggc   8220
cagcttctgc gcggcgataa agtcgcactt gctgaggtca tcaccgaagc gcttgaccag   8280
cccggccatc tcgctgcggt actcgtccag cgccgtgcgc cggtggcggc taagctgccg   8340
```

ctcgggcagt tcgaggctgg ccagcctgcg ggccttctcc tgctgccgct gggcctgctc 8400
gatctgctgg ccagcctgct gcaccagcgc cgggccagcg gtggcggtct tgcccttgga 8460
ttcacgcagc agcacccacg gctgataacc ggcgcgggtg gtgtgcttgt ccttgcggtt 8520
ggtgaagccc gccaagcggc catagtggcg gctgtcggcg ctggccgggt cggcgtcgta 8580
ctcgctggcc agcgtccggg caatctgccc ccgaagttca ccgcctgcgg cgtcggccac 8640
cttgacccat gcctgatagt tcttcgggct ggtttccact accagggcag gctcccggcc 8700
ctcggctttc atgtcatcca ggtcaaactc gctgaggtcg tccaccagca ccagaccatg 8760
ccgctcctgc tcggcgggcc tgatatacac gtcattgccc tgggcattca tccgcttgag 8820
ccatggcgtg ttctggagca cttcggcggc tgaccattcc cggttcatca tctggccggt 8880
ggtggcgtcc ctgacgccga tatcgaagcg ctcacagccc atggccttga gctgtcggcc 8940
tatggcctgc aaagtcctgt cgttcttcat cgggccacca agcgcagcca gatcgagccg 9000
tcctcggttg tcagtggcgt caggtcgagc aagagcaacg atgcgatcag cagcaccacc 9060
gtaggcatca tggaagccag catcacggtt agccatagct tccagtgcca cccccgcgac 9120
gcgctccggg cgctctgcgc ggcgctgctc acctcggcgg ctacctcccg caactctttg 9180
gccagctcca cccatgccgc ccctgtctgg cgctgggctt tcagccactc cgccgcctgc 9240
gcctcgctgg cctgctgggt ctggctcatg acctgccggg cttcgtcggc cagtgtcgcc 9300
atgctctggg ccagcggttc gatctgctcc gctaactcgt tgatgcctct ggatttcttc 9360
actctgtcga ttgcgttcat ggtctattgc ctcccggtat tcctgtaagt cgatgatctg 9420
ggcgttggcg gtgtcgatgt tcagggccac gtctgcccgg tcggtgcgga tgccccggcc 9480
ttccatctcc accacgttcg gccccaggtg aacaccgggc aggcgctcga tgccctgcgc 9540
ctcaagtgtt ctgtggtcaa tgcgggcgtc gtggccagcc cgctctaatg cccggttggc 9600
atggtcggcc catgcctcgc gggtctgctc aagccatgcc ttgggcttga gcgcttcggt 9660
cttctgtgcc ccgcccttct ccggggtctt gccgttgtac cgcttgaacc actgagcggc 9720
gggccgctcg atgccgtcat tgatccgctc ggagatcatc aggtggcagt gcgggttctc 9780
gccgccaccg gcatggatgg ccagcgtata cggcaggcgc tcggcaccgg tcaggtgctg 9840
ggcgaactcg gacgccagcg ccttctgctg gtcgagggtc agctcgaccg gcagggcaaa 9900
ttcgacctcc ttgaacagcc gcccattggc gcgttcatac aggtcggcag catcccagta 9960
gtcggcgggc cgctcgacga actccggcat gtgcccggat tcggcgtgca agacttcatc 10020
catgtcgcgg gcatacttgc cttcgcgctg gatgtagtcg gccttggccc tggccgattg 10080
gccgcccgac ctgctgccgg ttttcgccgt aaggtgataa atcgccatgc tgcctcgctg 10140
ttgcttttgc ttttcggctc catgcaatgg ccctcggaga gcgcaccgcc cgaagggtgg 10200
ccgttaggcc agtttctcga agagaaaccg gtaagtgcgc cctcccctac aaagtagggt 10260
cgggattgcc gccgctgtgc ctccatgata gcctacgaga cagcacatta acaatggggt 10320
gtcaagatgg ttaaggggag caacaaggcg gcggatcggc tggccaagct cgaagaacaa 10380
cgagcgcgaa tcaatgccga aattcagcgg gtgcgggcaa gggaacagca gcaagagcgc 10440
aagaacgaaa caaggcgcaa ggtgctggtg gggccatga ttttggccaa ggtgaacagc 10500
agcgagtggc cggaggatcg gctcatggcg gcaatggatg cgtaccttga acgcgaccac 10560
gaccgcgcct tgttcggtct gccgccacgc cagaaggatg agccgggctg aatgatcgac 10620
cgagacaggc cctgcggggc tgcacacgcg cccccaccct tcgggtaggg ggaaaggccg 10680

```
ctaaagcggc taaaagcgct ccagcgtatt tctgcggggt ttggtgtggg gtttagcggg  10740
ctttgcccgc ctttccccct gccgcgcagc ggtggggcgg tgtgtagcct agcgcagcga  10800
atagaccagc tatccggcct ctggccgggc atattgggca agggcagcag cgccccacaa  10860
gggcgctgat aaccgcgcct agtggattat tcttagataa tcatggatgg atttttccaa  10920
caccccgcca gcccccgccc ctgctgggtt tgcaggtttg ggggcgtgac agttattgca  10980
ggggttcgtg acagttattg caggggggcg tgacagttat tgcaggggtt cgtgacagtt  11040
agtacgggag tgacgggcac tggctggcaa tgtctagcaa cggcaggcat ttcggctgag  11100
ggtaaaagaa ctttccgcta agcgatagac tgtatgtaaa cacagtattg caaggacgcg  11160
gaacatgcct catgtggcgg ccaggacggc cagccgggat cgggatactg gtcgttacca  11220
gagccaccga cccgagcaaa cccttctcta tcagatcgtt gacgagtatt acccggcatt  11280
cgctgcgctt atggcagagc agggaaagga attgccgggc tatgtgcaac gggaatttga  11340
agaatttctc caatgcgggc ggctggagca tggctttcta cgggttcgct gcgagtcttg  11400
ccacgccgag cacctggtcg ctttcagctg taatccgggc agcgcaacgg aacattcatc  11460
agtgtaaaaa tggaatcaat aaagccctgc gcagcgcgca gggtcagcct gaatacgcgt  11520
gctcgaattg acataagcct gttcggttcg taaactgtaa tgcaagtagc gtatgcgctc  11580
acgcaactgg tccagaacct tgaccgaacg cagcggtggt aacggcgcag tggcggtttt  11640
catggcttgt tatgactgtt tttttgtaca gtctatgcct cgggcatcca agcagcaagc  11700
gcgttacgcc gtgggtcgat gtttgatgtt atggagcagc aacgatgtta cgcagcagca  11760
acgatgttac gcagcagggc agtcgcccta aaacaaagtt aggtggctca agtatgggca  11820
tcattcgcac atgtaggctc ggccctgacc aagtcaaatc catgcgggct gctcttgatc  11880
ttttcggtcg tgagttcgga gacgtagcca cctactccca acatcagccg gactccgatt  11940
acctcgggaa cttgctccgt agtaagacat tcatcgcgct tgctgccttc gaccaagaag  12000
cggttgttgg cgctctcgcg gcttacgttc tgcccaggtt tgagcagccg cgtagtgaga  12060
tctatatcta tgatctcgca gtctccggcg agcaccggag gcagggcatt gccaccgcgc  12120
tcatcaatct cctcaagcat gaggccaacg cgcttggtgc ttatgtgatc tacgtgcaag  12180
cagattacgg tgacgatccc gcagtggctc tctatacaaa gttgggcata cgggaagaag  12240
tgatgcactt tgatatcgac ccaagtaccg ccacctaaca attcgttcaa gccgagatcg  12300
gcttcccggc cctagacgcg tattcaggct gaccctgcgc gctgcgcagg gctttattga  12360
ttccattttt acactgatga atgttccgtt gcgctgcccg gattacagat cctctagaag  12420
aacagcaagg ccgccaatgc ctgacgatgc gtggagaccg aaaccttgcg ctcgttcgcc  12480
agccaggaca gaaatgcctc gacttcgctg ctgcccaagg ttgccgggtg acgcacaccg  12540
tggaaacgga tgaaggcacg aacccagtgg acataagcct gttcggttcg taagctgtaa  12600
tgcaagtagc gtatgcgctc acgcaactgg tccagaacct tgaccgaacg cagcggtggt  12660
aacggcgcag tggcggtttt catggcttgt tatgactgtt tttttggggt acagtctatg  12720
cctcgggcat ccaagcagca agcgcgttac gccgtgggtc gatgtttgat gttatggagc  12780
agcaacgatg ttacgcagca gggcagtcgc cctaaaacaa agttaaacat catgagggaa  12840
gcggtgatcg ccgaagtatc gactcaacta tcagaggtag ttggcgtcat cgagcgccat  12900
ctcgaaccga cgttgctggc cgtacatttg tacggctccg cagtggatgg cggcctgaag  12960
ccacacagtg atattgattt gctggttacg gtgaccgtaa ggcttgatga aacaacgcgg  13020
cgagctttga tcaacgacct tttggaaact tcggcttccc ctggagagag cgagattctc  13080
```

```
cgcgctgtag aagtcaccat tgttgtgcac gacgacatca ttccgtggcg ttatccagct  13140

aagcgcgaac tgcaatttgg agaatggcag cgcaatgaca ttcttgcagg tatcttcgag  13200

ccagccacga tcgacattga tctggctatc ttgctgacaa aagcaagaga acatagcgtt  13260

gccttggtag gtccagcggc ggaggaactc tttgatccgg ttcctgaaca ggatctattt  13320

gaggcgctaa atgaaacctt aacgctatgg aactcgccgc ccgactgggc tggcgatgag  13380

cgaaatgtag tgcttacgtt gtcccgcatt tggtacagcg cagtaaccgg caaaatcgcg  13440

ccgaaggatg tcgctgccga ctgggcaatg gagcgcctgc cggcccagta tcagcccgtc  13500

atacttgaag ctagacaggc ttatcttgga caagaagaag atcgcttggc ctcgcgcgca  13560

gatcagttgg aagaatttgt ccactacgtg aaaggcgaga tcaccaaggt agtcggcaaa  13620

taatgtctaa caattcgttc aagccgacgc cgcttcgcgg cgcggcttaa ctcaagctct  13680

agagtcgacg ggagtttgca aactccctca tattca                            13716
```

```
<210> SEQ ID NO 74
<211> LENGTH: 13727
<212> TYPE: DNA
<213> ORGANISM: Artificial
<220> FEATURE:
<223> OTHER INFORMATION: Synthetic vector construct #1379
      pVZ325a-nrsR-PnrsB-zpPDC_ter-corR-PcorT-zmPDCdeg_spf for
      transformation of Synechocystis sp. PCC6803

<400> SEQUENCE: 74
```

```
tcgacgggag tttgcaaact ccctcatatt catggcgata gggtgaaccg atagccttga     60

ccgggaactg ttttaattgg gcaaggacaa ttttgttgag ctagcttgcg tcgtatcaaa    120

cgcatttggg ccgccaccac attactcatg ggctcctcat caagatccca cagttgttgc    180

cggatcttgc taccggaaat gatccgctct gggttttgca tcagatattg aaaaatttga    240

aattctctta cggttaaagc aatttcctgt ctttctaggt ttagtggctc cgagatagtt    300

accgataaca gattattact gggatcaagg ctgaagttgc ccaaagttaa aatttgcggt    360

tggaattgtg gcgatcgccg ttgtagtgcc cgcagtcttg ctaatagctc tgccatcaca    420

aacggttttg ttagatagtc atctgccccg gcatctagtc cttcgacacg gttttccggt    480

tctcctaacg ctgttaacat caacaccggc aaggaattac cctgggttct cagtttttga    540

cagagttcca aacccgataa tcccggcagt aaccaatcca caatggcaag ggtgtattcc    600

gtccattgat tttccaaata atcccaagct tgggagccat ccgtcaccca atccaccaca    660

tacttttcac taactagcac tttcttaata gccattccca aatccgtctc atcttccacc    720

agcaaaattc gcatcgcctc tgcctttttt ataacggtct gatcttagcg ggggaaggag    780

attttcacct gaatttcata ccccctttgg cagactggga aaatcttgga caaattccca    840

atttgaggtg gtgtgatgaa ttcctatacc gttggtatgt acttggcaga acgcctagcc    900

cagatcggcc tgaaacacca ctttgccgtg gccggtgact acaacctggt gttgcttgat    960

cagctcctgc tgaacaaaga catggagcag gtctactgct gtaacgaact taactgcggc   1020

tttagcgccg aaggttacgc tcgtgcacgt ggtgccgccg ctgccatcgt cacgttcagc   1080

gtaggtgcta tctctgcaat gaacgccatc ggtggcgcct atgcagaaaa cctgccggtc   1140

atcctgatct ctggctcacc gaacaccaat gactacggca caggccacat cctgcaccac   1200

accattggta ctactgacta taactatcag ctggaaatgg taaaacacgt tacctgcgca   1260

cgtgaaagca tcgtttctgc cgaagaagca ccggcaaaaa tcgaccacgt catccgtacg   1320
```

-continued

```
gctctacgtg aacgcaaacc ggcttatctg gaaatcgcat gcaacgtcgc tggcgctgaa   1380
tgtgttcgtc cgggcccgat caatagcctg ctgcgtgaac tcgaagttga ccagaccagt   1440
gtcactgccg ctgtagatgc cgccgtagaa tggctgcagg accgccagaa cgtcgtcatg   1500
ctggtcggta gcaaactgcg tgccgctgcc gctgaaaaac aggctgttgc cctagcggac   1560
cgcctgggct gcgctgtcac gatcatggct gccgaaaaag gcttcttccc ggaagatcat   1620
ccgaacttcc gcggcctgta ctggggtgaa gtcagctccg aaggtgcaca ggaactggtt   1680
gaaaacgccg atgccatcct gtgtctggca ccggtattca acgactatgc taccgttggc   1740
tggaactcct ggccgaaagg cgacaatgtc atggtcatgg acaccgaccg cgtcactttc   1800
gcaggacagt ccttcgaagg tctgtcattg agcaccttcg ccgcagcact ggctgagaaa   1860
gcaccttctc gcccggcaac gactcaaggc actcaagcac cggtactggg tattgaggcc   1920
gcagagccca atgcaccgct gaccaatgac gaaatgacgc gtcagatcca gtcgctgatc   1980
acttccgaca ctactctgac agcagaaaca ggtgactctt ggttcaacgc ttctcgcatg   2040
ccgattcctg gcggtgctcg tgtcgaactg gaaatgcaat ggggtcatat cggttggtcc   2100
gtaccttctg cattcggtaa cgccgttggt tctccggagc gtcgccacat catgatggtc   2160
ggtgatggct ctttccagct gactgctcaa gaagttgctc agatgatccg ctatgaaatc   2220
ccggtcatca tcttcctgat caacaaccgc ggttacgtca tcgaaatcgc tatccatgac   2280
ggcccttaca actacatcaa aaactggaac tacgctggcc tgatcgacgt cttcaatgac   2340
gaagatggtc atggcctggg tctgaaagct tctactggtg cagaactaga aggcgctatc   2400
aagaaagcac tcgacaatcg tcgcggtccg acgctgatcg aatgtaacat cgctcaggac   2460
gactgcactg aaaccctgat tgcttggggt aaacgtgtag cagctaccaa ctctcgcaaa   2520
ccacaagcgt aagttgatgt agtgaattag gcggggccta ttagggcccc accacatagc   2580
ccctcttacg gcgcaatacc cgtaagaggg gctgttttat ataattaaaa ctagagtcga   2640
ccatgcgtcc aaaactttca ccatcctttc cctatcaacc tttactgcac taaagacaag   2700
tgagatagca gtggcaatct ggctttgcaa tcaatgtttc cactaaagcg tttagcgtta   2760
ctgcggctag aagtcctcca ccgaggctcc cctgaatggt gatatgggga atgggactgg   2820
tcatcagtcg tcgttttgcc cccggagcat gactaaaacc gatcggcatt ccgatcacaa   2880
gagccggctg aatatgttgt tgctctatca gcttacaggc agtgagtaaa acagaagggg   2940
catagccgat cgccagcaca catccttggg gaatctgttg taaccgctgt tgccaatggt   3000
catggtgcca aaaagcttgc tcggcttccc taagccctgt gatgtgaggg tcgtcaatca   3060
gcgttttaac cgtacatcct aaatgagcta accgagtttg atcaagagcc gcagccacaa   3120
ccggaacatc ggtgacgact ggacaccctg ctttcagtgc atctcgtgcc gaggcgatcg   3180
ctccctgact caatcgaacg gcgtttacca agctaacatc accacaggcc agcactaatt   3240
gatgtagtaa gtgaatggta atttcagagt aagccgataa atccggtagc aggtgtttga   3300
gggattcctg aaaggcttct ggatgagttg ttgtctccgc atctaggttc gtccacaact   3360
gatcgagttt tcctaacccc tcctggacat ccacatcaag ctgtttcagt tgggccagag   3420
cttccgcttg ggtaatctgg caactctggt cgcgtcccag taatccttct aaagcagatg   3480
cggtttggcg gagtcgagta atctgctgaa tcacagcctg atattgctgt tgcaactgca   3540
ccattagggt gggatcaagg ctctcttcag aatggctatc cagcagttgc cgaatatgag   3600
acaactgaaa gccctgctgt ttgagggcaa tgactcgttg gagccgttgt acgtcctgct   3660
gagtataaag gcggtagttg ccctctgagc gttgaacggg gggaagcaat cccagggtgt   3720
```

```
ggtaatggcg caccatgcga ggcgtaacgc cacctcccac tgcatctgtg agttctttaa   3780
tcgttaagtg attagtcttc atccctttag tttactcaaa accttgacat tgacactaat   3840
gttaaggttt aggctgagaa ggtaaaaatc caagttaaaa agcatgaatt cctacaccgt   3900
tggcacttac ctggctgaac gcttggttca gatcggctta aaacaccatt ttgctgttgc   3960
tggtgattat aatttggttt tgttagataa tttattgctc aataagaata tggaacaggt   4020
gtactgttgc aatgagttaa attgtggctt ttccgctgag ggctacgccc gtgctaaggg   4080
tgctgctgct gctgttgtga cttattctgt tggcgctttg agtgcttttg acgccattgg   4140
cggtgcttac gctgagaatt tgccagtgat tttaattagt ggcgccccaa ataataacga   4200
ccatgccgcc ggccatgtcc tccaccatgc cttgggtaag actgattacc attaccaact   4260
ggagatggct aaaaatatta ccgctgctgc cgaagctatc tatactcctg aggaagcccc   4320
agccaagatt gaccatgtca tcaagaccgc cttgcgggaa aaaaaaccag tgtacttaga   4380
gattgcctgt aatatcgcca gtatgccttg tgctgccccc ggtccagctt ctgctctctt   4440
taacgatgaa gcttctgatg aggccagtct caacgctgct gtggaggaaa ctttaaagtt   4500
tattgctaat cgtgataagg tggctgtttt agttggttct aaattacgtg ctgccggcgc   4560
cgaggaagcc gccgttaagt ttgccgacgc cttaggcggt gctgtggcca ctatggccgc   4620
cgctaagtct ttttttcctg aagagaatcc acactatatt ggcactagct ggggcgaggt   4680
ttcttaccca ggtgtggaga aaaccatgaa ggaggctgac gctgtgattg ccttagcccc   4740
ggtttttaat gattatagta ctaccggctg gaccgacatc ccggacccga aaaagttagt   4800
gttagccgaa ccacggagtg ttgttgtgaa tggtgtgcgt tttccttctg tgcacttaaa   4860
ggattactta actcggctcg cccagaaggt gagtaaaaag actggcgccc tcgatttttt   4920
taagagttta aacgctggcg agttaaaaaa ggctgcccca gccgacccat ccgcccccact   4980
cgttaatgct gaaattgctc ggcaggttga ggccttgtta actccaaata ccaccgtgat   5040
cgccgaaact ggcgatagtt ggtttaacgc ccaacgtatg aaattaccaa atggcgcccg   5100
tgtggagtac gagatgcaat ggggccatat tggctggagt gtgccggctg cttttggcta   5160
cgctgttggc gccccagagc ggcgtaatat tttaatggtg ggcgacggca gttttcagtt   5220
aaccgcccaa gaggttgccc aaatggtgcg tttaaagtta ccagtgatta tttttctcat   5280
taacaattac ggctatacta ttgaggtgat gattcacgac ggcccatata ataatattaa   5340
aaattgggac tacgctggct taatggaggt ctttaatggc aatggcggct acgattctgg   5400
cgccggcaag ggtttaaaag ccaagactgg cggtgagtta gctgaagcca ttaaagtggc   5460
cttagctaat actgatggtc ctactttaat tgagtgtttt attggccggg aagattgtac   5520
cgaggaactc gttaagtggg gcaaacgtgt ggccgctgct aattctcgga aacccgtgaa   5580
taaattatta tgaaatattt tagccgcccc agtcagtaat gactggggcg tttttttattg   5640
ggagctcctg caggagcaga agagcataca tctggaagca aagccaggaa agcggcctat   5700
ggagctgtgc ggcagcgctc agtaggcaat ttttcaaaat attgttaagc cttttctgag   5760
catggtattt ttcatggtat taccaattag caggaaaata agccattgaa tataaaagat   5820
aaaaatgtct tgtttacaat agagtggggg gggtcagcct gccgccttgg gccgggtgat   5880
gtcgtacttg cccgccgcga actcggttac cgtccagccc agcgcgacca gctccggcaa   5940
cgcctcgcgc acccgctggc ggcgcttgcg catggtcgaa ccactggcct ctgacggcca   6000
gacatagccg cacaaggtat ctatggaagc cttgccggtt ttgccggggt cgatccagcc   6060
```

-continued

```
acacagccgc tggtgcagca ggcgggcggt ttcgctgtcc agcgcccgca cctcgtccat   6120
gctgatgcgc acatgctggc cgccacccat gacggcctgc gcgatcaagg ggttcagggc   6180
cacgtacagg cgcccgtccg cctcgtcgct ggcgtactcc gacagcagcc gaaacccctg   6240
ccgcttgcgg ccattctggg cgatgatgga taccttccaa aggcgctcga tgcagtcctg   6300
tatgtgcttg agcgccccac cactatcgac ctctgccccg atttcctttg ccagcgcccg   6360
atagctacct ttgaccacat ggcattcagc ggtgacggcc tcccacttgg gttccaggaa   6420
cagccggagc tgccgtccgc cttcggtctt gggttccggg ccaagcacta ggccattagg   6480
cccagccatg gccaccagcc cttgcaggat gcgcagatca tcagcgccca gcggctccgg   6540
gccgctgaac tcgatccgct tgccgtcgcc gtagtcatac gtcacgtcca gcttgctgcg   6600
cttgcgctcg ccccgcttga gggcacggaa caggccgggg gccagacagt gcgccgggtc   6660
gtgccggacg tggctgaggc tgtgcttgtt cttaggcttc accacggggc accccccttgc   6720
tcttgcgctg cctctccagc acggcgggct tgagcacccc gccgtcatgc cgcctgaacc   6780
accgatcagc gaacggtgcg ccatagttgg ccttgctcac accgaagcgg acgaagaacc   6840
ggcgctggtc gtcgtccaca ccccattcct cggcctcggc gctggtcatg ctcgacaggt   6900
aggactgcca gcggatgtta tcgaccagta ccgagctgcc ccggctggcc tgctgctggt   6960
cgcctgcgcc catcatggcc gcgcccttgc tggcatggtg caggaacacg atagagcacc   7020
cggtatcggc ggcgatggcc tccatgcgac cgatgacctg ggccatgggg ccgctggcgt   7080
tttcttcctc gatgtggaac cggcgcagcg tgtccagcac catcaggcgg cggccctcgg   7140
cggcgcgctt gaggccgtcg aaccactccg gggccatgat gttgggcagg ctgccgatca   7200
gcggctggat cagcaggccg tcagccacgg cttgccgttc ctcggcgctg aggtgcgccc   7260
caagggcgtg caggcggtga tgaatggcgg tgggcgggtc ttcggcgggc aggtagatca   7320
ccgggccggt gggcagttcg cccacctcca gcagatccgg cccgcctgca atctgtgcgg   7380
ccagttgcag ggccagcatg gatttaccgg caccaccggg cgacaccagc gccccgaccg   7440
taccggccac catgttgggc aaaacgtagt ccagcggtgg cggcgctgct gcgaacgcct   7500
ccagaatatt gataggctta tgggtagcca ttgattgcct cctttgcagg cagttggtgg   7560
ttaggcgctg gcggggtcac taccccgcc ctgcgccgct ctgagttctt ccaggcactc   7620
gcgcagcgcc tcgtattcgt cgtcggtcag ccagaacttg cgctgacgca tccctttggc   7680
cttcatgcgc tcggcatatc gcgcttggcg tacagcgtca gggctggcca gcaggtcgcc   7740
ggtctgcttg tccttttggt ctttcatatc agtcaccgag aaacttgccg gggccgaaag   7800
gcttgtcttc gcggaacaag gacaaggtgc agccgtcaag gttaaggctg gccatatcag   7860
cgactgaaaa gcggccagcc tcggccttgt ttgacgtata accaaagcca ccgggcaacc   7920
aatagccctt gtcactttg atcaggtaga ccgaccctga agcgcttttt tcgtattcca   7980
taaaaccccc ttctgtgcgt gagtactcat agtataacag gcgtgagtac caacgcaagc   8040
actacatgct gaaatctggc ccgcccctgt ccatgcctcg ctggcggggt gccggtgccc   8100
gtgccagctc ggcccgcgca agctggacgc tgggcagacc catgaccttg ctgacggtgc   8160
gctcgatgta atccgcttcg tggccgggct tgcgctctgc cagcgctggg ctggcctcgg   8220
ccatggcctt gccgatttcc tcggcactgc ggccccggct ggccagcttc tgcgcggcga   8280
taaagtcgca cttgctgagg tcatcaccga agcgcttgac cagcccggcc atctcgctgc   8340
ggtactcgtc cagcgccgtg cgccggtggc ggctaagctg ccgctcgggc agttcgaggc   8400
tggccagcct gcgggccttc tcctgctgcc gctgggcctg ctcgatctgc tggccagcct   8460
```

gctgcaccag cgccgggcca gcggtggcgg tcttgccctt ggattcacgc agcagcaccc 8520
acggctgata accggcgcgg gtggtgtgct tgtccttgcg gttggtgaag cccgccaagc 8580
ggccatagtg gcggctgtcg gcgctggccg ggtcggcgtc gtactcgctg gccagcgtcc 8640
gggcaatctg cccccgaagt tcaccgcctg cggcgtcggc caccttgacc catgcctgat 8700
agttcttcgg gctggtttcc actaccaggg caggctcccg gccctcggct ttcatgtcat 8760
ccaggtcaaa ctcgctgagg tcgtccacca gcaccagacc atgccgctcc tgctcggcgg 8820
gcctgatata cacgtcattg ccctgggcat tcatccgctt gagccatggc gtgttctgga 8880
gcacttcggc ggctgaccat tcccggttca tcatctggcc ggtggtggcg tccctgacgc 8940
cgatatcgaa gcgctcacag cccatggcct tgagctgtcg gcctatggcc tgcaaagtcc 9000
tgtcgttctt catcgggcca ccaagcgcag ccagatcgag ccgtcctcgg ttgtcagtgg 9060
cgtcaggtcg agcaagagca acgatgcgat cagcagcacc accgtaggca tcatggaagc 9120
cagcatcacg gttagccata gcttccagtg ccacccccgc gacgcgctcc gggcgctctg 9180
cgcggcgctg ctcacctcgg cggctacctc ccgcaactct ttggccagct ccacccatgc 9240
cgcccctgtc tggcgctggg ctttcagcca ctccgccgcc tgcgcctcgc tggcctgctg 9300
ggtctggctc atgacctgcc gggcttcgtc ggccagtgtc gccatgctct gggccagcgg 9360
ttcgatctgc tccgctaact cgttgatgcc tctggatttc ttcactctgt cgattgcgtt 9420
catggtctat tgcctcccgg tattcctgta agtcgatgat ctgggcgttg gcggtgtcga 9480
tgttcagggc cacgtctgcc cggtcggtgc ggatgccccg gccttccatc tccaccacgt 9540
tcggccccag gtgaacaccg ggcaggcgct cgatgccctg cgcctcaagt gttctgtggt 9600
caatgcgggc gtcgtggcca gcccgctcta atgcccggtt ggcatggtcg gcccatgcct 9660
cgcgggtctg ctcaagccat gccttgggct tgagcgcttc ggtcttctgt gccccgccct 9720
tctccggggt cttgccgttg taccgcttga accactgagc ggcgggccgc tcgatgccgt 9780
cattgatccg ctcggagatc atcaggtggc agtgcgggtt ctcgccgcca ccggcatgga 9840
tggccagcgt atacggcagg cgctcggcac cggtcaggtg ctgggcgaac tcggacgcca 9900
gcgccttctg ctggtcgagg gtcagctcga ccggcagggc aaattcgacc tccttgaaca 9960
gccgcccatt ggcgcgttca tacaggtcgg cagcatccca gtagtcggcg ggccgctcga 10020
cgaactccgg catgtgcccg gattcggcgt gcaagacttc atccatgtcg cgggcatact 10080
tgccttcgcg ctggatgtag tcggccttgg ccctggccga ttggccgccc gacctgctgc 10140
cggttttcgc cgtaaggtga taaatcgcca tgctgcctcg ctgttgcttt tgcttttcgg 10200
ctccatgcaa tggccctcgg agagcgcacc gcccgaaggg tggccgttag gccagtttct 10260
cgaagagaaa ccggtaagtg cgccctcccc tacaaagtag ggtcgggatt gccgccgctg 10320
tgcctccatg atagcctacg agacagcaca ttaacaatgg ggtgtcaaga tggttaaggg 10380
gagcaacaag gcggcggatc ggctggccaa gctcgaagaa caacgagcgc gaatcaatgc 10440
cgaaattcag cgggtgcggg caagggaaca gcagcaagag cgcaagaacg aaacaaggcg 10500
caaggtgctg gtgggggcca tgattttggc caaggtgaac agcagcgagt ggccggagga 10560
tcggctcatg gcggcaatgg atgcgtacct tgaacgcgac cacgaccgcg ccttgttcgg 10620
tctgccgcca cgccagaagg atgagccggg ctgaatgatc gaccgagaca ggccctgcgg 10680
ggctgcacac gcgcccccac ccttcgggta gggggaaagg ccgctaaagc ggctaaaagc 10740
gctccagcgt atttctgcgg ggtttggtgt ggggtttagc gggctttgcc cgcctttccc 10800

```
cctgccgcgc agcggtgggg cggtgtgtag cctagcgcag cgaatagacc agctatccgg  10860
cctctggccg ggcatattgg gcaagggcag cagcgcccca caagggcgct gataaccgcg  10920
cctagtggat tattcttaga taatcatgga tggatttttc caacaccccg ccagcccccg  10980
cccctgctgg gtttgcaggt ttgggggcgt gacagttatt gcaggggttc gtgacagtta  11040
ttgcaggggg gcgtgacagt tattgcaggg gttcgtgaca gttagtacgg gagtgacggg  11100
cactggctgg caatgtctag caacggcagg catttcggct gagggtaaaa gaactttccg  11160
ctaagcgata gactgtatgt aaacacagta ttgcaaggac gcggaacatg cctcatgtgg  11220
cggccaggac ggccagccgg gatcgggata ctggtcgtta ccagagccac cgacccgagc  11280
aaacccttct ctatcagatc gttgacgagt attacccggc attcgctgcg cttatggcag  11340
agcagggaaa ggaattgccg ggctatgtgc aacgggaatt tgaagaattt ctccaatgcg  11400
ggcggctgga gcatggcttt ctacgggttc gctgcgagtc ttgccacgcc gagcacctgg  11460
tcgctttcag ctgtaatccg ggcagcgcaa cggaacattc atcagtgtaa aaatggaatc  11520
aataaagccc tgcgcagcgc gcagggtcag cctgaatacg cgtgctcgaa ttgacataag  11580
cctgttcggt tcgtaaactg taatgcaagt agcgtatgcg ctcacgcaac tggtccagaa  11640
ccttgaccga acgcagcggt ggtaacggcg cagtggcggt tttcatggct tgttatgact  11700
gtttttttgt acagtctatg cctcgggcat ccaagcagca agcgcgttac gccgtgggtc  11760
gatgtttgat gttatggagc agcaacgatg ttacgcagca gcaacgatgt tacgcagcag  11820
ggcagtcgcc ctaaaacaaa gttaggtggc tcaagtatgg gcatcattcg cacatgtagg  11880
ctcggccctg accaagtcaa atccatgcgg gctgctcttg atcttttcgg tcgtgagttc  11940
ggagacgtag ccacctactc ccaacatcag ccggactccg attacctcgg gaacttgctc  12000
cgtagtaaga cattcatcgc gcttgctgcc ttcgaccaag aagcggttgt tggcgctctc  12060
gcggcttacg ttctgcccag gtttgagcag ccgcgtagtg agatctatat ctatgatctc  12120
gcagtctccg gcgagcaccg gaggcagggc attgccaccg cgctcatcaa tctcctcaag  12180
catgaggcca acgcgcttgg tgcttatgtg atctacgtgc aagcagatta cggtgacgat  12240
cccgcagtgg ctctctatac aaagttgggc atacgggaag aagtgatgca ctttgatatc  12300
gacccaagta ccgccaccta acaattcgtt caagccgaga tcggcttccc ggccctagac  12360
gcgtattcag gctgaccctg cgcgctgcgc agggctttat tgattccatt tttacactga  12420
tgaatgttcc gttgcgctgc ccggattaca gatcctctag aagaacagca aggccgccaa  12480
tgcctgacga tgcgtggaga ccgaaacctt gcgctcgttc gccagccagg acagaaatgc  12540
ctcgacttcg ctgctgccca aggttgccgg gtgacgcaca ccgtggaaac ggatgaaggc  12600
acgaacccag tggacataag cctgttcggt tcgtaagctg taatgcaagt agcgtatgcg  12660
ctcacgcaac tggtccagaa ccttgaccga acgcagcggt ggtaacggcg cagtggcggt  12720
tttcatggct tgttatgact gtttttttgg ggtacagtct atgcctcggg catccaagca  12780
gcaagcgcgt tacgccgtgg gtcgatgttt gatgttatgg agcagcaacg atgttacgca  12840
gcagggcagt cgccctaaaa caaagttaaa catcatgagg gaagcggtga tcgccgaagt  12900
atcgactcaa ctatcagagg tagttggcgt catcgagcgc catctcgaac cgacgttgct  12960
ggccgtacat ttgtacggct ccgcagtgga tggcggcctg aagccacaca gtgatattga  13020
tttgctggtt acggtgaccg taaggcttga tgaaacaacg cggcgagctt tgatcaacga  13080
ccttttggaa acttcggctt cccctggaga gagcgagatt ctccgcgctg tagaagtcac  13140
cattgttgtg cacgacgaca tcattccgtg gcgttatcca gctaagcgcg aactgcaatt  13200
```

tggagaatgg cagcgcaatg acattcttgc aggtatcttc gagccagcca cgatcgacat 13260
tgatctggct atcttgctga caaaagcaag agaacatagc gttgccttgg taggtccagc 13320
ggcggaggaa ctctttgatc cggttcctga acaggatcta tttgaggcgc taaatgaaac 13380
cttaacgcta tggaactcgc cgcccgactg ggctggcgat gagcgaaatg tagtgcttac 13440
gttgtcccgc atttggtaca gcgcagtaac cggcaaaatc gcgccgaagg atgtcgctgc 13500
cgactgggca atggagcgcc tgccggccca gtatcagccc gtcatacttg aagctagaca 13560
ggcttatctt ggacaagaag aagatcgctt ggcctcgcgc gcagatcagt tggaagaatt 13620
tgtccactac gtgaaaggcg agatcaccaa ggtagtcggc aaataatgtc taacaattcg 13680
ttcaagccga cgccgcttcg cggcgcggct taactcaagc tctagag 13727

<210> SEQ ID NO 75
<211> LENGTH: 13304
<212> TYPE: DNA
<213> ORGANISM: Artificial
<220> FEATURE:
<223> OTHER INFORMATION: Synthetic vector construct #1356
pVZ325a-nrsRS-PnrsB*-zpPDC_ter-Prbc*-synADHdeg_oop for
transformation of Synechococcus sp. PCC7002

<400> SEQUENCE: 75
tcgaccctat atcgggcttt tctcaataaa atctttattt tttgaggtgc tttttagcca 60
taaataatca ctttagtata aaattttgac ggcgtaaagt tgataaaata gaattaagaa 120
tggactatcg gtacagaaaa aatgggtaac tggatggtga ataaacttcc cttacccaat 180
gcactctcca ccgttaaaga ccccctatgc ttaacggtga tcacctgggc aatggcgagt 240
cccaaccctg tcccccccgt tttgcgcgaa cgatctcgat taactcggta aaaacgctca 300
aaaatgtgtt cctgttggtc gggggcaatg ccgatgccgg tatcttgcac ggtgatgata 360
gccatctgtt catgggatgt cagggtaata tcaacacgtc ccccagcagt tgtgtattga 420
atggcgttgg caattaggtt tgagaccagt cgatagagtt gggattcatt accccaggcg 480
taaacttccc ctgaactcag atcactgctg agatcaatgt gggcggcgat cgctaattct 540
aaaaactctt cggtgaggtc actgactaaa tcatttaaac aacaaagccg ccaatcttcg 600
gcggtggttt cctgctctaa gcgacttagt agcaataaat ccgtaatcaa ttggcttaat 660
cgccttccct gtcgttcaac ggtatgtagc atggtgttaa tttctgggga atggcttgag 720
tcgatgcgta ataccgcttc caccgtggcc aacagactag ccaatggcga tcgtaattca 780
tgggctgcat tcgcggtgaa ttgttgttgt tgttggtagg actggtaaat gggacgcatg 840
gctaaccccg ctaagcccca actggagaag gcgaccaaac ccagggcaat gggaaaacta 900
agccctaaaa tccaaagaat acgtttattt tcggcatcaa aggctgccag gctccggcca 960
atttgtagat agccccagga agatttgtct gtattaccgg cgctatgcaa aatggtggtg 1020
aattgtcgat accgatcgcc ggttgggggg tgaatagtct gccaagtttc ctggttaaaa 1080
atggaggata gggaagccgg ttgattaggc gaaaaagcca gcaggttgcc ttgataatca 1140
aataaacgaa tgtaatataa actgcgatca ctaatgccca acgtgtgacg ttcaatcagg 1200
gtggggttga cctggcaggg ttggttgacc aaacacagat cgggcaacat tttttgtaat 1260
actccggtgg gactagcatt actcggcaac atcggctcta aactgtcatg caacgtcccg 1320
gcgatcgact ccacttctcg ctccaacgcc atccagttgg cctgcacaat ggcacgataa 1380
acccccaacc ccaacagggt aagaataccc cccattacta gggcatacca gaaagccaat 1440

```
tgcagacgac tacgggcaaa gaggcgacgg gtattcatgg cgatagggtg aaccgatagc   1500
cttgaccggg aactgtttta attgggcaag gacaattttg ttgagctagc ttgcgtcgta   1560
tcaaacgcat ttgggccgcc accacattac tcatgggctc ctcatcaaga tcccacagtt   1620
gttgccggat cttgctaccg gaaatgatcc gctctgggtt ttgcatcaga tattgaaaaa   1680
tttgaaattc tcttacggtt aaagcaattt cctgtctttc taggtttagt ggctccgaga   1740
tagttaccga taacagatta ttactgggat caaggctgaa gttgcccaaa gttaaaattt   1800
gcggttggaa ttgtggcgat cgccgttgta gtgcccgcag tcttgctaat agctctgcca   1860
tcacaaacgg ttttgttaga tagtcatctg ccccggcatc tagtccttcg acacggtttt   1920
ccggttctcc taacgctgtt aacatcaaca ccggcaagga attaccctgg gttctcagtt   1980
tttgacagag ttccaaaccc gataatcccg gcagtaacca atccacaatg gcaagggtgt   2040
attccgtcca ttgattttcc aaataatccc aagcttggga gccatccgtc acccaatcca   2100
ccacatactt ttcactaact agcactttct taatagccat tcccaaatcc gtctcatctt   2160
ccaccagcaa aattcgcatc gcctctgcct tttttataac ggtctgatct tagcgggggga   2220
aggagatttt cacctgaatt tcataccccc tttggcagac tgggaaaatc ttggacaaat   2280
tcccaatttg aggtggtgtg atgaattcct ataccgttgg tatgtacttg gcagaacgcc   2340
tagcccagat cggcctgaaa caccactttg ccgtggccgg tgactacaac ctggtgttgc   2400
ttgatcagct cctgctgaac aaagacatgg agcaggtcta ctgctgtaac gaacttaact   2460
gcggctttag cgccgaaggt tacgctcgtg cacgtggtgc cgccgctgcc atcgtcacgt   2520
tcagcgtagg tgctatctct gcaatgaacg ccatcggtgg cgcctatgca gaaaacctgc   2580
cggtcatcct gatctctggc tcaccgaaca ccaatgacta cggcacaggc cacatcctgc   2640
accacaccat tggtactact gactataact atcagctgga aatggtaaaa cacgttacct   2700
gcgcacgtga aagcatcgtt tctgccgaag aagcaccggc aaaaatcgac cacgtcatcc   2760
gtacggctct acgtgaacgc aaaccggctt atctggaaat cgcatgcaac gtcgctggcg   2820
ctgaatgtgt tcgtccgggc ccgatcaata gcctgctgcg tgaactcgaa gttgaccaga   2880
ccagtgtcac tgccgctgta gatgccgccg tagaatggct gcaggaccgc cagaacgtcg   2940
tcatgctggt cggtagcaaa ctgcgtgccg ctgccgctga aaaacaggct gttgccctag   3000
cggaccgcct gggctgcgct gtcacgatca tggctgccga aaaaggcttc ttcccggaag   3060
atcatccgaa cttccgcggc ctgtactggg gtgaagtcag ctccgaaggt gcacaggaac   3120
tggttgaaaa cgccgatgcc atcctgtgtc tggcaccggt attcaacgac tatgctaccg   3180
ttggctggaa ctcctggccg aaaggcgaca atgtcatggt catggacacc gaccgcgtca   3240
ctttcgcagg acagtccttc gaaggtctgt cattgagcac cttcgccgca gcactggctg   3300
agaaagcacc ttctcgcccg gcaacgactc aaggcactca agcaccggta ctgggtattg   3360
aggccgcaga gcccaatgca ccgctgacca atgacgaaat gacgcgtcag atccagtcgc   3420
tgatcacttc cgacactact ctgacagcag aaacaggtga ctcttggttc aacgcttctc   3480
gcatgccgat tcctggcggt gctcgtgtcg aactggaaat gcaatggggt catatcggtt   3540
ggtccgtacc ttctgcattc ggtaacgccg ttggttctcc ggagcgtcgc cacatcatga   3600
tggtcggtga tggctctttc cagctgactg ctcaagaagt tgctcagatg atccgctatg   3660
aaatcccggt catcatcttc ctgatcaaca accgcggtta cgtcatcgaa atcgctatcc   3720
atgacggccc ttacaactac atcaaaaact ggaactacgc tggcctgatc gacgtcttca   3780
atgacgaaga tggtcatggc ctgggtctga aagcttctac tggtgcagaa ctagaaggcg   3840
```

```
ctatcaagaa agcactcgac aatcgtcgcg gtccgacgct gatcgaatgt aacatcgctc   3900
aggacgactg cactgaaacc ctgattgctt ggggtaaacg tgtagcagct accaactctc   3960
gcaaaccaca agcgtaagtt gatgtagtga attaggcggg gcctattagg gccccaccac   4020
atagcccctc ttacggcgca atacccgtaa gaggggctgt tttatataat taaaactagt   4080
aacgcccggt tgccaccggg cgtttttat tccgacattg ccataagtaa aggcatcccc   4140
tgcgtgataa gattaccttc agtttatgga ggactgacca tatgatcaag gcttatgccg   4200
ctttagaggc taatggcaag ttgcagccgt tcgagtatga tccgggcgct ttaggcgcca   4260
acgaagttga aatcgaagtt caatactgcg gtgtttgtca ttccgacctc agtatgatca   4320
acaatgagtg ggtatcagt aactatccgt tggttcccgg ccacgaagtt gttggcaccg   4380
ttgctgctat gggtgagggt gttaatcacg tggaagttgg tgacctggtt ggtttaggct   4440
ggcacagtgg ttattgtatg acttgtcact cctgcctgag cggttatcat aatttgtgcg   4500
ctaccgccga gagtactatc gttggtcatt atggcggttt cggtgaccgt gtgcgtgcta   4560
aaggtgtgtc cgttgttaag ctgcccaagg gtatcgattt ggcttccgct ggtccgttgt   4620
tttgcggtgg tatcactgtg ttttccccca tggttgagtt atccctgaaa ccgaccgcca   4680
aggttgccgt tattggtatc ggtggtctcg gtcacctggc cgttcagttc ttgcgtgctt   4740
ggggttgcga ggttaccgct ttcactagct ccgctcgtaa acagaccgag gttctggagc   4800
tgggtgccca tcatattttg gacagtacta accccgaagc cattgcttcc gccgagggta   4860
agttcgatta catcattagt accgttaatt taaaattgga ttggaatctg tatatttcca   4920
ctttagcccc gcaaggtcac tttcatttcg tgggtgttgt tctcgaaccc ctcgacttga   4980
acttgttccc gttgctcatg ggtcagcgga gtgtgtccgc tagtccggtt ggctccccgg   5040
ctactatcgc tactatgctc gatttcgccg ttcggcacga tatcaagccg gttgttgagc   5100
agttctcctt cgaccaaatt aatgaagcca ttgctcactt ggagtccggt aaggctcact   5160
accgtgtggt tttgagtcac tccaagaact gaaacgctcg gttgccgccg ggcgtttttt   5220
attcctgcag gagcagaaga gcatacatct ggaagcaaag ccaggaaagc ggcctatgga   5280
gctgtgcggc agcgctcagt aggcaatttt tcaaaatatt gttaagcctt ttctgagcat   5340
ggtatttttc atggtattac caattagcag gaaaataagc cattgaatat aaaagataaa   5400
aatgtcttgt ttacaataga gtgggggggg tcagcctgcc gccttgggcc gggtgatgtc   5460
gtacttgccc gccgcgaact cggttaccgt ccagcccagc gcgaccagct ccggcaacgc   5520
ctcgcgcacc cgctggcggc gcttgcgcat ggtcgaacca ctggcctctg acggccagac   5580
atagccgcac aaggtatcta tggaagcctt gccggttttg ccggggtcga tccagccaca   5640
cagccgctgg tgcagcaggc gggcggtttc gctgtccagc gcccgcacct cgtccatgct   5700
gatgcgcaca tgctggccgc cacccatgac ggcctgcgcg atcaaggggt tcagggccac   5760
gtacaggcgc ccgtccgcct cgtcgctggc gtactccgac agcagccgaa acccctgccg   5820
cttgcggcca ttctgggcga tgatggatac cttccaaagg cgctcgatgc agtcctgtat   5880
gtgcttgagc gccccaccac tatcgacctc tgccccgatt tcctttgcca gcgcccgata   5940
gctacctttg accacatggc attcagcggt gacggcctcc cacttgggtt ccaggaacag   6000
ccggagctgc cgtccgcctt cggtcttggg ttccgggcca agcactaggc cattaggccc   6060
agccatggcc accagccctt gcaggatgcg cagatcatca gcgcccagcg gctccgggcc   6120
gctgaactcg atccgcttgc cgtcgccgta gtcatacgtc acgtccagct tgctgcgctt   6180
```

-continued

```
gcgctcgccc cgcttgaggg cacggaacag gccgggggcc agacagtgcg ccgggtcgtg   6240
ccggacgtgg ctgaggctgt gcttgttctt aggcttcacc acggggcacc cccttgctct   6300
tgcgctgcct ctccagcacg gcgggcttga gcaccccgcc gtcatgccgc ctgaaccacc   6360
gatcagcgaa cggtgcgcca tagttggcct tgctcacacc gaagcggacg aagaaccggc   6420
gctggtcgtc gtccacaccc cattcctcgg cctcggcgct ggtcatgctc gacaggtagg   6480
actgccagcg gatgttatcg accagtaccg agctgccccg gctggcctgc tgctggtcgc   6540
ctgcgcccat catggccgcg cccttgctgg catggtgcag gaacacgata gagcacccgg   6600
tatcggcggc gatggcctcc atgcgaccga tgacctgggc catggggccg ctggcgtttt   6660
cttcctcgat gtggaaccgg cgcagcgtgt ccagcaccat caggcggcgg ccctcggcgg   6720
cgcgcttgag gccgtcgaac cactccgggg ccatgatgtt gggcaggctg ccgatcagcg   6780
gctggatcag caggccgtca gccacggctt gccgttcctc ggcgctgagg tgcgccccaa   6840
gggcgtgcag gcggtgatga atggcggtgg gcgggtcttc ggcgggcagg tagatcaccg   6900
ggccggtggg cagttcgccc acctccagca gatccggccc gcctgcaatc tgtgcggcca   6960
gttgcagggc cagcatggat ttaccggcac caccgggcga caccagcgcc ccgaccgtac   7020
cggccaccat gttgggcaaa acgtagtcca gcggtggcgg cgctgctgcg aacgcctcca   7080
gaatattgat aggcttatgg gtagccattg attgcctcct ttgcaggcag ttggtggtta   7140
ggcgctggcg gggtcactac ccccgccctg cgccgctctg agttcttcca ggcactcgcg   7200
cagcgcctcg tattcgtcgt cggtcagcca gaacttgcgc tgacgcatcc ctttggcctt   7260
catgcgctcg gcatatcgcg cttggcgtac agcgtcaggg ctggccagca ggtcgccggt   7320
ctgcttgtcc ttttggtctt tcatatcagt caccgagaaa cttgccgggg ccgaaaggct   7380
tgtcttcgcg gaacaaggac aaggtgcagc cgtcaaggtt aaggctggcc atatcagcga   7440
ctgaaaagcg gccagcctcg gccttgtttg acgtataacc aaagccaccg ggcaaccaat   7500
agcccttgtc acttttgatc aggtagaccg accctgaagc gcttttttcg tattccataa   7560
aaccccccttc tgtgcgtgag tactcatagt ataacaggcg tgagtaccaa cgcaagcact   7620
acatgctgaa atctggcccg cccctgtcca tgcctcgctg gcggggtgcc ggtgcccgtg   7680
ccagctcggc ccgcgcaagc tggacgctgg gcagacccat gaccttgctg acggtgcgct   7740
cgatgtaatc cgcttcgtgg ccgggcttgc gctctgccag cgctgggctg gcctcggcca   7800
tggccttgcc gatttcctcg gcactgcggc cccggctggc cagcttctgc gcggcgataa   7860
agtcgcactt gctgaggtca tcaccgaagc gcttgaccag cccggccatc tcgctgcggt   7920
actcgtccag cgccgtgcgc cggtggcggc taagctgccg ctcgggcagt tcgaggctgg   7980
ccagcctgcg ggccttctcc tgctgccgct gggcctgctc gatctgctgg ccagcctgct   8040
gcaccagcgc cgggccagcg gtggcggtct tgcccttgga ttcacgcagc agcacccacg   8100
gctgataacc ggcgcgggtg gtgtgcttgt ccttgcggtt ggtgaagccc gccaagcggc   8160
catagtggcg gctgtcggcg ctggccgggt cggcgtcgta ctcgctggcc agcgtccggg   8220
caatctgccc ccgaagttca ccgcctgcgg cgtcggccac cttgacccat gcctgatagt   8280
tcttcgggct ggtttccact accagggcag gctcccggcc ctcggctttc atgtcatcca   8340
ggtcaaactc gctgaggtcg tccaccagca ccagaccatg ccgctcctgc tcggcgggcc   8400
tgatatacac gtcattgccc tgggcattca tccgcttgag ccatggcgtg ttctggagca   8460
cttcggcggc tgaccattcc cggttcatca tctggccggt ggtggcgtcc ctgacgccga   8520
tatcgaagcg ctcacagccc atggccttga gctgtcggcc tatggcctgc aaagtcctgt   8580
```

```
cgttcttcat cgggccacca agcgcagcca gatcgagccg tcctcggttg tcagtggcgt   8640
caggtcgagc aagagcaacg atgcgatcag cagcaccacc gtaggcatca tggaagccag   8700
catcacggtt agccatagct tccagtgcca cccccgcgac gcgctccggg cgctctgcgc   8760
ggcgctgctc acctcggcgg ctacctcccg caactctttg gccagctcca cccatgccgc   8820
ccctgtctgg cgctgggctt tcagccactc cgccgcctgc gcctcgctgg cctgctgggt   8880
ctggctcatg acctgccggg cttcgtcggc cagtgtcgcc atgctctggg ccagcggttc   8940
gatctgctcc gctaactcgt tgatgcctct ggatttcttc actctgtcga ttgcgttcat   9000
ggtctattgc ctcccggtat tcctgtaagt cgatgatctg ggcgttggcg gtgtcgatgt   9060
tcagggccac gtctgcccgg tcggtgcgga tgccccggcc ttccatctcc accacgttcg   9120
gccccaggtg aacaccgggc aggcgctcga tgccctgcgc ctcaagtgtt ctgtggtcaa   9180
tgcgggcgtc gtggccagcc cgctctaatg cccggttggc atggtcggcc catgcctcgc   9240
gggtctgctc aagccatgcc ttgggcttga gcgcttcggt cttctgtgcc ccgcccttct   9300
ccggggtctt gccgttgtac cgcttgaacc actgagcggc gggccgctcg atgccgtcat   9360
tgatccgctc ggagatcatc aggtggcagt gcgggttctc gccgccaccg gcatggatgg   9420
ccagcgtata cggcaggcgc tcggcaccgg tcaggtgctg ggcgaactcg gacgccagcg   9480
ccttctgctg gtcgagggtc agctcgaccg gcagggcaaa ttcgacctcc ttgaacagcc   9540
gcccattggc gcgttcatac aggtcggcag catcccagta gtcggcgggc cgctcgacga   9600
actccggcat gtgcccggat tcggcgtgca agacttcatc catgtcgcgg gcatacttgc   9660
cttcgcgctg gatgtagtcg gccttggccc tggccgattg gccgcccgac ctgctgccgg   9720
ttttcgccgt aaggtgataa atcgccatgc tgcctcgctg ttgcttttgc ttttcggctc   9780
catgcaatgg ccctcggaga gcgcaccgcc cgaagggtgg ccgttaggcc agtttctcga   9840
agagaaaccg gtaagtgcgc cctcccctac aaagtagggt cgggattgcc gccgctgtgc   9900
ctccatgata gcctacgaga cagcacatta acaatggggt gtcaagatgg ttaaggggag   9960
caacaaggcg gcggatcggc tggccaagct cgaagaacaa cgagcgcgaa tcaatgccga  10020
aattcagcgg gtgcgggcaa gggaacagca gcaagagcgc aagaacgaaa caaggcgcaa  10080
ggtgctggtg gggggccatga ttttggccaa ggtgaacagc agcgagtggc cggaggatcg  10140
gctcatggcg gcaatggatg cgtaccttga acgcgaccac gaccgcgcct tgttcggtct  10200
gccgccacgc cagaaggatg agccgggctg aatgatcgac cgagacaggc cctgcggggc  10260
tgcacacgcg cccccaccct tcgggtaggg ggaaaggccg ctaaagcggc taaaagcgct  10320
ccagcgtatt tctgcggggt ttggtgtggg gtttagcggg ctttgcccgc ctttcccccct  10380
gccgcgcagc ggtggggcgg tgtgtagcct agcgcagcga atagaccagc tatccggcct  10440
ctggccgggc atattgggca agggcagcag cgccccacaa gggcgctgat aaccgcgcct  10500
agtggattat tcttagataa tcatggatgg atttttccaa caccccgcca gcccccgccc  10560
ctgctgggtt tgcaggtttg ggggcgtgac agttattgca ggggttcgtg acagttattg  10620
caggggggcg tgacagttat tgcaggggtt cgtgacagtt agtacgggag tgacgggcac  10680
tggctggcaa tgtctagcaa cggcaggcat ttcggctgag ggtaaaagaa ctttccgcta  10740
agcgatagac tgtatgtaaa cacagtattg caaggacgcg gaacatgcct catgtggcgg  10800
ccaggacggc cagccgggat cgggatactg gtcgttacca gagccaccga cccgagcaaa  10860
cccttctcta tcagatcgtt gacgagtatt acccggcatt cgctgcgctt atggcagagc  10920
```

-continued

```
agggaaagga attgccgggc tatgtgcaac gggaatttga agaatttctc caatgcgggc  10980
ggctggagca tggctttcta cgggttcgct gcgagtcttg ccacgccgag cacctggtcg  11040
ctttcagctg taatccgggc agcgcaacgg aacattcatc agtgtaaaaa tggaatcaat  11100
aaagccctgc gcagcgcgca gggtcagcct gaatacgcgt gctcgaattg acataagcct  11160
gttcggttcg taaactgtaa tgcaagtagc gtatgcgctc acgcaactgg tccagaacct  11220
tgaccgaacg cagcggtggt aacggcgcag tggcggtttt catggcttgt tatgactgtt  11280
tttttgtaca gtctatgcct cgggcatcca agcagcaagc gcgttacgcc gtgggtcgat  11340
gtttgatgtt atggagcagc aacgatgtta cgcagcagca acgatgttac gcagcagggc  11400
agtcgcccta aaacaaagtt aggtggctca agtatgggca tcattcgcac atgtaggctc  11460
ggccctgacc aagtcaaatc catgcgggct gctcttgatc ttttcggtcg tgagttcgga  11520
gacgtagcca cctactccca acatcagccg gactccgatt acctcgggaa cttgctccgt  11580
agtaagacat tcatcgcgct tgctgccttc gaccaagaag cggttgttgg cgctctcgcg  11640
gcttacgttc tgcccaggtt tgagcagccg cgtagtgaga tctatatcta tgatctcgca  11700
gtctccggcg agcaccggag gcagggcatt gccaccgcgc tcatcaatct cctcaagcat  11760
gaggccaacg cgcttggtgc ttatgtgatc tacgtgcaag cagattacgg tgacgatccc  11820
gcagtggctc tctatacaaa gttgggcata cgggaagaag tgatgcactt tgatatcgac  11880
ccaagtaccg ccacctaaca attcgttcaa gccgagatcg gcttcccggc cctagacgcg  11940
tattcaggct gaccctgcgc gctgcgcagg gctttattga ttccattttt acactgatga  12000
atgttccgtt gcgctgcccg gattacagat cctctagaag aacagcaagg ccgccaatgc  12060
ctgacgatgc gtggagaccg aaaccttgcg ctcgttcgcc agccaggaca gaaatgcctc  12120
gacttcgctg ctgcccaagg ttgccgggtg acgcacaccg tggaaacgga tgaaggcacg  12180
aacccagtgg acataagcct gttcggttcg taagctgtaa tgcaagtagc gtatgcgctc  12240
acgcaactgg tccagaacct tgaccgaacg cagcggtggt aacggcgcag tggcggtttt  12300
catggcttgt tatgactgtt tttttggggt acagtctatg cctcgggcat ccaagcagca  12360
agcgcgttac gccgtgggtc gatgtttgat gttatggagc agcaacgatg ttacgcagca  12420
gggcagtcgc cctaaaacaa agttaaacat catgagggaa gcggtgatcg ccgaagtatc  12480
gactcaacta tcagaggtag ttggcgtcat cgagcgccat ctcgaaccga cgttgctggc  12540
cgtacatttg tacggctccg cagtggatgg cggcctgaag ccacacagtg atattgattt  12600
gctggttacg gtgaccgtaa ggcttgatga aacaacgcgg cgagctttga tcaacgacct  12660
tttggaaact tcggcttccc ctggagagag cgagattctc cgcgctgtag aagtcaccat  12720
tgttgtgcac gacgacatca ttccgtggcg ttatccagct aagcgcgaac tgcaatttgg  12780
agaatggcag cgcaatgaca ttcttgcagg tatcttcgag ccagccacga tcgacattga  12840
tctggctatc ttgctgacaa aagcaagaga acatagcgtt gccttggtag gtccagcggc  12900
ggaggaactc tttgatccgg ttcctgaaca ggatctattt gaggcgctaa atgaaacctt  12960
aacgctatgg aactcgccgc ccgactgggc tggcgatgag cgaaatgtag tgcttacgtt  13020
gtcccgcatt tggtacagcg cagtaaccgg caaaatcgcg ccgaaggatg tcgctgccga  13080
ctgggcaatg gagcgcctgc cggcccagta tcagcccgtc atacttgaag ctagacaggc  13140
ttatcttgga caagaagaag atcgcttggc ctcgcgcgca gatcagttgg aagaatttgt  13200
ccactacgtg aaaggcgaga tcaccaaggt agtcggcaaa taatgtctaa caattcgttc  13260
aagccgacgc cgcttcgcgg cgcggcttaa ctcaagctct agag                   13304
```

<210> SEQ ID NO 76
<211> LENGTH: 12256
<212> TYPE: DNA
<213> ORGANISM: Artificial
<220> FEATURE:
<223> OTHER INFORMATION: Synthetic vector construct #1217
pVZ325a-corR-PcorT-zmPDC_dsrA-Prbc*-synADHdeg_oop for
transformation of Synechocystis sp. PCC6803

<400> SEQUENCE: 76
tcgaccatgc gtccaaaact ttcaccatcc tttccctatc aacctttact gcactaaaga 60
caagtgagat agcagtggca atctggcttt gcaatcaatg tttccactaa agcgtttagc 120
gttactgcgg ctagaagtcc tccaccgagg ctcccctgaa tggtgatatg gggaatggga 180
ctggtcatca gtcgtcgttt tgcccccgga gcatgactaa aaccgatcgg cattccgatc 240
acaagagccg gctgaatatg ttgttgctct atcagcttac aggcagtgag taaaacagaa 300
ggggcatagc cgatcgccag cacacatcct tggggaatct gttgtaaccg ctgttgccaa 360
tggtcatggt gccaaaaagc ttgctcggct tccctaagcc ctgtgatgtg agggtcgtca 420
atcagcgttt taaccgtaca tcctaaatga gctaaccgag tttgatcaag agccgcagcc 480
acaaccggaa catcggtgac gactggacac cctgctttca gtgcatctcg tgccgaggcg 540
atcgctccct gactcaatcg aacggcgttt accaagctaa catcaccaca ggccagcact 600
aattgatgta gtaagtgaat ggtaatttca gagtaagccg ataaatccgg tagcaggtgt 660
ttgagggatt cctgaaaggc ttctggatga gttgttgtct ccgcatctag gttcgtccac 720
aactgatcga gttttcctaa cccctcctgg acatccacat caagctgttt cagttgggcc 780
agagcttccg cttgggtaat ctggcaactc tggtcgcgtc ccagtaatcc ttctaaagca 840
gatgcggttt ggcggagtcg agtaatctgc tgaatcacag cctgatattg ctgttgcaac 900
tgcaccatta gggtgggatc aaggctctct tcagaatggc tatccagcag ttgccgaata 960
tgagacaact gaaagccctg ctgtttgagg gcaatgactc gttggagccg ttgtacgtcc 1020
tgctgagtat aaaggcggta gttgccctct gagcgttgaa cgggggggaag caatcccagg 1080 gtgtggtaat ggcgcaccat gcgaggcgta acgccacctc ccactgcatc tgtgagttct 1140
ttaatcgtta agtgattagt cttcatccct ttagtttact caaaaccttg acattgacac 1200
taatgttaag gtttaggctg agaaggtaaa aatccaagtt aaaaagcatg aattcttata 1260
ctgtcggtac ctatttagcg gagcggcttg tccagattgg tctcaagcat cacttcgcag 1320
tcgcgggcga ctacaacctc gtccttcttg acaacctgct tttgaacaaa aacatggagc 1380
aggtttattg ctgtaacgaa ctgaactgcg gtttcagtgc agaaggttat gctcgtgcca 1440
aaggcgcagc agcagccgtc gttacctaca gcgtcggtgc gctttccgca tttgatgcta 1500
tcggtggcgc ctatgcagaa aaccttccgg ttatcctgat ctccggtgct ccgaacaaca 1560
atgatcacgc tgctggtcac gtgttgcatc acgctcttgg caaaaccgac tatcactatc 1620
agttggaaat ggccaagaac atcacggccg cagctgaagc gatttacacc ccagaagaag 1680
ctccggctaa aatcgatcac gtgattaaaa ctgctcttcg tgagaagaag ccggtttatc 1740
tcgaaatcgc ttgcaacatt gcttccatgc cctgcgccgc tcctggaccg gcaagcgcat 1800
tgttcaatga cgaagccagc gacgaagctt ctttgaatgc agcggttgaa gaaaccctga 1860
aattcatcgc caaccgcgac aaagttgccg tcctcgtcgg cagcaagctg cgcgcagctg 1920
gtgctgaaga agctgctgtc aaatttgctg atgctctcgg tggcgcagtt gctaccatgg 1980

```
ctgctgcaaa aagcttcttc ccagaagaaa acccgcatta catcggtacc tcatggggtg   2040
aagtcagcta tccgggcgtt gaaaagacga tgaaagaagc cgatgcggtt atcgctctgg   2100
ctcctgtctt caacgactac tccaccactg gttggacgga tattcctgat cctaagaaac   2160
tggttctcgc tgaaccgcgt tctgtcgtcg ttaacggcgt tcgcttcccc agcgttcatc   2220
tgaaagacta tctgacccgt ttggctcaga aagtttccaa gaaaaccggt gctttggact   2280
tcttcaaatc cctcaatgca ggtgaactga agaaagccgc tccggctgat ccgagtgctc   2340
cgttggtcaa cgcagaaatc gcccgtcagg tcgaagctct tctgaccccg aacacgacgg   2400
ttattgctga aaccggtgac tcttggttca atgctcagcg catgaagctc ccgaacggtg   2460
ctcgcgttga atatgaaatg cagtggggtc acatcggttg gtccgttcct gccgccttcg   2520
gttatgccgt cggtgctccg gaacgtcgca acatcctcat ggttggtgat ggttccttcc   2580
agctgacggc tcaggaagtc gctcagatgg ttcgcctgaa actgccggtt atcatcttct   2640
tgatcaataa ctatggttac accatcgaag ttatgatcca tgatggtccg tacaacaaca   2700
tcaagaactg ggattatgcc ggtctgatgg aagtgttcaa cggtaacggt ggttatgaca   2760
gcggtgctgg taaaggcctg aaggctaaaa ccggtggcga actggcagaa gctatcaagg   2820
ttgctctggc aaacaccgac ggcccaaccc tgatcgaatg cttcatcggt cgtgaagact   2880
gcactgaaga attggtcaaa tggggtaagc gcgttgctgc cgccaacagc cgtaagcctg   2940
ttaacaagct cctctagttt ttggggatca attcgagctc agcaagtttc atcccgaccc   3000
cctcagggtc gggatttttt tattgtacta gtaacgcccg gttgccaccg ggcgtttttt   3060
attccgacat tgccataagt aaaggcatcc cctgcgtgat aagattacct tcagtttatg   3120
gaggactgac catatgatca aggcttatgc cgctttagag gctaatggca agttgcagcc   3180
gttcgagtat gatccgggcg ctttaggcgc caacgaagtt gaaatcgaag ttcaatactg   3240
cggtgtttgt cattccgacc tcagtatgat caacaatgag tggggtatca gtaactatcc   3300
gttggttccc ggccacgaag ttgttggcac cgttgctgct atgggtgagg gtgttaatca   3360
cgtggaagtt ggtgacctgg ttggtttagg ctggcacagt ggttattgta tgacttgtca   3420
ctcctgcctg agcggttatc ataatttgtg cgctaccgcc gagagtacta tcgttggtca   3480
ttatggcggt ttcggtgacc gtgtgcgtgc taaaggtgtg tccgttgtta agctgcccaa   3540
gggtatcgat ttggcttccg ctggtccgtt gttttgcggt ggtatcactg tgtttttcccc   3600
catggttgag ttatccctga aaccgaccgc caaggttgcc gttattggta tcggtggtct   3660
cggtcacctg gccgttcagt tcttgcgtgc ttggggttgc gaggttaccg ctttcactag   3720
ctccgctcgt aaacagaccg aggttctgga gctgggtgcc catcatattt tggacagtac   3780
taaccccgaa gccattgctt ccgccgaggg taagttcgat tacatcatta gtaccgttaa   3840
tttaaaattg gattggaatc tgtatatttc cactttagcc ccgcaaggtc actttcattt   3900
cgtgggtgtt gttctcgaac ccctcgactt gaacttgttc ccgttgctca tgggtcagcg   3960
gagtgtgtcc gctagtccgg ttggctcccc ggctactatc gctactatgc tcgatttcgc   4020
cgttcggcac gatatcaagc cggttgttga gcagttctcc ttcgaccaaa ttaatgaagc   4080
cattgctcac ttggagtccg gtaaggctca ctaccgtgtg gttttgagtc actccaagaa   4140
ctgaaacgct cggttgccgc cgggcgtttt ttattcctgc aggagcagaa gagcatacat   4200
ctggaagcaa agccaggaaa gcggcctatg gagctgtgcg gcagcgctca gtaggcaatt   4260
tttcaaaata ttgttaagcc ttttctgagc atggtatttt tcatggtatt accaattagc   4320
aggaaaataa gccattgaat ataaaagata aaaatgtctt gtttacaata gagtgggggg   4380
```

```
ggtcagcctg ccgccttggg ccgggtgatg tcgtacttgc ccgccgcgaa ctcggttacc   4440
gtccagccca gcgcgaccag ctccggcaac gcctcgcgca cccgctggcg gcgcttgcgc   4500
atggtcgaac cactggcctc tgacggccag acatagccgc acaaggtatc tatggaagcc   4560
ttgccggttt tgccggggtc gatccagcca cacagccgct ggtgcagcag gcgggcggtt   4620
tcgctgtcca gcgcccgcac ctcgtccatg ctgatgcgca catgctggcc gccacccatg   4680
acggcctgcg cgatcaaggg gttcagggcc acgtacaggc gcccgtccgc ctcgtcgctg   4740
gcgtactccg acagcagccg aaacccctgc cgcttgcggc cattctgggc gatgatggat   4800
accttccaaa ggcgctcgat gcagtcctgt atgtgcttga gcgcccccacc actatcgacc  4860
tctgccccga tttcctttgc cagcgcccga tagctacctt tgaccacatg gcattcagcg   4920
gtgacggcct cccacttggg ttccaggaac agccggagct gccgtccgcc ttcggtcttg   4980
ggttccgggc caagcactag gccattaggc ccagccatgg ccaccagccc ttgcaggatg   5040
cgcagatcat cagcgcccag cggctccggg ccgctgaact cgatccgctt gccgtcgccg   5100
tagtcatacg tcacgtccag cttgctgcgc ttgcgctcgc cccgcttgag ggcacggaac   5160
aggccggggg ccagacagtg cgccgggtcg tgccggacgt ggctgaggct gtgcttgttc   5220
ttaggcttca ccacggggca ccccccttgct cttgcgctgc ctctccagca cggcgggctt  5280
gagcaccccg ccgtcatgcc gcctgaacca ccgatcagcg aacggtgcgc catagttggc   5340
cttgctcaca ccgaagcgga cgaagaaccg gcgctggtcg tcgtccacac cccattcctc   5400
ggcctcggcg ctggtcatgc tcgacaggta ggactgccag cggatgttat cgaccagtac   5460
cgagctgccc cggctggcct gctgctggtc gcctgcgccc atcatggccg cgcccttgct   5520
ggcatggtgc aggaacacga tagagcaccc ggtatcggcg gcgatggcct ccatgcgacc   5580
gatgacctgg gccatggggc cgctggcgtt ttcttcctcg atgtggaacc ggcgcagcgt   5640
gtccagcacc atcaggcggc ggccctcggc ggcgcgcttg aggccgtcga accactccgg   5700
ggccatgatg ttgggcaggc tgccgatcag cggctggatc agcaggccgt cagccacggc   5760
ttgccgttcc tcggcgctga ggtgcgcccc aagggcgtgc aggcggtgat gaatggcggt   5820
gggcgggtct tcggcgggca ggtagatcac cgggccggtg ggcagttcgc ccacctccag   5880
cagatccggc ccgcctgcaa tctgtgcggc cagttgcagg gccagcatgg atttaccggc   5940
accaccgggc gacaccagcg ccccgaccgt accggccacc atgttgggca aaacgtagtc   6000
cagcggtggc ggcgctgctg cgaacgcctc cagaatattg ataggcttat gggtagccat   6060
tgattgcctc ctttgcaggc agttggtggt taggcgctgg cggggtcact acccccgccc   6120
tgcgccgctc tgagttcttc caggcactcg cgcagcgcct cgtattcgtc gtcggtcagc   6180
cagaacttgc gctgacgcat ccctttggcc ttcatgcgct cggcatatcg cgcttggcgt   6240
acagcgtcag ggctggccag caggtcgccg gtctgcttgt ccttttggtc tttcatatca   6300
gtcaccgaga aacttgccgg ggccgaaagg cttgtcttcg cggaacaagg acaaggtgca   6360
gccgtcaagg ttaaggctgg ccatatcagc gactgaaaag cggccagcct cggccttgtt   6420
tgacgtataa ccaaagccac cgggcaacca atagcccttg tcacttttga tcaggtagac   6480
cgaccctgaa gcgctttttt cgtattccat aaaacccccct tctgtgcgtg agtactcata  6540
gtataacagg cgtgagtacc aacgcaagca ctacatgctg aaatctggcc cgcccctgtc   6600
catgcctcgc tggcggggtg ccggtgcccg tgccagctcg gcccgcgcaa gctggacgct   6660
gggcagaccc atgaccttgc tgacggtgcg ctcgatgtaa tccgcttcgt ggccgggctt   6720
```

gcgctctgcc agcgctgggc tggcctcggc catggccttg ccgatttcct cggcactgcg 6780
gccccggctg gccagcttct gcgcggcgat aaagtcgcac ttgctgaggt catcaccgaa 6840
gcgcttgacc agcccggcca tctcgctgcg gtactcgtcc agcgccgtgc gccggtggcg 6900
gctaagctgc cgctcgggca gttcgaggct ggccagcctg cgggccttct cctgctgccg 6960
ctgggcctgc tcgatctgct ggccagcctg ctgcaccagc gccgggccag cggtggcggt 7020
cttgcccttg gattcacgca gcagcaccca cggctgataa ccggcgcggg tggtgtgctt 7080
gtccttgcgg ttggtgaagc ccgccaagcg gccatagtgg cggctgtcgg cgctggccgg 7140
gtcggcgtcg tactcgctgg ccagcgtccg ggcaatctgc ccccgaagtt caccgcctgc 7200
ggcgtcggcc accttgaccc atgcctgata gttcttcggg ctggtttcca ctaccagggc 7260
aggctcccgg ccctcggctt tcatgtcatc caggtcaaac tcgctgaggt cgtccaccag 7320
caccagacca tgccgctcct gctcggcggg cctgatatac acgtcattgc cctgggcatt 7380
catccgcttg agccatggcg tgttctggag cacttcggcg gctgaccatt cccggttcat 7440
catctggccg gtggtggcgt ccctgacgcc gatatcgaag cgctcacagc ccatggcctt 7500
gagctgtcgg cctatggcct gcaaagtcct gtcgttcttc atcgggccac caagcgcagc 7560
cagatcgagc cgtcctcggt tgtcagtggc gtcaggtcga gcaagagcaa cgatgcgatc 7620
agcagcacca ccgtaggcat catggaagcc agcatcacgg ttagccatag cttccagtgc 7680
cacccccgcg acgcgctccg ggcgctctgc gcggcgctgc tcacctcggc ggctacctcc 7740
cgcaactctt tggccagctc cacccatgcc gcccctgtct ggcgctgggc tttcagccac 7800
tccgccgcct gcgcctcgct ggcctgctgg gtctggctca tgacctgccg ggcttcgtcg 7860
gccagtgtcg ccatgctctg ggccagcggt tcgatctgct ccgctaactc gttgatgcct 7920
ctggatttct tcactctgtc gattgcgttc atggtctatt gcctcccggt attcctgtaa 7980
gtcgatgatc tgggcgttgg cggtgtcgat gttcagggcc acgtctgccc ggtcggtgcg 8040
gatgccccgg ccttccatct ccaccacgtt cggccccagg tgaacaccgg gcaggcgctc 8100
gatgccctgc gcctcaagtg ttctgtggtc aatgcgggcg tcgtggccag cccgctctaa 8160
tgcccggttg gcatggtcgg cccatgcctc gcgggtctgc tcaagccatg ccttgggctt 8220
gagcgcttcg gtcttctgtg ccccgccctt ctccggggtc ttgccgttgt accgcttgaa 8280
ccactgagcg gcgggccgct cgatgccgtc attgatccgc tcggagatca tcaggtggca 8340
gtgcgggttc tcgccgccac cggcatggat ggccagcgta tacggcaggc gctcggcacc 8400
ggtcaggtgc tgggcgaact cggacgccag cgccttctgc tggtcgaggg tcagctcgac 8460
cggcagggca aattcgacct ccttgaacag ccgcccattg gcgcgttcat acaggtcggc 8520
agcatcccag tagtcggcgg gccgctcgac gaactccggc atgtgcccgg attcggcgtg 8580
caagacttca tccatgtcgc gggcatactt gccttcgcgc tggatgtagt cggccttggc 8640
cctggccgat tggccgcccg acctgctgcc ggttttcgcc gtaaggtgat aaatcgccat 8700
gctgcctcgc tgttgctttt gcttttcggc tccatgcaat ggccctcgga gagcgcaccg 8760
cccgaagggt ggccgttagg ccagtttctc gaagagaaac cggtaagtgc gccctcccct 8820
acaaagtagg gtcgggattg ccgccgctgt gcctccatga tagcctacga gacagcacat 8880
taacaatggg gtgtcaagat ggttaagggg agcaacaagg cggcggatcg gctggccaag 8940
ctcgaagaac aacgagcgcg aatcaatgcc gaaattcagc gggtgcgggc aagggaacag 9000
cagcaagagc gcaagaacga aacaaggcgc aaggtgctgg tgggggccat gattttggcc 9060
aaggtgaaca gcagcgagtg gccggaggat cggctcatgg cggcaatgga tgcgtacctt 9120

```
gaacgcgacc acgaccgcgc cttgttcggt ctgccgccac gccagaagga tgagccgggc   9180

tgaatgatcg accgagacag gccctgcggg gctgcacacg cgccccccacc cttcgggtag   9240

ggggaaaggc cgctaaagcg gctaaaagcg ctccagcgta tttctgcggg gtttggtgtg   9300

gggtttagcg ggctttgccc gcctttcccc ctgccgcgca gcggtggggc ggtgtgtagc   9360

ctagcgcagc gaatagacca gctatccggc ctctggccgg gcatattggg caagggcagc   9420

agcgccccac aagggcgctg ataaccgcgc ctagtggatt attcttagat aatcatggat   9480

ggatttttcc aacaccccgc cagcccccgc ccctgctggg tttgcaggtt tgggggcgtg   9540

acagttattg caggggttcg tgacagttat tgcagggggg cgtgacagtt attgcagggg   9600

ttcgtgacag ttagtacggg agtgacgggc actggctggc aatgtctagc aacggcaggc   9660

atttcggctg agggtaaaag aactttccgc taagcgatag actgtatgta aacacagtat   9720

tgcaaggacg cggaacatgc ctcatgtggc ggccaggacg gccagccggg atcgggatac   9780

tggtcgttac cagagccacc gacccgagca aacccttctc tatcagatcg ttgacgagta   9840

ttacccggca ttcgctgcgc ttatggcaga gcagggaaag gaattgccgg gctatgtgca   9900

acgggaattt gaagaatttc tccaatgcgg gcggctggag catggctttc tacgggttcg   9960

ctgcgagtct tgccacgccg agcacctggt cgctttcagc tgtaatccgg gcagcgcaac  10020

ggaacattca tcagtgtaaa aatggaatca ataaagccct gcgcagcgcg cagggtcagc  10080

ctgaatacgc gtgctcgaat tgacataagc ctgttcggtt cgtaaactgt aatgcaagta  10140

gcgtatgcgc tcacgcaact ggtccagaac cttgaccgaa cgcagcggtg gtaacggcgc  10200

agtggcggtt ttcatggctt gttatgactg tttttttgta cagtctatgc ctcgggcatc  10260

caagcagcaa gcgcgttacg ccgtgggtcg atgtttgatg ttatggagca gcaacgatgt  10320

tacgcagcag caacgatgtt acgcagcagg gcagtcgccc taaaacaaag ttaggtggct  10380

caagtatggg catcattcgc acatgtaggc tcggccctga ccaagtcaaa tccatgcggg  10440

ctgctcttga tcttttcggt cgtgagttcg gagacgtagc cacctactcc caacatcagc  10500

cggactccga ttacctcggg aacttgctcc gtagtaagac attcatcgcg cttgctgcct  10560

tcgaccaaga agcggttgtt ggcgctctcg cggcttacgt tctgcccagg tttgagcagc  10620

cgcgtagtga gatctatatc tatgatctcg cagtctccgg cgagcaccgg aggcagggca  10680

ttgccaccgc gctcatcaat ctcctcaagc atgaggccaa cgcgcttggt gcttatgtga  10740

tctacgtgca agcagattac ggtgacgatc ccgcagtggc tctctataca aagttgggca  10800

tacgggaaga agtgatgcac tttgatatcg acccaagtac cgccacctaa caattcgttc  10860

aagccgagat cggcttcccg gccctagacg cgtattcagg ctgaccctgc gcgctgcgca  10920

gggctttatt gattccattt ttacactgat gaatgttccg ttgcgctgcc cggattacag  10980

atcctctaga agaacagcaa ggccgccaat gcctgacgat gcgtggagac cgaaaccttg  11040

cgctcgttcg ccagccagga cagaaatgcc tcgacttcgc tgctgcccaa ggttgccggg  11100

tgacgcacac cgtggaaacg gatgaaggca cgaacccagt ggacataagc ctgttcggtt  11160

cgtaagctgt aatgcaagta gcgtatgcgc tcacgcaact ggtccagaac cttgaccgaa  11220

cgcagcggtg gtaacggcgc agtggcggtt ttcatggctt gttatgactg tttttttggg  11280

gtacagtcta tgcctcgggc atccaagcag caagcgcgtt acgccgtggg tcgatgtttg  11340

atgttatgga gcagcaacga tgttacgcag cagggcagtc gccctaaaac aaagttaaac  11400

atcatgaggg aagcggtgat cgccgaagta tcgactcaac tatcagaggt agttggcgtc  11460
```

atcgagcgcc atctcgaacc gacgttgctg gccgtacatt tgtacggctc cgcagtggat 11520
ggcggcctga agccacacag tgatattgat ttgctggtta cggtgaccgt aaggcttgat 11580
gaaacaacgc ggcgagcttt gatcaacgac cttttggaaa cttcggcttc ccctggagag 11640
agcgagattc tccgcgctgt agaagtcacc attgttgtgc acgacgacat cattccgtgg 11700
cgttatccag ctaagcgcga actgcaattt ggagaatggc agcgcaatga cattcttgca 11760
ggtatcttcg agccagccac gatcgacatt gatctggcta tcttgctgac aaaagcaaga 11820
gaacatagcg ttgccttggt aggtccagcg gcggaggaac tctttgatcc ggttcctgaa 11880
caggatctat ttgaggcgct aaatgaaacc ttaacgctat ggaactcgcc gcccgactgg 11940
gctggcgatg agcgaaatgt agtgcttacg ttgtcccgca tttggtacag cgcagtaacc 12000
ggcaaaatcg cgccgaagga tgtcgctgcc gactgggcaa tggagcgcct gccggcccag 12060
tatcagcccg tcatacttga agctagacag gcttatcttg gacaagaaga agatcgcttg 12120
gcctcgcgcg cagatcagtt ggaagaattt gtccactacg tgaaaggcga gatcaccaag 12180
gtagtcggca aataatgtct aacaattcgt tcaagccgac gccgcttcgc ggcgcggctt 12240
aactcaagct ctagag 12256

<210> SEQ ID NO 77
<211> LENGTH: 11864
<212> TYPE: DNA
<213> ORGANISM: Artificial
<220> FEATURE:
<223> OTHER INFORMATION: Synthetic vector construct #1227
pVZ325a-nrsR-PnrsB-PDC_dsrA-Prbc*-synADHdeg_oop for
transformation of Synechocystis sp. PCC6803

<400> SEQUENCE: 77
tcgacgggag tttgcaaact ccctcatatt catggcgata gggtgaaccg atagccttga 60
ccgggaactg ttttaattgg gcaaggacaa ttttgttgag ctagcttgcg tcgtatcaaa 120
cgcatttggg ccgccaccac attactcatg ggctcctcat caagatccca cagttgttgc 180
cggatcttgc taccggaaat gatccgctct gggttttgca tcagatattg aaaaatttga 240
aattctctta cggttaaagc aatttcctgt ctttctaggt ttagtggctc cgagatagtt 300
accgataaca gattattact gggatcaagg ctgaagttgc ccaaagttaa aatttgcggt 360
tggaattgtg gcgatcgccg ttgtagtgcc cgcagtcttg ctaatagctc tgccatcaca 420
aacggttttg ttagatagtc atctgccccg gcatctagtc cttcgacacg gttttccggt 480
tctcctaacg ctgttaacat caacaccggc aaggaattac cctgggttct cagtttttga 540
cagagttcca aacccgataa tcccggcagt aaccaatcca caatggcaag ggtgtattcc 600
gtccattgat tttccaaata atcccaagct tgggagccat ccgtcaccca atccaccaca 660
tacttttcac taactagcac tttcttaata gccattccca aatccgtctc atcttccacc 720
agcaaaattc gcatcgcctc tgcctttttt ataacggtct gatcttagcg ggggaaggag 780
attttcacct gaatttcata ccccctttgg cagactggga aaatcttgga caaattccca 840
atttgaggtg gtgtgatgaa ttcttatact gtcggtacct atttagcgga gcggcttgtc 900
cagattggtc tcaagcatca cttcgcagtc gcgggcgact acaacctcgt ccttcttgac 960
aacctgcttt tgaacaaaaa catggagcag gtttattgct gtaacgaact gaactgcggt 1020
ttcagtgcag aaggttatgc tcgtgccaaa ggcgcagcag cagccgtcgt tacctacagc 1080
gtcggtgcgc tttccgcatt tgatgctatc ggtggcgcct atgcagaaaa ccttccggtt 1140
atcctgatct ccggtgctcc gaacaacaat gatcacgctg ctggtcacgt gttgcatcac 1200

-continued

```
gctcttggca aaaccgacta tcactatcag ttggaaatgg ccaagaacat cacggccgca   1260
gctgaagcga tttacacccc agaagaagct ccggctaaaa tcgatcacgt gattaaaact   1320
gctcttcgtg agaagaagcc ggtttatctc gaaatcgctt gcaacattgc ttccatgccc   1380
tgcgccgctc ctggaccggc aagcgcattg ttcaatgacg aagccagcga cgaagcttct   1440
ttgaatgcag cggttgaaga aaccctgaaa ttcatcgcca accgcgacaa agttgccgtc   1500
ctcgtcggca gcaagctgcg cgcagctggt gctgaagaag ctgctgtcaa atttgctgat   1560
gctctcggtg gcgcagttgc taccatggct gctgcaaaaa gcttcttccc agaagaaaac   1620
ccgcattaca tcggtacctc atggggtgaa gtcagctatc cgggcgttga aaagacgatg   1680
aaagaagccg atgcggttat cgctctggct cctgtcttca acgactactc caccactggt   1740
tggacggata ttcctgatcc taagaaactg gttctcgctg aaccgcgttc tgtcgtcgtt   1800
aacggcgttc gcttccccag cgttcatctg aaagactatc tgacccgttt ggctcagaaa   1860
gtttccaaga aaaccggtgc tttggacttc ttcaaatccc tcaatgcagg tgaactgaag   1920
aaagccgctc cggctgatcc gagtgctccg ttggtcaacg cagaaatcgc ccgtcaggtc   1980
gaagctcttc tgaccccgaa cacgacggtt attgctgaaa ccggtgactc ttggttcaat   2040
gctcagcgca tgaagctccc gaacggtgct cgcgttgaat atgaaatgca gtggggtcac   2100
atcggttggt ccgttcctgc cgccttcggt tatgccgtcg gtgctccgga acgtcgcaac   2160
atcctcatgg ttggtgatgg ttccttccag ctgacggctc aggaagtcgc tcagatggtt   2220
cgcctgaaac tgccggttat catcttcttg atcaataact atggttacac catcgaagtt   2280
atgatccatg atggtccgta caacaacatc aagaactggg attatgccgg tctgatggaa   2340
gtgttcaacg gtaacggtgg ttatgacagc ggtgctggta aaggcctgaa ggctaaaacc   2400
ggtggcgaac tggcagaagc tatcaaggtt gctctggcaa acaccgacgg cccaaccctg   2460
atcgaatgct tcatcggtcg tgaagactgc actgaagaat tggtcaaatg gggtaagcgc   2520
gttgctgccg ccaacagccg taagcctgtt aacaagctcc tctagttttt ggggatcaat   2580
tcgagctcag caagtttcat cccgaccccc tcagggtcgg gatttttttta ttgtactagt   2640
aacgcccggt tgccaccggg cgttttttat tccgacattg ccataagtaa aggcatcccc   2700
tgcgtgataa gattaccttc agtttatgga ggactgacca tatgatcaag gcttatgccg   2760
ctttagaggc taatggcaag ttgcagccgt tcgagtatga tccgggcgct ttaggcgcca   2820
acgaagttga aatcgaagtt caatactgcg gtgtttgtca ttccgacctc agtatgatca   2880
acaatgagtg gggtatcagt aactatccgt tggttcccgg ccacgaagtt gttggcaccg   2940
ttgctgctat gggtgagggt gttaatcacg tggaagttgg tgacctggtt ggtttaggct   3000
ggcacagtgg ttattgtatg acttgtcact cctgcctgag cggttatcat aatttgtgcg   3060
ctaccgccga gagtactatc gttggtcatt atggcggttt cggtgaccgt gtgcgtgcta   3120
aaggtgtgtc cgttgttaag ctgcccaagg gtatcgattt ggcttccgct ggtccgttgt   3180
tttgcggtgg tatcactgtg ttttccccca tggttgagtt atccctgaaa ccgaccgcca   3240
aggttgccgt tattggtatc ggtggtctcg gtcacctggc cgttcagttc ttgcgtgctt   3300
ggggttgcga ggttaccgct ttcactagct ccgctcgtaa acagaccgag gttctggagc   3360
tgggtgccca tcatattttg gacagtacta accccgaagc cattgcttcc gccgagggta   3420
agttcgatta catcattagt accgttaatt taaaattgga ttggaatctg tatatttcca   3480
ctttagcccc gcaaggtcac tttcatttcg tgggtgttgt tctcgaaccc ctcgacttga   3540
```

-continued

```
acttgttccc gttgctcatg ggtcagcgga gtgtgtccgc tagtccggtt ggctccccgg   3600
ctactatcgc tactatgctc gatttcgccg ttcggcacga tatcaagccg gttgttgagc   3660
agttctcctt cgaccaaatt aatgaagcca ttgctcactt ggagtccggt aaggctcact   3720
accgtgtggt tttgagtcac tccaagaact gaaacgctcg gttgccgccg ggcgtttttt   3780
attcctgcag gagcagaaga gcatacatct ggaagcaaag ccaggaaagc ggcctatgga   3840
gctgtgcggc agcgctcagt aggcaatttt tcaaaatatt gttaagcctt ttctgagcat   3900
ggtatttttc atggtattac caattagcag gaaaataagc cattgaatat aaaagataaa   3960
aatgtcttgt ttacaataga gtgggggggg tcagcctgcc gccttgggcc gggtgatgtc   4020
gtacttgccc gccgcgaact cggttaccgt ccagcccagc gcgaccagct ccggcaacgc   4080
ctcgcgcacc cgctggcggc gcttgcgcat ggtcgaacca ctggcctctg acggccagac   4140
atagccgcac aaggtatcta tggaagcctt gccggttttg ccggggtcga tccagccaca   4200
cagccgctgg tgcagcaggc gggcggtttc gctgtccagc gcccgcacct cgtccatgct   4260
gatgcgcaca tgctggccgc cacccatgac ggcctgcgcg atcaaggggt tcagggccac   4320
gtacaggcgc ccgtccgcct cgtcgctggc gtactccgac agcagccgaa acccctgccg   4380
cttgcggcca ttctgggcga tgatggatac cttccaaagg cgctcgatgc agtcctgtat   4440
gtgcttgagc gccccaccac tatcgacctc tgccccgatt tcctttgcca gcgcccgata   4500
gctacctttg accacatggc attcagcggt gacggcctcc cacttgggtt ccaggaacag   4560
ccggagctgc cgtccgcctt cggtcttggg ttccgggcca agcactaggc cattaggccc   4620
agccatggcc accagccctt gcaggatgcg cagatcatca gcgcccagcg gctccgggcc   4680
gctgaactcg atccgcttgc cgtcgccgta gtcatacgtc acgtccagct tgctgcgctt   4740
gcgctcgccc cgcttgaggg cacggaacag gccgggggcc agacagtgcg ccgggtcgtg   4800
ccggacgtgg ctgaggctgt gcttgttctt aggcttcacc acggggcacc cccttgctct   4860
tgcgctgcct ctccagcacg gcgggcttga gcaccccgcc gtcatgccgc ctgaaccacc   4920
gatcagcgaa cggtgcgcca tagttggcct tgctcacacc gaagcggacg aagaaccggc   4980
gctggtcgtc gtccacaccc cattcctcgg cctcggcgct ggtcatgctc gacaggtagg   5040
actgccagcg gatgttatcg accagtaccg agctgccccg gctggcctgc tgctggtcgc   5100
ctgcgcccat catggccgcg cccttgctgg catggtgcag gaacacgata gagcaccccgg  5160
tatcggcggc gatggcctcc atgcgaccga tgacctgggc catggggccg ctggcgtttt   5220
cttcctcgat gtggaaccgg cgcagcgtgt ccagcaccat caggcggcgg ccctcggcgg   5280
cgcgcttgag gccgtcgaac cactccgggg ccatgatgtt gggcaggctg ccgatcagcg   5340
gctggatcag caggccgtca gccacggctt gccgttcctc ggcgctgagg tgcgccccaa   5400
gggcgtgcag gcggtgatga atggcggtgg gcgggtcttc ggcgggcagg tagatcaccg   5460
ggccggtggg cagttcgccc acctccagca gatccggccc gcctgcaatc tgtgcggcca   5520
gttgcagggc cagcatggat ttaccggcac caccgggcga caccagcgcc ccgaccgtac   5580
cggccaccat gttgggcaaa acgtagtcca gcggtggcgg cgctgctgcg aacgcctcca   5640
gaatattgat aggcttatgg gtagccattg attgcctcct ttgcaggcag ttggtggtta   5700
ggcgctggcg gggtcactac ccccgccctg cgccgctctg agttcttcca ggcactcgcg   5760
cagcgcctcg tattcgtcgt cggtcagcca gaacttgcgc tgacgcatcc ctttggcctt   5820
catgcgctcg gcatatcgcg cttggcgtac agcgtcaggg ctggccagca ggtcgccggt   5880
ctgcttgtcc ttttggtctt tcatatcagt caccgagaaa cttgccgggg ccgaaaggct   5940
```

```
tgtcttcgcg gaacaaggac aaggtgcagc cgtcaaggtt aaggctggcc atatcagcga   6000
ctgaaaagcg gccagcctcg gccttgtttg acgtataacc aaagccaccg ggcaaccaat   6060
agcccttgtc acttttgatc aggtagaccg accctgaagc gctttttttcg tattccataa   6120
aaccccccttc tgtgcgtgag tactcatagt ataacaggcg tgagtaccaa cgcaagcact   6180
acatgctgaa atctggcccg cccctgtcca tgcctcgctg gcggggtgcc ggtgcccgtg   6240
ccagctcggc ccgcgcaagc tggacgctgg gcagacccat gaccttgctg acggtgcgct   6300
cgatgtaatc cgcttcgtgg ccgggcttgc gctctgccag cgctgggctg gcctcggcca   6360
tggccttgcc gatttcctcg gcactgcggc cccggctggc cagcttctgc gcggcgataa   6420
agtcgcactt gctgaggtca tcaccgaagc gcttgaccag cccggccatc tcgctgcggt   6480
actcgtccag cgccgtgcgc cggtggcggc taagctgccg ctcgggcagt tcgaggctgg   6540
ccagcctgcg ggccttctcc tgctgccgct gggcctgctc gatctgctgg ccagcctgct   6600
gcaccagcgc cgggccagcg gtggcggtct tgcccttgga ttcacgcagc agcacccacg   6660
gctgataacc ggcgcgggtg gtgtgcttgt ccttgcggtt ggtgaagccc gccaagcggc   6720
catagtggcg gctgtcggcg ctggccgggt cggcgtcgta ctcgctggcc agcgtccggg   6780
caatctgccc ccgaagttca ccgcctgcgg cgtcggccac cttgacccat gcctgatagt   6840
tcttcgggct ggtttccact accagggcag gctcccggcc ctcggctttc atgtcatcca   6900
ggtcaaactc gctgaggtcg tccaccagca ccagaccatg ccgctcctgc tcggcgggcc   6960
tgatatacac gtcattgccc tgggcattca tccgcttgag ccatggcgtg ttctggagca   7020
cttcggcggc tgaccattcc cggttcatca tctggccggt ggtggcgtcc ctgacgccga   7080
tatcgaagcg ctcacagccc atggccttga gctgtcggcc tatggcctgc aaagtcctgt   7140
cgttcttcat cgggccacca agcgcagcca gatcgagccg tcctcggttg tcagtggcgt   7200
caggtcgagc aagagcaacg atgcgatcag cagcaccacc gtaggcatca tggaagccag   7260
catcacggtt agccatagct tccagtgcca cccccgcgac gcgctccggg cgctctgcgc   7320
ggcgctgctc acctcggcgg ctacctcccg caactctttg gccagctcca cccatgccgc   7380
ccctgtctgg cgctgggctt tcagccactc cgccgcctgc gcctcgctgg cctgctgggt   7440
ctggctcatg acctgccggg cttcgtcggc cagtgtcgcc atgctctggg ccagcggttc   7500
gatctgctcc gctaactcgt tgatgcctct ggatttcttc actctgtcga ttgcgttcat   7560
ggtctattgc ctcccggtat tcctgtaagt cgatgatctg ggcgttggcg gtgtcgatgt   7620
tcagggccac gtctgcccgg tcggtgcgga tgccccggcc ttccatctcc accacgttcg   7680
gccccaggtg aacaccgggc aggcgctcga tgccctgcgc ctcaagtgtt ctgtggtcaa   7740
tgcgggcgtc gtggccagcc cgctctaatg cccggttggc atggtcggcc catgcctcgc   7800
gggtctgctc aagccatgcc ttgggcttga gcgcttcggt cttctgtgcc ccgcccttct   7860
ccggggtctt gccgttgtac cgcttgaacc actgagcggc gggccgctcg atgccgtcat   7920
tgatccgctc ggagatcatc aggtggcagt gcgggttctc gccgccaccg gcatggatgg   7980
ccagcgtata cggcaggcgc tcggcaccgg tcaggtgctg ggcgaactcg gacgccagcg   8040
ccttctgctg gtcgagggtc agctcgaccg gcagggcaaa ttcgacctcc ttgaacagcc   8100
gcccattggc gcgttcatac aggtcggcag catcccagta gtcggcgggc cgctcgacga   8160
actccggcat gtgcccggat tcggcgtgca agacttcatc catgtcgcgg gcatacttgc   8220
cttcgcgctg gatgtagtcg gccttggccc tggccgattg gccgcccgac ctgctgccgg   8280
```

```
ttttcgccgt aaggtgataa atcgccatgc tgcctcgctg ttgcttttgc ttttcggctc   8340
catgcaatgg ccctcggaga gcgcaccgcc cgaagggtgg ccgttaggcc agtttctcga   8400
agagaaaccg gtaagtgcgc cctcccctac aaagtagggt cgggattgcc gccgctgtgc   8460
ctccatgata gcctacgaga cagcacatta acaatggggt gtcaagatgg ttaaggggag   8520
caacaaggcg gcggatcggc tggccaagct cgaagaacaa cgagcgcgaa tcaatgccga   8580
aattcagcgg gtgcgggcaa gggaacagca gcaagagcgc aagaacgaaa caaggcgcaa   8640
ggtgctggtg gggccatga ttttggccaa ggtgaacagc agcgagtggc cggaggatcg   8700
gctcatggcg gcaatggatg cgtaccttga acgcgaccac gaccgcgcct tgttcggtct   8760
gccgccacgc cagaaggatg agccgggctg aatgatcgac cgagacaggc cctgcggggc   8820
tgcacacgcg cccccaccct tcgggtaggg ggaaaggccg ctaaagcggc taaaagcgct   8880
ccagcgtatt tctgcggggt ttggtgtggg gtttagcggg ctttgcccgc ctttcccct   8940
gccgcgcagc ggtggggcgg tgtgtagcct agcgcagcga atagaccagc tatccggcct   9000
ctggccgggc atattgggca agggcagcag cgccccacaa gggcgctgat aaccgcgcct   9060
agtggattat tcttagataa tcatggatgg atttttccaa caccccgcca gcccccgccc   9120
ctgctgggtt tgcaggtttg ggggcgtgac agttattgca ggggttcgtg acagttattg   9180
caggggggcg tgacagttat tgcaggggtt cgtgacagtt agtacgggag tgacgggcac   9240
tggctggcaa tgtctagcaa cggcaggcat ttcggctgag ggtaaaagaa ctttccgcta   9300
agcgatagac tgtatgtaaa cacagtattg caaggacgcg gaacatgcct catgtggcgg   9360
ccaggacggc cagccgggat cgggatactg gtcgttacca gagccaccga cccgagcaaa   9420
cccttctcta tcagatcgtt gacgagtatt acccggcatt cgctgcgctt atggcagagc   9480
agggaaagga attgccgggc tatgtgcaac gggaatttga agaatttctc caatgcgggc   9540
ggctggagca tggctttcta cgggttcgct gcgagtcttg ccacgccgag cacctggtcg   9600
ctttcagctg taatccgggc agcgcaacgg aacattcatc agtgtaaaaa tggaatcaat   9660
aaagccctgc gcagcgcgca gggtcagcct gaatacgcgt gctcgaattg acataagcct   9720
gttcggttcg taaactgtaa tgcaagtagc gtatgcgctc acgcaactgg tccagaacct   9780
tgaccgaacg cagcggtggt aacggcgcag tggcggtttt catggcttgt tatgactgtt   9840
tttttgtaca gtctatgcct cgggcatcca agcagcaagc gcgttacgcc gtgggtcgat   9900
gtttgatgtt atggagcagc aacgatgtta cgcagcagca acgatgttac gcagcagggc   9960
agtcgcccta aaacaaagtt aggtggctca agtatgggca tcattcgcac atgtaggctc  10020
ggccctgacc aagtcaaatc catgcgggct gctcttgatc ttttcggtcg tgagttcgga  10080
gacgtagcca cctactccca acatcagccg gactccgatt acctcgggaa cttgctccgt  10140
agtaagacat tcatcgcgct tgctgccttc gaccaagaag cggttgttgg cgctctcgcg  10200
gcttacgttc tgcccaggtt tgagcagccg cgtagtgaga tctatatcta tgatctcgca  10260
gtctccggcg agcaccggag gcagggcatt gccaccgcgc tcatcaatct cctcaagcat  10320
gaggccaacg cgcttggtgc ttatgtgatc tacgtgcaag cagattacgg tgacgatccc  10380
gcagtggctc tctatacaaa gttgggcata cgggaagaag tgatgcactt tgatatcgac  10440
ccaagtaccg ccacctaaca attcgttcaa gccgagatcg gcttcccggc cctagacgcg  10500
tattcaggct gaccctgcgc gctgcgcagg gctttattga ttccattttt acactgatga  10560
atgttccgtt gcgctgcccg gattacagat cctctagaag aacagcaagg ccgccaatgc  10620
ctgacgatgc gtggagaccg aaaccttgcg ctcgttcgcc agccaggaca gaaatgcctc  10680
```

gacttcgctg ctgcccaagg ttgccgggtg acgcacaccg tggaaacgga tgaaggcacg 10740
aacccagtgg acataagcct gttcggttcg taagctgtaa tgcaagtagc gtatgcgctc 10800
acgcaactgg tccagaacct tgaccgaacg cagcggtggt aacggcgcag tggcggtttt 10860
catggcttgt tatgactgtt tttttggggt acagtctatg cctcgggcat ccaagcagca 10920
agcgcgttac gccgtgggtc gatgtttgat gttatggagc agcaacgatg ttacgcagca 10980
gggcagtcgc cctaaaacaa agttaaacat catgagggaa gcggtgatcg ccgaagtatc 11040
gactcaacta tcagaggtag ttggcgtcat cgagcgccat ctcgaaccga cgttgctggc 11100
cgtacatttg tacggctccg cagtggatgg cggcctgaag ccacacagtg atattgattt 11160
gctggttacg gtgaccgtaa ggcttgatga aacaacgcgg cgagctttga tcaacgacct 11220
tttggaaact tcggcttccc ctggagagag cgagattctc cgcgctgtag aagtcaccat 11280
tgttgtgcac gacgacatca ttccgtggcg ttatccagct aagcgcgaac tgcaatttgg 11340
agaatggcag cgcaatgaca ttcttgcagg tatcttcgag ccagccacga tcgacattga 11400
tctggctatc ttgctgacaa aagcaagaga acatagcgtt gccttggtag gtccagcggc 11460
ggaggaactc tttgatccgg ttcctgaaca ggatctattt gaggcgctaa atgaaacctt 11520
aacgctatgg aactcgccgc ccgactgggc tggcgatgag cgaaatgtag tgcttacgtt 11580
gtcccgcatt tggtacagcg cagtaaccgg caaaatcgcg ccgaaggatg tcgctgccga 11640
ctgggcaatg gagcgcctgc cggcccagta tcagcccgtc atacttgaag ctagacaggc 11700
ttatcttgga caagaagaag atcgcttggc ctcgcgcgca gatcagttgg aagaatttgt 11760
ccactacgtg aaaggcgaga tcaccaaggt agtcggcaaa taatgtctaa caattcgttc 11820
aagccgacgc cgcttcgcgg cgcggcttaa ctcaagctct agag 11864

<210> SEQ ID NO 78
<211> LENGTH: 9235
<212> TYPE: DNA
<213> ORGANISM: Artificial
<220> FEATURE:
<223> OTHER INFORMATION: Synthetic vector construct #1480 pAQ3-aztR-PaztA-zmPDCdeg_spf-Prbc*-synADH_oop for integration into the endogenous pAQ3 plasmid of Synechococcus sp. PCC7002

<400> SEQUENCE: 78
tcgactaaat cgtaatacct aaatcagcca acaaaattta gcacaattgc acaggggaga 60
agttcagatt aatacattta tactattaat ttgcgatcac cctgtgccag ttgcgtaagt 120
attgttttcc actaaagagc gatataagtt aatgacgtga ctgtcagcca aactataata 180
aacattccga ccttctcgac gatagctgac taaacgcata gctttcaata accgcagctg 240
atgacaaaca gctgattcac tcattttggt taatgcagct agatcgcaaa cacacaactc 300
actagaagcc aaagctgata ggaggcgtat acggtttgta tctgctaaca ccccaaaaat 360
ttctgccatt tgttgtgctt tatctgtcgg taagatttga gcctgagatg agcgtacatt 420
atctagatgc accagatgag tatcacaggt aggggtatca gaactttgaa ttaagtctaa 480
gtcctgcttt ttcttgtgct tattcatagc aagttttact tagcaatagt tatcaatctc 540
aataatacct aaaatgataa ccattgtaca attgaatagt tgttcaattg ttgtattaga 600
atattggcag ttaacttttt gccttaattc taaagctgct atgaattcct acaccgttgg 660
cacttacctg gctgaacgct tggttcagat cggcttaaaa caccattttg ctgttgctgg 720
tgattataat ttggttttgt tagataattt attgctcaat aagaatatgg aacaggtgta 780

```
ctgttgcaat gagttaaatt gtggcttttc cgctgagggc tacgcccgtg ctaagggtgc    840
tgctgctgct gttgtgactt attctgttgg cgctttgagt gcttttgacg ccattggcgg    900
tgcttacgct gagaatttgc cagtgatttt aattagtggc gccccaaata ataacgacca    960
tgccgccggc catgtcctcc accatgcctt gggtaagact gattaccatt accaactgga   1020
gatggctaaa aatattaccg ctgctgccga agctatctat actcctgagg aagccccagc   1080
caagattgac catgtcatca agaccgcctt gcgggaaaaa aaaccagtgt acttagagat   1140
tgcctgtaat atcgccagta tgccttgtgc tgcccccggt ccagcttctg ctctctttaa   1200
cgatgaagct tctgatgagg ccagtctcaa cgctgctgtg gaggaaactt taaagtttat   1260
tgctaatcgt gataaggtgg ctgttttagt tggttctaaa ttacgtgctg ccggcgccga   1320
ggaagccgcc gttaagtttg ccgacgcctt aggcggtgct gtggccacta tggccgccgc   1380
taagtctttt tttcctgaag agaatccaca ctatattggc actagctggg gcgaggtttc   1440
ttacccaggt gtggagaaaa ccatgaagga ggctgacgct gtgattgcct tagccccggt   1500
ttttaatgat tatagtacta ccggctggac cgacatcccg gacccgaaaa agttagtgtt   1560
agccgaacca cggagtgttg ttgtgaatgg tgtgcgtttt ccttctgtgc acttaaagga   1620
ttacttaact cggctcgccc agaaggtgag taaaaagact ggcgccctcg attttttttaa   1680
gagtttaaac gctggcgagt taaaaaaggc tgccccagcc gacccatccg ccccactcgt   1740
taatgctgaa attgctcggc aggttgaggc cttgttaact ccaaatacca ccgtgatcgc   1800
cgaaactggc gatagttggt ttaacgccca acgtatgaaa ttaccaaatg gcgcccgtgt   1860
ggagtacgag atgcaatggg gccatattgg ctggagtgtg ccggctgctt ttggctacgc   1920
tgttggcgcc ccagagcggc gtaatatttt aatggtgggc gacggcagtt ttcagttaac   1980
cgcccaagag gttgcccaaa tggtgcgttt aaagttacca gtgattattt ttctcattaa   2040
caattacggc tatactattg aggtgatgat tcacgacggc ccatataata atattaaaaa   2100
ttgggactac gctggcttaa tggaggtctt taatggcaat ggcggctacg attctggcgc   2160
cggcaagggt ttaaaagcca agactggcgg tgagttagct gaagccatta aagtggcctt   2220
agctaatact gatggtccta ctttaattga gtgttttatt ggccgggaag attgtaccga   2280
ggaactcgtt aagtggggca aacgtgtggc cgctgctaat tctcggaaac ccgtgaataa   2340
attattatga aatattttag ccgccccagt cagtaatgac tggggcgttt tttattggga   2400
gctcactagt cgatcgacat tgccataagt aaaggcatcc cctgcgtgat aagattacct   2460
tcagtttatg gaggactgac catatgatta aagcctacgc tgccctggaa gccaacggaa   2520
aactccaacc ctttgaatac gaccccggtg ccctgggtgc taatgaggtg gagattgagg   2580
tgcagtattg tggggtgtgc cacagtgatt tgtccatgat taataacgaa tggggcattt   2640
ccaattaccc cctagtgccg ggtcatgagg tggtgggtac tgtggccgcc atgggcgaag   2700
gggtgaacca tgttgaggtg ggggatttag tggggctggg ttggcattcg ggctactgca   2760
tgacctgcca tagttgttta tctggctacc acaacctttg tgccacggcg gaatcgacca   2820
ttgtgggcca ctacggtggc tttggcgatc gggttcgggc caagggagtc agcgtggtga   2880
aattacctaa aggcattgac ctagccagtg ccgggcccct tttctgtgga ggaattaccg   2940
ttttcagtcc tatggtggaa ctgagtttaa agcccactgc aaaagtggca gtgatcggca   3000
ttgggggctt gggccattta gcggtgcaat ttctccgggc ctggggctgt gaagtgactg   3060
cctttacctc cagtgccagg aagcaaacgg aagtgttgga attgggcgct caccacatac   3120
tagattccac caatccagag gcgatcgcca gtgcggaagg caaatttgac tatattatct   3180
```

ccactgtgaa cctgaagctt gactggaact tatacatcag caccctggcg ccccagggac 3240
atttccactt tgttggggtg gtgttggagc ctttggatct aaatcttttt ccccttttga 3300
tgggacaacg ctccgtttct gcctccccag tgggtagtcc cgccaccatt gccaccatgt 3360
tggactttgc tgtgcgccat gacattaaac ccgtggtgga acaatttagc tttgatcaga 3420
tcaacgaggc gatcgcccat ctagaaagcg gcaaagccca ttatcgggta gtgctcagcc 3480
atagtaaaaa ttagctctgc aaaggttgct tctgggtccg tggaacgctc ggttgccgcc 3540
gggcgttttt tattcctgca ggatccacag gacgggtgtg gtcgccatga tcgcgtagtc 3600
gatagtggct ccaagtagcg aagcgagcag gactgggcgg cggccaaagc ggtcggacag 3660
tgctccgaga acgggtgcgc atagaaattg catcaacgca tatagcgcta gcagcacgcc 3720
atagtgactg gcgatgctgt cggaatggac gatcgaattg gccgcggcgt tgtgacaatt 3780
taccgaacaa ctccgcggcc gggaagccga tctcggcttg aacgaattgt taggtggcgg 3840
tacttgggtc gatatcaaag tgcatcactt cttcccgtat gcccaacttt gtatagagag 3900
ccactgcggg atcgtcaccg taatctgctt gcacgtagat cacataagca ccaagcgcgt 3960
tggcctcatg cttgaggaga ttgatgagcg cggtggcaat gccctgcctc cggtgctcgc 4020
cggagactgc gagatcatag atatagatct cactacgcgg ctgctcaaac ttgggcagaa 4080
cgtaagccgc gagagcgcca acaaccgctt cttggtcgaa ggcagcaagc gcgatgaatg 4140
tcttactacg gagcaagttc ccgaggtaat cggagtccgg ctgatgttgg gagtaggtgg 4200
ctacgtctcc gaactcacga ccgaaaagat caagagcagc ccgcatggat ttgacttggt 4260
cagggccgag cctacatgtg cgaatgatgc ccatacttga gccacctaac tttgttttag 4320
ggcgactgcc ctgctgcgta acatcgttgc tgctgcgtaa catcgttgct gctccataac 4380
atcaaacatc gacccacggc gtaacgcgct tgctgcttgg atgcccgagg catagactgt 4440
acaaaaaaac agtcataaca agccatgaaa accgccactg cgccgttacc accgctgcgt 4500
tcggtcaagg ttctggacca gttgcgtgag cgcatacgct acttgcatta cagtttacga 4560
accgaacagg cttatgtcaa ttcgagcatc gattgtatgg gaagcccgat gcgccagagt 4620
tgtttctgaa acatggcaaa ggtagcgttg ccaatgatgt tacagatgag atggtcagac 4680
taaactggct gacggaattt atgcctcttc cgaccatcaa gcattttatc cgtactcctg 4740
atgatgcatg gttactcacc actgcgatcc ccgatccccc cctcgatcaa ggcaggcaac 4800
gcccccggcg atcgccgtcc ttttttatgc cacatcttcg gtatataaat ccgcctgaaa 4860
atctgcgaat acttgaccga tatcctgacc caagatcact aaaccttcat taacggtttg 4920
gtatttgatt tcgatgaggg taggcagttt cccccgatca agttcctcca ctccttctcg 4980
aatgtattgg tctaggacaa aatctaaaaa ttcttgctgc tttccggtgt acttcgagaa 5040
aatcagatct cgatgcttaa ttactcgctc ttctctgcta atgggtttgg tgttgtaggc 5100
aacccaagtc aggacatcat agacatcact tttttccgct tcggcaatgc gtgcgatcgc 5160
cttcagttgg gtgtcaccgt agcctttttc cgcgagtccg gtcaggaacg atttacgggt 5220
atcgggtttc ccccagatgg tgcgtagttc ggcttcatcc ttgaagaggt cgggcaggtc 5280
gccaaatagc ttttcgataa attcttgggc ggaaatgggt ttaccatcag catcccaaaa 5340
agttgtggat gcatagcttg agtattctat agtgtcacct aaatagcttg gcgtaatcat 5400
ggtcatagct gtttcctgtg tgaaattgtt atccgctcac aattccacac aacatacgag 5460
ccggaagcat aaagtgtaaa gcctggggtg cctaatgagt gagctaactc acattaattg 5520
cgttgcgctc actgcccgct ttccagtcgg gaaacctgtc gtgccagctg cattaatgaa 5580
tcggccaacg cgcggggaga ggcggtttgc gtattgggcg ctcttccgct tcctcgctca 5640
ctgactcgct gcgctcggtc gttcggctgc ggcgagcggt atcagctcac tcaaaggcgg 5700
taatacggtt atccacagaa tcaggggata acgcaggaaa gaacatgtga gcaaaaggcc 5760
agcaaaaggc caggaaccgt aaaaaggccg cgttgctggc gtttttccat aggctccgcc 5820
cccctgacga gcatcacaaa aatcgacgct caagtcagag gtggcgaaac ccgacaggac 5880
tataaagata ccaggcgttt ccccctggaa gctccctcgt gcgctctcct gttccgaccc 5940
tgccgcttac cggatacctg tccgcctttc tcccttcggg aagcgtggcg ctttctcata 6000
gctcacgctg taggtatctc agttcggtgt aggtcgttcg ctccaagctg ggctgtgtgc 6060
acgaaccccc cgttcagccc gaccgctgcg ccttatccgg taactatcgt cttgagtcca 6120
acccggtaag acacgactta tcgccactgg cagcagccac tggtaacagg attagcagag 6180
cgaggtatgt aggcggtgct acagagttct tgaagtggtg gcctaactac ggctacacta 6240
gaaggacagt atttggtatc tgcgctctgc tgaagccagt taccttcgga aaaagagttg 6300
gtagctcttg atccggcaaa caaaccaccg ctggtagcgg tggttttttt gtttgcaagc 6360
agcagattac gcgcagaaaa aaaggatctc aagaagatcc tttgatcttt tctacggggt 6420
ctgacgctca gtggaacgaa aactcacgtt aagggatttt ggtcatgaga ttatcaaaaa 6480
ggatcttcac ctagatcctt ttaaattaaa aatgaagttt taaatcaatc taaagtatat 6540
atgagtaaac ttggtctgac agttaccaat gcttaatcag tgaggcacct atctcagcga 6600
tctgtctatt tcgttcatcc atagttgcct gactccccgt cgtgtagata actacgatac 6660
gggagggctt accatctggc cccagtgctg caatgatacc gcgagaccca cgctcaccgg 6720
ctccagattt atcagcaata aaccagccag ccggaagggc cgagcgcaga agtggtcctg 6780
caactttatc cgcctccatc cagtctatta attgttgccg ggaagctaga gtaagtagtt 6840
cgccagttaa tagtttgcgc aacgttgttg gcattgctac aggcatcgtg gtgtcacgct 6900
cgtcgtttgg tatggcttca ttcagctccg gttcccaacg atcaaggcga gttacatgat 6960
cccccatgtt gtgcaaaaaa gcggttagct ccttcggtcc tccgatcgtt gtcagaagta 7020
agttggccgc agtgttatca ctcatggtta tggcagcact gcataattct cttactgtca 7080
tgccatccgt aagatgcttt tctgtgactg gtgagtactc aaccaagtca ttctgagaat 7140
agtgtatgcg gcgaccgagt tgctcttgcc cggcgtcaat acgggataat accgcgccac 7200
atagcagaac tttaaaagtg ctcatcattg gaaaacgttc ttcggggcga aaactctcaa 7260
ggatcttacc gctgttgaga tccagttcga tgtaacccac tcgtgcaccc aactgatctt 7320
cagcatcttt tactttcacc agcgtttctg ggtgagcaaa aacaggaagg caaaatgccg 7380
caaaaaaggg aataagggcg acacggaaat gttgaatact catactcttc ctttttcaat 7440
attattgaag catttatcag ggttattgtc tcatgagcgg atacatattt gaatgtattt 7500
agaaaaataa acaaataggg gttccgcgca catttccccg aaaagtgcca cctgtatgcg 7560
gtgtgaaata ccgcacagat gcgtaaggag aaaataccgc atcaggcgaa attgtaaacg 7620
ttaatatttt gttaaaattc gcgttaaata tttgttaaat cagctcattt tttaaccaat 7680
aggccgaaat cggcaaaatc ccttataaat caaaagaata gaccgagata gggttgagtg 7740
ttgttccagt ttggaacaag agtccactat taaagaacgt ggactccaac gtcaaagggc 7800
gaaaaaccgt ctatcagggc gatggcccac tacgtgaacc atcacccaaa tcaagttttt 7860
tgcggtcgag gtgccgtaaa gctctaaatc ggaaccctaa agggagcccc cgatttagag 7920
cttgacgggg aaagccggcg aacgtggcga gaaaggaagg gaagaaagcg aaaggagcgg 7980
gcgctagggc gctggcaagt gtagcggtca cgctgcgcgt aaccaccaca cccgccgcgc 8040
ttaatgcgcc gctacagggc gcgtccattc gccattcagg ctgcgcaact gttgggaagg 8100
gcgatcggtg cgggcctctt cgctattacg ccagctggcg aaagggggat gtgctgcaag 8160
gcgattaagt tgggtaacgc cagggttttc ccagtcacga cgttgtaaaa cgacggccag 8220
tgaattgtaa tacgactcac tatagggcga attgggcccg acgtcgcatg ctcccggccg 8280
ccatcactag tttggagata atcgcctttg ggcagttatc tagaatgtac acaaatttat 8340
taccatctaa gacacgacaa aaaatacata ctcatttcca attacctaac aagtttttta 8400
tatcttggtt acggtctttg tcgcatatta gaaatatttg cgctcatcat tcaaggctct 8460
ggaatataca gctaggagaa tcacctaaat tgcctgatag gttaaaagga aaatggctct 8520
ctagagaagt attggaggat attaatcaaa gaaacagccg taaaattttc actggcttat 8580
gttgtattca gtatctctta gacagaatta aaccagagca taattttgca cagcatttaa 8640
aaagaacttt tgagatgtat ccagaaatag aatctaaaaa cttaggcttt cccaaagatt 8700
gggaaaatca gcctctctgg aaataatcta agagtcagaa ttttaatttg tcataactct 8760
ttctcgttca aggcagggcg gcctgcacat actgggaagc atattcttcg atgcgcttaa 8820
agttttgccg tggtagttta gcttgatgct cttccacgtt gaaacctgct aagtagttac 8880
atacggctga cagcggcaaa aaatgtttga gtataaggcc atagttgatg cttgttggaa 8940
ttaaattttt aataaaattc ctgtctcagt ttcctgaagc ttgctctaaa cctcgttcaa 9000
aaaaaatgca gaataaagtt ggtcaagagg aacatattga atatttagct cgtagttttc 9060
atgagagtcg attgccaaga aaacccacgc cacctacaac ggttcctgat gaggtggtta 9120
gcatagttct taatataagt tttaatatac agcctgaaaa tcttgagaga ataaaagaag 9180
aacatcgatt ttccatggca gctgagaata ttgtaggaga tcttctagaa agatg 9235

<210> SEQ ID NO 79
<211> LENGTH: 10291
<212> TYPE: DNA
<213> ORGANISM: Artificial
<220> FEATURE:
<223> OTHER INFORMATION: Synthetic vector construct #1563
pGEM-gpA::smtB-PsmtA-zmPDC_dsrA-Prbc*-synADH_oop for genomic
integration into Synechococcus sp. PCC7002 between gene loci
A0124 and A0125

<400> SEQUENCE: 79
tcgacgggca aactttatga agcagatcaa gcctatatcc gccaagcaac cggcagccgc 60
gttgattagt gggtgtgtcc atcctctggt tcgtctaggt gctccgaagc gtcacgatag 120
agattaagaa tgtggtgatc cttgaggcga taaatcacat tccgcccttc cttgcgatag 180
ctcactaaac gtgctgtgcg cagggttctt agttggtgag agacagccga ttcactcatt 240
tcaacggcgg cggcgagttc ccccacccgc atctctccag tggccagggc cgaaagaata 300
cgccagcggt tggcatcccc caagacacca aaaaattcgg ccatccgttg ggccttggct 360
tggttcaaga ttttgccact gtggtctgtc attgttcgct gatctaaaca atacctgaat 420
aattgttcat gtgttaatct aaaaatgtga acaatcgttc aactatttaa gacaataacct 480 tggaggttta aaccatgaat tcttatactg tcggtaccta tttagcggag cggcttgtcc 540
agattggtct caagcatcac ttcgcagtcg cgggcgacta caacctcgtc cttcttgaca 600
acctgctttt gaacaaaaac atggagcagg tttattgctg taacgaactg aactgcggtt 660

```
tcagtgcaga aggttatgct cgtgccaaag gcgcagcagc agccgtcgtt acctacagcg    720
tcggtgcgct ttccgcattt gatgctatcg gtggcgccta tgcagaaaac cttccggtta    780
tcctgatctc cggtgctccg aacaacaatg atcacgctgc tggtcacgtg ttgcatcacg    840
ctcttggcaa aaccgactat cactatcagt tggaaatggc caagaacatc acggccgcag    900
ctgaagcgat ttacacccca gaagaagctc cggctaaaat cgatcacgtg attaaaactg    960
ctcttcgtga gaagaagccg gtttatctcg aaatcgcttg caacattgct tccatgccct   1020
gcgccgctcc tggaccggca agcgcattgt tcaatgacga agccagcgac gaagcttctt   1080
tgaatgcagc ggttgaagaa accctgaaat tcatcgccaa ccgcgacaaa gttgccgtcc   1140
tcgtcggcag caagctgcgc gcagctggtg ctgaagaagc tgctgtcaaa tttgctgatg   1200
ctctcggtgg cgcagttgct accatggctg ctgcaaaaag cttcttccca gaagaaaacc   1260
cgcattacat cggtacctca tggggtgaag tcagctatcc gggcgttgaa aagacgatga   1320
aagaagccga tgcggttatc gctctggctc ctgtcttcaa cgactactcc accactggtt   1380
ggacggatat tcctgatcct aagaaactgg ttctcgctga accgcgttct gtcgtcgtta   1440
acggcgttcg cttccccagc gttcatctga aagactatct gacccgtttg gctcagaaag   1500
tttccaagaa aaccggtgct ttggacttct tcaaatccct caatgcaggt gaactgaaga   1560
aagccgctcc ggctgatccg agtgctccgt tggtcaacgc agaaatcgcc cgtcaggtcg   1620
aagctcttct gaccccgaac acgacggtta ttgctgaaac cggtgactct tggttcaatg   1680
ctcagcgcat gaagctcccg aacggtgctc gcgttgaata tgaaatgcag tggggtcaca   1740
tcggttggtc cgttcctgcc gccttcggtt atgccgtcgg tgctccggaa cgtcgcaaca   1800
tcctcatggt tggtgatggt tccttccagc tgacggctca ggaagtcgct cagatggttc   1860
gcctgaaact gccggttatc atcttcttga tcaataacta tggttacacc atcgaagtta   1920
tgatccatga tggtccgtac aacaacatca agaactggga ttatgccggt ctgatggaag   1980
tgttcaacgg taacggtggt tatgacagcg gtgctggtaa aggcctgaag gctaaaaccg   2040
gtggcgaact ggcagaagct atcaaggttg ctctggcaaa caccgacggc ccaaccctga   2100
tcgaatgctt catcggtcgt gaagactgca ctgaagaatt ggtcaaatgg ggtaagcgcg   2160
ttgctgccgc caacagccgt aagcctgtta acaagctcct ctagtttcaa gtttcatccc   2220
gacccccctca gggtcgggat ttttttattg agctcactag tcgatcgaca ttgccataag   2280
taaaggcatc ccctgcgtga taagattacc ttcagtttat ggaggactga ccatatgatt   2340
aaagcctacg ctgccctgga agccaacgga aaactccaac cctttgaata cgaccccggt   2400
gccctgggtg ctaatgaggt ggagattgag gtgcagtatt gtggggtgtg ccacagtgat   2460
ttgtccatga ttaataacga atggggcatt tccaattacc ccctagtgcc gggtcatgag   2520
gtggtgggta ctgtggccgc catgggcgaa ggggtgaacc atgttgaggt gggggattta   2580
gtggggctgg gttggcattc gggctactgc atgacctgcc atagttgttt atctggctac   2640
cacaaccttt gtgccacggc ggaatcgacc attgtgggcc actacggtgg ctttggcgat   2700
cgggttcggg ccaagggagt cagcgtggtg aaattaccta aaggcattga cctagccagt   2760
gccgggcccc ttttctgtgg aggaattacc gttttcagtc ctatggtgga actgagttta   2820
aagcccactg caaaagtggc agtgatcggc attgggggct tgggccattt agcggtgcaa   2880
tttctccggg cctggggctg tgaagtgact gcctttacct ccagtgccag gaagcaaacg   2940
gaagtgttgg aattgggcgc tcaccacata ctagattcca ccaatccaga ggcgatcgcc   3000
```

-continued

```
agtgcggaag gcaaatttga ctatattatc tccactgtga acctgaagct tgactggaac   3060
ttatacatca gcaccctggc gccccaggga catttccact ttgttggggt ggtgttggag   3120
cctttggatc taaatctttt tccccttttg atgggacaac gctccgtttc tgcctcccca   3180
gtgggtagtc ccgccaccat tgccaccatg ttggactttg ctgtgcgcca tgacattaaa   3240
cccgtggtgg aacaatttag ctttgatcag atcaacgagg cgatcgccca tctagaaagc   3300
ggcaaagccc attatcgggt agtgctcagc catagtaaaa attagctctg caaaggttgc   3360
ttctgggtcc gtggaacgct cggttgccgc cgggcgtttt ttattcctgc agccttgctc   3420
tagaagaaca gcaaggccgc caatgcctga cgatgcgtgg agaccgaaac cttgcgctcg   3480
ttcgccagcc aggacagaaa tgcctcgact tcgctgctgc ccaaggttgc cgggtgacgc   3540
acaccgtgga aacggatgaa ggcacgaacc cagtggacat aagcctgttc ggttcgtaag   3600
ctgtaatgca agtagcgtat gcgctcacgc aactggtcca gaaccttgac cgaacgcagc   3660
ggtggtaacg gcgcagtggc ggttttcatg gcttgttatg actgtttttt tggggtacag   3720
tctatgcctc gggcatccaa gcagcaagcg cgttacgccg tgggtcgatg tttgatgtta   3780
tggagcagca acgatgttac gcagcagggc agtcgcccta aaacaaagtt aaacatcatg   3840
agggaagcgg tgatcgccga agtatcgact caactatcag aggtagttgg cgtcatcgag   3900
cgccatctcg aaccgacgtt gctggccgta catttgtacg gctccgcagt ggatggcggc   3960
ctgaagccac acagtgatat tgatttgctg gttacggtga ccgtaaggct tgatgaaaca   4020
acgcggcgag ctttgatcaa cgaccttttg gaaacttcgg cttcccctgg agagagcgag   4080
attctccgcg ctgtagaagt caccattgtt gtgcacgacg acatcattcc gtggcgttat   4140
ccagctaagc gcgaactgca atttggagaa tggcagcgca atgacattct tgcaggtatc   4200
ttcgagccag ccacgatcga cattgatctg gctatcttgc tgacaaaagc aagagaacat   4260
agcgttgcct tggtaggtcc agcggcggag gaactctttg atccggttcc tgaacaggat   4320
ctatttgagg cgctaaatga aaccttaacg ctatggaact cgccgcccga ctgggctggc   4380
gatgagcgaa atgtagtgct tacgttgtcc cgcatttggt acagcgcagt aaccggcaaa   4440
atcgcgccga aggatgtcgc tgccgactgg gcaatggagc gcctgccggc ccagtatcag   4500
cccgtcatac ttgaagctag acaggcttat cttggacaag aagaagatcg cttggcctcg   4560
cgcgcagatc agttggaaga atttgtccac tacgtgaaag gcgagatcac caaggtagtc   4620
ggcaaataat gtctaacaat tcgttcaagc cgacgccgct tcgcggcgcg gcttaactca   4680
agcgttagat gcactaccgg tatctttcta gaagatcctc tagttctaga gcggccgcag   4740
gagcgatctg agtcactccc tttatttctc taattatttt ggcgatttgt tggtcagcct   4800
aaattcatta ccgcaacaca ggatttttca tggattcttc catcgccatt tgaggaagtc   4860
cttgggattt cgtgtagtgg gtcgagtaca gcagcgcacc gatgaagata ccaccaccaa   4920
taatgttccc aatcgtcaca ggtaggaaat cccagaagac catatccata ccagagatcg   4980
gcgcaccgag aaccatacca gtcaagataa agaacatatt gaccacgatg tgctccaggc   5040
cgagggtgac gaacgcgaag atcgggaacc agcagcccat aaatttacct gggacggact   5100
tactcaccat gcccatcatc acagccaaac aaactaggaa gttacagaaa ataccacgga   5160
caatgaagag aaagaagcca ttggtgccca tttctttcac tgccacggtc ttggagaggg   5220
cgatttcgat aatttttttca cccacggggc tggggtcagc cgtcccacca ttggtaaggg   5280
agaaccccat caacagggcc acaaacaaac aacctaaaaa attacccaga taaacccaaa   5340
gccaattatt aataactctg ccaaacctca ctcgtctcgc caacattgcc gatgtcatca   5400
```

gcgcaaagtt gccagttacc agttccatcc caaagagcac gatggaggca aatccccaag 5460
ggaagagaag tgctccgagg aatggcagac cactttgtac ggcgacggta acagcgaggg 5520
tggtggcaac gccaagggcc agaccagagt agaagccacg gatgagcaga tctttgacgg 5580
aaagacgtgc ttttgtttcg cctgctttga tactggcatc tactagttct ttggggatta 5640
cgtagtccat tattttctcc taatttaaaa ccgatgggga aacaaaaggg tcattggttt 5700
ttctaaagtc aatgcgcttt gagattaact tttaaaccac agataaattg ttcatgaaga 5760
acttaatttc acttttccgg aatttaattt caaaagttta gctctggatt tttgttctgc 5820
tgtgatattc agccatgaac gtcccttgat ctaggtcaaa gccaagtaat acaatgcttt 5880
tgaggaattc acccaaagaa agatactttt aaataaaatc agtctccagt cacaattaaa 5940
gctccatttt ctgaccaact gcaaaaaata tagaggattc aaattgttta gaagaaagta 6000
atcttcagtt ggttttgcta agaaaataat aatccttggc aaagtagaga acgagctgca 6060
tgcgacgtcg ggcccaattc gccctatagt gagtcgtatt acaattcact ggccgtcgtt 6120
ttacaacgtc gtgactggga aaaccctggc gttacccaac ttaatcgcct tgcagcacat 6180
ccccctttcg ccagctggcg taatagcgaa gaggcccgca ccgatcgccc ttcccaacag 6240
ttgcgcagcc tgaatggcga atggacgcgc cctgtagcgg cgcattaagc gcggcgggtg 6300
tggtggttac gcgcagcgtg accgctacac ttgccagcgc cctagcgccc gctcctttcg 6360
ctttcttccc ttcctttctc gccacgttcg ccggctttcc ccgtcaagct ctaaatcggg 6420
ggctcccttt agggttccga tttagagctt tacggcacct cgaccgcaaa aaacttgatt 6480
tgggtgatgg ttcacgtagt gggccatcgc cctgatagac ggtttttcgc cctttgacgt 6540
tggagtccac gttctttaat agtggactct tgttccaaac tggaacaaca ctcaacccta 6600
tctcggtcta ttcttttgat ttataaggga ttttgccgat ttcggcctat tggttaaaaa 6660
atgagctgat ttaacaaata tttaacgcga attttaacaa aatattaacg tttacaattt 6720
cgcctgatgc ggtattttct ccttacgcat ctgtgcggta tttcacaccg catacaggtg 6780
gcacttttcg gggaaatgtg cgcggaaccc ctatttgttt atttttctaa atacattcaa 6840
atatgtatcc gctcatgaga caataaccct gataaatgct tcaataatat tgaaaaagga 6900
agagtatgag tattcaacat ttccgtgtcg cccttattcc cttttttgcg gcattttgcc 6960
ttcctgtttt tgctcaccca gaaacgctgg tgaaagtaaa agatgctgaa gatcagttgg 7020
gtgcacgagt gggttacatc gaactggatc tcaacagcgg taagatcctt gagagttttc 7080
gccccgaaga acgttttcca atgatgagca cttttaaagt tctgctatgt ggcgcggtat 7140
tatcccgtat tgacgccggg caagagcaac tcggtcgccg catacactat tctcagaatg 7200
acttggttga gtactcacca gtcacagaaa agcatcttac ggatggcatg acagtaagag 7260
aattatgcag tgctgccata accatgagtg ataacactgc ggccaactta cttctgacaa 7320
cgatcggagg accgaaggag ctaaccgctt ttttgcacaa catgggggat catgtaactc 7380
gccttgatcg ttgggaaccg gagctgaatg aagccatacc aaacgacgag cgtgacacca 7440
cgatgcctgt agcaatgcca acaacgttgc gcaaactatt aactggcgaa ctacttactc 7500
tagcttcccg gcaacaatta atagactgga tggaggcgga taaagttgca ggaccacttc 7560
tgcgctcggc ccttccggct ggctggttta ttgctgataa atctggagcc ggtgagcgtg 7620
ggtctcgcgg tatcattgca gcactggggc cagatggtaa gccctcccgt atcgtagtta 7680
tctacacgac ggggagtcag gcaactatgg atgaacgaaa tagacagatc gctgagatag 7740
gtgcctcact gattaagcat tggtaactgt cagaccaagt ttactcatat atactttaga 7800
ttgatttaaa acttcatttt taatttaaaa ggatctaggt gaagatcctt tttgataatc 7860
tcatgaccaa aatcccttaa cgtgagtttt cgttccactg agcgtcagac cccgtagaaa 7920
agatcaaagg atcttcttga gatccttttt ttctgcgcgt aatctgctgc ttgcaaacaa 7980
aaaaaccacc gctaccagcg gtggtttgtt tgccggatca agagctacca actctttttc 8040
cgaaggtaac tggcttcagc agagcgcaga taccaaatac tgtccttcta gtgtagccgt 8100
agttaggcca ccacttcaag aactctgtag caccgcctac atacctcgct ctgctaatcc 8160
tgttaccagt ggctgctgcc agtggcgata agtcgtgtct taccgggttg gactcaagac 8220
gatagttacc ggataaggcg cagcggtcgg gctgaacggg gggttcgtgc acacagccca 8280
gcttggagcg aacgacctac accgaactga gatacctaca gcgtgagcta tgagaaagcg 8340
ccacgcttcc cgaagggaga aaggcggaca ggtatccggt aagcggcagg gtcggaacag 8400
gagagcgcac gagggagctt ccagggggaa acgcctggta tctttatagt cctgtcgggt 8460
ttcgccacct ctgacttgag cgtcgatttt tgtgatgctc gtcagggggg cggagcctat 8520
ggaaaaacgc cagcaacgcg gcctttttac ggttcctggc cttttgctgg ccttttgctc 8580
acatgttctt tcctgcgtta tcccctgatt ctgtggataa ccgtattacc gcctttgagt 8640
gagctgatac cgctcgccgc agccgaacga ccgagcgcag cgagtcagtg agcgaggaag 8700
cggaagagcg cccaatacgc aaaccgcctc tccccgcgcg ttggccgatt cattaatgca 8760
gctggcacga caggtttccc gactggaaag cgggcagtga gcgcaacgca attaatgtga 8820
gttagctcac tcattaggca ccccaggctt tacactttat gcttccggct cgtatgttgt 8880
gtggaattgt gagcggataa caatttcaca caggaaacag ctatgaccat gattacgcca 8940
agctatttag gtgacactat agaatactca agctatgcat gcacagacga tacactgaag 9000
ggcatctttg tctgggacac taggctctat gtcttctgaa aaaatgtcgc catcgtcacc 9060
cccctatgat ctaatcgtgg tgggggccac tggttttgtg ggccaaatta tttgccgcta 9120
tctttgtgac catgccgaac gtgaattgtt tacttgggcg atcgccggcc gttcagccga 9180
aaaattagcc caactcaagc actctttggg catcccaggg gagaccttag caacctttgt 9240
cgttgatgtg tttgatcaag gggcagtgac ggccctctgc gagcaaacga aggtgatcct 9300
cacaacggtc ggcccctaca gtctttatgg agaaaccttg ctccgggcct gtgccacaac 9360
gggaaccgat tattgcgatc tgaccgggga agtccagtgg gtcaaaaaga tggtgactaa 9420
atatgaggcg atcgcccaac agtcgggggc acggatcgtc cattgttgcg gctttgattc 9480
ggtgccgtct gaccttgggg tgtatttttt gcaacagcgg gctttaaaac gattcggaaa 9540
accctgtcgc caaattaaga tgcgcgttaa gacagcccag ggaggcattt ccgggggggac 9600
ggcggccagc ggcgtaaatc tgatcaaaga ggcgatcgcc gactcagaga tcaaaacact 9660
attggctaat ccctatgccc tctgtcccaa agctcccaat ccccagcacc cagctcccct 9720
aatcccggta caaatcgacc acatttttgg cgaatgggtg acacccttta tcatggcagc 9780
ggtgaatacg cctattgtgc tgcgctccaa tgccctacaa aactgggcct atggtgagca 9840
gttccagtac gacgaagggc tgcttacggg ggtcagtgtt gggggttggt tgaaagccca 9900
gggtctaagc ctattactta aaatcctggg aggaactgcg gcgatcgacc ctagtctcct 9960
cgaaaaaatt gtcccggccc ccggcgaagg gccttccccc agccaacagc aagccggttt 10020
ttatgatcta cgcttttggg gcattactac ttcgggtgaa gttcttatgg caaaagtcac 10080
tggcgatcgc gaccctggct atggttccac cgcaaaaatt atcgcccaag caggactctg 10140
tttagccaaa gataatctat cccgatccgg tggcttctgg acgccagcca cagccatggg 10200
tgaacatctt atcgatcgcc tcaccgctta cagtggctta accttcagca tcctttgagt 10260
tgatcttggt ccctcacaat tcaaaacata g 10291

<210> SEQ ID NO 80
<211> LENGTH: 9516
<212> TYPE: DNA
<213> ORGANISM: Artificial
<220> FEATURE:
<223> OTHER INFORMATION: Synthetic vector construct #1568
pGEM-gpB::smtB-PsmtA-zmPDCdeg_spf-Prbc*-synADH_oop for
chromosomal integration between gene loci A1330 and A1331 of
Synechococcus sp.PCC7002

<400> SEQUENCE: 80
tcgacgggca aactttatga agcagatcaa gcctatatcc gccaagcaac cggcagccgc 60
gttgattagt gggtgtgtcc atcctctggt tcgtctaggt gctccgaagc gtcacgatag 120
agattaagaa tgtggtgatc cttgaggcga taaatcacat tccgcccttc cttgcgatag 180
ctcactaaac gtgctgtgcg cagggttctt agttggtgag agacagccga ttcactcatt 240
tcaacggcgg cggcgagttc ccccacccgc atctctccag tggccagggc cgaaagaata 300
cgccagcggt tggcatcccc caagacacca aaaaattcgg ccatccgttg ggccttggct 360
tggttcaaga ttttgccact gtggtctgtc attgttcgct gatctaaaca atacctgaat 420
aattgttcat gtgttaatct aaaaatgtga acaatcgttc aactatttaa gacaatacct 480
tggaggttta aaccatgaat tcctacaccg ttggcactta cctggctgaa cgcttggttc 540
agatcggctt aaaacaccat tttgctgttg ctggtgatta taatttggtt ttgttagata 600
atttattgct caataagaat atggaacagg tgtactgttg caatgagtta aattgtggct 660
tttccgctga gggctacgcc cgtgctaagg gtgctgctgc tgctgttgtg acttattctg 720
ttggcgcttt gagtgctttt gacgccattg gcggtgctta cgctgagaat ttgccagtga 780
ttttaattag tggcgcccca aataataacg accatgccgc cggccatgtc ctccaccatg 840
ccttgggtaa gactgattac cattaccaac tggagatggc taaaaatatt accgctgctg 900
ccgaagctat ctatactcct gaggaagccc cagccaagat tgaccatgtc atcaagaccg 960
ccttgcggga aaaaaaacca gtgtacttag agattgcctg taatatcgcc agtatgcctt 1020
gtgctgcccc cggtccagct tctgctctct ttaacgatga agcttctgat gaggccagtc 1080
tcaacgctgc tgtggaggaa actttaaagt ttattgctaa tcgtgataag gtggctgttt 1140
tagttggttc taaattacgt gctgccggcg ccgaggaagc cgccgttaag tttgccgacg 1200
ccttaggcgg tgctgtggcc actatggccg ccgctaagtc ttttttttcct gaagagaatc 1260 cacactatat tggcactagc tggggcgagg tttcttaccc aggtgtggag aaaaccatga 1320
aggaggctga cgctgtgatt gccttagccc cggtttttaa tgattatagt actaccggct 1380
ggaccgacat cccggacccg aaaaagttag tgttagccga accacggagt gttgttgtga 1440
atggtgtgcg ttttccttct gtgcacttaa aggattactt aactcggctc gcccagaagg 1500
tgagtaaaaa gactggcgcc ctcgattttt ttaagagttt aaacgctggc gagttaaaaa 1560
aggctgcccc agccgaccca tccgccccac tcgttaatgc tgaaattgct cggcaggttg 1620
aggccttgtt aactccaaat accaccgtga tcgccgaaac tggcgatagt tggtttaacg 1680
cccaacgtat gaaattacca aatggcgccc gtgtggagta cgagatgcaa tggggccata 1740
ttggctggag tgtgccggct gcttttggct acgctgttgg cgccccagag cggcgtaata 1800
ttttaatggt gggcgacggc agttttcagt taaccgccca agaggttgcc caaatggtgc 1860
gtttaaagtt accagtgatt atttttctca ttaacaatta cggctatact attgaggtga 1920
tgattcacga cggcccatat aataatatta aaaattggga ctacgctggc ttaatggagg 1980
tctttaatgg caatggcggc tacgattctg gcgccggcaa gggtttaaaa gccaagactg 2040
gcggtgagtt agctgaagcc attaaagtgg ccttagctaa tactgatggt cctactttaa 2100
ttgagtgttt tattggccgg gaagattgta ccgaggaact cgttaagtgg ggcaaacgtg 2160
tggccgctgc taattctcgg aaacccgtga ataaattatt atgaaatatt ttagccgccc 2220
cagtcagtaa tgactggggc gttttttatt gggagctcac tagtcgatcg acattgccat 2280
aagtaaaggc atcccctgcg tgataagatt accttcagtt tatggaggac tgaccatatg 2340
attaaagcct acgctgccct ggaagccaac ggaaaactcc aaccctttga atacgacccc 2400
ggtgccctgg gtgctaatga ggtggagatt gaggtgcagt attgtggggt gtgccacagt 2460
gatttgtcca tgattaataa cgaatggggc atttccaatt acccccctagt gccgggtcat 2520
gaggtggtgg gtactgtggc cgccatgggc gaaggggtga accatgttga ggtgggggat 2580
ttagtggggc tgggttggca ttcgggctac tgcatgacct gccatagttg tttatctggc 2640
taccacaacc tttgtgccac ggcggaatcg accattgtgg gccactacgg tggctttggc 2700
gatcgggttc gggccaaggg agtcagcgtg gtgaaattac ctaaaggcat tgacctagcc 2760
agtgccgggc cccttttctg tggaggaatt accgttttca gtcctatggt ggaactgagt 2820
ttaaagccca ctgcaaaagt ggcagtgatc ggcattgggg gcttgggcca tttagcggtg 2880
caatttctcc gggcctgggg ctgtgaagtg actgccttta cctccagtgc caggaagcaa 2940
acggaagtgt tggaattggg cgctcaccac atactagatt ccaccaatcc agaggcgatc 3000
gccagtgcgg aaggcaaatt tgactatatt atctccactg tgaacctgaa gcttgactgg 3060
aacttataca tcagcaccct ggcgccccag ggacatttcc actttgttgg ggtggtgttg 3120
gagcctttgg atctaaatct tttccccctt ttgatgggac aacgctccgt ttctgcctcc 3180
ccagtgggta gtcccgccac cattgccacc atgttggact ttgctgtgcg ccatgacatt 3240
aaacccgtgg tggaacaatt tagctttgat cagatcaacg aggcgatcgc ccatctagaa 3300
agcggcaaag cccattatcg ggtagtgctc agccatagta aaaattagct ctgcaaaggt 3360
tgcttctggg tccgtggaac gctcggttgc cgccgggcgt tttttattcc tgcaggatcc 3420
acaggacggg tgtggtcgcc atgatcgcgt agtcgatagt ggctccaagt agcgaagcga 3480
gcaggactgg gcggcggcca aagcggtcgg acagtgctcc gagaacgggt gcgcatagaa 3540
attgcatcaa cgcatatagc gctagcagca cgccatagtg actggcgatg ctgtcggaat 3600
ggacgatcga attggccgcg gcgttgtgac aatttaccga acaactccgc ggccgggaag 3660
ccgatctcgg cttgaacgaa ttgttaggtg gcggtacttg ggtcgatatc aaagtgcatc 3720
acttcttccc gtatgcccaa ctttgtatag agagccactg cgggatcgtc accgtaatct 3780
gcttgcacgt agatcacata agcaccaagc gcgttggcct catgcttgag gagattgatg 3840
agcgcggtgg caatgccctg cctccggtgc tcgccggaga ctgcgagatc atagatatag 3900
atctcactac gcggctgctc aaacttgggc agaacgtaag ccgcgagagc gccaacaacc 3960
gcttcttggt cgaaggcagc aagcgcgatg aatgtcttac tacggagcaa gttcccgagg 4020
taatcggagt ccggctgatg ttgggagtag gtggctacgt ctccgaactc acgaccgaaa 4080
agatcaagag cagcccgcat ggatttgact tggtcagggc cgagcctaca tgtgcgaatg 4140

-continued

```
atgcccatac ttgagccacc taactttgtt ttagggcgac tgccctgctg cgtaacatcg   4200
ttgctgctgc gtaacatcgt tgctgctcca taacatcaaa catcgaccca cggcgtaacg   4260
cgcttgctgc ttggatgccc gaggcataga ctgtacaaaa aaacagtcat aacaagccat   4320
gaaaaccgcc actgcgccgt taccaccgct gcgttcggtc aaggttctgg accagttgcg   4380
tgagcgcata cgctacttgc attacagttt acgaaccgaa caggcttatg tcaattcgag   4440
catcgatata gaaatttgcc ctagcaaata tcctcctgag tgaattggtt ttgttaagct   4500
ttacaggctt caatgacgca aatttcctcg gcggttctaa caatgcgcgt cagttttaag   4560
tctgccgccg ccaacagggt ttcaaactca gcggcggtgc gttctttgcc accgggacac   4620
atcaccagca tattgatatc gagcattttt gcgccactag gttgatttcc ctctggaacc   4680
accgcttcac agatcaagat tttgccgtca tccggcagta cagcgcgaca attttgcaaa   4740
atggcgatcg cctggtcatc gccccaatcg tgaataatgt gtttgagcaa ataggcatcg   4800
ccccccgccg gaattgttct aaagaaactg ccgccaatcc gttgacagcg atcgccgacc   4860
ccatggcggt ttaacgtcgg agcagcatta tccaccacat aatcttcatc gaacaaaata   4920
ccttgtaatt ggggatattt cgccaaaatg ctgccgagca attccccgta gcccccaccc   4980
acatcaacga tggttgaaaa agccgaaaaa tcataatggg ccaaaatttc cggctcttca   5040
ttcctggaga aactgttcat cgcctcttca aaaatcgccg ccgcttctgg atgattgccg   5100
aaatattcaa acacccccctg gccatagcga tggtcaaagg caggttcacc ggttttaacg   5160
ctgtggagaa tattactcca ggcttcgtaa tgctctggtt cccccaacat caccacagaa   5220
cctcgcatgg agcggggatg atcactgcgg agaaaatcgg ctagcggtgt cagggcaaag   5280
gtttgggagg ctgtttcttg gaaaataccc acactggcca aggcccggag aatgcgatac   5340
aaagccgttt cgtctgtttc ggtgagatgg gctaacgcac ggcaaggttg ttctccggct   5400
ttgaggtgat cggcgatcgc caattttgcc gccacataaa tgcactggga aagccaataa   5460
ccagaggcca tttggagcaa ttgggtatgg agagggaggg ttggcggttc catagcgtga   5520
aaaatcctga tgcatagctt gagtattcta tagtgtcacc taaatagctt ggcgtaatca   5580
tggtcatagc tgtttcctgt gtgaaattgt tatccgctca caattccaca caacatacga   5640
gccggaagca taaagtgtaa agcctggggt gcctaatgag tgagctaact cacattaatt   5700
gcgttgcgct cactgcccgc tttccagtcg ggaaacctgt cgtgccagct gcattaatga   5760
atcggccaac gcgcggggag aggcggtttg cgtattgggc gctcttccgc ttcctcgctc   5820
actgactcgc tgcgctcggt cgttcggctg cggcgagcgg tatcagctca ctcaaaggcg   5880
gtaatacggt tatccacaga atcaggggat aacgcaggaa agaacatgtg agcaaaaggc   5940
cagcaaaagg ccaggaaccg taaaaaggcc gcgttgctgg cgtttttcca taggctccgc   6000
ccccctgacg agcatcacaa aaatcgacgc tcaagtcaga ggtggcgaaa cccgacagga   6060
ctataaagat accaggcgtt tccccctgga agctccctcg tgcgctctcc tgttccgacc   6120
ctgccgctta ccggatacct gtccgccttt ctcccttcgg gaagcgtggc gctttctcat   6180
agctcacgct gtaggtatct cagttcggtg taggtcgttc gctccaagct gggctgtgtg   6240
cacgaacccc ccgttcagcc cgaccgctgc gccttatccg gtaactatcg tcttgagtcc   6300
aacccggtaa gacacgactt atcgccactg gcagcagcca ctggtaacag gattagcaga   6360
gcgaggtatg taggcggtgc tacagagttc ttgaagtggt ggcctaacta cggctacact   6420
agaaggacag tatttggtat ctgcgctctg ctgaagccag ttaccttcgg aaaaagagtt   6480
ggtagctctt gatccggcaa acaaaccacc gctggtagcg gtggtttttt tgtttgcaag   6540
```

cagcagatta cgcgcagaaa aaaaggatct caagaagatc ctttgatctt ttctacgggg 6600
tctgacgctc agtggaacga aaactcacgt taagggattt tggtcatgag attatcaaaa 6660
aggatcttca cctagatcct tttaaattaa aaatgaagtt ttaaatcaat ctaaagtata 6720
tatgagtaaa cttggtctga cagttaccaa tgcttaatca gtgaggcacc tatctcagcg 6780
atctgtctat ttcgttcatc catagttgcc tgactccccg tcgtgtagat aactacgata 6840
cgggagggct taccatctgg ccccagtgct gcaatgatac cgcgagaccc acgctcaccg 6900
gctccagatt tatcagcaat aaaccagcca gccggaaggg ccgagcgcag aagtggtcct 6960
gcaactttat ccgcctccat ccagtctatt aattgttgcc gggaagctag agtaagtagt 7020
tcgccagtta atagtttgcg caacgttgtt ggcattgcta caggcatcgt ggtgtcacgc 7080
tcgtcgtttg gtatggcttc attcagctcc ggttcccaac gatcaaggcg agttacatga 7140
tcccccatgt tgtgcaaaaa agcggttagc tccttcggtc ctccgatcgt tgtcagaagt 7200
aagttggccg cagtgttatc actcatggtt atggcagcac tgcataattc tcttactgtc 7260
atgccatccg taagatgctt ttctgtgact ggtgagtact caaccaagtc attctgagaa 7320
tagtgtatgc ggcgaccgag ttgctcttgc ccggcgtcaa tacgggataa taccgcgcca 7380
catagcagaa ctttaaaagt gctcatcatt ggaaaacgtt cttcggggcg aaaactctca 7440
aggatcttac cgctgttgag atccagttcg atgtaaccca ctcgtgcacc caactgatct 7500
tcagcatctt ttactttcac cagcgtttct gggtgagcaa aaacaggaag gcaaaatgcc 7560
gcaaaaaagg gaataagggc gacacggaaa tgttgaatac tcatactctt cctttttcaa 7620
tattattgaa gcatttatca gggttattgt ctcatgagcg gatacatatt tgaatgtatt 7680
tagaaaaata aacaaatagg ggttccgcgc acatttcccc gaaaagtgcc acctgtatgc 7740
ggtgtgaaat accgcacaga tgcgtaagga gaaaataccg catcaggcga aattgtaaac 7800
gttaatattt tgttaaaatt cgcgttaaat atttgttaaa tcagctcatt ttttaaccaa 7860
taggccgaaa tcggcaaaat cccttataaa tcaaaagaat agaccgagat agggttgagt 7920
gttgttccag tttggaacaa gagtccacta ttaaagaacg tggactccaa cgtcaaaggg 7980
cgaaaaaccg tctatcaggg cgatggccca ctacgtgaac catcacccaa atcaagtttt 8040
ttgcggtcga ggtgccgtaa agctctaaat cggaacccta aagggagccc ccgatttaga 8100
gcttgacggg gaaagccggc gaacgtggcg agaaaggaag ggaagaaagc gaaaggagcg 8160
ggcgctaggg cgctggcaag tgtagcggtc acgctgcgcg taaccaccac acccgccgcg 8220
cttaatgcgc cgctacaggg cgcgtccatt cgccattcag gctgcgcaac tgttgggaag 8280
ggcgatcggt gcgggcctct tcgctattac gccagctggc gaaaggggga tgtgctgcaa 8340
ggcgattaag ttgggtaacg ccagggtttt cccagtcacg acgttgtaaa acgacggcca 8400
gtgaattgta atacgactca ctatagggcg aattgggccc gacgtcgcat gctggggctt 8460
gatagaatag atctcaggat ttttacgcag cacatttaac aattcaatca tgattaaacg 8520
gttttttat ggggcgatcg ccattgtctt ggcctttacc ctgatcttta ccccagcgga 8580
taatgcttgg gcggcccgca gtggaggacg cattggtggc ggttccttcc gcagtgcccc 8640
tagtcgcagt ttttcccctg gcccagcacg acgggctccc gttgggggtg gctatggtta 8700
cggatttggg ggtggatttg ggttcccctt cctgctgcct ttcttcggat tcggtggttt 8760
tagcggcatt ttcggtcttt tcattatgtt ggcgatcgcc ggcttccttg tccgcacctt 8820
ccagaacgtg atggggggtg gcatgaacga gggcgacagt ctcggttact ctgcccccag 8880
tagcaaaatt tctgtggcga aggtacaggt ggggctgttg gcccaagcac gggatctcca 8940
gcaggatcta aatcgcctgg cgagcaccgc tgatactggc accccggctg gacgcgctaa 9000
ggttcttcaa gaatcgactc tggccctgtt gcgccaccca gaatattggg tctatggtgc 9060
gagcgaatcc ctcgaagctg gggttgatgc tgccgaagcc aagtttaatc aattggccct 9120
gaacgagcgg agtaaattta ccgccgagac ccttagtaac gttgacaacg aacgggatgt 9180
ggctgggaaa agtgggagtg ctgatttggt aaaaagcgac gatacaccga acgaatacat 9240
catggtgaca atcatcgctg ggccatgggg gaaagttgag ttaccgaaag tgaccgattc 9300
ccaatccctc gaacaagcga tccgtcaaat tggtgccctt ggtggcgatc gccttttggc 9360
cctcgaagtt ttatggacgc cccaagcgat tggtgacacc ctcagcactg acgatatttt 9420
gacctattac cccgacatta atctcgtata actaggccaa aatctaaaac aattcaacgc 9480
aaatcatggc gatttaaaga atcccctcaa tacagg 9516

<210> SEQ ID NO 81
<211> LENGTH: 10553
<212> TYPE: DNA
<213> ORGANISM: Artificial
<220> FEATURE:
<223> OTHER INFORMATION: Synthetic vector construct #1692
pGEM-gpC::smtB-PsmtA-zmPDC_oop-PrbcL-synADHdeg_oop for
chromosomal integration between gene loci A2578 and A2579 of
Synechococcus sp. PCC7002

<400> SEQUENCE: 81
tcgacgggca aactttatga agcagatcaa gcctatatcc gccaagcaac cggcagccgc 60
gttgattagt gggtgtgtcc atcctctggt tcgtctaggt gctccgaagc gtcacgatag 120
agattaagaa tgtggtgatc cttgaggcga taaatcacat tccgcccttc cttgcgatag 180
ctcactaaac gtgctgtgcg cagggttctt agttggtgag agacagccga ttcactcatt 240
tcaacggcgg cggcgagttc ccccacccgc atctctccag tggccagggc cgaaagaata 300
cgccagcggt tggcatcccc caagacacca aaaaattcgg ccatccgttg ggccttggct 360
tggttcaaga ttttgccact gtggtctgtc attgttcgct gatctaaaca atacctgaat 420
aattgttcat gtgttaatct aaaaatgtga acaatcgttc aactatttaa gacaatacct 480
tggaggttta aaccatgaat tcttatactg tcggtaccta tttagcggag cggcttgtcc 540
agattggtct caagcatcac ttcgcagtcg cgggcgacta caacctcgtc cttcttgaca 600
acctgctttt gaacaaaaac atggagcagg tttattgctg taacgaactg aactgcggtt 660
tcagtgcaga aggttatgct cgtgccaaag gcgcagcagc agccgtcgtt acctacagcg 720
tcggtgcgct ttccgcattt gatgctatcg gtggcgccta tgcagaaaac cttccggtta 780
tcctgatctc cggtgctccg aacaacaatg atcacgctgc tggtcacgtg ttgcatcacg 840
ctcttggcaa aaccgactat cactatcagt tggaaatggc caagaacatc acggccgcag 900
ctgaagcgat ttacacccca gaagaagctc cggctaaaat cgatcacgtg attaaaactg 960
ctcttcgtga gaagaagccg gtttatctcg aaatcgcttg caacattgct tccatgccct 1020
gcgccgctcc tggaccggca agcgcattgt tcaatgacga agccagcgac gaagcttctt 1080
tgaatgcagc ggttgaagaa accctgaaat tcatcgccaa ccgcgacaaa gttgccgtcc 1140
tcgtcggcag caagctgcgc gcagctggtg ctgaagaagc tgctgtcaaa tttgctgatg 1200
ctctcggtgg cgcagttgct accatggctg ctgcaaaaag cttcttccca gaagaaaacc 1260
cgcattacat cggtacctca tggggtgaag tcagctatcc gggcgttgaa aagacgatga 1320
aagaagccga tgcggttatc gctctggctc ctgtcttcaa cgactactcc accactggtt 1380
ggacggatat tcctgatcct aagaaactgg ttctcgctga accgcgttct gtcgtcgtta 1440
acggcgttcg cttccccagc gttcatctga aagactatct gacccgtttg gctcagaaag 1500
tttccaagaa aaccggtgct ttggacttct tcaaatccct caatgcaggt gaactgaaga 1560
aagccgctcc ggctgatccg agtgctccgt tggtcaacgc agaaatcgcc cgtcaggtcg 1620
aagctcttct gaccccgaac acgacggtta ttgctgaaac cggtgactct tggttcaatg 1680
ctcagcgcat gaagctcccg aacggtgctc gcgttgaata tgaaatgcag tggggtcaca 1740
tcggttggtc cgttcctgcc gccttcggtt atgccgtcgg tgctccggaa cgtcgcaaca 1800
tcctcatggt tggtgatggt tccttccagc tgacggctca ggaagtcgct cagatggttc 1860
gcctgaaact gccggttatc atcttcttga tcaataacta tggttacacc atcgaagtta 1920
tgatccatga tggtccgtac aacaacatca agaactggga ttatgccggt ctgatggaag 1980
tgttcaacgg taacggtggt tatgacagcg gtgctggtaa aggcctgaag gctaaaaccg 2040
gtggcgaact ggcagaagct atcaaggttg ctctggcaaa caccgacggc ccaaccctga 2100
tcgaatgctt catcggtcgt gaagactgca ctgaagaatt ggtcaaatgg ggtaagcgcg 2160
ttgctgccgc caacagccgt aagcctgtta acaagctcct ctagtttttg ggatcaatt 2220 cgagctcggt acccaaacta gtaacgctcg gttgccgccg ggcgtttttt attccgacat 2280
caggaattgt aattagaaag tccaaaaatt gtaatttaaa aaacagtcaa tggagagcat 2340
tgccataagt aaaggcatcc cctgcgtgat aagattacct tcagaaaaca gatagttgct 2400
gggttatcgc agatttttct cgcaaccaaa taactgtaaa taataactgt ctctggggcg 2460
acggtaggct ttatattgcc aaatttcgcc cgtgggagaa agctaggcta ttcaatgttt 2520
atggaggact gacccatatg atcaaggctt atgccgcttt agaggctaat ggcaagttgc 2580
agccgttcga gtatgatccg ggcgctttag gcgccaacga agttgaaatc gaagttcaat 2640
actgcggtgt ttgtcattcc gacctcagta tgatcaacaa tgagtggggt atcagtaact 2700
atccgttggt tcccggccac gaagttgttg gcaccgttgc tgctatgggt gagggtgtta 2760
atcacgtgga agttggtgac ctggttggtt taggctggca cagtggttat tgtatgactt 2820
gtcactcctg cctgagcggt tatcataatt tgtgcgctac cgccgagagt actatcgttg 2880
gtcattatgg cggtttcggt gaccgtgtgc gtgctaaagg tgtgtccgtt gttaagctgc 2940
ccaagggtat cgatttggct tccgctggtc cgttgttttg cggtggtatc actgtgtttt 3000
cccccatggt tgagttatcc ctgaaaccga ccgccaaggt tgccgttatt ggtatcggtg 3060
gtctcggtca cctggccgtt cagttcttgc gtgcttgggg ttgcgaggtt accgctttca 3120
ctagctccgc tcgtaaacag accgaggttc tggagctggg tgcccatcat attttggaca 3180
gtactaaccc cgaagccatt gcttccgccg agggtaagtt cgattacatc attagtaccg 3240
ttaatttaaa attggattgg aatctgtata tttccacttt agccccgcaa ggtcactttc 3300
atttcgtggg tgttgttctc gaacccctcg acttgaactt gttcccgttg ctcatgggtc 3360
agcggagtgt gtccgctagt ccggttggct ccccggctac tatcgctact atgctcgatt 3420
tcgccgttcg gcacgatatc aagccggttg ttgagcagtt ctccttcgac caaattaatg 3480
aagccattgc tcacttggag tccggtaagg ctcactaccg tgtggttttg agtcactcca 3540
agaactgaaa cgctcggttg ccgccgggcg ttttttattc ctgcaggccc cccgggggat 3600
ccactagagg atctcaatga atattggttg acacgggcgt ataagacatg ttatactgtt 3660
gaataacaag gacggatctg atcaagagac aggatgagga tcgtttcgca tgattgaaca 3720
agatggattg cacgcaggtt ctccggccgc ttgggtggag aggctattcg gctatgactg 3780
ggcacaacag acaatcggct gctctgatgc cgccgtgttc cggctgtcag cgcaggggcg 3840
cccggttctt tttgtcaaga ccgacctgtc cggtgccctg aatgaactgc aggacgaggc 3900
agcgcggcta tcgtggctgg ccacgacggg cgttccttgc gcagctgtgc tcgacgttgt 3960
cactgaagcg ggaagggact ggctgctatt gggcgaagtg ccggggcagg atctcctgtc 4020
atctcacctt gctcctgccg agaaagtatc catcatggct gatgcaatgc ggcggctgca 4080
tacgcttgat ccggctacct gcccattcga ccaccaagcg aaacatcgca tcgagcgagc 4140
acgtactcgg atggaagccg gtcttgtcga tcaggatgat ctggacgaag agcatcaggg 4200
gctcgcgcca gccgaactgt tcgccaggct caaggcgcgc atgcccgacg gcgaggatct 4260
cgtcgtgacc catggcgatg cctgcttgcc gaatatcatg gtggaaaatg gccgcttttc 4320
tggattcatc gactgtggcc ggctgggtgt ggcggaccgc tatcaggaca tagcgttggc 4380
tacccgtgat attgctgaag agcttggcgg cgaatgggct gaccgcttcc tcgtgcttta 4440
cggtatcgcc gctcccgatt cgcagcgcat cgccttctat cgccttcttg acgagttctt 4500
ctgagcggga ctctggggtt cgaaatgacc gaccaagcga cgcccaacct gccatcacga 4560
gatttcgatt ccaccgccgc cttctatgaa aggttgggct tcggaatcgt tttccgggac 4620
gccggctgga tgatcctcca gcgcggggat ctcatgctgg agttcttcgc ccaccgggga 4680
tcctctagtt ctagactgct ttagattaac ttttgtcatg tggcaatttt tagaagctaa 4740
catgttctta gaatttagat gatcacaaaa aatgtaacat ctattcgaaa aaataagaaa 4800
tttgtttttg tatccaaaaa agcttgataa aacgaattca tcaagccata aaaagaaggc 4860
ctagaataat atttaatatc taagcctttg aaaaatagat tatcgaacta aatacctaaa 4920
cagtattagt cgtcaccaat agtgaattcg atgacttctt cttcaccatc gaaggggttg 4980
atttcgttaa cttcgataaa tacagaagta tcgtcattac ctagggcata accagaggtc 5040
agtacgacat cgggaccgaa aggaacctga agggcagcag caccagttgc agcagcagca 5100
tagccatcac caaaggcaac ggagccagaa aagccagtga tgtcagccgt tagcagtggt 5160
gtcgatgtct acgaaggaga cggaagcagc gaattcagcc tttgcggaag aggcaaagcc 5220
taaagagaga gcggcagcac cagcagcaac agcagcgatt tttgcaaagt tcatttttgt 5280
ttctccaata atcaaaattt tgaatgtgta attggatgga gattatactt agaatatata 5340
accccttact ttagtaaata taccccactt ctcaaaagaa acgatcattc tttataagaa 5400
attcacgttt aattgttgtg agcaattaat attttgtttg ttaagaatca gtcaaattaa 5460
caactacatt gaaagccttt ttttttcaag tatcccaggg aacaatcttt acgtaagtat 5520
aactttgaca gcaagggcag ttagttttcg tgtactgctt atgggtttgg gttgttaatt 5580
agattgtttt tggccaaaaa taaagattga agtttccata acaccttgca tttgtgagag 5640
ttactaaatt tttatatagt catttattca aaatttggcg atcgcctttt ttccttttcc 5700
tctcctcctg cctgctggtg atcagcctta gccttggatt gcagcaacca gcgggggcaa 5760
tttttggcct acccttaccg gaagcagatc taggggaggt gttgccgaac aatggtcagg 5820
agctaatcgt cgatcggtgt gtgtatttgg atggccactg tatttttaag gtggcggccg 5880
catcatcaat ccccgtgatg tttcagtccc gtagtcggga tttagtggtt ggaaagcgga 5940
acgtcgcgcc gaaaccatcg ccaggacggg tttcagtccc gtagtcggga tttagtggtt 6000
ggaaagtgat tatgttcaag aaatcacaac gcaaaagaaa aagtttcagt cccgtagtcg 6060
ggatttagtg gttggaaagt caagcgagat acccaccaga aagcctttga cctggtttca 6120
gtcccgagtc gggatttagt ggttggaaag gcggcggctg atgtcgccaa tgcggttatc 6180
gatggccagt ttcagtcccg tagtcgggat ttagtggttg gaaagtccca agggggacag 6240
ggcggtgatc ctcgatgttg cgtgtttcag tcccgtagtc gggatttagt ggttggaaag 6300
actcgtctat atatacagag attactacag agatgtttca gtcccgtagt cgggatttag 6360
tggttggaaa gcgggaaagt agcctgtttt gtggagaatt gcaggcgttt cagtactagt 6420
gatggcggcc gggagcatgc gacgtcgggc ccaattcgcc ctatagtgag tcgtattaca 6480
attcactggc cgtcgtttta caacgtcgtg actgggaaaa ccctggcgtt acccaactta 6540
atcgccttgc agcacatccc cctttcgcca gctggcgtaa tagcgaagag gcccgcaccg 6600
atcgcccttc ccaacagttg cgcagcctga atggcgaatg gacgcgccct gtagcggcgc 6660
attaagcgcg gcgggtgtgg tggttacgcg cagcgtgacc gctacacttg ccagcgccct 6720
agcgcccgct cctttcgctt tcttcccttc ctttctcgcc acgttcgccg gctttccccg 6780
tcaagctcta aatcgggggc tccctttagg gttccgattt agagctttac ggcacctcga 6840
ccgcaaaaaa cttgatttgg gtgatggttc acgtagtggg ccatcgccct gatagacggt 6900
ttttcgccct ttgacgttgg agtccacgtt ctttaatagt ggactcttgt tccaaactgg 6960
aacaacactc aaccctatct cggtctattc ttttgattta taagggattt tgccgatttc 7020
ggcctattgg ttaaaaaatg agctgattta acaaatattt aacgcgaatt ttaacaaaat 7080
attaacgttt acaatttcgc ctgatgcggt attttctcct tacgcatctg tgcggtattt 7140
cacaccgcat acaggtggca cttttcgggg aaatgtgcgc ggaaccccta tttgtttatt 7200
tttctaaata cattcaaata tgtatccgct catgagacaa taaccctgat aaatgcttca 7260
ataatattga aaaaggaaga gtatgagtat tcaacatttc cgtgtcgccc ttattccctt 7320
ttttgcggca ttttgccttc ctgtttttgc tcacccagaa acgctggtga aagtaaaaga 7380
tgctgaagat cagttgggtg cacgagtggg ttacatcgaa ctggatctca acagcggtaa 7440
gatccttgag agttttcgcc ccgaagaacg ttttccaatg atgagcactt ttaaagttct 7500
gctatgtggc gcggtattat cccgtattga cgccgggcaa gagcaactcg gtcgccgcat 7560
acactattct cagaatgact tggttgagta ctcaccagtc acagaaaagc atcttacgga 7620
tggcatgaca gtaagagaat tatgcagtgc tgccataacc atgagtgata acactgcggc 7680
caacttactt ctgacaacga tcggaggacc gaaggagcta accgcttttt tgcacaacat 7740
gggggatcat gtaactcgcc ttgatcgttg ggaaccggag ctgaatgaag ccataccaaa 7800
cgacgagcgt gacaccacga tgcctgtagc aatgccaaca acgttgcgca aactattaac 7860
tggcgaacta cttactctag cttcccggca acaattaata gactggatgg aggcggataa 7920
agttgcagga ccacttctgc gctcggccct tccggctggc tggtttattg ctgataaatc 7980
tggagccggt gagcgtgggt ctcgcggtat cattgcagca ctggggccag atggtaagcc 8040
ctcccgtatc gtagttatct acacgacggg gagtcaggca actatggatg aacgaaatag 8100
acagatcgct gagataggtg cctcactgat taagcattgg taactgtcag accaagttta 8160
ctcatatata ctttagattg atttaaaact tcatttttaa tttaaaagga tctaggtgaa 8220
gatccttttt gataatctca tgaccaaaat cccttaacgt gagttttcgt tccactgagc 8280
gtcagacccc gtagaaaaga tcaaaggatc ttcttgagat cctttttttc tgcgcgtaat 8340
ctgctgcttg caaacaaaaa aaccaccgct accagcggtg gtttgtttgc cggatcaaga 8400
gctaccaact ctttttccga aggtaactgg cttcagcaga gcgcagatac caaatactgt 8460
ccttctagtg tagccgtagt taggccacca cttcaagaac tctgtagcac cgcctacata 8520
cctcgctctg ctaatcctgt taccagtggc tgctgccagt ggcgataagt cgtgtcttac 8580
cgggttggac tcaagacgat agttaccgga taaggcgcag cggtcgggct gaacgggggg 8640
ttcgtgcaca cagcccagct tggagcgaac gacctacacc gaactgagat acctacagcg 8700
tgagctatga gaaagcgcca cgcttcccga agggagaaag gcggacaggt atccggtaag 8760
cggcagggtc ggaacaggag agcgcacgag ggagcttcca gggggaaacg cctggtatct 8820
ttatagtcct gtcgggtttc gccacctctg acttgagcgt cgatttttgt gatgctcgtc 8880
aggggggcgg agcctatgga aaaacgccag caacgcggcc tttttacggt tcctggcctt 8940
ttgctggcct tttgctcaca tgttctttcc tgcgttatcc cctgattctg tggataaccg 9000
tattaccgcc tttgagtgag ctgataccgc tcgccgcagc cgaacgaccg agcgcagcga 9060
gtcagtgagc gaggaagcgg aagagcgccc aatacgcaaa ccgcctctcc ccgcgcgttg 9120
gccgattcat taatgcagct ggcacgacag gtttcccgac tggaaagcgg gcagtgagcg 9180
caacgcaatt aatgtgagtt agctcactca ttaggcaccc caggctttac actttatgct 9240
tccggctcgt atgttgtgtg gaattgtgag cggataacaa tttcacacag gaaacagcta 9300
tgaccatgat tacgccaagc tatttaggtg acactataga atactcaagc tatgcatctc 9360
tgcgccgcgt ttagtagatt ctgtgtttga ggaagccggt tcagctgatc ttgacgaaga 9420
agatatcaat gttgatattt ttggtctctt tttggatgaa tttggggagg tcgaggatat 9480
tgttgatttc gatttcagtg acattcccga tgcttatact caggtaggtc tcgatctttt 9540
tgagagagat gcgatcgccc ccaatactgt tgtatttcgg gaaagaacaa actatgtacc 9600
ccacgtaagt tttaccggaa ctaaagttga tgcccgtaat caaaaacgtt attatactgg 9660
tctactttgg gattataccg aaggagagtc agggcaaaag tttcgttctt acttgggagc 9720
tgactaccag tatcgcaatc cagagaaagg tgtacgggcc ttcactggtg taattggtta 9780
cattaatcct gatcgagact actacagtca agtttggggt gaaattgcta aaacattcag 9840
ttctgctgat aaaaatactg ctttcacact aggcacctca atggtctatg ctatcgacca 9900
agcggatgat gtgggtgacg atgtttttgt tgatgcagat gccagtaagt tcttattgag 9960
tgcgggggct cgctttggtt ccatcagact aggtgttgat cataacattg actttttccc 10020
taattctgat gatgcgagta ctgttttatc cgctggcatt gacttcggtg agaatgttac 10080
ttttgctggt ttttacacac cttatgatga gggatcaaat gttgccttgg taggggccaa 10140
ccttggtttc cgctttggta ctgattacaa tagcccaaga ttatctttgg gttggagtca 10200
aaatgagtat cgatttgaca ccaataactt cattgacaat cgctacacgt tgaccttccg 10260
cgtgggtcgt cctggcaatc cgtttggccc tcagtaaaaa ccaatttaat ttctctattt 10320
atagaaaaaa agatggtgaa gattgtctca ccatcttttt ttgattacgt gaacagataa 10380
caatttacac ataaaaaaag ctttgccaat aaaaaaatat tgttaaaagc ttattttttt 10440
gccttttaat gaaaatcaat aaaccataga tacaaagact taaacatagc aacagcaata 10500
ttactcagaa aaaatacact tctaaaaatc cgcgactttt taatcagcag tag 10553

<210> SEQ ID NO 82
<211> LENGTH: 11044
<212> TYPE: DNA
<213> ORGANISM: Artificial
<220> FEATURE:
<223> OTHER INFORMATION: Synthetic vector construct #1564
pGEM-gpA::corR-PcorT-zmPDC_dsrA-Prbc*synADH_oop for chromosomal -continued integration between gene loci A0124 and A0125 of Synechococcus sp. PCC7002

<400> SEQUENCE: 82

```
tcgaccatgc gtccaaaact ttcaccatcc tttccctatc aacctttact gcactaaaga     60
caagtgagat agcagtggca atctggcttt gcaatcaatg tttccactaa agcgtttagc    120
gttactgcgg ctagaagtcc tccaccgagg ctcccctgaa tggtgatatg gggaatggga    180
ctggtcatca gtcgtcgttt tgcccccgga gcatgactaa aaccgatcgg cattccgatc    240
acaagagccg gctgaatatg ttgttgctct atcagcttac aggcagtgag taaaacagaa    300
ggggcatagc cgatcgccag cacacatcct tggggaatct gttgtaaccg ctgttgccaa    360
tggtcatggt gccaaaaagc ttgctcggct tccctaagcc ctgtgatgtg agggtcgtca    420
atcagcgttt taaccgtaca tcctaaatga gctaaccgag tttgatcaag agccgcagcc    480
acaaccggaa catcggtgac gactggacac cctgctttca gtgcatctcg tgccgaggcg    540
atcgctccct gactcaatcg aacggcgttt accaagctaa catcaccaca ggccagcact    600
aattgatgta gtaagtgaat ggtaatttca gagtaagccg ataaatccgg tagcaggtgt    660
ttgagggatt cctgaaaggc ttctggatga gttgttgtct ccgcatctag gttcgtccac    720
aactgatcga gttttcctaa cccctcctgg acatccacat caagctgttt cagttgggcc    780
agagcttccg cttgggtaat ctggcaactc tggtcgcgtc ccagtaatcc ttctaaagca    840
gatgcggttt ggcggagtcg agtaatctgc tgaatcacag cctgatattg ctgttgcaac    900
tgcaccatta gggtgggatc aaggctctct tcagaatggc tatccagcag ttgccgaata    960
tgagacaact gaaagccctg ctgtttgagg gcaatgactc gttggagccg ttgtacgtcc   1020
tgctgagtat aaaggcggta gttgccctct gagcgttgaa cggggggaag caatcccagg   1080
gtgtggtaat ggcgcaccat gcgaggcgta acgccacctc ccactgcatc tgtgagttct   1140
ttaatcgtta agtgattagt cttcatccct ttagtttact caaaaccttg acattgacac   1200
taatgttaag gtttaggctg agaaggtaaa aatccaagtt aaaaagcatg aattcttata   1260
ctgtcggtac ctatttagcg gagcggcttg tccagattgg tctcaagcat cacttcgcag   1320
tcgcgggcga ctacaacctc gtccttcttg acaacctgct tttgaacaaa aacatggagc   1380
aggtttattg ctgtaacgaa ctgaactgcg gtttcagtgc agaaggttat gctcgtgcca   1440
aaggcgcagc agcagccgtc gttacctaca gcgtcggtgc gctttccgca tttgatgcta   1500
tcggtggcgc ctatgcagaa aaccttccgg ttatcctgat ctccggtgct ccgaacaaca   1560
atgatcacgc tgctggtcac gtgttgcatc acgctcttgg caaaaccgac tatcactatc   1620
agttggaaat ggccaagaac atcacggccg cagctgaagc gatttacacc ccagaagaag   1680
ctccggctaa aatcgatcac gtgattaaaa ctgctcttcg tgagaagaag ccggtttatc   1740
tcgaaatcgc ttgcaacatt gcttccatgc cctgcgccgc tcctggaccg gcaagcgcat   1800
tgttcaatga cgaagccagc gacgaagctt ctttgaatgc agcggttgaa gaaaccctga   1860
aattcatcgc caaccgcgac aaagttgccg tcctcgtcgg cagcaagctg cgcgcagctg   1920
gtgctgaaga agctgctgtc aaatttgctg atgctctcgg tggcgcagtt gctaccatgg   1980
ctgctgcaaa aagcttcttc ccagaagaaa acccgcatta catcggtacc tcatggggtg   2040
aagtcagcta tccgggcgtt gaaaagacga tgaaagaagc cgatgcggtt atcgctctgg   2100
ctcctgtctt caacgactac tccaccactg gttggacgga tattcctgat cctaagaaac   2160
tggttctcgc tgaaccgcgt tctgtcgtcg ttaacggcgt tcgcttcccc agcgttcatc   2220
```

-continued

```
tgaaagacta tctgacccgt ttggctcaga aagtttccaa gaaaaccggt gctttggact   2280
tcttcaaatc cctcaatgca ggtgaactga agaaagccgc tccggctgat ccgagtgctc   2340
cgttggtcaa cgcagaaatc gcccgtcagg tcgaagctct tctgaccccg aacacgacgg   2400
ttattgctga aaccggtgac tcttggttca atgctcagcg catgaagctc ccgaacggtg   2460
ctcgcgttga atatgaaatg cagtggggtc acatcggttg gtccgttcct gccgccttcg   2520
gttatgccgt cggtgctccg gaacgtcgca acatcctcat ggttggtgat ggttccttcc   2580
agctgacggc tcaggaagtc gctcagatgg ttcgcctgaa actgccggtt atcatcttct   2640
tgatcaataa ctatggttac accatcgaag ttatgatcca tgatggtccg tacaacaaca   2700
tcaagaactg ggattatgcc ggtctgatgg aagtgttcaa cggtaacggt ggttatgaca   2760
gcggtgctgg taaaggcctg aaggctaaaa ccggtggcga actggcagaa gctatcaagg   2820
ttgctctggc aaacaccgac ggcccaaccc tgatcgaatg cttcatcggt cgtgaagact   2880
gcactgaaga attggtcaaa tggggtaagc gcgttgctgc cgccaacagc cgtaagcctg   2940
ttaacaagct cctctagttt caagtttcat cccgaccccc tcagggtcgg gatttttta    3000
ttgagctcac tagtcgatcg acattgccat aagtaaaggc atcccctgcg tgataagatt   3060
accttcagtt tatggaggac tgaccatatg attaaagcct acgctgccct ggaagccaac   3120
ggaaaactcc aaccctttga atacgacccc ggtgccctgg gtgctaatga ggtggagatt   3180
gaggtgcagt attgtggggt gtgccacagt gatttgtcca tgattaataa cgaatggggc   3240
atttccaatt accccctagt gccgggtcat gaggtggtgg gtactgtggc cgccatgggc   3300
gaaggggtga accatgttga ggtgggggat ttagtggggc tgggttggca ttcgggctac   3360
tgcatgacct gccatagttg tttatctggc taccacaacc tttgtgccac ggcggaatcg   3420
accattgtgg gccactacgg tggctttggc gatcgggttc gggccaaggg agtcagcgtg   3480
gtgaaattac ctaaaggcat tgacctagcc agtgccgggc ccctttttctg tggaggaatt  3540
accgttttca gtcctatggt ggaactgagt ttaaagccca ctgcaaaagt ggcagtgatc   3600
ggcattgggg gcttgggcca tttagcggtg caatttctcc gggcctgggg ctgtgaagtg   3660
actgccttta cctccagtgc caggaagcaa acggaagtgt tggaattggg cgctcaccac   3720
atactagatt ccaccaatcc agaggcgatc gccagtgcgg aaggcaaatt tgactatatt   3780
atctccactg tgaacctgaa gcttgactgg aacttataca tcagcaccct ggcgccccag   3840
ggacatttcc actttgttgg ggtggtgttg gagcctttgg atctaaatct tttttcccctt  3900
ttgatgggac aacgctccgt ttctgcctcc ccagtgggta gtcccgccac cattgccacc   3960
atgttggact ttgctgtgcg ccatgacatt aaacccgtgg tggaacaatt tagctttgat   4020
cagatcaacg aggcgatcgc ccatctagaa agcggcaaag cccattatcg ggtagtgctc   4080
agccatagta aaaattagct ctgcaaaggt tgcttctggg tccgtggaac gctcggttgc   4140
cgccgggcgt tttttattcc tgcagccttg ctctagaaga acagcaaggc cgccaatgcc   4200
tgacgatgcg tggagaccga aaccttgcgc tcgttcgcca gccaggacag aaatgcctcg   4260
acttcgctgc tgcccaaggt tgccgggtga cgcacaccgt ggaaacggat gaaggcacga   4320
acccagtgga cataagcctg ttcggttcgt aagctgtaat gcaagtagcg tatgcgctca   4380
cgcaactggt ccagaacctt gaccgaacgc agcggtggta acggcgcagt ggcggttttc   4440
atggcttgtt atgactgttt ttttggggta cagtctatgc ctcgggcatc caagcagcaa   4500
gcgcgttacg ccgtgggtcg atgtttgatg ttatggagca gcaacgatgt tacgcagcag   4560
ggcagtcgcc ctaaaacaaa gttaaacatc atgagggaag cggtgatcgc cgaagtatcg   4620
```

actcaactat cagaggtagt tggcgtcatc gagcgccatc tcgaaccgac gttgctggcc 4680
gtacatttgt acggctccgc agtggatggc ggcctgaagc cacacagtga tattgatttg 4740
ctggttacgg tgaccgtaag gcttgatgaa acaacgcggc gagctttgat caacgacctt 4800
ttggaaactt cggcttcccc tggagagagc gagattctcc gcgctgtaga agtcaccatt 4860
gttgtgcacg acgacatcat tccgtggcgt tatccagcta agcgcgaact gcaatttgga 4920
gaatggcagc gcaatgacat tcttgcaggt atcttcgagc cagccacgat cgacattgat 4980
ctggctatct tgctgacaaa agcaagagaa catagcgttg ccttggtagg tccagcggcg 5040
gaggaactct ttgatccggt tcctgaacag gatctatttg aggcgctaaa tgaaacctta 5100
acgctatgga actcgccgcc cgactgggct ggcgatgagc gaaatgtagt gcttacgttg 5160
tcccgcattt ggtacagcgc agtaaccggc aaaatcgcgc cgaaggatgt cgctgccgac 5220
tgggcaatgg agcgcctgcc ggcccagtat cagcccgtca tacttgaagc tagacaggct 5280
tatcttggac aagaagaaga tcgcttggcc tcgcgcgcag atcagttgga agaatttgtc 5340
cactacgtga aaggcgagat caccaaggta gtcggcaaat aatgtctaac aattcgttca 5400
agccgacgcc gcttcgcggc gcggcttaac tcaagcgtta gatgcactac cggtatcttt 5460
ctagaagatc ctctagttct agagcggccg caggagcgat ctgagtcact ccctttattt 5520
ctctaattat tttggcgatt tgttggtcag cctaaattca ttaccgcaac acaggatttt 5580
tcatggattc ttccatcgcc atttgaggaa gtccttggga tttcgtgtag tgggtcgagt 5640
acagcagcgc accgatgaag ataccaccac caataatgtt cccaatcgtc acaggtagga 5700
aatcccagaa gaccatatcc ataccagaga tcggcgcacc gagaaccata ccagtcaaga 5760
taaagaacat attgaccacg atgtgctcca ggccgagggt gacgaacgcg aagatcggga 5820
accagcagcc cataaattta cctgggacgg acttactcac catgcccatc atcacagcca 5880
aacaaactag gaagttacag aaaataccac ggacaatgaa gagaaagaag ccattggtgc 5940
ccatttcttt cactgccacg gtcttggaga gggcgatttc gataattttt tcacccacgg 6000
ggctggggtc agccgtccca ccattggtaa gggagaaccc catcaacagg gccacaaaca 6060
aacaacctaa aaaattaccc agataaaccc aaagccaatt attaataact ctgccaaacc 6120
tcactcgtct cgccaacatt gccgatgtca tcagcgcaaa gttgccagtt accagttcca 6180
tcccaaagag cacgatggag gcaaatcccc aagggaagag aagtgctccg aggaatggca 6240
gaccactttg tacggcgacg gtaacagcga gggtggtggc aacgccaagg gccagaccag 6300
agtagaagcc acggatgagc agatctttga cggaaagacg tgcttttgtt tcgcctgctt 6360
tgatactggc atctactagt tctttgggga ttacgtagtc cattattttc tcctaattta 6420
aaaccgatgg ggaaacaaaa gggtcattgg tttttctaaa gtcaatgcgc tttgagatta 6480
acttttaaac cacagataaa ttgttcatga agaacttaat ttcacttttc cggaatttaa 6540
tttcaaaagt ttagctctgg atttttgttc tgctgtgata ttcagccatg aacgtccctt 6600
gatctaggtc aaagccaagt aatacaatgc ttttgaggaa ttcacccaaa gaaagatact 6660
tttaaataaa atcagtctcc agtcacaatt aaagctccat ttctgacca actgcaaaaa 6720
atatagagga ttcaaattgt ttagaagaaa gtaatcttca gttggttttg ctaagaaaat 6780
aataatcctt ggcaaagtag agaacgagct gcatgcgacg tcgggcccaa ttcgccctat 6840
agtgagtcgt attacaattc actggccgtc gttttacaac gtcgtgactg ggaaaaccct 6900
ggcgttaccc aacttaatcg ccttgcagca catcccccctt tcgccagctg gcgtaatagc 6960
gaagaggccc gcaccgatcg cccttcccaa cagttgcgca gcctgaatgg cgaatggacg 7020
cgccctgtag cggcgcatta agcgcggcgg gtgtggtggt tacgcgcagc gtgaccgcta 7080
cacttgccag cgccctagcg cccgctcctt tcgctttctt cccttccttt ctcgccacgt 7140
tcgccggctt tccccgtcaa gctctaaatc gggggctccc tttagggttc cgatttagag 7200
ctttacggca cctcgaccgc aaaaaacttg atttgggtga tggttcacgt agtgggccat 7260
cgccctgata gacggttttt cgccctttga cgttggagtc cacgttcttt aatagtggac 7320
tcttgttcca aactggaaca acactcaacc ctatctcggt ctattctttt gatttataag 7380
ggattttgcc gatttcggcc tattggttaa aaaatgagct gatttaacaa atatttaacg 7440
cgaattttaa caaaatatta acgtttacaa tttcgcctga tgcggtattt tctccttacg 7500
catctgtgcg gtatttcaca ccgcatacag gtggcacttt tcggggaaat gtgcgcggaa 7560
cccctatttg tttatttttc taaatacatt caaatatgta tccgctcatg agacaataac 7620
cctgataaat gcttcaataa tattgaaaaa ggaagagtat gagtattcaa catttccgtg 7680
tcgcccttat tccctttttt gcggcatttt gccttcctgt ttttgctcac ccagaaacgc 7740
tggtgaaagt aaaagatgct gaagatcagt tgggtgcacg agtgggttac atcgaactgg 7800
atctcaacag cggtaagatc cttgagagtt ttcgccccga agaacgtttt ccaatgatga 7860
gcacttttaa agttctgcta tgtggcgcgg tattatcccg tattgacgcc gggcaagagc 7920
aactcggtcg ccgcatacac tattctcaga atgacttggt tgagtactca ccagtcacag 7980
aaaagcatct tacggatggc atgacagtaa gagaattatg cagtgctgcc ataaccatga 8040
gtgataacac tgcggccaac ttacttctga caacgatcgg aggaccgaag gagctaaccg 8100
cttttttgca caacatgggg gatcatgtaa ctcgccttga tcgttgggaa ccggagctga 8160
atgaagccat accaaacgac gagcgtgaca ccacgatgcc tgtagcaatg ccaacaacgt 8220
tgcgcaaact attaactggc gaactactta ctctagcttc ccggcaacaa ttaatagact 8280
ggatggaggc ggataaagtt gcaggaccac ttctgcgctc ggcccttccg gctggctggt 8340
ttattgctga taaatctgga gccggtgagc gtgggtctcg cggtatcatt gcagcactgg 8400
ggccagatgg taagccctcc cgtatcgtag ttatctacac gacggggagt caggcaacta 8460
tggatgaacg aaatagacag atcgctgaga taggtgcctc actgattaag cattggtaac 8520
tgtcagacca agtttactca tatatacttt agattgattt aaaacttcat ttttaattta 8580
aaaggatcta ggtgaagatc ctttttgata atctcatgac caaaatccct taacgtgagt 8640
tttcgttcca ctgagcgtca gaccccgtag aaaagatcaa aggatcttct tgagatcctt 8700
tttttctgcg cgtaatctgc tgcttgcaaa caaaaaaacc accgctacca gcggtggttt 8760
gtttgccgga tcaagagcta ccaactcttt ttccgaaggt aactggcttc agcagagcgc 8820
agataccaaa tactgtcctt ctagtgtagc cgtagttagg ccaccacttc aagaactctg 8880
tagcaccgcc tacatacctc gctctgctaa tcctgttacc agtggctgct gccagtggcg 8940
ataagtcgtg tcttaccggg ttggactcaa gacgatagtt accggataag gcgcagcggt 9000
cgggctgaac ggggggttcg tgcacacagc ccagcttgga gcgaacgacc tacaccgaac 9060
tgagatacct acagcgtgag ctatgagaaa gcgccacgct tcccgaaggg agaaaggcgg 9120
acaggtatcc ggtaagcggc agggtcggaa caggagagcg cacgagggag cttccagggg 9180
gaaacgcctg gtatctttat agtcctgtcg ggtttcgcca cctctgactt gagcgtcgat 9240
ttttgtgatg ctcgtcaggg gggcggagcc tatggaaaaa cgccagcaac gcggcctttt 9300
tacggttcct ggccttttgc tggccttttg ctcacatgtt ctttcctgcg ttatcccctg 9360
attctgtgga taaccgtatt accgcctttg agtgagctga taccgctcgc cgcagccgaa 9420
cgaccgagcg cagcgagtca gtgagcgagg aagcggaaga gcgcccaata cgcaaaccgc 9480
ctctccccgc gcgttggccg attcattaat gcagctggca cgacaggttt cccgactgga 9540
aagcgggcag tgagcgcaac gcaattaatg tgagttagct cactcattag gcaccccagg 9600
ctttacactt tatgcttccg gctcgtatgt tgtgtggaat tgtgagcgga taacaatttc 9660
acacaggaaa cagctatgac catgattacg ccaagctatt taggtgacac tatagaatac 9720
tcaagctatg catgcacaga cgatacactg aagggcatct ttgtctggga cactaggctc 9780
tatgtcttct gaaaaaatgt cgccatcgtc acccccctat gatctaatcg tggtgggggc 9840
cactggtttt gtgggccaaa ttatttgccg ctatctttgt gaccatgccg aacgtgaatt 9900
gtttacttgg gcgatcgccg gccgttcagc cgaaaaatta gcccaactca agcactcttt 9960
gggcatccca ggggagacct tagcaacctt tgtcgttgat gtgtttgatc aaggggcagt 10020
gacggccctc tgcgagcaaa cgaaggtgat cctcacaacg gtcggcccct acagtcttta 10080
tggagaaacc ttgctccggg cctgtgccac aacgggaacc gattattgcg atctgaccgg 10140
ggaagtccag tgggtcaaaa agatggtgac taaatatgag gcgatcgccc aacagtcggg 10200
ggcacggatc gtccattgtt gcggctttga ttcggtgccg tctgaccttg ggtgtgtattt 10260 tttgcaacag cgggctttaa aacgattcgg aaaaccctgt cgccaaatta agatgcgcgt 10320
taagacagcc cagggaggca tttccggggg gacggcggcc agcggcgtaa atctgatcaa 10380
agaggcgatc gccgactcag agatcaaaac actattggct aatccctatg ccctctgtcc 10440
caaagctccc aatccccagc acccagctcc cctaatcccg gtacaaatcg accacatttt 10500
tggcgaatgg gtgacaccct ttatcatggc agcggtgaat acgcctattg tgctgcgctc 10560
caatgcccta caaaactggg cctatggtga gcagttccag tacgacgaag ggctgcttac 10620
gggggtcagt gttgggggtt ggttgaaagc ccagggtcta agcctattac ttaaaatcct 10680
gggaggaact gcggcgatcg accctagtct cctcgaaaaa attgtcccgg cccccggcga 10740
agggccttcc cccagccaac agcaagccgg tttttatgat ctacgctttt ggggcattac 10800
tacttcgggt gaagttctta tggcaaaagt cactggcgat cgcgaccctg gctatggttc 10860
caccgcaaaa attatcgccc aagcaggact ctgtttagcc aaagataatc tatcccgatc 10920
cggtggcttc tggacgccag ccacagccat gggtgaacat cttatcgatc gcctcaccgc 10980
ttacagtggc ttaaccttca gcatcctttg agttgatctt ggtccctcac aattcaaaac 11040
atag 11044

<210> SEQ ID NO 83
<211> LENGTH: 10269
<212> TYPE: DNA
<213> ORGANISM: Artificial
<220> FEATURE:
<223> OTHER INFORMATION: Synthetic vector construct #1633
pGEM-gpB::corR-PcorT*1-zmPDCdeg_spf-Prbc*-synADH_oop for
chromosomal integration into Synechococcus sp. PCC7002 between
gene loci A1330 and A1331

<400> SEQUENCE: 83
tcgaccatgc gtccaaaact ttcaccatcc tttccctatc aacctttact gcactaaaga 60
caagtgagat agcagtggca atctggcttt gcaatcaatg tttccactaa agcgtttagc 120
gttactgcgg ctagaagtcc tccaccgagg ctcccctgaa tggtgatatg gggaatggga 180
ctggtcatca gtcgtcgttt tgcccccgga gcatgactaa aaccgatcgg cattccgatc 240

```
acaagagccg gctgaatatg ttgttgctct atcagcttac aggcagtgag taaaacagaa    300
ggggcatagc cgatcgccag cacacatcct tggggaatct gttgtaaccg ctgttgccaa    360
tggtcatggt gccaaaaagc ttgctcggct tccctaagcc ctgtgatgtg agggtcgtca    420
atcagcgttt taaccgtaca tcctaaatga gctaaccgag tttgatcaag agccgcagcc    480
acaaccggaa catcggtgac gactggacac cctgctttca gtgcatctcg tgccgaggcg    540
atcgctccct gactcaatcg aacggcgttt accaagctaa catcaccaca ggccagcact    600
aattgatgta gtaagtgaat ggtaatttca gagtaagccg ataaatccgg tagcaggtgt    660
ttgagggatt cctgaaaggc ttctggatga gttgttgtct ccgcatctag gttcgtccac    720
aactgatcga gttttcctaa cccctcctgg acatccacat caagctgttt cagttgggcc    780
agagcttccg cttgggtaat ctggcaactc tggtcgcgtc ccagtaatcc ttctaaagca    840
gatgcggttt ggcggagtcg agtaatctgc tgaatcacag cctgatattg ctgttgcaac    900
tgcaccatta gggtgggatc aaggctctct tcagaatggc tatccagcag ttgccgaata    960
tgagacaact gaaagccctg ctgtttgagg gcaatgactc gttggagccg ttgtacgtcc   1020
tgctgagtat aaaggcggta gttgccctct gagcgttgaa cggggggaag caatcccagg   1080
gtgtggtaat ggcgcaccat gcgaggcgta acgccacctc ccactgcatc tgtgagttct   1140
ttaatcgtta agtgattagt cttcatgact ttagtttact caaaaccttg acattgacac   1200
taatgttaag gtttaggctg agaaggtaaa aatcgaggat aaaaagcatg aattcctaca   1260
ccgttggcac ttacctggct gaacgcttgg ttcagatcgg cttaaaacac cattttgctg   1320
ttgctggtga ttataatttg gttttgttag ataatttatt gctcaataag aatatggaac   1380
aggtgtactg ttgcaatgag ttaaattgtg gcttttccgc tgagggctac gcccgtgcta   1440
agggtgctgc tgctgctgtt gtgacttatt ctgttggcgc tttgagtgct tttgacgcca   1500
ttggcggtgc ttacgctgag aatttgccag tgattttaat tagtggcgcc ccaaataata   1560
acgaccatgc cgccggccat gtcctccacc atgccttggg taagactgat taccattacc   1620
aactggagat ggctaaaaat attaccgctg ctgccgaagc tatctatact cctgaggaag   1680
ccccagccaa gattgaccat gtcatcaaga ccgccttgcg ggaaaaaaaa ccagtgtact   1740
tagagattgc ctgtaatatc gccagtatgc cttgtgctgc cccccggtcca gcttctgctc   1800
tctttaacga tgaagcttct gatgaggcca gtctcaacgc tgctgtggag gaaactttaa   1860
agtttattgc taatcgtgat aaggtggctg ttttagttgg ttctaaatta cgtgctgccg   1920
gcgccgagga agccgccgtt aagtttgccg acgccttagg cggtgctgtg gccactatgg   1980
ccgccgctaa gtcttttttt cctgaagaga atccacacta tattggcact agctggggcg   2040
aggtttctta cccaggtgtg gagaaaacca tgaaggaggc tgacgctgtg attgccttag   2100
ccccggtttt taatgattat agtactaccg gctggaccga catcccggac ccgaaaaagt   2160
tagtgttagc cgaaccacgg agtgttgttg tgaatggtgt gcgttttcct tctgtgcact   2220
taaaggatta cttaactcgg ctcgcccaga aggtgagtaa aaagactggc gccctcgatt   2280
tttttaagag tttaaacgct ggcgagttaa aaaaggctgc cccagccgac ccatccgccc   2340
cactcgttaa tgctgaaatt gctcggcagg ttgaggcctt gttaactcca aataccaccg   2400
tgatcgccga aactggcgat agttggttta acgcccaacg tatgaaatta ccaaatggcg   2460
cccgtgtgga gtacgagatg caatggggcc atattggctg gagtgtgccg gctgcttttg   2520
gctacgctgt tggcgcccca gagcggcgta atattttaat ggtgggcgac ggcagttttc   2580
```

agttaaccgc ccaagaggtt gcccaaatgg tgcgtttaaa gttaccagtg attatttttc 2640
tcattaacaa ttacggctat actattgagg tgatgattca cgacggccca tataataata 2700
ttaaaaattg ggactacgct ggcttaatgg aggtctttaa tggcaatggc ggctacgatt 2760
ctggcgccgg caagggttta aaagccaaga ctggcggtga gttagctgaa gccattaaag 2820
tggccttagc taatactgat ggtcctactt taattgagtg ttttattggc cgggaagatt 2880
gtaccgagga actcgttaag tggggcaaac gtgtggccgc tgctaattct cggaaacccg 2940
tgaataaatt attatgaaat attttagccg ccccagtcag taatgactgg ggcgtttttt 3000
attgggagct cactagtcga tcgacattgc cataagtaaa ggcatcccct gcgtgataag 3060
attaccttca gtttatggag gactgaccat atgattaaag cctacgctgc cctggaagcc 3120
aacggaaaac tccaaccctt tgaatacgac cccggtgccc tgggtgctaa tgaggtggag 3180
attgaggtgc agtattgtgg ggtgtgccac agtgatttgt ccatgattaa taacgaatgg 3240
ggcatttcca attacccct agtgccgggt catgaggtgg tgggtactgt ggccgccatg 3300
ggcgaagggg tgaaccatgt tgaggtgggg gatttagtgg ggctgggttg gcattcgggc 3360
tactgcatga cctgccatag ttgtttatct ggctaccaca acctttgtgc cacggcggaa 3420
tcgaccattg tgggccacta cggtggcttt ggcgatcggg ttcgggccaa gggagtcagc 3480
gtggtgaaat tacctaaagg cattgaccta gccagtgccg ggcccctttt ctgtggagga 3540
attaccgttt tcagtcctat ggtggaactg agtttaaagc ccactgcaaa agtggcagtg 3600
atcggcattg gggcttggg ccatttagcg gtgcaatttc tccgggcctg ggctgtgaa 3660
gtgactgcct ttacctccag tgccaggaag caaacggaag tgttggaatt gggcgctcac 3720
cacatactag attccaccaa tccagaggcg atcgccagtg cggaaggcaa atttgactat 3780
attatctcca ctgtgaacct gaagcttgac tggaacttat acatcagcac cctggcgccc 3840
cagggacatt tccactttgt tggggtggtg ttggagcctt tggatctaaa tctttttccc 3900
cttttgatgg gacaacgctc cgtttctgcc tccccagtgg gtagtcccgc caccattgcc 3960
accatgttgg actttgctgt gcgccatgac attaaacccg tggtggaaca atttagcttt 4020
gatcagatca acgaggcgat cgcccatcta gaaagcggca aagcccatta tcgggtagtg 4080
ctcagccata gtaaaaatta gctctgcaaa ggttgcttct gggtccgtgg aacgctcggt 4140
tgccgccggg cgttttttat tcctgcagga tccacaggac gggtgtggtc gccatgatcg 4200
cgtagtcgat agtggctcca agtagcgaag cgagcaggac tgggcggcgg ccaaagcggt 4260
cggacagtgc tccgagaacg ggtgcgcata gaaattgcat caacgcatat agcgctagca 4320
gcacgccata gtgactggcg atgctgtcgg aatggacgat cgaattggcc gcggcgttgt 4380
gacaatttac cgaacaactc cgcggccggg aagccgatct cggcttgaac gaattgttag 4440
gtggcggtac ttgggtcgat atcaaagtgc atcacttctt cccgtatgcc caactttgta 4500
tagagagcca ctgcgggatc gtcaccgtaa tctgcttgca cgtagatcac ataagcacca 4560
agcgcgttgg cctcatgctt gaggagattg atgagcgcgg tggcaatgcc ctgcctccgg 4620
tgctcgccgg agactgcgag atcatagata tagatctcac tacgcggctg ctcaaacttg 4680
ggcagaacgt aagccgcgag agcgccaaca accgcttctt ggtcgaaggc agcaagcgcg 4740
atgaatgtct tactacggag caagttcccg aggtaatcgg agtccggctg atgttgggag 4800
taggtggcta cgtctccgaa ctcacgaccg aaaagatcaa gagcagcccg catggatttg 4860
acttggtcag ggccgagcct acatgtgcga atgatgccca tacttgagcc acctaacttt 4920
gttttagggc gactgccctg ctgcgtaaca tcgttgctgc tgcgtaacat cgttgctgct 4980
ccataacatc aaacatcgac ccacggcgta acgcgcttgc tgcttggatg cccgaggcat 5040
agactgtaca aaaaaacagt cataacaagc catgaaaacc gccactgcgc cgttaccacc 5100
gctgcgttcg gtcaaggttc tggaccagtt gcgtgagcgc atacgctact tgcattacag 5160
tttacgaacc gaacaggctt atgtcaattc gagcatcgat atagaaattt gccctagcaa 5220
atatcctcct gagtgaattg gttttgttaa gctttacagg cttcaatgac gcaaatttcc 5280
tcggcggttc taacaatgcg cgtcagtttt aagtctgccg ccgccaacag ggtttcaaac 5340
tcagcggcgg tgcgttcttt gccaccggga cacatcacca gcatattgat atcgagcatt 5400
tttgcgccac taggttgatt tccctctgga accaccgctt cacagatcaa gattttgccg 5460
tcatccggca gtacagcgcg acaattttgc aaaatggcga tcgcctggtc atcgccccaa 5520
tcgtgaataa tgtgtttgag caaataggca tcgccccccg ccggaattgt tctaaagaaa 5580
ctgccgccaa tccgttgaca gcgatcgccg accccatggc ggtttaacgt cggagcagca 5640
ttatccacca cataatcttc atcgaacaaa ataccttgta attggggata tttcgccaaa 5700
atgctgccga gcaattcccc gtagccccca cccacatcaa cgatggttga aaaagccgaa 5760
aaatcataat gggccaaaat ttccggctct tcattcctgg agaaactgtt catcgcctct 5820
tcaaaaatcg ccgccgcttc tggatgattg ccgaaatatt caaacacccc ctggccatag 5880
cgatggtcaa aggcaggttc accggtttta acgctgtgga gaatattact ccaggcttcg 5940
taatgctctg gttcccccaa catcaccaca gaacctcgca tggagcgggg atgatcactg 6000
cggagaaaat cggctagcgg tgtcagggca aaggtttggg aggctgtttc ttggaaaata 6060
cccacactgg ccaaggcccg gagaatgcga tacaaagccg tttcgtctgt ttcggtgaga 6120
tgggctaacg cacggcaagg ttgttctccg gctttgaggt gatcggcgat cgccaatttt 6180
gccgccacat aaatgcactg ggaaagccaa taaccagagg ccatttggag caattgggta 6240
tggagaggga gggttggcgg ttccatagcg tgaaaaatcc tgatgcatag cttgagtatt 6300
ctatagtgtc acctaaatag cttggcgtaa tcatggtcat agctgtttcc tgtgtgaaat 6360
tgttatccgc tcacaattcc acacaacata cgagccggaa gcataaagtg taaagcctgg 6420
ggtgcctaat gagtgagcta actcacatta attgcgttgc gctcactgcc cgctttccag 6480
tcgggaaacc tgtcgtgcca gctgcattaa tgaatcggcc aacgcgcggg gagaggcggt 6540
ttgcgtattg ggcgctcttc cgcttcctcg ctcactgact cgctgcgctc ggtcgttcgg 6600
ctgcggcgag cggtatcagc tcactcaaag gcggtaatac ggttatccac agaatcaggg 6660
gataacgcag gaaagaacat gtgagcaaaa ggccagcaaa aggccaggaa ccgtaaaaag 6720
gccgcgttgc tggcgttttt ccataggctc cgcccccctg acgagcatca caaaaatcga 6780
cgctcaagtc agaggtggcg aaacccgaca ggactataaa gataccaggc gtttccccct 6840
ggaagctccc tcgtgcgctc tcctgttccg accctgccgc ttaccggata cctgtccgcc 6900
tttctccctt cgggaagcgt ggcgctttct catagctcac gctgtaggta tctcagttcg 6960
gtgtaggtcg ttcgctccaa gctgggctgt gtgcacgaac cccccgttca gcccgaccgc 7020
tgcgccttat ccggtaacta tcgtcttgag tccaacccgg taagacacga cttatcgcca 7080
ctggcagcag ccactggtaa caggattagc agagcgaggt atgtaggcgg tgctacagag 7140
ttcttgaagt ggtggcctaa ctacggctac actagaagga cagtatttgg tatctgcgct 7200
ctgctgaagc cagttacctt cggaaaaaga gttggtagct cttgatccgg caaacaaacc 7260
accgctggta gcggtggttt ttttgtttgc aagcagcaga ttacgcgcag aaaaaaagga 7320

-continued

```
tctcaagaag atcctttgat cttttctacg gggtctgacg ctcagtggaa cgaaaactca   7380
cgttaaggga ttttggtcat gagattatca aaaaggatct tcacctagat ccttttaaat   7440
taaaaatgaa gttttaaatc aatctaaagt atatatgagt aaacttggtc tgacagttac   7500
caatgcttaa tcagtgaggc acctatctca gcgatctgtc tatttcgttc atccatagtt   7560
gcctgactcc ccgtcgtgta gataactacg atacgggagg gcttaccatc tggccccagt   7620
gctgcaatga taccgcgaga cccacgctca ccggctccag atttatcagc aataaaccag   7680
ccagccggaa gggccgagcg cagaagtggt cctgcaactt tatccgcctc catccagtct   7740
attaattgtt gccgggaagc tagagtaagt agttcgccag ttaatagttt gcgcaacgtt   7800
gttggcattg ctacaggcat cgtggtgtca cgctcgtcgt ttggtatggc ttcattcagc   7860
tccggttccc aacgatcaag gcgagttaca tgatccccca tgttgtgcaa aaaagcggtt   7920
agctccttcg gtcctccgat cgttgtcaga agtaagttgg ccgcagtgtt atcactcatg   7980
gttatggcag cactgcataa ttctcttact gtcatgccat ccgtaagatg cttttctgtg   8040
actggtgagt actcaaccaa gtcattctga gaatagtgta tgcggcgacc gagttgctct   8100
tgcccggcgt caatacggga taataccgcg ccacatagca gaactttaaa agtgctcatc   8160
attggaaaac gttcttcggg gcgaaaactc tcaaggatct taccgctgtt gagatccagt   8220
tcgatgtaac ccactcgtgc acccaactga tcttcagcat cttttacttt caccagcgtt   8280
tctgggtgag caaaaacagg aaggcaaaat gccgcaaaaa agggaataag ggcgacacgg   8340
aaatgttgaa tactcatact cttccttttt caatattatt gaagcattta tcagggttat   8400
tgtctcatga gcggatacat atttgaatgt atttagaaaa ataaacaaat aggggttccg   8460
cgcacatttc cccgaaaagt gccacctgta tgcggtgtga aataccgcac agatgcgtaa   8520
ggagaaaata ccgcatcagg cgaaattgta aacgttaata ttttgttaaa attcgcgtta   8580
aatatttgtt aaatcagctc attttttaac caataggccg aaatcggcaa aatcccttat   8640
aaatcaaaag aatagaccga gatagggttg agtgttgttc cagtttggaa caagagtcca   8700
ctattaaaga acgtggactc caacgtcaaa gggcgaaaaa ccgtctatca gggcgatggc   8760
ccactacgtg aaccatcacc caaatcaagt tttttgcggt cgaggtgccg taaagctcta   8820
aatcggaacc ctaaagggag cccccgattt agagcttgac ggggaaagcc ggcgaacgtg   8880
gcgagaaagg aagggaagaa agcgaaagga gcgggcgcta gggcgctggc aagtgtagcg   8940
gtcacgctgc gcgtaaccac cacacccgcc gcgcttaatg cgccgctaca gggcgcgtcc   9000
attcgccatt caggctgcgc aactgttggg aagggcgatc ggtgcgggcc tcttcgctat   9060
tacgccagct ggcgaaaggg ggatgtgctg caaggcgatt aagttgggta acgccagggt   9120
tttcccagtc acgacgttgt aaaacgacgg ccagtgaatt gtaatacgac tcactatagg   9180
gcgaattggg cccgacgtcg catgctgggg cttgatagaa tagatctcag gatttttacg   9240
cagcacattt aacaattcaa tcatgattaa acggtttttt tatggggcga tcgccattgt   9300
cttggccttt accctgatct ttaccccagc ggataatgct tgggcggccc gcagtggagg   9360
acgcattggt ggcggttcct tccgcagtgc ccctagtcgc agtttttccc ctggcccagc   9420
acgacgggct cccgttgggg gtggctatgg ttacggattt gggggtggat ttgggttccc   9480
cttcctgctg cctttcttcg gattcggtgg ttttagcggc attttcggtc ttttcattat   9540
gttggcgatc gccggcttcc ttgtccgcac cttccagaac gtgatggggg gtggcatgaa   9600
cgagggcgac agtctcggtt actctgcccc cagtagcaaa atttctgtgg cgaaggtaca   9660
ggtggggctg ttggcccaag cacgggatct ccagcaggat ctaaatcgcc tggcgagcac   9720
```

cgctgatact ggcaccccgg ctggacgcgc taaggttctt caagaatcga ctctggccct 9780
gttgcgccac ccagaatatt gggtctatgg tgcgagcgaa tccctcgaag ctggggttga 9840
tgctgccgaa gccaagttta atcaattggc cctgaacgag cggagtaaat ttaccgccga 9900
gacccttagt aacgttgaca acgaacggga tgtggctggg aaaagtggga gtgctgattt 9960
ggtaaaaagc gacgatacac cgaacgaata catcatggtg acaatcatcg ctggggccat 10020
ggggaaagtt gagttaccga aagtgaccga ttcccaatcc ctcgaacaag cgatccgtca 10080
aattggtgcc cttggtggcg atcgcctttt ggccctcgaa gttttatgga cgccccaagc 10140
gattggtgac accctcagca ctgacgatat tttgacctat taccccgaca ttaatctcgt 10200
ataactaggc caaaatctaa aacaattcaa cgcaaatcat ggcgatttaa agaatcccct 10260
caatacagg 10269

<210> SEQ ID NO 84
<211> LENGTH: 11121
<212> TYPE: DNA
<213> ORGANISM: Artificial
<220> FEATURE:
<223> OTHER INFORMATION: Synthetic vector construct #1574
pGEM-gpC::corR-PcorT-zpPDC_ter-Prbc*-synADHdeg_oop for
chromosomal integration into Synechococcus sp. PCC7002 between
gene loci A2578 and A2579

<400> SEQUENCE: 84
tcgaccatgc gtccaaactt tcaccatcct ttccctatca acctttactg cactaaagac 60
aagtgagata gcagtggcaa tctggctttg caatcaatgt ttccactaaa gcgtttagcg 120
ttactgcggc tagaagtcct ccaccgaggc tcccctgaat ggtgatatgg ggaatgggac 180
tggtcatcag tcgtcgtttt gcccccggag catgactaaa accgatcggc attccgatca 240
caagagccgg ctgaatatgt tgttgctcta tcagcttaca ggcagtgagt aaaacagaag 300
gggcatagcc gatcgccagc acacatcctt ggggaatctg ttgtaaccgc tgttgccaat 360
ggtcatggtg ccaaaaagct tgctcggctt ccctaagccc tgtgatgtga gggtcgtcaa 420
tcagcgtttt aaccgtacat cctaaatgag ctaaccgagt ttgatcaaga gccgcagcca 480
caaccggaac atcggtgacg actggacacc ctgctttcag tgcatctcgt gccgaggcga 540
tcgctccctg actcaatcga acggcgttta ccaagctaac atcaccacag gccagcacta 600
attgatgtag taagtgaatg gtaatttcag agtaagccga taaatccggt agcaggtgtt 660
tgagggattc ctgaaaggct tctggatgag ttgttgtctc cgcatctagg ttcgtccaca 720
actgatcgag ttttcctaac ccctcctgga catccacatc aagctgtttc agttgggcca 780
gagcttccgc ttgggtaatc tggcaactct ggtcgcgtcc cagtaatcct tctaaagcag 840
atgcggtttg gcggagtcga gtaatctgct gaatcacagc ctgatattgc tgttgcaact 900
gcaccattag ggtgggatca aggctctctt cagaatggct atccagcagt tgccgaatat 960
gagacaactg aaagccctgc tgtttgaggg caatgactcg ttggagccgt tgtacgtcct 1020
gctgagtata aaggcggtag ttgccctctg agcgttgaac ggggggaagc aatcccaggg 1080
tgtggtaatg gcgcaccatg cgaggcgtaa cgccacctcc cactgcatct gtgagttctt 1140
taatcgttaa gtgattagtc ttcatccctt tagtttactc aaaaccttga cattgacact 1200
aatgttaagg tttaggctga gaaggtaaaa atccaagtta aaaagcatga attcctatac 1260
cgttggtatg tacttggcag aacgcctagc ccagatcggc ctgaaacacc actttgccgt 1320
ggccggtgac tacaacctgg tgttgcttga tcagctcctg ctgaacaaag acatggagca 1380

-continued

```
ggtctactgc tgtaacgaac ttaactgcgg ctttagcgcc gaaggttacg ctcgtgcacg   1440
tggtgccgcc gctgccatcg tcacgttcag cgtaggtgct atctctgcaa tgaacgccat   1500
cggtggcgcc tatgcagaaa acctgccggt catcctgatc tctggctcac cgaacaccaa   1560
tgactacggc acaggccaca tcctgcacca caccattggt actactgact ataactatca   1620
gctggaaatg gtaaaacacg ttacctgcgc agctgaaagc atcgtttctg ccgaagaagc   1680
accggcaaaa atcgaccacg tcatccgtac ggctctacgt gaacgcaaac cggcttatct   1740
ggaaatcgca tgcaacgtcg ctggcgctga atgtgttcgt ccgggcccga tcaatagcct   1800
gctgcgtgaa ctcgaagttg accagaccag tgtcactgcc gctgtagatg ccgccgtaga   1860
atggctgcag gaccgccaga acgtcgtcat gctggtcggt agcaaactgc gtgccgctgc   1920
cgctgaaaaa caggctgttg ccctagcgga ccgcctgggc tgcgctgtca cgatcatggc   1980
tgccgcaaaa ggcttcttcc cggaagatca tccgaacttc cgcggcctgt actggggtga   2040
agtcagctcc gaaggtgcac aggaactggt tgaaaacgcc gatgccatcc tgtgtctggc   2100
accggtattc aacgactatg ctaccgttgg ctggaactcc tggccgaaag gcgacaatgt   2160
catggtcatg gacaccgacc gcgtcacttt cgcaggacag tccttcgaag gtctgtcatt   2220
gagcaccttc gccgcagcac tggctgagaa agcaccttct cgcccggcaa cgactcaagg   2280
cactcaagca ccggtactgg gtattgaggc cgcagagccc aatgcaccgc tgaccaatga   2340
cgaaatgacg cgtcagatcc agtcgctgat cacttccgac actactctga cagcagaaac   2400
aggtgactct tggttcaacg cttctcgcat gccgattcct ggcggtgctc gtgtcgaact   2460
ggaaatgcaa tggggtcata tcggttggtc cgtaccttct gcattcggta acgccgttgg   2520
ttctccggag cgtcgccaca tcatgatggt cggtgatggc tctttccagc tgactgctca   2580
agaagttgct cagatgatcc gctatgaaat cccggtcatc atcttcctga tcaacaaccg   2640
cggttacgtc atcgaaatcg ctatccatga cggcccttac aactacatca aaaactggaa   2700
ctacgctggc ctgatcgacg tcttcaatga cgaagatggt catggcctgg gtctgaaagc   2760
ttctactggt gcagaactag aaggcgctat caagaaagca ctcgacaatc gtcgcggtcc   2820
gacgctgatc gaatgtaaca tcgctcagga cgactgcact gaaaccctga ttgcttgggg   2880
taaacgtgta gcagctacca actctcgcaa accacaagcg taagttgatg tagtgaatta   2940
ggcggggcct attagggccc caccacatag cccctcttac ggcgcaatac ccgtaagagg   3000
ggctgtttta tataattaaa gagctcacta gtcgatcgac attgccataa gtaaaggcat   3060
cccctgcgtg ataagattac cttcagttta tggaggactg accatatgat caaggcttat   3120
gccgctttag aggctaatgg caagttgcag ccgttcgagt atgatccggg cgctttaggc   3180
gccaacgaag ttgaaatcga agttcaatac tgcggtgttt gtcattccga cctcagtatg   3240
atcaacaatg agtggggtat cagtaactat ccgttggttc ccggccacga agttgttggc   3300
accgttgctg ctatgggtga gggtgttaat cacgtggaag ttggtgacct ggttggttta   3360
ggctggcaca gtggttattg tatgacttgt cactcctgcc tgagcggtta tcataatttg   3420
tgcgctaccg ccgagagtac tatcgttggt cattatggcg gtttcggtga ccgtgtgcgt   3480
gctaaaggtg tgtccgttgt taagctgccc aagggtatcg atttggcttc cgctggtccg   3540
ttgttttgcg gtggtatcac tgtgttttcc cccatggttg agttatccct gaaaccgacc   3600
gccaaggttg ccgttattgg tatcggtggt ctcggtcacc tggccgttca gttcttgcgt   3660
gcttggggtt gcgaggttac cgctttcact agctccgctc gtaaacagac cgaggttctg   3720
```

-continued

```
gagctgggtg cccatcatat tttggacagt actaaccccg aagccattgc ttccgccgag   3780
ggtaagttcg attacatcat tagtaccgtt aatttaaaat tggattggaa tctgtatatt   3840
tccactttag ccccgcaagg tcactttcat ttcgtgggtg ttgttctcga acccctcgac   3900
ttgaacttgt tcccgttgct catgggtcag cggagtgtgt ccgctagtcc ggttggctcc   3960
ccggctacta tcgctactat gctcgatttc gccgttcggc acgatatcaa gccggttgtt   4020
gagcagttct ccttcgacca aattaatgaa gccattgctc acttggagtc cggtaaggct   4080
cactaccgtg tggttttgag tcactccaag aactgaaacg ctcggttgcc gccgggcgtt   4140
ttttattcct gcaggccccc cgggggatcc actagaggat ctcaatgaat attggttgac   4200
acgggcgtat aagacatgtt atactgttga ataacaagga cggatctgat caagagacag   4260
gatgaggatc gtttcgcatg attgaacaag atggattgca cgcaggttct ccggccgctt   4320
gggtggagag gctattcggc tatgactggg cacaacagac aatcggctgc tctgatgccg   4380
ccgtgttccg gctgtcagcg caggggcgcc cggttctttt tgtcaagacc gacctgtccg   4440
gtgccctgaa tgaactgcag gacgaggcag cgcggctatc gtggctggcc acgacgggcg   4500
ttccttgcgc agctgtgctc gacgttgtca ctgaagcggg aagggactgg ctgctattgg   4560
gcgaagtgcc ggggcaggat ctcctgtcat ctcaccttgc tcctgccgag aaagtatcca   4620
tcatggctga tgcaatgcgg cggctgcata cgcttgatcc ggctacctgc ccattcgacc   4680
accaagcgaa acatcgcatc gagcgagcac gtactcggat ggaagccggt cttgtcgatc   4740
aggatgatct ggacgaagag catcaggggc tcgcgccagc cgaactgttc gccaggctca   4800
aggcgcgcat gcccgacggc gaggatctcg tcgtgaccca tggcgatgcc tgcttgccga   4860
atatcatggt ggaaaatggc cgcttttctg gattcatcga ctgtggccgg ctgggtgtgg   4920
cggaccgcta tcaggacata gcgttggcta cccgtgatat tgctgaagag cttggcggcg   4980
aatgggctga ccgcttcctc gtgctttacg gtatcgccgc tcccgattcg cagcgcatcg   5040
ccttctatcg ccttcttgac gagttcttct gagcgggact ctggggttcg aaatgaccga   5100
ccaagcgacg cccaacctgc catcacgaga tttcgattcc accgccgcct tctatgaaag   5160
gttgggcttc ggaatcgttt tccgggacgc cggctggatg atcctccagc gcggggatct   5220
catgctggag ttcttcgccc accggggatc ctctagttct agactgcttt agattaactt   5280
ttgtcatgtg gcaattttta gaagctaaca tgttcttaga atttagatga tcacaaaaaa   5340
tgtaacatct attcgaaaaa ataagaaatt tgtttttgta tccaaaaaag cttgataaaa   5400
cgaattcatc aagccataaa aagaaggcct agaataatat ttaatatcta agcctttgaa   5460
aaatagatta tcgaactaaa tacctaaaca gtattagtcg tcaccaatag tgaattcgat   5520
gacttcttct tcaccatcga aggggttgat ttcgttaact tcgataaata cagaagtatc   5580
gtcattacct agggcataac cagaggtcag tacgacatcg ggaccgaaag gaacctgaag   5640
ggcagcagca ccagttgcag cagcagcata gccatcacca aaggcaacgg agccagaaaa   5700
gccagtgatg tcagccgtta gcagtggtgt cgatgtctac gaaggagacg gaagcagcga   5760
attcagcctt tgcggaagag gcaaagccta aagagagagc ggcagcacca gcagcaacag   5820
cagcgatttt tgcaaagttc atttttgttt ctccaataat caaaattttg aatgtgtaat   5880
tggatggaga ttatacttag aatatataac cccttacttt agtaaatata ccccacttct   5940
caaaagaaac gatcattctt tataagaaat tcacgtttaa ttgttgtgag caattaatat   6000
tttgtttgtt aagaatcagt caaattaaca actacattga aagccttttt ttttcaagta   6060
tcccagggaa caatctttac gtaagtataa ctttgacagc aagggcagtt agttttcgtg   6120
```

```
tactgcttat gggtttgggt tgttaattag attgtttttg gccaaaaata aagattgaag   6180
tttccataac accttgcatt tgtgagagtt actaaatttt tatatagtca tttattcaaa   6240
atttggcgat cgcctttttt ccttttcctc tcctcctgcc tgctggtgat cagccttagc   6300
cttggattgc agcaaccagc gggggcaatt tttggcctac ccttaccgga agcagatcta   6360
ggggaggtgt tgccgaacaa tggtcaggag ctaatcgtcg atcggtgtgt gtatttggat   6420
ggccactgta tttttaaggt ggcggccgca tcatcaatcc ccgtgatgtt tcagtcccgt   6480
agtcgggatt tagtggttgg aaagcggaac gtcgcgccga aaccatcgcc aggacgggtt   6540
tcagtcccgt agtcgggatt tagtggttgg aaagtgatta tgttcaagaa atcacaacgc   6600
aaaagaaaaa gtttcagtcc cgtagtcggg atttagtggt tggaaagtca agcgagatac   6660
ccaccagaaa gcctttgacc tggtttcagt cccgagtcgg gatttagtgg ttggaaaggc   6720
ggcggctgat gtcgccaatg cggttatcga tggccagttt cagtcccgta gtcgggattt   6780
agtggttgga aagtcccaag gggacaggg  cggtgatcct cgatgttgcg tgtttcagtc   6840
ccgtagtcgg gatttagtgg ttggaaagac tcgtctatat atacagagat tactacagag   6900
atgtttcagt cccgtagtcg ggatttagtg gttggaaagc gggaaagtag cctgttttgt   6960
ggagaattgc aggcgtttca gtactagtga tggcggccgg gagcatgcga cgtcgggccc   7020
aattcgccct atagtgagtc gtattacaat tcactggccg tcgttttaca acgtcgtgac   7080
tgggaaaacc ctggcgttac ccaacttaat cgccttgcag cacatccccc tttcgccagc   7140
tggcgtaata gcgaagaggc ccgcaccgat cgcccttccc aacagttgcg cagcctgaat   7200
ggcgaatgga cgcgccctgt agcggcgcat taagcgcggc gggtgtggtg gttacgcgca   7260
gcgtgaccgc tacacttgcc agcgccctag cgcccgctcc tttcgctttc ttcccttcct   7320
ttctcgccac gttcgccggc tttccccgtc aagctctaaa tcgggggctc cctttagggt   7380
tccgatttag agctttacgg cacctcgacc gcaaaaaact tgatttgggt gatggttcac   7440
gtagtgggcc atcgccctga tagacggttt ttcgcccttt gacgttggag tccacgttct   7500
ttaatagtgg actcttgttc caaactggaa caacactcaa ccctatctcg gtctattctt   7560
ttgatttata agggattttg ccgatttcgg cctattggtt aaaaaatgag ctgatttaac   7620
aaatatttaa cgcgaatttt aacaaaatat taacgtttac aatttcgcct gatgcggtat   7680
tttctcctta cgcatctgtg cggtatttca caccgcatac aggtggcact tttcggggaa   7740
atgtgcgcgg aacccctatt tgtttatttt tctaaataca ttcaaatatg tatccgctca   7800
tgagacaata accctgataa atgcttcaat aatattgaaa aaggaagagt atgagtattc   7860
aacatttccg tgtcgccctt attccctttt ttgcggcatt ttgccttcct gtttttgctc   7920
acccagaaac gctggtgaaa gtaaaagatg ctgaagatca gttgggtgca cgagtgggtt   7980
acatcgaact ggatctcaac agcggtaaga tccttgagag ttttcgcccc gaagaacgtt   8040
ttccaatgat gagcactttt aaagttctgc tatgtggcgc ggtattatcc cgtattgacg   8100
ccgggcaaga gcaactcggt cgccgcatac actattctca gaatgacttg gttgagtact   8160
caccagtcac agaaaagcat cttacggatg gcatgacagt aagagaatta tgcagtgctg   8220
ccataaccat gagtgataac actgcggcca acttacttct gacaacgatc ggaggaccga   8280
aggagctaac cgcttttttg cacaacatgg gggatcatgt aactcgcctt gatcgttggg   8340
aaccggagct gaatgaagcc ataccaaacg acgagcgtga caccacgatg cctgtagcaa   8400
tgccaacaac gttgcgcaaa ctattaactg gcgaactact tactctagct tcccggcaac   8460
```

-continued

```
aattaataga ctggatggag gcggataaag ttgcaggacc acttctgcgc tcggcccttc   8520
cggctggctg gtttattgct gataaatctg gagccggtga gcgtgggtct cgcggtatca   8580
ttgcagcact ggggccagat ggtaagccct cccgtatcgt agttatctac acgacgggga   8640
gtcaggcaac tatggatgaa cgaaatagac agatcgctga gataggtgcc tcactgatta   8700
agcattggta actgtcagac caagtttact catatatact ttagattgat ttaaaacttc   8760
atttttaatt taaaaggatc taggtgaaga tcctttttga taatctcatg accaaaatcc   8820
cttaacgtga gttttcgttc cactgagcgt cagaccccgt agaaaagatc aaaggatctt   8880
cttgagatcc tttttttctg cgcgtaatct gctgcttgca aacaaaaaaa ccaccgctac   8940
cagcggtggt ttgtttgccg gatcaagagc taccaactct ttttccgaag gtaactggct   9000
tcagcagagc gcagatacca aatactgtcc ttctagtgta gccgtagtta ggccaccact   9060
tcaagaactc tgtagcaccg cctacatacc tcgctctgct aatcctgtta ccagtggctg   9120
ctgccagtgg cgataagtcg tgtcttaccg ggttggactc aagacgatag ttaccggata   9180
aggcgcagcg gtcgggctga acggggggtt cgtgcacaca gcccagcttg gagcgaacga   9240
cctacaccga actgagatac ctacagcgtg agctatgaga aagcgccacg cttcccgaag   9300
ggagaaaggc ggacaggtat ccggtaagcg gcagggtcgg aacaggagag cgcacgaggg   9360
agcttccagg gggaaacgcc tggtatcttt atagtcctgt cgggtttcgc cacctctgac   9420
ttgagcgtcg atttttgtga tgctcgtcag gggggcggag cctatggaaa aacgccagca   9480
acgcggcctt tttacggttc ctggcctttt gctggccttt tgctcacatg ttctttcctg   9540
cgttatcccc tgattctgtg gataaccgta ttaccgcctt tgagtgagct gataccgctc   9600
gccgcagccg aacgaccgag cgcagcgagt cagtgagcga ggaagcggaa gagcgcccaa   9660
tacgcaaacc gcctctcccc gcgcgttggc cgattcatta atgcagctgg cacgacaggt   9720
ttcccgactg gaaagcgggc agtgagcgca acgcaattaa tgtgagttag ctcactcatt   9780
aggcacccca ggctttacac tttatgcttc cggctcgtat gttgtgtgga attgtgagcg   9840
gataacaatt tcacacagga aacagctatg accatgatta cgccaagcta tttaggtgac   9900
actatagaat actcaagcta tgcatctctg cgccgcgttt agtagattct gtgtttgagg   9960
aagccggttc agctgatctt gacgaagaag atatcaatgt tgatattttt ggtctctttt  10020
tggatgaatt tggggaggtc gaggatattg ttgatttcga tttcagtgac attcccgatg  10080
cttatactca ggtaggtctc gatctttttg agagagatgc gatcgccccc aatactgttg  10140
tatttcggga aagaacaaac tatgtacccc acgtaagttt taccggaact aaagttgatg  10200
cccgtaatca aaaacgttat tatactggtc tactttggga ttataccgaa ggagagtcag  10260
ggcaaaagtt tcgttcttac ttgggagctg actaccagta tcgcaatcca gagaaaggtg  10320
tacgggcctt cactggtgta attggttaca ttaatcctga tcgagactac tacagtcaag  10380
tttggggtga aattgctaaa acattcagtt ctgctgataa aaatactgct ttcacactag  10440
gcacctcaat ggtctatgct atcgaccaag cggatgatgt gggtgacgat gtttttgttg  10500
atgcagatgc cagtaagttc ttattgagtg cgggggctcg ctttggttcc atcagactag  10560
gtgttgatca taacattgac tttttcccta attctgatga tgcgagtact gttttatccg  10620
ctggcattga cttcggtgag aatgttactt ttgctggttt ttacacacct tatgatgagg  10680
gatcaaatgt tgccttggta ggggccaacc ttggtttccg ctttggtact gattacaata  10740
gcccaagatt atctttgggt tggagtcaaa atgagtatcg atttgacacc aataacttca  10800
ttgacaatcg ctacacgttg accttccgcg tgggtcgtcc tggcaatccg tttggccctc  10860
```

-continued

```
agtaaaaacc aatttaattt ctctatttat agaaaaaaag atggtgaaga ttgtctcacc  10920

atcttttttt gattacgtga acagataaca atttacacat aaaaaaagct ttgccaataa  10980

aaaaatattg ttaaaagctt atttttttgc cttttaatga aaatcaataa accatagata  11040

caaagactta aacatagcaa cagcaatatt actcagaaaa aatacacttc taaaaatccg  11100

cgacttttta atcagcagta g                                            11121
```